US012446874B2

(12) United States Patent
Shelton, IV et al.

(10) Patent No.: US 12,446,874 B2
(45) Date of Patent: Oct. 21, 2025

(54) CARTRIDGE ASSEMBLIES WITH ABSORBABLE METAL STAPLES AND ABSORBABLE IMPLANTABLE ADJUNCTS

(71) Applicant: Cilag GmbH International, Zug (CH)

(72) Inventors: Frederick E. Shelton, IV, Hillsboro, OH (US); Jason L. Harris, Lebanon, OH (US); Chad E. Eckert, Terrace Park, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 17/718,879

(22) Filed: Apr. 12, 2022

(65) Prior Publication Data

US 2022/0361872 A1 Nov. 17, 2022

Related U.S. Application Data

(60) Provisional application No. 63/186,519, filed on May 10, 2021.

(51) Int. Cl.
*A61B 17/72* (2006.01)
*A61B 17/064* (2006.01)
(Continued)

(52) U.S. Cl.
CPC ........ *A61B 17/0644* (2013.01); *A61B 17/064* (2013.01); *A61B 17/072* (2013.01);
(Continued)

(58) Field of Classification Search
CPC ............ A61B 17/07292; A61B 17/072; A61B 17/0644
(Continued)

(56) References Cited

U.S. PATENT DOCUMENTS 4,448,613 A 5/1984 Sherby et al.
5,403,312 A 4/1995 Yates et al.
(Continued)

FOREIGN PATENT DOCUMENTS

CA 2673914 C 8/2008
CN 209360781 U 9/2019
(Continued)

OTHER PUBLICATIONS

Myrissa et al., "In vitro and in vivo comparison of binary Mg alloys and pure Mg," Materials Science and Engineering C 61 (2016) 865-874.
(Continued)

*Primary Examiner* — Gloria R Weeks
(74) *Attorney, Agent, or Firm* — Troutman Pepper Locke LLP

(57) ABSTRACT

A staple cartridge assembly includes a cartridge body with a deck, a longitudinal slot defined in the deck, and staple cavities defined in the deck. The staple cartridge assembly includes staples removably stored in the staple cavities, wherein the staples are deployable from the staple cavities into tissue of a patient, and wherein the staples comprise substrates comprised of metal that degrades when exposed to a degradation source in the patient. The staple cartridge assembly includes an implantable adjunct, wherein the staples are configured to hold the implantable adjunct to the tissue, and wherein the implantable adjunct is configured to delay an initiation of the degradation of regions of the metal in contact with the implantable adjunct in the patient, and wherein the implantable adjunct is configured to modify a local environment surrounding the staples to control a degradation rate of the staples after the initial delay.

19 Claims, 126 Drawing Sheets

(51) Int. Cl.

| | |
|---|---|
| ***A61B 17/072*** | (2006.01) |
| ***A61B 17/10*** | (2006.01) |
| ***A61B 50/30*** | (2016.01) |
| ***A61B 90/98*** | (2016.01) |
| ***A61L 31/02*** | (2006.01) |
| ***A61L 31/04*** | (2006.01) |
| ***A61L 31/10*** | (2006.01) |
| ***A61L 31/14*** | (2006.01) |
| ***A61L 31/16*** | (2006.01) |
| *A61B 17/00* | (2006.01) |
| *A61B 17/068* | (2006.01) |
| *A61B 90/00* | (2016.01) |

(52) U.S. Cl.
CPC ...... *A61B 17/07207* (2013.01); *A61B 17/105* (2013.01); *A61B 50/3001* (2016.02); *A61B 90/98* (2016.02); *A61L 31/022* (2013.01); *A61L 31/028* (2013.01); *A61L 31/042* (2013.01); *A61L 31/048* (2013.01); *A61L 31/10* (2013.01); *A61L 31/148* (2013.01); *A61L 31/16* (2013.01); *A61B 2017/00004* (2013.01); *A61B 2017/00022* (2013.01); *A61B 2017/00084* (2013.01); *A61B 2017/00119* (2013.01); *A61B 2017/00845* (2013.01); *A61B 17/0686* (2013.01); *A61B 2017/0688* (2013.01); *A61B 2017/07228* (2013.01); *A61B 2017/07235* (2013.01); *A61B 2017/07257* (2013.01); *A61B 2017/07264* (2013.01); *A61B 2017/07271* (2013.01); *A61B 2017/07278* (2013.01); *A61B 2017/07285* (2013.01); *A61B 2050/3004* (2016.02); *A61B 2090/0807* (2016.02)

(58) Field of Classification Search
USPC .......................................................... 606/219
See application file for complete search history.

(56) References Cited

U.S. PATENT DOCUMENTS 6,652,621 B1 11/2003 Oishibashi et al.
6,780,261 B2 8/2004 Trozera
6,854,172 B2 2/2005 Kaese et al.
6,978,921 B2 12/2005 Shelton, IV et al.
7,000,818 B2 2/2006 Shelton, IV et al.
7,422,139 B2 9/2008 Shelton, IV et al.
7,438,209 B1 * 10/2008 Hess .................... A61B 17/105 227/176.1
7,464,849 B2 12/2008 Shelton, IV et al.
7,556,865 B2 7/2009 Drillet et al.
7,572,298 B2 8/2009 Roller et al.
7,621,952 B2 11/2009 Truckai et al.
7,666,351 B2 2/2010 Nishikawa et al.
7,670,334 B2 3/2010 Hueil et al.
7,673,781 B2 3/2010 Swayze et al.
7,753,245 B2 7/2010 Boudreaux et al.
7,845,537 B2 12/2010 Shelton, IV et al.
7,879,367 B2 2/2011 Heublein et al.
7,905,902 B2 * 3/2011 Huitema ............ A61B 17/0644 606/220
7,939,146 B2 5/2011 Borck et al.
7,966,799 B2 * 6/2011 Morgan ............. A61B 17/1155 411/469
7,976,650 B2 7/2011 Drillet et al.
7,980,443 B2 7/2011 Scheib et al.
8,002,909 B2 8/2011 Craig
8,034,101 B2 10/2011 Yamamoto et al.
8,057,536 B2 11/2011 Mueller et al.
8,137,380 B2 3/2012 Green et al.
8,172,908 B2 5/2012 Ip et al.
8,206,837 B2 6/2012 Mishima
8,210,411 B2 7/2012 Yates et al.
8,220,688 B2 7/2012 Laurent et al.
8,246,762 B2 8/2012 Janko et al.
8,267,992 B2 9/2012 Atanasoska et al.
8,268,235 B2 9/2012 Gerold
8,293,031 B2 10/2012 Gerold et al.
8,308,040 B2 11/2012 Huang et al.
8,365,976 B2 2/2013 Hess et al.
8,372,144 B2 2/2013 Mueller et al.
8,382,824 B2 2/2013 Weber
8,393,514 B2 3/2013 Shelton, IV et al.
8,419,785 B2 4/2013 Kramer-Brown et al.
8,435,281 B2 5/2013 Weber
8,561,870 B2 10/2013 Baxter, III et al.
8,562,664 B2 10/2013 Kramer et al.
8,591,672 B2 11/2013 Janko et al.
8,608,045 B2 12/2013 Smith et al.
8,709,073 B2 4/2014 Klocke et al.
8,733,613 B2 5/2014 Huitema et al.
8,741,073 B2 6/2014 Bayer et al.
8,801,778 B2 8/2014 Becher et al.
8,852,622 B2 10/2014 Borck
8,871,829 B2 10/2014 Gerold et al.
8,888,841 B2 11/2014 Pandelidis et al.
8,926,772 B2 1/2015 Bouzekri et al.
8,956,403 B2 2/2015 Gregorich et al.
8,974,541 B2 3/2015 Nies et al.
8,986,369 B2 3/2015 Steckel et al.
8,992,600 B2 3/2015 Goetzen et al.
9,045,816 B2 6/2015 Oishi et al.
9,050,083 B2 6/2015 Yates et al.
9,072,535 B2 7/2015 Shelton, IV et al.
9,072,618 B2 7/2015 Doerr et al.
9,072,810 B2 7/2015 Ip et al.
9,089,408 B2 7/2015 Xu
9,090,955 B2 7/2015 Xu et al.
9,095,642 B2 8/2015 Harder et al.
9,101,358 B2 8/2015 Kerr et al.
9,119,906 B2 9/2015 Tomantschger et al.
9,125,649 B2 * 9/2015 Bruewer .......... A61B 17/07207
9,155,816 B2 10/2015 Hiromoto et al.
9,200,355 B2 12/2015 Scott et al.
9,211,120 B2 12/2015 Scheib et al.
9,259,516 B2 2/2016 Bayer
9,283,305 B2 3/2016 Birdsall et al.
9,307,986 B2 4/2016 Hall et al.
9,307,989 B2 4/2016 Shelton, IV et al.
9,326,767 B2 5/2016 Koch, Jr. et al.
9,332,987 B2 5/2016 Leimbach et al.
9,345,481 B2 5/2016 Hall et al.
9,351,726 B2 5/2016 Leimbach et al.
9,351,727 B2 5/2016 Leimbach et al.
9,358,003 B2 6/2016 Hall et al.
9,364,312 B2 6/2016 Xu
9,364,581 B2 6/2016 Kurze et al.
9,398,911 B2 7/2016 Auld
9,445,902 B2 9/2016 Klein et al.
9,446,174 B2 9/2016 Weber et al.
9,452,243 B2 9/2016 Gratz et al.
9,463,260 B2 * 10/2016 Stopek ............... A61B 17/0644
9,468,438 B2 10/2016 Baber et al.
9,480,585 B2 11/2016 Gerold et al.
9,486,337 B2 11/2016 Bayer et al.
9,504,554 B2 11/2016 Bayer et al.
9,510,884 B2 12/2016 Tamai et al.
9,554,794 B2 1/2017 Baber et al.
9,561,308 B2 2/2017 Schaffer
9,629,623 B2 4/2017 Lytle, IV et al.
9,629,629 B2 4/2017 Leimbach et al.
9,636,160 B2 5/2017 Honda et al.
9,649,110 B2 5/2017 Parihar et al.
9,676,026 B2 6/2017 Witte et al.
9,687,230 B2 6/2017 Leimbach et al.
9,690,362 B2 6/2017 Leimbach et al.
9,700,309 B2 7/2017 Jaworek et al.
9,700,311 B2 7/2017 Shelton, IV et al.
9,700,652 B2 7/2017 Loeffler et al.
9,700,657 B2 7/2017 Kühn et al.
9,724,094 B2 8/2017 Baber et al.

(56) References Cited

U.S. PATENT DOCUMENTS 9,733,663 B2 8/2017 Leimbach et al.
9,737,301 B2 8/2017 Baber et al.
9,743,929 B2 8/2017 Leimbach et al.
9,750,499 B2 9/2017 Leimbach et al.
9,757,128 B2 9/2017 Baber et al.
9,782,169 B2 10/2017 Kimsey et al.
9,788,836 B2 10/2017 Overmyer et al.
9,789,663 B2 10/2017 Zhang et al.
9,801,626 B2 10/2017 Parihar et al.
9,801,628 B2 * 10/2017 Harris .................. A61B 17/072
9,804,618 B2 10/2017 Leimbach et al.
9,808,244 B2 11/2017 Leimbach et al.
9,808,246 B2 11/2017 Shelton, IV et al.
9,814,460 B2 11/2017 Kimsey et al.
9,820,738 B2 11/2017 Lytle, IV et al.
9,826,976 B2 11/2017 Parihar et al.
9,826,977 B2 11/2017 Leimbach et al.
9,833,241 B2 12/2017 Huitema et al.
9,839,420 B2 12/2017 Shelton, IV et al.
9,844,368 B2 12/2017 Boudreaux et al.
9,844,369 B2 12/2017 Huitema et al.
9,844,374 B2 12/2017 Lytle, IV et al.
9,844,375 B2 12/2017 Overmyer et al.
9,849,008 B2 12/2017 Steckel et al.
9,861,361 B2 1/2018 Aronhalt et al.
9,867,612 B2 1/2018 Parihar et al.
9,877,721 B2 1/2018 Schellin et al.
9,883,860 B2 2/2018 Leimbach et al.
9,888,919 B2 2/2018 Leimbach et al.
9,895,148 B2 2/2018 Shelton, IV et al.
9,901,342 B2 2/2018 Shelton, IV et al.
9,913,707 B2 3/2018 Bayer et al.
9,924,944 B2 3/2018 Shelton, IV et al.
9,924,961 B2 3/2018 Shelton, IV et al.
9,931,118 B2 4/2018 Shelton, IV et al.
9,937,283 B2 * 4/2018 Shelton, IV ..... A61B 17/07207
9,943,309 B2 4/2018 Shelton, IV et al.
9,943,625 B2 4/2018 Koo et al.
9,968,355 B2 5/2018 Shelton, IV et al.
9,987,000 B2 6/2018 Shelton, IV et al.
9,993,248 B2 6/2018 Shelton, IV et al.
9,993,258 B2 6/2018 Shelton, IV et al.
10,004,497 B2 6/2018 Overmyer et al.
10,004,501 B2 6/2018 Shelton, IV et al.
D822,206 S 7/2018 Shelton, IV et al.
10,010,324 B2 7/2018 Huitema et al.
10,010,652 B2 7/2018 Dingeldein et al.
10,013,049 B2 7/2018 Leimbach et al.
10,016,199 B2 7/2018 Baber et al.
10,022,164 B2 7/2018 Mangiardi
10,022,165 B2 7/2018 Mangiardi
10,022,470 B2 7/2018 Decker et al.
10,028,761 B2 7/2018 Leimbach et al.
D826,405 S 8/2018 Shelton, IV et al.
10,045,776 B2 8/2018 Shelton, IV et al.
10,045,779 B2 8/2018 Savage et al.
10,046,094 B1 8/2018 Munroe et al.
10,052,044 B2 8/2018 Shelton, IV et al.
10,052,102 B2 8/2018 Baxter, III et al.
10,052,188 B2 8/2018 Kalb et al.
10,052,405 B2 8/2018 Koo et al.
10,076,329 B2 * 9/2018 Shelton, IV ..... A61B 17/07292
10,077,492 B2 9/2018 Li et al.
10,085,748 B2 10/2018 Morgan et al.
10,085,860 B2 10/2018 Steckel et al.
10,098,642 B2 10/2018 Baxter, III et al.
10,111,679 B2 10/2018 Baber et al.
D833,608 S 11/2018 Miller et al.
10,117,649 B2 11/2018 Baxter, III et al.
10,135,242 B2 11/2018 Baber et al.
10,136,887 B2 11/2018 Shelton, IV et al.
D836,198 S 12/2018 Harris et al.
10,149,680 B2 12/2018 Parihar et al.
10,154,841 B2 12/2018 Weaner et al.
10,154,865 B2 12/2018 Bayer et al.
10,159,483 B2 12/2018 Beckman et al.
10,166,105 B2 1/2019 Thorwarth et al.
10,178,992 B2 1/2019 Wise et al.
10,180,463 B2 1/2019 Beckman et al.
10,182,816 B2 1/2019 Shelton, IV et al.
10,182,818 B2 1/2019 Hensel et al.
10,188,385 B2 1/2019 Kerr et al.
10,188,394 B2 1/2019 Shelton, IV et al.
10,194,904 B2 2/2019 Viola et al.
10,201,364 B2 2/2019 Leimbach et al.
10,226,250 B2 3/2019 Beckman et al.
10,245,027 B2 4/2019 Shelton, IV et al.
10,245,028 B2 4/2019 Shelton, IV et al.
10,245,029 B2 4/2019 Hunter et al.
10,245,030 B2 4/2019 Hunter et al.
10,245,033 B2 4/2019 Overmyer et al.
10,258,331 B2 4/2019 Shelton, IV et al.
10,265,068 B2 4/2019 Harris et al.
10,266,922 B2 4/2019 Manuel et al.
10,271,851 B2 4/2019 Shelton, IV et al.
10,271,971 B2 4/2019 Hanada et al.
10,272,183 B2 4/2019 Bayer et al.
D847,989 S 5/2019 Shelton, IV et al.
10,285,705 B2 5/2019 Shelton, IV et al.
10,292,704 B2 5/2019 Harris et al.
10,299,792 B2 5/2019 Huitema et al.
D850,617 S 6/2019 Shelton, IV et al.
10,307,159 B2 6/2019 Harris et al.
10,314,582 B2 6/2019 Shelton, IV et al.
10,321,907 B2 6/2019 Shelton, IV et al.
10,335,149 B2 7/2019 Baxter, III et al.
10,342,543 B2 7/2019 Shelton, IV et al.
10,357,246 B2 7/2019 Shelton, IV et al.
10,357,596 B2 7/2019 Sager et al.
10,368,861 B2 8/2019 Baxter, III et al.
10,368,865 B2 8/2019 Harris et al.
10,376,263 B2 8/2019 Morgan et al.
10,390,829 B2 * 8/2019 Eckert .................. A61B 17/105
10,405,857 B2 9/2019 Shelton, IV et al.
10,405,863 B2 9/2019 Wise et al.
10,413,291 B2 9/2019 Worthington et al.
10,413,293 B2 9/2019 Shelton, IV et al.
10,413,297 B2 9/2019 Harris et al.
10,420,552 B2 9/2019 Shelton, IV et al.
10,426,471 B2 10/2019 Shelton, IV et al.
10,433,837 B2 10/2019 Worthington et al.
10,433,849 B2 10/2019 Shelton, IV et al.
10,441,279 B2 10/2019 Shelton, IV et al.
10,448,948 B2 10/2019 Shelton, IV et al.
10,448,950 B2 10/2019 Shelton, IV et al.
10,456,140 B2 10/2019 Shelton, IV et al.
10,463,771 B2 11/2019 Kopp et al.
10,470,762 B2 11/2019 Leimbach et al.
10,470,764 B2 11/2019 Baxter, III et al.
10,470,768 B2 11/2019 Harris et al.
10,478,190 B2 11/2019 Miller et al.
10,478,236 B2 11/2019 Tacktill
10,478,280 B2 * 11/2019 Vendely ................. A61B 17/29
10,478,529 B2 11/2019 Imwinkelried et al.
10,485,542 B2 11/2019 Shelton, IV et al.
10,485,543 B2 11/2019 Shelton, IV et al.
10,492,785 B2 12/2019 Overmyer et al.
10,499,914 B2 12/2019 Huang et al.
10,512,712 B2 12/2019 Klocke et al.
10,517,595 B2 12/2019 Hunter et al.
10,517,596 B2 12/2019 Hunter et al.
10,524,789 B2 1/2020 Swayze et al.
10,525,173 B2 1/2020 Qin et al.
10,531,874 B2 1/2020 Morgan et al.
10,532,134 B2 1/2020 Zhou et al.
10,537,324 B2 1/2020 Shelton, IV et al.
10,537,325 B2 1/2020 Bakos et al.
10,542,979 B2 1/2020 Shelton, IV et al.
10,542,982 B2 1/2020 Beckman et al.
10,542,991 B2 1/2020 Shelton, IV et al.
10,548,504 B2 2/2020 Shelton, IV et al.
10,561,422 B2 2/2020 Schellin et al.
10,568,625 B2 2/2020 Harris et al.
10,568,626 B2 2/2020 Shelton, IV et al.

(56) References Cited

U.S. PATENT DOCUMENTS 10,568,632 B2 2/2020 Miller et al.
10,569,071 B2 * 2/2020 Harris .................. A61M 37/00
10,582,928 B2 3/2020 Hunter et al.
10,588,625 B2 3/2020 Weaner et al.
10,588,630 B2 3/2020 Shelton, IV et al.
10,588,631 B2 3/2020 Shelton, IV et al.
10,588,632 B2 3/2020 Shelton, IV et al.
10,603,036 B2 3/2020 Hunter et al.
10,610,224 B2 4/2020 Shelton, IV et al.
10,617,412 B2 4/2020 Shelton, IV et al.
10,617,414 B2 4/2020 Shelton, IV et al.
10,617,418 B2 * 4/2020 Barton .................... A61L 31/16
10,624,635 B2 4/2020 Harris et al.
10,639,034 B2 5/2020 Harris et al.
10,639,035 B2 5/2020 Shelton, IV et al.
10,653,413 B2 5/2020 Worthington et al.
10,667,809 B2 6/2020 Bakos et al.
10,667,810 B2 6/2020 Shelton, IV et al.
10,667,811 B2 6/2020 Harris et al.
10,675,021 B2 6/2020 Harris et al.
10,675,024 B2 6/2020 Shelton, IV et al.
10,675,025 B2 6/2020 Swayze et al.
10,675,026 B2 6/2020 Harris et al.
10,682,136 B2 6/2020 Harris et al.
10,682,138 B2 6/2020 Shelton, IV et al.
10,687,806 B2 6/2020 Shelton, IV et al.
10,687,809 B2 6/2020 Shelton, IV et al.
10,687,810 B2 6/2020 Shelton, IV et al.
10,695,055 B2 6/2020 Shelton, IV et al.
10,702,270 B2 7/2020 Shelton, IV et al.
10,709,446 B2 7/2020 Harris et al.
10,709,816 B2 7/2020 Andersen et al.
10,716,564 B2 * 7/2020 Shelton, IV ..... A61B 17/07292
10,736,629 B2 8/2020 Shelton, IV et al.
10,758,229 B2 9/2020 Shelton, IV et al.
10,758,230 B2 9/2020 Shelton, IV et al.
10,765,775 B2 9/2020 Radisch et al.
10,779,821 B2 9/2020 Harris et al.
10,779,823 B2 9/2020 Shelton, IV et al.
10,781,521 B2 9/2020 Lee et al.
10,799,237 B2 * 10/2020 Shelton, IV ............ A61L 31/04
10,813,638 B2 10/2020 Shelton, IV et al.
10,835,245 B2 11/2020 Swayze et al.
10,835,246 B2 11/2020 Shelton, IV et al.
10,835,247 B2 11/2020 Shelton, IV et al.
10,842,492 B2 11/2020 Shelton, IV et al.
10,849,697 B2 12/2020 Yates et al.
10,856,867 B2 12/2020 Shelton, IV et al.
10,856,868 B2 12/2020 Shelton, IV et al.
10,856,870 B2 12/2020 Harris et al.
10,869,663 B2 * 12/2020 Shelton, IV ......... A61B 17/072
10,881,399 B2 1/2021 Shelton, IV et al.
10,881,401 B2 1/2021 Baber et al.
10,888,322 B2 1/2021 Morgan et al.
10,892,899 B2 1/2021 Shelton, IV et al.
10,893,863 B2 1/2021 Shelton, IV et al.
10,893,864 B2 1/2021 Harris et al.
10,898,186 B2 1/2021 Bakos et al.
10,912,559 B2 2/2021 Harris et al.
10,918,385 B2 2/2021 Overmyer et al.
D914,878 S 3/2021 Shelton, IV et al.
10,932,872 B2 3/2021 Shelton, IV et al.
10,939,911 B2 3/2021 Huitema et al.
10,944,728 B2 3/2021 Wiener et al.
10,945,727 B2 3/2021 Shelton, IV et al.
10,959,727 B2 3/2021 Hunter et al.
10,966,791 B2 4/2021 Harris et al.
10,973,516 B2 4/2021 Shelton, IV et al.
10,980,536 B2 4/2021 Weaner et al.
10,980,538 B2 4/2021 Nalagatla et al.
10,987,178 B2 4/2021 Shelton, IV et al.
10,993,712 B2 5/2021 Lahteenkorva et al.
10,993,715 B2 5/2021 Shelton, IV et al.
11,000,278 B2 5/2021 Shelton, IV et al.
11,013,563 B2 5/2021 Shelton, IV et al.
11,026,751 B2 6/2021 Shelton, IV et al.
11,039,834 B2 6/2021 Harris et al.
11,045,191 B2 6/2021 Shelton, IV et al.
11,045,192 B2 6/2021 Harris et al.
D926,318 S 7/2021 Posey et al.
11,051,958 B2 7/2021 Mangiardi
11,053,572 B2 7/2021 Manuel et al.
11,058,498 B2 7/2021 Shelton, IV et al.
11,058,804 B2 * 7/2021 Widenhouse .... A61B 17/07292
11,064,997 B2 7/2021 Shelton, IV et al.
11,065,135 B2 7/2021 Hanada et al.
11,069,012 B2 7/2021 Shelton, IV et al.
11,076,921 B2 8/2021 Shelton, IV et al.
11,083,458 B2 8/2021 Harris et al.
11,090,048 B2 8/2021 Fanelli et al.
11,096,688 B2 8/2021 Shelton, IV et al.
11,100,631 B2 8/2021 Yates et al.
11,129,611 B2 9/2021 Shelton, IV et al.
11,132,462 B2 9/2021 Shelton, IV et al.
11,134,942 B2 10/2021 Harris et al.
11,149,166 B2 10/2021 Kumta et al.
11,160,551 B2 11/2021 Shelton, IV et al.
11,166,716 B2 11/2021 Shelton, IV et al.
11,166,772 B2 11/2021 Shelton, IV et al.
11,179,155 B2 11/2021 Shelton, IV et al.
11,179,208 B2 11/2021 Yates et al.
11,185,330 B2 11/2021 Huitema et al.
11,191,539 B2 12/2021 Overmyer et al.
11,191,540 B2 12/2021 Aronhalt et al.
11,197,668 B2 12/2021 Shelton, IV et al.
11,202,570 B2 12/2021 Shelton, IV et al.
11,207,065 B2 12/2021 Harris et al.
11,207,067 B2 12/2021 Shelton, IV et al.
11,213,293 B2 1/2022 Worthington et al.
11,213,294 B2 1/2022 Shelton, IV et al.
11,213,359 B2 1/2022 Shelton, IV et al.
11,219,453 B2 1/2022 Shelton, IV et al.
11,224,426 B2 1/2022 Shelton, IV et al.
11,229,437 B2 1/2022 Shelton, IV et al.
11,253,254 B2 2/2022 Kimball et al.
11,253,256 B2 2/2022 Harris et al.
11,259,806 B2 3/2022 Shelton, IV et al.
11,266,468 B2 3/2022 Shelton, IV et al.
11,278,280 B2 3/2022 Shelton, IV et al.
11,284,890 B2 3/2022 Nalagatla et al.
11,284,988 B2 3/2022 Kalb et al.
11,291,440 B2 4/2022 Harris et al.
11,324,862 B2 5/2022 Calisse
11,406,382 B2 8/2022 Shelton, IV et al.
11,410,259 B2 8/2022 Harris et al.
11,419,606 B2 8/2022 Overmyer et al.
11,419,630 B2 8/2022 Yates et al.
11,426,251 B2 8/2022 Kimball et al.
11,432,816 B2 9/2022 Leimbach et al.
11,432,885 B2 9/2022 Shelton, IV et al.
11,452,526 B2 9/2022 Ross et al.
11,452,528 B2 9/2022 Leimbach et al.
D967,421 S 10/2022 Shelton, IV et al.
11,471,156 B2 10/2022 Shelton, IV et al.
11,471,157 B2 10/2022 Baxter, III et al.
11,478,355 B2 10/2022 Tadic et al.
11,497,538 B2 11/2022 Mitchell et al.
11,517,315 B2 12/2022 Huitema et al.
11,517,390 B2 12/2022 Baxter, III
11,534,259 B2 12/2022 Leimbach et al.
D974,560 S 1/2023 Shelton, IV et al.
11,571,210 B2 2/2023 Shelton, IV et al.
11,589,865 B2 2/2023 Shelton, IV et al.
11,627,961 B2 * 4/2023 Shelton, IV ..... A61B 17/07292
227/175.1
11,779,341 B2 * 10/2023 Shelton, V ....... A61B 17/07207
227/177.1
2004/0167572 A1 * 8/2004 Roth ................ A61B 17/12181
606/219
2004/0167632 A1 8/2004 Wen et al.
2005/0079088 A1 4/2005 Wirth et al.
2006/0052824 A1 3/2006 Ransick et al.
2006/0052825 A1 3/2006 Ransick et al.
2006/0069069 A1 3/2006 Kajander et al.

(56) References Cited

U.S. PATENT DOCUMENTS

2006/0085081 A1 4/2006 Shadduck et al.
2006/0130947 A1 6/2006 Oishi et al.
2006/0198869 A1 9/2006 Furst et al.
2006/0229711 A1* 10/2006 Yan .......................... A61F 2/82 623/1.38
2007/0055305 A1 3/2007 Schnyder et al.
2007/0169858 A1 7/2007 Oishi et al.
2007/0175955 A1 8/2007 Shelton et al.
2007/0224244 A1 9/2007 Weber et al.
2007/0243227 A1 10/2007 Gertner
2007/0250155 A1 10/2007 Simpson
2008/0015578 A1 1/2008 Erickson et al.
2008/0033530 A1 2/2008 Zberg et al.
2008/0033538 A1 2/2008 Borck et al.
2008/0033576 A1 2/2008 Gerold et al.
2008/0051335 A1 2/2008 Kleiner et al.
2008/0051872 A1* 2/2008 Borck ..................... A61L 31/10 523/121
2008/0058923 A1 3/2008 Bertsch et al.
2008/0082126 A1* 4/2008 Murray ............ A61B 17/07292 606/221
2008/0086195 A1 4/2008 Atanasoka et al.
2008/0110961 A1* 5/2008 Voegele ............... A61B 17/115 606/220
2008/0175885 A1 7/2008 Asgari
2008/0177378 A1 7/2008 Asgari
2008/0195189 A1 8/2008 Asgari
2008/0243242 A1 10/2008 Kappelt et al.
2008/0248086 A1 10/2008 Asgari
2008/0249564 A1* 10/2008 Hadba .................. A61B 17/064 606/219
2008/0249637 A1 10/2008 Asgari
2008/0249638 A1 10/2008 Asgari
2009/0048660 A1 2/2009 Adden
2009/0068249 A1* 3/2009 Furst ....................... C22C 27/04 606/151
2009/0081313 A1 3/2009 Aghion et al.
2009/0131540 A1 5/2009 Hiromoto et al.
2009/0164002 A1 6/2009 Becher et al.
2009/0192594 A1 7/2009 Borck
2009/0192595 A1 7/2009 Nagura et al.
2009/0192596 A1 7/2009 Adden
2009/0269237 A1 10/2009 Satoh et al.
2009/0287301 A1 11/2009 Weber
2009/0306725 A1 12/2009 Hiromoto et al.
2010/0023112 A1 1/2010 Borck et al.
2010/0023116 A1 1/2010 Borck et al.
2010/0047109 A1 2/2010 Nishikawa et al.
2010/0075162 A1 3/2010 Yang et al.
2010/0089973 A1 4/2010 Kostrzewski
2010/0131052 A1 5/2010 Kappelt et al.
2010/0145432 A1 6/2010 Bayer et al.
2010/0249900 A1 9/2010 Sager et al.
2010/0256747 A1 10/2010 Hausbeck et al.
2010/0331966 A1 12/2010 Borck
2011/0027188 A1 2/2011 Kleiner et al.
2011/0034926 A1 2/2011 Menneking et al.
2011/0034990 A1 2/2011 Borck
2011/0054629 A1 3/2011 Seok et al.
2011/0060419 A1 3/2011 Choi et al.
2011/0076319 A1 3/2011 Orlowski et al.
2011/0313527 A1 12/2011 Witte et al.
2012/0035740 A1 2/2012 Koo et al.
2012/0046732 A1 2/2012 Sillekens et al.
2012/0150281 A1 6/2012 Klocke et al.
2012/0150282 A1 6/2012 Adden et al.
2012/0172997 A1 7/2012 Thorwarth et al.
2012/0187179 A1* 7/2012 Gleiman .............. A61B 17/072 227/181.1
2012/0241491 A1 9/2012 Aldridge
2012/0277007 A1 11/2012 Oishi et al.
2013/0041455 A1 2/2013 Gerold
2013/0060348 A1 3/2013 Hodgkinson et al.
2013/0131814 A1 5/2013 Koo et al.
2013/0172929 A1 7/2013 Hess
2013/0195711 A1 8/2013 Araoka et al.
2013/0231727 A1 9/2013 Carlson et al.
2013/0256373 A1* 10/2013 Schmid ............ A61B 17/07207 227/176.1
2013/0256375 A1 10/2013 Shelton, IV
2014/0119987 A1 5/2014 Ogawa
2014/0152238 A1 6/2014 Shelton, IV
2014/0228967 A1 8/2014 Wittchow
2014/0228968 A1 8/2014 Wittchow
2014/0246475 A1 9/2014 Hall et al.
2014/0249557 A1 9/2014 Koch, Jr. et al.
2014/0263541 A1 9/2014 Leimbach et al.
2014/0263552 A1 9/2014 Hall et al.
2014/0271334 A1 9/2014 Kim et al.
2014/0271768 A1 9/2014 Radisch et al.
2014/0277184 A1 9/2014 Janko et al.
2014/0332581 A1 11/2014 Dudai
2014/0363330 A1 12/2014 Ogawa
2015/0136832 A1 5/2015 Baxter, III
2015/0140352 A1 5/2015 Bayer et al.
2015/0182674 A1 7/2015 Schaffer
2015/0272557 A1 10/2015 Overmyer et al.
2015/0272571 A1 10/2015 Leimbach et al.
2015/0272580 A1 10/2015 Leimbach et al.
2015/0272582 A1 10/2015 Leimbach et al.
2015/0272753 A1 10/2015 Steckel et al.
2015/0289979 A1 10/2015 Gabele et al.
2015/0351754 A1* 12/2015 Harris ................ A61B 17/0686 227/176.1
2015/0351757 A1* 12/2015 Harris .............. A61B 17/07292 227/176.1
2016/0000554 A1 1/2016 Woo et al.
2016/0066913 A1 3/2016 Swayze et al.
2016/0095592 A1 4/2016 Levinson et al.
2016/0106435 A1 4/2016 Brenner
2016/0138147 A1 5/2016 Jarvis et al.
2016/0220254 A1 8/2016 Baxter, III
2016/0249910 A1 9/2016 Shelton, IV et al.
2017/0014169 A1 1/2017 Dean et al.
2017/0014548 A1 1/2017 Sfeir et al.
2017/0028103 A1 2/2017 Song et al.
2017/0055986 A1 3/2017 Harrison
2017/0055996 A1 3/2017 Baxter, III
2017/0056007 A1* 3/2017 Eckert .................. A61B 17/105
2017/0157299 A1 6/2017 Janko et al.
2017/0224332 A1 8/2017 Hunter et al.
2017/0231628 A1 8/2017 Shelton, IV et al.
2017/0281186 A1 10/2017 Shelton, IV et al.
2017/0296213 A1 10/2017 Swensgard et al.
2017/0312102 A1 11/2017 Mangiardi
2018/0015203 A1 1/2018 Beniash et al.
2018/0140299 A1 5/2018 Weaner et al.
2018/0168575 A1 6/2018 Simms et al.
2018/0168577 A1 6/2018 Aronhalt et al.
2018/0168579 A1 6/2018 Aronhalt et al.
2018/0168598 A1 6/2018 Shelton, IV et al.
2018/0168608 A1 6/2018 Shelton, IV et al.
2018/0168609 A1 6/2018 Fanelli et al.
2018/0168615 A1 6/2018 Shelton, IV et al.
2018/0168618 A1 6/2018 Scott et al.
2018/0168619 A1 6/2018 Scott et al.
2018/0168623 A1 6/2018 Simms et al.
2018/0168625 A1 6/2018 Posada et al.
2018/0168633 A1 6/2018 Shelton, IV et al.
2018/0168647 A1 6/2018 Shelton, IV et al.
2018/0168648 A1 6/2018 Shelton, IV et al.
2018/0168650 A1 6/2018 Shelton, IV et al.
2018/0235617 A1* 8/2018 Shelton, IV ......... A61B 17/068
2018/0254670 A1* 9/2018 Tsukamoto ............. H02J 50/80
2018/0353174 A1 12/2018 Widenhouse et al.
2019/0001027 A1 1/2019 Ibrahim et al.
2019/0083683 A1 3/2019 Janko et al.
2019/0200905 A1 7/2019 Shelton, IV et al.
2019/0200906 A1 7/2019 Shelton, IV et al.
2019/0200981 A1 7/2019 Harris et al.
2019/0201104 A1 7/2019 Shelton, IV et al.
2019/0201112 A1 7/2019 Wiener et al.
2019/0201113 A1 7/2019 Shelton, IV et al.

(56) References Cited

U.S. PATENT DOCUMENTS

| | | | |
|---|---|---|---|
| 2019/0201115 A1 | 7/2019 | Shelton, IV et al. | |
| 2019/0201118 A1 | 7/2019 | Shelton, IV et al. | |
| 2019/0201139 A1 | 7/2019 | Shelton, IV et al. | |
| 2019/0201140 A1 | 7/2019 | Yates et al. | |
| 2019/0201142 A1 | 7/2019 | Shelton, IV et al. | |
| 2019/0205001 A1 | 7/2019 | Messerly et al. | |
| 2019/0205567 A1 | 7/2019 | Shelton, IV et al. | |
| 2019/0206551 A1 | 7/2019 | Yates et al. | |
| 2019/0206555 A1 | 7/2019 | Morgan et al. | |
| 2019/0206561 A1 | 7/2019 | Shelton, IV et al. | |
| 2019/0206565 A1 | 7/2019 | Shelton, IV | |
| 2019/0249286 A1 | 8/2019 | Kim et al. | |
| 2019/0298353 A1 | 10/2019 | Shelton, IV et al. | |
| 2019/0314016 A1 | 10/2019 | Huitema et al. | |
| 2019/0365957 A1 | 12/2019 | Paquin et al. | |
| 2020/0032372 A1 | 1/2020 | Bayer et al. | |
| 2020/0038018 A1* | 2/2020 | Shelton, IV ......... | A61B 17/068 |
| 2020/0054321 A1 | 2/2020 | Harris et al. | |
| 2020/0123636 A1 | 4/2020 | Eliezer et al. | |
| 2020/0197006 A1 | 6/2020 | Shelton, IV | |
| 2020/0205825 A1 | 7/2020 | Vendely | |
| 2020/0246002 A1 | 8/2020 | Holsten | |
| 2020/0261080 A1 | 8/2020 | Bakos | |
| 2020/0330642 A1 | 10/2020 | Qin et al. | |
| 2020/0345353 A1 | 11/2020 | Leimbach et al. | |
| 2020/0345356 A1 | 11/2020 | Leimbach et al. | |
| 2020/0345357 A1 | 11/2020 | Leimbach et al. | |
| 2020/0345358 A1 | 11/2020 | Jenkins | |
| 2020/0345359 A1 | 11/2020 | Baxter, III et al. | |
| 2020/0384160 A1 | 12/2020 | Decker et al. | |
| 2020/0390443 A1 | 12/2020 | Thompson | |
| 2020/0405296 A1 | 12/2020 | Shelton, IV et al. | |
| 2020/0405301 A1 | 12/2020 | Shelton, IV | |
| 2021/0252198 A1 | 8/2021 | Goepfert | |
| 2021/0338889 A1 | 11/2021 | Shashkov et al. | |
| 2021/0393268 A1 | 12/2021 | Shelton, IV et al. | |
| 2022/0016315 A1 | 1/2022 | Kopp | |
| 2022/0031310 A1* | 2/2022 | De La Rosa ...... | A61B 17/0684 |
| 2022/0133299 A1 | 5/2022 | Baxter, III | |
| 2022/0133300 A1 | 5/2022 | Leimbach et al. | |
| 2022/0133301 A1 | 5/2022 | Leimbach | |
| 2022/0133302 A1 | 5/2022 | Zerkle et al. | |
| 2022/0133303 A1 | 5/2022 | Huang | |
| 2022/0133304 A1 | 5/2022 | Leimbach et al. | |
| 2022/0133311 A1 | 5/2022 | Huang | |
| 2022/0133312 A1 | 5/2022 | Huang | |
| 2022/0133322 A1* | 5/2022 | Shelton, IV ..... | A61B 17/07207 227/176.1 |
| 2022/0152280 A1 | 5/2022 | Stolle et al. | |
| 2022/0251688 A1 | 8/2022 | Griebel et al. | |
| 2022/0273291 A1 | 9/2022 | Shelton, IV et al. | |
| 2022/0273292 A1 | 9/2022 | Shelton, IV et al. | |
| 2022/0273293 A1 | 9/2022 | Shelton, IV et al. | |
| 2022/0273294 A1 | 9/2022 | Creamer et al. | |
| 2022/0273299 A1 | 9/2022 | Shelton, IV et al. | |
| 2022/0273300 A1 | 9/2022 | Shelton, IV et al. | |
| 2022/0273301 A1 | 9/2022 | Creamer et al. | |
| 2022/0273302 A1 | 9/2022 | Shelton, IV et al. | |
| 2022/0273303 A1 | 9/2022 | Creamer et al. | |
| 2022/0273304 A1 | 9/2022 | Shelton, IV et al. | |
| 2022/0273305 A1 | 9/2022 | Shelton, IV et al. | |
| 2022/0273306 A1 | 9/2022 | Shelton, IV et al. | |
| 2022/0273307 A1 | 9/2022 | Shelton, IV et al. | |
| 2022/0273308 A1 | 9/2022 | Shelton, IV et al. | |
| 2022/0275477 A1 | 9/2022 | Luo et al. | |
| 2022/0278438 A1 | 9/2022 | Shelton, IV et al. | |
| 2022/0346781 A1 | 11/2022 | Shelton, IV et al. | |
| 2022/0354486 A1 | 11/2022 | Harris et al. | |
| 2022/0354487 A1* | 11/2022 | Rector ............. | A61B 17/07207 |
| 2022/0354488 A1 | 11/2022 | Harris et al. | |
| 2022/0354489 A1 | 11/2022 | Rector, IV et al. | |
| 2022/0354490 A1 | 11/2022 | Harris et al. | |
| 2022/0354498 A1 | 11/2022 | Rector et al. | |
| 2022/0354607 A1 | 11/2022 | Rector et al. | |
| 2022/0354999 A1* | 11/2022 | Rector .................. | A61L 31/022 |
| 2022/0361874 A1 | 11/2022 | Shelton, IV et al. | |
| 2022/0370064 A1 | 11/2022 | Harris et al. | |
| 2022/0370065 A1 | 11/2022 | Shelton, IV et al. | |
| 2022/0370691 A1 | 11/2022 | Rector et al. | |

FOREIGN PATENT DOCUMENTS

| | | | |
|---|---|---|---|
| CN | 110952038 | A | 4/2020 |
| CN | 213076762 | U | 4/2021 |
| EP | 0947592 | A1 | 10/1999 |
| EP | 1183402 | B1 | 11/2003 |
| EP | 1171643 | B1 | 6/2004 |
| EP | 1607048 | A1 | 12/2005 |
| EP | 2116196 | A2 | 11/2009 |
| EP | 2149414 | A1 | 2/2010 |
| EP | 2308387 | A2 | 4/2011 |
| EP | 1667748 | B1 | 5/2011 |
| EP | 2644114 | A2 | 10/2013 |
| EP | 1711213 | B1 | 11/2014 |
| EP | 2954854 | A2 | 12/2015 |
| EP | 3047806 | A1 | 7/2016 |
| EP | 3135207 | A1 | 3/2017 |
| EP | 3135208 | A2 | 3/2017 |
| EP | 3338697 | A1 | 6/2018 |
| EP | 3415176 | A1 | 12/2018 |
| EP | 2593152 | B1 | 5/2019 |
| EP | 3482695 | A1 | 5/2019 |
| EP | 3498192 | A1 | 6/2019 |
| EP | 3733084 | A1 | 11/2020 |
| EP | 3791798 | A2 | 2/2021 |
| EP | 3338814 | B1 | 3/2021 |
| EP | 3470001 | B1 | 4/2021 |
| EP | 3808283 | A1 | 4/2021 |
| EP | 3954301 | A2 | 2/2022 |
| WO | 2005030285 | A1 | 4/2005 |
| WO | 2009143227 | A1 | 11/2009 |
| WO | WO-2015137911 | A1 | 9/2015 |
| WO | WO-2017204803 | A1 | 11/2017 |
| WO | 2019116273 | A1 | 6/2019 |
| WO | WO-2020038956 | A1 | 2/2020 |
| WO | WO-2020109222 | A1 | 6/2020 |
| WO | 2020261047 | A1 | 10/2020 |
| WO | 2020261072 | A1 | 12/2020 |

OTHER PUBLICATIONS

Incesu et al., "Biocorrosion and Mechanical Properties of ZXM100 and ZXM120 Magnesium Alloys, International Journal of Metalworking," vol. 13, Issue 4, pp. 905-914 (2019).

Zheng et al., "Biodegradable Metals," Materials and Science Engineering R 77 (2014) 1-34.

Walker, Jemimah et al., "Magnesium alloys: Predicting in vivo corrosion with in vitro immersion testing," Journal of Biomedical Materials Research B: Applied Biomaterials, May 2012, vol. 100B, Issue 4, pp. 1134-1141.

Salem, H.A. et al., Influence of Intense Plastic Straining on Room Temperature Mechanical Properties of Al—Cu—Li Base Alloys, Current Advances in Mechanical Design and Production, Seventh Cairo University International MDP Conference, Cairo, Feb. 15-17, 2000, pp. 357-368.

Horn et al., "Strain Localization during Equal-Channel Angular Pressing Analyzed by Finite Element Simulations," Metals, vol. 8, No. 55 (2018), pp. 1-18.

Lin, Pei-Hui et al., "Zinc in Wound Healing Modulation," Nutrients, vol. 10, No. 16 (2018), pp. 1-20.

Yufeng Zheng, Magnesium Alloys as Degradable Biomaterials, Taylor & Francis Group LLC, Boca Raton, FL, published 2016—book not attached.

* cited by examiner

CARTRIDGE ASSEMBLIES WITH ABSORBABLE METAL STAPLES AND ABSORBABLE IMPLANTABLE ADJUNCTS

CROSS REFERENCE TO RELATED APPLICATION

This application claims the benefit under 35 U.S.C. § 119(e) of U.S. Provisional Patent Application Ser. No. 63/186,519, entitled ABSORBABLE METAL STAPLE, filed May 10, 2021, the entire disclosure of which is hereby incorporated by reference herein.

BACKGROUND

The present invention relates to surgical staples that compress and appose patient tissue. During a surgical procedure, a clinician can utilize a surgical stapling instrument to staple, and cut, the patient tissue. The surgical stapling instrument can include a staple cartridge that includes staples removably stored therein that are deployed into the patient tissue by a firing drive of the surgical stapling instrument. When deployed, the staples puncture a first side of the tissue and are then deformed by an anvil of the surgical stapling instrument positioned on a second, or opposite, side of the tissue. The deformed staples clench, or compress, the tissue to prevent, or at least reduce, bleeding from the incision created by the stapling instrument.

The staples can be made of a bioabsorbable material such that the staples can dissolve and release the tissue after a sufficient amount of time has elapsed following the surgical procedure. While it is desirable that the staples ultimately dissolve and release the tissue, the staples must maintain their structural integrity for an amount of time, i.e., the biocorrosion timeframe, to allow for sufficient healing of the tissue. When selecting appropriate bioabsorbable materials such that the staples can meet the biocorrosion timeframe, many factors are considered, such as the stiffness of the staples, the strength of the staples, the ductility of the staple materials, the safety of the materials being utilized (such as toxicity concerns), and/or the compatibility of the materials with electrosurgical instruments, for example. Comparatively, stents which are often implanted to hold open an artery, for example, are often comprised of alloys which resist or impede biocorrosion of the underlying structure eventhough a surface of the stent may comprise a dissolvable coating.

BRIEF DESCRIPTION OF THE DRAWINGS

Various features of the embodiments described herein, together with advantages thereof, may be understood in accordance with the following description taken in conjunction with the accompanying drawings as follows:

FIG. 104 is a partial perspective view of the stapled tissue of FIG. 102;

FIG. 105 illustrates a degradation sequence of a staple and an implantable adjunct portion held to a tissue portion by the staple, in accordance with at least one aspect of the present disclosure;

FIG. 106 is a top view of an implantable adjunct including implantable adjunct portions, and staples deployed from a staple cartridge into the implantable adjunct portions, in accordance with at least one aspect of the present disclosure;

FIG. 107 is a top view of an implantable adjunct including implantable adjunct portions, and staples deployed from a staple cartridge into the implantable adjunct portions, in accordance with at least one aspect of the present disclosure;

FIG. 108 is perspective view of a stapled tissue showing multiple firings of a surgical stapler, with overlapping staples from subsequent firings, in accordance with at least one aspect of the present disclosure;

FIG. 109 is a perspective view of an end effector assembly configured to engage, cut, staple, and apply an implantable adjunct material containing a medicament to tissue, in accordance with at least one aspect of the present disclosure;

FIG. 110 illustrates a degradation sequence of a staple including a material configured to yield a radiotherapy to stapled tissue, in accordance with at least one aspect of the present disclosure;

FIG. 111 is a perspective view of a surgical stapling instrument comprising a handle, a shaft assembly, and a surgical end effector;

FIG. 112 is a perspective view of a portion of the shaft assembly and handle of FIG. 1;

FIG. 113 is an exploded assembly view of the surgical end effector of FIG. 1;

FIG. 114 is a perspective view of the surgical end effector of FIG. 1 with an anvil thereof in an open position, and wherein a cartridge/retainer assembly comprising a staple retainer attached to a surgical staple cartridge is illustrated removed from a channel of the surgical end effector;

FIG. 115 is perspective view of the surgical end effector of FIG. 114, with the surgical staple cartridge of the cartridge/retainer assembly seated in the channel of the surgical end effector, and with the staple retainer removed from the surgical staple cartridge;

Figure 114:
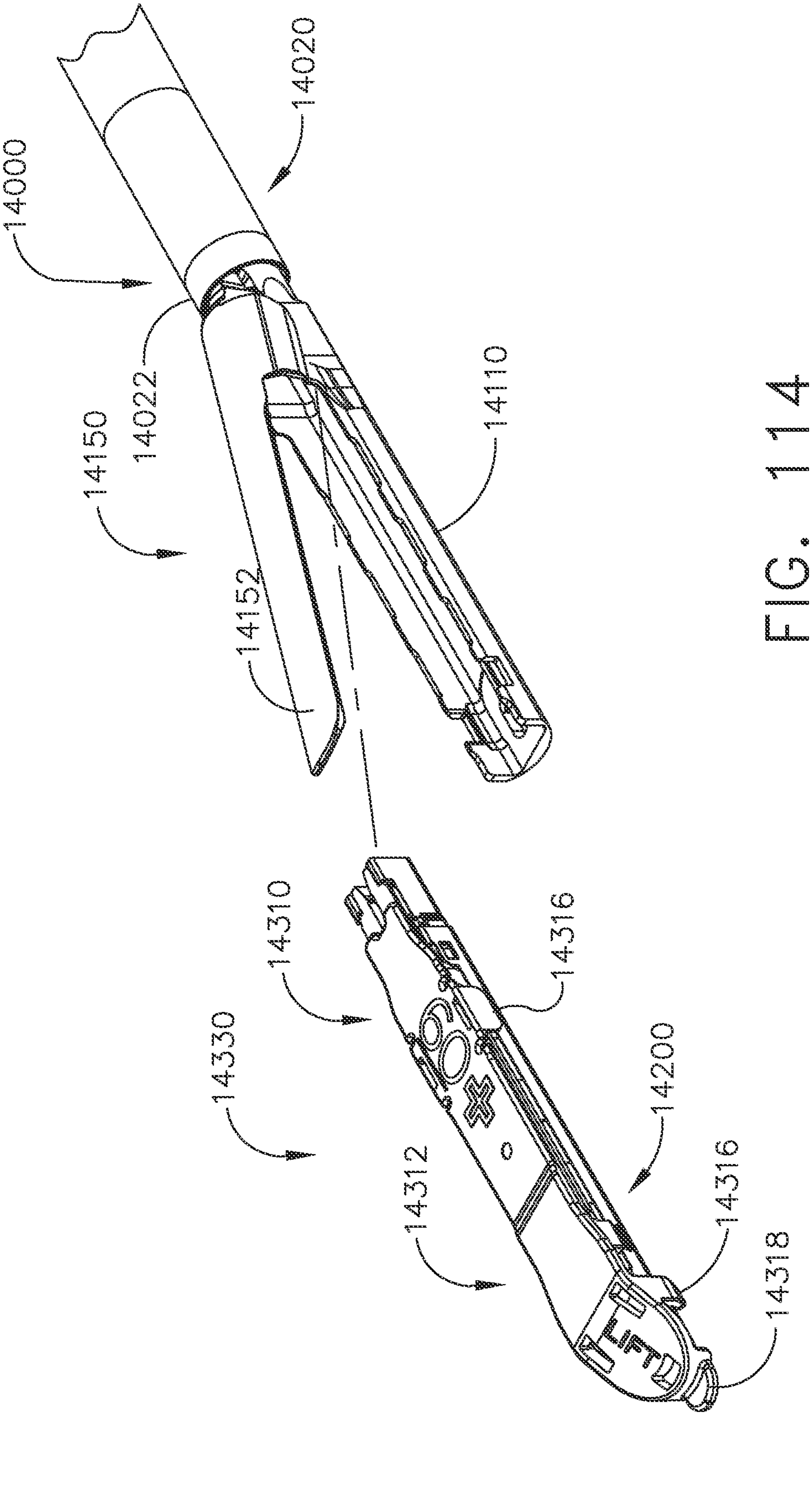
Figure 115:
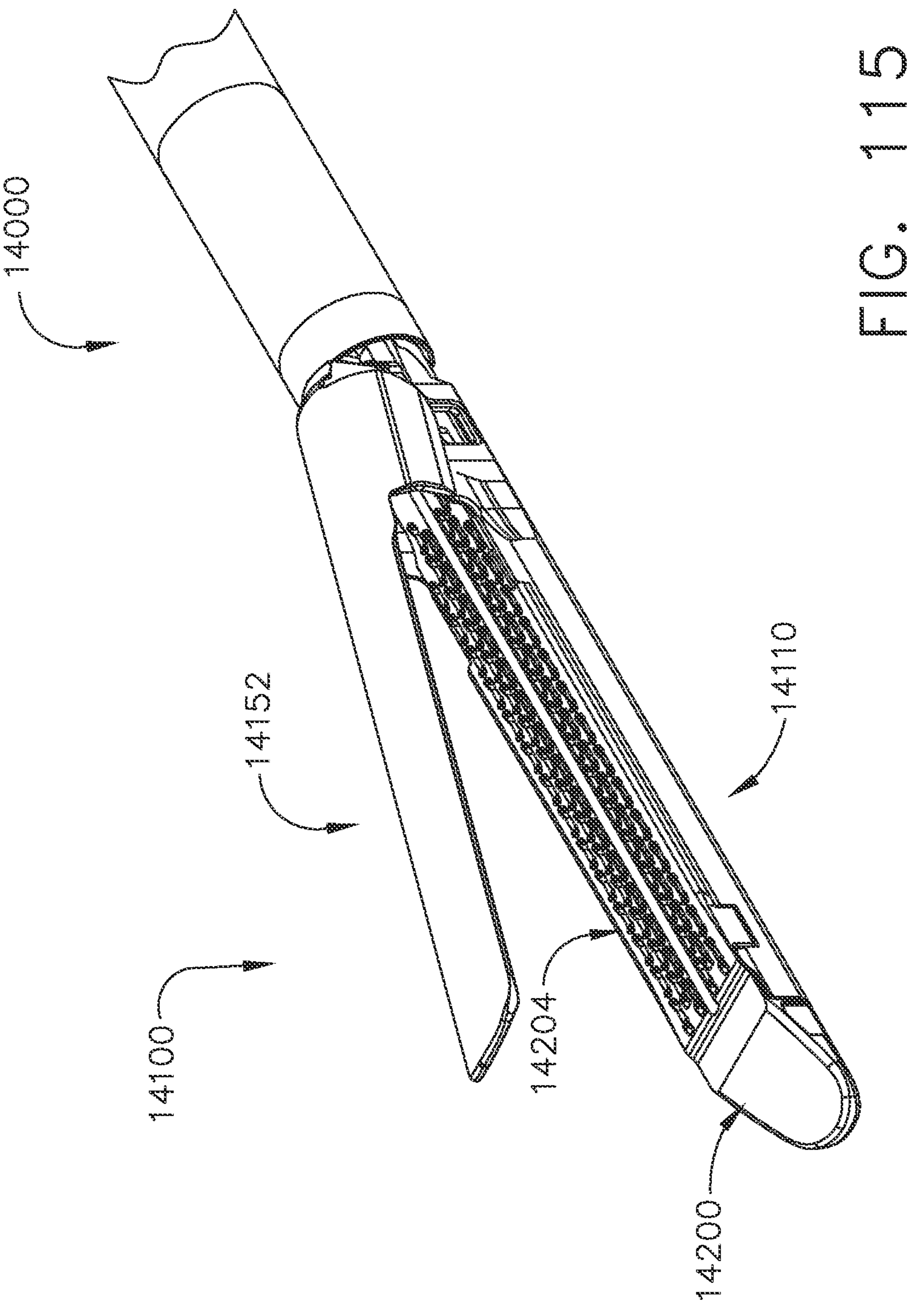
Figure 116:
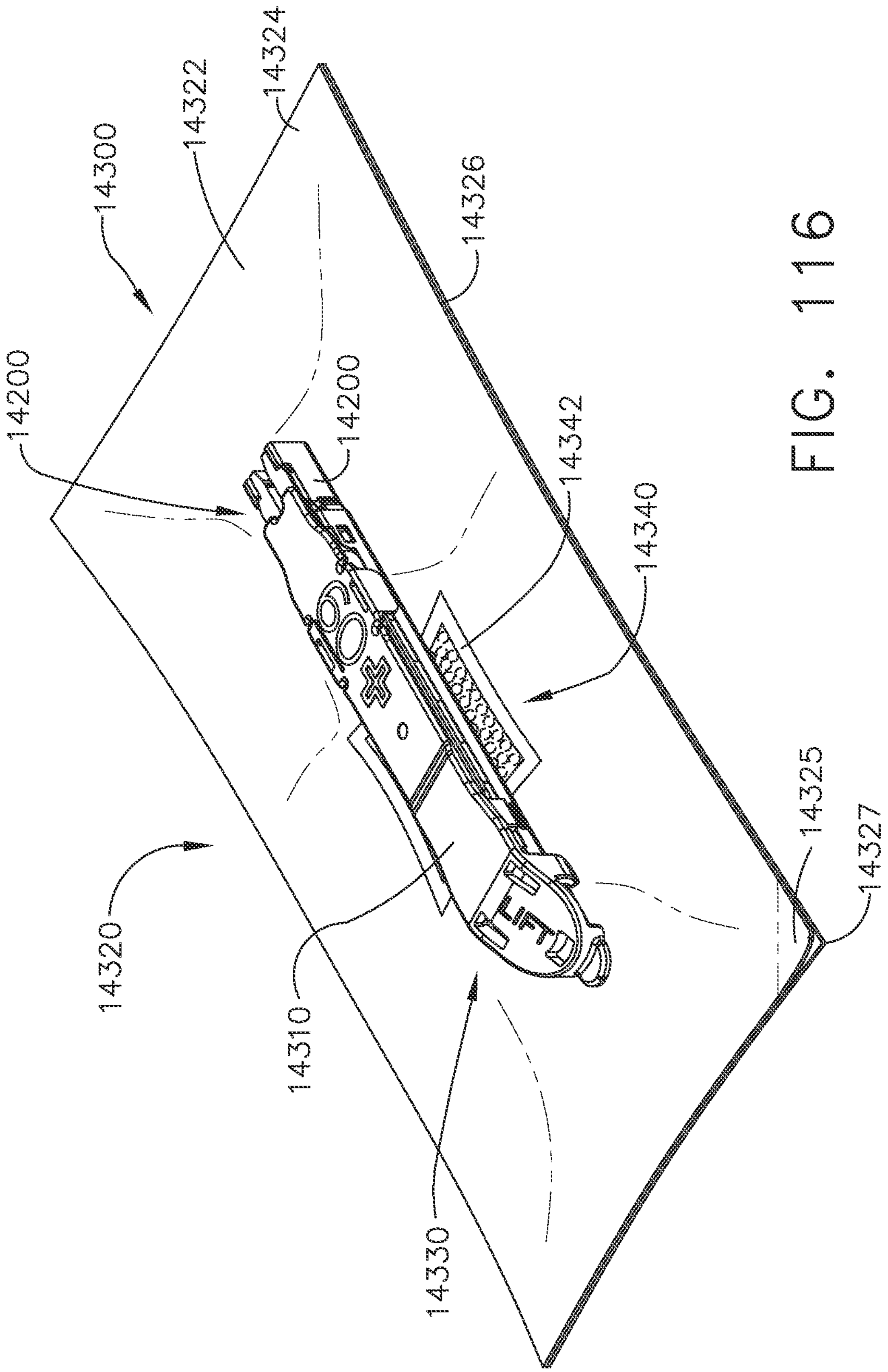
Figure 117:
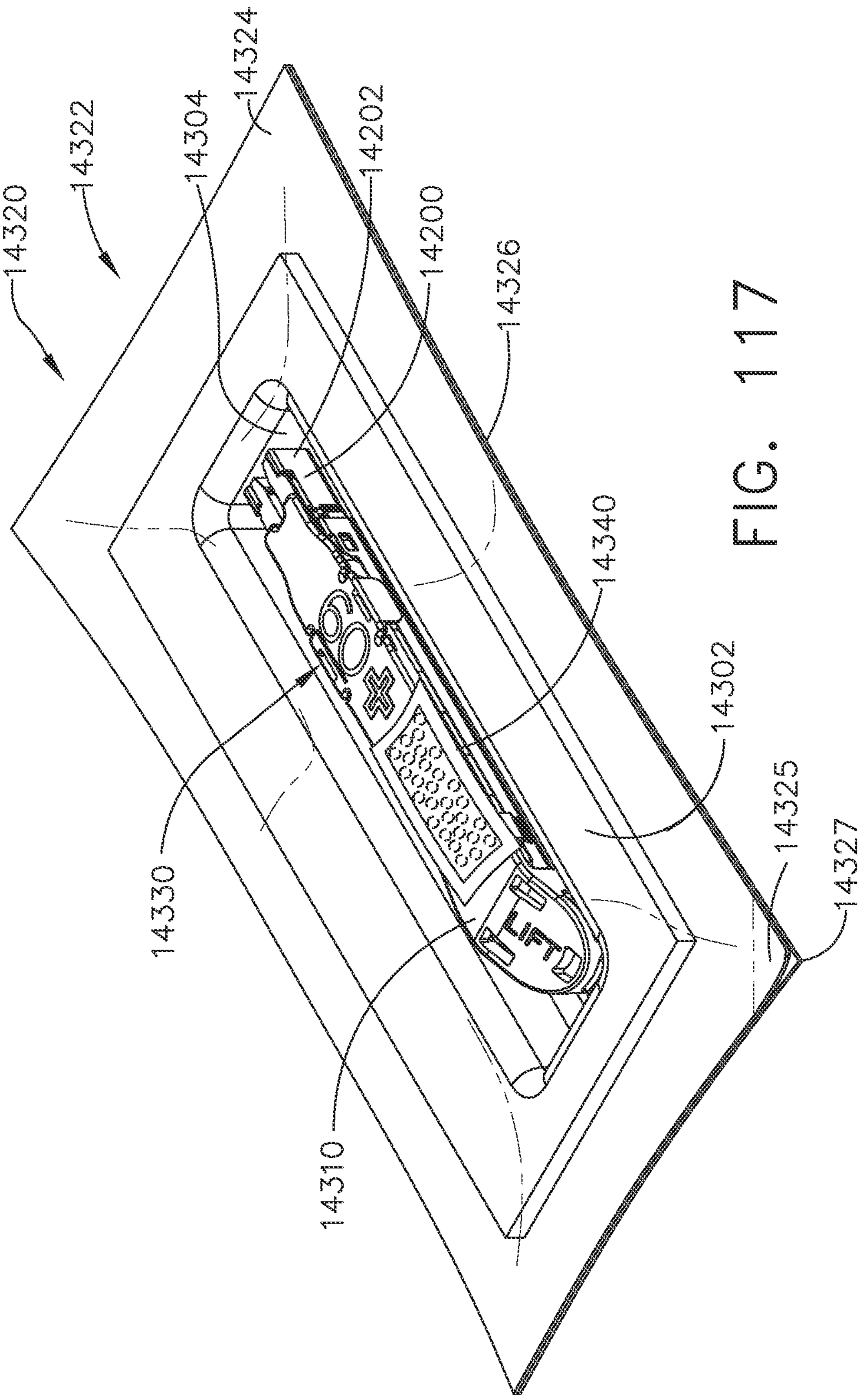
Figure 118:
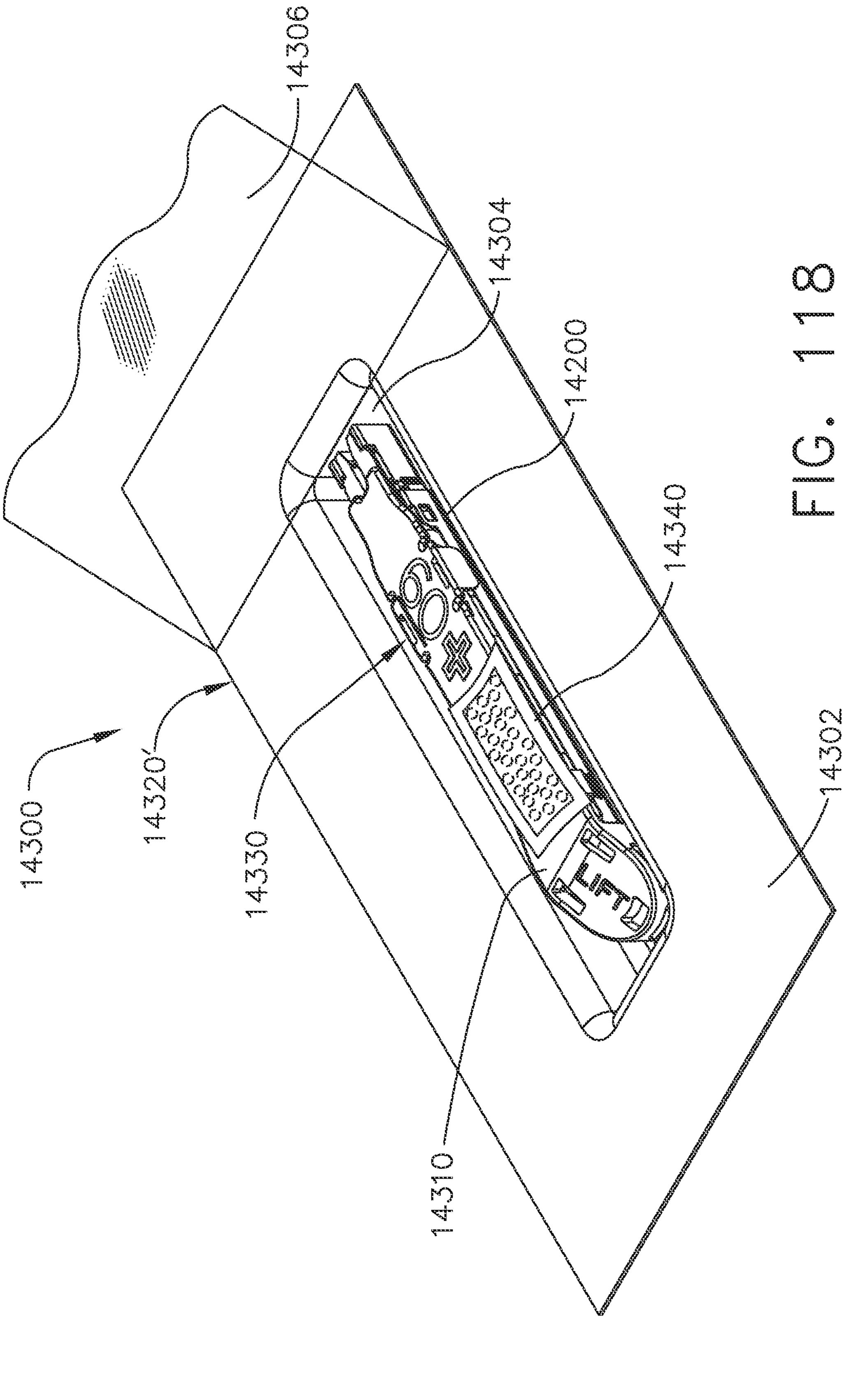
Figure 119:
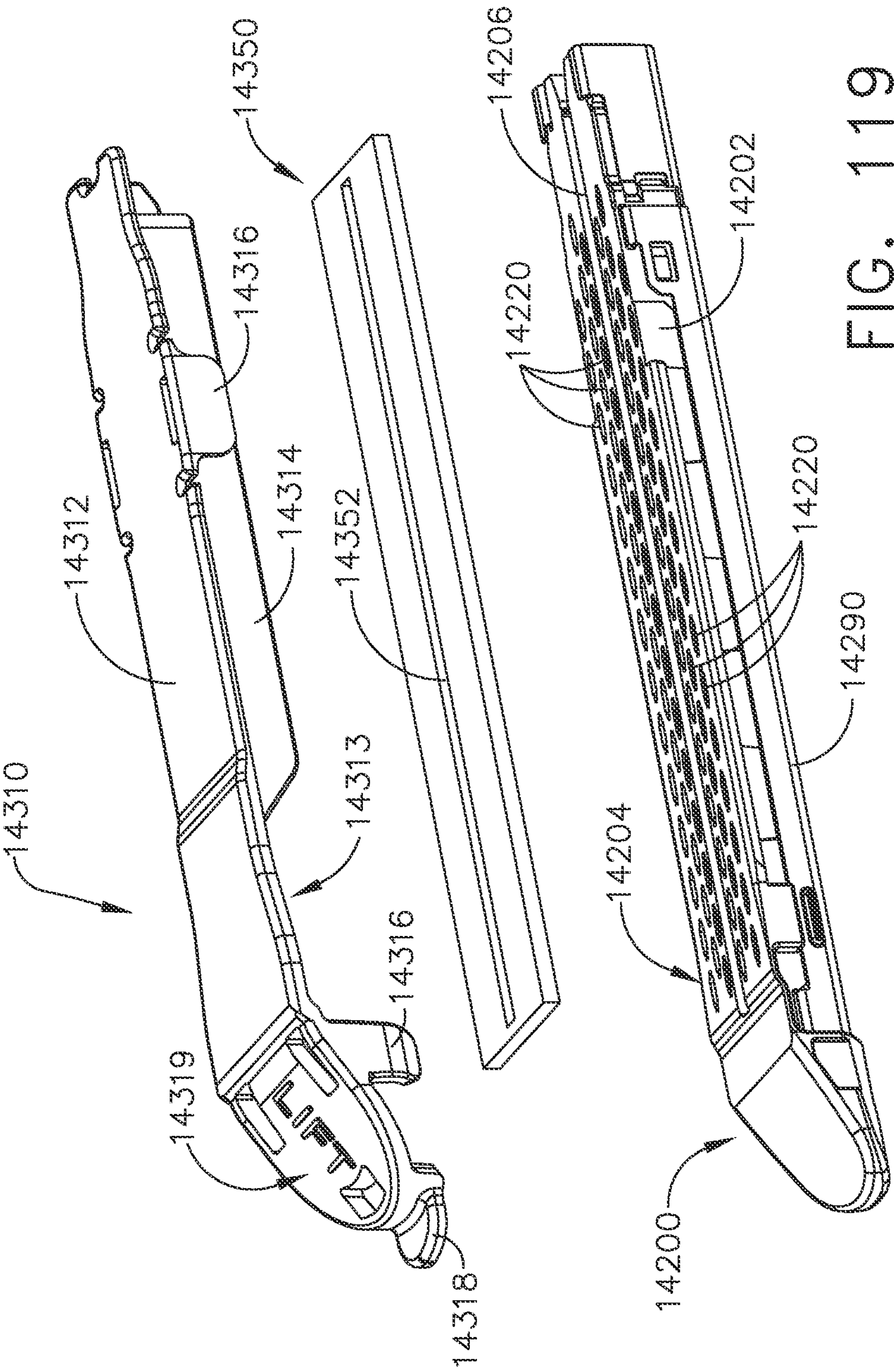
Figure 120:
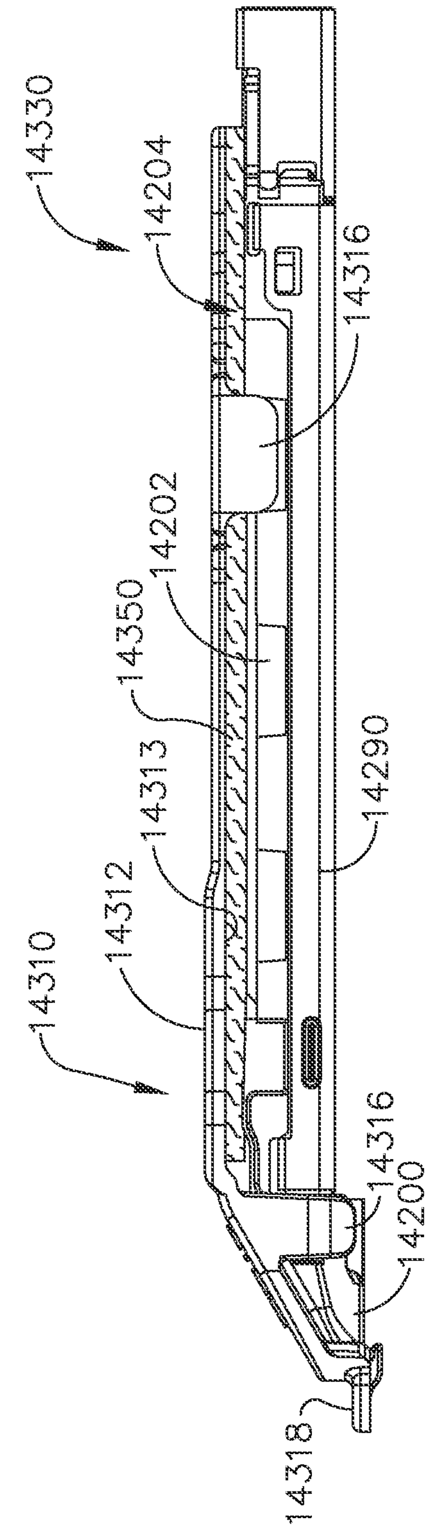
Figure 121:
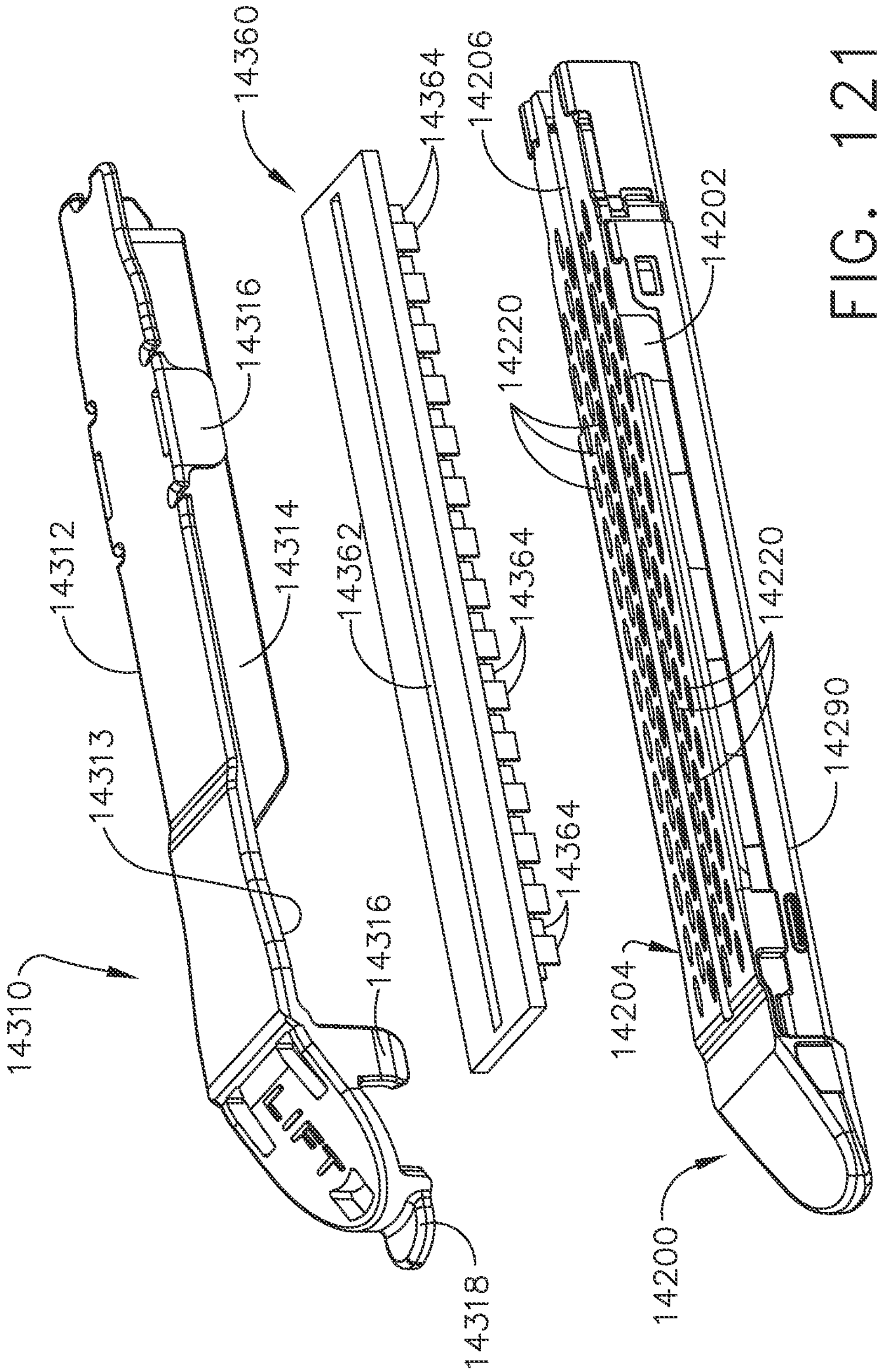
Figure 122:
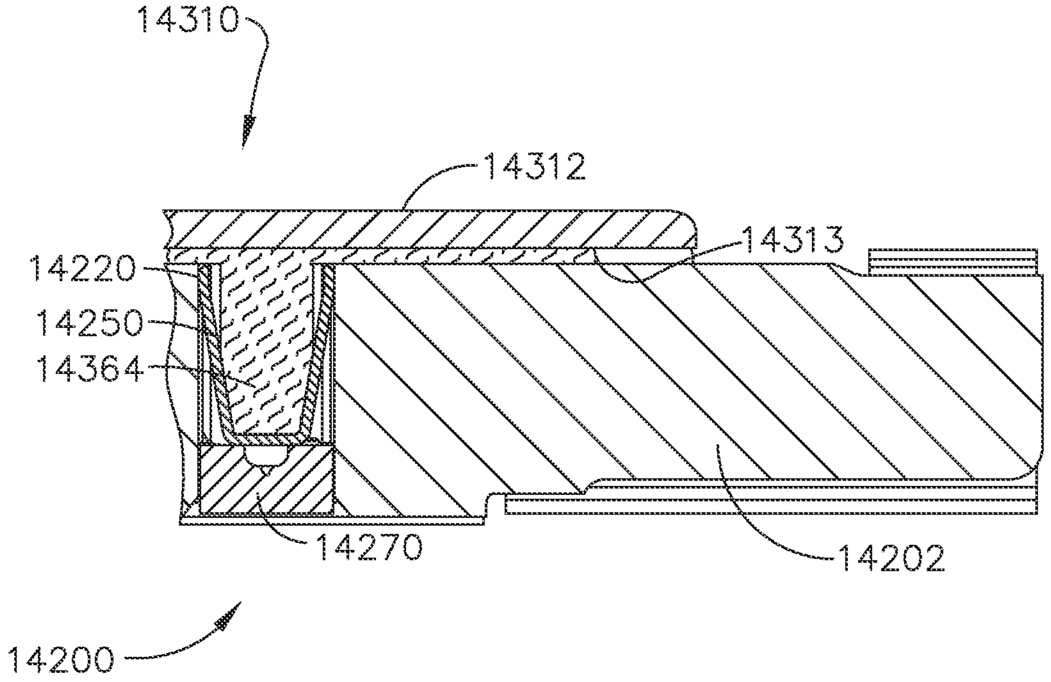
Figure 123:
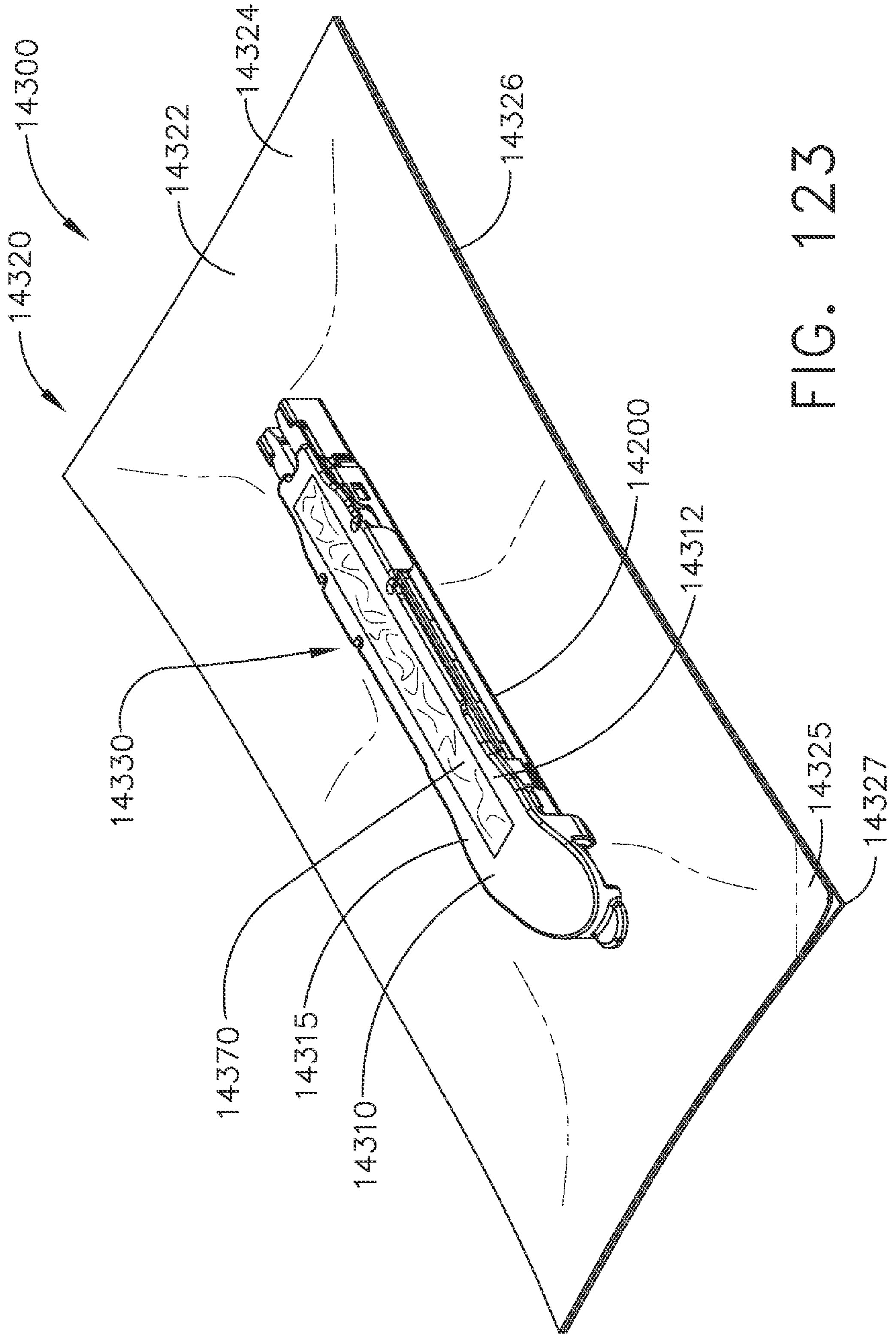
Figure 124:
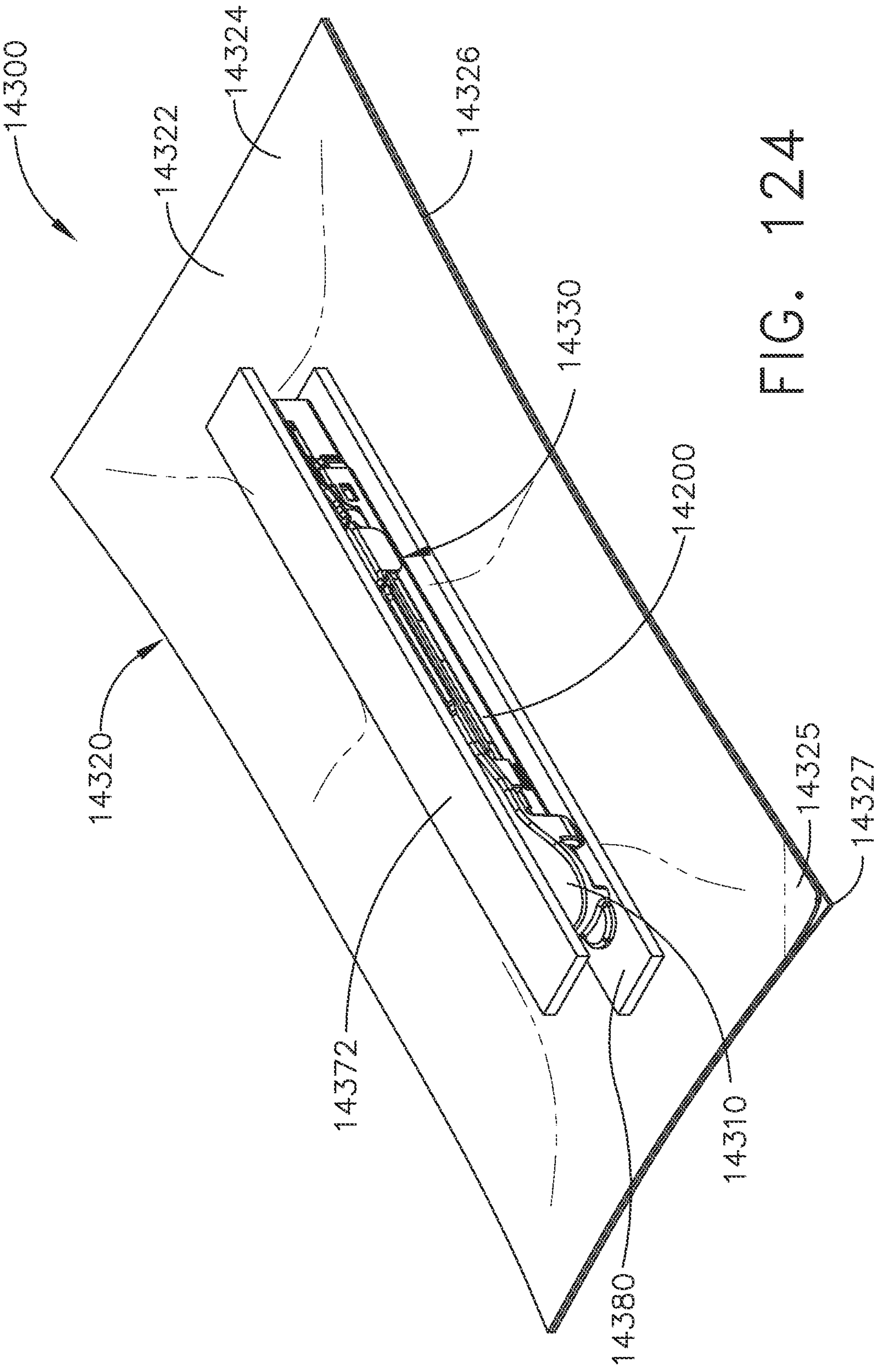
Figure 125:
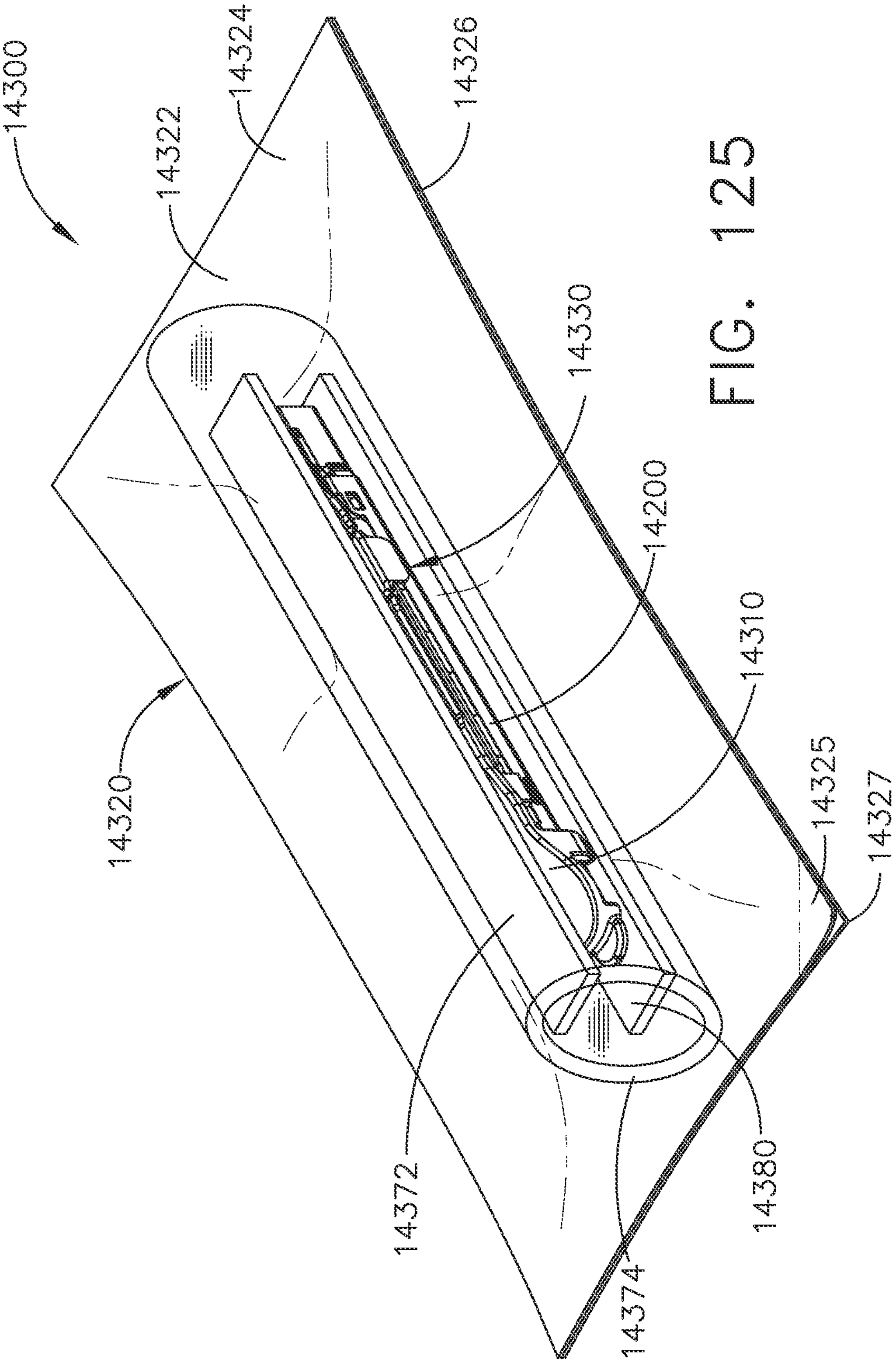
Figure 126:
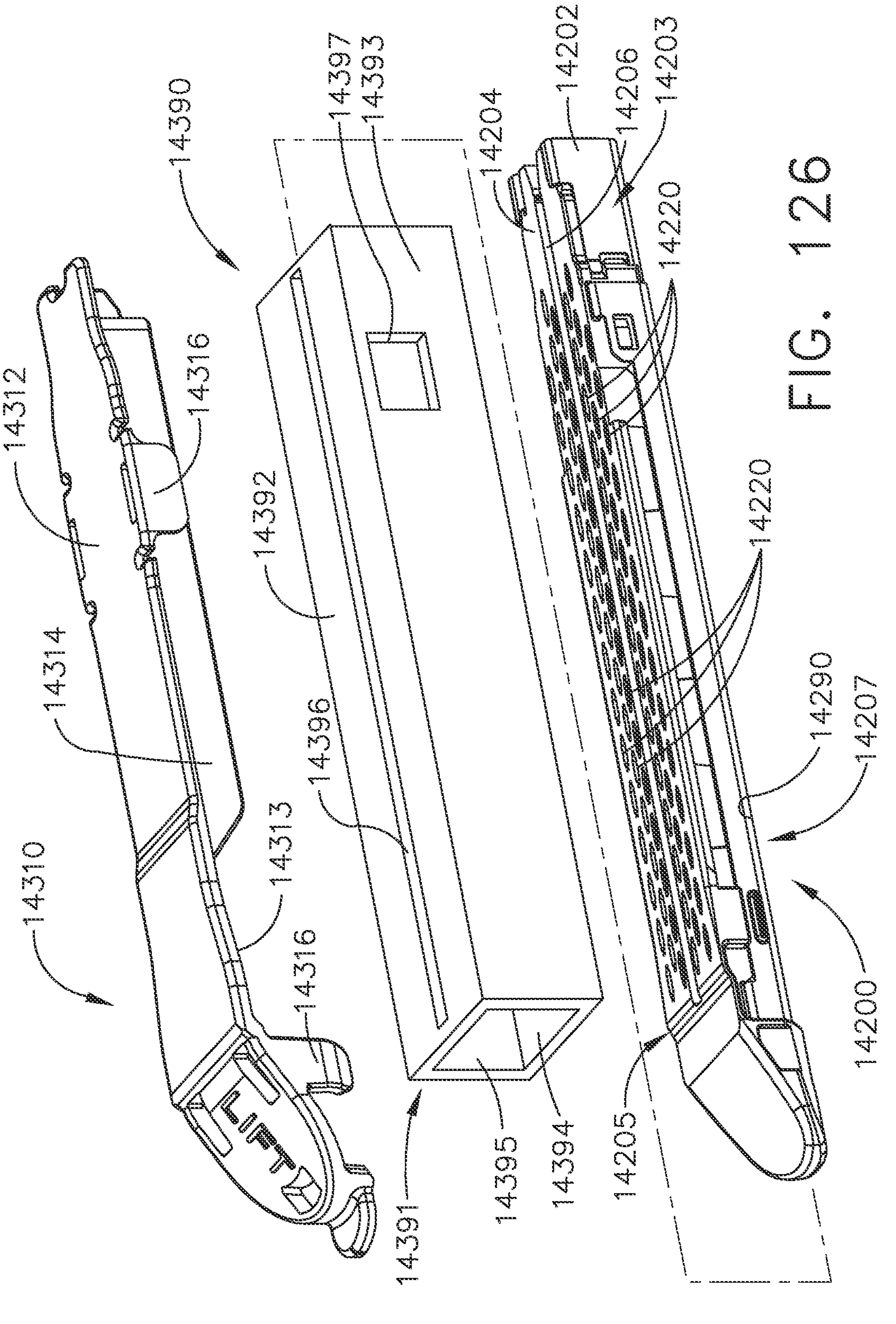
Figure 127:
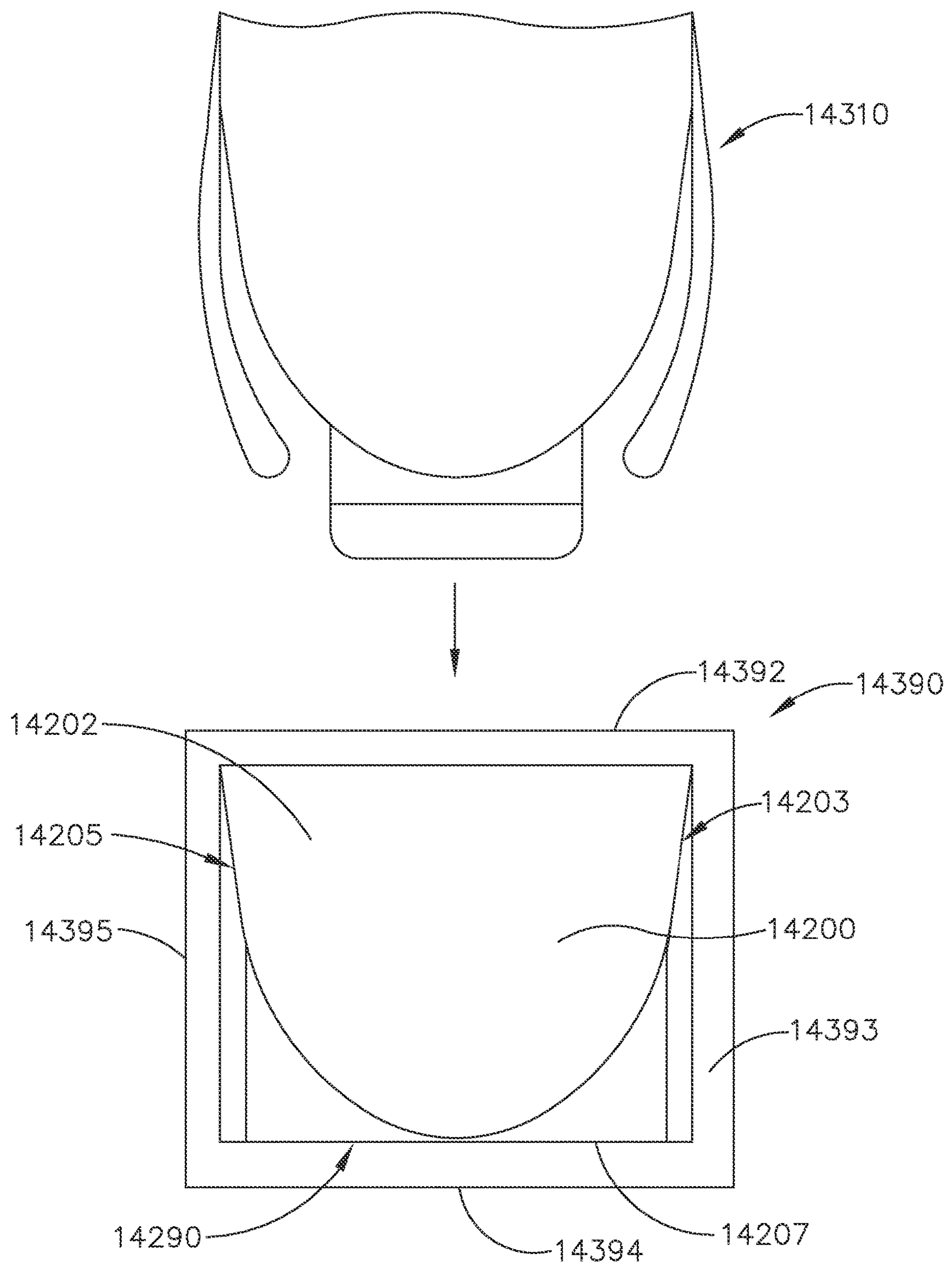
Figure 128:
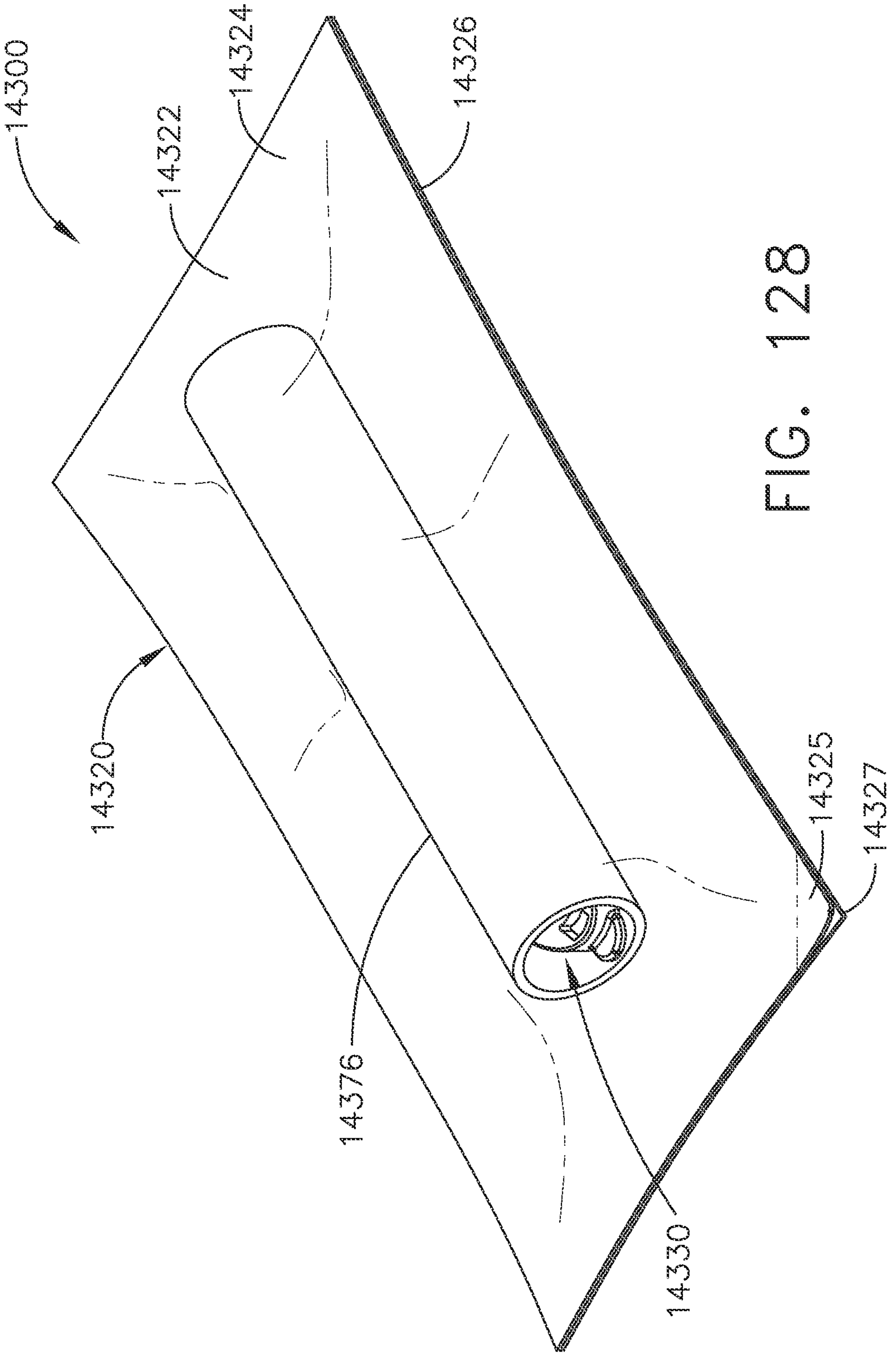
Figure 129:
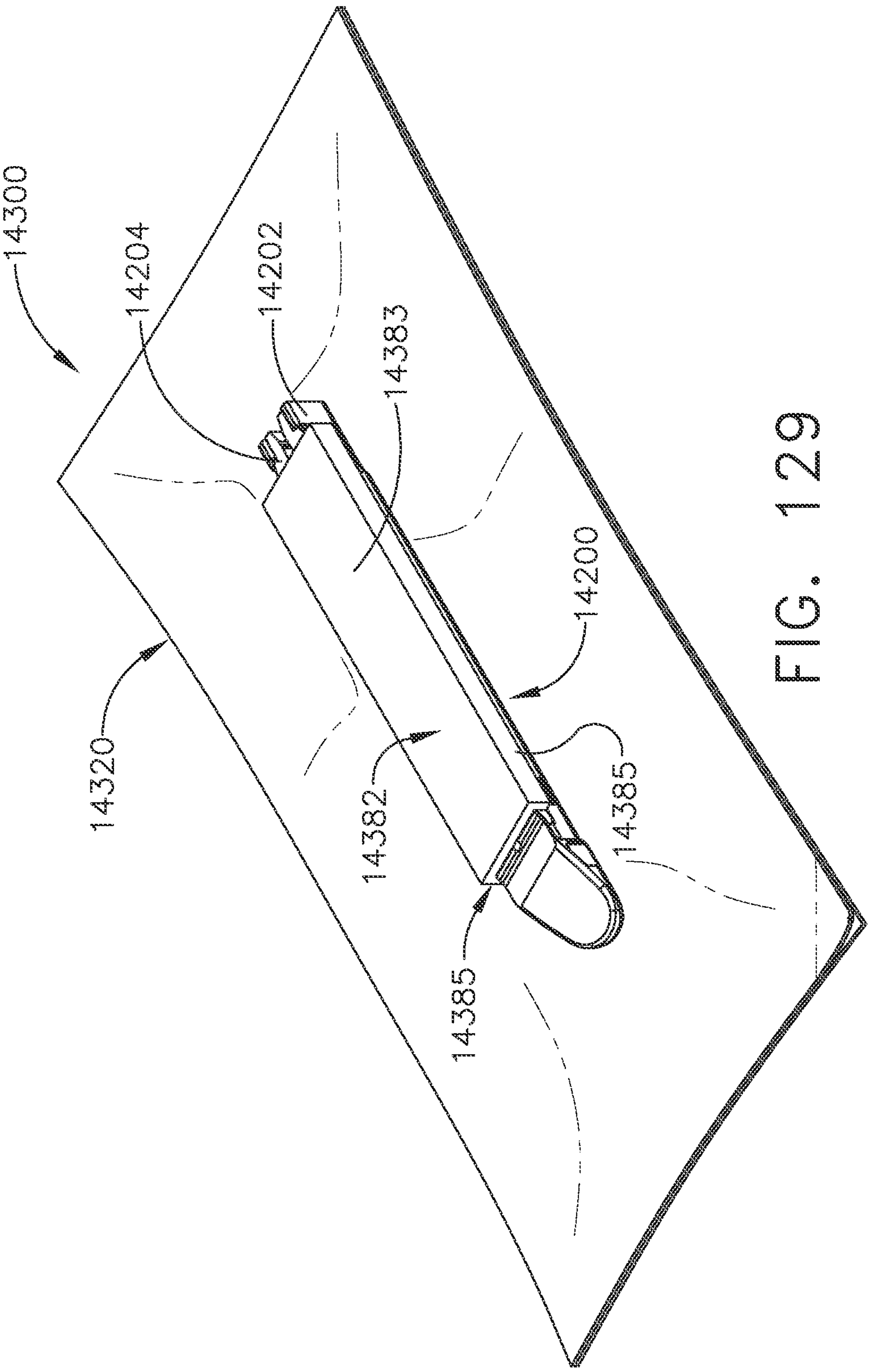
Figure 130:
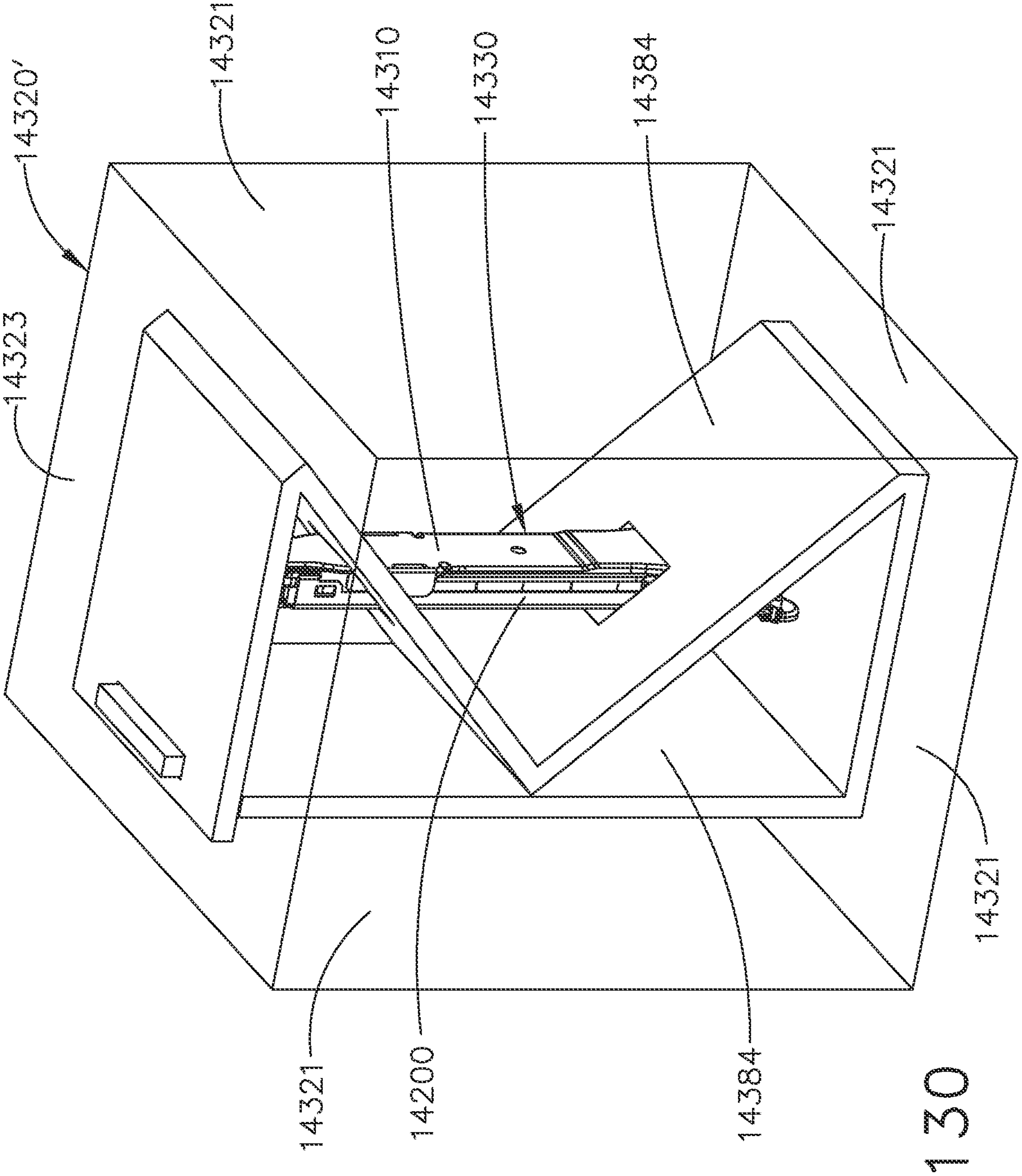
Figure 131:
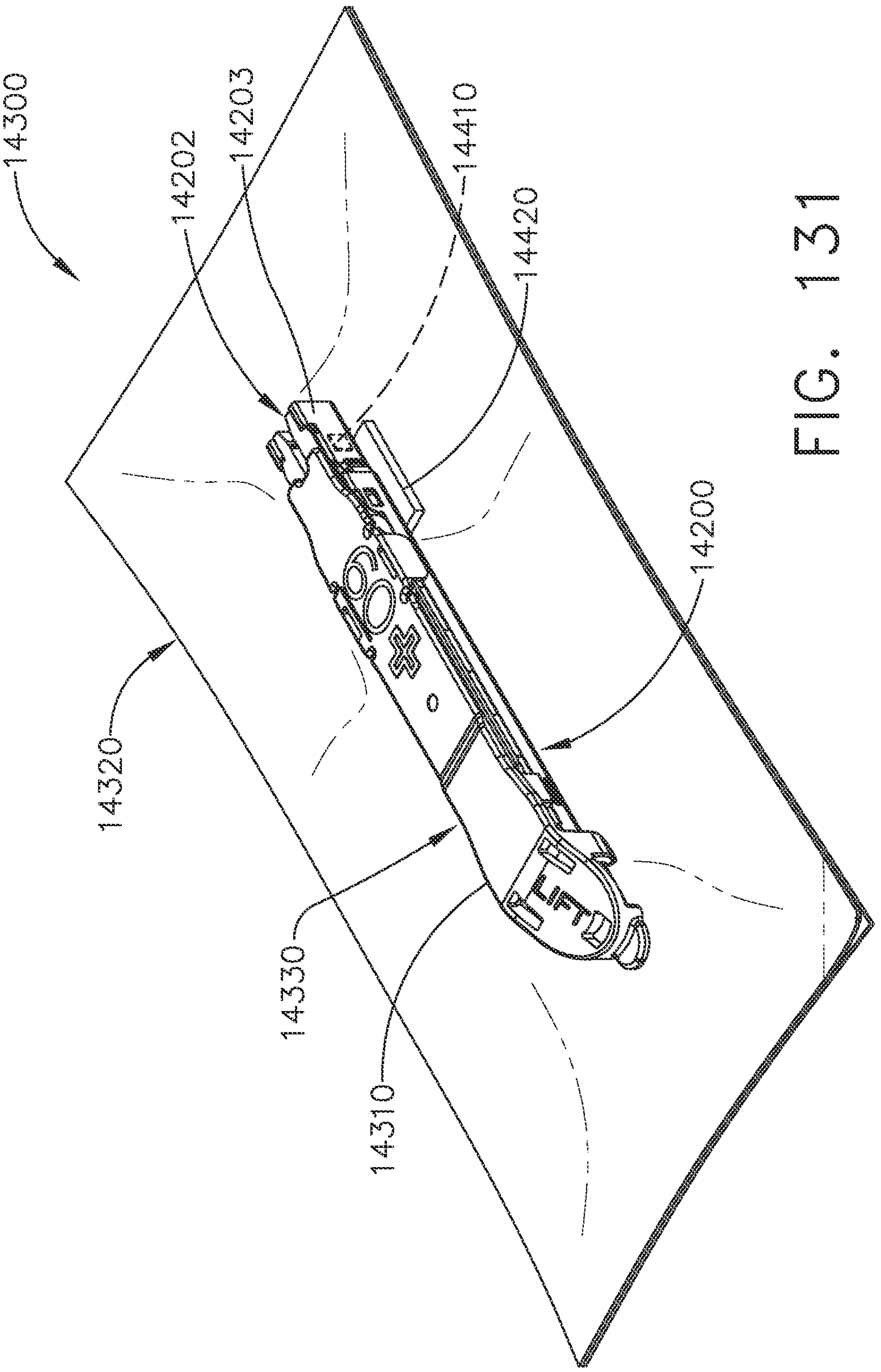
Figure 132:
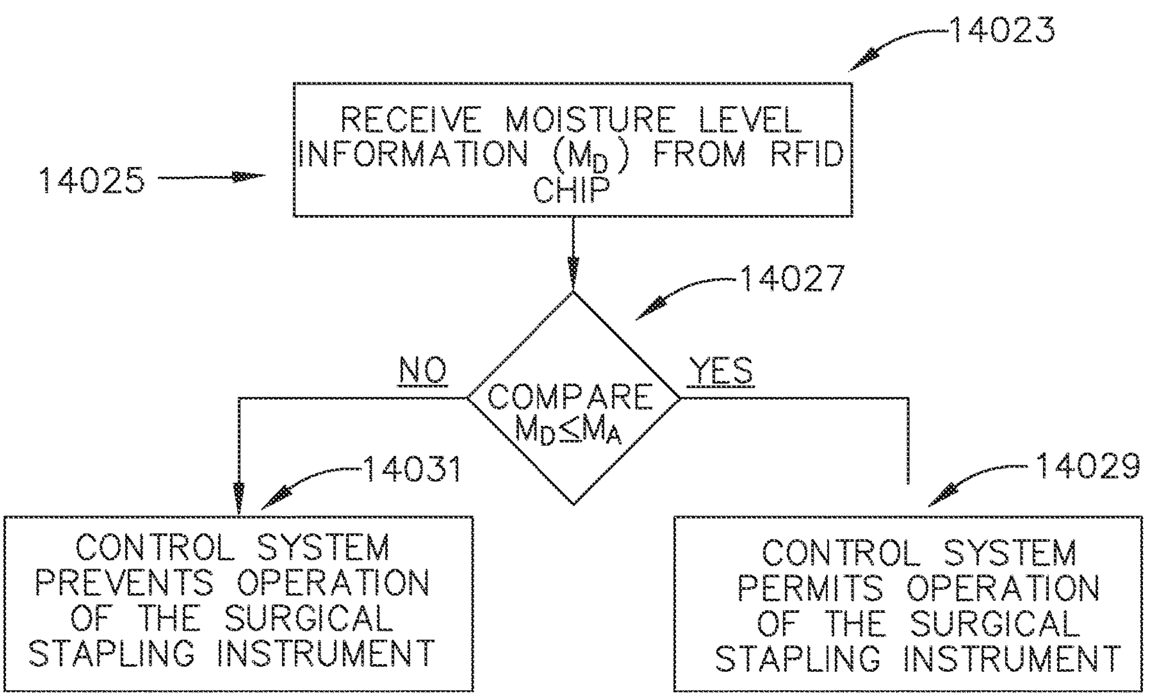
Figure 133:
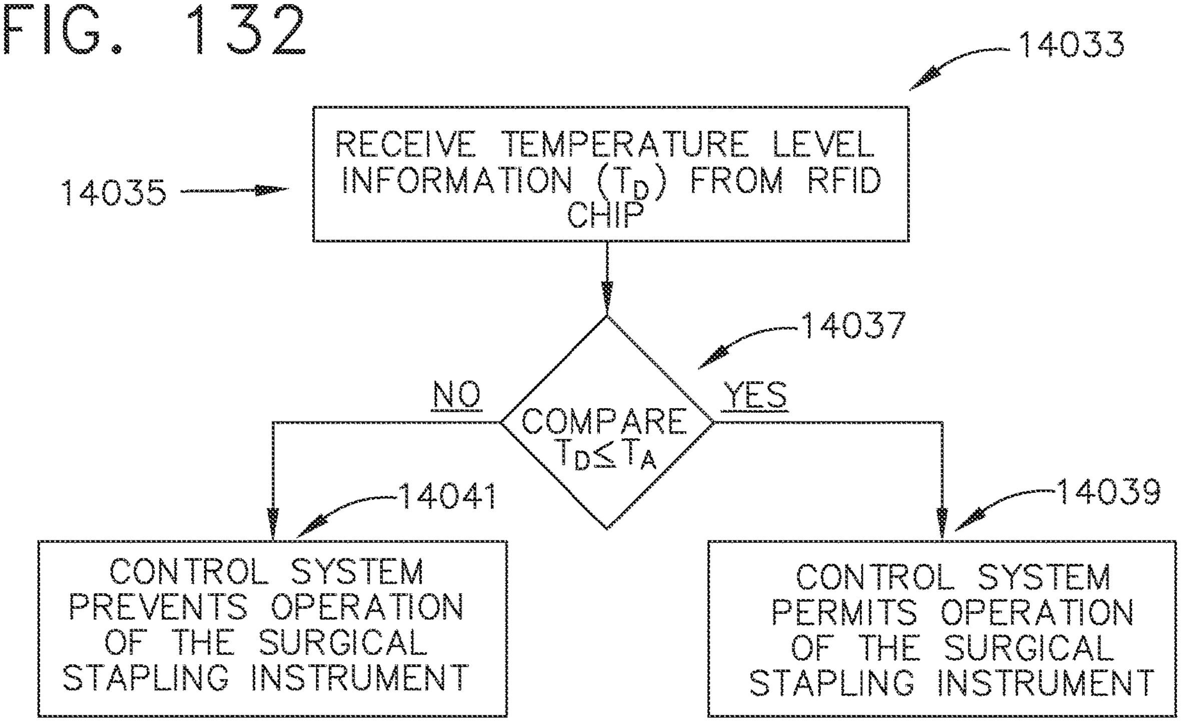
Figure 134:
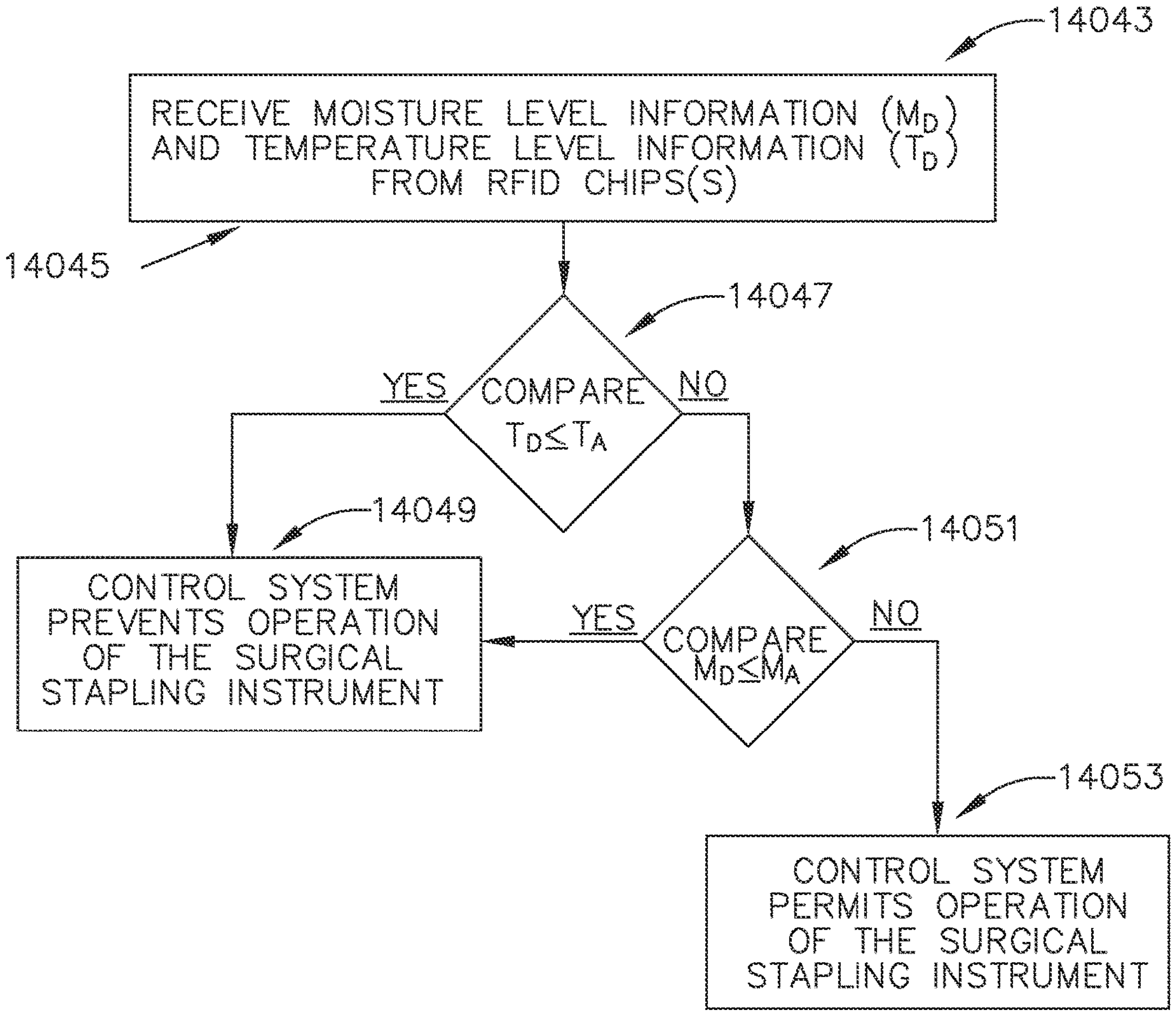
Figure 135:
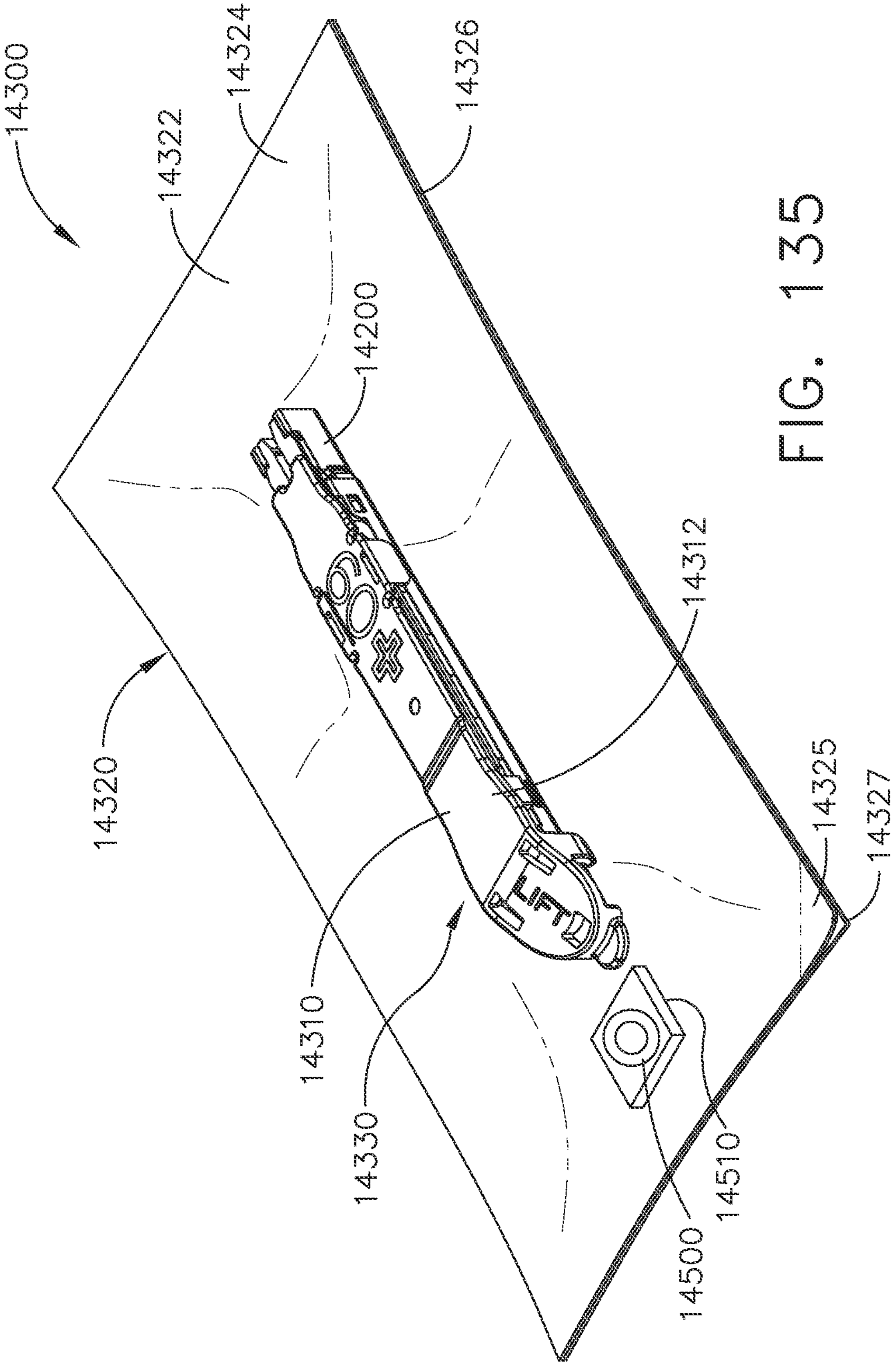
Figure 136:
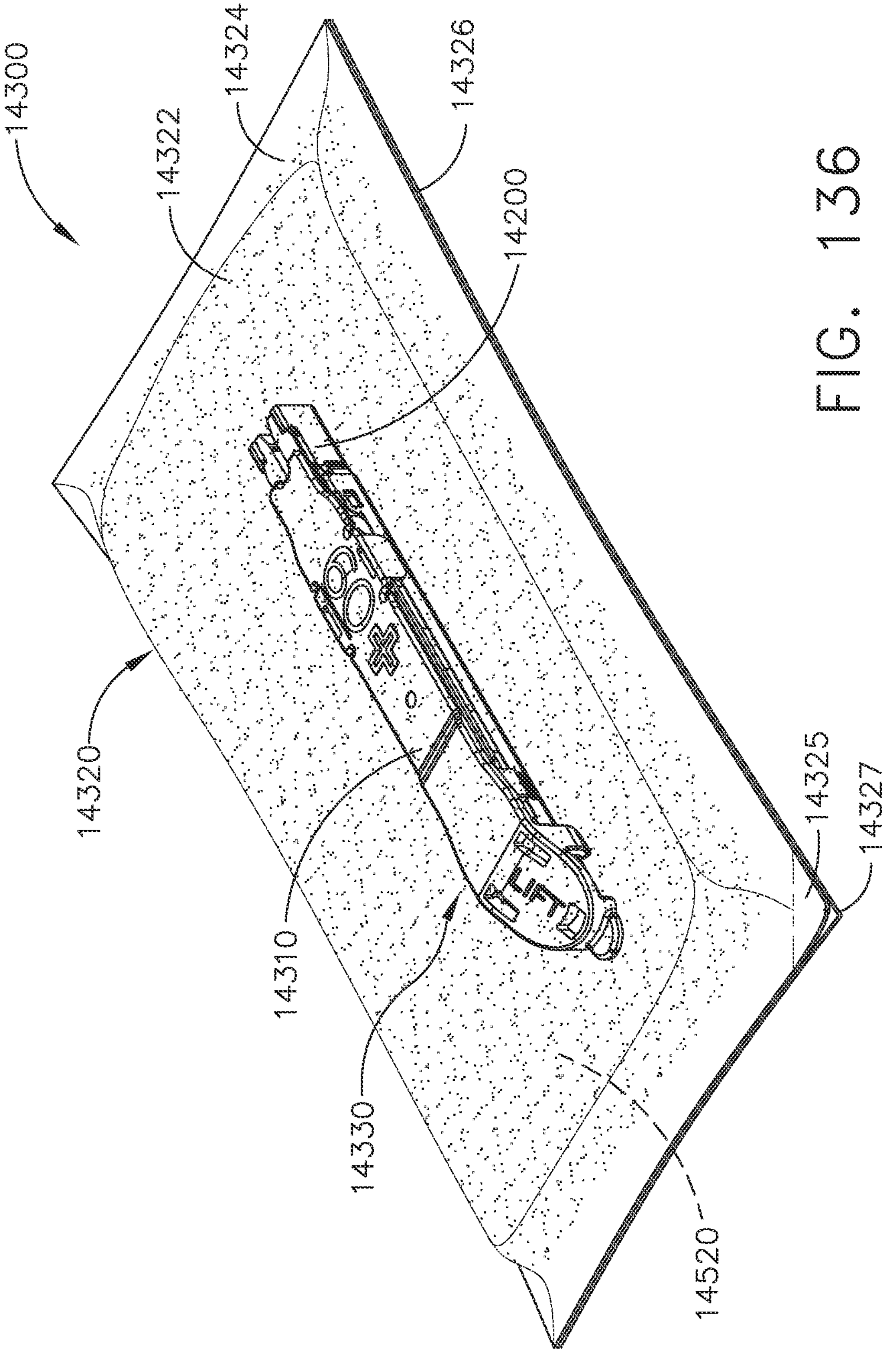
Figure 137:
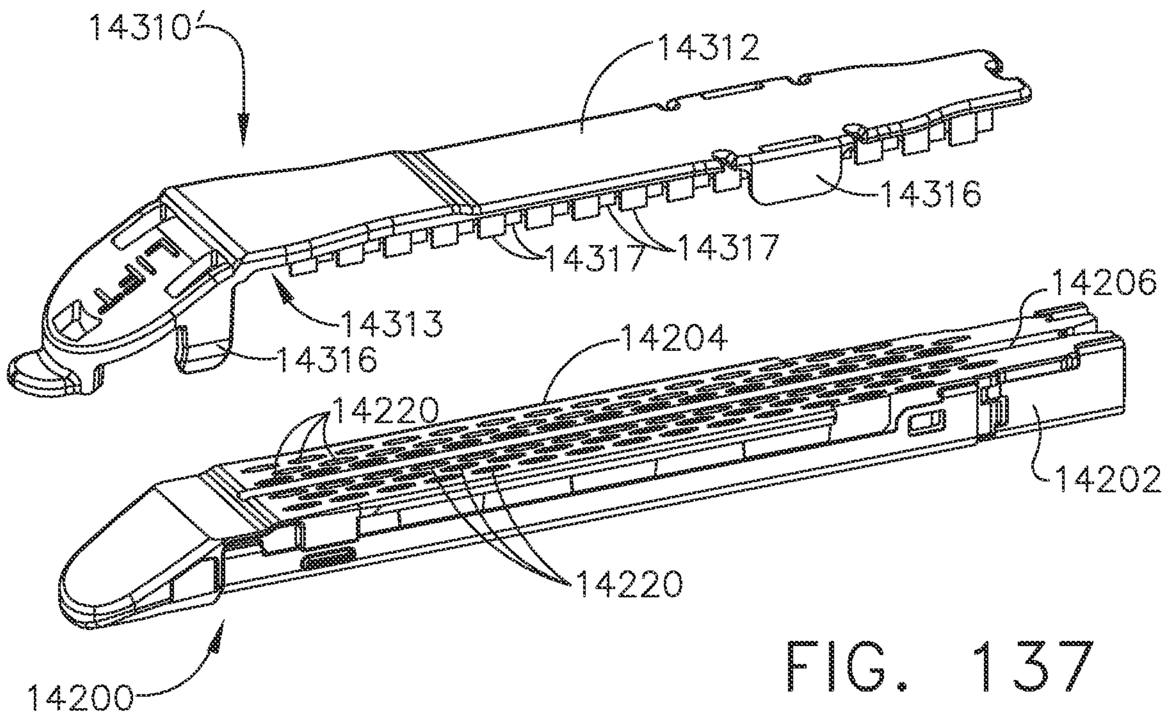
Figure 138:
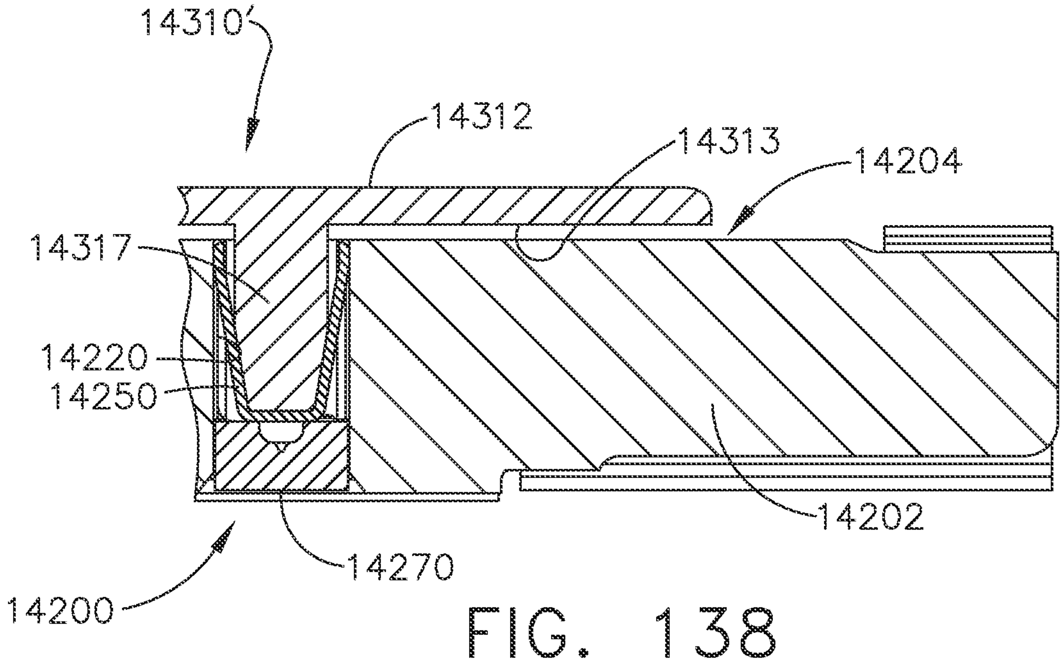
Figure 139:
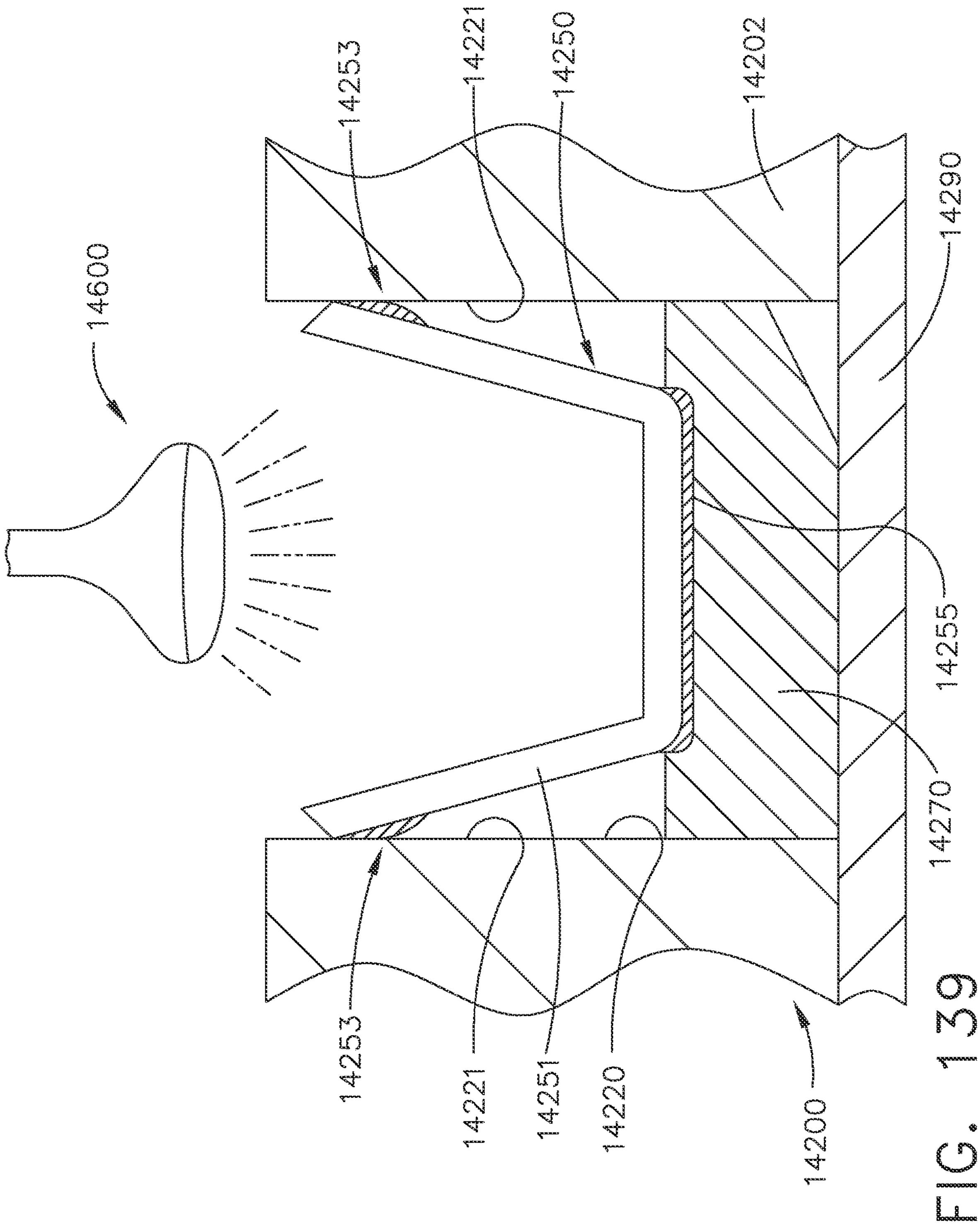
Figure 140:
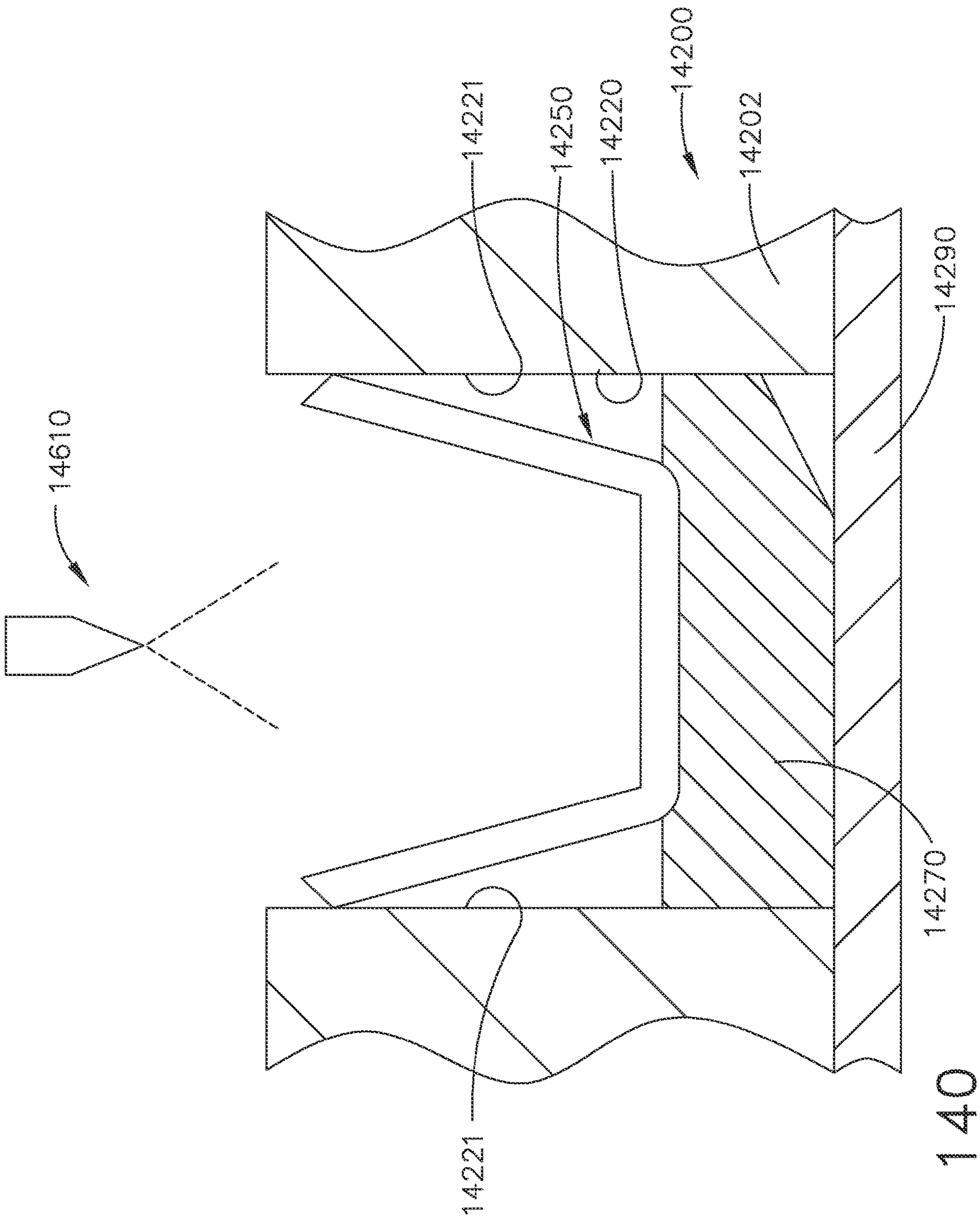
Figure 141:
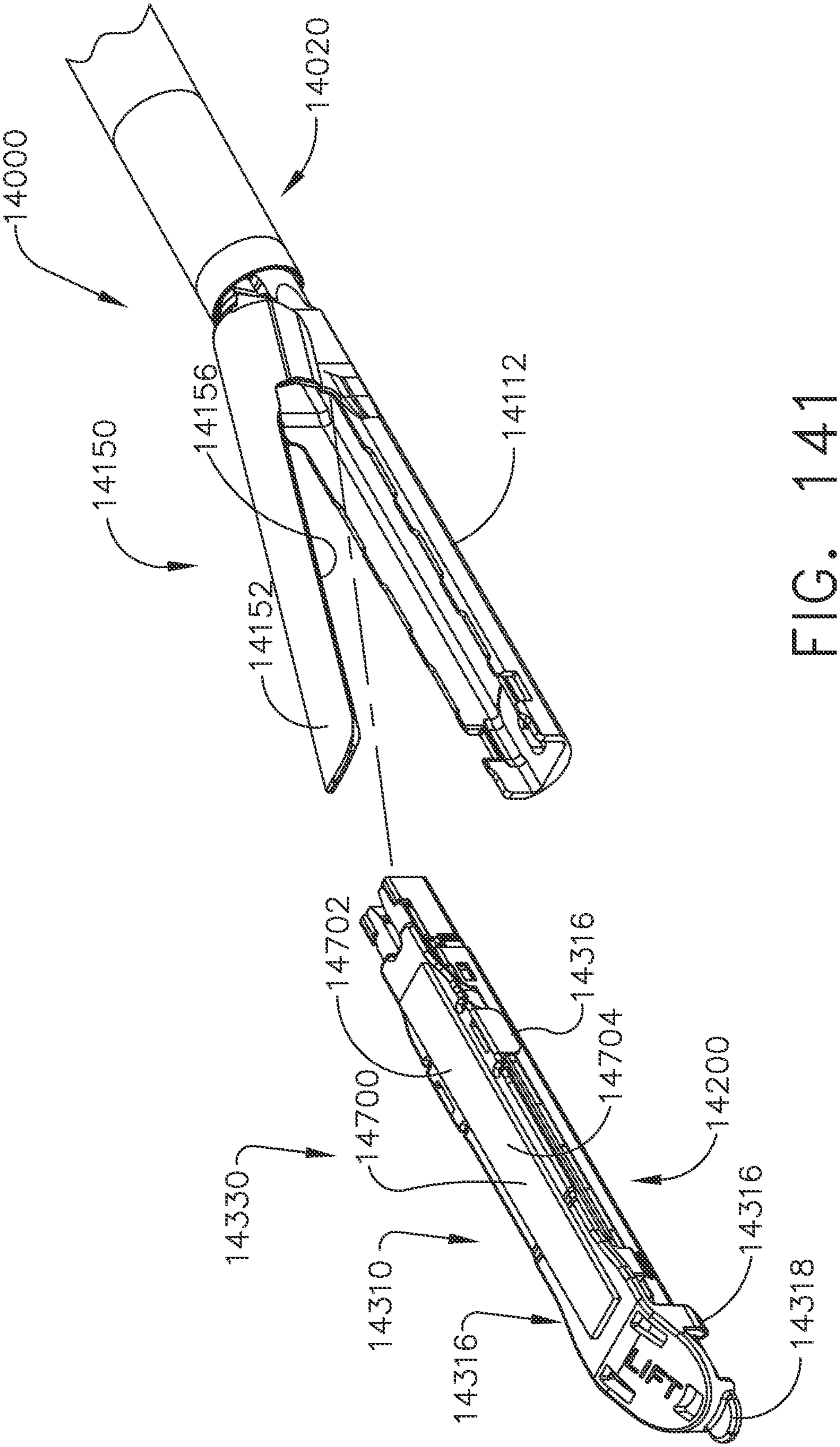
Figure 142A:
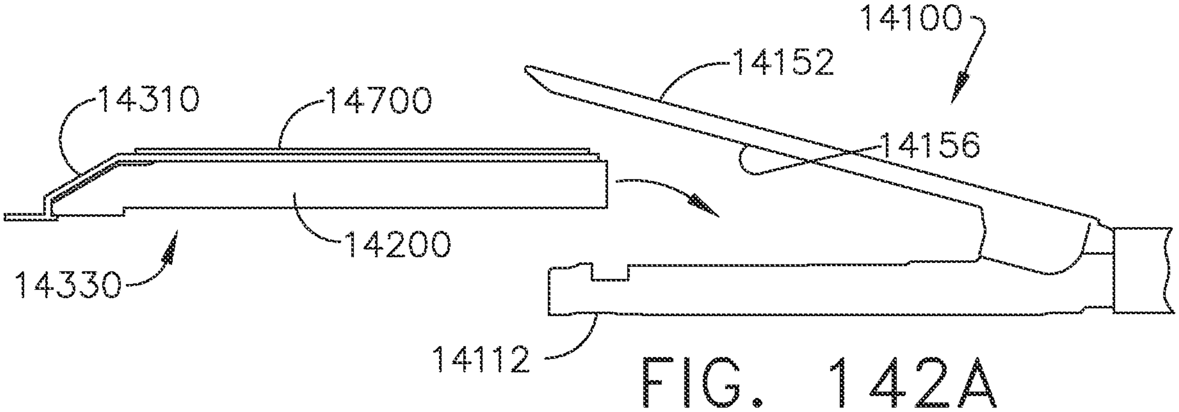
Figure 142B:
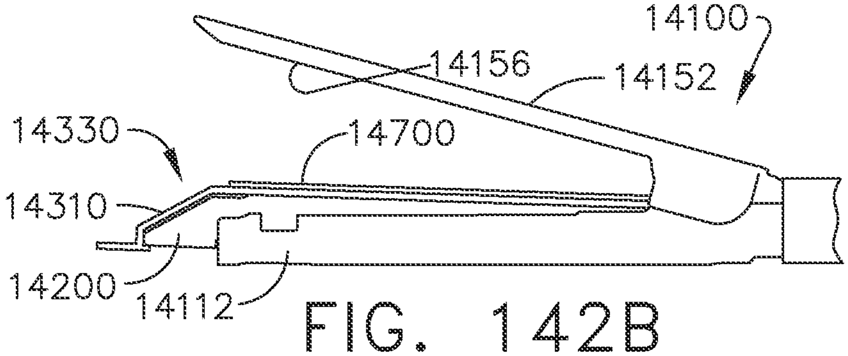
Figure 142C:
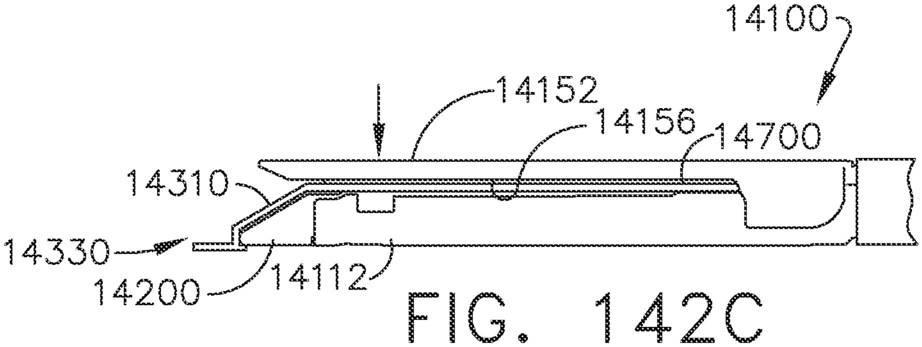
Figure 142D:
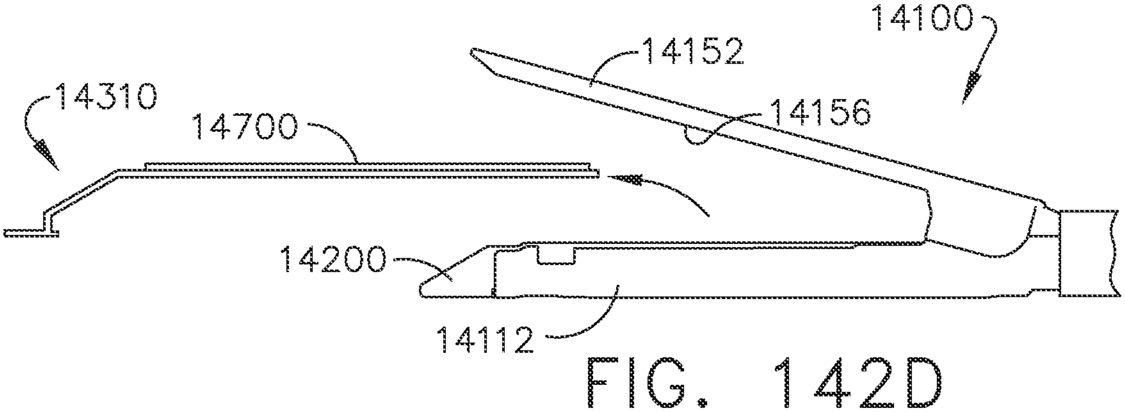
Figure 143:
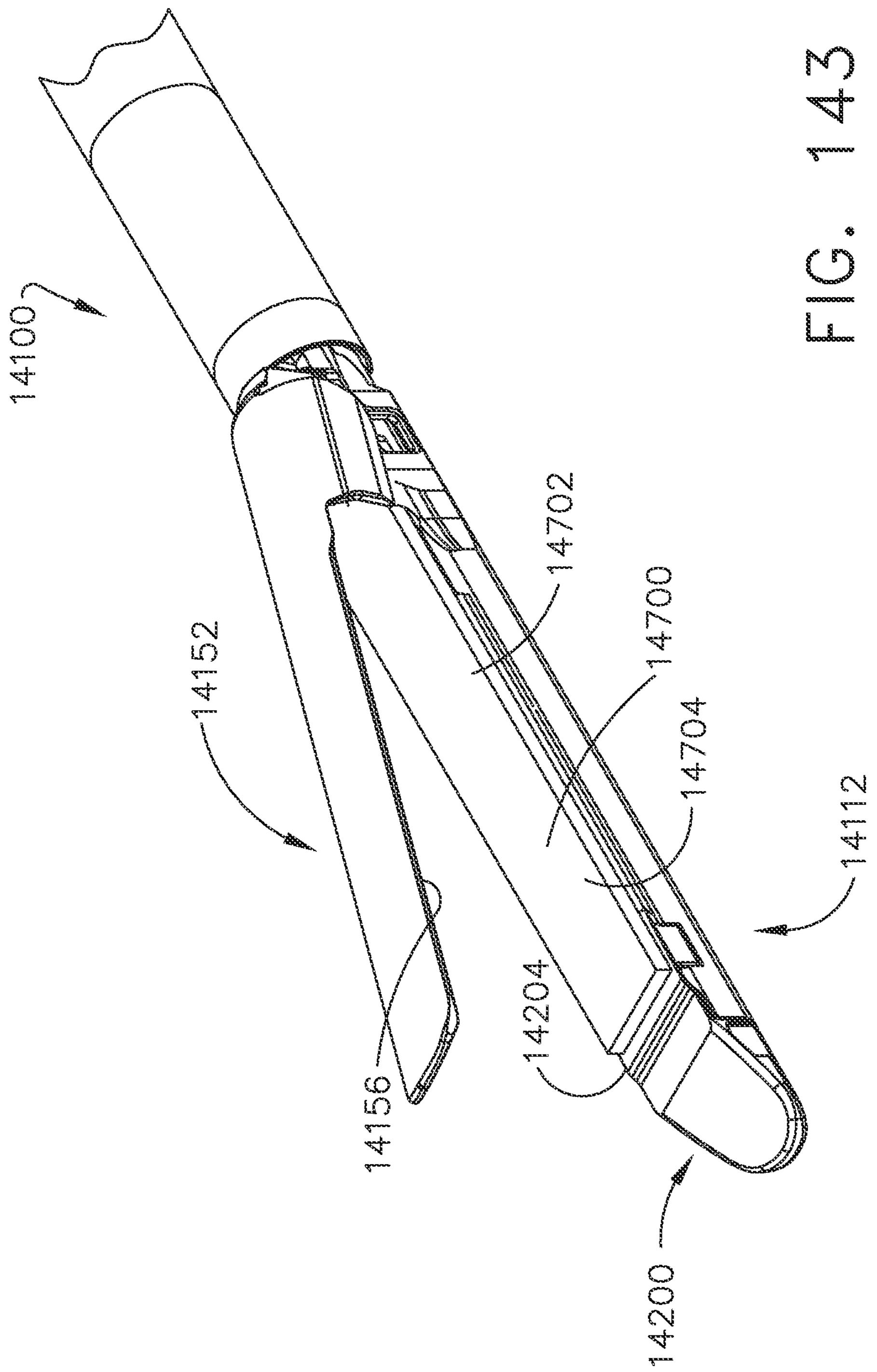
Figure 144A:
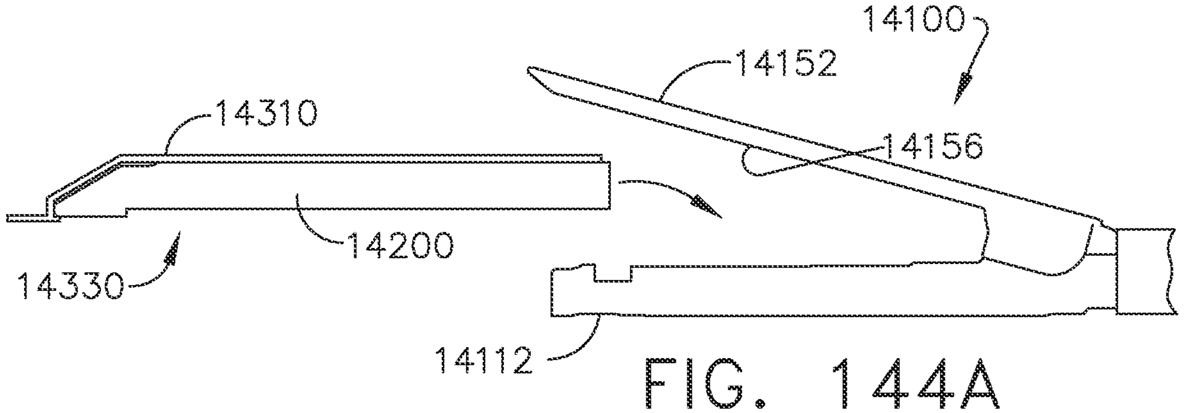
Figure 144B:
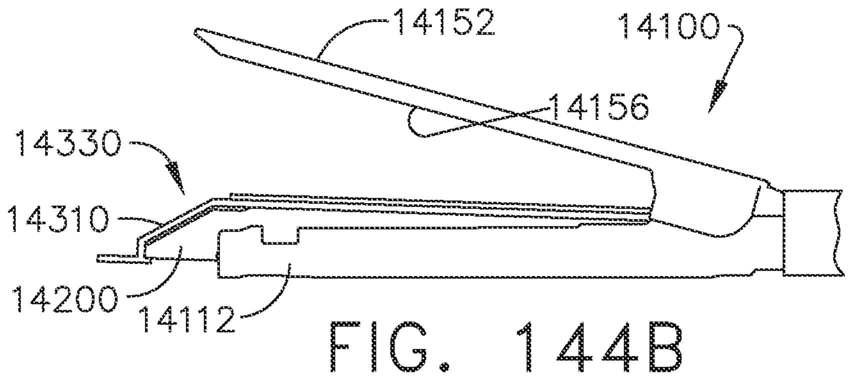
Figure 144C:
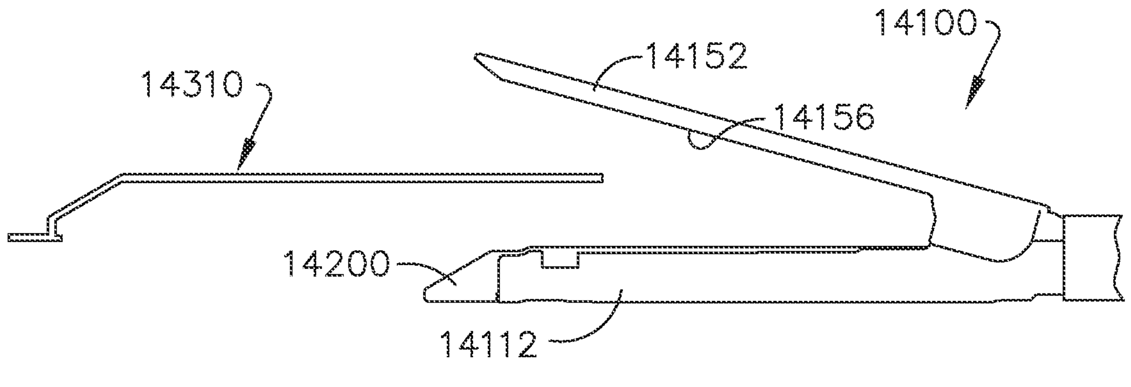
Figure 144D:
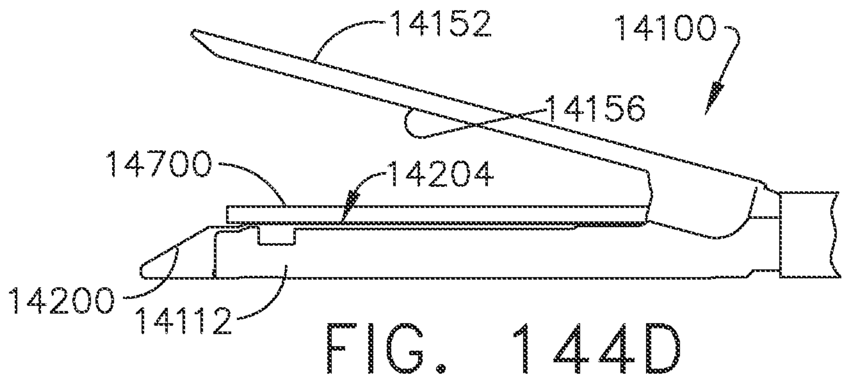
Figure 144E:
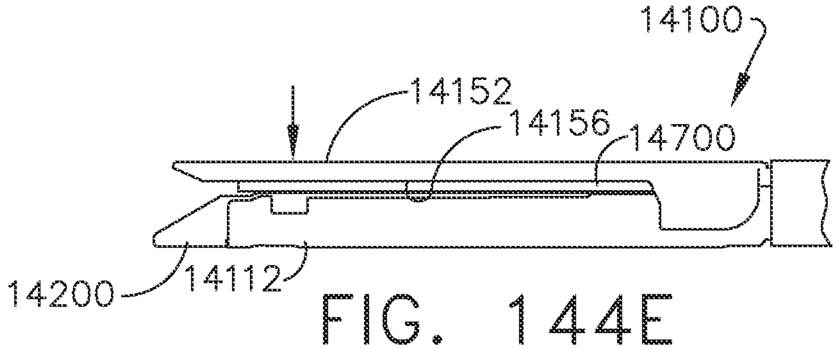
Figure 144F:
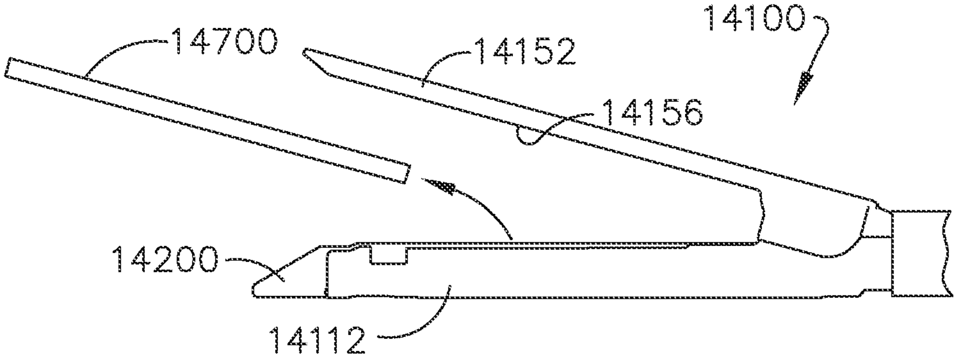
Figure 145:
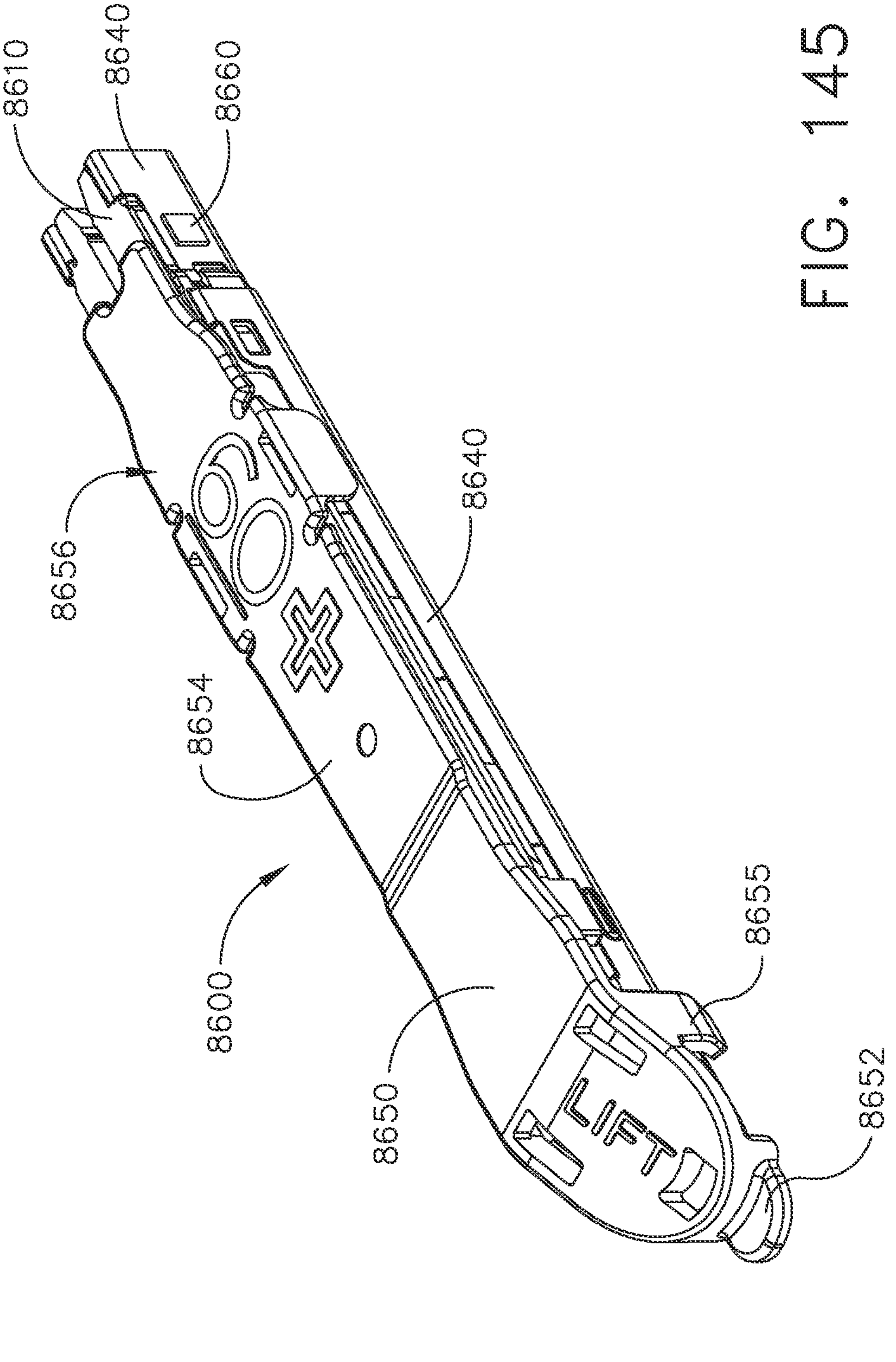
Figure 146:
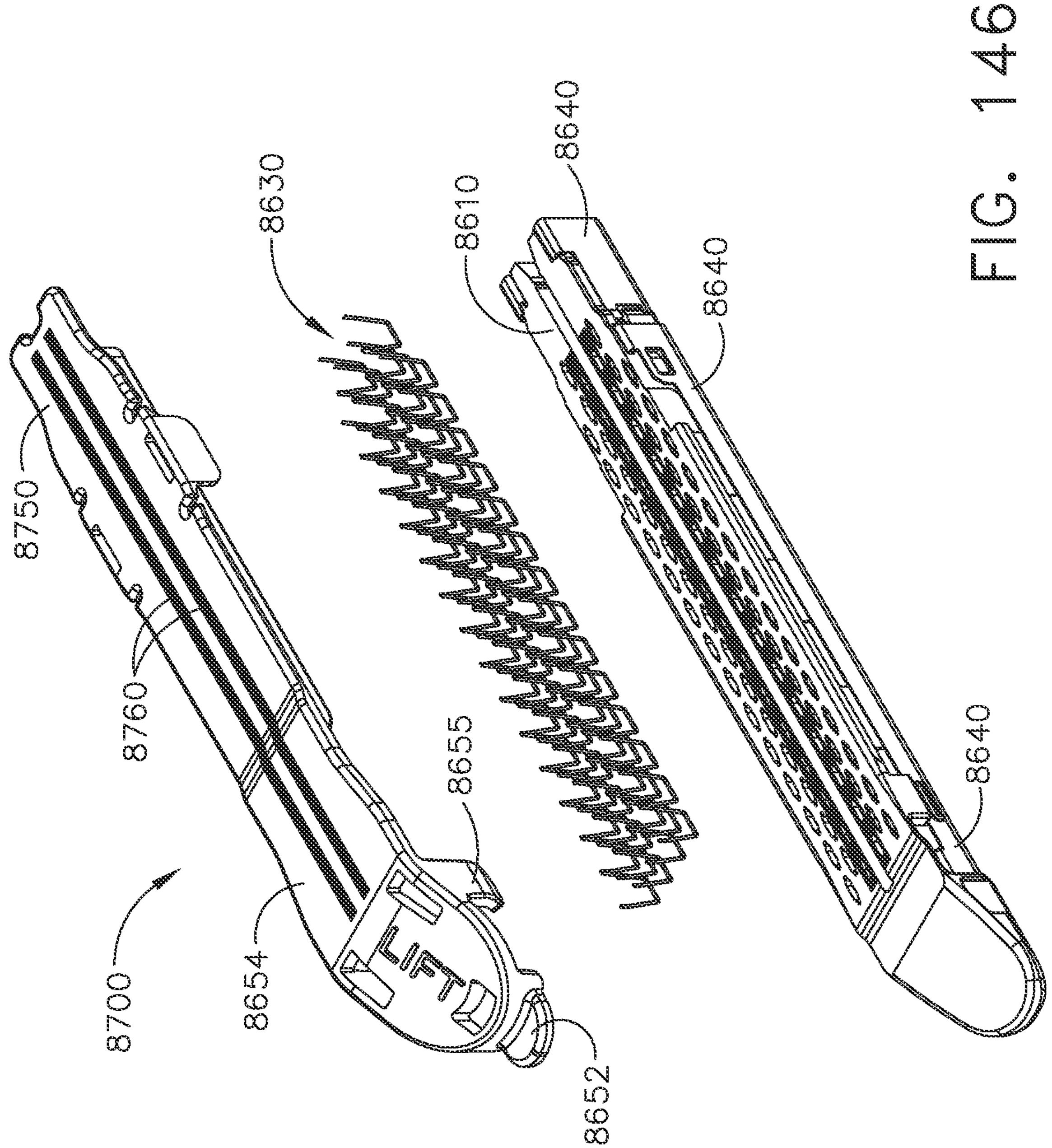
Figure 146A:
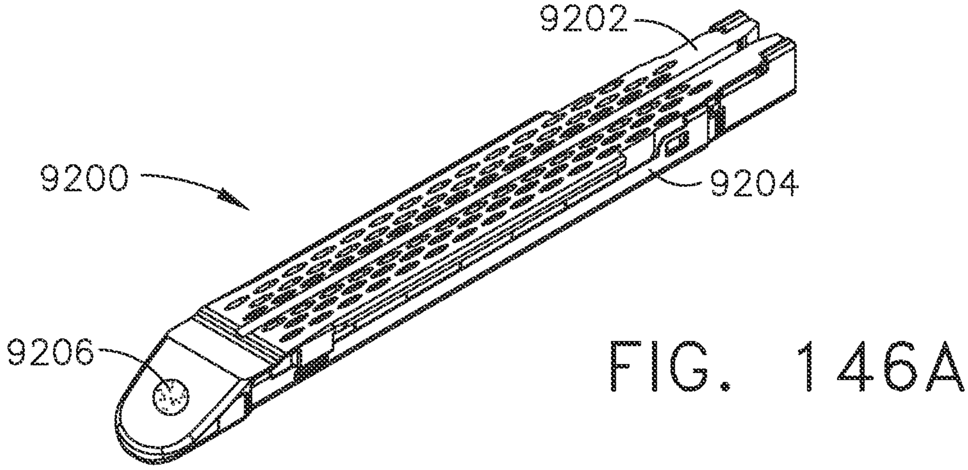
Figure 146B:
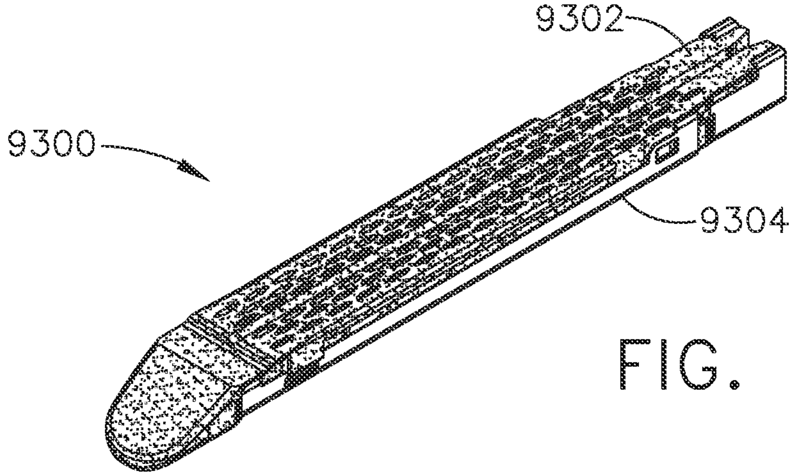
Figure 146C:
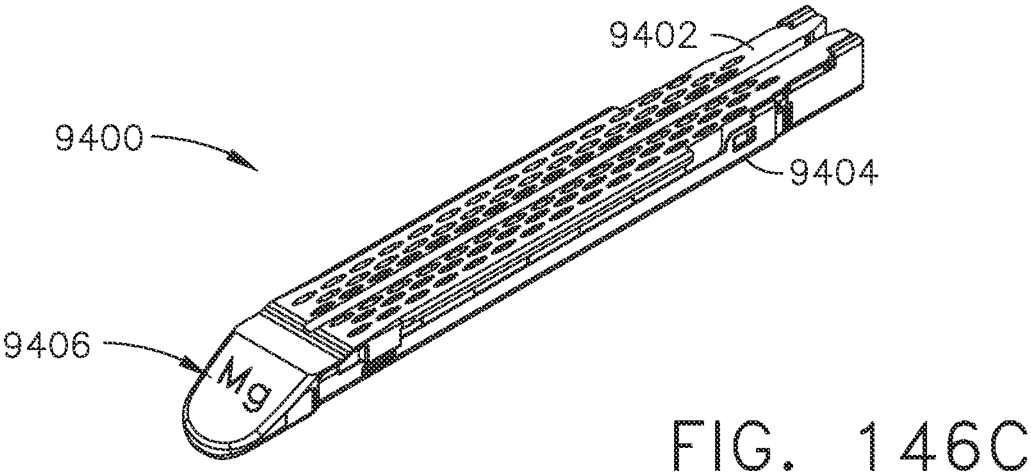
Figure 146D:
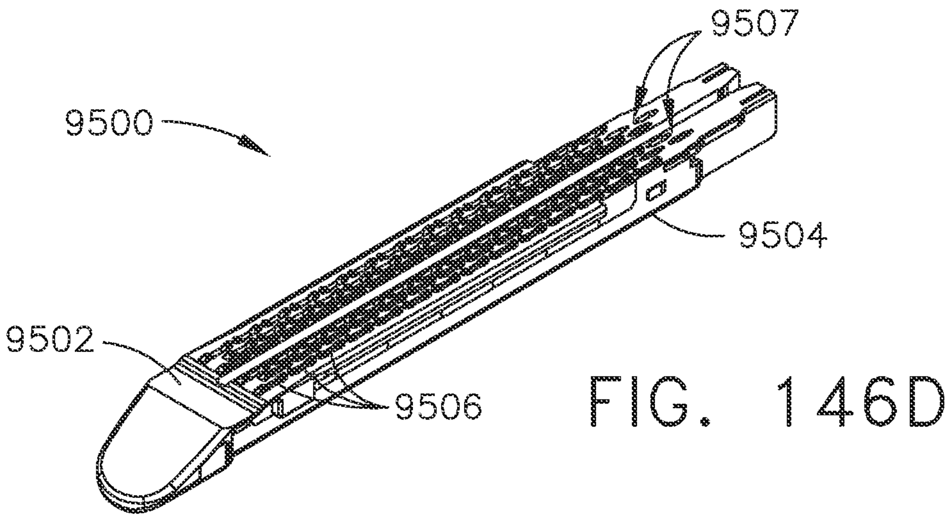
Figure 146E:
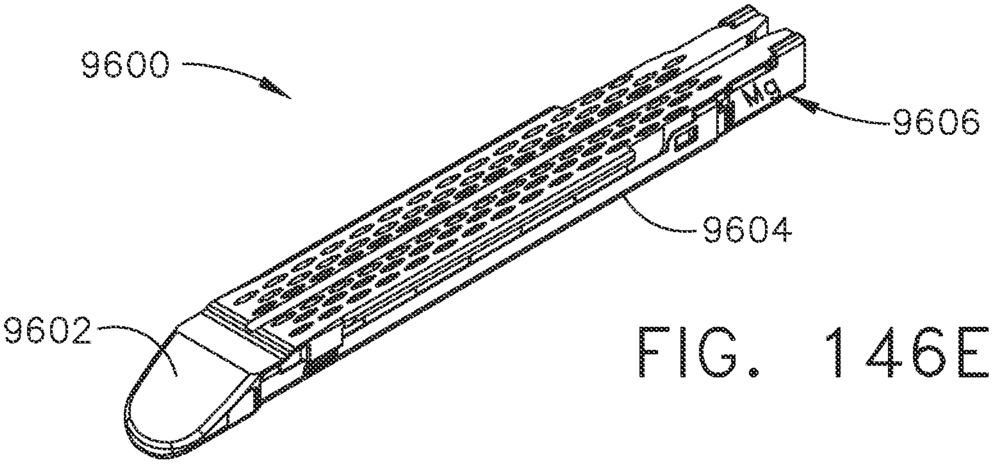
Figure 146F:
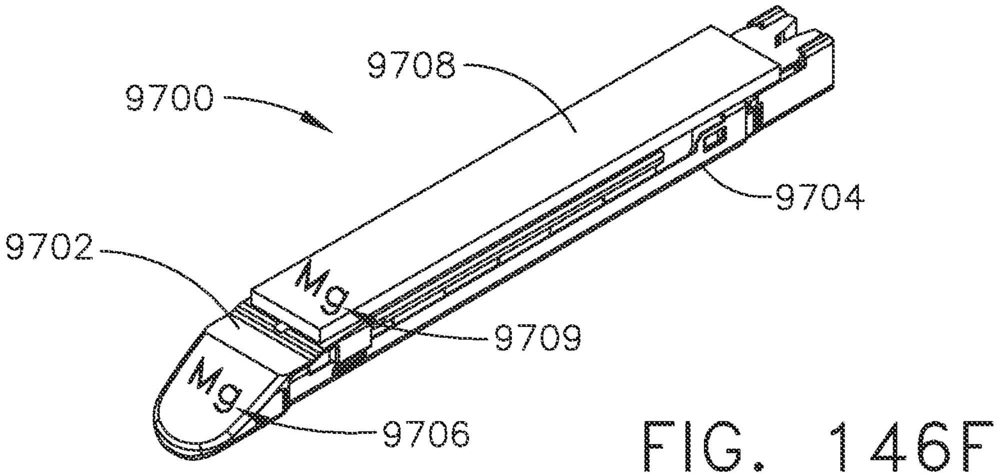
Figure 147:
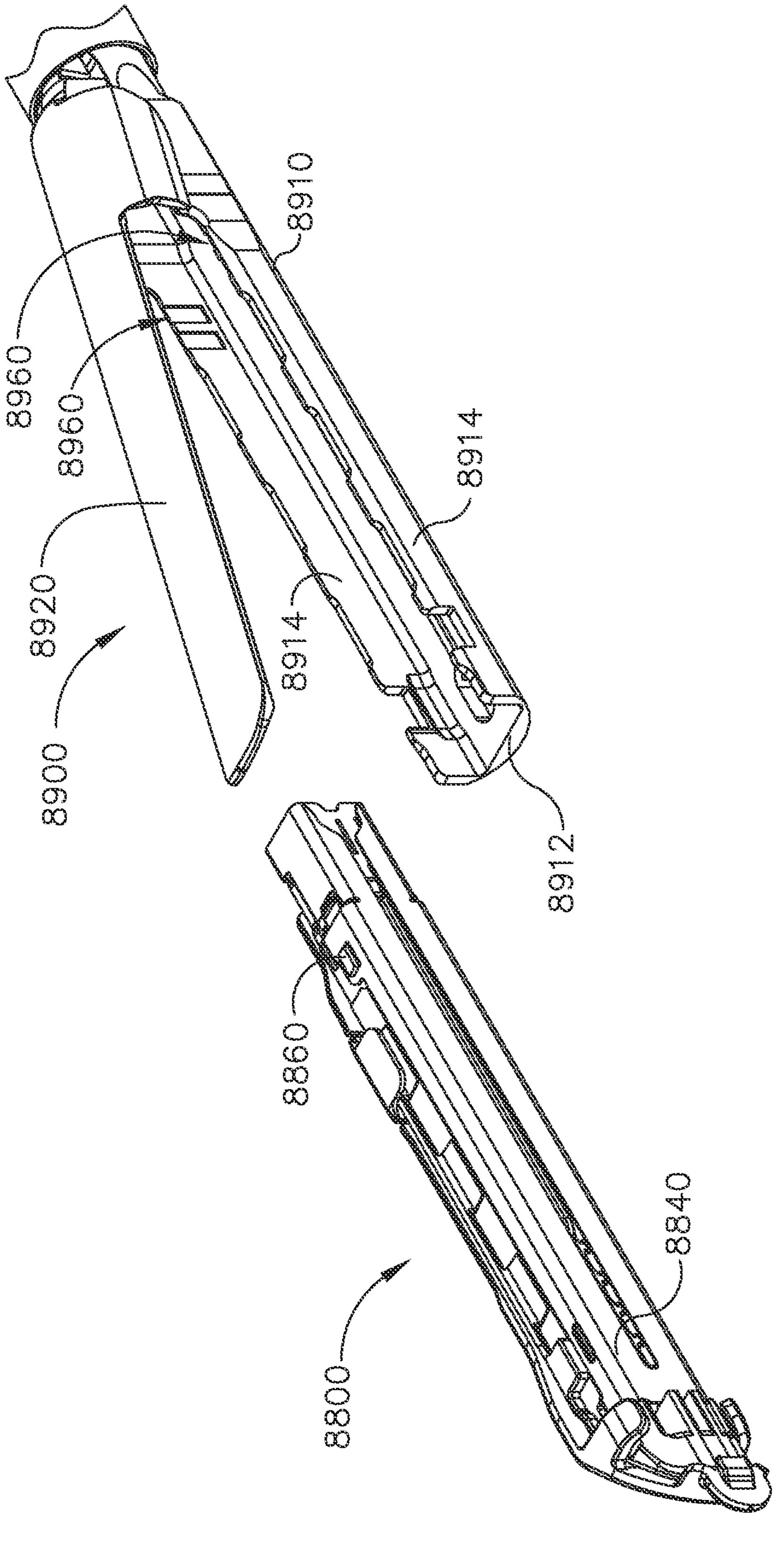
Figure 148:
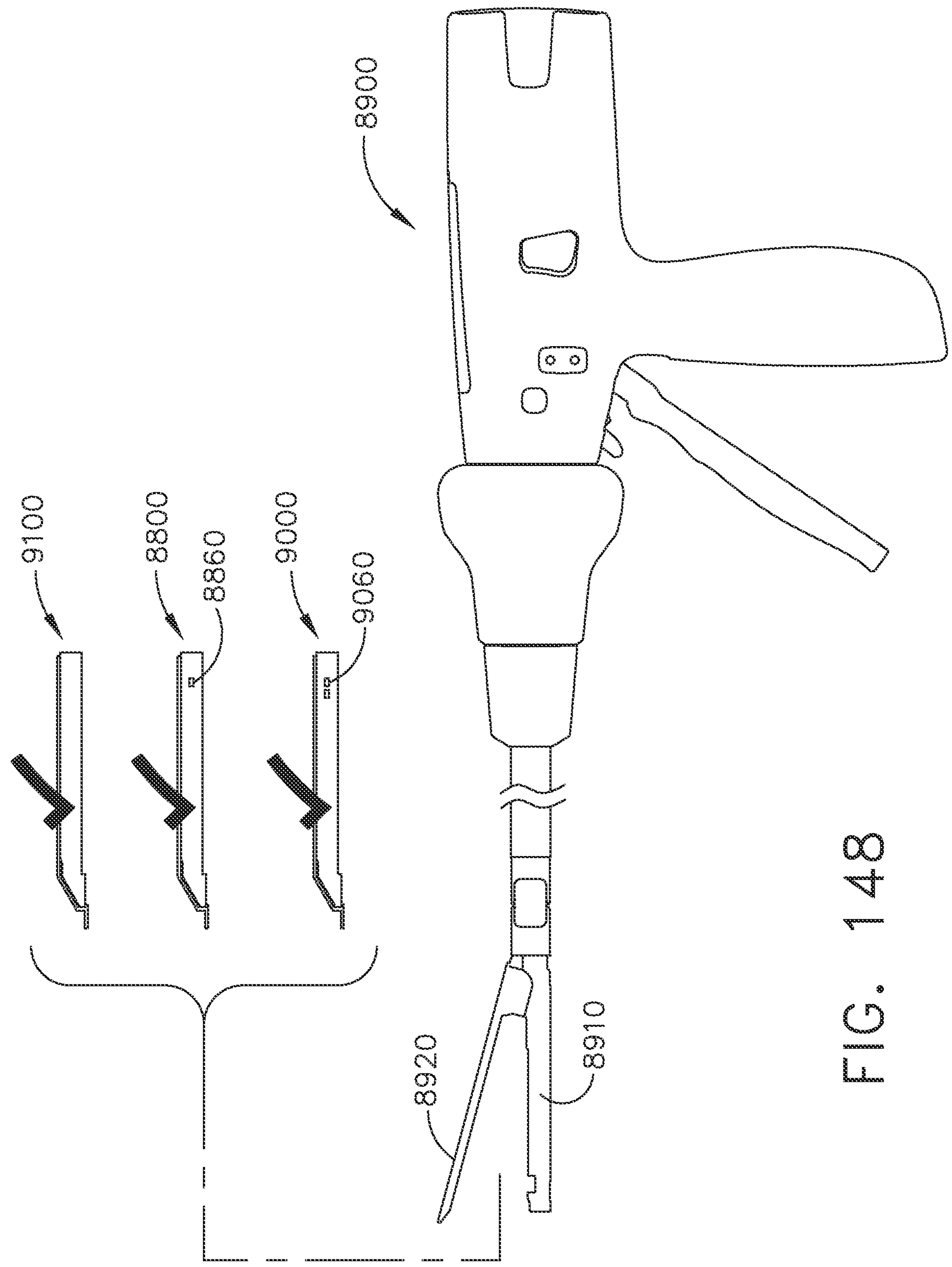
Figure 149:
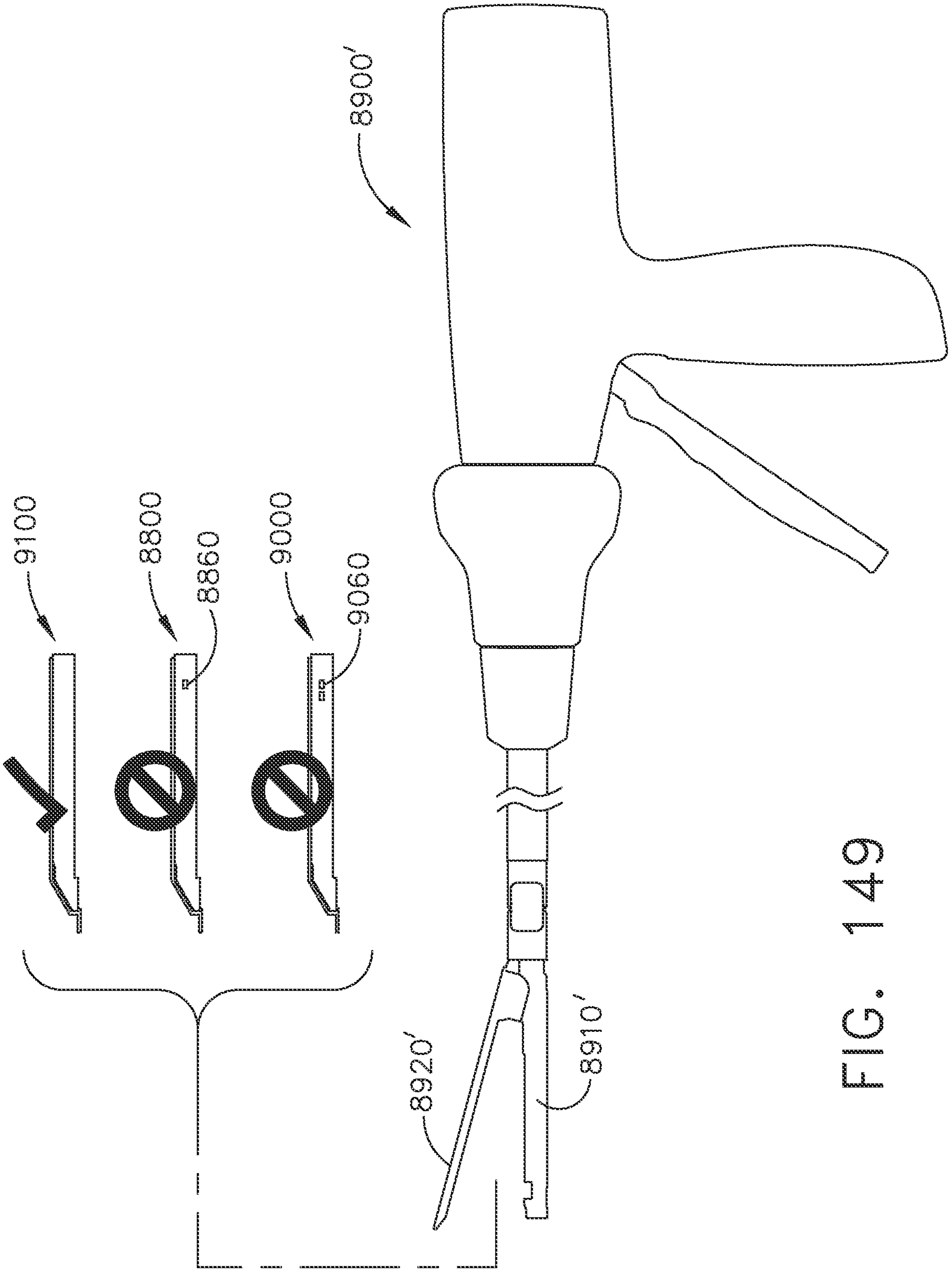
Figure 149A:
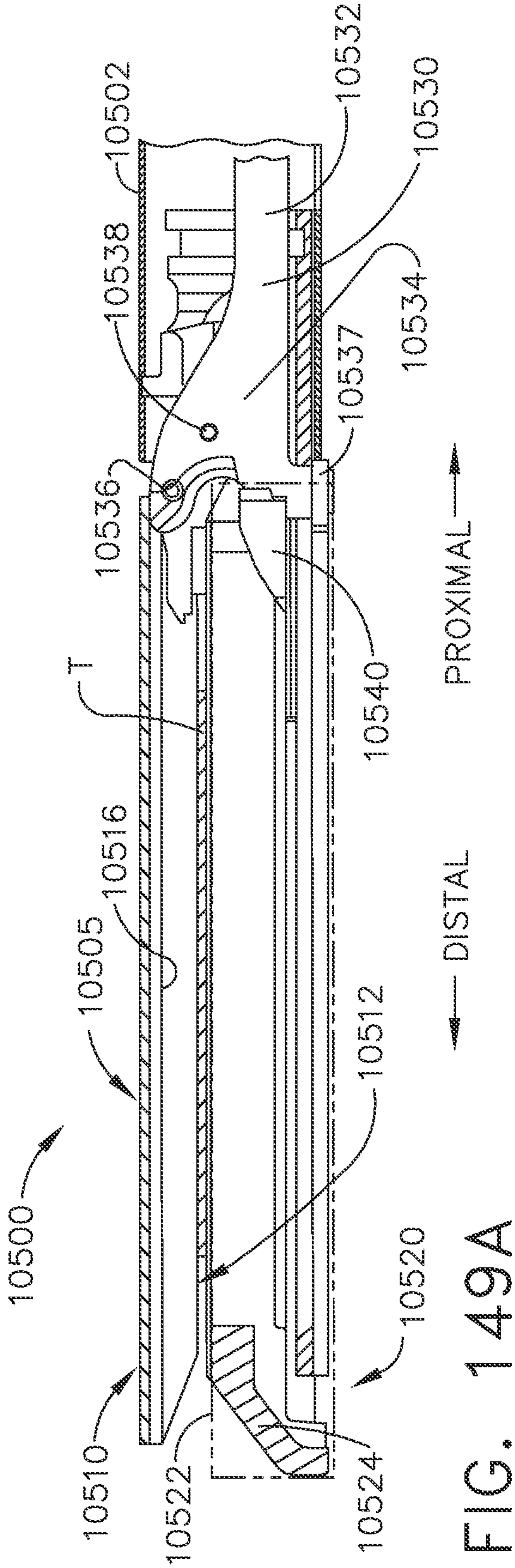
Figure 149B:
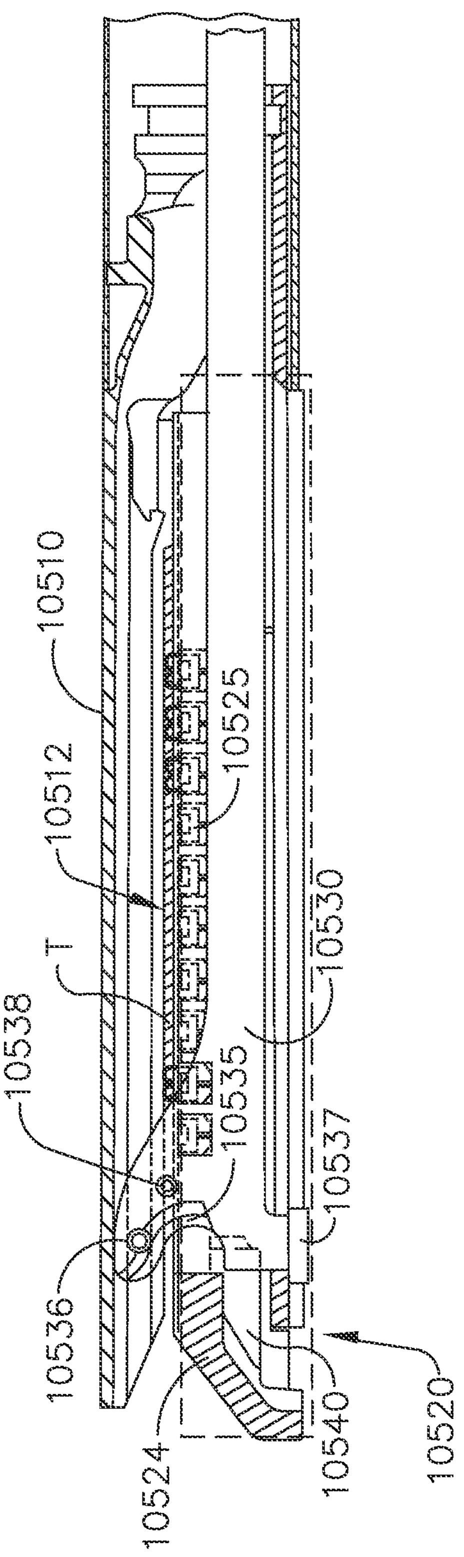
Figure 149C:
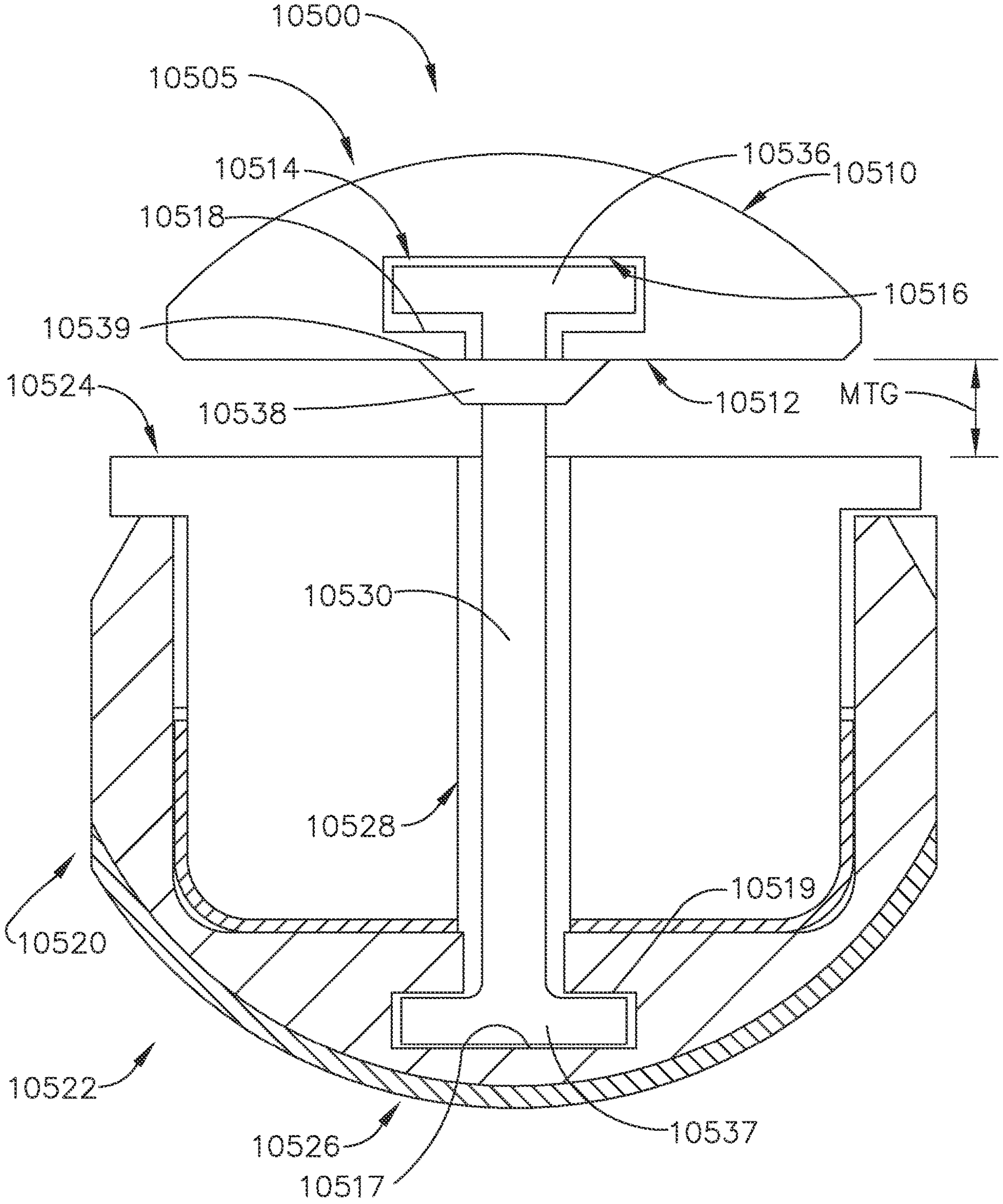
Figure 150:
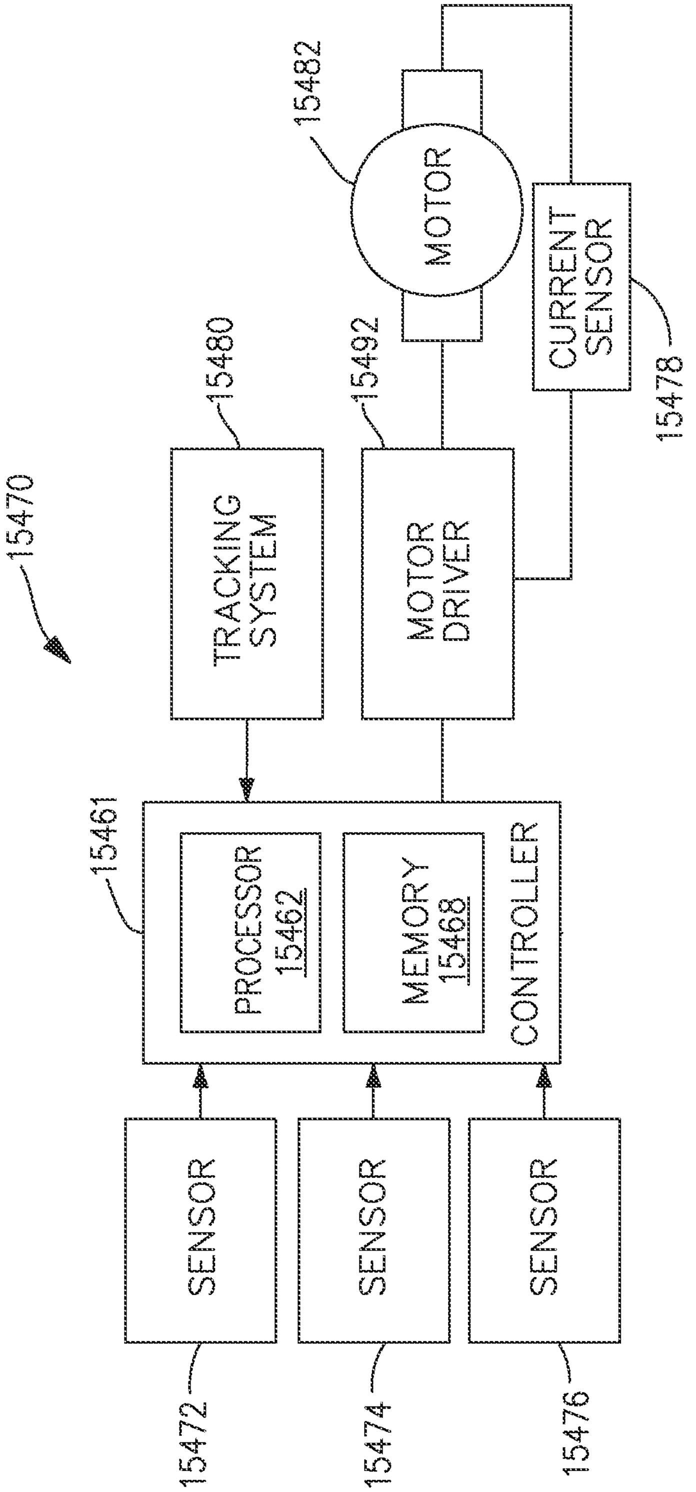
Figure 151:
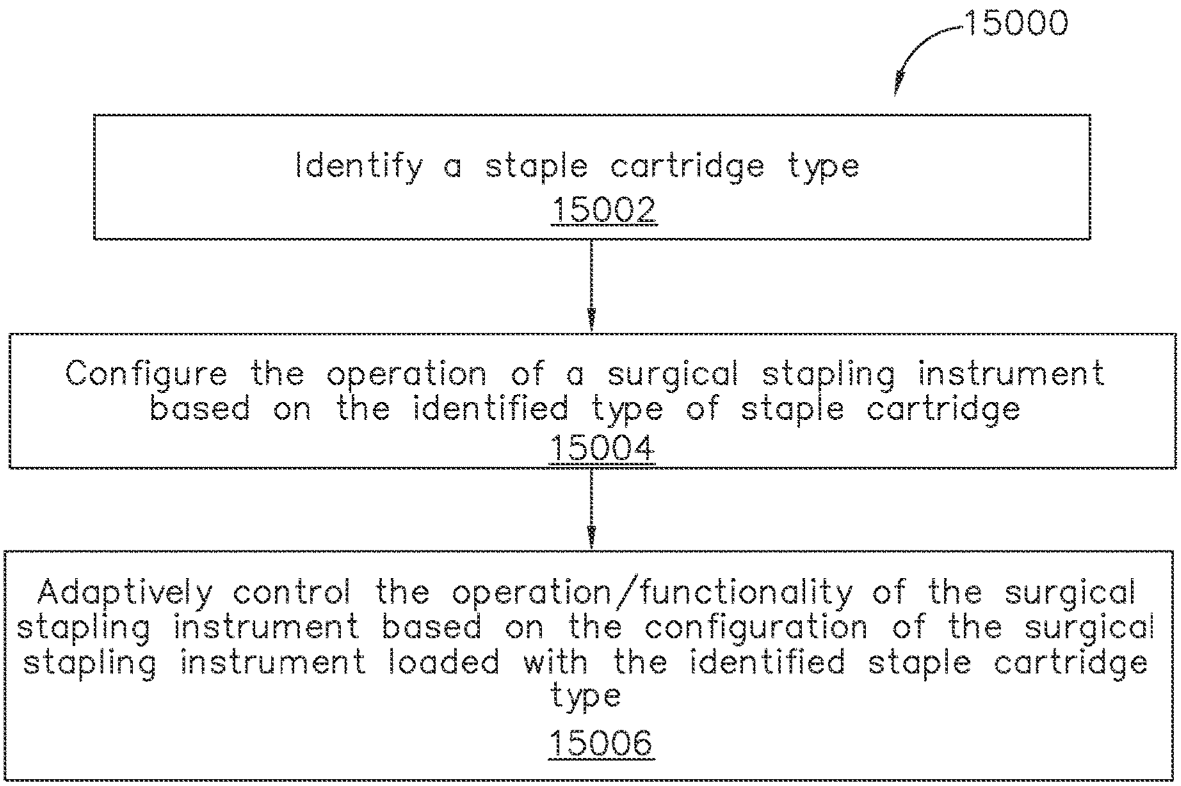

FIG. 116 is a perspective view of a packaging assembly embodiment comprising the cartridge/retainer assembly of FIG. 114 stored inside a hermetically-sealed container comprising a pouch, and wherein a desiccant element is also contained within the hermetically-sealed pouch;

FIG. 117 is a perspective view of another packaging assembly embodiment, wherein a cartridge/retainer assembly is non-movably seated in a cartridge tray that is stored within a hermetically-sealed container comprising a pouch, and wherein a desiccant element is also contained within the hermetically-sealed pouch;

FIG. 118 is a perspective view of another packaging assembly embodiment, wherein a cartridge/retainer assembly is non-movably seated in a cartridge tray component of a hermetically-sealable container and the container further comprises a top member in a partially opened position that is attached to the cartridge tray and configured to establish a hermetic seal therewith, and wherein the container further includes a desiccant element therein;

FIG. 119 is an exploded assembly view of a staple retainer embodiment, a desiccant element, and a surgical staple cartridge, wherein the desiccant element is positioned between the staple retainer and the surgical staple cartridge;

FIG. 120 is a side view of the staple retainer of FIG. 119 coupled to the surgical staple cartridge, and wherein the desiccant element of FIG. 119 is captured between the staple retainer and a deck of the surgical staple cartridge to form a cartridge/retainer assembly;

FIG. 121 is an exploded assembly view of the staple retainer of 119, wherein another desiccant element embodiment is positioned between the staple retainer and a surgical staple cartridge, wherein the desiccant element is formed with a plurality of staple retention protrusions configured to be inserted into corresponding staple cavities in the surgical staple cartridge to restrain the staples therein;

FIG. 122 is a cross-sectional view of a portion of the staple retainer of FIG. 121 coupled to the surgical staple cartridge of FIG. 121, wherein the desiccant element of FIG. 121 is captured between the staple retainer and a deck of the surgical staple cartridge, and wherein a staple retention protrusion of the staple retainer is received within a corresponding staple cavity of the surgical staple cartridge to restrain the staple contained therein on a corresponding staple driver;

FIG. 123 is a perspective view of another packaging assembly embodiment comprising a cartridge/retainer assembly stored inside a hermetically-sealed container comprising a pouch, wherein the cartridge/retainer assembly comprises a staple retainer coupled to a surgical staple cartridge, and wherein a desiccant element is attached to the staple retainer;

FIG. 124 is a perspective view of another packaging assembly embodiment comprising a cartridge/retainer assembly stored inside a container comprising a hermetically-sealed pouch, wherein the cartridge/retainer assembly comprises a staple retainer coupled to a surgical staple cartridge, and wherein the cartridge/retainer assembly is received between an upper desiccant element and a lower desiccant element supported within the hermetically-sealed pouch;

FIG. 125 is a perspective view of another packaging assembly embodiment, wherein the cartridge/retainer assembly of FIG. 124 and the upper desiccant element and lower desiccant element of FIG. 124 are contained within a retainer tube stored within a container comprising a hermetically-sealed pouch;

FIG. 126 is an exploded assembly view of a staple retainer, a tubular desiccant element, and a surgical staple cartridge wherein the surgical staple cartridge is to be received within the tubular desiccant element and the staple retainer is to be attached to the surgical staple cartridge to capture a portion of the tubular desiccant element between the staple retainer and a deck surface of the surgical staple cartridge;

FIG. 127 is an end exploded view of the staple retainer, tubular desiccant element, and surgical staple cartridge of FIG. 126, and wherein the surgical staple cartridge has been inserted into the tubular desiccant element;

FIG. 128 is a perspective view of another packaging assembly embodiment comprising a staple retainer attached to a surgical staple cartridge to form a cartridge/retainer assembly, wherein the cartridge/retainer assembly is received within a tubular desiccant element and is stored inside a container comprising a hermetically-sealed pouch;

FIG. 129 is a perspective view of another desiccant element embodiment, wherein the desiccant element is removably mounted to a deck surface of a surgical staple cartridge, and wherein the surgical staple cartridge is stored in a hermetically-sealed container;

FIG. 130 is a perspective view of another desiccant element embodiment that is configured to non-movably support a cartridge/retainer assembly within a hermetically-sealable container for storage and shipment purposes;

FIG. 131 is a perspective view of another packaging assembly embodiment comprising a staple retainer attached to a surgical staple cartridge to form a cartridge/retainer assembly, wherein the cartridge/retainer assembly is stored inside a container comprising a hermetically-sealed pouch, and wherein the surgical staple cartridge comprises an RFID chip associated with a sensor;

FIG. 132 is a flow chart representative of a process of controller of a surgical stapling instrument, wherein a sensor communicating with the controller monitors an amount of moisture experienced by the surgical staple cartridge of FIG. 131 while stored within the hermetically-sealed pouch of FIG. 131, and wherein the controller prevents operation of the surgical stapling instrument when a detected amount of moisture exceeds a predetermined acceptable moisture level;

FIG. 133 is a flow chart representative of another process of controller of a surgical stapling instrument, wherein a sensor communicating with the controller monitors an amount of temperature experienced by the surgical staple cartridge of FIG. 131 while stored within the hermetically-sealed pouch of FIG. 131, and wherein the controller prevents operation of the surgical stapling instrument when a detected amount of temperature exceeds a predetermined acceptable temperature level;

FIG. 134 is a flow chart representative of another process of controller of a surgical stapling instrument, wherein a sensor communicating with the controller monitors an amount of moisture and temperature experienced by the surgical staple cartridge of FIG. 131 while stored within the hermetically-sealed pouch of FIG. 131, and wherein the controller prevents operation of the surgical stapling instrument when a detected amount of moisture exceeds a predetermined moisture level and/or a detected amount of temperature exceeds a predetermined temperature level;

FIG. 135 is a perspective view of another packaging assembly embodiment comprising a staple retainer attached to a surgical staple cartridge to form a cartridge/retainer assembly, wherein the cartridge/retainer assembly is stored inside a container comprising a hermetically-sealed pouch, and wherein the pouch comprises an indicator associated with a sensor;

FIG. 136 is a perspective view of another packaging assembly embodiment comprising a staple retainer attached to a surgical staple cartridge to form a cartridge/retainer assembly, wherein the cartridge/retainer assembly is stored inside a container comprising a hermetically-sealed pouch, and wherein the pouch is filled with a Nitrogen or Argon gas;

FIG. 137 is an exploded assembly view of another staple retainer embodiment and surgical staple cartridge, wherein the staple retainer comprises a plurality of staple retention protrusions protruding from an undersurface thereof, and wherein the staple retention protrusions are configured to be inserted into corresponding staple cavities in the surgical staple cartridge to restrain the staples therein;

FIG. 138 is a cross-sectional view pf a portion of the staple retainer of FIG. 137 coupled to the surgical staple cartridge of FIG. 137, wherein a staple retention protrusion of the staple retainer is received within a corresponding staple cavity of the surgical staple cartridge to restrain the staple contained therein in position on a staple driver;

FIG. 139 is cross-sectional view of a portion of a cartridge body of a surgical staple cartridge, wherein a bio-absorbable staple is received within a corresponding staple cavity in the cartridge body that comprises inner cavity walls, wherein the bio-absorbable staple is supported on a staple driver within the staple cavity, wherein the bio-absorbable staple comprises a staple coating, and wherein heat is applied to the bio-absorbable staple to cause portions of the staple coating to become tacky to temporarily adhere portions of the bio-absorbable staple to corresponding portions of the inner cavity walls and the staple driver;

FIG. 140 is cross-sectional view of a portion of a cartridge body of another surgical staple cartridge, wherein a bio-absorbable staple is received within a corresponding staple cavity in the cartridge body, wherein the bio-absorbable staple is supported on a staple driver within the staple cavity, and wherein a Vapor Corrosion Inhibitor is applied to the bio-absorbable staple while in the staple cavity;

FIG. 141 is an exploded assembly view of a cartridge/retainer assembly and a surgical end effector of a surgical stapling instrument, wherein an anvil of the surgical end effector is in an open position, wherein the cartridge/retainer assembly comprises a staple retainer coupled to a surgical staple cartridge, and wherein a pretreatment element is attached to the staple retainer and is saturated with a pretreatment medium configured to treat a staple-forming undersurface of the anvil;

FIG. 142A is a side view of the cartridge/retainer assembly of FIG. 141 being positioned for insertion into the surgical end effector of FIG. 141;

FIG. 142B is another side view of the cartridge/retainer assembly of FIG. 141 partially inserted into a channel of the surgical end effector of FIG. 141;

FIG. 142C is another side view of the cartridge/retainer assembly of FIG. 141, wherein the anvil of the surgical end effector has been closed onto the pretreatment element to cause the surgical staple cartridge to be seated in the channel and the pretreatment medium to be transferred to the staple-forming undersurface of the anvil;

FIG. 142D is another side view of the cartridge/retainer assembly of FIG. 141 after the anvil has been moved to an open position and the staple retainer has been detached from the surgical staple cartridge;

FIG. 143 is a perspective view of a surgical staple cartridge seated in a channel of a surgical end effector of a surgical stapling instrument, wherein an anvil thereof is in an open position, wherein a pretreatment element is positioned on a deck surface of the surgical staple cartridge, and wherein the pretreatment element is saturated with a pretreatment medium configured to treat a staple-forming undersurface of the anvil;

FIG. 144A is a side view of the surgical end effector of FIG. 143, wherein the anvil thereof is in the open position, wherein a cartridge/retainer assembly is being positioned for insertion into a channel of the surgical end effector, and wherein the cartridge/retainer assembly comprises a staple retainer attached to the surgical staple cartridge of FIG. 143;

FIG. 144B is another side view of the surgical end effector of FIG. 144A with the cartridge/retainer assembly partially seated in the channel;

FIG. 144C is another side view of the surgical end effector of FIG. 144A after the surgical staple cartridge has been seated in the channel and the staple retainer has been detached from the surgical staple cartridge;

FIG. 144D is another side view of the surgical end effector, surgical staple cartridge, and pretreatment element of FIG. 143;

FIG. 144E is another side view of the surgical end effector, surgical staple cartridge and pretreatment element of FIG. 143, wherein the anvil has been moved to a closed position to cause the pretreatment medium to be transferred to a staple-forming undersurface of the anvil;

FIG. 144F is another side view of the surgical end effector and surgical staple cartridge of FIG. 143 after the anvil has been moved to an open position and the pretreatment element has been removed from the deck of the surgical staple cartridge;

FIG. 145 is a perspective view of a staple cartridge assembly including an identifying chip in accordance with at least one embodiment;

FIG. 146 is an exploded view of a staple cartridge assembly including a visual indicia thereon for identifying the bioabsorbability of the staples contained therein in accordance with at least one embodiment;

FIG. 146A is a perspective view of a staple cartridge including an identification feature on its distal end;

FIG. 146B is a perspective view of a staple cartridge including a cartridge body molded with metallic flakes for identification purposes;

FIG. 146C is a perspective view of a staple cartridge including a cartridge body comprising an identification symbol;

FIG. 146D is a perspective view of a staple cartridge including a cartridge body comprising protrusions selectively positioned for identification purposes;

FIG. 146E is a perspective view of a staple cartridge having a cartridge body and a cartridge pan where the cartridge pan includes an identification symbol;

FIG. 146F is a perspective view of a staple cartridge assembly including an implantable layer having an identification symbol;

FIG. 147 is a perspective view of a staple cartridge that is insertable into an end effector of a surgical stapling instrument in accordance with at least one embodiment;

FIG. 148 depicts the compatibility of certain staple cartridges with the surgical stapling instrument of FIG. 147;

FIG. 149 depicts the compatibility and incompatibility of the staple cartridges of FIG. 148 with a different surgical stapling instrument;

FIG. 149A illustrates a side-elevation view of a surgical instrument including an end effector and a firing member where the end effector is in a closed or clamped position and the firing member is in a proximal or unfired position;

FIG. 149B illustrates a side-elevation view of the surgical instrument of FIG. 149A with the end effector in the closed or clamped position and the firing member in a distal or fired position;

FIG. 149C illustrates a cross-section end view of the surgical instrument of FIG. 149A with the end effector in the closed or clamped position;

FIG. 150 illustrates a logic diagram of a control system of a surgical instrument or tool, in accordance with at least one aspect of the present disclosure; and FIG. 151 illustrates a method of adaptively controlling a surgical stapling instrument based on the type of staple cartridge identified by a clinician or a control circuit, in accordance with at least one aspect of the present disclosure.

Corresponding reference characters indicate corresponding parts throughout the several views. The exemplifications set out herein illustrate various embodiments of the invention, in one form, and such exemplifications are not to be construed as limiting the scope of the invention in any manner.

DETAILED DESCRIPTION

Applicant of the present application also owns the following U.S. Patent Applications that were filed on even date herewith and which are each herein incorporated by reference in their respective entireties:

- U.S. Patent Application entitled METHOD FOR IMPLEMENTING A STAPLE SYSTEM;
- U.S. Patent Application entitled ADAPTIVE CONTROL OF SURGICAL STAPLING INSTRUMENT BASED ON STAPLE CARTRIDGE TYPE;
- U.S. Patent Application entitled BIOABSORBABLE STAPLE COMPRISING MECHANISMS FOR SLOWING THE ABSORPTION OF THE STAPLE;
- U.S. Patent Application entitled BIOABSORBABLE STAPLE COMPRISING MECHANISM FOR DELAYING THE ABSORPTION OF THE STAPLE;
- U.S. Patent Application entitled SYSTEM OF SURGICAL STAPLE CARTRIDGES COMPRISING ABSORBABLE STAPLES;
- U.S. Patent Application entitled ABSORBABLE SURGICAL STAPLES COMPRISING SUFFICIENT STRUCTURAL PROPERTIES DURING A TISSUE HEALING WINDOW;
- U.S. Patent Application entitled METHOD FOR DELIVERING A STAPLE IN SITU PAIRED TO THE IN SITU ENVIRONMENT;
- U.S. Patent Application entitled ABSORBABLE STAPLE COMPRISING STRAIN LIMITING FEATURES;
- U.S. Patent Application entitled ABSORBABLE SURGICAL STAPLE COMPRISING AT LEAST TWO COATINGS;
- U.S. Patent Application entitled STAPLE CARTRIDGE COMPRISING LUBRICATED STAPLES;
- U.S. Patent Application entitled DISSIMILAR STAPLE CARTRIDGES WITH DIFFERENT BIOABSORBABLE COMPONENTS; and
- U.S. Patent Application entitled PACKAGING ASSEMBLIES FOR SURGICAL STAPLE CARTRIDGES CONTAINING BIO-ABSORBABLE STAPLES.

Applicant of the present application also owns the following U.S. Patent Applications that were filed on Feb. 26, 2021 and which are each herein incorporated by reference in their respective entireties:

- U.S. patent application Ser. No. 17/186,269, entitled METHOD OF POWERING AND COMMUNICATING WITH A STAPLE CARTRIDGE;
- U.S. patent application Ser. No. 17/186,273, entitled METHOD OF POWERING AND COMMUNICATING WITH A STAPLE CARTRIDGE;
- U.S. patent application Ser. No. 17/186,276, entitled ADJUSTABLE COMMUNICATION BASED ON AVAILABLE BANDWIDTH AND POWER CAPACITY;
- U.S. patent application Ser. No. 17/186,283, entitled ADJUSTMENT TO TRANSFER PARAMETERS TO IMPROVE AVAILABLE POWER;
- U.S. patent application Ser. No. 17/186,345, entitled MONITORING OF MANUFACTURING LIFE-CYCLE;
- U.S. patent application Ser. No. 17/186,350, entitled MONITORING OF MULTIPLE SENSORS OVER TIME TO DETECT MOVING CHARACTERISTICS OF TISSUE;
- U.S. patent application Ser. No. 17/186,353, entitled MONITORING OF INTERNAL SYSTEMS TO DETECT AND TRACK CARTRIDGE MOTION STATUS;
- U.S. patent application Ser. No. 17/186,357, entitled DISTAL COMMUNICATION ARRAY TO TUNE FREQUENCY OF RF SYSTEMS;
- U.S. patent application Ser. No. 17/186,364, entitled STAPLE CARTRIDGE COMPRISING A SENSOR ARRAY;
- U.S. patent application Ser. No. 17/186,373, entitled STAPLE CARTRIDGE COMPRISING A SENSING ARRAY AND A TEMPERATURE CONTROL SYSTEM;
- U.S. patent application Ser. No. 17/186,378, entitled STAPLE CARTRIDGE COMPRISING AN INFORMATION ACCESS CONTROL SYSTEM;
- U.S. patent application Ser. No. 17/186,407, entitled STAPLE CARTRIDGE COMPRISING A POWER MANAGEMENT CIRCUIT;

U.S. patent application Ser. No. 17/186,421, entitled STAPLING INSTRUMENT COMPRISING A SEPARATE POWER ANTENNA AND A DATA TRANSFER ANTENNA;

U.S. patent application Ser. No. 17/186,438, entitled SURGICAL INSTRUMENT SYSTEM COMPRISING A POWER TRANSFER COIL; and U.S. patent application Ser. No. 17/186,451, entitled STAPLING INSTRUMENT COMPRISING A SIGNAL ANTENNA.

Applicant of the present application also owns the following U.S. Patent Applications that were filed on Oct. 29, 2020 and which are each herein incorporated by reference in their respective entireties:

U.S. patent application Ser. No. 17/084,179, entitled SURGICAL INSTRUMENT COMPRISING A RELEASABLE CLOSURE DRIVE LOCK;

U.S. patent application Ser. No. 17/084,190, entitled SURGICAL INSTRUMENT COMPRISING A STOWED CLOSURE ACTUATOR STOP;

U.S. patent application Ser. No. 17/084,198, entitled SURGICAL INSTRUMENT COMPRISING AN INDICATOR WHICH INDICATES THAT AN ARTICULATION DRIVE IS ACTUATABLE;

U.S. patent application Ser. No. 17/084,205, entitled SURGICAL INSTRUMENT COMPRISING AN ARTICULATION INDICATOR;

U.S. patent application Ser. No. 17/084,258, entitled METHOD FOR OPERATING A SURGICAL INSTRUMENT;

U.S. patent application Ser. No. 17/084,206, entitled SURGICAL INSTRUMENT COMPRISING AN ARTICULATION LOCK;

U.S. patent application Ser. No. 17/084,215, entitled SURGICAL INSTRUMENT COMPRISING A JAW ALIGNMENT SYSTEM;

U.S. patent application Ser. No. 17/084,229, entitled SURGICAL INSTRUMENT COMPRISING SEALABLE INTERFACE;

U.S. patent application Ser. No. 17/084,180, entitled SURGICAL INSTRUMENT COMPRISING A LIMITED TRAVEL SWITCH;

U.S. Design patent application Ser. No. 29/756,615, Application entitled SURGICAL STAPLING ASSEMBLY;

U.S. Design patent application Ser. No. 29/756,620, entitled SURGICAL STAPLING ASSEMBLY;

U.S. patent application Ser. No. 17/084,188, entitled SURGICAL INSTRUMENT COMPRISING A STAGED VOLTAGE REGULATION START-UP SYSTEM; and U.S. patent application Ser. No. 17/084,193, entitled SURGICAL INSTRUMENT COMPRISING A SENSOR CONFIGURED TO SENSE WHETHER AN ARTICULATION DRIVE OF THE SURGICAL INSTRUMENT IS ACTUATABLE.

Applicant of the present application also owns the following U.S. Patent Applications that were filed on Apr. 11, 2020 and which are each herein incorporated by reference in their respective entireties:

U.S. patent application Ser. No. 16/846,303, entitled METHODS FOR STAPLING TISSUE USING A SURGICAL INSTRUMENT, now U.S. Patent Application Publication No. 2020/0345353;

U.S. patent application Ser. No. 16/846,304, entitled ARTICULATION ACTUATORS FOR A SURGICAL INSTRUMENT, now U.S. Patent Application Publication No. 2020/0345354;

U.S. patent application Ser. No. 16/846,305, entitled ARTICULATION DIRECTIONAL LIGHTS ON A SURGICAL INSTRUMENT, now U.S. Patent Application Publication No. 2020/0345446;

U.S. patent application Ser. No. 16/846,307, entitled SHAFT ROTATION ACTUATOR ON A SURGICAL INSTRUMENT, now U.S. Patent Application Publication No. 2020/03453549;

U.S. patent application Ser. No. 16/846,308, entitled ARTICULATION CONTROL MAPPING FOR A SURGICAL INSTRUMENT, now U.S. Patent Application Publication No. 2020/0345355;

U.S. patent application Ser. No. 16/846,309, entitled INTELLIGENT FIRING ASSOCIATED WITH A SURGICAL INSTRUMENT, now U.S. Patent Application Publication No. 2020/0345356;

U.S. patent application Ser. No. 16/846,310, entitled INTELLIGENT FIRING ASSOCIATED WITH A SURGICAL INSTRUMENT, now U.S. Patent Application Publication No. 2020/0345357;

U.S. patent application Ser. No. 16/846,311, entitled ROTATABLE JAW TIP FOR A SURGICAL INSTRUMENT, now U.S. Patent Application Publication No. 2020/0345358;

U.S. patent application Ser. No. 16/846,312, entitled TISSUE STOP FOR A SURGICAL INSTRUMENT, now U.S. Patent Application Publication No. 2020/0345359; and U.S. patent application Ser. No. 16/846,313, entitled ARTICULATION PIN FOR A SURGICAL INSTRUMENT, now U.S. Patent Application Publication No. 2020/0345360.

The entire disclosure of U.S. Provisional Patent Application Ser. No. 62/840,715, entitled SURGICAL INSTRUMENT COMPRISING AN ADAPTIVE CONTROL SYSTEM, filed Apr. 30, 2019, is hereby incorporated by reference herein.

Applicant of the present application owns the following U.S. Patent Applications that were filed on Feb. 21, 2019 and which are each herein incorporated by reference in their respective entireties:

U.S. patent application Ser. No. 16/281,658, entitled METHODS FOR CONTROLLING A POWERED SURGICAL STAPLER THAT HAS SEPARATE ROTARY CLOSURE AND FIRING SYSTEMS, now U.S. Patent Application Publication No. 2019/0298350;

U.S. patent application Ser. No. 16/281,670, entitled STAPLE CARTRIDGE COMPRISING A LOCKOUT KEY CONFIGURED TO LIFT A FIRING MEMBER, now U.S. Patent Application Publication No. 2019/0298340;

U.S. patent application Ser. No. 16/281,675, entitled SURGICAL STAPLERS WITH ARRANGEMENTS FOR MAINTAINING A FIRING MEMBER THEREOF IN A LOCKED CONFIGURATION UNLESS A COMPATIBLE CARTRIDGE HAS BEEN INSTALLED THEREIN, now U.S. Patent Application Publication No. 2019/0298354;

U.S. patent application Ser. No. 16/281,685, entitled SURGICAL INSTRUMENT COMPRISING CO-OPERATING LOCKOUT FEATURES, now U.S. Patent Application Publication No. 2019/0298341;

U.S. patent application Ser. No. 16/281,693, entitled SURGICAL STAPLING ASSEMBLY COMPRISING A LOCKOUT AND AN EXTERIOR ACCESS ORIFICE TO PERMIT ARTIFICIAL UNLOCKING OF THE LOCKOUT, now U.S. Patent Application Publication No. 2019/0298342;

U.S. patent application Ser. No. 16/281,704, entitled SURGICAL STAPLING DEVICES WITH FEATURES FOR BLOCKING ADVANCEMENT OF A CAMMING ASSEMBLY OF AN INCOMPATIBLE CARTRIDGE INSTALLED THEREIN, now U.S. Patent Application Publication No. 2019/0298356;

U.S. patent application Ser. No. 16/281,707, entitled STAPLING INSTRUMENT COMPRISING A DEACTIVATABLE LOCKOUT, now U.S. Patent Application Publication No. 2019/0298347;

U.S. patent application Ser. No. 16/281,741, entitled SURGICAL INSTRUMENT COMPRISING A JAW CLOSURE LOCKOUT, now U.S. Patent Application Publication No. 2019/0298357;

U.S. patent application Ser. No. 16/281,762, entitled SURGICAL STAPLING DEVICES WITH CARTRIDGE COMPATIBLE CLOSURE AND FIRING LOCKOUT ARRANGEMENTS, now U.S. Patent Application Publication No. 2019/0298343;

U.S. patent application Ser. No. 16/281,666, entitled SURGICAL STAPLING DEVICES WITH IMPROVED ROTARY DRIVEN CLOSURE SYSTEMS, now U.S. Patent Application Publication No. 2019/0298352;

U.S. patent application Ser. No. 16/281,672, entitled SURGICAL STAPLING DEVICES WITH ASYMMETRIC CLOSURE FEATURES, now U.S. Patent Application Publication No. 2019/0298353;

U.S. patent application Ser. No. 16/281,678, entitled ROTARY DRIVEN FIRING MEMBERS WITH DIFFERENT ANVIL AND CHANNEL ENGAGEMENT FEATURES, now U.S. Patent Application Publication No. 2019/0298355; and U.S. patent application Ser. No. 16/281,682, entitled SURGICAL STAPLING DEVICE WITH SEPARATE ROTARY DRIVEN CLOSURE AND FIRING SYSTEMS AND FIRING MEMBER THAT ENGAGES BOTH JAWS WHILE FIRING, now U.S. Patent Application Publication No. 2019/0298346.

Applicant of the present application owns the following U.S. Provisional Patent Applications that were filed on Feb. 19, 2019 and which are each herein incorporated by reference in their respective entireties:

U.S. Provisional Patent Application Ser. No. 62/807,310, entitled METHODS FOR CONTROLLING A POWERED SURGICAL STAPLER THAT HAS SEPARATE ROTARY CLOSURE AND FIRING SYSTEMS;

U.S. Provisional Patent Application Ser. No. 62/807,319, entitled SURGICAL STAPLING DEVICES WITH IMPROVED LOCKOUT SYSTEMS; and U.S. Provisional Patent Application Ser. No. 62/807,309, entitled SURGICAL STAPLING DEVICES WITH IMPROVED ROTARY DRIVEN CLOSURE SYSTEMS.

Applicant of the present application owns the following U.S. Provisional Patent Applications, filed on Mar. 28, 2018, each of which is herein incorporated by reference in its entirety:

U.S. Provisional Patent Application Ser. No. 62/649,302, entitled INTERACTIVE SURGICAL SYSTEMS WITH ENCRYPTED COMMUNICATION CAPABILITIES;

U.S. Provisional Patent Application Ser. No. 62/649,294, entitled DATA STRIPPING METHOD TO INTERROGATE PATIENT RECORDS AND CREATE ANONYMIZED RECORD;

U.S. Provisional Patent Application Ser. No. 62/649,300, entitled SURGICAL HUB SITUATIONAL AWARENESS;

U.S. Provisional Patent Application Ser. No. 62/649,309, entitled SURGICAL HUB SPATIAL AWARENESS TO DETERMINE DEVICES IN OPERATING THEATER;

U.S. Provisional Patent Application Ser. No. 62/649,310, entitled COMPUTER IMPLEMENTED INTERACTIVE SURGICAL SYSTEMS;

U.S. Provisional Patent Application Ser. No. 62/649,291, entitled USE OF LASER LIGHT AND RED-GREEN-BLUE COLORATION TO DETERMINE PROPERTIES OF BACK SCATTERED LIGHT;

U.S. Provisional Patent Application Ser. No. 62/649,296, entitled ADAPTIVE CONTROL PROGRAM UPDATES FOR SURGICAL DEVICES;

U.S. Provisional Patent Application Ser. No. 62/649,333, entitled CLOUD-BASED MEDICAL ANALYTICS FOR CUSTOMIZATION AND RECOMMENDATIONS TO A USER;

U.S. Provisional Patent Application Ser. No. 62/649,327, entitled CLOUD-BASED MEDICAL ANALYTICS FOR SECURITY AND AUTHENTICATION TRENDS AND REACTIVE MEASURES;

U.S. Provisional Patent Application Ser. No. 62/649,315, entitled DATA HANDLING AND PRIORITIZATION IN A CLOUD ANALYTICS NETWORK;

U.S. Provisional Patent Application Ser. No. 62/649,313, entitled CLOUD INTERFACE FOR COUPLED SURGICAL DEVICES;

U.S. Provisional Patent Application Ser. No. 62/649,320, entitled DRIVE ARRANGEMENTS FOR ROBOT-ASSISTED SURGICAL PLATFORMS;

U.S. Provisional Patent Application Ser. No. 62/649,307, entitled AUTOMATIC TOOL ADJUSTMENTS FOR ROBOT-ASSISTED SURGICAL PLATFORMS; and U.S. Provisional Patent Application Ser. No. 62/649,323, entitled SENSING ARRANGEMENTS FOR ROBOT-ASSISTED SURGICAL PLATFORMS.

Applicant of the present application owns the following U.S. Provisional Patent Application, filed on Mar. 30, 2018, which is herein incorporated by reference in its entirety:

U.S. Provisional Patent Application Ser. No. 62/650,887, entitled SURGICAL SYSTEMS WITH OPTIMIZED SENSING CAPABILITIES.

Applicant of the present application owns the following U.S. Patent Application, filed on Dec. 4, 2018, which is herein incorporated by reference in its entirety:

U.S. patent application Ser. No. 16/209,423, entitled METHOD OF COMPRESSING TISSUE WITHIN A STAPLING DEVICE AND SIMULTANEOUSLY DISPLAYING THE LOCATION OF THE TISSUE WITHIN THE JAWS, now U.S. Patent Application Publication No. 2019/0200981.

Applicant of the present application owns the following U.S. Patent Applications that were filed on Aug. 20, 2018 and which are each herein incorporated by reference in their respective entireties:

- U.S. patent application Ser. No. 16/105,101, entitled METHOD FOR FABRICATING SURGICAL STAPLER ANVILS, now U.S. Patent Application Publication No. 2020/0054323;
- U.S. patent application Ser. No. 16/105,183, entitled REINFORCED DEFORMABLE ANVIL TIP FOR SURGICAL STAPLER ANVIL, now U.S. Pat. No. 10,912,559;
- U.S. patent application Ser. No. 16/105,150, entitled SURGICAL STAPLER ANVILS WITH STAPLE DIRECTING PROTRUSIONS AND TISSUE STABILITY FEATURES, now U.S. Patent Application Publication No. 2020/0054326;
- U.S. patent application Ser. No. 16/105,098, entitled FABRICATING TECHNIQUES FOR SURGICAL STAPLER ANVILS, now U.S. Patent Application Publication No. 2020/0054322;
- U.S. patent application Ser. No. 16/105,140, entitled SURGICAL STAPLER ANVILS WITH TISSUE STOP FEATURES CONFIGURED TO AVOID TISSUE PINCH, now U.S. Pat. No. 10,779,821;
- U.S. patent application Ser. No. 16/105,081, entitled METHOD FOR OPERATING A POWERED ARTICULATABLE SURGICAL INSTRUMENT, now U.S. Patent Application Publication No. 2020/0054320;
- U.S. patent application Ser. No. 16/105,094, entitled SURGICAL INSTRUMENTS WITH PROGRESSIVE JAW CLOSURE ARRANGEMENTS, now U.S. Patent Application Publication No. 2020/0054321;
- U.S. patent application Ser. No. 16/105,097, entitled POWERED SURGICAL INSTRUMENTS WITH CLUTCHING ARRANGEMENTS TO CONVERT LINEAR DRIVE MOTIONS TO ROTARY DRIVE MOTIONS, now U.S. Patent Application Publication No. 2020/0054328;
- U.S. patent application Ser. No. 16/105,104, entitled POWERED ARTICULATABLE SURGICAL INSTRUMENTS WITH CLUTCHING AND LOCKING ARRANGEMENTS FOR LINKING AN ARTICULATION DRIVE SYSTEM TO A FIRING DRIVE SYSTEM, now U.S. Pat. No. 10,842,492;
- U.S. patent application Ser. No. 16/105,119, entitled ARTICULATABLE MOTOR POWERED SURGICAL INSTRUMENTS WITH DEDICATED ARTICULATION MOTOR ARRANGEMENTS, now U.S. Patent Application Publication No. 2020/0054330;
- U.S. patent application Ser. No. 16/105,160, entitled SWITCHING ARRANGEMENTS FOR MOTOR POWERED ARTICULATABLE SURGICAL INSTRUMENTS, now U.S. Pat. No. 10,856,870; and
- U.S. Design patent application Ser. No. 29/660,252, entitled SURGICAL STAPLER ANVILS.

Applicant of the present application owns the following U.S. Patent Applications and U.S. Patents that are each herein incorporated by reference in their respective entireties:

- U.S. patent application Ser. No. 15/386,185, entitled SURGICAL STAPLING INSTRUMENTS AND REPLACEABLE TOOL ASSEMBLIES THEREOF, now U.S. Pat. No. 10,639,035;
- U.S. patent application Ser. No. 15/386,230, entitled ARTICULATABLE SURGICAL STAPLING INSTRUMENTS, now U.S. Patent Application Publication No. 2018/0168649;
- U.S. patent application Ser. No. 15/386,221, entitled LOCKOUT ARRANGEMENTS FOR SURGICAL END EFFECTORS, now U.S. Pat. No. 10,835,247;
- U.S. patent application Ser. No. 15/386,209, entitled SURGICAL END EFFECTORS AND FIRING MEMBERS THEREOF, now U.S. Pat. No. 10,588,632;
- U.S. patent application Ser. No. 15/386,198, entitled LOCKOUT ARRANGEMENTS FOR SURGICAL END EFFECTORS AND REPLACEABLE TOOL ASSEMBLIES, now U.S. Pat. No. 10,610,224;
- U.S. patent application Ser. No. 15/386,240, entitled SURGICAL END EFFECTORS AND ADAPTABLE FIRING MEMBERS THEREFOR, now U.S. Patent Application Publication No. 2018/0168651;
- U.S. patent application Ser. No. 15/385,939, entitled STAPLE CARTRIDGES AND ARRANGEMENTS OF STAPLES AND STAPLE CAVITIES THEREIN, now U.S. Pat. No. 10,835,246;
- U.S. patent application Ser. No. 15/385,941, entitled SURGICAL TOOL ASSEMBLIES WITH CLUTCHING ARRANGEMENTS FOR SHIFTING BETWEEN CLOSURE SYSTEMS WITH CLOSURE STROKE REDUCTION FEATURES AND ARTICULATION AND FIRING SYSTEMS, now U.S. Pat. No. 10,736,629;
- U.S. patent application Ser. No. 15/385,943, entitled SURGICAL STAPLING INSTRUMENTS AND STAPLE-FORMING ANVILS, now U.S. Pat. No. 10,667,811;
- U.S. patent application Ser. No. 15/385,950, entitled SURGICAL TOOL ASSEMBLIES WITH CLOSURE STROKE REDUCTION FEATURES, now U.S. Pat. No. 10,588,630;
- U.S. patent application Ser. No. 15/385,945, entitled STAPLE CARTRIDGES AND ARRANGEMENTS OF STAPLES AND STAPLE CAVITIES THEREIN, now U.S. Pat. No. 10,893,864;
- U.S. patent application Ser. No. 15/385,946, entitled SURGICAL STAPLING INSTRUMENTS AND STAPLE-FORMING ANVILS, now U.S. Patent Application Publication No. 2018/0168633;
- U.S. patent application Ser. No. 15/385,951, entitled SURGICAL INSTRUMENTS WITH JAW OPENING FEATURES FOR INCREASING A JAW OPENING DISTANCE, now U.S. Pat. No. 10,568,626;
- U.S. patent application Ser. No. 15/385,953, entitled METHODS OF STAPLING TISSUE, now U.S. Pat. No. 10,675,026;
- U.S. patent application Ser. No. 15/385,954, entitled FIRING MEMBERS WITH NON-PARALLEL JAW ENGAGEMENT FEATURES FOR SURGICAL END EFFECTORS, now U.S. Pat. No. 10,624,635;
- U.S. patent application Ser. No. 15/385,955, entitled SURGICAL END EFFECTORS WITH EXPANDABLE TISSUE STOP ARRANGEMENTS, now U.S. Pat. No. 10,813,638;
- U.S. patent application Ser. No. 15/385,948, entitled SURGICAL STAPLING INSTRUMENTS AND STAPLE-FORMING ANVILS, now U.S. Patent Application Publication No. 2018/0168584;
- U.S. patent application Ser. No. 15/385,956, entitled SURGICAL INSTRUMENTS WITH POSITIVE JAW OPENING FEATURES, now U.S. Pat. No. 10,588,631;
- U.S. patent application Ser. No. 15/385,958, entitled SURGICAL INSTRUMENTS WITH LOCKOUT ARRANGEMENTS FOR PREVENTING FIRING SYSTEM ACTUATION UNLESS AN UNSPENT STAPLE CARTRIDGE IS PRESENT, now U.S. Pat. No. 10,639,034;

U.S. patent application Ser. No. 15/385,947, entitled STAPLE CARTRIDGES AND ARRANGEMENTS OF STAPLES AND STAPLE CAVITIES THEREIN, now U.S. Pat. No. 10,568,625;

U.S. patent application Ser. No. 15/385,896, entitled METHOD FOR RESETTING A FUSE OF A SURGICAL INSTRUMENT SHAFT, now U.S. Patent Application Publication No. 2018/0168597;

U.S. patent application Ser. No. 15/385,898, entitled STAPLE-FORMING POCKET ARRANGEMENT TO ACCOMMODATE DIFFERENT TYPES OF STAPLES, now U.S. Pat. No. 10,537,325;

U.S. patent application Ser. No. 15/385,899, entitled SURGICAL INSTRUMENT COMPRISING IMPROVED JAW CONTROL, now U.S. Pat. No. 10,758,229;

U.S. patent application Ser. No. 15/385,901, entitled STAPLE CARTRIDGE AND STAPLE CARTRIDGE CHANNEL COMPRISING WINDOWS DEFINED THEREIN, now U.S. Pat. No. 10,667,809;

U.S. patent application Ser. No. 15/385,902, entitled SURGICAL INSTRUMENT COMPRISING A CUTTING MEMBER, now U.S. Pat. No. 10,888,322;

U.S. patent application Ser. No. 15/385,904, entitled STAPLE FIRING MEMBER COMPRISING A MISSING CARTRIDGE AND/OR SPENT CARTRIDGE LOCKOUT, now U.S. Pat. No. 10,881,401;

U.S. patent application Ser. No. 15/385,905, entitled FIRING ASSEMBLY COMPRISING A LOCKOUT, now U.S. Pat. No. 10,695,055;

U.S. patent application Ser. No. 15/385,907, entitled SURGICAL INSTRUMENT SYSTEM COMPRISING AN END EFFECTOR LOCKOUT AND A FIRING ASSEMBLY LOCKOUT, now U.S. Patent Application Publication No. 2018/0168608;

U.S. patent application Ser. No. 15/385,908, entitled FIRING ASSEMBLY COMPRISING A FUSE, now U.S. Patent Application Publication No. 2018/0168609;

U.S. patent application Ser. No. 15/385,909, entitled FIRING ASSEMBLY COMPRISING A MULTIPLE FAILED-STATE FUSE, now U.S. Patent Application Publication No. 2018/0168610;

U.S. patent application Ser. No. 15/385,920, entitled STAPLE-FORMING POCKET ARRANGEMENTS, now U.S. Pat. No. 10,499,914;

U.S. patent application Ser. No. 15/385,913, entitled ANVIL ARRANGEMENTS FOR SURGICAL STAPLERS, now U.S. Patent Application Publication No. 2018/0168614;

U.S. patent application Ser. No. 15/385,914, entitled METHOD OF DEFORMING STAPLES FROM TWO DIFFERENT TYPES OF STAPLE CARTRIDGES WITH THE SAME SURGICAL STAPLING INSTRUMENT, now U.S. Patent Application Publication No. 2018/0168615;

U.S. patent application Ser. No. 15/385,893, entitled BILATERALLY ASYMMETRIC STAPLE-FORMING POCKET PAIRS, now U.S. Pat. No. 10,682,138;

U.S. patent application Ser. No. 15/385,929, entitled CLOSURE MEMBERS WITH CAM SURFACE ARRANGEMENTS FOR SURGICAL INSTRUMENTS WITH SEPARATE AND DISTINCT CLOSURE AND FIRING SYSTEMS, now U.S. Pat. No. 10,667,810;

U.S. patent application Ser. No. 15/385,911, entitled SURGICAL STAPLERS WITH INDEPENDENTLY ACTUATABLE CLOSING AND FIRING SYSTEMS, now U.S. Pat. No. 10,448,950;

U.S. patent application Ser. No. 15/385,927, entitled SURGICAL STAPLING INSTRUMENTS WITH SMART STAPLE CARTRIDGES, now U.S. Patent Application Publication No. 2018/0168625;

U.S. patent application Ser. No. 15/385,917, entitled STAPLE CARTRIDGE COMPRISING STAPLES WITH DIFFERENT CLAMPING BREADTHS, now U.S. Patent Application Publication No. 2018/0168617;

U.S. patent application Ser. No. 15/385,900, entitled STAPLE-FORMING POCKET ARRANGEMENTS COMPRISING PRIMARY SIDEWALLS AND POCKET SIDEWALLS, now U.S. Pat. No. 10,898,186;

U.S. patent application Ser. No. 15/385,931, entitled NO-CARTRIDGE AND SPENT CARTRIDGE LOCKOUT ARRANGEMENTS FOR SURGICAL STAPLERS, now U.S. Patent Application Publication No. 2018/0168627;

U.S. patent application Ser. No. 15/385,915, entitled FIRING MEMBER PIN ANGLE, now U.S. Pat. No. 10,779,823;

U.S. patent application Ser. No. 15/385,897, entitled STAPLE-FORMING POCKET ARRANGEMENTS COMPRISING ZONED FORMING SURFACE GROOVES, now U.S. Patent Application Publication No. 2018/0168598;

U.S. patent application Ser. No. 15/385,922, entitled SURGICAL INSTRUMENT WITH MULTIPLE FAILURE RESPONSE MODES, now U.S. Pat. No. 10,426,471;

U.S. patent application Ser. No. 15/385,924, entitled SURGICAL INSTRUMENT WITH PRIMARY AND SAFETY PROCESSORS, now U.S. Pat. No. 10,758,230;

U.S. patent application Ser. No. 15/385,910, entitled ANVIL HAVING A KNIFE SLOT WIDTH, now U.S. Pat. No. 10,485,543;

U.S. patent application Ser. No. 15/385,903, entitled CLOSURE MEMBER ARRANGEMENTS FOR SURGICAL INSTRUMENTS, now U.S. Pat. No. 10,617,414;

U.S. patent application Ser. No. 15/385,906, entitled FIRING MEMBER PIN CONFIGURATIONS, now U.S. Pat. No. 10,856,868;

U.S. patent application Ser. No. 15/386,188, entitled STEPPED STAPLE CARTRIDGE WITH ASYMMETRICAL STAPLES, now U.S. Pat. No. 10,537,324;

U.S. patent application Ser. No. 15/386,192, entitled STEPPED STAPLE CARTRIDGE WITH TISSUE RETENTION AND GAP SETTING FEATURES, now U.S. Pat. No. 10,687,810;

U.S. patent application Ser. No. 15/386,206, entitled STAPLE CARTRIDGE WITH DEFORMABLE DRIVER RETENTION FEATURES, now U.S. Patent Application Publication No. 2018/0168586;

U.S. patent application Ser. No. 15/386,226, entitled DURABILITY FEATURES FOR END EFFECTORS AND FIRING ASSEMBLIES OF SURGICAL STA- PLING INSTRUMENTS, now U.S. Patent Application Publication No. 2018/0168648;

U.S. patent application Ser. No. 15/386,222, entitled SURGICAL STAPLING INSTRUMENTS HAVING END EFFECTORS WITH POSITIVE OPENING FEATURES, now U.S. Patent Application Publication No. 2018/0168647;

U.S. patent application Ser. No. 15/386,236, entitled CONNECTION PORTIONS FOR DEPOSABLE LOADING UNITS FOR SURGICAL STAPLING INSTRUMENTS, now U.S. Patent Application Publication No. 2018/0168650;

U.S. patent application Ser. No. 15/385,887, entitled METHOD FOR ATTACHING A SHAFT ASSEMBLY TO A SURGICAL INSTRUMENT AND, ALTERNATIVELY, TO A SURGICAL ROBOT, now U.S. Pat. No. 10,835,245;

U.S. patent application Ser. No. 15/385,889, entitled SHAFT ASSEMBLY COMPRISING A MANUALLY-OPERABLE RETRACTION SYSTEM FOR USE WITH A MOTORIZED SURGICAL INSTRUMENT SYSTEM, now U.S. Patent Application Publication No. 2018/0168590;

U.S. patent application Ser. No. 15/385,890, entitled SHAFT ASSEMBLY COMPRISING SEPARATELY ACTUATABLE AND RETRACTABLE SYSTEMS, now U.S. Pat. No. 10,675,025;

U.S. patent application Ser. No. 15/385,891, entitled SHAFT ASSEMBLY COMPRISING A CLUTCH CONFIGURED TO ADAPT THE OUTPUT OF A ROTARY FIRING MEMBER TO TWO DIFFERENT SYSTEMS, now U.S. Patent Application Publication No. 2018/0168592;

U.S. patent application Ser. No. 15/385,892, entitled SURGICAL SYSTEM COMPRISING A FIRING MEMBER ROTATABLE INTO AN ARTICULATION STATE TO ARTICULATE AN END EFFECTOR OF THE SURGICAL SYSTEM, now U.S. Pat. No. 10,918,385;

U.S. patent application Ser. No. 15/385,894, entitled SHAFT ASSEMBLY COMPRISING A LOCKOUT, now U.S. Pat. No. 10,492,785;

U.S. patent application Ser. No. 15/385,895, entitled SHAFT ASSEMBLY COMPRISING FIRST AND SECOND ARTICULATION LOCKOUTS, now U.S. Pat. No. 10,542,982;

U.S. patent application Ser. No. 15/385,916, entitled SURGICAL STAPLING SYSTEMS, now U.S. Patent Application Publication No. 2018/0168575;

U.S. patent application Ser. No. 15/385,918, entitled SURGICAL STAPLING SYSTEMS, now U.S. Patent Application Publication No. 2018/0168618;

U.S. patent application Ser. No. 15/385,919, entitled SURGICAL STAPLING SYSTEMS, now U.S. Patent Application Publication No. 2018/0168619;

U.S. patent application Ser. No. 15/385,921, entitled SURGICAL STAPLE CARTRIDGE WITH MOVABLE CAMMING MEMBER CONFIGURED TO DISENGAGE FIRING MEMBER LOCKOUT FEATURES, now U.S. Pat. No. 10,687,809;

U.S. patent application Ser. No. 15/385,923, entitled SURGICAL STAPLING SYSTEMS, now U.S. Patent Application Publication No. 2018/0168623;

U.S. patent application Ser. No. 15/385,925, entitled JAW ACTUATED LOCK ARRANGEMENTS FOR PREVENTING ADVANCEMENT OF A FIRING MEMBER IN A SURGICAL END EFFECTOR UNLESS AN UNFIRED CARTRIDGE IS INSTALLED IN THE END EFFECTOR, now U.S. Pat. No. 10,517,595;

U.S. patent application Ser. No. 15/385,926, entitled AXIALLY MOVABLE CLOSURE SYSTEM ARRANGEMENTS FOR APPLYING CLOSURE MOTIONS TO JAWS OF SURGICAL INSTRUMENTS, now U.S. Patent Application Publication No. 2018/0168577;

U.S. patent application Ser. No. 15/385,928, entitled PROTECTIVE COVER ARRANGEMENTS FOR A JOINT INTERFACE BETWEEN A MOVABLE JAW AND ACTUATOR SHAFT OF A SURGICAL INSTRUMENT, now U.S. Patent Application Publication No. 2018/0168578;

U.S. patent application Ser. No. 15/385,930, entitled SURGICAL END EFFECTOR WITH TWO SEPARATE COOPERATING OPENING FEATURES FOR OPENING AND CLOSING END EFFECTOR JAWS, now U.S. Patent Application Publication No. 2018/0168579;

U.S. patent application Ser. No. 15/385,932, entitled ARTICULATABLE SURGICAL END EFFECTOR WITH ASYMMETRIC SHAFT ARRANGEMENT, now U.S. Patent Application Publication No. 2018/0168628;

U.S. patent application Ser. No. 15/385,933, entitled ARTICULATABLE SURGICAL INSTRUMENT WITH INDEPENDENT PIVOTABLE LINKAGE DISTAL OF AN ARTICULATION LOCK, now U.S. Pat. No. 10,603,036;

U.S. patent application Ser. No. 15/385,934, entitled ARTICULATION LOCK ARRANGEMENTS FOR LOCKING AN END EFFECTOR IN AN ARTICULATED POSITION IN RESPONSE TO ACTUATION OF A JAW CLOSURE SYSTEM, now U.S. Pat. No. 10,582,928;

U.S. patent application Ser. No. 15/385,935, entitled LATERALLY ACTUATABLE ARTICULATION LOCK ARRANGEMENTS FOR LOCKING AN END EFFECTOR OF A SURGICAL INSTRUMENT IN AN ARTICULATED CONFIGURATION, now U.S. Pat. No. 10,524,789;

U.S. patent application Ser. No. 15/385,936, entitled ARTICULATABLE SURGICAL INSTRUMENTS WITH ARTICULATION STROKE AMPLIFICATION FEATURES, now U.S. Pat. No. 10,517,596;

U.S. patent application Ser. No. 14/318,996, entitled FASTENER CARTRIDGES INCLUDING EXTENSIONS HAVING DIFFERENT CONFIGURATIONS, now U.S. Patent Application Publication No. 2015/0297228;

U.S. patent application Ser. No. 14/319,006, entitled FASTENER CARTRIDGE COMPRISING FASTENER CAVITIES INCLUDING FASTENER CONTROL FEATURES, now U.S. Pat. No. 10,010,324;

U.S. patent application Ser. No. 14/318,991, entitled SURGICAL FASTENER CARTRIDGES WITH DRIVER STABILIZING ARRANGEMENTS, now U.S. Pat. No. 9,833,241;

U.S. patent application Ser. No. 14/319,004, entitled SURGICAL END EFFECTORS WITH FIRING ELEMENT MONITORING ARRANGEMENTS, now U.S. Pat. No. 9,844,369;

U.S. patent application Ser. No. 14/319,008, entitled FASTENER CARTRIDGE COMPRISING NON-UNIFORM FASTENERS, now U.S. Pat. No. 10,299,792;

- U.S. patent application Ser. No. 14/318,997, entitled FASTENER CARTRIDGE COMPRISING DEPLOYABLE TISSUE ENGAGING MEMBERS, now U.S. Pat. No. 10,561,422;
- U.S. patent application Ser. No. 14/319,002, entitled FASTENER CARTRIDGE COMPRISING TISSUE CONTROL FEATURES, now U.S. Pat. No. 9,877,721;
- U.S. patent application Ser. No. 14/319,013, entitled FASTENER CARTRIDGE ASSEMBLIES AND STAPLE RETAINER COVER ARRANGEMENTS, now U.S. Patent Application Publication No. 2015/0297233; and
- U.S. patent application Ser. No. 14/319,016, entitled FASTENER CARTRIDGE INCLUDING A LAYER ATTACHED THERETO, now U.S. Pat. No. 10,470,768.

Applicant of the present application owns the following U.S. Patent Applications that were filed on Jun. 24, 2016 and which are each herein incorporated by reference in their respective entireties:

- U.S. patent application Ser. No. 15/191,775, entitled STAPLE CARTRIDGE COMPRISING WIRE STAPLES AND STAMPED STAPLES, now U.S. Patent Application Publication No. 2017/0367695;
- U.S. patent application Ser. No. 15/191,807, entitled STAPLING SYSTEM FOR USE WITH WIRE STAPLES AND STAMPED STAPLES, now U.S. Pat. No. 10,702,270;
- U.S. patent application Ser. No. 15/191,834, entitled STAMPED STAPLES AND STAPLE CARTRIDGES USING THE SAME, now U.S. Pat. No. 10,542,979;
- U.S. patent application Ser. No. 15/191,788, entitled STAPLE CARTRIDGE COMPRISING OVERDRIVEN STAPLES, now U.S. Pat. No. 10,675,024; and
- U.S. patent application Ser. No. 15/191,818, entitled STAPLE CARTRIDGE COMPRISING OFFSET LONGITUDINAL STAPLE ROWS, now U.S. Pat. No. 10,893,863.

Applicant of the present application owns the following U.S. Patent Applications that were filed on Jun. 24, 2016 and which are each herein incorporated by reference in their respective entireties:

- U.S. Design Patent Application Ser. No. 29/569,218, entitled SURGICAL FASTENER, now U.S. Design Pat. No. D826,405;
- U.S. Design Patent Application Ser. No. 29/569,227, entitled SURGICAL FASTENER, now U.S. Design Pat. No. D822,206;
- U.S. Design Patent Application Ser. No. 29/569,259, entitled SURGICAL FASTENER CARTRIDGE, now U.S. Design Pat. No. D847,989; and
- U.S. Design Patent Application Ser. No. 29/569,264, entitled SURGICAL FASTENER CARTRIDGE, now U.S. Design Pat. No. D850,617.

Applicant of the present application owns the following patent applications that were filed on Apr. 1, 2016 and which are each herein incorporated by reference in their respective entirety:

- U.S. patent application Ser. No. 15/089,325, entitled METHOD FOR OPERATING A SURGICAL STAPLING SYSTEM, now U.S. Patent Application Publication No. 2017/0281171;
- U.S. patent application Ser. No. 15/089,321, entitled MODULAR SURGICAL STAPLING SYSTEM COMPRISING A DISPLAY, now U.S. Pat. No. 10,271,851;
- U.S. patent application Ser. No. 15/089,326, entitled SURGICAL STAPLING SYSTEM COMPRISING A DISPLAY INCLUDING A RE-ORIENTABLE DISPLAY FIELD, now U.S. Pat. No. 10,433,849;
- U.S. patent application Ser. No. 15/089,263, entitled SURGICAL INSTRUMENT HANDLE ASSEMBLY WITH RECONFIGURABLE GRIP PORTION, now U.S. Pat. No. 10,307,159;
- U.S. patent application Ser. No. 15/089,262, entitled ROTARY POWERED SURGICAL INSTRUMENT WITH MANUALLY ACTUATABLE BAILOUT SYSTEM, now U.S. Pat. No. 10,357,246;
- U.S. patent application Ser. No. 15/089,277, entitled SURGICAL CUTTING AND STAPLING END EFFECTOR WITH ANVIL CONCENTRIC DRIVE MEMBER, now U.S. Pat. No. 10,531,874;
- U.S. patent application Ser. No. 15/089,296, entitled INTERCHANGEABLE SURGICAL TOOL ASSEMBLY WITH A SURGICAL END EFFECTOR THAT IS SELECTIVELY ROTATABLE ABOUT A SHAFT AXIS, now U.S. Pat. No. 10,413,293;
- U.S. patent application Ser. No. 15/089,258, entitled SURGICAL STAPLING SYSTEM COMPRISING A SHIFTABLE TRANSMISSION, now U.S. Pat. No. 10,342,543;
- U.S. patent application Ser. No. 15/089,278, entitled SURGICAL STAPLING SYSTEM CONFIGURED TO PROVIDE SELECTIVE CUTTING OF TISSUE, now U.S. Pat. No. 10,420,552;
- U.S. patent application Ser. No. 15/089,284, entitled SURGICAL STAPLING SYSTEM COMPRISING A CONTOURABLE SHAFT, now U.S. Patent Application Publication No. 2017/0281186;
- U.S. patent application Ser. No. 15/089,295, entitled SURGICAL STAPLING SYSTEM COMPRISING A TISSUE COMPRESSION LOCKOUT, now U.S. Pat. No. 10,856,867;
- U.S. patent application Ser. No. 15/089,300, entitled SURGICAL STAPLING SYSTEM COMPRISING AN UNCLAMPING LOCKOUT, now U.S. Pat. No. 10,456,140;
- U.S. patent application Ser. No. 15/089,196, entitled SURGICAL STAPLING SYSTEM COMPRISING A JAW CLOSURE LOCKOUT, now U.S. Pat. No. 10,568,632;
- U.S. patent application Ser. No. 15/089,203, entitled SURGICAL STAPLING SYSTEM COMPRISING A JAW ATTACHMENT LOCKOUT, now U.S. Pat. No. 10,542,991;
- U.S. patent application Ser. No. 15/089,210, entitled SURGICAL STAPLING SYSTEM COMPRISING A SPENT CARTRIDGE LOCKOUT, now U.S. Pat. No. 10,478,190;
- U.S. patent application Ser. No. 15/089,324, entitled SURGICAL INSTRUMENT COMPRISING A SHIFTING MECHANISM, now U.S. Pat. No. 10,314,582;
- U.S. patent application Ser. No. 15/089,335, entitled SURGICAL STAPLING INSTRUMENT COMPRISING MULTIPLE LOCKOUTS, now U.S. Pat. No. 10,485,542;
- U.S. patent application Ser. No. 15/089,339, entitled SURGICAL STAPLING INSTRUMENT, now U.S. Patent Application Publication No. 2017/0281173;
- U.S. patent application Ser. No. 15/089,253, entitled SURGICAL STAPLING SYSTEM CONFIGURED TO APPLY ANNULAR ROWS OF STAPLES HAVING DIFFERENT HEIGHTS, now U.S. Pat. No. 10,413,297;

U.S. patent application Ser. No. 15/089,304, entitled SURGICAL STAPLING SYSTEM COMPRISING A GROOVED FORMING POCKET, now U.S. Pat. No. 10,285,705;

U.S. patent application Ser. No. 15/089,331, entitled ANVIL MODIFICATION MEMBERS FOR SURGICAL STAPLERS, now U.S. Pat. No. 10,376,263;

U.S. patent application Ser. No. 15/089,336, entitled STAPLE CARTRIDGES WITH ATRAUMATIC FEATURES, now U.S. Pat. No. 10,709,446;

U.S. patent application Ser. No. 15/089,312, entitled CIRCULAR STAPLING SYSTEM COMPRISING AN INCISABLE TISSUE SUPPORT, now U.S. Patent Application Publication No. 2017/0281189;

U.S. patent application Ser. No. 15/089,309, entitled CIRCULAR STAPLING SYSTEM COMPRISING ROTARY FIRING SYSTEM, now U.S. Pat. No. 10,675,021; and U.S. patent application Ser. No. 15/089,349, entitled CIRCULAR STAPLING SYSTEM COMPRISING LOAD CONTROL, now U.S. Pat. No. 10,682,136.

Applicant of the present application also owns the U.S. Patent Applications identified below which were filed on Dec. 30, 2015 which are each herein incorporated by reference in their respective entirety:

U.S. patent application Ser. No. 14/984,488, entitled MECHANISMS FOR COMPENSATING FOR BATTERY PACK FAILURE IN POWERED SURGICAL INSTRUMENTS, now U.S. Pat. No. 10,292,704;

U.S. patent application Ser. No. 14/984,525, entitled MECHANISMS FOR COMPENSATING FOR DRIVETRAIN FAILURE IN POWERED SURGICAL INSTRUMENTS, now U.S. Pat. No. 10,368,865; and U.S. patent application Ser. No. 14/984,552, entitled SURGICAL INSTRUMENTS WITH SEPARABLE MOTORS AND MOTOR CONTROL CIRCUITS, now U.S. Pat. No. 10,265,068.

Applicant of the present application also owns the U.S. Patent Applications identified below which were filed on Feb. 9, 2016, which are each herein incorporated by reference in their respective entirety:

U.S. patent application Ser. No. 15/019,220, entitled SURGICAL INSTRUMENT WITH ARTICULATING AND AXIALLY TRANSLATABLE END EFFECTOR, now U.S. Pat. No. 10,245,029;

U.S. patent application Ser. No. 15/019,228, entitled SURGICAL INSTRUMENTS WITH MULTIPLE LINK ARTICULATION ARRANGEMENTS, now U.S. Patent No. 10,433,837;

U.S. patent application Ser. No. 15/019,196, entitled SURGICAL INSTRUMENT ARTICULATION MECHANISM WITH SLOTTED SECONDARY CONSTRAINT, now U.S. Pat. No. 10,413,291;

U.S. patent application Ser. No. 15/019,206, entitled SURGICAL INSTRUMENTS WITH AN END EFFECTOR THAT IS HIGHLY ARTICULATABLE RELATIVE TO AN ELONGATE SHAFT ASSEMBLY, now U.S. Pat. No. 10,653,413;

U.S. patent application Ser. No. 15/019,215, entitled SURGICAL INSTRUMENTS WITH NON-SYMMETRICAL ARTICULATION ARRANGEMENTS, now U.S. Patent Application Publication No. 2017/0224332;

U.S. patent application Ser. No. 15/019,227, entitled ARTICULATABLE SURGICAL INSTRUMENTS WITH SINGLE ARTICULATION LINK ARRANGEMENTS, now U.S. Patent Application Publication No. 2017/0224334;

U.S. patent application Ser. No. 15/019,235, entitled SURGICAL INSTRUMENTS WITH TENSIONING ARRANGEMENTS FOR CABLE DRIVEN ARTICULATION SYSTEMS, now U.S. Pat. No. 10,245,030;

U.S. patent application Ser. No. 15/019,230, entitled ARTICULATABLE SURGICAL INSTRUMENTS WITH OFF-AXIS FIRING BEAM ARRANGEMENTS, now U.S. Pat. No. 10,588,625; and U.S. patent application Ser. No. 15/019,245, entitled SURGICAL INSTRUMENTS WITH CLOSURE STROKE REDUCTION ARRANGEMENTS, now U.S. Pat. No. 10,470,764.

Applicant of the present application also owns the U.S. Patent Applications identified below which were filed on Feb. 12, 2016, which are each herein incorporated by reference in their respective entirety:

U.S. patent application Ser. No. 15/043,254, entitled MECHANISMS FOR COMPENSATING FOR DRIVETRAIN FAILURE IN POWERED SURGICAL INSTRUMENTS, now U.S. Pat. No. 10,258,331;

U.S. patent application Ser. No. 15/043,259, entitled MECHANISMS FOR COMPENSATING FOR DRIVETRAIN FAILURE IN POWERED SURGICAL INSTRUMENTS, now U.S. Pat. No. 10,448,948;

U.S. patent application Ser. No. 15/043,275, entitled MECHANISMS FOR COMPENSATING FOR DRIVETRAIN FAILURE IN POWERED SURGICAL INSTRUMENTS, now U.S. Patent Application Publication No. 2017/0231627; and U.S. patent application Ser. No. 15/043,289, entitled MECHANISMS FOR COMPENSATING FOR DRIVETRAIN FAILURE IN POWERED SURGICAL INSTRUMENTS, now U.S. Patent Application Publication No. 2017/0231628.

Applicant of the present application owns the following patent applications that were filed on Jun. 18, 2015 and which are each herein incorporated by reference in their respective entirety:

U.S. patent application Ser. No. 14/742,925, entitled SURGICAL END EFFECTORS WITH POSITIVE JAW OPENING ARRANGEMENTS, now U.S. Pat. No. 10,182,818;

U.S. patent application Ser. No. 14/742,941, entitled SURGICAL END EFFECTORS WITH DUAL CAM ACTUATED JAW CLOSING FEATURES, now U.S. Pat. No. 10,052,102;

U.S. patent application Ser. No. 14/742,933, entitled SURGICAL STAPLING INSTRUMENTS WITH LOCKOUT ARRANGEMENTS FOR PREVENTING FIRING SYSTEM ACTUATION WHEN A CARTRIDGE IS SPENT OR MISSING, now U.S. Pat. No. 10,154,841;

U.S. patent application Ser. No. 14/742,914, entitled MOVABLE FIRING BEAM SUPPORT ARRANGEMENTS FOR ARTICULATABLE SURGICAL INSTRUMENTS, now U.S. Pat. No. 10,405,863;

U.S. patent application Ser. No. 14/742,900, entitled ARTICULATABLE SURGICAL INSTRUMENTS WITH COMPOSITE FIRING BEAM STRUCTURES WITH CENTER FIRING SUPPORT MEMBER FOR ARTICULATION SUPPORT, now U.S. Pat. No. 10,335,149;

U.S. patent application Ser. No. 14/742,885, entitled DUAL ARTICULATION DRIVE SYSTEM ARRANGEMENTS FOR ARTICULATABLE SURGICAL INSTRUMENTS, now U.S. Pat. No. 10,368,861; and U.S. patent application Ser. No. 14/742,876, entitled PUSH/PULL ARTICULATION DRIVE SYSTEMS FOR ARTICULATABLE SURGICAL INSTRUMENTS, now U.S. Pat. No. 10,178,992.

Applicant of the present application owns the following patent applications that were filed on Mar. 6, 2015 and which are each herein incorporated by reference in their respective entirety:

U.S. patent application Ser. No. 14/640,746, entitled POWERED SURGICAL INSTRUMENT, now U.S. Pat. No. 9,808,246;

U.S. patent application Ser. No. 14/640,795, entitled MULTIPLE LEVEL THRESHOLDS TO MODIFY OPERATION OF POWERED SURGICAL INSTRUMENTS, now U.S. Pat. No. 10,441,279;

U.S. patent application Ser. No. 14/640,832, entitled ADAPTIVE TISSUE COMPRESSION TECHNIQUES TO ADJUST CLOSURE RATES FOR MULTIPLE TISSUE TYPES, now U.S. Pat. No. 10,687,806;

U.S. patent application Ser. No. 14/640,935, entitled OVERLAID MULTI SENSOR RADIO FREQUENCY (RF) ELECTRODE SYSTEM TO MEASURE TISSUE COMPRESSION, now U.S. Pat. No. 10,548,504;

U.S. patent application Ser. No. 14/640,831, entitled MONITORING SPEED CONTROL AND PRECISION INCREMENTING OF MOTOR FOR POWERED SURGICAL INSTRUMENTS, now U.S. Pat. No. 9,895,148;

U.S. patent application Ser. No. 14/640,859, entitled TIME DEPENDENT EVALUATION OF SENSOR DATA TO DETERMINE STABILITY, CREEP, AND VISCOELASTIC ELEMENTS OF MEASURES, now U.S. Pat. No. 10,052,044;

U.S. patent application Ser. No. 14/640,817, entitled INTERACTIVE FEEDBACK SYSTEM FOR POWERED SURGICAL INSTRUMENTS, now U.S. Pat. No. 9,924,961;

U.S. patent application Ser. No. 14/640,844, entitled CONTROL TECHNIQUES AND SUB-PROCESSOR CONTAINED WITHIN MODULAR SHAFT WITH SELECT CONTROL PROCESSING FROM HANDLE, now U.S. Pat. No. 10,045,776;

U.S. patent application Ser. No. 14/640,837, entitled SMART SENSORS WITH LOCAL SIGNAL PROCESSING, now U.S. Pat. No. 9,993,248;

U.S. patent application Ser. No. 14/640,765, entitled SYSTEM FOR DETECTING THE MIS-INSERTION OF A STAPLE CARTRIDGE INTO A SURGICAL STAPLER, now U.S. Pat. No. 10,617,412;

U.S. patent application Ser. No. 14/640,799, entitled SIGNAL AND POWER COMMUNICATION SYSTEM POSITIONED ON A ROTATABLE SHAFT, now U.S. Pat. No. 9,901,342; and U.S. patent application Ser. No. 14/640,780, entitled SURGICAL INSTRUMENT COMPRISING A LOCKABLE BATTERY HOUSING, now U.S. Pat. No. 10,245,033.

Applicant of the present application owns the following patent applications that were filed on Feb. 27, 2015, and which are each herein incorporated by reference in their respective entirety:

U.S. patent application Ser. No. 14/633,576, entitled SURGICAL INSTRUMENT SYSTEM COMPRISING AN INSPECTION STATION, now U.S. Pat. No. 10,045,779;

U.S. patent application Ser. No. 14/633,546, entitled SURGICAL APPARATUS CONFIGURED TO ASSESS WHETHER A PERFORMANCE PARAMETER OF THE SURGICAL APPARATUS IS WITHIN AN ACCEPTABLE PERFORMANCE BAND, now U.S. Pat. No. 10,180,463;

U.S. patent application Ser. No. 14/633,560, entitled SURGICAL CHARGING SYSTEM THAT CHARGES AND/OR CONDITIONS ONE OR MORE BATTERIES, now U.S. Patent Application Publication No. 2016/0249910;

U.S. patent application Ser. No. 14/633,566, entitled CHARGING SYSTEM THAT ENABLES EMERGENCY RESOLUTIONS FOR CHARGING A BATTERY, now U.S. Pat. No. 10,182,816;

U.S. patent application Ser. No. 14/633,555, entitled SYSTEM FOR MONITORING WHETHER A SURGICAL INSTRUMENT NEEDS TO BE SERVICED, now U.S. Pat. No. 10,321,907;

U.S. patent application Ser. No. 14/633,542, entitled REINFORCED BATTERY FOR A SURGICAL INSTRUMENT, now U.S. Pat. No. 9,931,118;

U.S. patent application Ser. No. 14/633,548, entitled POWER ADAPTER FOR A SURGICAL INSTRUMENT, now U.S. Pat. No. 10,245,028;

U.S. patent application Ser. No. 14/633,526, entitled ADAPTABLE SURGICAL INSTRUMENT HANDLE, now U.S. Pat. No. 9,993,258;

U.S. patent application Ser. No. 14/633,541, entitled MODULAR STAPLING ASSEMBLY, now U.S. Pat. No. 10,226,250; and U.S. patent application Ser. No. 14/633,562, entitled SURGICAL APPARATUS CONFIGURED TO TRACK AN END-OF-LIFE PARAMETER, now U.S. Pat. No. 10,159,483.

Applicant of the present application owns the following patent applications that were filed on Dec. 18, 2014 and which are each herein incorporated by reference in their respective entirety:

U.S. patent application Ser. No. 14/574,478, entitled SURGICAL INSTRUMENT SYSTEMS COMPRISING AN ARTICULATABLE END EFFECTOR AND MEANS FOR ADJUSTING THE FIRING STROKE OF A FIRING MEMBER, now U.S. Pat. No. 9,844,374;

U.S. patent application Ser. No. 14/574,483, entitled SURGICAL INSTRUMENT ASSEMBLY COMPRISING LOCKABLE SYSTEMS, now U.S. Pat. No. 10,188,385;

U.S. patent application Ser. No. 14/575,139, entitled DRIVE ARRANGEMENTS FOR ARTICULATABLE SURGICAL INSTRUMENTS, now U.S. Pat. No. 9,844,375;

U.S. patent application Ser. No. 14/575,148, entitled LOCKING ARRANGEMENTS FOR DETACHABLE SHAFT ASSEMBLIES WITH ARTICULATABLE SURGICAL END EFFECTORS, now U.S. Pat. No. 10,085,748;

U.S. patent application Ser. No. 14/575,130, entitled SURGICAL INSTRUMENT WITH AN ANVIL THAT IS SELECTIVELY MOVABLE ABOUT A DISCRETE NON-MOVABLE AXIS RELATIVE TO A STAPLE CARTRIDGE, now U.S. Pat. No. 10,245,027;

U.S. patent application Ser. No. 14/575,143, entitled SURGICAL INSTRUMENTS WITH IMPROVED CLOSURE ARRANGEMENTS, now U.S. Pat. No. 10,004,501;

U.S. patent application Ser. No. 14/575,117, entitled SURGICAL INSTRUMENTS WITH ARTICULATABLE END EFFECTORS AND MOVABLE FIRING BEAM SUPPORT ARRANGEMENTS, now U.S. Pat. No. 9,943,309;

U.S. patent application Ser. No. 14/575,154, entitled SURGICAL INSTRUMENTS WITH ARTICULATABLE END EFFECTORS AND IMPROVED FIRING BEAM SUPPORT ARRANGEMENTS, now U.S. Pat. No. 9,968,355;

U.S. patent application Ser. No. 14/574,493, entitled SURGICAL INSTRUMENT ASSEMBLY COMPRISING A FLEXIBLE ARTICULATION SYSTEM, now U.S. Pat. No. 9,987,000; and U.S. patent application Ser. No. 14/574,500, entitled SURGICAL INSTRUMENT ASSEMBLY COMPRISING A LOCKABLE ARTICULATION SYSTEM, now U.S. Pat. No. 10,117,649.

Applicant of the present application owns the following patent applications that were filed on Mar. 1, 2013 and which are each herein incorporated by reference in their respective entirety:

U.S. patent application Ser. No. 13/782,295, entitled ARTICULATABLE SURGICAL INSTRUMENTS WITH CONDUCTIVE PATHWAYS FOR SIGNAL COMMUNICATION, now U.S. Pat. No. 9,700,309;

U.S. patent application Ser. No. 13/782,323, entitled ROTARY POWERED ARTICULATION JOINTS FOR SURGICAL INSTRUMENTS, now U.S. Pat. No. 9,782,169;

U.S. patent application Ser. No. 13/782,338, entitled THUMBWHEEL SWITCH ARRANGEMENTS FOR SURGICAL INSTRUMENTS, now U.S. Patent Application Publication No. 2014/0249557;

U.S. patent application Ser. No. 13/782,499, entitled ELECTROMECHANICAL SURGICAL DEVICE WITH SIGNAL RELAY ARRANGEMENT, now U.S. Pat. No. 9,358,003;

U.S. patent application Ser. No. 13/782,460, entitled MULTIPLE PROCESSOR MOTOR CONTROL FOR MODULAR SURGICAL INSTRUMENTS, now U.S. Pat. No. 9,554,794;

U.S. patent application Ser. No. 13/782,358, entitled JOYSTICK SWITCH ASSEMBLIES FOR SURGICAL INSTRUMENTS, now U.S. Pat. No. 9,326,767;

U.S. patent application Ser. No. 13/782,481, entitled SENSOR STRAIGHTENED END EFFECTOR DURING REMOVAL THROUGH TROCAR, now U.S. Pat. No. 9,468,438;

U.S. patent application Ser. No. 13/782,518, entitled CONTROL METHODS FOR SURGICAL INSTRUMENTS WITH REMOVABLE IMPLEMENT PORTIONS, now U.S. Patent Application Publication No. 2014/0246475;

U.S. patent application Ser. No. 13/782,375, entitled ROTARY POWERED SURGICAL INSTRUMENTS WITH MULTIPLE DEGREES OF FREEDOM, now U.S. Pat. No. 9,398,911; and U.S. patent application Ser. No. 13/782,536, entitled SURGICAL INSTRUMENT SOFT STOP, now U.S. Pat. No. 9,307,986.

Applicant of the present application also owns the following patent applications that were filed on Mar. 14, 2013 and which are each herein incorporated by reference in their respective entirety:

U.S. patent application Ser. No. 13/803,097, entitled ARTICULATABLE SURGICAL INSTRUMENT COMPRISING A FIRING DRIVE, now U.S. Pat. No. 9,687,230;

U.S. patent application Ser. No. 13/803,193, entitled CONTROL ARRANGEMENTS FOR A DRIVE MEMBER OF A SURGICAL INSTRUMENT, now U.S. Pat. No. 9,332,987;

U.S. patent application Ser. No. 13/803,053, entitled INTERCHANGEABLE SHAFT ASSEMBLIES FOR USE WITH A SURGICAL INSTRUMENT, now U.S. Pat. No. 9,883,860;

U.S. patent application Ser. No. 13/803,086, entitled ARTICULATABLE SURGICAL INSTRUMENT COMPRISING AN ARTICULATION LOCK, now U.S. Patent Application Publication No. 2014/0263541;

U.S. patent application Ser. No. 13/803,210, entitled SENSOR ARRANGEMENTS FOR ABSOLUTE POSITIONING SYSTEM FOR SURGICAL INSTRUMENTS, now U.S. Pat. No. 9,808,244;

U.S. patent application Ser. No. 13/803,148, entitled MULTI-FUNCTION MOTOR FOR A SURGICAL INSTRUMENT, now U.S. Pat. No. 10,470,762;

U.S. patent application Ser. No. 13/803,066, entitled DRIVE SYSTEM LOCKOUT ARRANGEMENTS FOR MODULAR SURGICAL INSTRUMENTS, now U.S. Pat. No. 9,629,623;

U.S. patent application Ser. No. 13/803,117, entitled ARTICULATION CONTROL SYSTEM FOR ARTICULATABLE SURGICAL INSTRUMENTS, now U.S. Pat. No. 9,351,726;

U.S. patent application Ser. No. 13/803,130, entitled DRIVE TRAIN CONTROL ARRANGEMENTS FOR MODULAR SURGICAL INSTRUMENTS, now U.S. Pat. No. 9,351,727; and U.S. patent application Ser. No. 13/803,159, entitled METHOD AND SYSTEM FOR OPERATING A SURGICAL INSTRUMENT, now U.S. Pat. No. 9,888,919.

Applicant of the present application also owns the following patent application that was filed on Mar. 7, 2014 and is herein incorporated by reference in its entirety:

U.S. patent application Ser. No. 14/200,111, entitled CONTROL SYSTEMS FOR SURGICAL INSTRUMENTS, now U.S. Pat. No. 9,629,629.

Applicant of the present application also owns the following patent applications that were filed on Mar. 26, 2014 and are each herein incorporated by reference in their respective entirety:

U.S. patent application Ser. No. 14/226,106, entitled POWER MANAGEMENT CONTROL SYSTEMS FOR SURGICAL INSTRUMENTS, now U.S. Patent Application Publication No. 2015/0272582;

U.S. patent application Ser. No. 14/226,099, entitled STERILIZATION VERIFICATION CIRCUIT, now U.S. Pat. No. 9,826,977;

U.S. patent application Ser. No. 14/226,094, entitled VERIFICATION OF NUMBER OF BATTERY EXCHANGES/PROCEDURE COUNT, now U.S. Patent Application Publication No. 2015/0272580;

U.S. patent application Ser. No. 14/226,117, entitled POWER MANAGEMENT THROUGH SLEEP OPTIONS OF SEGMENTED CIRCUIT AND WAKE UP CONTROL, now U.S. Pat. No. 10,013,049;
- U.S. patent application Ser. No. 14/226,075, entitled MODULAR POWERED SURGICAL INSTRUMENT WITH DETACHABLE SHAFT ASSEMBLIES, now U.S. Pat. No. 9,743,929;
- U.S. patent application Ser. No. 14/226,093, entitled FEEDBACK ALGORITHMS FOR MANUAL BAIL-OUT SYSTEMS FOR SURGICAL INSTRUMENTS, now U.S. Pat. No. 10,028,761;
- U.S. patent application Ser. No. 14/226,116, entitled SURGICAL INSTRUMENT UTILIZING SENSOR ADAPTATION, now U.S. Patent Application Publication No. 2015/0272571;
- U.S. patent application Ser. No. 14/226,071, entitled SURGICAL INSTRUMENT CONTROL CIRCUIT HAVING A SAFETY PROCESSOR, now U.S. Pat. No. 9,690,362;
- U.S. patent application Ser. No. 14/226,097, entitled SURGICAL INSTRUMENT COMPRISING INTERACTIVE SYSTEMS, now U.S. Pat. No. 9,820,738;
- U.S. patent application Ser. No. 14/226,126, entitled INTERFACE SYSTEMS FOR USE WITH SURGICAL INSTRUMENTS, now U.S. Pat. No. 10,004,497;
- U.S. patent application Ser. No. 14/226,133, entitled MODULAR SURGICAL INSTRUMENT SYSTEM, now U.S. Patent Application Publication No. 2015/0272557;
- U.S. patent application Ser. No. 14/226,081, entitled SYSTEMS AND METHODS FOR CONTROLLING A SEGMENTED CIRCUIT, now U.S. Pat. No. 9,804,618;
- U.S. patent application Ser. No. 14/226,076, entitled POWER MANAGEMENT THROUGH SEGMENTED CIRCUIT AND VARIABLE VOLTAGE PROTECTION, now U.S. Pat. No. 9,733,663;
- U.S. patent application Ser. No. 14/226,111, entitled SURGICAL STAPLING INSTRUMENT SYSTEM, now U.S. Pat. No. 9,750,499; and
- U.S. patent application Ser. No. 14/226,125, entitled SURGICAL INSTRUMENT COMPRISING A ROTATABLE SHAFT, now U.S. Pat. No. 10,201,364.

Applicant of the present application also owns the following patent applications that were filed on Sep. 5, 2014 and which are each herein incorporated by reference in their respective entirety:
- U.S. patent application Ser. No. 14/479,103, entitled CIRCUITRY AND SENSORS FOR POWERED MEDICAL DEVICE, now U.S. Pat. No. 10,111,679;
- U.S. patent application Ser. No. 14/479,119, entitled ADJUNCT WITH INTEGRATED SENSORS TO QUANTIFY TISSUE COMPRESSION, now U.S. Pat. No. 9,724,094;
- U.S. patent application Ser. No. 14/478,908, entitled MONITORING DEVICE DEGRADATION BASED ON COMPONENT EVALUATION, now U.S. Pat. No. 9,737,301;
- U.S. patent application Ser. No. 14/478,895, entitled MULTIPLE SENSORS WITH ONE SENSOR AFFECTING A SECOND SENSOR'S OUTPUT OR INTERPRETATION, now U.S. Pat. No. 9,757,128;
- U.S. patent application Ser. No. 14/479,110, entitled POLARITY OF HALL MAGNET TO IDENTIFY CARTRIDGE TYPE, now U.S. Pat. No. 10,016,199;
- U.S. patent application Ser. No. 14/479,098, entitled SMART CARTRIDGE WAKE UP OPERATION AND DATA RETENTION, now U.S. Pat. No. 10,135,242;
- U.S. patent application Ser. No. 14/479,115, entitled MULTIPLE MOTOR CONTROL FOR POWERED MEDICAL DEVICE, now U.S. Pat. No. 9,788,836; and U.S. patent application Ser. No. 14/479,108, entitled LOCAL DISPLAY OF TISSUE PARAMETER STABILIZATION, now U.S. Patent Application Publication No. 2016/0066913.

Applicant of the present application also owns the following patent applications that were filed on Apr. 9, 2014 and which are each herein incorporated by reference in their respective entirety:
- U.S. patent application Ser. No. 14/248,590, entitled MOTOR DRIVEN SURGICAL INSTRUMENTS WITH LOCKABLE DUAL DRIVE SHAFTS, now U.S. Pat. No. 9,826,976;
- U.S. patent application Ser. No. 14/248,581, entitled SURGICAL INSTRUMENT COMPRISING A CLOSING DRIVE AND A FIRING DRIVE OPERATED FROM THE SAME ROTATABLE OUTPUT, now U.S. Pat. No. 9,649,110;
- U.S. patent application Ser. No. 14/248,595, entitled SURGICAL SYSTEM COMPRISING FIRST AND SECOND DRIVE SYSTEMS, now U.S. Pat. No. 9,844,368;
- U.S. patent application Ser. No. 14/248,588, entitled POWERED LINEAR SURGICAL STAPLER, now U.S. Pat. No. 10,405,857;
- U.S. patent application Ser. No. 14/248,591, entitled SURGICAL INSTRUMENT COMPRISING A GAP SETTING SYSTEM, now U.S. Pat. No. 10,149,680;
- U.S. patent application Ser. No. 14/248,584, entitled MODULAR MOTOR DRIVEN SURGICAL INSTRUMENTS WITH ALIGNMENT FEATURES FOR ALIGNING ROTARY DRIVE SHAFTS WITH SURGICAL END EFFECTOR SHAFTS, now U.S. Pat. No. 9,801,626;
- U.S. patent application Ser. No. 14/248,587, entitled POWERED SURGICAL STAPLER, now U.S. Pat. No. 9,867,612;
- U.S. patent application Ser. No. 14/248,586, entitled DRIVE SYSTEM DECOUPLING ARRANGEMENT FOR A SURGICAL INSTRUMENT, now U.S. Pat. No. 10,136,887; and
- U.S. patent application Ser. No. 14/248,607, entitled MODULAR MOTOR DRIVEN SURGICAL INSTRUMENTS WITH STATUS INDICATION ARRANGEMENTS, now U.S. Pat. No. 9,814,460.

Applicant of the present application also owns the following patent applications that were filed on Apr. 16, 2013 and which are each herein incorporated by reference in their respective entirety:
- U.S. Provisional Patent Application Ser. No. 61/812,365, entitled SURGICAL INSTRUMENT WITH MULTIPLE FUNCTIONS PERFORMED BY A SINGLE MOTOR;
- U.S. Provisional Patent Application Ser. No. 61/812,376, entitled LINEAR CUTTER WITH POWER;
- U.S. Provisional Patent Application Ser. No. 61/812,382, entitled LINEAR CUTTER WITH MOTOR AND PISTOL GRIP;
- U.S. Provisional Patent Application Ser. No. 61/812,385, entitled SURGICAL INSTRUMENT HANDLE WITH MULTIPLE ACTUATION MOTORS AND MOTOR CONTROL; and U.S. Provisional Patent Application Ser. No. 61/812,372, entitled SURGICAL INSTRUMENT WITH MULTIPLE FUNCTIONS PERFORMED BY A SINGLE MOTOR.

Applicant of the present application owns the following U.S. Provisional Patent Applications, filed on Dec. 28, 2017, the disclosure of each of which is herein incorporated by reference in its entirety:

U.S. Provisional Patent Application Ser. No. 62/611,341, entitled INTERACTIVE SURGICAL PLATFORM;

U.S. Provisional Patent Application Ser. No. 62/611,340, entitled CLOUD-BASED MEDICAL ANALYTICS; and U.S. Provisional Patent Application Ser. No. 62/611,339, entitled ROBOT ASSISTED SURGICAL PLATFORM.

Applicant of the present application owns the following U.S. Provisional Patent Applications, filed on Mar. 28, 2018, each of which is herein incorporated by reference in its entirety:

U.S. Provisional Patent Application Ser. No. 62/649,302, entitled INTERACTIVE SURGICAL SYSTEMS WITH ENCRYPTED COMMUNICATION CAPABILITIES;

U.S. Provisional Patent Application Ser. No. 62/649,294, entitled DATA STRIPPING METHOD TO INTERROGATE PATIENT RECORDS AND CREATE ANONYMIZED RECORD;

U.S. Provisional Patent Application Ser. No. 62/649,300, entitled SURGICAL HUB SITUATIONAL AWARENESS;

U.S. Provisional Patent Application Ser. No. 62/649,309, entitled SURGICAL HUB SPATIAL AWARENESS TO DETERMINE DEVICES IN OPERATING THEATER;

U.S. Provisional Patent Application Ser. No. 62/649,310, entitled COMPUTER IMPLEMENTED INTERACTIVE SURGICAL SYSTEMS;

U.S. Provisional Patent Application Ser. No. 62/649,291, entitled USE OF LASER LIGHT AND RED-GREEN-BLUE COLORATION TO DETERMINE PROPERTIES OF BACK SCATTERED LIGHT;

U.S. Provisional Patent Application Ser. No. 62/649,296, entitled ADAPTIVE CONTROL PROGRAM UPDATES FOR SURGICAL DEVICES;

U.S. Provisional Patent Application Ser. No. 62/649,333, entitled CLOUD-BASED MEDICAL ANALYTICS FOR CUSTOMIZATION AND RECOMMENDATIONS TO A USER;

U.S. Provisional Patent Application Ser. No. 62/649,327, entitled CLOUD-BASED MEDICAL ANALYTICS FOR SECURITY AND AUTHENTICATION TRENDS AND REACTIVE MEASURES;

U.S. Provisional Patent Application Ser. No. 62/649,315, entitled DATA HANDLING AND PRIORITIZATION IN A CLOUD ANALYTICS NETWORK;

U.S. Provisional Patent Application Ser. No. 62/649,313, entitled CLOUD INTERFACE FOR COUPLED SURGICAL DEVICES;

U.S. Provisional Patent Application Ser. No. 62/649,320, entitled DRIVE ARRANGEMENTS FOR ROBOT-ASSISTED SURGICAL PLATFORMS;

U.S. Provisional Patent Application Ser. No. 62/649,307, entitled AUTOMATIC TOOL ADJUSTMENTS FOR ROBOT-ASSISTED SURGICAL PLATFORMS; and U.S. Provisional Patent Application Ser. No. 62/649,323, entitled SENSING ARRANGEMENTS FOR ROBOT-ASSISTED SURGICAL PLATFORMS.

Applicant of the present application owns the following U.S. Patent Applications, filed on Mar. 29, 2018, each of which is herein incorporated by reference in its entirety:

U.S. patent application Ser. No. 15/940,641, entitled INTERACTIVE SURGICAL SYSTEMS WITH ENCRYPTED COMMUNICATION CAPABILITIES, now U.S. Patent Application Publication No. 2019/0207911;

U.S. patent application Ser. No. 15/940,648, entitled INTERACTIVE SURGICAL SYSTEMS WITH CONDITION HANDLING OF DEVICES AND DATA CAPABILITIES, now U.S. Patent Application Publication No. 2019/0206004;

U.S. patent application Ser. No. 15/940,656, entitled SURGICAL HUB COORDINATION OF CONTROL AND COMMUNICATION OF OPERATING ROOM DEVICES, now U.S. Patent Application Publication No. 2019/0201141;

U.S. patent application Ser. No. 15/940,666, entitled SPATIAL AWARENESS OF SURGICAL HUBS IN OPERATING ROOMS, now U.S. Patent Application Publication No. 2019/0206551;

U.S. patent application Ser. No. 15/940,670, entitled COOPERATIVE UTILIZATION OF DATA DERIVED FROM SECONDARY SOURCES BY INTELLIGENT SURGICAL HUBS, now U.S. Patent Application Publication No. 2019/0201116;

U.S. patent application Ser. No. 15/940,677, entitled SURGICAL HUB CONTROL ARRANGEMENTS, now U.S. Patent Application Publication No. 2019/0201143;

U.S. patent application Ser. No. 15/940,632, entitled DATA STRIPPING METHOD TO INTERROGATE PATIENT RECORDS AND CREATE ANONYMIZED RECORD, now U.S. Patent Application Publication No. 2019/0205566;

U.S. patent application Ser. No. 15/940,640, entitled COMMUNICATION HUB AND STORAGE DEVICE FOR STORING PARAMETERS AND STATUS OF A SURGICAL DEVICE TO BE SHARED WITH CLOUD BASED ANALYTICS SYSTEMS, now U.S. Patent Application Publication No. 2019/0200863;

U.S. patent application Ser. No. 15/940,645, entitled SELF DESCRIBING DATA PACKETS GENERATED AT AN ISSUING INSTRUMENT, now U.S. Pat. No. 10,892,899;

U.S. patent application Ser. No. 15/940,649, entitled DATA PAIRING TO INTERCONNECT A DEVICE MEASURED PARAMETER WITH AN OUTCOME, now U.S. Patent Application Publication No. 2019/0205567;

U.S. patent application Ser. No. 15/940,654, entitled SURGICAL HUB SITUATIONAL AWARENESS, now U.S. Patent Application Publication No. 2019/0201140;

U.S. patent application Ser. No. 15/940,663, entitled SURGICAL SYSTEM DISTRIBUTED PROCESSING, now U.S. Patent Application Publication No. 2019/0201033;

U.S. patent application Ser. No. 15/940,668, entitled AGGREGATION AND REPORTING OF SURGICAL HUB DATA, now U.S. Patent Application Publication No. 2019/0201115;

U.S. patent application Ser. No. 15/940,671, entitled SURGICAL HUB SPATIAL AWARENESS TO DETERMINE DEVICES IN OPERATING THEATER, now U.S. Patent Application Publication No. 2019/0201104;

U.S. patent application Ser. No. 15/940,686, entitled DISPLAY OF ALIGNMENT OF STAPLE CARTRIDGE TO PRIOR LINEAR STAPLE LINE, now U.S. Patent Application Publication No. 2019/0201105;

U.S. patent application Ser. No. 15/940,700, entitled STERILE FIELD INTERACTIVE CONTROL DISPLAYS, now U.S. Patent Application Publication No. 2019/0205001;

U.S. patent application Ser. No. 15/940,629, entitled COMPUTER IMPLEMENTED INTERACTIVE SURGICAL SYSTEMS, now U.S. Patent Application Publication No. 2019/0201112;

U.S. patent application Ser. No. 15/940,704, entitled USE OF LASER LIGHT AND RED-GREEN-BLUE COLORATION TO DETERMINE PROPERTIES OF BACK SCATTERED LIGHT, now U.S. Patent Application Publication No. 2019/0206050;

U.S. patent application Ser. No. 15/940,722, entitled CHARACTERIZATION OF TISSUE IRREGULARITIES THROUGH THE USE OF MONO-CHROMATIC LIGHT REFRACTIVITY, now U.S. Patent Application Publication No. 2019/0200905; and U.S. patent application Ser. No. 15/940,742, entitled DUAL CMOS ARRAY IMAGING, now U.S. Patent Application Publication No. 2019/0200906.

Applicant of the present application owns the following U.S. Patent Applications, filed on Mar. 29, 2018, each of which is herein incorporated by reference in its entirety:

U.S. patent application Ser. No. 15/940,636, entitled ADAPTIVE CONTROL PROGRAM UPDATES FOR SURGICAL DEVICES, now U.S. Patent Application Publication No. 2019/0206003;

U.S. patent application Ser. No. 15/940,653, entitled ADAPTIVE CONTROL PROGRAM UPDATES FOR SURGICAL HUBS, now U.S. Patent Application Publication No. 2019/0201114;

U.S. patent application Ser. No. 15/940,660, entitled CLOUD-BASED MEDICAL ANALYTICS FOR CUSTOMIZATION AND RECOMMENDATIONS TO A USER, now U.S. Patent Application Publication No. 2019/0206555;

U.S. patent application Ser. No. 15/940,679, entitled CLOUD-BASED MEDICAL ANALYTICS FOR LINKING OF LOCAL USAGE TRENDS WITH THE RESOURCE ACQUISITION BEHAVIORS OF LARGER DATA SET, now U.S. Patent Application Publication No. 2019/0201144;

U.S. patent application Ser. No. 15/940,694, entitled CLOUD-BASED MEDICAL ANALYTICS FOR MEDICAL FACILITY SEGMENTED INDIVIDUALIZATION OF INSTRUMENT FUNCTION, now U.S. Patent Application Publication No. 2019/0201119;

U.S. patent application Ser. No. 15/940,634, entitled CLOUD-BASED MEDICAL ANALYTICS FOR SECURITY AND AUTHENTICATION TRENDS AND REACTIVE MEASURES, now U.S. Patent Application Publication No. 2019/0201138;

U.S. patent application Ser. No. 15/940,706, entitled DATA HANDLING AND PRIORITIZATION IN A CLOUD ANALYTICS NETWORK, now U.S. Patent Application Publication No. 2019/0206561; and U.S. patent application Ser. No. 15/940,675, entitled CLOUD INTERFACE FOR COUPLED SURGICAL DEVICES, now U.S. Pat. No. 10,849,697.

Applicant of the present application owns the following U.S. Patent Applications, filed on Mar. 29, 2018, each of which is herein incorporated by reference in its entirety:

U.S. patent application Ser. No. 15/940,627, entitled DRIVE ARRANGEMENTS FOR ROBOT-ASSISTED SURGICAL PLATFORMS, now U.S. Patent Application Publication No. 2019/0201111;

U.S. patent application Ser. No. 15/940,637, entitled COMMUNICATION ARRANGEMENTS FOR ROBOT-ASSISTED SURGICAL PLATFORMS, now U.S. Patent Application Publication No. 2019/0201139;

U.S. patent application Ser. No. 15/940,642, entitled CONTROLS FOR ROBOT-ASSISTED SURGICAL PLATFORMS, now U.S. Patent Application Publication No. 2019/0201113;

U.S. patent application Ser. No. 15/940,676, entitled AUTOMATIC TOOL ADJUSTMENTS FOR ROBOT-ASSISTED SURGICAL PLATFORMS, now U.S. Patent Application Publication No. 2019/0201142;

U.S. patent application Ser. No. 15/940,680, entitled CONTROLLERS FOR ROBOT-ASSISTED SURGICAL PLATFORMS, now U.S. Patent Application Publication No. 2019/0201135;

U.S. patent application Ser. No. 15/940,683, entitled COOPERATIVE SURGICAL ACTIONS FOR ROBOT-ASSISTED SURGICAL PLATFORMS, now U.S. Patent Application Publication No. 2019/0201145;

U.S. patent application Ser. No. 15/940,690, entitled DISPLAY ARRANGEMENTS FOR ROBOT-ASSISTED SURGICAL PLATFORMS, now U.S. Patent Application Publication No. 2019/0201118; and U.S. patent application Ser. No. 15/940,711, entitled SENSING ARRANGEMENTS FOR ROBOT-ASSISTED SURGICAL PLATFORMS, now U.S. Patent Application Publication No. 2019/0201120.

Numerous specific details are set forth to provide a thorough understanding of the overall structure, function, manufacture, and use of the embodiments as described in the specification and illustrated in the accompanying drawings. Well-known operations, components, and elements have not been described in detail so as not to obscure the embodiments described in the specification. The reader will understand that the embodiments described and illustrated herein are non-limiting examples, and thus it can be appreciated that the specific structural and functional details disclosed herein may be representative and illustrative. Variations and changes thereto may be made without departing from the scope of the claims.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a surgical system, device, or apparatus that "comprises," "has," "includes" or "contains" one or more elements possesses those one or more elements, but is not limited to possessing only those one or more elements. Likewise, an element of a system, device, or apparatus that "comprises," "has," "includes" or "contains" one or more features possesses those one or more features, but is not limited to possessing only those one or more features.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the reader will readily appreciate that the various methods and devices disclosed herein can be used in numerous surgical procedures and applications including, for example, in connection with open surgical procedures. As the present Detailed Description proceeds, the reader will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongate shaft of a surgical instrument can be advanced.

A surgical stapling system can comprise a shaft and an end effector extending from the shaft. The end effector comprises a first jaw and a second jaw. The first jaw comprises a staple cartridge. The staple cartridge is insertable into and removable from the first jaw; however, other embodiments are envisioned in which a staple cartridge is not removable from, or at least readily replaceable from, the first jaw. The second jaw comprises an anvil configured to deform staples ejected from the staple cartridge. The second jaw is pivotable relative to the first jaw about a closure axis; however, other embodiments are envisioned in which the first jaw is pivotable relative to the second jaw. The surgical stapling system further comprises an articulation joint configured to permit the end effector to be rotated, or articulated, relative to the shaft. The end effector is rotatable about an articulation axis extending through the articulation joint. Other embodiments are envisioned which do not include an articulation joint.

The staple cartridge comprises a cartridge body. The cartridge body includes a proximal end, a distal end, and a deck extending between the proximal end and the distal end. In use, the staple cartridge is positioned on a first side of the tissue to be stapled and the anvil is positioned on a second side of the tissue. The anvil is moved toward the staple cartridge to compress and clamp the tissue against the deck. Thereafter, staples removably stored in the cartridge body can be deployed into the tissue. The cartridge body includes staple cavities defined therein wherein staples are removably stored in the staple cavities. The staple cavities are arranged in six longitudinal rows. Three rows of staple cavities are positioned on a first side of a longitudinal slot and three rows of staple cavities are positioned on a second side of the longitudinal slot. Other arrangements of staple cavities and staples may be possible.

The staples are supported by staple drivers in the cartridge body. The drivers are movable between a first, or unfired position, and a second, or fired, position to eject the staples from the staple cavities. The drivers are retained in the cartridge body by a retainer which extends around the bottom of the cartridge body and includes resilient members configured to grip the cartridge body and hold the retainer to the cartridge body. The drivers are movable between their unfired positions and their fired positions by a sled. The sled is movable between a proximal position adjacent the proximal end and a distal position adjacent the distal end. The sled comprises a plurality of ramped surfaces configured to slide under the drivers and lift the drivers, and the staples supported thereon, toward the anvil.

Further to the above, the sled is moved distally by a firing member. The firing member is configured to contact the sled and push the sled toward the distal end. The longitudinal slot defined in the cartridge body is configured to receive the firing member. The anvil also includes a slot configured to receive the firing member. The firing member further comprises a first cam which engages the first jaw and a second cam which engages the second jaw. As the firing member is advanced distally, the first cam and the second cam can control the distance, or tissue gap, between the deck of the staple cartridge and the anvil. The firing member also comprises a knife configured to incise the tissue captured intermediate the staple cartridge and the anvil. It is desirable for the knife to be positioned at least partially proximal to the ramped surfaces such that the staples are ejected ahead of the knife.

Various staples disclosed herein comprise a flat-formed staple which can be cut and/or stamped from a sheet of material, for example. The sheet of material can be metallic and can comprise stainless steel and/or titanium, for example. In at least one instance, outlines can be traced, etched, and/or cut into the sheet of material which are machined and/or laser cut to form the staples into a manufactured shape. The staples comprise a pair of staple legs and a staple base portion, or crown, from which the staple legs extend. Each staple leg comprises a staple tip, or piercing portion, which is configured to pierce the tissue and contact a corresponding forming pocket of the anvil of the surgical stapling instrument. The staple legs are configured to be deformed to assume a formed configuration to fasten the tissue. The staple legs define a plane which is laterally offset from but at least substantially parallel to a plane defined by the base of the staple. Embodiments are envisioned where the first and second planes are not parallel.

A stamped staple 100 is depicted in FIGS. 1-4. The staple 100 comprises a proximal staple leg 110, a distal staple leg 120, and a staple base portion 130. The staple 100 further comprises vertical transition portions, or bends, 118, 128 and lateral transition portions, or bends, 116, 126. The vertical transition portions 118, 128 bend, or extend, the legs 110, 120 vertically, or upward, from the staple base portion 130. The lateral transition portions 116, 126 extend the staple legs 110, 120 laterally outward, or at least substantially perpendicularly with respect to the staple base portion 130. The staple legs 110, 120 define a first plane and the staple base portion 130 defines a second plane. Together, the vertical transition portions 118, 128 and the lateral transition portions 116, 126 permit the staple legs 110, 120 to be laterally offset and parallel with respect to the staple base portion 130. Stated another way, the first plane is offset from and at least substantially parallel to the second plane. In FIGS. 1-4, the first plane is offset in a negative Y direction, which is orthogonal to a vertical Z direction. Other staples may be used in conjunction with a plurality of staples 100 where the other staples comprise a first plane which is offset in the positive Y direction. The use of both types of staples permits staple rows to be nested, or interwoven, where staple legs of neighboring rows may be at least substantially aligned and/or share a common longitudinal axis. In various instances, the staple rows can be nested to provide denser staple rows.

Further to the above, the proximal staple leg 110 comprises a generally rectangular cross-section including flat surfaces and corners. The corners of the cross-section comprise bevels, radiuses, and/or coined edges 114 which reduce the exposure of sharp edges to the patient tissue. That said, the proximal staple leg 110 comprises a sharp tip 112 configured to incise the patient tissue. Similarly, the distal staple leg 120 comprises a generally rectangular cross-section including flat surfaces 125 and corners 124 which are beveled, radiused, and/or coined to reduce the exposure of sharp edges to the patient tissue. Like the proximal leg 110, the distal staple leg 120 comprises a sharp tip 122 configured to incise the patient tissue.

The staple base 130 comprises an upper portion 136 configured to contact and support patient tissue. The upper portion 136 of the staple base 130 comprises tissue contacting surfaces 137, 138, and 139 and edges 134 which are beveled, radiused, and/or coined to reduce the exposure of the sharp edges to the patient tissue. The staple base 130 further comprises a lower portion 135 which includes a drive cam 132 configured to be directly engaged by a sled. The lower portion 135 further comprises a bottom edge 131 which rides over the apex of a sled rail and a distal shoulder 133 which loses contact with the sled rail as the sled moves distally.

Further to the above, the legs 110 and 120 of the staple 100 extend in a first plane and the drive cam 132 of the staple 100 is defined in a second plane. The second plane is parallel to, or at least substantially parallel to, the first plane. When the legs 110 and 120 are deformed, the legs 110 and 120 capture patient tissue within the staple 100 outside of the second plane. Among other things, such an arrangement allows a larger volume of tissue to be captured within the staple 100 as compared to wire staples that are defined in a single plane. That said, such wire staples are desirable in many instances and, in some instances, can be used in conjunction with stamped staples.

Figure 5:
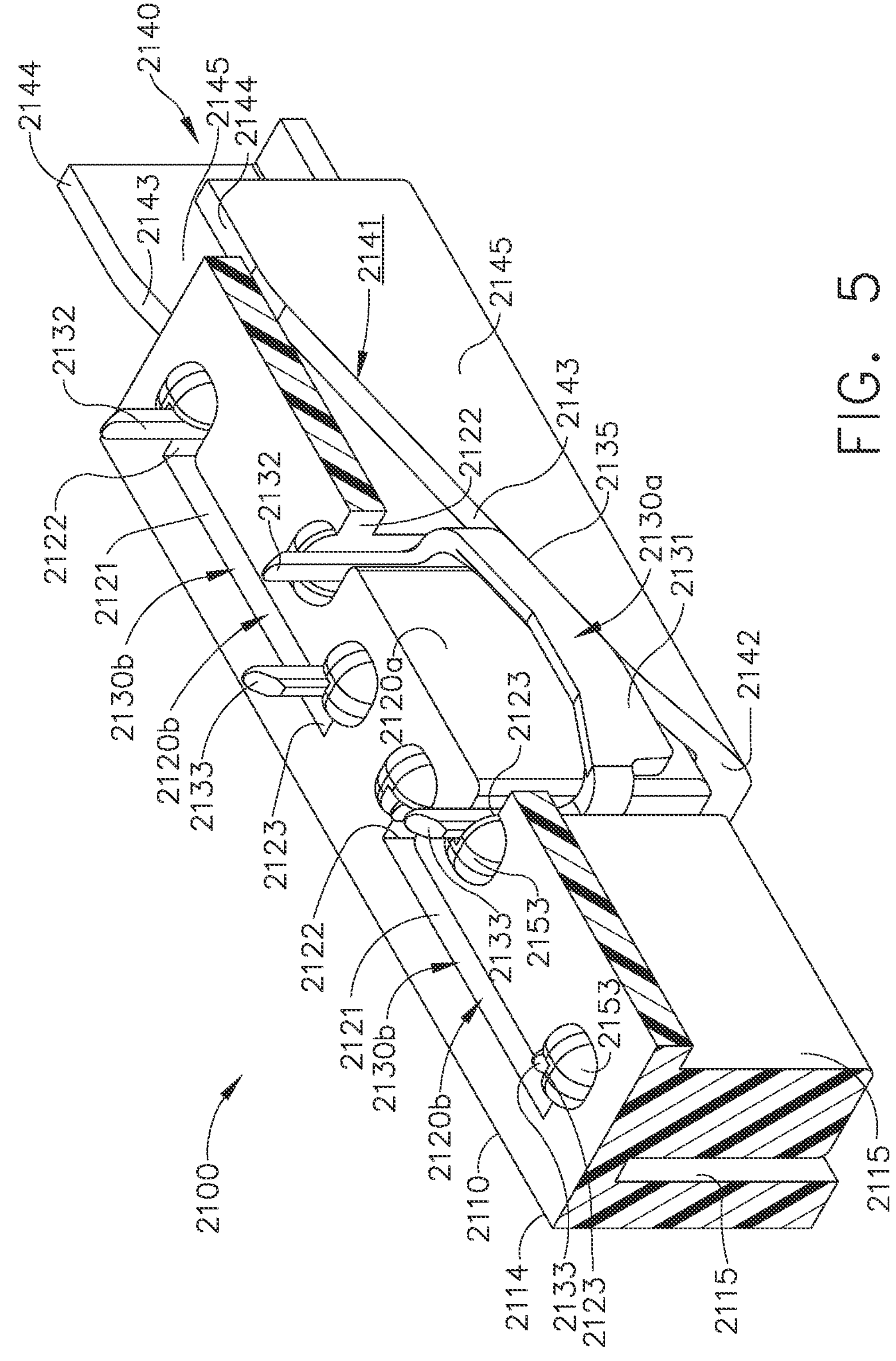
FIG. 5 is a partial cross-sectional perspective view of a staple cartridge assembly illustrating staples being ejected from the staple cartridge assembly by a firing member.

A staple cartridge 2100 is illustrated in FIG. 5 comprising a cartridge body 2110. The cartridge body 2110 comprises a deck 2114, a plurality of staple cavities 2120*a*, and a plurality of staple cavities 2120*b*. The staple cavities 2120*a* are similar to the staple cavities 2120*b* in many respects. For instance, the staple cavities 2120*a* and 2120*b* both comprise a central slot 2121 having a proximal end and a distal end, a proximal staple leg guide 2122 extending laterally from the proximal end of the central slot 2121, and a distal staple leg guide 2123 extending laterally from the distal end of the central slot 2121. That said, the staple cavities 2120*a* and the staple cavities 2120*b* are oriented in different directions. More particularly, the staple leg guides 2122, 2123 of the staple cavities 2120*a* extend toward the staple cavities 2120*b* and, similarly, the staple leg guides 2122, 2123 of the staple cavities 2120*b* extend toward the staple cavities 2120*a*; however, any suitable arrangement can be utilized.

A staple 2130*a*, which is similar to staple 100 in many respects, is positioned in each staple cavity 2120*a* and a staple 2130*b*, which is also similar to staple 100 in many respects, is positioned in each staple cavity 2120*b*. Moreover, the staples 2130*a* and the staples 2130*b* are similar to one another in many respects. For instance, each staple 2130*a* comprises a base, or crown, 2131, a proximal leg 2132 extending from a proximal end of the base 2131, and a distal leg 2133 extending from a distal end of the base 2131. That said, the staples 2130*a*, 2130*b* are adapted in a manner to fit within the staple cavities 2120*a*, 2120*b*, respectively. For example, when the staples 2130*a* are positioned in the staple cavities 2120*a* and the staples 2130*b* are positioned in the staple cavities 2120*b*, the legs 2132, 2133 of the staples 2130*a* extend toward the staples 2130*b* and the legs 2132, 2133 of the staples 2130*b* extend toward the staples 2130*a*; however, other arrangements are possible.

The staples 2130 are driven from unfired positions to fired positions by a firing member, such as sled 2140, for example. The sled 2140 comprises wedges 2145 which are configured to directly engage the staples 2130 and lift the staples 2130 toward an anvil, such as anvil 2190, for example. The sled 2140 comprises a wedge, or rail, 2145 for each longitudinal row of staples 2130; however, the sled 2140 may have any suitable number of wedges 2145. Each wedge 2145 comprises an angled drive surface 2141 which slides under the staples 2130 as the sled 2140 is advanced from the proximal end of the staple cartridge 2100 toward the distal end of the staple cartridge 2100. The base 2131 of each staple 2130 comprises an angled drive surface 2135 which is directly contacted by a drive surface 2141. Stated another way, each staple 2130 comprises its own integrally-formed driver having a drive surface 2135. The staples 2130 are comprised of metal and, as a result, the integrally-formed driver is also comprised of metal. That said, the staples disclosed herein can be comprised of any suitable material. Additional details can be found in U.S. Patent Application Ser. No. 14/836,411, which issued on Jul. 23, 2019 as U.S. Pat. No. 10,357,251, which is hereby incorporated by reference in its entirety herein.

Figure 6:
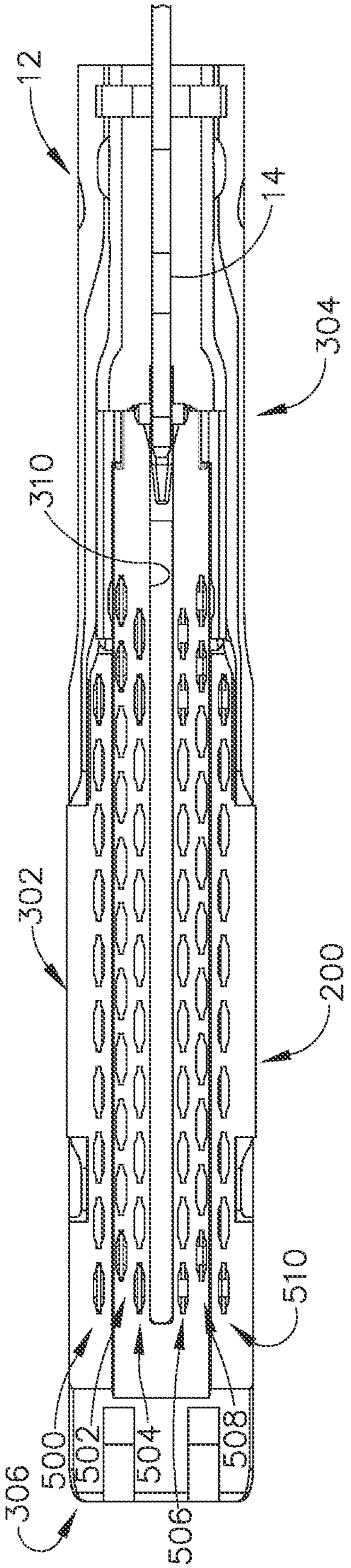
FIG. 6 depicts a plan view of a staple cartridge installed in an end effector.
Figure 7:
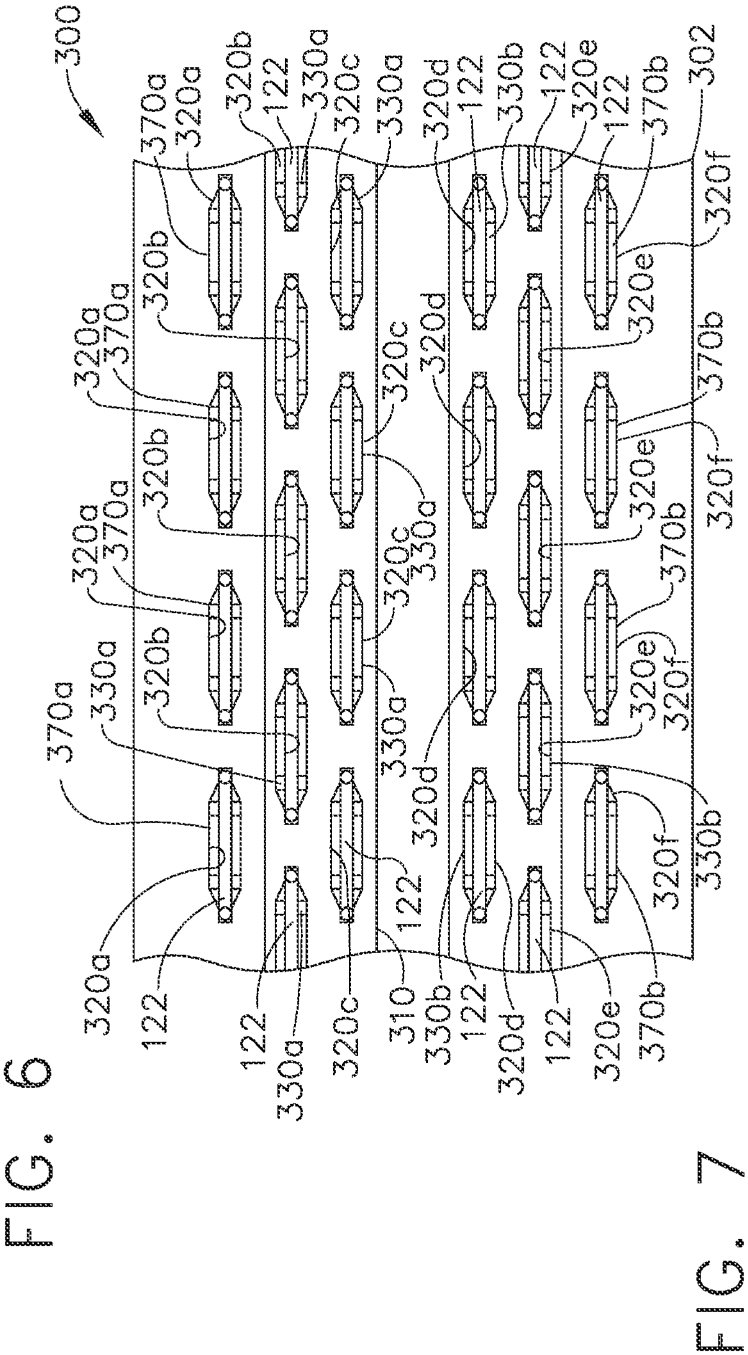
FIG. 7 is an enlarged plan view of a portion of a staple cartridge.
Figure 8:
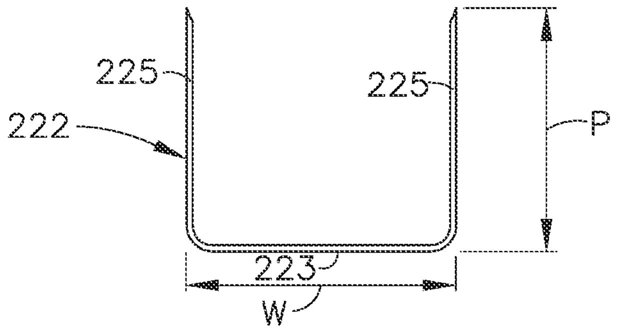
FIG. 8 is a side view of a wire staple.

FIG. 6 depicts a staple cartridge 300 that includes staple cavities 320*a*-320*f* formed within a cartridge body 302 that are arranged in six laterally-spaced longitudinal rows 500, 502, 504, 506, 508, 510, with three rows on each side of an elongated slot 310 defined in the cartridge body 302. A staple 222, seen in FIG. 8, is positioned in each staple cavity 320*a*-320*f*. The staple cartridge 300 further includes four laterally-spaced longitudinal rows of staple drivers 330*a*, 330*b*, 370*a*, and 370*b*, as shown in FIG. 7. The inside staple drivers 330*a* are slideably mounted within corresponding staple cavities 320*b* and 320*c* such that each driver 330*a* supports two staples 222—one in a staple cavity 320*b* and one in a staple cavity 320*c*. Likewise, the inside drivers 330*b* are slideably mounted within staple cavities 320*d* and 320*e* such that each driver 330*b* supports two staples 222—one in a staple cavity 320*d* and one in a staple cavity 320*e*. The outside drivers 370*a* and 370*b* are slideably mounted within the staple cavities 320*a* and 320*f*, respectively. Each of the outside drivers 370*a* and 370*b* supports a single staple 222.

Figure 9:
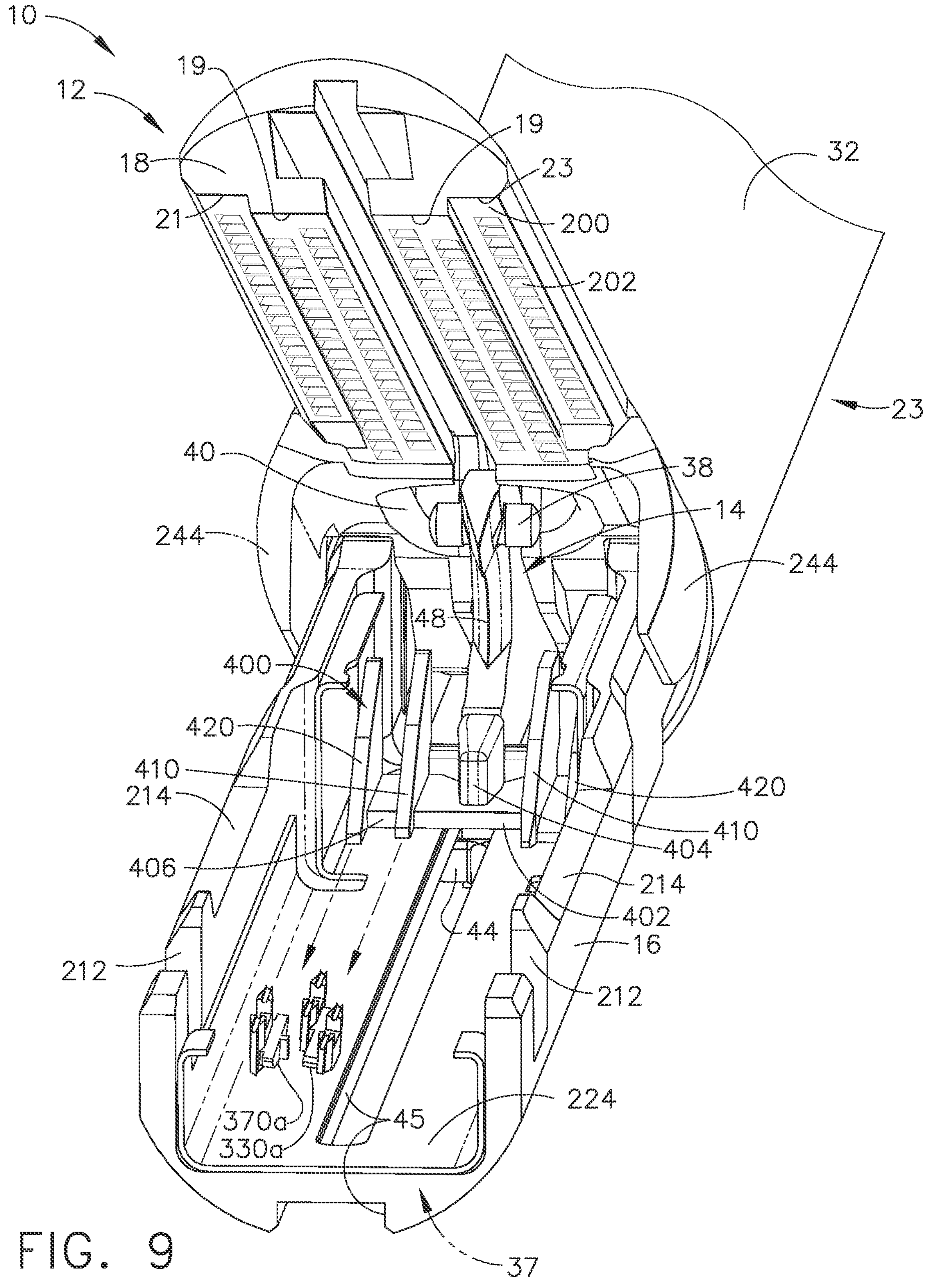
FIG. 9 is an isometric view of an end effector of a surgical stapling instrument comprising an anvil illustrated in an open position.

With particular reference to FIG. 9, a portion of the staple cartridge 300 is removed to expose portions of the elongate channel 16, such as recesses 212, 214 and to expose some components of the staple cartridge 300 in their unfired positions. In particular, the cartridge body 302 has been removed. A wedge sled 400 is shown in its proximal, unfired position and is in longitudinal sliding contact upon a cartridge tray, or pan, 224 of the staple cartridge 300. The wedge sled 400 includes wedges sled cams 410, 420 that force upward the double drivers 330*a*, 330*b* and the single drivers 370*b*, 370*b* as the wedge sled 400 moves distally. Staples 222 (not shown in FIG. 9) resting upon the drivers 330*a*, 330*b*, 370*a*, 370*b* are thus also forced upward into contact with anvil forming pockets 202 defined in an anvil 18 to form closed staples. Additional details can be found in U.S. Patent Application Ser. No. 11/216,562, which issued on Mar. 2, 2010 as U.S. Pat. No. 7,669,746, the entire disclosure of which is hereby incorporated by reference in its entirety.

Figure 10:
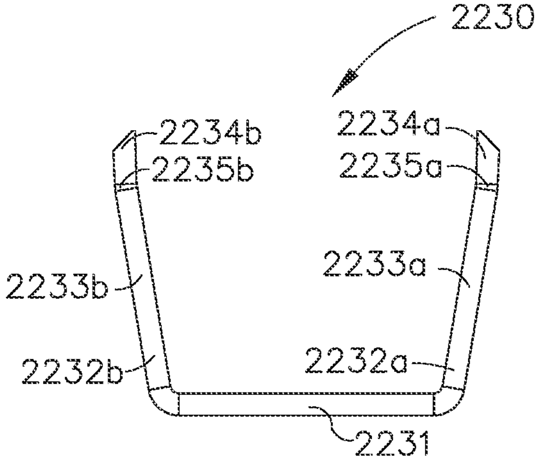
FIG. 10 is an elevational view of a staple.

A staple 2230 is illustrated in FIG. 10. The staple 2230 comprises a base 2231, a first leg 2232*a* extending from the base 2231, and a second leg 2232*b* extending from the base 2231. The first leg 2232*a* comprises a first portion 2233*a* connected to the base 2231 and a second portion 2234*a* extending from the first portion 2233*a*. The second leg 2232*b* comprises a first portion 2233*b* connected to the base 2231 and a second portion 2234*b* extending from the first portion 2233*b*. The base 2231, the first portion 2233*a*, and the first portion 2233*b* can comprise a generally V-shaped configuration, for example. In various instances, the second portion 2234*a* extends inwardly from the first portion 2233*a* at a joint 2235*a* and, similarly, the second portion 2234*b* extends inwardly from the first portion 2233*b* at a joint 2235*b*. The base 2231, the first leg 2232*a*, and the second leg 2232*b* can be configured and arranged such that the staple 2230 is symmetrical in its unformed, or unfired, configuration illustrated in FIG. 10. In various instances, the first leg 2232*a* is positioned distally with respect to the second leg 2232*b*. Alternatively, the first leg 2232*a* is positioned proximally with respect to the second leg 2232*b*.

Figure 11:
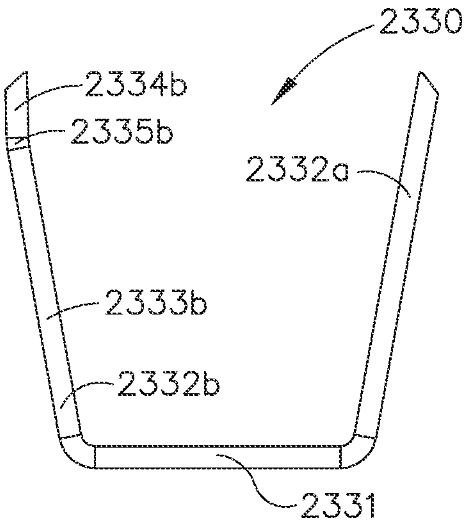
FIG. 11 is an elevational view of an asymmetrical staple.

A staple 2330 is illustrated in FIG. 11. The staple 2330 comprises a base 2331, a first leg 2332*a* extending from the base 2331, and a second leg 2332*b* extending from the base 2331. The first leg 2332*a* comprises a straight portion 2333 a connected to the base 2331 which extends along an axis. The second leg 2332*b* comprises a first portion 2333*b* connected to the base 2331 and a second portion 2334*b* extending from the first portion 2333*b*. The base 2331, the straight portion 2333*a*, and the first portion 2333*b* comprise a generally V-shaped configuration, for example. In various instances, the second portion 2334*b* extends inwardly from the first portion 2333*b* at a joint 2335*b*. The base 2331, the first leg 2332*a*, and the second leg 2332*b* can be configured and arranged such that the staple 2330 is asymmetrical in its unformed, or unfired, configuration illustrated in FIG. 11. In various instances, the first leg 2332*a* is positioned distally with respect to the second leg 2332*b*. Alternatively, the first leg 2332*a* is positioned proximally with respect to the second leg 2332*b*.

Figure 12:
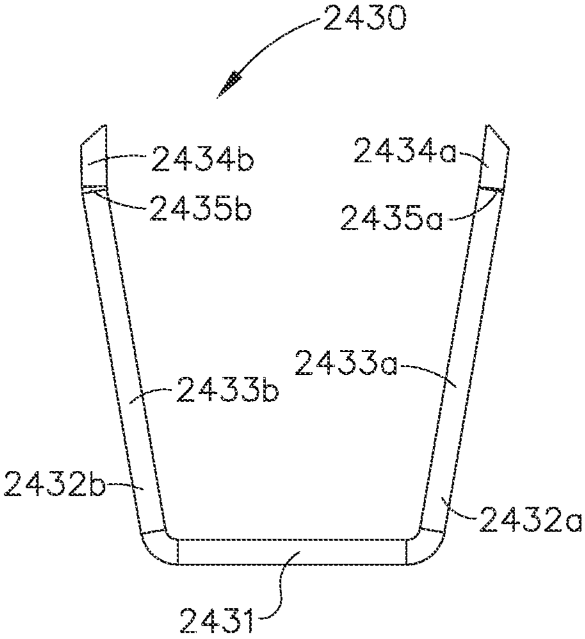
FIG. 12 is an elevational view of another asymmetrical staple.

A staple 2430 is illustrated in FIG. 12. The staple 2430 comprises a base 2431, a first leg 2432*a* extending from the base 2431, and a second leg 2432*b* extending from the base 2431. The first leg 2432*a* comprises a first portion 2433*a* connected to the base 2431 and a second portion 2434*a* extending from the first portion 2433*a*. The second leg 2432*b* comprises a first portion 2433*b* connected to the base 2431 and a second portion 2434*b* extending from the first portion 2433*b*. The base 2431, the first portion 2433*a*, and the first portion 2433*b* comprise a generally V-shaped configuration, for example. In various instances, the second portion 2434*a* extends inwardly from the first portion 2433*a* at a first angle at a joint 2435*a* and, similarly, the second portion 2434*b* extends inwardly from the first portion 2433*b* at a second angle at a joint 2435*b*. The first angle and the second angle can be different. The base 2431, the first leg 2432*a*, and the second leg 2432*b* can be configured and arranged such that the staple 2430 is asymmetrical in its unformed, or unfired, configuration illustrated in FIG. 12. In various instances, the first leg 2432*a* is positioned distally with respect to the second leg 2432*b*. Alternatively, the first leg 2432*a* is positioned proximally with respect to the second leg 2432*b*.

Figure 13:
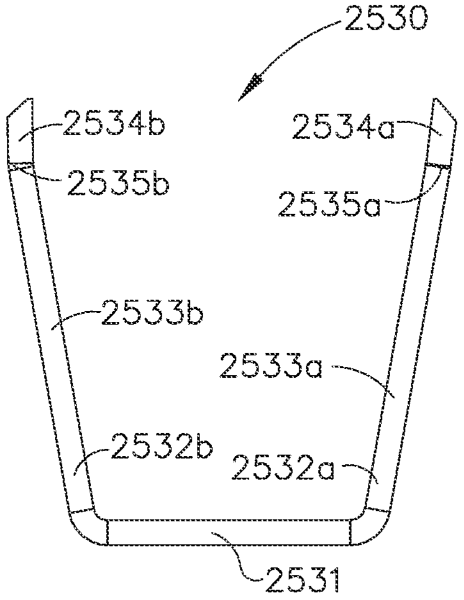
FIG. 13 is an elevational view of another asymmetrical staple.

A staple 2530 is illustrated in FIG. 13. The staple 2530 comprises a base 2531, a first leg 2532*a* extending from the base 2531, and a second leg 2532*b* extending from the base 2531. The first leg 2532*a* comprises a first portion 2533*a* connected to the base 2531 and a second portion 2534*a* extending from the first portion 2533*a*. The second leg 2532*b* comprises a first portion 2533*b* connected to the base 2531 and a second portion 2534*b* extending from the first portion 2533*b*. The base 2531, the first portion 2533*a*, and the first portion 2533*b* comprise a generally V-shaped configuration, for example. In various instances, the second portion 2534*a* extends inwardly from the first portion 2533*a* at a first angle at a joint 2535*a* and, similarly, the second portion 2534*b* extends inwardly from the first portion 2533*b* at a second angle at a joint 2535*b*. The first angle and the second angle can be different. The base 2531, the first leg 2532*a*, and the second leg 2532*b* are configured and arranged such that the staple 2530 is asymmetrical in its unformed, or unfired, configuration illustrated in FIG. 13. The staple 2530 can be similar to the staple 2430 in many respects and, in at least one instance, can include a wider base 2531 than the base 2431, for example. In certain instances, a wider staple base can be accommodated within a given staple cavity when the staple leg 2532*a* and/or the staple leg 2532*b* extend in directions which are closer to the vertical direction. In various instances, the first leg 2532*a* is positioned distally with respect to the second leg 2532*b*. Alternatively, the first leg 2532*a* is positioned proximally with respect to the second leg 2532*b*. Additional details can be found in U.S. patent application Ser. No. 14/318,996, which published on Oct. 22, 2015 as U.S. Patent Application Publication No. 2015/0297228, the entire disclosure of which is hereby incorporated by reference in its entirety.

Figure 14:
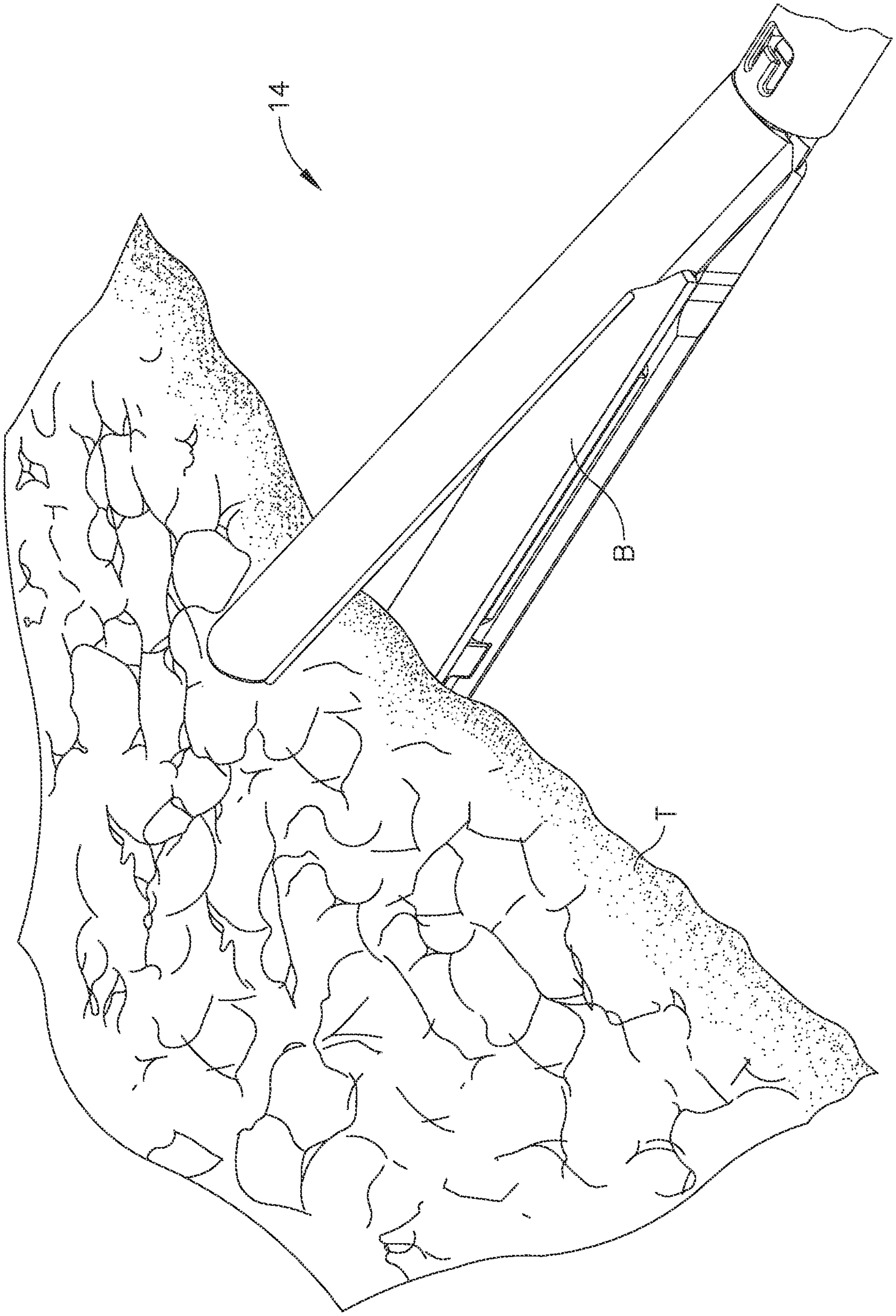
FIG. 14 is a perspective view of an end effector assembly configured to engage, cut, staple, and apply a piece of buttress material to tissue.
Figure 15:
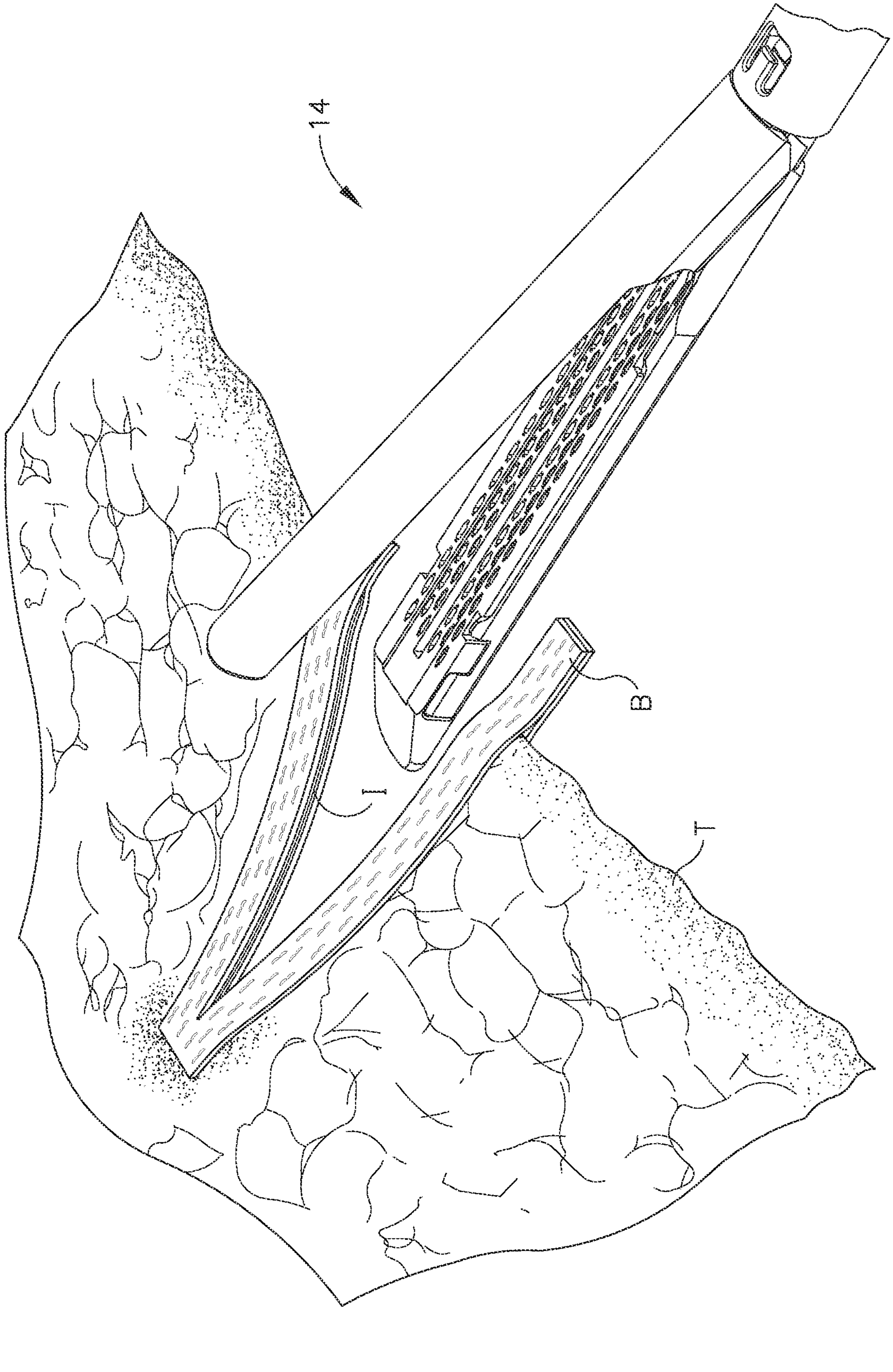
FIG. 15 is a perspective view of the end effector assembly of FIG. 14 after the end effector has been utilized to engage, cut, staple, and apply the piece of buttress material to the tissue.

In various embodiments, referring to FIGS. 14 and 15, an end effector of a surgical instrument can include at least one implantable adjunct, such as a piece of buttress material "B", releasably attached thereto. In at least one embodiment, the end effector is configured to engage and clamp tissue "T", deploy staples into the tissue, and cut the tissue and the piece of buttress material. In such an embodiment, the end effector can then be removed from the tissue leaving the staples and the piece of buttress material attached to the tissue on both sides of an incision "I". Additional details regarding the buttress material "B" can be found in U.S. Patent Application Ser. No. 12/032,002, which issued on Feb. 12, 2013 as U.S. Pat. No. 8,371,491, the entire disclosure of which is hereby incorporated by reference in its entirety.

The staples of a staple cartridge can be comprised of any suitable material to provide a desired biocorrosion time-frame of the staples. In many instances, it may be desirable that this amount of time be within a year of the surgical procedure and, in some instances, within 6 months. In other instances, it may be desirable that this amount of time be about 3-4 months and/or any other suitable amount of time. In various embodiments, the staples can be comprised of magnesium, iron, zinc, and/or alloys thereof, for example. In addition to or in lieu of the above, the staples of a staple cartridge can comprise a coating, coatings, and/or an at least partial coating which can increase and/or otherwise control the rate in which the staples bioabsorb after being implanted in the patient tissue. In various embodiments, a staple cartridge can comprise an implantable adjunct, or layer, which is implanted against the patient tissue by the staples which increases and/or otherwise controls the rate in which the implanted staples bioabsorb.

In various embodiments, as described above, the staples of a staple cartridge are comprised of a metal material that biocorrodes, or degrades, after being implanted in patient tissue owing to the bioabsorption of the staples. As also described above, it is desirable for the staples to degrade within a specific time frame. For instance, it is desirable that the staples retain a sufficient amount of strength while the tissue heals such that the staples do not release the tissue prior to the tissue being sufficiently healed. In many instances, the tissue healing window is about 30 days, depending on the type of tissue such as lung tissue, colon tissue, and/or stomach tissue, for example. Moreover, it is desirable for the staples to release the tissue after the tissue heals such that the tissue regains its flexibility, or at least a substantial portion of its flexibility, after being stapled. Thus, as a result, the tissue healing window is a factor that can be used to define both ends of the desired biocorrosion time frame.

Further to the above, many metal materials have an intrinsic biocorrosion rate. As discussed in greater detail below, this biocorrosion rate can be affected by the presence of other metals and/or impurities within the base metal material. The biocorrosion rate of magnesium, for example, can vary over orders of magnitude owing to the presence of other metals within the magnesium. Therefore, a base metal can be alloyed to tune the degradation properties of the base metal and control the biocorrosion time frame of the staples. As described in greater detail below, magnesium, for example, can be alloyed with lithium, zinc, iron, tin, aluminum, silver, zirconium, strontium, and/or calcium, for example, to tune the degradation rate of the magnesium. In other instances, magnesium can be alloyed into other metals, such as zinc, for example, to tune the degradation rate of the zinc.

In various instances, the electrode potential of pure magnesium, or high-purity magnesium (HP—Mg), can be reduced by the introduction of one or more other elements to increase the degradation rate of the magnesium. In at least one instance, the presence of another element within magnesium can create a duplex microstructure which establishes microgalvanic cells within the alloy. The presence of these other elements can create secondary phases within the magnesium which act as cathodes and accelerate the anodic dissolution, or biocorrosion, of the magnesium. For instance, microgalvanic corrosion can be employed by alloying magnesium with iron. Iron at >170 ppm within high-purity magnesium, for example, greatly increases the corrosion rate of the magnesium as compared to high-purity magnesium. As a result, small additions of iron into magnesium alloys and/or pure magnesium can be used to tune the degradation properties of magnesium-based absorbable staples owing to the galvanic effect created by the secondary iron phase within the primary magnesium phase. In at least one embodiment, a staple can be comprised of a Mg—Al—Fe alloy, for example. In at least one such embodiment, the aluminum is between 3-8 wt % and the iron is between 5-7 wt %. In at least one embodiment, a staple is comprised of magnesium-iron alloy, such as Mg-0.1Fe and/or Mg-0.5Fe, for example. In at least one embodiment, the staples of a staple cartridge are comprised of a magnesium-iron alloy including 1 wt % or less iron. In at least one embodiment, the staples of a staple cartridge are comprised of a magnesium-iron alloy including 1 wt % iron. In at least one embodiment, the staples of a staple cartridge are comprised of a magnesium-iron alloy including 0.5 wt % iron. In at least one embodiment, the staples of a staple cartridge are comprised of a magnesium-iron alloy including 0.1 wt % iron. In some embodiments, annealing the magnesium-iron alloy can increase the presence of iron precipitates within the magnesium and, therefore, increase the degradation rate of the staples. Moreover, annealing can be used to control the grain size within the magnesium-iron staple alloy which, as a result, can control the corrosion rate of the staples.

In various embodiments, microgalvanic corrosion can be employed by alloying magnesium with lithium. In certain embodiments, lithium-containing magnesium alloys can comprise a duplex structure of α-Mg and β-Li phases which establishes galvanic cells. In at least one embodiment, the staples of a staple cartridge are comprised of a magnesium-lithium alloy containing lithium between 1 wt % and 11 wt %, for example. In at least one embodiment, the staples of a staple cartridge are comprised of Mg-9Li. In at least one embodiment, the staples of a staple cartridge are comprised of a magnesium-lithium alloy containing lithium between 8 wt % and 14 wt % for example. Lithium-containing magnesium alloys with greater than 11 wt % lithium may comprise excellent mechanical properties; however, such alloys sometimes corrode slower than magnesium-lithium alloys comprising less than 6 wt % lithium, which may be due to pH effects. In at least one embodiment, the staples of a staple cartridge are comprised of a magnesium-lithium alloy comprised of 2 wt % lithium. That said, an alloy can be selected to satisfy many parameters including, but not limited to, the degradation rate, ductility, and creep-resistance of the staple. Moreover, alloying magnesium with lithium can lower the electrode potential of the alloy in addition to creating microgalvanic corrosion within the staples. In at least one embodiment, the staples of a staple cartridge are comprised of a magnesium-lithium alloy including aluminum, such as Mg-14Li-1Al, for example. In at least one embodiment, the staples of a staple cartridge are comprised of LA141 alloy, for example.

In various embodiments, microgalvanic corrosion can be employed by alloying magnesium with zinc. In various embodiments, the zinc within magnesium alloys containing above 6.5 wt % zinc provide an accelerating effect on corrosion. That said, magnesium alloys containing below 6.5 wt % zinc, such as 3 wt % zinc, for example, can have a desirable degradation rate. In at least one embodiment, a staple is comprised of a magnesium alloy containing between 6 wt % and 10 wt % zinc, such as Mg-6Zn, for example. In at least one embodiment, a staple is comprised of a magnesium alloy containing between 5 wt % and 15 wt % zinc, such as Mg-14Zn, for example. In at least one embodiment, a staple is comprised of a magnesium-zinc-zirconium alloy, such as Mg-6Zn-0.1Zr and/or Mg-3Zn-0.6Zr, for example. In at least one such embodiment, zirconium is added to magnesium-zinc alloy at 1 wt % or less for grain refinement which, in various instances, can increase the degradation rate of the magnesium-zinc alloy. In at least one embodiment, the staples of a staple cartridge are comprised of ZK30 alloy, for example. The addition of zirconium can also increase the resistivity of the magnesium alloy which can have various other benefits, discussed further below. In at least one embodiment, a staple is comprised of a magnesium-zinc-zirconium-iron alloy, such as Mg-6Zn-0.1Zr-0.1Fe, for example. As discussed above, the addition of iron to a magnesium alloy can increase the degradation rate of the alloy. In various embodiments, the staples of a staple cartridge are comprised of a magnesium-zinc-zirconium alloy comprising 3 wt % zinc and less than 1 wt % zirconium, for example.

In various embodiments, the staples of a staple cartridge are comprised of a magnesium-manganese alloy, such as Mg-1Mn, for example. In at least one embodiment, magnesium alloys containing 1 wt % manganese or less have a desirable degradation rate and ductility. In at least one embodiment, the staples of a staple cartridge are comprised of a magnesium-manganese alloy comprising 1 wt % manganese. In at least one embodiment, the staples of a staple cartridge are comprised of Mg-1Zn-0.3Ca-0.15Mn, for example. In at least one embodiment, the staples of a staple cartridge are comprised of a magnesium-manganese alloy comprising 0.15 wt % manganese. That said, staples can be comprised of a magnesium-manganese alloy having more than 1 wt % manganese.

In various instances, further to the above, a magnesium alloy can include aluminum. In at least one embodiment, the staples of a staple cartridge are comprised of Mg-2Al-1Zn, for example, which has a high degradation rate. In at least one embodiment, the staples of a staple cartridge are comprised of Mg-3Al-1Zn, for example, which also has a high degradation rate.

In various embodiments, a staple is comprised of an magnesium-zinc-calcium alloy. In at least one such embodiment, calcium is added to a magnesium-zinc alloy at 1 wt % or more which can provide grain refinement and can increase the degradation rate of the magnesium-zinc alloy. In various embodiments, calcium is added to a magnesium-zinc alloy between 0.1 wt % and 2 wt %, for example. In at least one embodiment, the staples of a staple cartridge are comprised of Mg-1.34Ca-3Zn, for example. In at least one embodiment, the staples of a staple cartridge are comprised of ZX10 alloy, for example. In at least one embodiment, the staples of a staple cartridge are comprised of ZX20 alloy, for example. In at least one embodiment, the staples of a staple cartridge are comprised of ZX50 alloy, for example. In at least one embodiment, the staples of a staple cartridge are comprised of Mg-1.0Zn-0.3Ca. In at least one embodiment, the staples of a staple cartridge are comprised of Mg-1.5Zn-0.25Ca. In at least one embodiment, the staples of a staple cartridge are comprised of Mg-5Zn-0.3Ca.

In various instances, the staples implanted within a patient are exposed to electrical energy during a surgical procedure. In at least one such instance, a monopolar instrument can come into contact with the staples and transmit electricity to the staples. Such electricity heats the staples and can ignite the staples depending on the metal comprising the staples and how hot the staples get. Adding calcium to magnesium and/or a magnesium alloy increases the ignition temperature thereof which can prevent the ignition of the staples. Moreover, the calcium comprises a less noble secondary phase within the magnesium which creates galvanic corrosion. In at least one embodiment, the staples of a staple cartridge are comprised of Mg-0.8Ca, for example. In various embodiments, calcium is added to magnesium between 0.1 wt % and 2 wt %, for example. In at least one embodiment, the staples of a staple cartridge are comprised of a magnesium-calcium alloy comprising 1 wt % or greater of calcium. Moreover, adding tin, aluminum, and/or zinc, for example, to magnesium and/or a magnesium alloy increases the resistivity thereof which can increase the time before the staples can ignite thereby possibly preventing the ignition of the staples.

As discussed above, staples can be comprised of zinc. In at least one embodiment, a staple can be comprised of wrought zinc, for example. In various embodiments, microgalvanic corrosion can be employed within zinc staples by alloying the zinc with magnesium, for example. The difference in nobility between the zinc and the magnesium in a zinc-magnesium alloy can create an anodic-cathodic relationship between the two elements. In at least one embodiment, the magnesium in the zinc-magnesium alloy can be greater than or equal to 0.1 wt %, for example. In at least one embodiment, the magnesium in the zinc-magnesium alloy can be between 0.1 wt % and 1 wt %, for example. In at least one embodiment, the magnesium in the zinc-magnesium alloy is 1 wt %, for example. Zinc-magnesium alloys comprising less than 0.1 wt % magnesium are also envisioned but such alloys may or may not be sufficiently ductile for every application. That said, manganese can be alloyed with an alloy of zinc and magnesium to improve the ductility of the zinc-magnesium alloy. In at least one embodiment, a zinc-magnesium staple alloy comprises 1 wt % magnesium, for example. In certain embodiments, a zinc-magnesium staple alloy comprises between 0.1 wt % and 5 wt % magnesium, for example. In various embodiments, the degradation rate of the zinc can be increased by alloying zinc with calcium, strontium, and/or iron, for example. In at least one embodiment, a zinc-iron staple alloy comprises 1 wt % or less iron. In at least one embodiment, a zinc-iron staple alloy comprises 1 wt % iron. In at least one embodiment, a zinc-iron staple alloy comprises 0.5 wt % iron. In at least one embodiment, a zinc-iron staple alloy comprises 0.1 wt % iron. In at least one embodiment, a zinc-strontium staple alloy comprises 1 wt % strontium, for example. In certain embodiments, a zinc-strontium staple alloy comprises between 0.1 wt % and 5 wt % strontium, for example. In at least one embodiment, a zinc-calcium staple alloy comprises 1 wt % calcium, for example. In certain embodiments, a zinc-calcium staple alloy comprises between 0.1 wt % and 5 wt % calcium, for example. In at least one embodiment, a staple is comprised of Zn—Mg-0.1Ca, for example. In at least one embodiment, a staple is comprised of a zinc-calcium alloy including 0.1 wt % calcium. In various embodiments, the degradation rate of zinc can be increased by alloying the zinc with aluminum, for example. Such embodiments can produce staples having excellent ductility.

In various instances, staples comprised of zinc and/or zinc alloys can slowly relax, or creep, into a partially open configuration owing to the natural body temperature of the patient, i.e., around 98 degrees F. In various embodiments, alloying zinc with copper can create staples that do not open, or at least substantially open, owing to creep. Moreover, alloying the zinc with copper can create microgalvanic corrosion within the staple and/or otherwise increase the degradation rate of the staple. In at least one embodiment, the copper in the zinc-copper alloy can be 1 wt %, for example. In certain embodiments, the copper in the zinc-copper alloy can be greater than or equal to 1 wt %, for example. In at least one embodiment, the copper in the zinc-copper staple alloy can be between 0.1 wt % and 2 wt %, for example. Adding titanium to a zinc-copper staple alloy can also reduce the creep of the implanted staples. In at least one embodiment, a zinc-copper-titanium alloy comprises 0.1 wt % titanium, for example. In certain embodiments, a zinc-copper-titanium alloy comprises between 0.1 wt % and 1.0 wt % titanium, for example. In at least one embodiment, the zinc-copper-titanium alloy comprises 1 wt % copper and 0.1 wt % titanium, for example. In various embodiments, a staple can be comprised of Z41320 alloy and/or Z41321 alloy, for example. In various embodiments, a zinc-copper alloy can comprise titanium, manganese, and/or magnesium, for example.

Magnesium and/or magnesium alloy staples can also experience creep after being implanted in a patient. In various embodiments, the staples can be comprised of a magnesium alloy including rare earth elements, such as gadolinium, for example. Such alloys can be resistant, or at least more resistant, to creep. In at least one embodiment, the staples are comprised of ZXM100 (1.07Zn-0.21Ca-0.31Mn) and/or ZXM120 (1.01Zn-1.63Ca-0.30Mn), for example. The entire disclosure of BIOCORROSION AND MECHANICAL PROPERTIES OF ZXM100 AND ZXM120 MAGNESIUM ALLOYS, which published on Jan. 25, 2019 in International Journal of Metalcasting is incorporated by reference herein. The entire disclosure of International Patent Application Publication No. WO2020/247383A1, entitled MAGNESIUM-BASED ABSORBABLE ALLOYS is incorporated by reference herein. The entire disclosure of BIODEGRADABLE METALS by Y. F. Zheng, X. N. Gu, and F. Witte, which published in MATERIALS SCIENCE AND ENGINEERING R and became available online on Mar. 6, 2014, is incorporated by reference herein. The entire disclosure of MAGNESIUM ALLOYS AS DEGRADABLE BIOMATERIALS by Yufeng Zheng, published in 2016 by Taylor & Francis Group LLC, Boca Raton, FL is incorporated by reference herein.

In various embodiments, the staples of a staple cartridge are comprised of Mg-10Dy-1Nd-1Zn-0.2Zr, for example. In certain instances, the Mg-10Dy-1Nd-1Zn-0.2Zr alloy may be further tuned and/or alloyed as described herein to achieve a desired degradation rate. In various embodiments, the staples of a staple cartridge are comprised of Mg-2.5Nd-1Y, for example. Similar to the above, the Mg-2.5Nd-1Y alloy may be further tuned and/or alloyed as described herein to achieve a desired degradation rate. In various embodiments, the staples of a staple cartridge are comprised of a magnesium alloy including yttrium, zirconium, and/or rare earth metals, for example. Similar to the above, such alloys may be further tuned and/or alloyed as described herein to achieve a desired degradation rate. In various embodiments, the staples of a staple cartridge are comprised of WE43, for example. Similar to the above, the WE43 alloy may be further tuned and/or alloyed as described herein to achieve a desired degradation rate, among other things.

The staple materials disclosed herein can be alloyed with silver and/or electroplated with silver, for example. Silver has various antiseptic benefits. In at least one embodiment, magnesium is alloyed with silver, for example. Moreover, silver is highly soluble in magnesium and, as a result, a Mg—Ag alloy may be stronger than pure magnesium. Moreover, electroplating a staple can create a smooth surface which can prevent, or at least inhibit, the deposit of minerals and/or materials onto the staple. As a result, the degradation rate, or biocorrosion of, the staple will not be inhibited, or at least substantially inhibited, by deposited materials.

In various embodiments, a staple cartridge comprises a cartridge body and a longitudinal slot defined in the cartridge body configured to receive a tissue cutting knife. The staple cartridge further comprises longitudinal rows of staple cavities defined in the cartridge body on both sides of the longitudinal slot. For instance, a staple cartridge can comprise three longitudinal rows of staple cavities on a first side of the longitudinal slot and three longitudinal rows of staple cavities on a second, or opposite, side of the longitudinal slot. On each side of the longitudinal slot, in at least one such embodiment, the longitudinal rows of staple cavities are arranged in an inner row adjacent the longitudinal slot, an intermediate row adjacent the inner row, and an outer row adjacent the intermediate row. In various embodiments, the staples positioned in the inner rows, intermediate rows, and outer rows are comprised of the same material. In at least one such instance, all of the staples in the staple cartridge are comprised of the same magnesium alloy, for example.

In various alternative embodiments, further to the above, the staples in the inner rows are comprised of a material that is different than the staples in the intermediate rows and the outer rows. In at least one such embodiment, the staples in the inner rows are comprised of a material that has a slower degradation rate, or biocorrosion rate, than the staples in the intermediate rows and the outer rows, for example. In such embodiments, the staples closest to the incision may be the last staples to release the patient tissue. As a result, the intermediate and outer rows of staples can release the patient tissue before the inner rows of staples which re-introduces flexibility into the patient tissue before the tissue at the incision margin is released by the inner rows of staples. Such an arrangement can provide the tissue at the incision margin additional time to heal. In certain embodiments, the staples in the intermediate rows are comprised of a material that is different than the staples in the inner rows and the outer rows. In at least one such embodiment, the staples in the intermediate rows are comprised of a material that has a faster degradation rate than the staples in the inner rows but a slower degradation rate than the staples in the outer rows, for example. In at least one such embodiment, the outer rows of staples can release the patient tissue before the intermediate rows of staples and, likewise, the intermediate rows of staples can release the patient tissue before the inner rows of staples. In such instances, the rows of staples can progressively release the patient tissue which, as a result, progressively re-introduces flexibility into the patient tissue as it heals. In at least one embodiment, the staples in the outer rows are comprised of a material that is different than the staples in the inner rows and the intermediate rows. In at least one such embodiment, the staples in the outer rows are comprised of a material that has a faster degradation rate than the staples in the intermediate rows and inner rows, for example.

In various instances, further to the above, the physiological and/or environmental response of a patient can affect the corrosion process of the staples implanted within the patient. For instance, phosphates and/or carbonates, for example, can precipitate on the surface of the staples during the biocorrosion process, thereby slowing the rate in which the staples degrade, or biocorrode. In at least one such instance, the biocorrosion of magnesium staples can lead to an increase in local pH which lowers the solubility of the corrosion products and the physiological phosphates, carbonates, and/or organics. Preventing, or at least substantially minimizing, the deposition of such phosphates, carbonates, and/or organics on the staples during the healing process can increase or at least maintain the biocorrosion rate of the staples to meet the desired biocorrosion timeframe.

In various embodiments, further to the above, the staples comprise a coating that includes an absorbable polymer, such as polylactic acid (PLA), polylactic-co-glycolic acid (PLGA), and/or polyglycolic acid (PGA), for example. The absorbable polymer improves the solubility of the corrosion products and minerals by generating acid which maintains a lower local pH, thereby increasing the corrosion rate of the staples. In various embodiments, the staples comprise a coating that includes a calcification inhibitor, such as Fetuin A, citrate, and/or a chelating agent, such as phytic acid, for example. After such staples have been implanted, the calcification inhibitor can slowly release from the staples. The calcification inhibitor binds with calcium and phosphate ions to form calciprotein particles (CPP). These keep the ions in solution and prevent, or at least significantly decrease, the extent of mineral deposition on the staples, thereby preserving and/or increasing the corrosion rate thereof. In various embodiments, the calcification inhibitor is embedded within the absorbable polymer. In at least one such embodiment, the calcification inhibitor is continuously released as the absorbable polymer is bioabsorbed.

In various embodiments, the staples comprise a coating that includes proteins that bind to magnesium ions to prevent, or at least significantly decrease, the formation of phosphates and carbonates thereon. Such coatings keep the ions in solution and prevent, or at least significantly decrease, the extent of mineral deposition on the staples so as to preserve and/or increase the corrosion rate thereof.

In various instances, the staples of a staple cartridge comprise a coating that can block nucleation sites thereon. In various embodiments, the staples comprise a coating that includes inorganic ions, such as pyrophosphate or bisphosphonates (polyphosphates), for example. Such inorganic ions comprise a potent inhibitor of calcium crystallization and can bind to newly forming hydroxyapatite crystals and prevent further growth thereof, thereby preserving and/or increasing the corrosion rate of the staples. In various embodiments, the staples comprise a coating that includes polymers of acrylic acid that inhibit the precipitation of calcium phosphate by surface adsorption, thereby preserving and/or increasing the corrosion rate of the staples. In various embodiments, the staples comprise a coating that includes polycarboxylic acids, which can inhibit the precipitation of calcium phosphate by surface adsorption, thereby preserving and/or increasing the corrosion rate of the staples.

In various embodiments, the staples comprise a coating that includes osteopontin, which has been shown to be an inhibitor of calcification in blood vessel walls.

In various embodiments, the staples comprise a coating that includes inorganic ions, such as $Mg2+$ ions, for example, which inhibit the formation of the most stable calcium phosphate polymorph (hydroxyapatite) and also stabilize the amorphous calcium phosphate polymorph, thereby preserving and/or increasing the corrosion rate of the staples.

In various embodiments, the staples comprise a coating that encourages movement of the dissolved metal, phosphate, and carbonate ions away from the staple, making corrosion products less likely to form directly on the surface thereof. In various embodiments, the staples comprise a coating that diverts, or encourages movement, of the corrosion products onto a buttress that is implanted in the patient tissue with the staples. As a magnesium staple dissolves, magnesium ions are freed to form molecules and/or bonds with other elements surrounding the staple. In various embodiments, magnesium staples are at least partially-coated with a chlorine ion eluding material. In such embodiments, the magnesium ions from the dissolving staple and the chlorine ions that elude from the coating form magnesium chloride. Magnesium chloride is a salt that tends to lower the pH of the surrounding environment and, moreover, is readily absorbed by the surrounding patient tissue. As such, the magnesium chloride created around the magnesium staples lowers the pH around the staples and, also, reduces the accumulation of scale on the staples. In many instances, scale can impede the absorption of the staples within a desired time window; however, owing to the chlorine-eluding coating on the staples, the effect of the scale can be reduced.

In various embodiments, the staples comprise a coating that includes an acid that removes corrosion products from the staples and/or destabilizes corrosion products on the staples. Metal carbonates, for example, react with acids to produce soluble products, such as salts, carbon dioxide and/or water, for example. Moreover, in various instances, a low pH will aid the dissolution of some of the corrosion products deposited on the staples. As referenced above, PLA, PGLA, and/or PGA, for example, lower the pH of the environment surrounding the staples. When PLA, PGLA, and/or PGA dissolve, more specifically, they generate acid which maintains a lower local pH, thereby increasing the corrosion rate of the staples.

In certain embodiments, further to the above, the absorbable polymer comprises a layer, or an at least partial layer, on the metal staple material and the calcification inhibitor comprises a layer, or an at least partial layer, on the absorbable polymer layer. In at least one such embodiment, the calcification inhibitor is immediately released, or at least quickly released, into the environment immediately surrounding the staples. In certain embodiments, the absorbable polymer comprises a partial layer on a first portion of the staples and the calcification inhibitor comprises a partial layer on a second, or different, portion of the staples. In at least one such embodiment, the calcification inhibitor can release from the staples at a rate which is faster than the rate in which the absorbable polymer is bioabsorbed. In such instances, the calcification inhibitor deploys quickly to prevent, or at least inhibit, the calcification of the absorbable polymer and/or the underlying metal staple material.

In various embodiments, the staples comprise a coating that decreases the early degradation rate thereof. A rapid early degradation rate of the staples can be responsible for a dramatic change in the local conditions surrounding the staples, creating a strong initial driving force for mineral deposition onto the staples which, as discussed above, can slow the degradation rate of the staples. A slower fundamental or initial degradation rate of the staples, via surface coatings, can result in a faster overall bioabsorption of the staples in many instances. Moreover, surface coatings can create a more uniform initial corrosion of the staple, i.e., immediately after the staple is implanted or within a few weeks of it being implanted. In various instances, the staple coating delays galvanic corrosion of the staple and the bioabsorption and/or dissolution of the coating exposes the underlying metal structure of the staple to the surrounding environment thereby initiating galvanic corrosion. In various embodiments, the coating is applied on top of a metal wire and/or stamped metal structure of the staple. In at least one such embodiment, the coating is comprised of one or more polymers, such as PGA, for example. In various embodiments, the staple coating comprises a conversion coating of the underlying base metal of the staple. In at least one such embodiment, the outer surface of a magnesium staple is coated with and/or otherwise exposed to fluorine ions, for example, which converts the outer surface of the magnesium staple to magnesium fluoride, $MgF2$, for example. Coating the staples with a conversion coating may result in little, if any, change to the diameter of the underlying metal wire of the staples, for example.

In various embodiments, a staple cartridge can further comprise an implantable adjunct, such as a buttress, for example, that is secured to the patient tissue by the deployed staples. In at least one embodiment, the implantable adjunct comprises a layer releasably secured to a top surface, or deck, of the staple cartridge. During the staple firing stroke, the legs of the staples pass through the implantable adjunct and the patient tissue and, as the staples are deformed against the anvil positioned opposite the staple cartridge, the staples secure the implantable adjunct against the patient tissue. The implantable adjunct is configured to release from the staple cartridge during the staple firing stroke and/or as the staple cartridge is moved away from the stapled tissue. Once the staples are implanted, various portions of the staple are in contact with the implanted adjunct and other portions of the staple are in contact with the patient tissue. In various embodiments, the adjunct is comprised of an absorbable polymer and/or a calcification inhibitor which can further decrease the local pH and decrease the extent of mineral deposition on the staples.

In various instances, the corrosion rate of a staple can be increased by altering the physical design of the staple. In one aspect, the corrosion rate of a staple is based on the volume/surface area ratio of the staple. In various embodiments, a staple can further comprise notches and/or recesses defined therein which increases surface area of the staple and lowers the volume, for example. In another aspect, the geometry of the staple can affect the propensity of the staple to exhibit stress corrosion cracking. Further to the above, the notches and/or recesses in the staples can comprise stress risers, or amplifiers, which can induce failure in the staples at the notches and recesses. In at least one such embodiment, the notches and/or recesses can be present in the staple legs, for example. In at least one embodiment, the notches and/or recesses can be present in the joints connecting the staple legs to the staple base.

In various embodiment, a staple comprises hollow portions defining a recess therein. In at least one embodiment, a staple comprises a base, a first leg extending from a first end of the base, and a second leg extending from a second end of the base. In at least one such embodiment, the staples are comprised of a hollow wire which is cut to length and then bent into its unfired configuration. In various embodiments, the hollow staples are formed by a hollow extrusion process followed by a tube drawing process to reduce wall thickness and diameter, for example. In various embodiments, the staples are stamped from metal sheets. In at least one such embodiment, the bases of the staples are solid, i.e., they do not comprise an internal aperture defined therein, and the first staple leg and/or the second staple leg comprise an internal aperture defined therein. In at least one such embodiment, the legs of the staples are stamped flat and, during a secondary forming process, rolled into a round circumference defining the internal aperture therein. In various instances, a hollow staple design enables a staple to have sufficient stiffness, but with a lower volume/surface area ratio which permits the staple to biocorrode and release the patient tissue within a desired window of time.

In various embodiments, further to the above, staples are comprised of round wire including a metal outer circumference defining an internal aperture and an inner core positioned in the internal aperture. In at least one such embodiment, the wire is formed by a hollow extrusion process which co-extrudes the metal outer perimeter and a polymer inset. In at least one embodiment, the metal outer portion is extruded and the inner core is filled during an injection molding process, for example. In various embodiments, the staples are formed using a polymer extrusion process to create the inset which is then coated with metal using at least one of an electroplating process and/or a sputtering process, for example. In various embodiments, the hollow staples comprise a filler positioned in the internal apertures which is released as the staples are corroded. In various instances, the filler can be selected to mitigate and/or induce a physiological response within the patient. In at least one embodiment, the filler can comprise an absorbable polymer, such as PLA, PLGA, and/or PGA, for example. In at least one embodiment, the filler comprises a lithium carbonate layer, for example.

In various embodiments, the staples can comprise a smooth surface. In various instances, corrosion products are more likely to adhere to rough surfaces of the staples, thereby lowering the corrosion rate of the staples. Maintaining a smooth staple surface on the staples will encourage the corrosion products to fall off the staples and/or not adhere to the staples. In various embodiments, an electroplating process is used to create the smoothness of the staples.

In various embodiments, a staple cartridge comprises staples stored therein which have the same unformed height. By the same unformed height, the staples can have the exact same unformed height and/or an unformed height within a manufacturing tolerance range. In at least one embodiment, the staples have an unformed height of 3.5 mm. In at least one such embodiment, the staples are comprised of wire having a wire diameter of 0.20 mm, for example. In at least one embodiment, the staples have an unformed height of 3.8 mm. In at least one such embodiment, the staples have a wire diameter of 0.22 mm, for example. In at least one embodiment, the staples have an unformed height of 4.1 mm. In at least once such embodiment, the staples have a wire diameter of 0.22 mm, for example.

Further to the above, various embodiments are envisioned in which a staple cartridge comprises staples have different unformed heights. In at least one embodiment, a staple cartridge comprises a longitudinal slot configured to receive a tissue cutting knife therein and three longitudinal rows of staple cavities on each side of the longitudinal slot. Each side of the longitudinal slot comprises an inner row adjacent the longitudinal slot, an intermediate row adjacent the inner row, and an outer row adjacent the intermediate row. In at least one such embodiment, the staples in the inner row of staple cavities comprise a first unformed height, the staples in the intermediate row of staple cavities comprise a second unformed height which is taller than the first unformed height, and the staples in the outer row of staple cavities comprise a third unformed height is taller than the second unformed height. For instance, the staples in the inner row have an unformed height of 3.5 mm, the staples in the intermediate row have an unformed height of 3.8 mm, and the staples in the outer row have an unformed height of 4.1 mm.

In various embodiments, further to the above, the staples of a staple cartridge are deformed to the same formed height. By the same formed height, the staples can have the exact same formed height and/or a formed height within a tolerance range. In at least one embodiment, staples having an unformed height of 3.5 mm are deformed to a 1.5 mm formed height, for example. In at least one embodiment, staples having an unformed height of 3.8 mm are deformed to a 1.8 mm formed height, for example. In at least one embodiment, staples having an unformed height of 4.1 mm are deformed to a 2.0 mm formed height, for example. As a result of different formed heights, the formed staples can apply different clamping pressures to the tissue. For instance, the staples formed to 1.5 mm formed height apply about 78 kPa, the staples formed to 1.8 mm apply about 59 kPA, and the staples formed to 2.0 mm apply about 30 kPa, for example. Such pressures can be referred to as initial, or as-fired, clamping pressures. Such embodiments apply the largest clamping pressure to the tissue adjacent the incised tissue margin which can, as a result, prevent, or at least reduce, bleeding therefrom, although other embodiments are envisioned in which larger pressures are applied by staples further away from the tissue incision. In any event, as the staples biocorrode, the clamping pressure that they apply to the patient tissue drops. Stated another way, the staples disclosed herein gradually relax the clamping pressure being applied to the patient tissue as the patient tissue heals.

As discussed above, the staples of a staple cartridge can be formed to one or more formed heights. Such formed heights can be referred to as final formed heights. Stated another way, a staple deforms both plastically and elastically as it is being deformed and, after the staple has been deformed to an as-formed height, the staple height thereafter grows from its as-formed height to its final formed height as a result of the release of the elastic energy stored in the staple. Such a process can be referred to as spingback. Notably, absent other considerations, titanium staples have more springback than magnesium staples. Thus, in various instances, titanium staples may need to be fired to a smaller as-fired height to arrive at the same final formed height as magnesium staples.

Many examples are disclosed in the Subject Application. Many of these examples comprise a percentage of one material that is included within another material. For instance, as provided above, calcium can be added to a magnesium-zinc alloy between 0.1 wt % and 2 wt % in some embodiments. That said, for all embodiments disclosed in the Subject Application as having a specific percentage of a material, the Subject Application also includes embodiments having about that percentage of the material. With regard to the preceding example, for instance, the Subject Application also discloses that calcium can be added to a magnesium-zinc alloy between about 0.1 wt % and about 2 wt %. The term about includes a range of 20% of the given value on each side of the given value. Thus, the percentage of about 0.1 wt % includes a range of 0.08 wt % to 0.12 wt %. Moreover, the percentage of about 2 wt % includes a range of 1.6 wt % to 2.4 wt %.

As discussed above, a wire can be deformed to manufacture a staple. Such deformation typically includes both elastic deformation and plastic deformation. The elastic deformation of the wire created during the manufacturing process naturally relieves itself when the forces applied to the wire by the manufacturing process are relieved. The plastic deformation of the wire during the manufacturing process does not resiliently relieve itself. Thus, when wire is bent to form a substantially V-shaped staple, for example, the staple includes a crown and two legs where each leg is connected to the crown by a bend. These bends are the result of large plastic deformations and can include high residual stresses—especially on the inside surfaces of the bends. The inside surfaces of the bends have a smaller radius than the outside surfaces and, in various instances, the inner surfaces can undergo larger amounts of work hardening than the outside surfaces. Such work hardening can create cracks in the wire along the inner surfaces of the bends, especially when the wire is comprised of magnesium, for example. More specifically, the inner surfaces of the bends undergo compression when the V-shaped staple is manufactured while the outer surfaces of the bends undergo tension and, as a result, the inner radius bends may be more susceptible to cracking as magnesium and magnesium alloys may have a lower strength in compression that in tension, for example. This phenomenon is more prevalent in staples have a thicker wire diameter than a thinner wire diameter owing to the larger moment arm between the inner surface of the bend and the center of mass.

In at least one example, further to the above, the staples can be annealed to reduce the residual stresses contained therein and/or toughen them. In at least one instance, the staples are heated and then allowed to cool slowly before the staples are loaded into a staple cartridge. In at least one other instance, the staples are loaded into a staple cartridge and then the whole staple cartridge is heated to anneal the staples while they are in the staple cartridge. In such instances, the plastic parts of the staple cartridge are comprised of a high-performance plastic that is able to withstand elevated temperatures without substantial degradation, such as polyether ether ketone, for example. After the staple cartridge has been heated, the staple cartridge is permitted to cool before it is used. In any event, the annealing processes described above anneal the entire staple. In other examples, only portions of the staples may be treated to relieve residual stress and/or improve the toughness of the portions. In at least one such process, for instance, the bends of the staples are heated with a laser.

Figure 19:
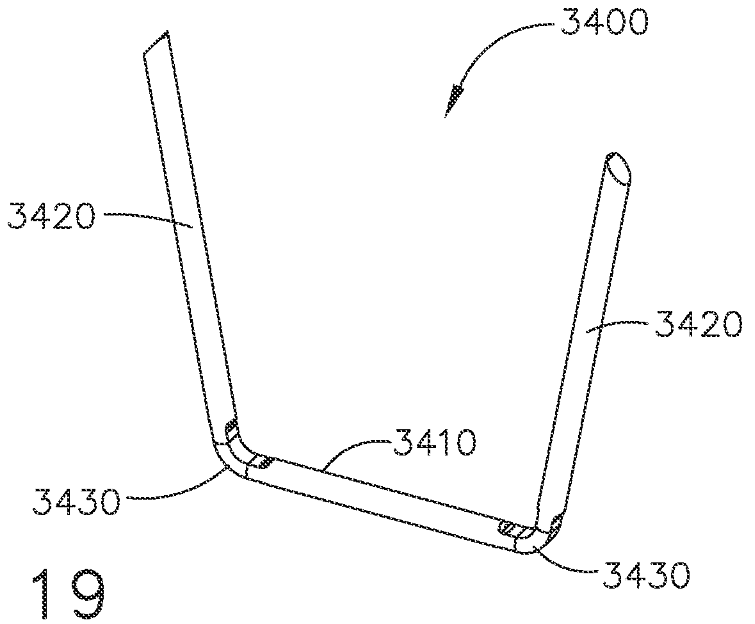
FIG. 19 is a perspective view of a wire staple comprising stamped spots defined therein in accordance with at least one embodiment.
Figure 20:
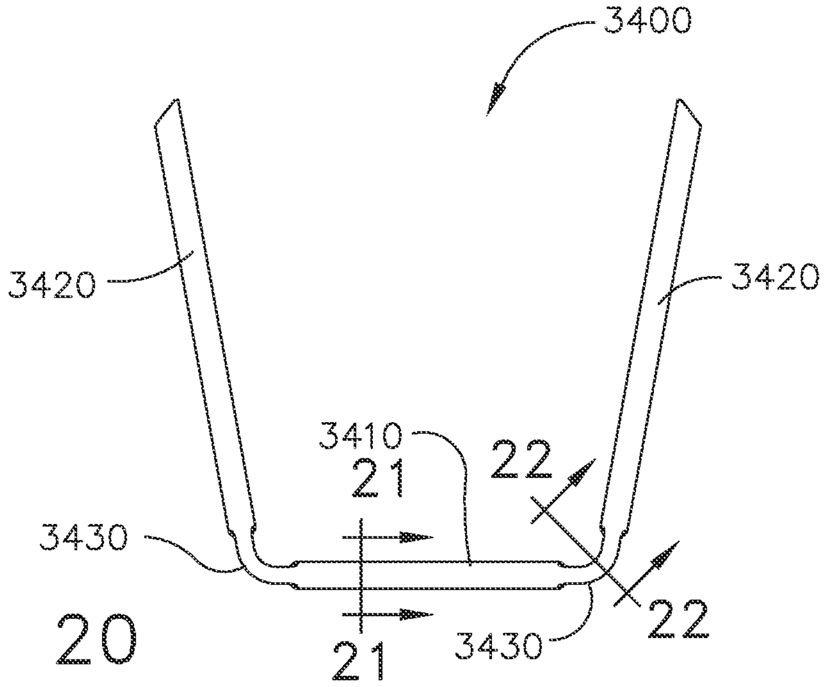
FIG. 20 is an elevational view of the wire staple of FIG. 19.
Figure 21:
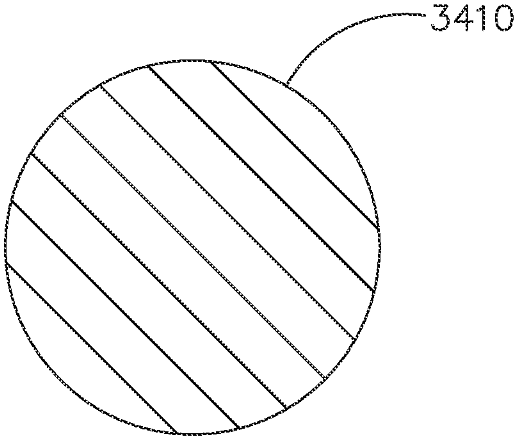
FIG. 21 is a cross-sectional view of the wire staple of FIG. 19 taken along line 21-21 in FIG. 20.
Figure 22:
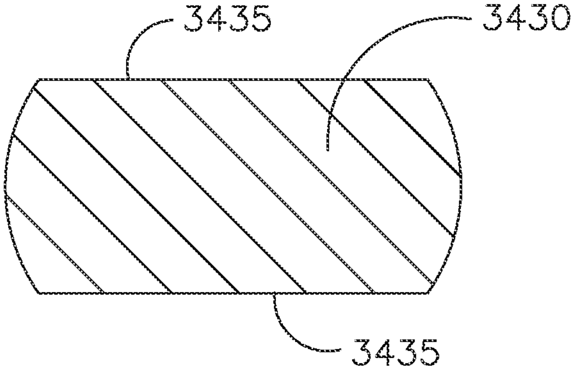
FIG. 22 is a cross-sectional view of the wire staple of FIG. 19 taken along line 22-22 in FIG. 20.

In various instances, further to the above, the wire used to form a staple has a constant cross-sectional thickness or diameter along the length thereof. In various examples, the cross-section of the wire can be changed to reduce the residual stress within the wire and/or reduce the possibility of the wire cracking and/or fracturing at a particular location. In at least one such example, the inside surface of the bends can be flattened. For instance, one or more flat spots can be stamped into a wire before it is deformed into a staple such that, once the wire is deformed into the staple, the flat spots are in the inside surfaces of the bends. Referring to FIGS. 19 and 20, a staple 3400 comprises a wire substrate including a crown 3410, legs 3420, and bends 3430 connecting the legs 3420 to the crown 3410. Referring to FIG. 21, the wire substrate of the staple 3400 comprises a round cross-section that is present in the crown 3410 and the legs 3420 and, referring to FIG. 22, a flattened cross-section including flat spots 3435 in the bends 3430. In at least one example, the portions of the wire that will become the bends are worked to have a smaller cross-sectional area or diameter than the portions of the wire that will become the crown and the staple legs. Such a process creates wire staples having a crown and staple legs which have larger cross-sections than the bends, or at least part of the bends, that connect them. As a result of the above, the bends are less likely to crack and/or fracture. In at least one other embodiment, the portions of the wire that will become the bends and the staple legs are worked to have a smaller cross-sectional area or diameter than the portion of the wire that will become the crown.

As discussed above, wire staples can be heated and then permitted to cool slowly to reduce residual stresses within the wire and/or toughen the wire. In other instances, wire staples can be heated and then cooled quickly. In at least one instance, the staples are quenched in a liquid. In at least one example, the staples of a staple cartridge are comprised of magnesium glass which comprises magnesium or a magnesium alloy that is heated and then cooled so quickly that the metal does not have time to form crystals, or a substantial amount of crystals, such that the metal has an amorphous, or an at least substantially amorphous, grain structure.

In at least one example, the staples of a staple cartridge are comprises of a magnesium shape-memory alloy. In at least one such example, the staples are comprised of a magnesium-scandium alloy, for example. The staples are bent into a substantially V-shaped configuration from a wire comprised of a magnesium shape-memory alloy with residual stresses and strains locked therein. The staples are then loaded into a staple cartridge and implanted in a patient. Applying heat to the staples unlocks the residual stresses and strains in the staples such that the staples move into a closed, or substantially B-shaped, configuration where the legs of the staples deflect inwardly to trap patient tissue within the staples.

In various instances, further to the above, forming, or closing, the staples ejected from a staple cartridge during a staple firing process comprises pushing the legs of the staples against an anvil positioned opposite the staple cartridge. In at least one example, the staple cartridge comprises drivers which are pushed upwardly toward the anvil by a sled moving from a proximal end of the staple cartridge toward a distal end of the staple cartridge. In any event, the anvil comprises forming pockets that guide the staple legs inwardly toward one another as the legs are being deformed to create a closed, or substantially B-shaped, fired configuration. In some instances, however, one or both of the staple legs may be bent outwardly during the staple firing process. Although malformed, the staples may still be able to apply a sufficient clamping pressure to the tissue. Whether formed correctly of incorrectly, the staples undergo a significant amount of stress and strain during the formation process. Such stress and strain may cause the bends of the staples between the crown and the legs to crack and/or fracture even if they did not crack and/or fracture during the staple manufacturing process. Discussed below are configurations of the staples and/or staple drivers that reduce the possibility of and/or reduce the severity of such cracking and/or fracturing.

Figure 16:
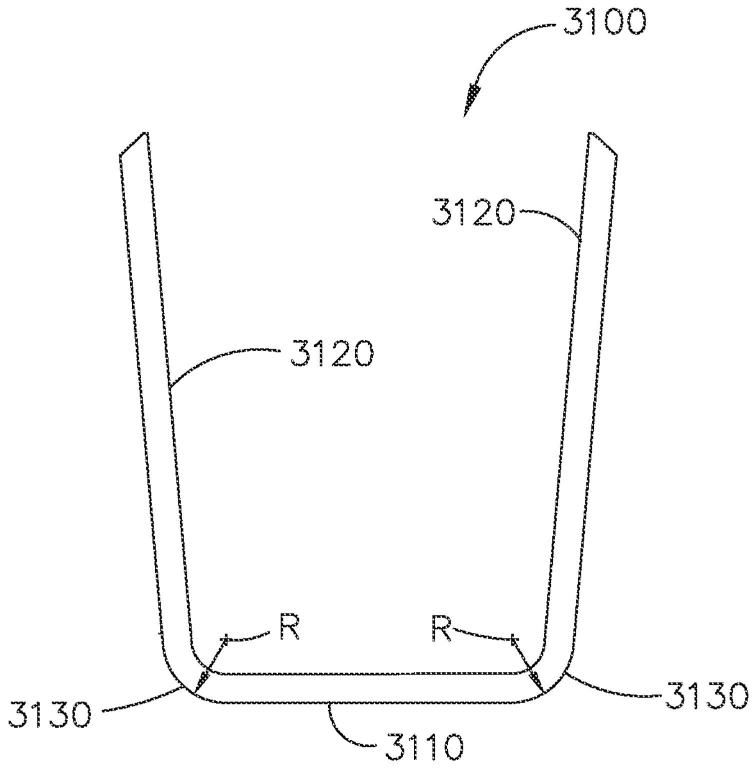
FIG. 16 is an elevational view of a staple having round corners in accordance with at least one embodiment.
Figure 16A:
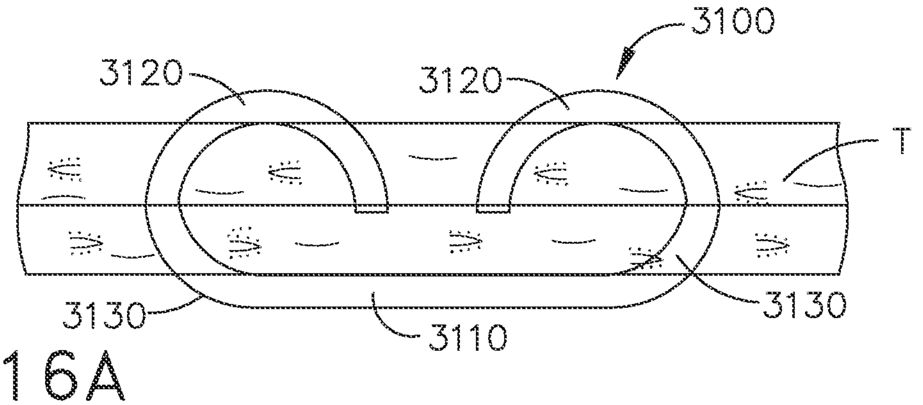
FIG. 16A illustrates a wire staple implanted in patient tissue in accordance with at least one embodiment.
Figure 16B:
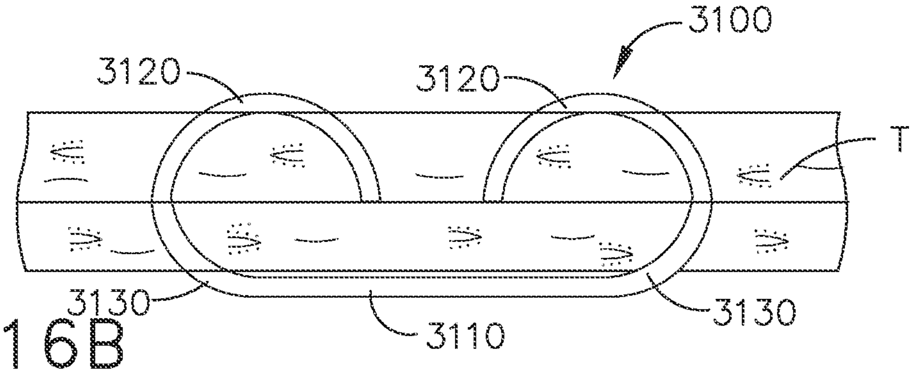
FIG. 16B illustrates the wire staple of FIG. 16A in a partially-dissolved functional state.
Figure 16C:
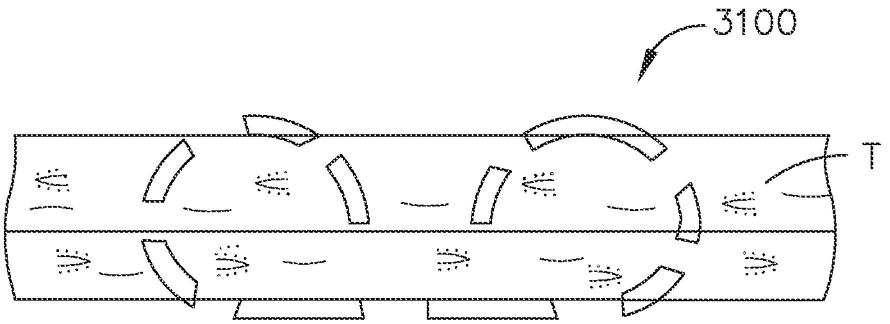
FIG. 16C illustrates the wire staple of FIG. 16A in a mostly-dissolved non-functional state.
Figure 16D:
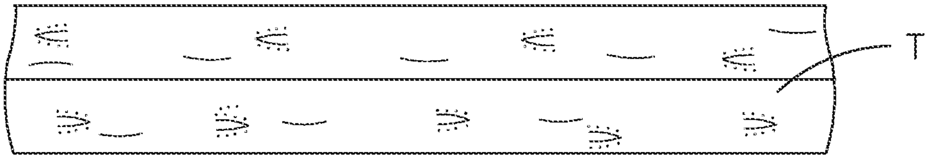
FIG. 16D illustrates the wire staple of FIG. 16A in a completely-dissolved state.

In at least one example, referring to FIG. 16, a staple 3100 comprises a crown 3110, a first leg 3120, a first bend 3130 connecting the first leg 3120 to a first end of the crown 3110, a second leg 3120, and a second bend 3130 connecting the second leg 3120 to a second end of the crown 3110. The first leg 3120, the second leg 3120, and the crown 3110 each comprises a straight, or an at least substantially straight, segment; however, examples are envisioned in which one or more of these segments is not straight. In this example, the first bend 3130 is defined by a constant radius of curvature. The first bend 3130 extends between the crown 3110 and the first leg 3120 along a continuous constant radius. Similarly, the second bend 3130 is also defined by a constant radius of curvature. Like the first bend 3130, the second bend 3130 extends between the crown 3110 and the second leg 3120 along a continuous constant radius. In this example, the radius defining the first bend 3130 is the same as the radius defining the second bend 3130. Such an arrangement can create a symmetrically-formed staple. See FIG. 16A. That being said, it is often the case that one of the staple legs 3120 may experience different forming mechanics than the other leg 3120 during the staple firing process. To accommodate this, in at least one example, a staple can comprise a first bend defined by a first constant radius and a second bend defined by a second constant radius that is different than the first constant radius. The second constant radius can be larger than or smaller than the first constant radius. In any event, the constant-radius bends reduce the possibility of the bends cracking and/or fracturing during the staple firing process.

In at least one example, a staple comprises a substantially V-shaped configuration including a crown, a first leg, a first connection portion connecting the first leg to the crown, a second leg, and a second connection portion connecting the second leg to the crown. The staple 3100 of FIG. 16 is substantially V-shaped, for example. The first leg, the second leg, and the crown each comprise a straight, or an at least substantially straight, segment; however, examples are envisioned in which one or more of these segments are not straight. In any event, the first connection portion comprises two bends and an intermediate portion—a first bend connects the first leg to the intermediate portion and a second bend connects the intermediate portion to the crown. Each of the first and second bends within the first connection portion provides at least one degree of freedom within the staple permits the first staple leg to be bent into a closed, or fired, configuration while reducing the possibility of the first connection portion cracking and/or fracturing during the staple firing process. The second connection portion comprises a similar arrangement to that of the first connection portion; however, various examples are envisioned in which the multi-bend connection portions described above may only be used to connect one of the staple legs to crown. Such an example may be useful when one of the staple legs experiences more stress and strain than the other.

In at least one example, further to the above, a wire staple comprises a crown, a first leg, a first bend connecting the first leg to the crown, a second leg, and a second bend connecting the second leg to the crown. In at least one such example, the crown comprises a wire diameter and extends along a line that is parallel to, or at least substantially parallel to, a deck, or top, surface of a staple cartridge when the staple is positioned in a staple cavity defined in the staple cartridge. The staple cartridge comprises a driver that includes a seat defined in a top portion of the driver that supports the crown of the staple. The seat comprises a trough or recess including a first sidewall that extends longitudinally along a first side of the staple and a second sidewall that extends longitudinally along a second side of the staple. In at least one embodiment, the seat of the staple driver is configured to support the entire bottom surface of the staple when the staple is in its unfired position and then push upwardly on the bottom surface of the staple as the staple driver is driven upwardly toward an anvil positioned opposite the staple cartridge during a staple firing stroke. In such an example, the drive surface of the seat that contacts the bottom surface of the staple is flat which matches the flat bottom surface of the crown.

Figure 24:
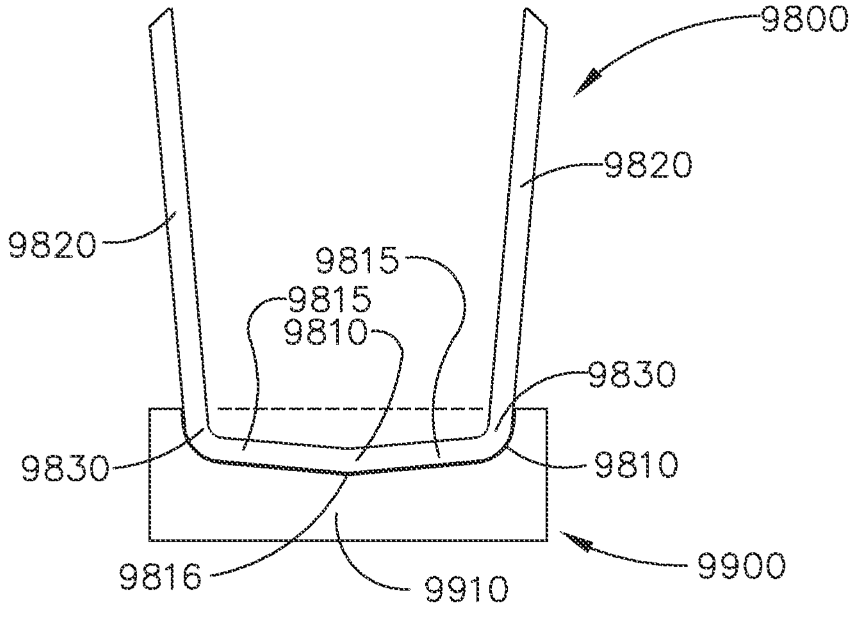
FIG. 24 is an elevational view of a wire staple and a staple driver in accordance with at least one embodiment.

In various embodiments, referring to FIG. 24, a staple 9800 comprises a crown 9810 that has a downwardly-extending first portion 9815 and a downwardly-extending second portion 9815 that are connected at an intermediate vertex 9816. The first portion 9815 comprises a linear segment of the crown 9810 that extends downwardly at about −5 degrees from a bend 9830 and the second portion 9815 also comprises a linear segment that extends downwardly at about −5 degrees from an opposite bend 9830. That said, the linear segments 9815 can extend downwardly at any suitable angle. In any event, the staple 9800 is driveable by a staple driver 9900. The seat 9910 of the staple driver 9900 comprises a drive surface that matches the bottom surface of the staple 9800 as well as angled sidewalls that sufficiently envelop the crown 9810 of the staple 9800 to limit relative movement between the staple 9800 and the staple driver 9900. In various other examples, the downwardly-descending first and second portions 9815 may be non-linear, and may be curved, for example. In any event, the seat of the corresponding staple driver is shaped to match the contours of the staple crown.

Figure 23:
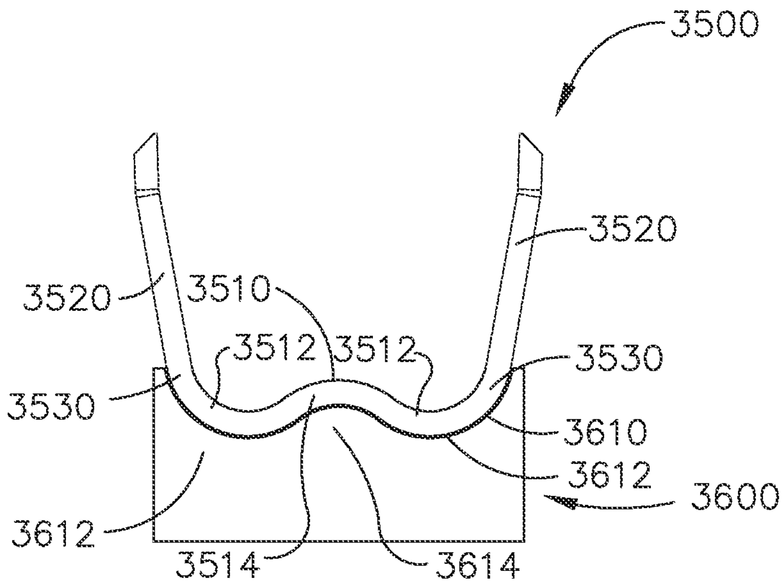
FIG. 23 is an elevational view of a wire staple and a staple driver in accordance with at least one embodiment.

In at least one example, referring to FIG. 23, a staple 3500 comprises a crown 3510, a first leg 3520 extending from the crown 3510, and a second leg 3520 extending from the crown 3510. The crown 3510 comprises three curved portions—a first curved portion 3512 connected to the first leg 3520, a second curved portion 3512 connected to the second leg 3520, and an intermediate curved portion 3514 intermediate the first curved portion 3512 and the second curved portion 3512. The first curved portion 3512 and the second curved portion 3512 have a concave shape and the intermediate curved portion 3514 has a convex shape. A staple driver 3600 used to drive the staple 3500 toward an anvil comprises a seat 3610 that matches, or at substantially matches, the undulating profile of the crown 3510. For instance, the seat 3610 comprises first and second convex portions 3612 aligned with the first and second concave portions 3512 of the staple crown 3510 and, also, an intermediate concave portion 3614 aligned with the convex intermediate portion 3514 of the staple crown 3510.

Figure 25:
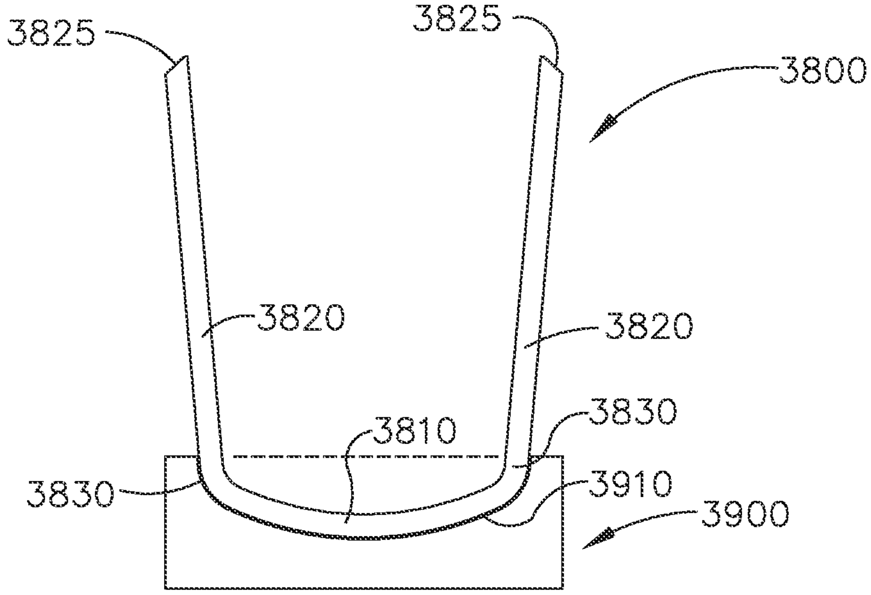
FIG. 25 is an elevational view of a wire staple and a staple driver in accordance with at least one embodiment.

In at least one example, referring to FIG. 25, a wire staple 3800 comprises a crown 3810, a first leg 3820 extending from the crown 3810, and a second leg 3820 extending from the crown 3810. The wire staple 3800 comprises bends 3830 that connect the legs 3820 to the crown 3810. The crown 3810 comprises a curved portion and the first and second legs 3820 extend from the ends of the curved portion. The curved portion comprises a catenary shape, but could comprise any suitable shape. Similar to the above, the staple 3800 is driveable by a corresponding staple driver 3900 configured to drive the staple 3800 out of a staple cartridge which comprises a seat 3910 that pushes on a bottom surface of the staple 3800. The driver seat 3910 is in full contact with the staple crown 3810 such that there are no gaps between the driver seat 3910 and the staple crown 3810.

Figure 35:
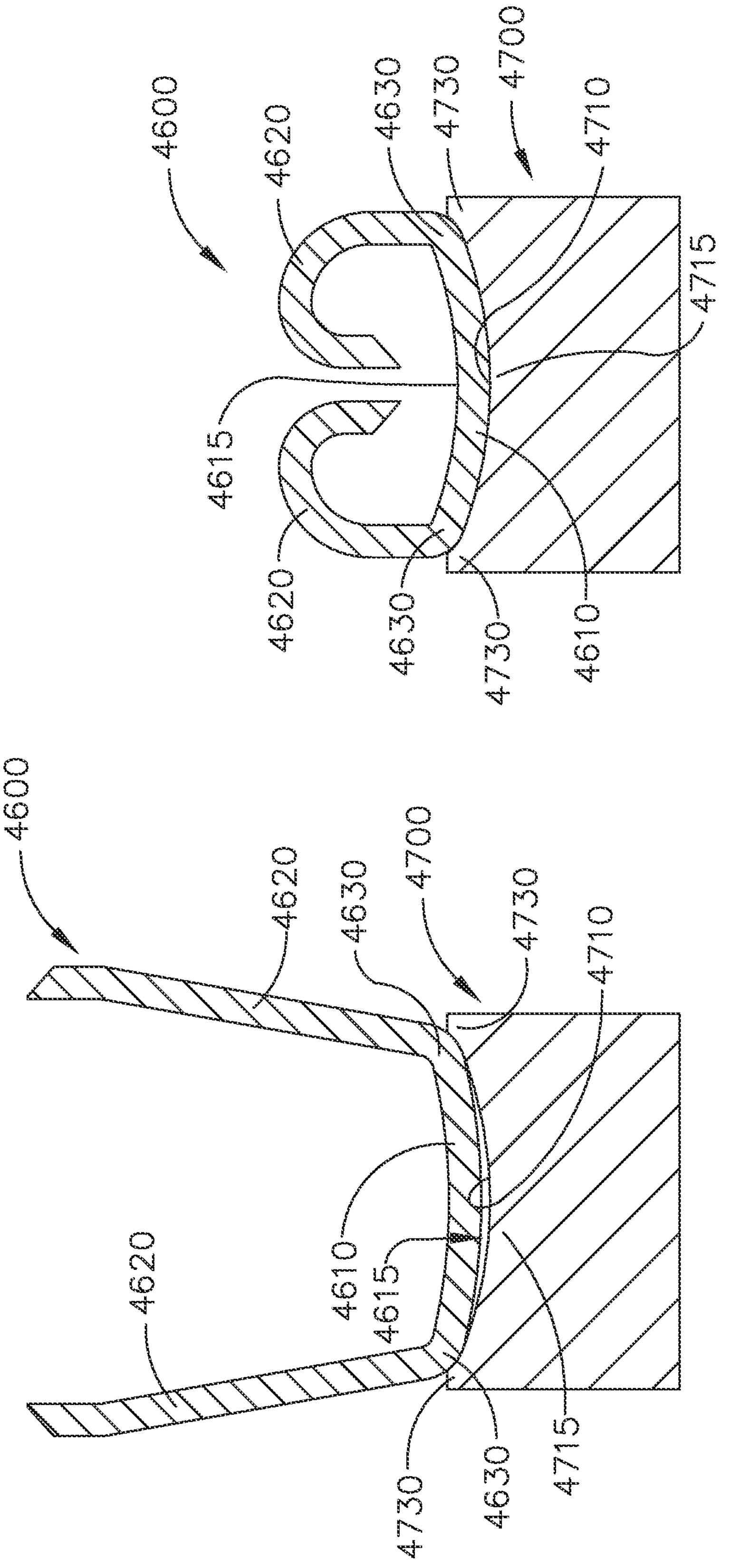
FIG. 35 is a cross-sectional view of a wire staple and a staple driver in accordance with at least one embodiment illustrating the wire staple deflecting into contact with the staple driver during the staple firing process.

In various embodiments, referring to FIG. 35, a wire staple 4600 is configured to be driven by a staple driver 4700 during a staple firing stroke that deflects relative to the staple driver 4700. The staple 4600 comprises a crown 4610, legs 4620, and bends 4630 that connect the legs 4620 to the crown 4610. The staple driver 4700 comprises a seat 4710 defined therein configured to receive the staple crown 4610. As illustrated in FIG. 35, the driver seat 4710 does not fully contact the bottom surface of the staple crown 4610, at least not when the driver 4700 and the staple 4600 are in their unfired positions. Rather, only the ends 4730 of the driver seat 4710 are in contact, or are capable of contacting, the bottom drive surface of the staple 4600 while the driver 4700 and the staple 4600 are in their unfired position. Stated another way, the middle 4715 of the driver seat 4710 is not in contact with the bottom drive surface of the staple 4600 when the driver 4700 and the staple 4600 are in their unfired positions. As the driver 4700 is lifted upwardly to fire the staple 4600, the ends 4730 of the driver seat 4710 push the staple 4600 upwardly toward and anvil while the middle portion 4715 of the driver seat 4710 does not contact the staple 4600 until the staple legs 4620 contact the anvil. More specifically, the middle 4615 of the staple crown 4610 deflects into contact with the middle 4715 of the staple driver 4710 after the staple legs 4620 come into contact with the anvil and a significant firing force is transmitted through the staple 4600. Once the middle portion 4615 of the staple crown 4610 deflects into contact with the driver seat 4710, the entire driver seat 4710, or substantially all of the driver seat 4710, is in contact with staple crown 4610 such that the firing force is distributed across the crown 4610. Such an arrangement reduces the possibility of the staple bends 4630 cracking and/or fracturing during the staple firing process. In at least one example, the downward deflection of the staple crown 4610 causes plastic deformation within the crown 4610 such that the crown 4610 at least partially permanently assumes the shape of the driver seat 4710 during the staple firing process.

Figure 36:
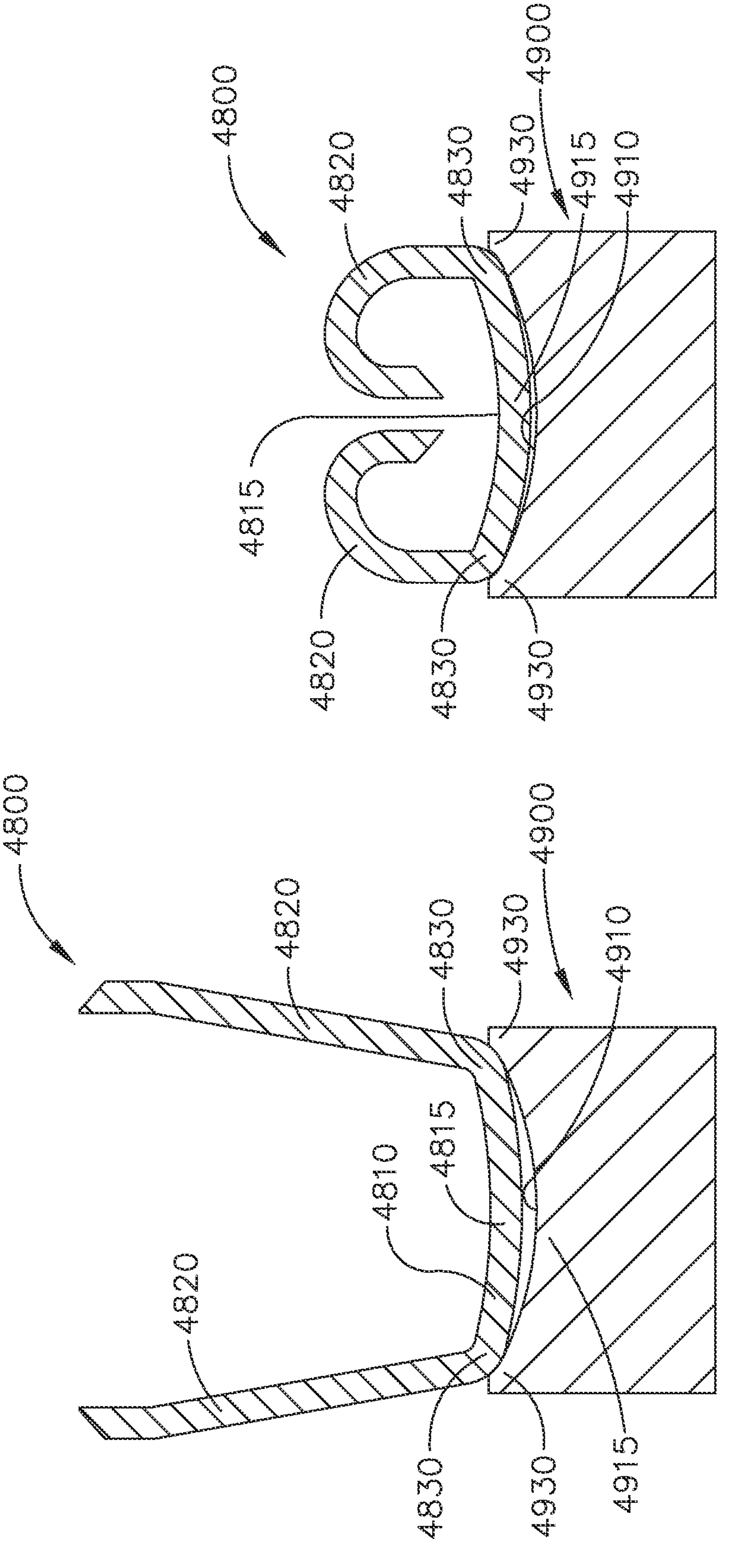
FIG. 36 is a cross-sectional view of a wire staple and a staple driver in accordance with at least one embodiment illustrating the wire staple deflecting downwardly toward a seat of the staple driver during the staple firing process.

In various other embodiments, further to the above, a wire staple 4800 is driven by a staple driver 4900 where, although the staple 4800 deflects downwardly toward the staple driver 4900 during the staple firing process, the entire crown of the staple 4800 does not come into contact with the staple driver 4900. Referring to FIG. 36, the staple 4800 comprises a crown 4810, legs 4820, and bends 4830 that connect the legs 4820 to the crown 4810. The staple driver 4900 comprises a seat 4910 defined therein including seat ends 4930 which are in contact with the bends 4830 of the staple 4800 when the staple 4800 and the driver 4900 are in their unfired positions. Notably, the center 4815 of the crown 4810 is not in contact with the center 4915 of the driver seat 4910 when the staple 4800 and the driver 4900 are in their unfired positions. As the staple 4800 is lifted upwardly by the driver 4900 and deformed against an anvil, the center 4815 of the crown 4810 deflects downwardly toward the center 4915 of the driver seat 4910 but does not come into contact with the driver seat 4910.

In at least one example, in contrast with the above, the middle of the staple crown is in contact with the middle of the staple driver and the ends of the staple crown are not in contact with the driver when the driver and the staple are in their unfired positions. As the driver is lifted upwardly toward the anvil, the driver seat pushes on the middle of the staple crown until the staple legs contact the anvil. At such point, the bends connecting the staple legs to the crown are pushed down into contact with the driver seat such that the entire bottom drive surface of the staple, or nearly all of the bottom drive surface, is in contact with the staple driver such that the firing force transmitted through the staple is distributed across the crown. Such an arrangement reduces the possibility of the staple bends cracking and/or fracturing during the staple firing process. In at least one example, the downward deflection of the staple crown causes plastic deformation within the crown such that the crown at least partially permanently assumes the shape of the driver seat during the staple firing process. In addition, the bends of the staple can be contoured by the driver seat as the staple is being deformed against the anvil. In at least one instance, the bends of the staple have a large radius of curvature when the staple is loaded into the staple cartridge which is reduced as the staple is being deformed.

Figure 34:
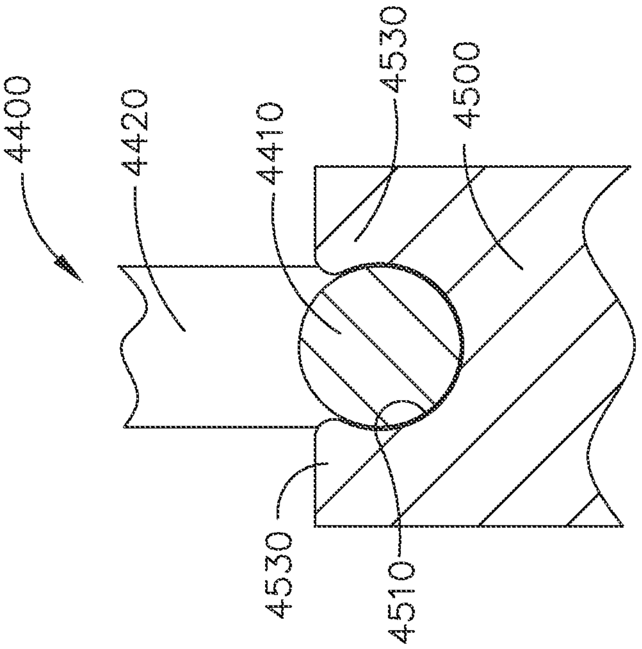
FIG. 34 is a cross-sectional view of a wire staple positioned in a different staple driver in accordance with at least one embodiment.

In at least one example, referring to FIGS. 27-32, a staple cartridge comprises a staple driver 4100 includes a seat 4110 that releasably holds a wire staple 4000 in the driver seat 4110. The staple 4000 comprises a crown 4010, legs 4020, and bends 4030 connecting the legs 4020 to the crown 4010. In addition to the seat 4110, the staple driver 4100 further comprises a cam portion 4120 configured to be engaged by a sled during a staple firing stroke to lift the staple driver 4100 and the staple 4000 toward an anvil positioned opposite the staple cartridge. The staple driver 4100 further comprises guides 4130 that interface with slots defined in the staple cartridge that keep the staple driver 4100 and the staple 4000 aligned with forming pockets positioned opposite the staple 4000. The driver seat 4110 further comprises a first seat end that holds a first bend 4030 of the staple 4000 and a second seat end that holds a second bend 4030 of the staple 4000. The first seat end comprises an internal slot that receives the first bend 4030 that is at least partially defined by sidewalls 4112 and 4114 forming a wedge configuration. The distance between the sidewalls 4112 and 4114 is the same as, or slightly smaller than, the diameter of the staple wire such that there is an interference fit between the staple 4000 and the driver seat 4110. The second seat end comprises a similar arrangement. As a result, the staple driver 4100 grips and holds the staple 4000 thereby limiting relative movement between the staple 4000 and the staple driver 4100 during the staple firing process. Such an arrangement reduces the possibility of the staple 4000 slipping or sliding relative to the staple driver 4100. The driver 4100 detaches from the staple 4000 during the staple firing process or, in various instances, the driver 4100 detaches from the staple 4000 after the staple firing process when the jaws of the stapler are opened and the staple cartridge is moved away from the stapled tissue. In this example, the walls of the staple seat 4110 hold the staple 4000 from the sides and do not extend over any portion of the staple 4000. In at least one other example, referring to FIG. 34, a staple driver 4500 comprises a seat 4510 including a wall and/or catch 4530 that extends over the crown 4410 of a staple 4400, for example, that releasably holds the staple 4400 to the staple driver 4500. In at least one such example, the catch 4530 deflects during the staple firing process to release the staple 4400 from the staple driver 4500.

In at least one example, a material is inserted into the staple cavities of a staple cartridge to hold the staples in their unfired position. In at least one example, a mixture including sodium stearate and water is poured and/or otherwise deposited into the staple cavities of a staple cartridge. The mixture flows down over the staples and then dries. Once dried, or at least partially dried, the sodium stearate releasably holds the staples in their unfired positions and prevents, or at least inhibits, the staples from falling out of their staple cavities. When the staple cartridge is loaded into a stapling instrument and then inserted into a patient, fluids within the patient may come into contact with the dried sodium stearate and soften it. Whether or not the sodium stearate is softened, the staples break free from the sodium stearate as the staples are being fired. In various instances, portions of the sodium stearate may remain attached to the staples after the staples have been implanted.

Further to the above, certain portions of a staple can undergo a hardening process while other portions of the staple can undergo a softening process. For instance, a staple comprises a crown, legs, and bends connecting the legs to the crown wherein the bends are softened through an annealing process and the tips of the legs are hardened through a quenching process, for example. In at least one such instance, the entire staple is heated which is permitted to cool slowly except for the tips of the staple legs which are exposed to a cold fluid such as cold gaseous nitrogen and/or dipped in a cold hydrocarbon, for example. In other processes, only portions of the staple are heated. In at least one such instance, only the bends and the staple tips are heated with only the staple tips being actively cooled in a cooling process. Such processes can create staples having staple tips which are hard enough to interact with a metal anvil and bends capable of enduring the staple firing process without cracking or fracturing.

In at least one example, the tips of the staple legs are coated with a hard lubricious material to reduce the friction between the staple legs and the anvil. In at least one instance, a staple is comprised of a magnesium or magnesium alloy wire having staple legs at least partially covered with magnesium nitride. In other instances, boron nitride could be used, for example. In at least one instance, a sputtering process can be used to deposit the coating on the staple legs. In at least one example, only the tips of the staple legs are covered with the coating. In at least one such example, the portions of the staple that are not to be coated are masked and/or otherwise covered during the coating application process. In various instances, a process, such as a sputtering process, for example, can apply the coating on the metal wire substrate in a stippled, or dot, pattern. In at least one instance, the coating is applied to the metal wire substrate at a constant density, or an at least substantially constant density, across the covered surface. In at least one other example, the density of the coating on a first section of the metal wire substrate has a first density and the density of the coating on a second section of the metal wire substrate has a second density than the first density. In at least one instance, the density of the coating at the tips of the staple legs is the highest and the density of the coating gradually decreases away from the tips of the staple legs.

In addition to or in lieu of a hard lubricious coating on a staple, further to the above, an anvil can be at least partially coated with a hard lubricious coating. In at least one embodiment, the coating on the anvil is harder than the coating on the staples and harder than the metal wire substrate of the staples deformed against the anvil. In at least one instance, the anvil is comprised of at least one of stainless steel and titanium and at least portions of the anvil is coated with titanium nitride. In at least one such instance, the anvil has forming pockets configured to receive and deform the legs of the staples and only the forming pockets are coated with titanium nitride, for example.

In at least one example, further to the above, a length of metal wire is drawn form a spool of wire and cut to length. As part of this cutting process, the metal is sheared such that the ends of the wire length have sharp ends which become the staple tips when the wire length is formed into a staple. In at least one instance, the cutting process creates a transverse angled cut within the metal wire to create an angled flat penetration surface at each staple tip. The angled flat penetration surfaces face outwardly but, in other embodiments, the angled flat penetration surfaces face inwardly. Referring to FIG. 25, a staple 3800 comprises legs 3825 having tips 3825 that have outwardly facing surfaces. In at least one example, the angled flat penetration surfaces extend at an angle that is larger than 45 degrees from a plane extending through the tips of the staple legs. In at least one example, the angle is about 50 degrees, for example. In another example, the angle is about 60 degrees, for example. In a different example, the angle is about 70 degrees, for example. In another example, the angle is about 80 degrees, for example. In at least one other example, the staple tips comprise a non-linear penetration surface, such as curved penetration surface, for example. In at least one instance, the curved penetration surface comprises a concave penetration surface while, in other instances, the curved penetration surface comprises a convex penetration surface. In at least one other example, each staple tip comprises two linear portions that define a penetration surface.

Figure 26:
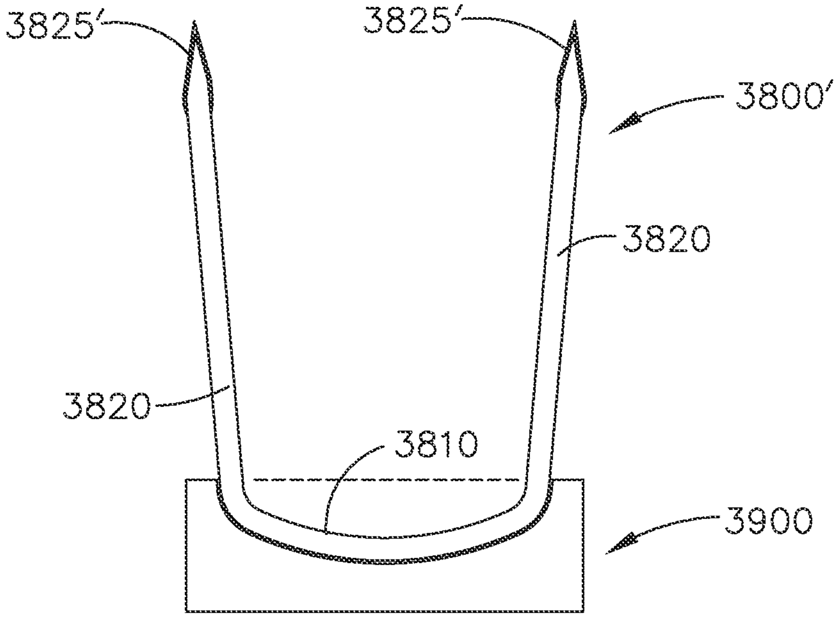
FIG. 26 is an elevational view of a wire staple in accordance with at least one embodiment comprising staple tips that are sharper than the staple tips of the staple of FIG. 25.
Figure 27:
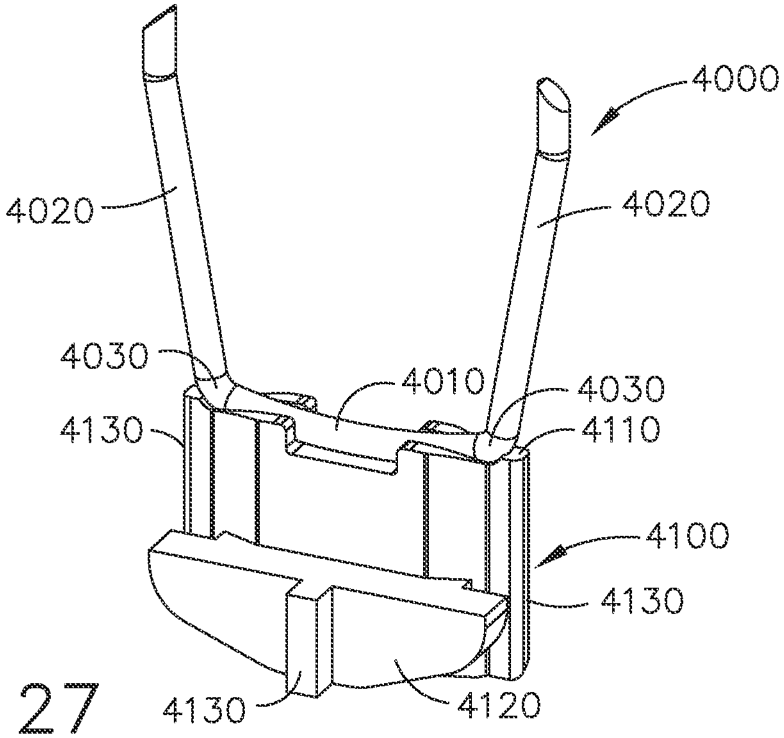
FIG. 27 is a perspective view of a wire staple and a staple driver in accordance with at least one embodiment.
Figure 28:
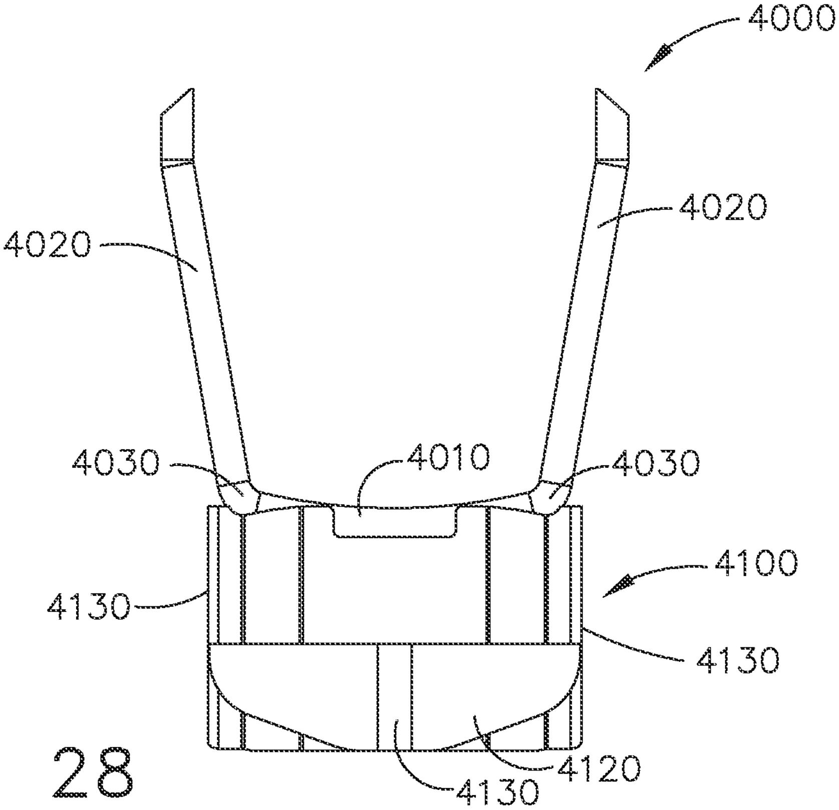
FIG. 28 is an elevational view of the wire staple and staple driver of FIG. 27.
Figure 29:
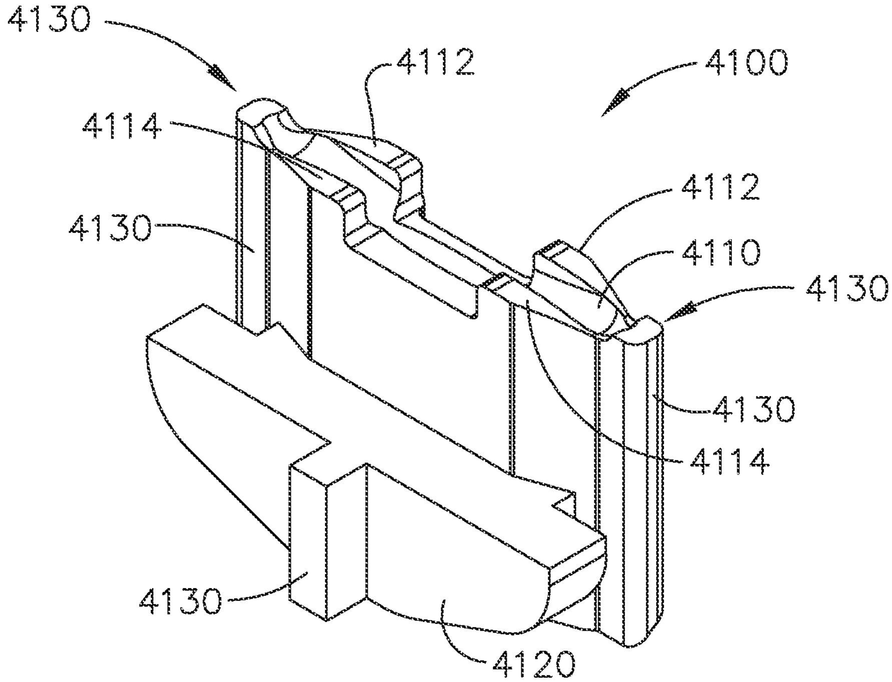
FIG. 29 is a perspective view of the staple driver of FIG. 27.
Figure 30:
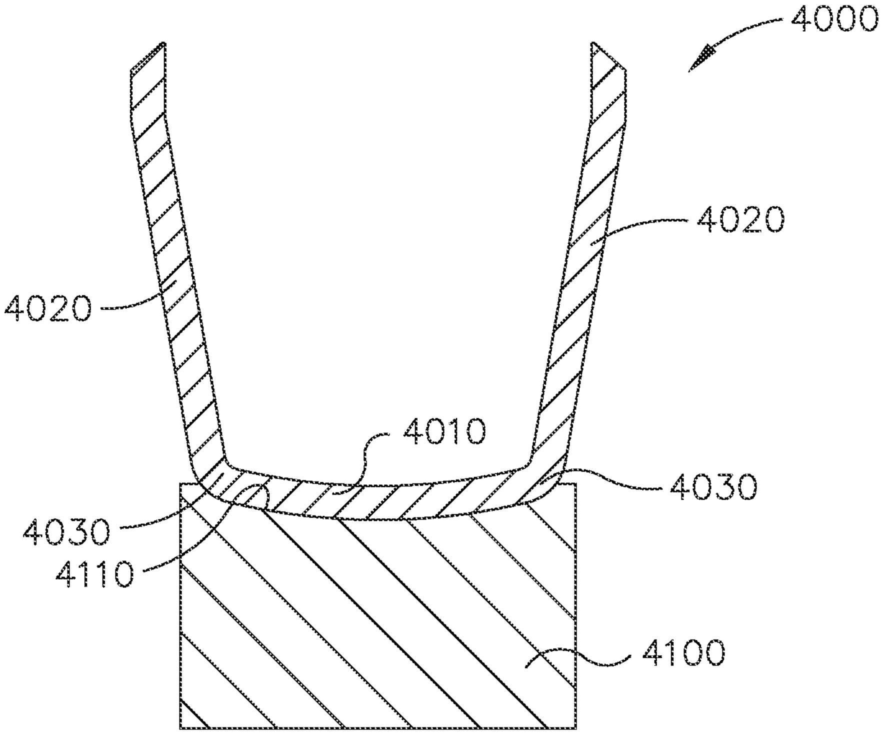
FIG. 30 is a cross-sectional view of the wire staple and staple driver of FIG. 27.
Figure 31:
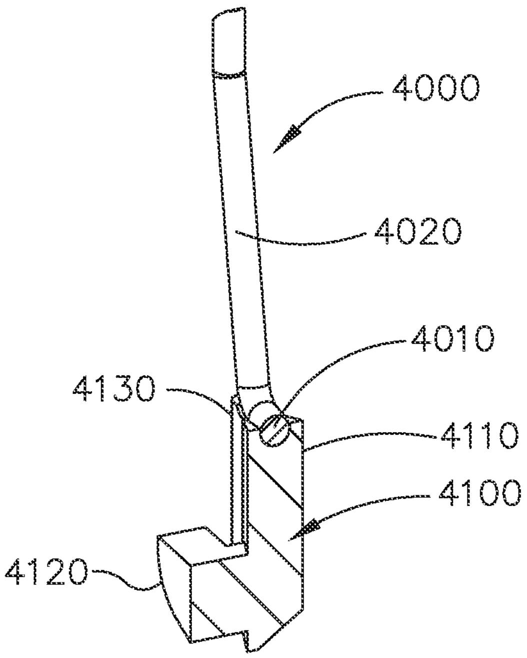
FIG. 31 is a cross-sectional view of the wire staple and staple driver of FIG. 27.
Figure 32:
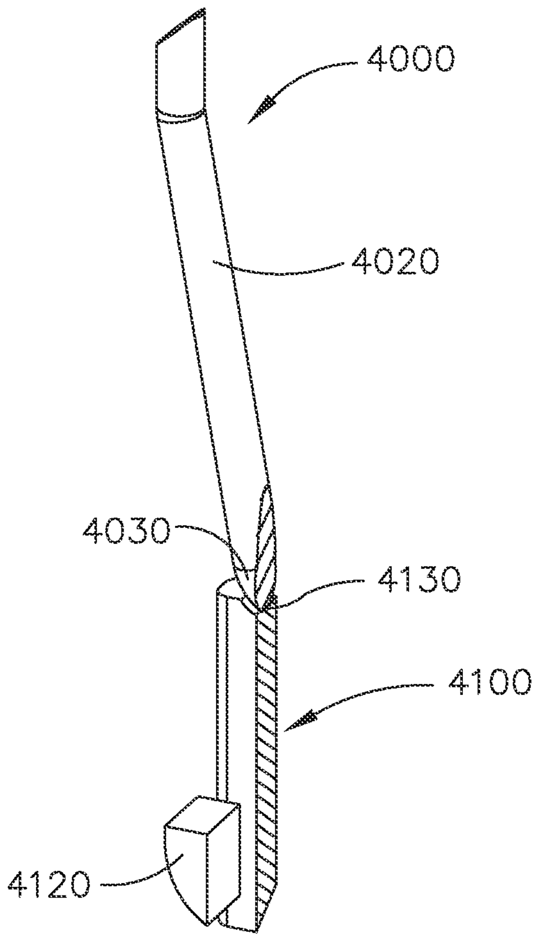
FIG. 32 is a cross-sectional view of the wire staple and staple driver of FIG. 27.

Referring to FIG. 26, a staple 3800' comprises leg tips 3825' that are each defined by two flat surfaces that meet at a sharp point. Such embodiments are useful for penetrating tough tissue, especially when the metal comprising the substrate of the staple is soft and/or brittle, for example. Such embodiments are useful for staples comprised of pure magnesium, magnesium alloys, zinc, zinc alloys, iron, and/or iron alloys, for example. In various embodiments, the leg tips 3825' are coated with a hard material such as a nitride, for example, to facilitate the insertion of the leg tips 3825' through the patient tissue such that the leg tips 3825' properly engage the anvil forming pockets during the staple firing process.

As discussed above, various staple cartridges comprise a cartridge body and staples removably stored in the cartridge body. In various embodiments, the cartridge body comprises a proximal end, a distal end, and a deck extending between the proximal end and the distal end. The deck is configured to support the patient tissue clamped against the staple cartridge and includes longitudinal rows of staple cavities defined in the deck. The deck further comprises a longitudinal slot extending from the proximal end toward the distal end that is configured to receive a tissue cutting knife. The longitudinal slot extends between three longitudinal rows of staple cavities defined on one side of the longitudinal slot and three longitudinal rows of staple cavities on the opposite side of the longitudinal slot. In various examples, a single staple is stored in each staple cavity. The staple cartridge further comprises a sled that is moved from the proximal end toward the distal end during a firing stroke that sequentially ejects the staples from the staple cartridges as the sled progressively moves distally from the proximal end. An anvil positioned opposite the staple cartridge comprises six longitudinal rows of forming pockets where each of the forming pockets is registered with a staple cavity defined in the staple cartridge such that each forming pocket deforms a single staple.

As described above, the staples stored within a staple cartridge are moved from an unfired position to a fired position during a staple firing stroke. In various examples, the tips of the staple legs are positioned below the deck of the staple cartridge when the staples are in their unfired position. As the staples are pushed into their fired positions, the tips of the staple legs emerge above the deck of the staple cartridge and puncture the patient tissue positioned above the staple. The tips of the staple legs then exit the patient tissue and contact the anvil and are deformed back toward the tissue. In various instances, the tips of the staple legs re-puncture the patient tissue as the staple is being deformed into its fully-fired configuration. Depending on the thickness of the tissue being stapled and/or the force used to deform the staples, among other things, the staples may assume a lightly-clenched formed configuration, a highly-clenched formed configuration, or somewhere in-between. All such formed configurations can be referred to as a B-shaped formed configuration; however, the lightly-clenched formed staples have a loose B-shaped configuration while the highly-clenched formed staples have a tight B-shaped configuration. In a highly-clenched configuration, for instance, the tips of the staple legs may approach the crown of the staple during the forming process. In many instances, it is desirable for the staple tips to not be deformed past the crown.

Figure 33:
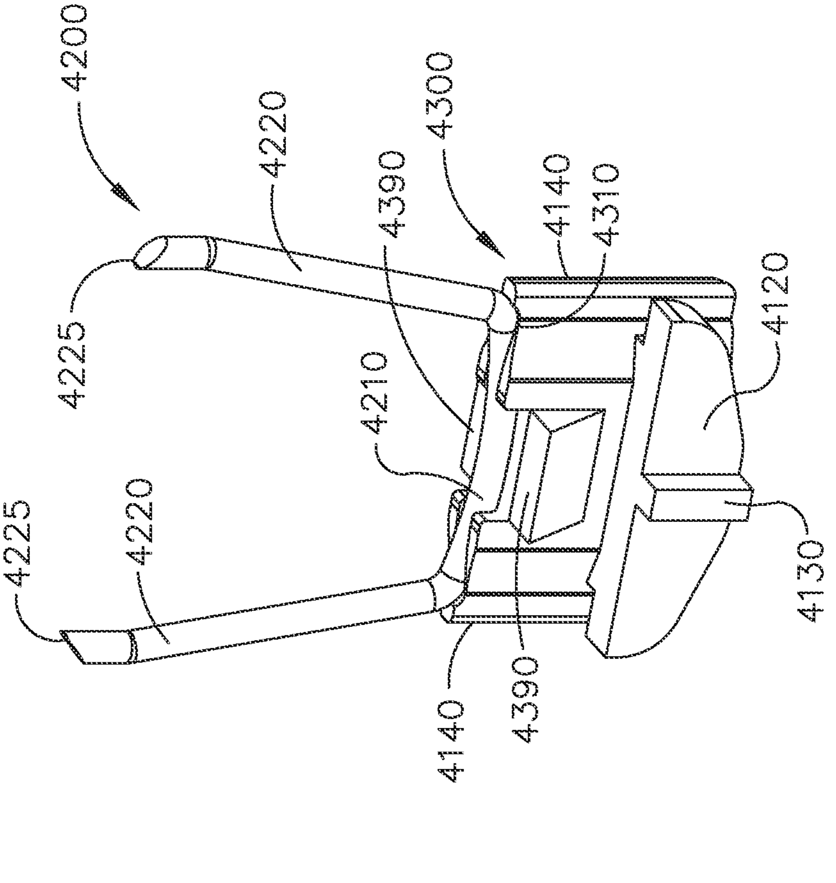
FIG. 33 is a perspective view of a wire staple and a staple driver in accordance with at least one embodiment.

In various embodiments, referring to FIG. 33, a staple driver 4300 is configured to drive a staple 4200 during a staple firing stroke. The staple 4200 comprises a crown 4210 and legs 4220 extending from the crown 4210 where each leg 4220 comprises a sharp staple tip 4225. The staple driver 4300 comprises a seat 4310 that receives and pushes on the crown 4210 of the staple 4200. The staple driver 4300 further comprises a platform and/or lateral flanges 4390 which comprise stop surfaces for the staple tips 4225 such that the staple 4200 does not become over-clenched during the staple firing process. In at least one such embodiment, the staple driver 4300 is comprised of metal, such as stainless steel and/or titanium, for example, which is strong enough to stop further clenching of the staple 4200. In at least one embodiment, the staple drivers 4300 are comprised of plastic that is plated and/or coated with metal.

In various embodiments, further to the above, a staple cartridge is configured to prevent the staples deployed therefrom from being over-deformed or over-clenched. In at least one embodiment, a staple cartridge comprises a stop extending upwardly from the distal end of the staple cartridge. The stop is sized and configured to set a minimum gap between the staple cartridge and an anvil positioned opposite the staple cartridge such that, when the staples are deformed against the anvil, the staples are formed to a desired height. In at least one such embodiment, the stop is positioned distally with respect to all of the staple cavities. In at least one such embodiment, one or more stops are positioned at the distal ends of the staple rows. In at least one embodiment, a staple cartridge comprises gap setting elements that are deployed during the staple firing stroke which, when lifted, can push the anvil to a desired minimum distance away from the staple cartridge. In at least one such embodiment, the gap setting elements are positioned in a staple cavity in the outermost staple rows, for example, and are pushed upwardly toward the anvil by a sled moving distally during the staple firing stroke. In at least one such embodiment, the deployable gap setting elements are comprised of solid plastic. In at least one such embodiment, a deployable gap setting element comprises a first component, a second component, and a spring element positioned intermediate the first component and the second component which can provide for a variable gap height setting element.

In various instances, further to the above, the staple legs may begin to splay outwardly as the staple legs emerge above the deck. More specifically, the staples have a substantially V-shaped configuration before being loaded into the staple cavities that is resiliently deflected into a substantially U-shaped configuration as the staples are loaded into the staple cavities such that the staple legs, absent more, resiliently splay outwardly as they emerge from the constraints of the staple cavity side walls. In most instances, the splaying staple legs still contact the appropriate, or registered, forming pockets in the anvil during the staple firing process. That said, the splaying staple legs can be further deflected by the patient tissue and can miss the registered forming pockets in some instances. Discussed below are embodiments that limit and/or control the leg splay.

Figure 38:
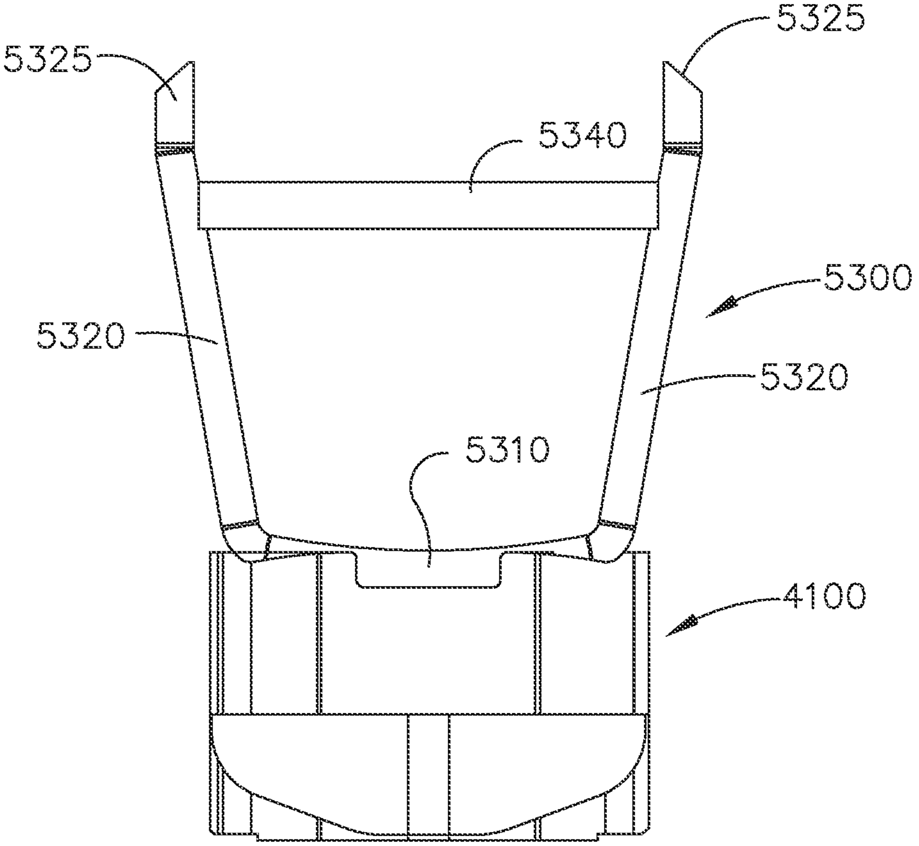
FIG. 38 is a perspective view of a staple and a staple driver in accordance with at least one embodiment.
Figure 38A:
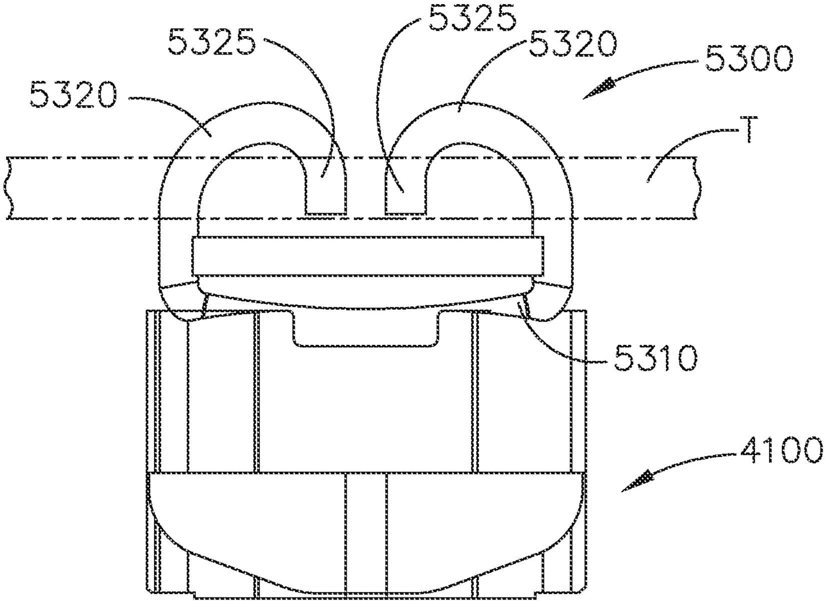
FIG. 38A depicts the staple of FIG. 38 in a fired configuration.

In at least one embodiment, referring to FIG. 38, a staple 5300 comprises a crown 5310, legs 5320 extending from the crown 5310 comprising leg tips 5325, and a connector 5340 positioned above the crown 5310 that connects the legs 5320. In at least one example, the crown 5310 and the legs 5320 are comprised of a metal wire and the connector 5340 comprises an absorbable polymer such as PGA and/or PLLA, for example. The connector 5340 is positioned below the deck of a staple cartridge when the staple 5300 is in its unfired position and emerges above the deck as the staple 5300 is being fired, or pushed upwardly toward an anvil by a staple driver 4100. The connector 5340 prevents, or at least substantially limits, the staple legs 5320 from splaying outwardly until the connector 5340 contacts the patient tissue T. When the connector 5340 contacts the patient tissue T, in at least one example, the connector 5340 slides down the staple legs 5320 which allows the staple legs to splay outwardly. In at least one such example, the connector 5340 is parallel, or at least substantially parallel, to the crown 5310 and slides down toward the crown 5310 in a parallel manner. In at least one other example, one end of the connector 5340 is higher than the other. In at least one example, the connector 5340 is frangible and is configured to break when the connector 5340 touches the patient tissue T. In various instances, the connector 5340 completely detaches from the staple legs 5320 during the staple firing process. In some instances, one or more portions of the connector 5340 remain attached to the staple legs 5320 which can slide down the staple legs 5320 as the staple 5300 is being fired.

Figure 37:
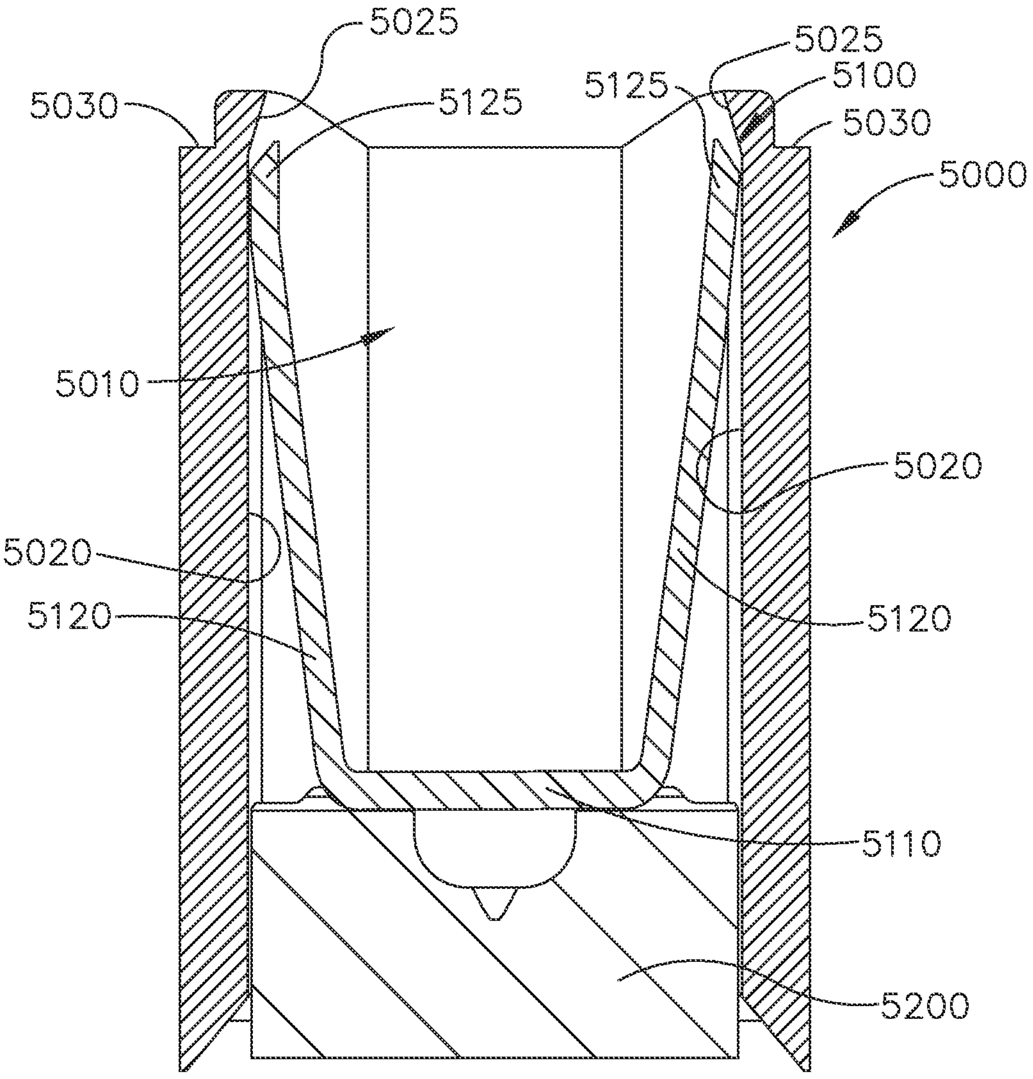
FIG. 37 is a partial cross-sectional view of a staple cartridge include staple cavities, staple drivers movably positioned within the staple cavities, and staples ejectable from the staple cavities.

In addition to or in lieu of the above, referring to FIG. 37, a staple cartridge comprises a cartridge body 5000 including a deck 5030 and staple cavities 5010 defined in the deck 5030, staples 5100 removably stored in the staple cavities 5010, and staple drivers 5200 configured to drive the staples 5100 out of the staple cavities 5010. Each staple 5100 comprises a crown 5110 and legs 5120 extending upwardly and outwardly from the crown 5120. The staple legs 5120 are in contact with sidewalls 5020 of the staple cavities and are resiliently deflected inwardly by the sidewalls 5020. of a staple cartridge comprises staple cavity extenders 5025 which extend upwardly from a deck 5030 of the cartridge body 5000. The cartridge body 5000 further comprises staple cavity extenders 5025 that prevent, or at least inhibit, the staple legs 5120 from splaying outwardly and/or otherwise becoming misaligned with the forming pockets in the anvil positioned opposite the staple cartridge during the staple firing process. In at least one example, the staple cavity extenders 5025 extend the sidewalls 5020 of the staple cavities 5010 above the deck 5030 such that the sidewalls 5020 extend in a continuous direction through the staple cavity extenders 5025. In at least one other example, the sidewalls 5020 of the staple cavities 5010 extending through the staple cavity extenders 5025 extend inwardly to camber the legs 5020 inwardly during the staple firing process to provide a greater control over the staple legs 5020. In either event, the tips 5125 of the staple legs 5120 are positioned in and/or aligned with the staple cavity extenders 5025 when the staples 5100 are in their unfired position, as illustrated in FIG. 37. Thus, the staple cavity extenders 5125 can maintain control of the staple legs 5120 throughout the staple firing process or at least until the staples 5100 are overdriven out of the staple cavities 5010 above the deck 5030.

In various embodiments, further to the above, the staple cavity extenders at the distal ends of the staple lines are taller than other staple cavity extenders in the staple lines. The taller staple cavity extenders serve an additional purpose of setting a minimum tissue gap between the staple cartridge and the anvil.

In various embodiments, a surgical stapling instrument comprises an end effector including first and second jaws, a motor-driven jaw closure system, and a separate and distinct motor-driven staple firing system. The surgical stapling instrument further comprises a control system including a closure actuator that, when actuated, causes the jaw closure system to close the jaws of the end effector and a firing actuator that, when actuated, fires the staples from a staple cartridge seated in the end effector. In use, the motor-driven jaw closure system is actuated until the jaws are completely closed and then the motor-driven staple firing system is actuated. In some instances, however, the completely closed jaws, depending on the thickness of the tissue captured between the jaws, may have a narrow gap therebetween resulting in the staples being overformed during the staple firing stroke. In at least one embodiment, the control system of the surgical stapling instrument is configured to run the closure drive in reverse to at least slightly back off or reduce the clamping pressure on the patient tissue while the staple firing stroke is being performed. Owing to the closure drive being partially backed up, the gap between the anvil and staple cartridge can increase thereby reducing the possibility of the staples being overformed during the staple firing stroke. In at least one instance, the closure drive is backed up at the beginning of the staple firing stroke. In at least one instance, the closure drive is backed up during the last half of the staple firing stroke. In at least another instance, the closure drive is backed up during the last quarter of the staple firing stroke. The appropriate time for selecting when to back up the closure drive can be based off of previously collected data and/or real-time data collected by the control system during the staple firing stroke. In at least one such instance, the control system comprises a circuit configured to detect the electric current to the motor and, when the current exceeds a predetermined threshold, back up the closure drive a predetermined distance and/or back up the closure drive until the current to the motor falls below the predetermined threshold, for example.

Various staples disclosed herein are comprised of metal or metal alloys such as stainless steel, titanium, magnesium, and/or magnesium alloy, for example. In various instances, a staple is manufactured by cutting and forming a wire which is then positioned in a staple cartridge. In other instances, staples are manufactured from a sheet of material that is cut and/or stamped which are then positioned in a staple cartridge. During the manufacturing and assembly processes, the staples may be exposed to water, air, oxygen, carbon dioxide, or corrosive agents which can degrade the integrity of the raw material and/or the staple. In use, the staples are exposed to bodily fluids when implanted in a patient which can corrode the staples. For one or more reasons, it is advantageous to coat the staples during a staple manufacturing process, during an assembly processes in which the staples are positioned in a staple cartridge, and/or after the staples have been assembled into the staple cartridge.

In various embodiments, further to the above, an initial coating and/or lubricant is applied to wire stock before it is cut and formed into staples. Once the wire stock is cut and formed into staples, additional coatings and/or lubricants can be applied to the staples. The additional coatings and/or lubricants may be the same or different than the initial coating and/or lubricant, for example. Further, once the staples are placed into a staple cartridge, additional coatings and/or lubricants can be applied to the staples and/or portions of the staple cartridge, for example. The coatings and/or lubricants applied during assembly may be the same or different than the previously-applied coatings and/or lubricants. In view of the above, various combinations of coatings and/or lubricants can be utilized during the manufacture of surgical staples and/or the assembly of surgical staple cartridges.

In various embodiments, a lubricant, such as a soap, for example, is applied to a staple at various stages of its manufacture, during its assembly into a staple cartridge, and/or in use. The lubricant can be applied directly onto the substrate of the staple if there is no coating already present on the staple or on top of an absorbable coating already on the substrate. In various embodiments, a lubricant can include, but is not limited to magnesium stearate, sodium stearate, calcium stearate, ethyl lauroyl arginate (LAE), a solution of LAE and sodium stearate, a solution of LAE and calcium stearate, a solution of LAE and magnesium stearate, and/or combinations thereof. Ethyl lauroyl arginate LAE is a lubricant which acts as both an anti-microbial material and as a dried soap lubrication. Further, when LAE is combined with sodium stearate, calcium stearate, and/or magnesium stearate in a solution, the resulting solution may be thinner, have a more consistent drying rate, and may better adhere to the staple surfaces it is applied to—and/or dried on—as compared to such substances without the use of LAE.

In various embodiments, a lubricant, such as those described above, is applied to the staple using a soap solution which can comprise water, alcohol, and/or other solvents which are aqueous, for example. In such embodiments, the soap solution further comprises a solute which is non aqueous. After the lubricant, or soap solution, is coated onto its intended surface, the solvent will eventually evaporate leaving the solute behind to coat the surfaces covered in the soap solution. In various embodiments, the sodium stearate, LAE, sodium stearate with LAE, calcium stearate with LAE, magnesium stearate with LAE, and/or combinations thereof, for example, are left behind on the staples and/or staple cartridge. In various embodiments, the soap solution, or lubricant, is applied onto wire stock or a sheet of material, whether previously coated or uncoated, and is dried, or permitted to dry, before it is cut and formed into staples. In other embodiments, the lubricant is still wet when the staples formed which can reduce damage to the substrate and/or coating during the staple manufacturing process. In addition to or in lieu of the above, the formed staples are coated with a lubricant before the formed staples are loaded into a staple cartridge. In various instances, the lubricant is still wet when the staples are loaded into the staple cartridge which can facilitate the insertion of the staples into the staple cartridge. In addition to or in lieu of the above, the staples are coated with a lubricant after the staples are loaded into the staple cartridge. In such instances, the lubricant can cover any exposed surfaces and facilitate the ejection of the staples from the staple cartridge.

Figure 68:
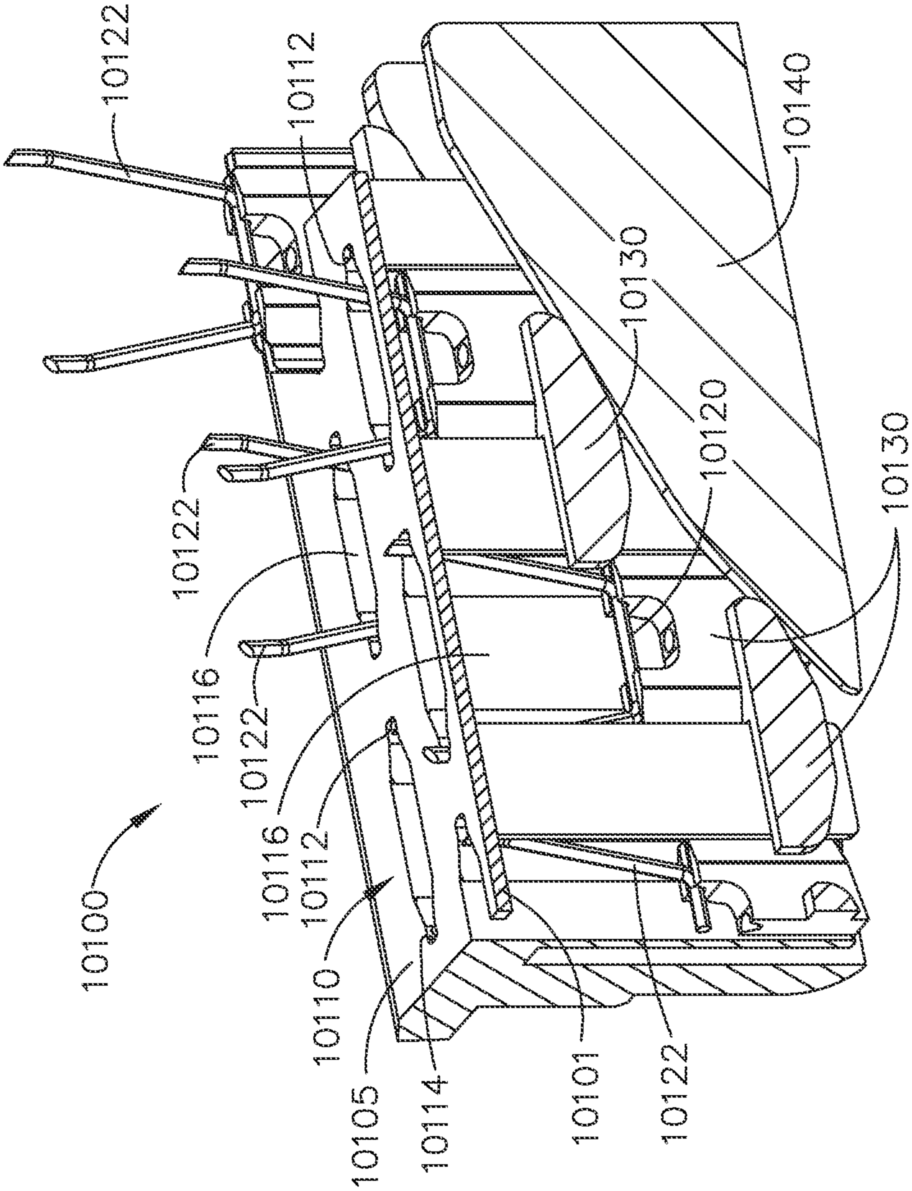
FIG. 68 is a perspective view of a surgical staple cartridge including staples, staple drivers, and a sled configured to eject the staples from the staple cartridge.

FIG. 68 illustrates a staple cartridge 10100 including a cartridge body 10101 and staples 10120 positioned in staple cavities 10110 defined in the cartridge body 10101. The staples 10120 are wire staples formed from a wire which has been cut and bent to form the staples 10120. In other embodiments, the staples 10120 are stamped from a sheet of material. In at least one embodiment, the staples 10120 are positioned into the cavities 10110 using a staple assembly tool 10310 illustrated in FIG. 70. The staple cavities 10110 define openings in a staple deck surface 10105 of the cartridge body 10101 and the staples 10120 are configured to be ejected through the openings. Each staple cavity 10110 comprises a proximal end wall 10112, a distal end wall 10114, and two opposing lateral sidewalls 10116 which form the staple cavity 10110. When each staple 10120 is positioned in its respective staple cavity 10110, staple legs 10122 of the staple 10120 are pressed, or resiliently biased, against the proximal and distal end walls 10112, 10114 to at least partially retain the staples 10120 in the staple cavities 10110. When the staples 10120 and the staple drivers 10130 are in an unfired position, the staples 10120 rest on staple drivers 10130 positioned within the cartridge body 10101 of the staple cartridge 10100. The staple drivers 10130 are movable from an unfired position (FIG. 68) to a fired position by a sled 10140 to eject the staples 10120 from the staple cavities 10110. Each staple 10120 comprises staple legs 10122 that extend above the staple deck 10105 when the staples 10120 are in their unfired positions in the cartridge body 10101. Other embodiments are envisioned where the staple legs 10122 do not extend above the staple deck 10105 when the staples 10120 are in their unfired position. Various combinations of different wire staple sizes and shapes as well as different driver sizes and shapes can determine whether or not the staple legs 10122 extend above the deck surface 10105.

Figure 69:
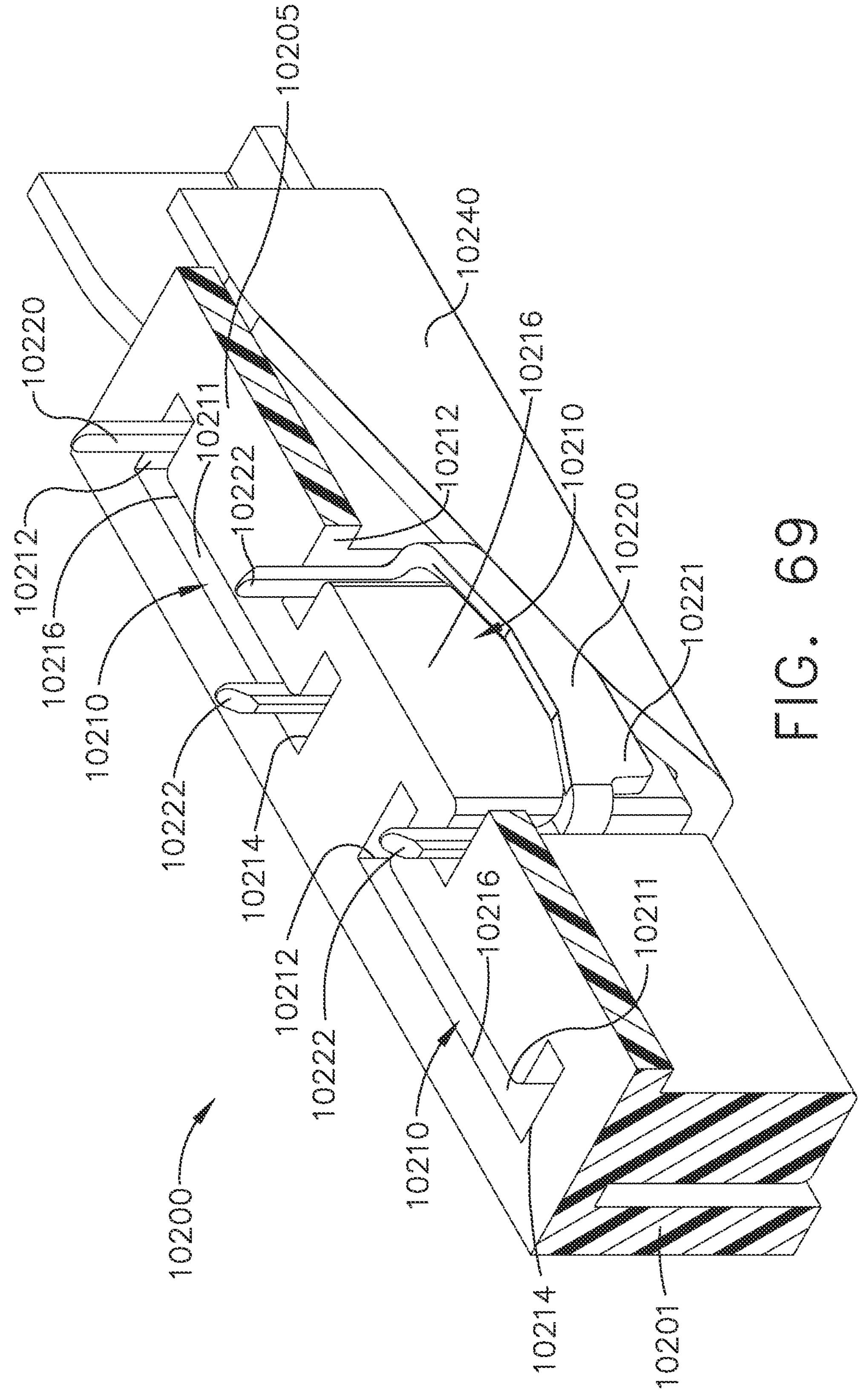
FIG. 69 is a perspective view of another surgical staple cartridge including staples having integral staple drivers, and a sled configured to eject the staples from the staple cartridge.

FIG. 69 illustrates a staple cartridge 10200 comprising a cartridge body 10201 and staples 10220 positioned in staple cavities 10210 defined in the cartridge body 10201. The staples 10120 are stamped staples formed from a sheet of material which is cut and/or stamped and then bent to form the staples 10120. The stamped staples 10220 comprise integral staple drivers 10221, or ramps, formed thereon to facilitate ejection of the staples 10220. In at least one embodiment, the staples 10220 are positioned into the cavities 10210 using the staple assembly tool 10310 illustrated in FIG. 70. In any event, the staple cavities 10210 define a plurality of openings 10211 in a staple deck surface 10205 of the cartridge body 10201 and the staples 10220 are configured to be ejected through the openings 10211. Each staple cavity 10210 comprises a proximal end wall 10212, a distal end wall 10214, and two opposing lateral sidewalls 10216 which form the staple cavity 10210. When each staple 10220 is inserted into its respective staple cavity 10210, staple legs 10222 of the staple 10220 press against, or are resiliently biased against, the proximal and distal end walls 10212, 10214 to at least partially retain the staples 10220 in the staple cavities 10210. During a staple firing stroke, the staples 10220 are ejected toward the deck 10205 of the cartridge body 10201 by a sled 10240 as the sled 10240 is moved distally and engages the integral drivers 10221 of the staples 10220. Each staple 10220 comprises staple legs 10222 that extend above the staple deck 10205 when the staples 10220 are in their unfired positions in the cartridge body 10201. However, other embodiments are envisioned where the staple legs 10222 do not extend above the deck 10205 when the staples 10220 are in their unfired positions in the cartridge body 10201. Various combinations of different stamped staple sizes and shapes as well as different integral driver sizes and shapes can determine whether or not the staple legs 10222 extend above the deck surface 10205, for example.

Further to the above, the uncoated staple tips and/or uncoated portions of a staple resulting from the staple manufacturing process may be coated and/or lubricated after the staple has been loaded into a staple cartridge. In various embodiments, the staples 10120, 10220 illustrated in FIGS. 68 and 69 comprise uncoated and/or unlubricated portions due to the manufacturing process discussed above. The staples 10120, 10220 are fully seated within the staple cavities 10110, 10210 of the staple cartridges 10100, 10200 and the uncoated and/or unlubricated staple tips extend above the deck surface 10105, 10205. In various embodiments, a second lubricant is applied to the exposed uncoated and/or unlubricated portions of the staples 10120, 10220 after the staples 10120, 10220 are positioned in the staple cartridge 10100, 10200. The second lubricant may be the same, similar, or different than the lubricants applied prior to assembling the staples into the staple cartridge.

In various embodiments, the second lubricant is applied by dipping the deck surface 10105, 10205 and exposed staple tips of the staples 10120, 10220 into the lubricant and then letting the lubricant dry. Other embodiments are envisioned where the second lubricant is sprayed onto the deck surface 10105 and the uncoated portions of the staples 10120, 10220, for example. In any event, once the second lubricant has dried, the uncoated portions of the staples and portions of the staple cartridges 10100, 10200 will be coated with the second lubricant. In various instances, the staples 10120, 10220 are at least partially retained in the staple cavities 10110, 10210 by the dried second lubricant.

Further to the above, other embodiments are envisioned where the staples 10120, 10220 are not fully seated within the staple cavities 10110, 10210 when the second lubricant is applied to the deck surface 10105, 10205 and the exposed uncoated staple tips of the staples 10120, 10220. In such an arrangement, the staples 10120, 10220 can be pushed down into their fully seated positions within the staple cavities 10110, 10210 before the second lubricant has dried. As such, the second lubricant is positioned between the staple legs 10122, 10222 and the staple cavity walls 10112, 10114, 10116, 10212, 10214, 10216 to at least partially retain the staples 10120, 10220 within the staple cavities 10110, 10210.

Further to the above, other embodiments are envisioned where the uncoated staple tips of the staples 10120, 10220 are positioned below the deck surface 10105, 10205 but are still accessible due to the staple cavity openings in the staple deck 10105, 10205. In such an arrangement, the second lubricant is applied to the staple deck 10105 and dripped or injected into the staple cavities 10110, 10210 to coat the uncoated portions of the staples 10120, 10220 and at least partially retain the staple 10120, 10220 within the staple cavity 10110, 10210 once dried.

Other embodiments are envisioned where the staples 10120, 10220 having uncoated and/or unlubricated portions may be positioned in the staple cartridge either fully or partially, and then the entire staple cartridge 10100, 10200 could be dipped or sprayed with the second lubricant. After the second lubricant is applied, and prior to the second lubricant drying, the staples 10120, 10220 are be pushed down into their fully seated position. Once the second lubricant dries it will at least partially retain the staples 10120, 10220 in the staple cavities 10110, 10210.

In various embodiments, the staple cartridge, the stock used for making staples, and/or the staple themselves are coated with different adhesive polymers and/or lubricated with different lubricants and/or solutions of adhesive soap. In one embodiment, the stock material is coated with an adhesive polymer and then lubricated with a first lubricant, such as those described herein, prior to inserting the staples into a staple cartridge. After seating the staples into the staple cavities of a staple cartridge, a second lubricant is applied to the staples which is different than the first lubricant. However, other embodiments are envisioned wherein the first lubricant and the second lubricant are the same.

In at least one embodiment, the staples are lubricated with a first lubricant, such as those described herein, prior to inserting the staples into a staple cartridge. After fully seating the staples into the staple cavities of a staple cartridge, the staples are lubricated with a second lubricant that is different than the first lubricant. Other embodiments are envisioned where the first and second lubricant are the same. The second lubricant is applied to the staples such that the second lubricant is not positioned intermediate the legs of the staples and the staple cavity walls.

In at least one embodiment, the stock material is coated with an adhesive polymer and then lubricated with a first lubricant, such as those described herein, prior to inserting the staples into a staple cartridge. The staples are then positioned in a staple cartridge but not fully seated in the staple cartridge. At that point, the staples are lubricated with a second lubricant and then pressed down into the stapled cartridge into a fully seated position prior to the second lubricant drying. The second lubricant is different than the first lubricant; however, other embodiments are envisioned wherein the first and second lubricants are the same.

In at least one embodiment, the staples are lubricated with a first lubricant, such as those described herein, prior to inserting the staples into a staple cartridge. The staples are then positioned in a staple cartridge but not fully seated in the staple cartridge. The staples in the staple cartridge are lubricated with a second lubricant and then pressed down into the stapled cartridge to fully seated position prior to the second lubricant drying. The second lubricant is different than the first lubricant. However, other embodiments are envisioned wherein the first and second lubricants are the same.

In at least one embodiment, the stock material is coated with an adhesive polymer and then lubricated with an initial lubricant, such as those lubricants described herein, for example. After the stock material is formed into staples and prior to inserting the staples into a staple cartridge, an intermediate lubricant is applied to the staples. After positioning the staples into the staple cavities of a staple cartridge, a final lubricant is applied to the staples and/or portions of the staple cartridge. In at least one embodiment, the initial lubricant, the intermediate lubricant, and the final lubricant are the same. However, other embodiments are envisioned wherein the initial lubricant, the intermediate lubricant, and the final lubricant are different. Other embodiments are envisioned where the stock material is not coated with an adhesive polymer and is only lubricated with the initial lubricant.

Further to the above, the staples of a staple cartridge can be coated, or at least partially coated, with a first lubricant and a second lubricant. In various embodiments, the second lubricant is an entirely different type of lubricant than the first lubricant. In at least one embodiment, the first lubricant is a solution of LAE and sodium stearate, and the second lubricant is a solution of LAE and calcium stearate, for example. Other embodiments are envisioned where the first lubricant and the second lubricant are the same type of lubricant but have different concentrations. In other words, the first and second lubricant solutions are made up of the same solvent(s) and solute(s) but have different concentrations of each. In at least one embodiment, the first lubricant is a solution of LAE and sodium stearate comprising a first ratio of LAE to sodium stearate, and the second lubricant is a solution of LAE and sodium stearate comprising a second ratio of LAE to sodium stearate that is different than the first ratio. In at least one embodiment, the first lubricant is a more diluted soap solution than the soap solution of the second lubricant.

Further to the above, the stock material and/or staples are made of a high silicone metal alloy that is coated using a lubricant that is highly anhygroscopic to limit bodily fluid infiltration to the underlying silicone metal. Examples of lubricants that can be applied to the stock material and/or staples include magnesium stearate, among other lubricants and/or coatings described herein. In at least one embodiment, the stock material and/or staples are lubricated and dried to form a coating with a thin layer of LAE, a thin layer of LAE and sodium, and/or a thin layer of LAE and calcium stearate, for example.

In various instances, a thin layer of coating is applied to staples before they are loaded into a staple cartridge. Once the pre-coated staples are positioned in the staple cavities of a staple cartridge, in various instances, a thicker more robust layer of lubricant is applied to the staples. The thicker layer of lubricant is then dried, or permitted to dry, to produce a thicker coating on the staples. In various instances, the thin coating applied to the staples before the staples are inserted into the staple cartridge is comprised of a different material than the thick coating applied to the staples while the staples are stored in the staple cartridge. In some instances, the thin coating and the thick coating are comprised of the same material but in different concentrations, for example. In any event, a thicker layer of lubrication on the staples, and the staple cartridge, can be more resistant to larger volumes of water.

As discussed herein in connection with various embodiments, staples used in surgical procedures are metallic. In various embodiments, the stock material used to make the staples is impregnated or alloyed to make the staples more hydrophobic which slows or reduces the degradation of the staples when the staples are exposed to bodily fluids and/or other corrosive substances, for example. In certain embodiments, polyether ether ketone (PEEK), polylactic acid (PLA), polyglycolide (PGA), and/or tamoxifen citrate (TMC) are used to impregnate the grain structure of the staple material to aid in sealing the pores in the material. In various embodiments, a magnesium or magnesium alloy is impregnated with PEEK, PLA, PGA, TMC, and/or combinations thereof, to produce a more hydrophobic staple that has reduced or slower degradation when exposed to bodily fluids and/or other corrosive elements. In various instances, the stock material is impregnated before the staples are made and/or the staples are impregnated after they have been formed from the stock material. Further to the above, the impregnated staples can be coated with one or more coatings or lubricants before the staple are loaded into a staple cartridge and/or one or more coatings or lubricants after the staples are loaded into the staple cartridge.

To reduce or slow the degradation of a metal or metal alloy staple, in various embodiments, a less noble metal than the staple metal is placed in contact with the staple via a conductive solution and/or lubricant to serve as a sacrificial anode. In at least one embodiment, the sacrificial anode prevents or limits corrosion of a magnesium or magnesium alloy staple, for example. The sacrificial anode comprising a less noble metal may be part of the staple cartridge or part of the staple loading equipment in the form of a conductive solution in contact with the magnesium or magnesium alloy staple. In at least one embodiment, a solution of less noble metal is used to lubricate the staple prior to insertion into the staple cartridge. In at least one embodiment, a solution of less noble metal in lubricant form is poured into the cavities containing the staples and dried. The less noble material in lubricant solution, once dried, will act as a sacrificial anode to reduce the corrosion of the more noble staple material positioned in the staple cavity. In various embodiments, the staple is magnesium alloy and a lubricant solution of magnesium or magnesium stearate is poured into the staple cavities to encapsulate the magnesium alloy staple. The lubricant solution, once dried, will act as a sacrificial anode to limit corrosion of the magnesium alloy staple. Other embodiments are envisioned with sodium (Na) and/or potassium (K) solutions to form lubricants that can be dried onto the staples prior to loading the staples into the staple cartridge and/or within the staple cavities after the staples are loaded into the staple cartridge to create sacrificial anodes.

In various embodiments, a lubricant is poured into or onto portions of a staple cartridge containing staples therein and then freeze dried to retain the lubricant and/or staples in position. Such an arrangement allows the staples to be retained in the staple cavities with a solution or lubricant freeze dried around the staples, for example. In other embodiments, the lubricant is freeze dried into the staple cavities prior to the insertion of the staples into the staple cavities. In such embodiments, the staples are inserted into the freeze dried lubricant to encapsulate the staples within the lubricant and retain the staples within the staple cavities.

In various embodiments, a conductive lubricant is positioned around the staples within the staple cavities of a staple cartridge that can have an applied electrical voltage to prevent corrosion of the staples while the voltage is applied to the conductive lubricant. Removing the voltage from the conductive lubricant will enable corrosion of the staples to proceed. In at least one embodiment, a conductive lubricant is flowed onto the staples prior to the staples being loaded into a staple cartridge. The conductive lubricant can have an electrical voltage applied thereto from a power source, such as a battery, for example, by way of a wire connection, an electrical conduit, and/or any suitable electrical connection. In any event, the electrical voltage will prevent or at least reduce the oxidation and/or corrosion of the staples until the staples are ready to be loaded into a staple cartridge and then packaged. In various instances, the conductive lubricant can be flowed onto the staple cartridge and onto the staples positioned therein once the staples are loaded into a staple cartridge. In at least one such instance, a power source, such as a battery, for example, is in electrical communication with the conductive lubricant via one or more conductive pathways in the staple cartridge. In at least one instance, the staple cartridge does not have the power source; instead, the power source is in the staple cartridge packaging which is placed in electrical communication with the conductive pathways in the staple cartridge when the staple cartridge is loaded into the staple cartridge packaging. In any event, the electrical voltage is supplied from the power source to the conductive pathways in the staple cartridge and to the conductive lubricant coating on the staples to prevent the staples from degrading until the staple cartridge is loaded into a stapling instrument and/or even while the staple cartridge is loaded in a stapling instrument depending on the availability of a power source.

In various embodiments, further to the above, the staples immersed in the conductive coating are comprised of a magnesium alloy while the conductive coating contains a high concentration of magnesium ions, for example. In at least one embodiment, the voltage applied to the conductive coating is based on the half-cell potential related to a Pourbaix diagram of magnesium.

In various embodiments, a lubricant that contains a high concentration of magnesium ions is applied to the stock material prior to creating the staples, the staples, and/or the staple cartridge and staples once the staples are inserted into the staple cartridge. In various embodiments, the staple material is magnesium or magnesium alloy and the lubricant contains a high concentration of magnesium ions such as magnesium stearate and/or magnesium lauryl sulfate, among others. The lubricant provides enough magnesium ions to reduce or inhibit further corrosion of the magnesium staples once the lubricant is applied to and/or dried on the magnesium or magnesium alloy staple material. This is based on the Nernst equation, for example.

Figure 70:
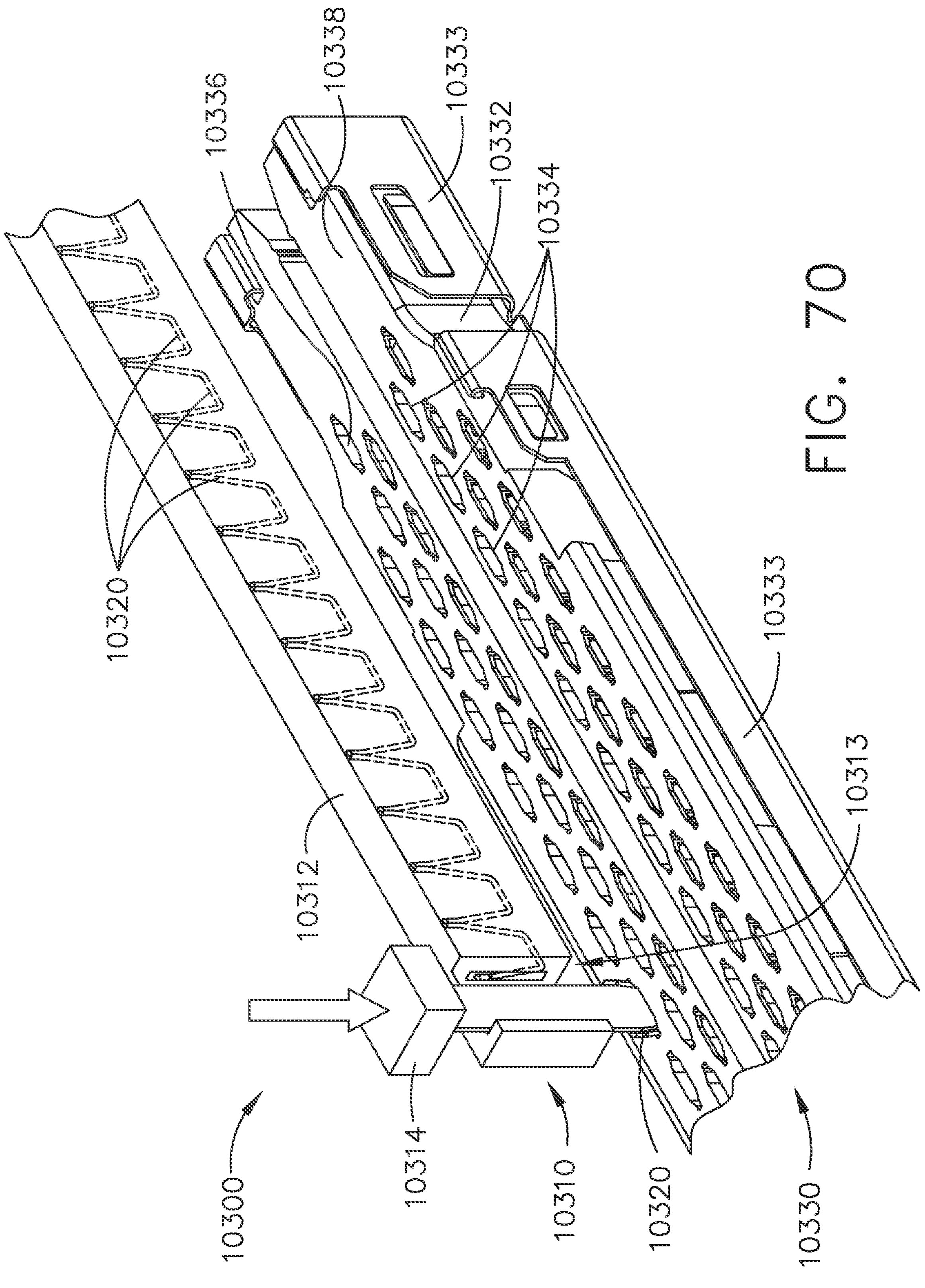
FIG. 70 is a perspective view of a surgical system including a staple assembly tool for inserting staples into a staple cartridge.

FIG. 70 illustrates a surgical system 10300 comprising a staple assembly tool 10310 configured to insert staples 10320 stored therein into a staple cartridge 10330. The staple cartridge 10330 may be the same or similar to the staple cartridge 10100 and/or the staple cartridge 10200 discussed above, for example. The staple cartridge 10330 comprises a body portion 10332, a cartridge pan 10333, and a plurality of staple cavities 10334 defined in the body portion 10332. Each staple cavity 10334 defines an opening 10336 in a deck surface 10338 of the body portion 10332. The staple cavities 10334 are configured to receive the staples 10320 therein and the cartridge pan 10333 is configured to prevent the staples 10320 and staple drivers, if present, from falling out of the bottom of the staple cartridge 10330. The staples 10320 are configured to be placed into the staple cartridge 10330 by the staple assembly tool 10310, as discussed in greater detail below.

The staple assembly tool 10310 comprises a staple magazine 10312 which stores a plurality of the staples 10320 therein and a reciprocating staple stitcher 10314. The staples 10320 may be the same or similar to the staples 10120 and/or the staples 10220 discussed above, for example. The staples 10320 are spring loaded into the magazine 10312 such that the staples 10320 are biased toward an opening 10313 in the staple magazine 10312. When the opening 10313 is clear of the staple stitcher 10314, a staple 10320 is biased into the opening 10313 and held in place due to the spring loaded nature of the magazine 10312. The staple stitcher 10314 is displaceable toward the staple cartridge 10330 from a first position into a second position (FIG. 70). The staple stitcher 10314 is then retracted toward the staple magazine 10312 from the second position toward the first position. In the illustrated embodiment, the staple stitcher 10314 is manually actuatable between the first and second position by a user of the staple assembly tool 10310, for example. However, other embodiments are envisioned where the reciprocating staple stitcher 10314 of the staple assembly tool 10310 is actuated using an electric motor, a solenoid, and/or any other suitable actuating means.

In use, the staple assembly tool 10310 is positioned above the staple cartridge 10330 such that the opening 10313 and the staple stitcher 10314 are aligned with one of the staple cavities 10334. The staple stitcher 10314 is then moved from the first position toward the second position to insert the staple 10320 positioned in the opening 10313 into one of the staple cavities 10334 of the staple cartridge 10330. The staple stitcher 10314 is retracted toward the first position and another staple 10320 is biased into the opening 10313 once the opening 10313 is clear of the staple stitcher 10314. The staple assembly tool 10310 is then moved to another location above the staple cartridge 10330 such that the opening 10313 and staple stitcher 10314 are aligned with a different staple cavity 10334. The staple stitcher 10314 is actuated again from the first position toward the second position to place another staple 10320 into the different staple cavity 10334. This process can be repeated until all of the staple cavities 10334 are filled with staples 10320, for example.

In various embodiments, further to the above, a staple cartridge comprises a cover, or staple retainer, removably attached to the cartridge body that extends over the deck of the cartridge body and prevents, or at least inhibits, staples from falling out of the staple cavities while the staple retainer is attached to the cartridge body. In use, the stapler retainer is removed from the staple cartridge after the staple cartridge has been seated in a surgical stapling instrument but before the surgical stapling instrument is inserted into the patient. In at least one embodiment, the staple retainer comprises projections that extend downwardly into the staple cavities that not only prevent the staples from falling out of the staple cavities but also hold the staples in their unfired position, at least until the staple retainer is removed from the staple cartridge. In at least one such embodiment, the staple retainer comprises a plastic portion that extends over the deck and metal portions attached to and/or embedded within the plastic portion that comprise the downwardly-extending projections. The metal portions prevent, or at least inhibit, the staples from becoming stuck in the staple retainer and being removed from the staple cartridge when the stapler retainer is removed.

Various embodiments are disclosed herein where the geometry, material, and/or material characteristics the staples stored in a staple cartridge are tuned to provide a desired performance once implanted in a patient. In many instances, it is desirable to delay the biodegradation of the staples, or at least certain staples, until after a certain time period has elapsed. As discussed below, this time period can comprise the healing window needed for the patient tissue to heal after being stapled and cut. In certain instances, it is desirable to slow the biodegradation of the staples, or at least certain staples, such that the staples become non-functional and/or entirely dissolved within a desired time period, as discussed in greater detail below.

The staples disclosed herein comprise a chemical makeup that provides for absorption of the staples at an appropriate rate during the tissue healing window. The absorbable staples are comprised of materials that compliment and support the natural tissue wound healing process. Moreover, the staples absorb at an absorption rate that is complimentary to, and coincides with, the natural wound healing process.

Various absorbable staples disclosed herein comprise three stages of absorption/degradation. The first stage involves staples which are structurally complete and have not yet begun the absorption/degradation process. The second stage involves staples which have begun the absorption/degradation process, but are still structurally present at the wound healing site. By the third and final stage, the staples have been fully absorbed by the body at the wound healing site. The absorbable staples comprise sub-elements, whether metal-based or polymer-based, which do not cause the wound healing site to become toxic as a result of excess oxidation of the staple materials. The sub-elements of the absorbable staples also comprise absorption/degradation rates which coincide with the natural wound healing timeline, as will be discussed in greater detail below. In many instances, the absorbable staples support the healing tissue up until the organ tissue is self-sustaining as a result of the wound healing process. The staples are configred to completely absorb into the wound healing site once the tissue is self-sustaining.

Embodiments of absorbable staples can comprise zinc and magnesium in some instances. Moreover, embodiments can comprise staples made of various alloys including zinc, magnesium, and/or other trace elements. Both zinc and magnesium have implications on bodily electrolyte levels and wound healing. Other trace elements can affect the wound healing process. Slightly elevated levels of zinc and magnesium can be beneficial and postively affect wound healing. However, drastically high levels and drastically low levels of zinc and magnesium negatively affect the would healing process. By way of background, zinc is a micronutrient that is essential to human health. Zinc plays a major role in regulating every phase of the wound healing process; ranging from membrane repair, oxidative stress, coagulation, inflammation and immune defense, tissue re-epithelialization, angiogenesis, to fibrosis/scar formation. The phases of the physiologic wound healing process will be described in greater detail below. Moreover, zinc supplementation has proven to be an overwhelming success in managing the delay of wound healing after surgery, which continues to be the frontline worry for surgeons. However, excess zinc, as well as zinc-deficiency, can hinder microbial elimination which can negatively affect wound healing. Signs of too much zinc include nausea, vomiting, loss of appetite, stomach cramps, diarrhea, and headaches. An excess of zinc in the body for an extended period of time can lead to problems such as low copper levels, lower immunity, and low levels of HDL cholesterol.

Magnesium is a mineral the body uses as an electrolyte, meaning it carries electric charges around the body when dissolved in the blood. Magnesium levels impact bone health, cardiovascular function, and neurotransmission, among other functions. Most magnesium is stored in the bones. Hypermagnesemia occurs when there are excess levels of magnesium in the body. Patients with symptomatic hypermagnesemia can present different clinical manifestations depending on the level and the time in which the electrolytic disturbance has occurred. The most frequent symptoms and signs may include weakness, nausea, dizziness, and confusion.

Figure 39:
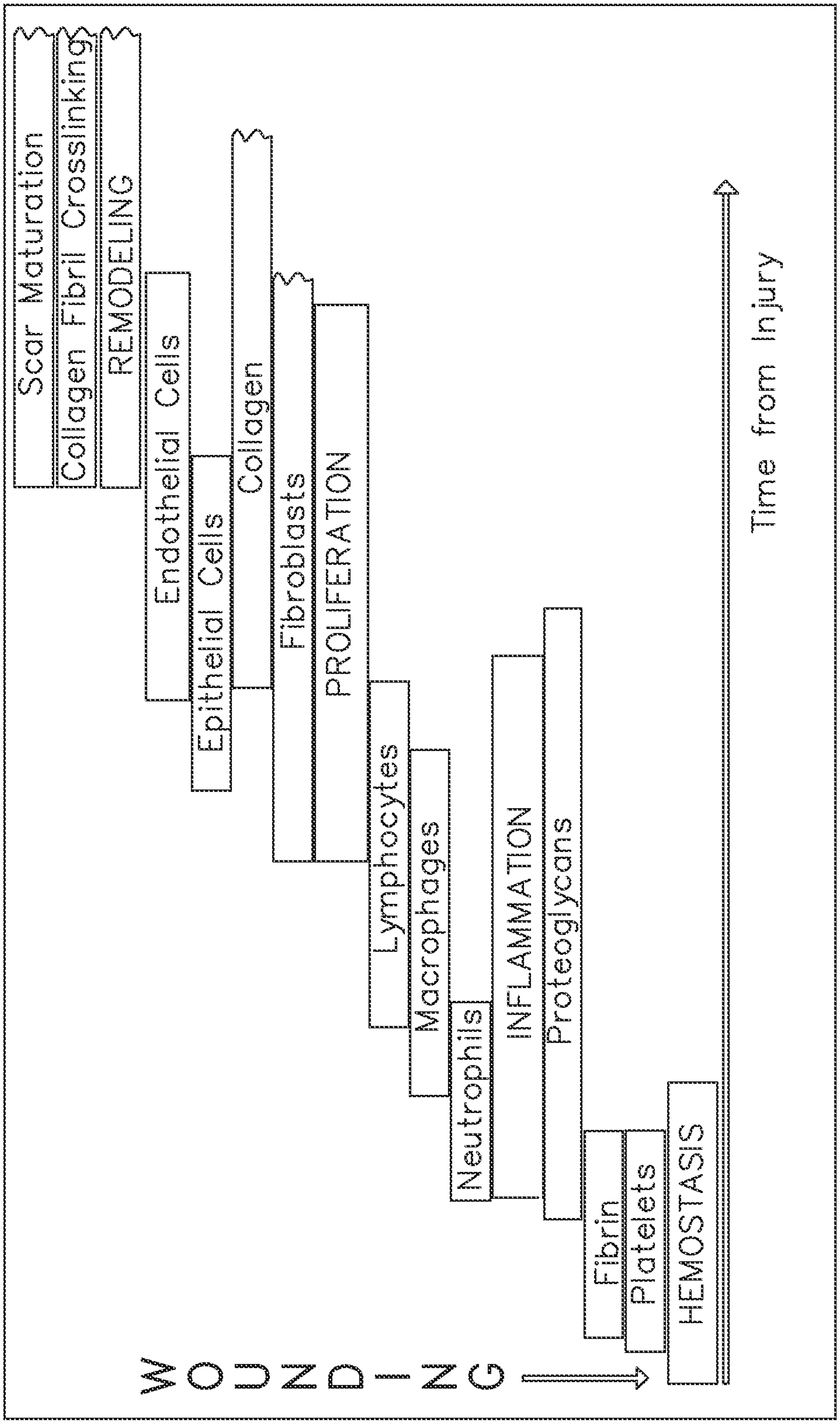
FIG. 39 is a graph depicting the healing time of tissue.

Turning now to FIG. 39, the four stages of physiologic wound healing are illustrated. Hemostasis is the first phase of wound healing which occurs immediately, or shortly after, bodily tissue sustaining an injury. Hemostasis involves the use of clotting factors to prevent further blood loss and to lay the foundation for the generation of tissue during the healing process. Fibrin and platelets play an essential role in forming blood clots during the hemostasis phase. Platelets gather at the injury site during hemostasis and adhere to the injury site within the injured blood vessel. During hemostasis, activated platelets form fibrins on the surface, which form a net-like structure across the injury site.

Figure 40:
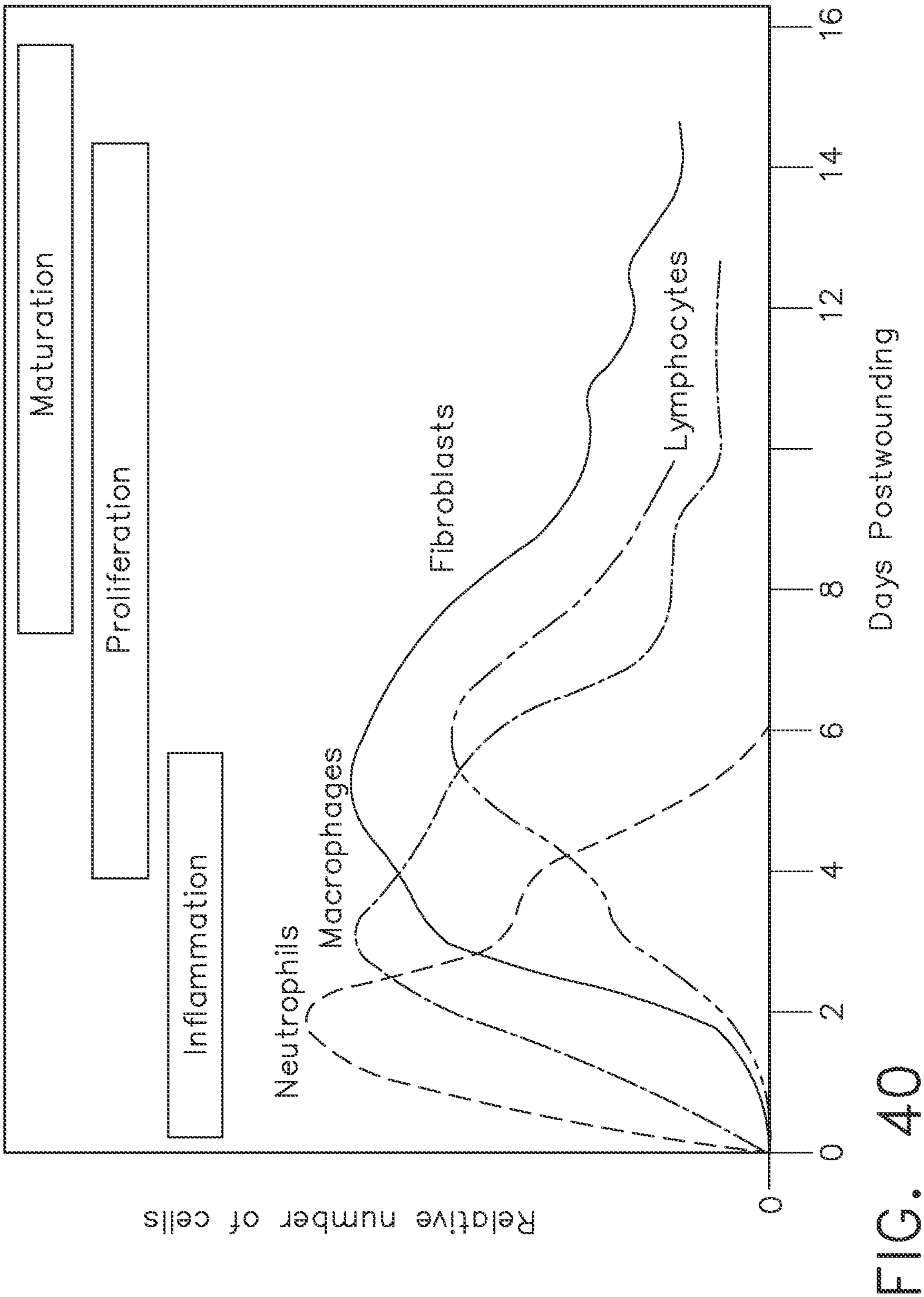
FIG. 40 is a graph depicting the healing of tissue.

Inflammation is the second stage of physiologic wound healing. The inflammation stage can partially overlap with the hemostasis stage, as illustrated in FIGS. 39 and 40. Proteoglycans play a crucial role in the inflammation stage. Proteoglycans comprise a protein chain component called glycosaminoglycan in the extracellular matrix of tissue. Glycosaminoglycan chains provide for hydration and swelling in the tissue during the inflammation stage by attracting water into the extracellular matrix. The tissue swelling allows for the tissue to withstand compressional forces.

Proliferation is the third stage of physiologic wound healing. The proliferation stage can partially overlap with the inflammation stage, as illustrated in FIGS. 39 and 40. The proliferation stage corresponds to the formation of granulation tissue and angiogenesis, or blood vessel formation. Granulation tissue is new connective tissue and microscopic blood vessels that form on the surfaces of a wound. The proliferation stage also includes production of fibroblasts, which are the most prominent type of cell found in connective tissue. Fibroblasts assist in maintaining the structural framework of tissue by secreting collagen proteins.

Phagocytes, such as neutrophils, are able to destroy intracellular pathogens via reactive oxygen species (ROS). Enzymes important for the generation of ROS precursors and bacterial clearance are nicotinamide adenine dinucleotide phosphate (NADPH)-oxidases. Neutrophils play an essential role in the body's immune response during the inflammation and the proliferation phases by acting as a barrier between the tissue would healing site and any microbial infections or pathogens. Neutrophils remove any microbial infections and/or pathogens by way of phagocytosis. An excess level of zinc can inhibit the production of NADPH— oxidases.

Similarly, macrophages serve a more than one role at this stage during the wound healing process. Macrophages boost host immune defenses and remove dead cells in order to promote tissue restoration during the inflammation and proliferation phases. Lymphocytes are white blood cells that are part of the body's immune response. There are two types of lymphocytes— B cells and T cells. B cells produce antibodies and T cells fight directly fight foreign invaders and serve to produce cytokines which activate other parts of the immune system.

Figure 41:
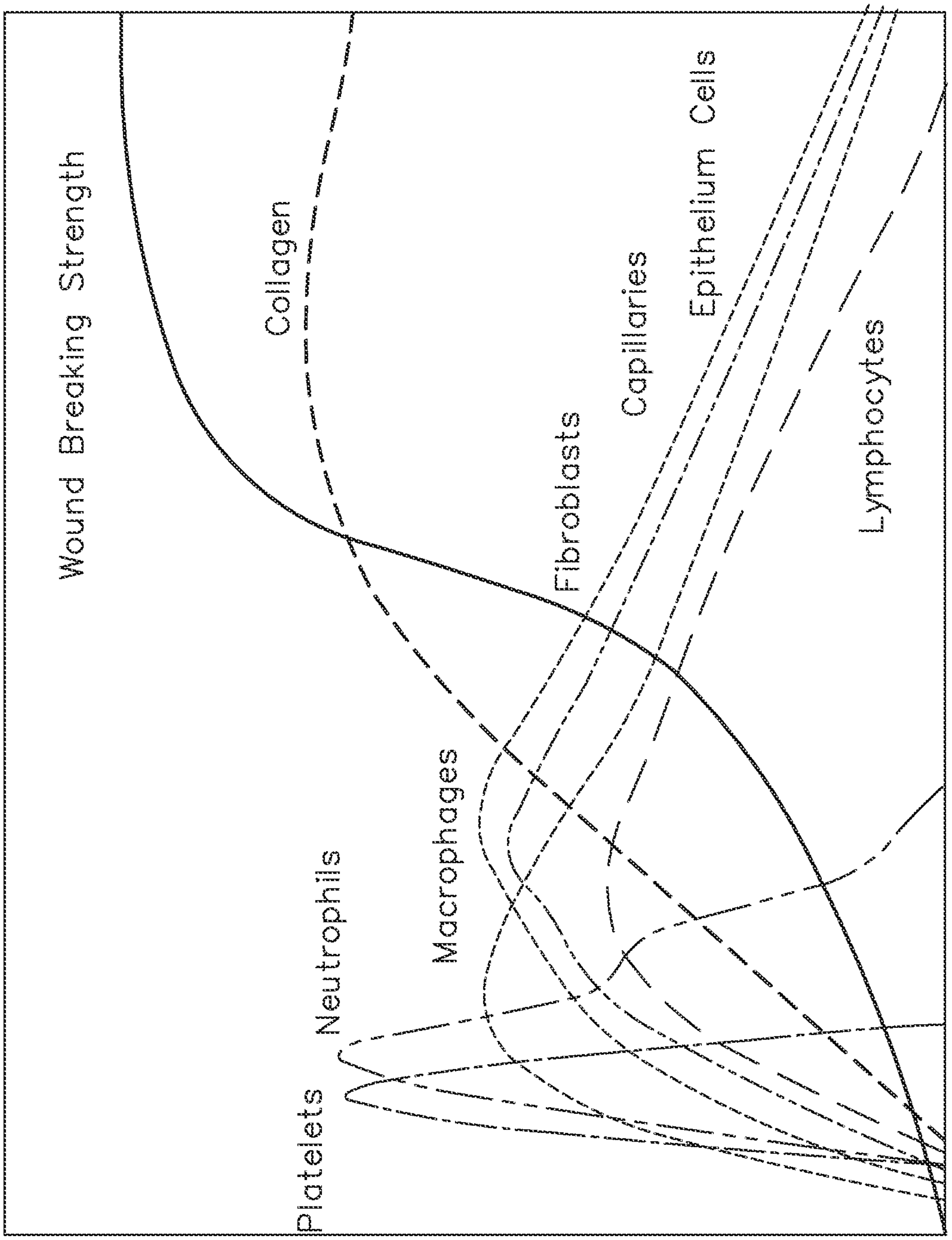
FIG. 41 is a graph depicting the strength of tissue during the healing process.
Figure 42:
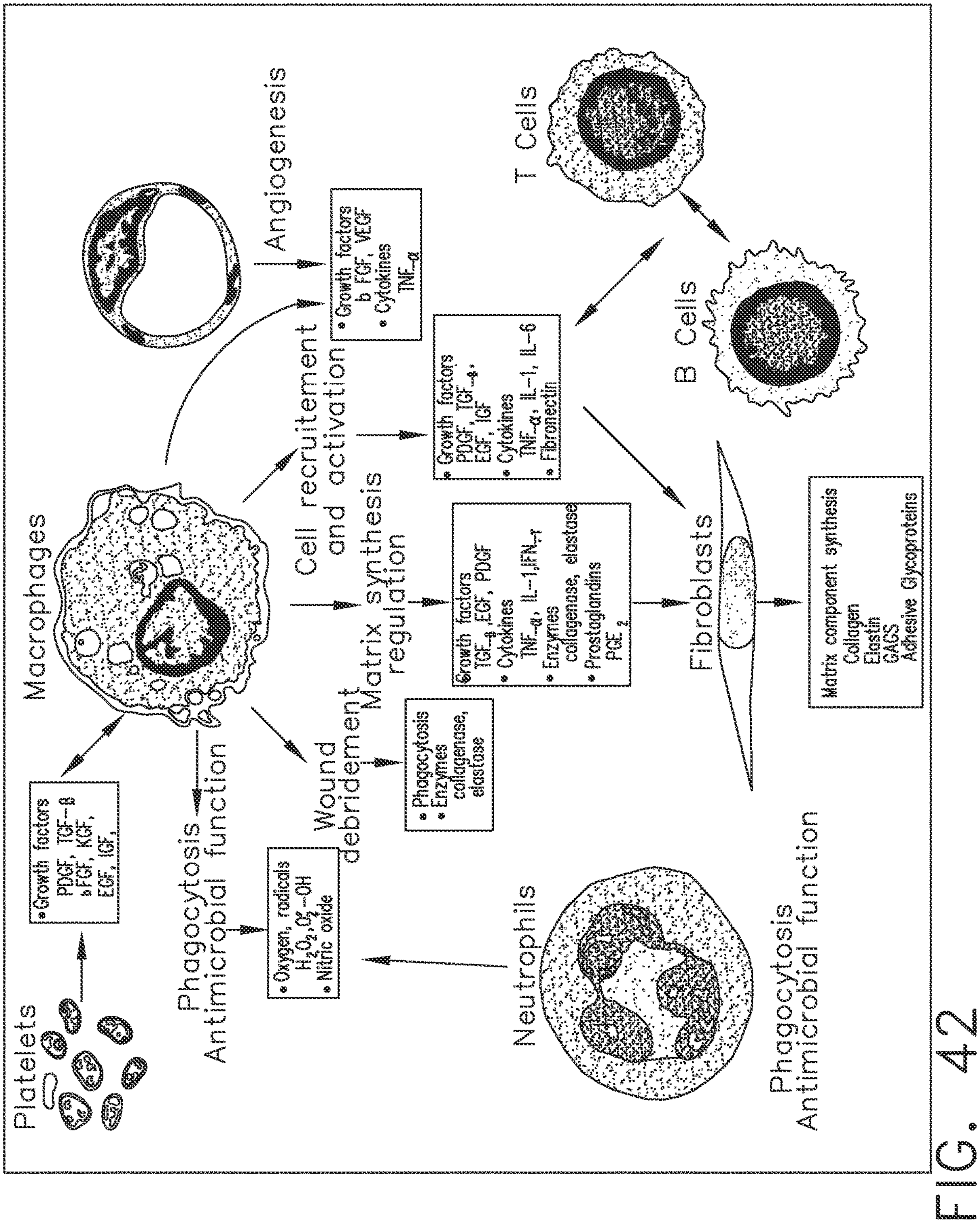
FIG. 42 depicts the healing process of tissue.

FIGS. 40 and 41 generally illustrate the increase in specific types of cells at various stages during the physiologic wound healing process. For example, neutrophil production peaks around day two of the wound healing process. Macrophages appear to peak around day three of the wound healing process. Fibroblasts peak around days five to six of the wound healing process. Lymphocytes also appear to peak around day six of the wound healing process. Similarly, FIG. 40 also illustrates how different levels of neutrophils, macrophages, fibroblasts, and lymphocytes coincide with the sequential stages of the wound healing process. FIG. 42 illustrates the interplay among various cell types discussed above at different stages during the wound healing process. In various embodiments, the bio-corrosion rates of staples situated in a tissue environment can be altered. In one aspect, the bio-corrosion rates of staples can be altered by introducing a secondary material that causes acceleration or deceleration of the bio-corrosion rates of the staples. In some embodiments, introduction of one or more other elements or materials can establish microgalvanic cells within the staple material to alter the electrode potential thereof, causing an increase or decrease of the bio-corrosion rate. Other embodiments regarding introduction of secondary materials or elements to alter bio-corrosion rates of staples in tissue environments are described elsewhere herein.

In various embodiments, the staples comprise a coating that keeps body fluids away from the surfaces of the staples and inhibits the onset of oxidation thereon. In various embodiments, the coating comprises $MgF_2$. In various embodiments, the coating comprises a polymer coating. In various embodiments, the coating comprises an organic-inorganic hybrid coating. In various embodiments, the coating comprises a naturally formed protective layer of magnesium hydroxide. In various embodiments, the coating comprises a naturally formed protective layer of magnesium carbonate. In various embodiments, the coating comprises a naturally formed protective layer of magnesium hydroxy carbonate. In various embodiments, the coating comprises a naturally formed protective layer of magnesium phosphate. In various embodiments, the coating can comprise one of magnesium hydroxide, magnesium carbonate, magnesium hydroxy carbonate, or magnesium phosphate, alone or in combination in the presence of $CO_3^{-2}$ and $PO_4^{-3}$. In various embodiments, the staples comprise a coating that captures deposition thereon.

In another aspect, the bio-corrosion rates of staples can be altered by changing the pH level or the ionic aspect of the local fluid in the tissue environment, thereby changing the bio-corrosion rates of the staples. In one aspect, the pH level or the ionic aspect of the local fluid can be altered by altering the staples. In one embodiment, an active element is applied to the staple and then predetermined amount of time is waited. After the predetermined amount of time, a neutralizing or stabilizing element added to the staple.

In one aspect, the bio-corrosion rates of staples can be altered by integrating an adjunct into the tissue environment with the staples. In various embodiments, a system is provided that includes a first staple cartridge and a second staple cartridge. The first staple cartridge comprises first staples comprised of a staple material and a first adjunct comprised of a first adjunct material. The second staple cartridge comprises second staples comprised of the staple material and a second adjunct comprised of a second adjunct material that is different than the first adjunct material. When implanted in a tissue environment, the first adjunct causes the first staples to bio-corrode at a first rate. When implanted in the tissue environment, the second adjunct causes the second staples to bio-corrode at a second rate that is different than the first rate. Accordingly, the system provides a clinician with the ability to select between staple cartridges that include staples comprised of the same material, but that will bio-corrode at different rates based on the adjunct that is provided with the staple cartridge.

In various embodiments, the material of the adjunct can be selected to increase or decrease the absorption rates of the staples depending on the particular application. In one aspect, the adjunct is comprised of a material that adjusts the pH level of the tissue environment in which the staples are situated, thus increasing or decreasing the bio-absorption rate of the staples. In one embodiment, the adjunct is comprised of a material that can lower the local pH of the tissue environment, making the tissue environment more acidic, thus increasing or decreasing the bio-corrosion rates of the staples. In one embodiment, the adjunct is comprised of a material that can increase the local pH of the tissue environment, making the tissue environment more basic, thus increasing or decreasing the bio-corrosion rates of the staples.

In one embodiment, the adjunct is comprised of pure magnesium that acts as an anode within the tissue environment, thereby increasing or decreasing the absorption rates of the staples. In one embodiment, the adjunct is comprised of a material, such as zinc or iron, as examples, that cause magnesium-based staples, to degrade at a faster rate.

In one aspect, the staples comprise interrupters, such as a coating, a surface treatment, a surrounding material, or combinations thereof. The interrupters interrupt materials, such as body fluid, within the tissue environment from coming into direct contact with the staples. In some embodiments, the interrupters inhibit onset of local oxidation, increasing the bio-corrosion rates of the staples. In some embodiments, the interrupters capture ions that drive oxidation and corrosion, thereby increasing or decreasing the bio-corrosion rates of the staples. In some embodiments, the interrupters include a catalyst that causes a change in the local tissue environment, thereby increasing or decreasing the bio-corrosion rates of the staples.

In various embodiments, the staples comprise a coating that increases or decreases the rate of bio-corrosion rates of the staples based on the mechanism of action. In one aspect, the mechanism of action can comprise oxidation. In one aspect, the mechanism of action can comprise hydrolysis. In one aspect, the mechanism of action can comprise galvanic corrosion, as described elsewhere herein. In one aspect, the mechanism of action can comprise a single replacement reaction between magnesium and hydrochloric acid. In one aspect, the mechanism of action can comprise stress corrosion.

In various embodiments, the staples are coated with a coating at the time of manufacture. In various embodiments, the staples are coated with a coating after the staples have been implanted within a tissue environment. In one embodiment, the staples are sprayed with a coating once they have been implanted in the tissue environment. In some embodiments, the staples are coated at a time after leaving the manufacturing facility, but prior to being implanted in a tissue environment. In one embodiment, the staples are coating while the staple cartridge is in the operating room. In various embodiments, the coating is applied in-situ through an adjunct. In various embodiments, the staples are partially coated with a coating at the time of manufacture and partially coated with a coating after the staples have been implanted within a tissue environment. In various embodiments, the staples are coated with a coating comprised of a first material at the time of manufacture and coated with a coating comprised of a second material different than the first material after the staples have been implanted in the tissue environment.

A first experiment was performed in which pure magnesium (HP—Mg) and five alloys (AZ31, Mg-0.8Ca, Mg-1Zn, Mg-1Mn, Mg-1.34Ca-3Zn) were implanted in vivo in a subcutaneous environment in Lewis rats. After 21 days, the materials were removed and an assessment of corrosion by weight loss was performed to determine a weight loss rate of the respective materials, as shown below:

TABLE 1

| First Experiment | |
|---|---|
| Material | Weight Loss (mm/year) |
| Mg—1.34Ca—3Zn | 1.001 |
| Mg—0.8Ca | 0.351 |
| Mg—1Mn | 0.252 |
| AZ31 | 0.223 |
| HP—Mg | 0.221 |
| Mg—1Zn | 0.164 |

More information regarding the experiment can be found in Walker, Jemimah, et al. "Magnesium alloys: predicting in vivo corrosion with in vitro immersion testing." Journal of Biomedical Materials Research Part B: Applied Biomaterials 100.4 (2012): 1134-1141, which is hereby incorporated by reference in its entirety herein.

In light of the results of the experiment, an embodiment is disclosed in which a system is provided to a user, such as a clinician, that includes a plurality of staple cartridges. The plurality of staple cartridges comprises a first staple cartridge including first staples that degrade at a first rate in a tissue environment and a second staple cartridge including second staples that degrade at a second rate that is different than the first rate in the tissue environment. In various other embodiments, the system can comprise additional staple cartridges that include staples that degrade at different rates in the tissue environment. In various embodiments, the system can comprise six staple cartridges including staples comprised of one of the aforementioned materials listed in Table 1. Other embodiments are envisioned where the system comprises any number of staple cartridges including staples comprised of any of the materials disclosed by the present disclosure.

In various embodiments, the staple cartridges are positioned in a respective packaging that includes an indicia thereon to inform the clinician of the degradation rates of the staples of the respective staple cartridges. Accordingly, when determining which staple cartridge to use for a particular stapling operation, a clinician can decide how fast or slow they want the staples to degrade. Based on the decision, the clinician can select a staple cartridge from among the plurality of staple cartridge according to their estimated degradation rates. For example, should a clinician decide they want staples to remain in the tissue environment for a longer period of time, the system provides the clinician with the ability to select a staple cartridge with a slower degradation rate compared to other staple cartridges of the system that have faster degradation rates.

In various embodiments, the indicia of the package can comprise numbers, letters, words, symbols, and/or colors, as examples, that correspond to the degradation rate of the staples of the staple cartridge positioned in the packaging. This indicia provides the clinician with a quick way of determining the degradation rates of the staples when making their selection of which staple cartridge to use for the stapling operation. In one aspect, the indicia can comprise an indicia that informs the clinician of the rate of degradation of the staples relative to the other provided staple cartridges of the system, as will be described in more detail below.

In various embodiments, the system can include a first packaging with a green indicia that indicates the staple cartridge in the packaging includes staples that degrade the fastest from among all of the staple cartridges in the system. The system can further include a second packaging with a yellow indicia that indicates the staple cartridge in the packaging includes staples that degrade slower than the green package staple cartridge. In addition, the system can include a third packaging with a red indicia that indicates that the staple cartridge in the packaging includes staples that degrade the slowest from among all of the staple cartridges in the system. In various embodiments, the color-based indicia can be based on a transition from green to red, as referenced above, where green is the fastest, red is the slowest, and transitional shades from green to red, such as orange, yellow, etc., can be used to order intermediate degradation speeds. In various embodiments, the color-based indicia can be based on the natural light wavelength bandwidth where red is the fastest, violet is the slowest, and intermediate colors and shades, such as orange, yellow, green, etc. can be used to order intermediate degradation speeds. Any suitable color-based indicia are contemplated by the present disclosure to indicate a relative speed of degradation rates to the clinician.

In various embodiments, the system can include a first packaging with a first symbol, such as a rabbit, that indicates the staple cartridge in the packaging includes staples that degrade the fastest from among all of the staple cartridges in the system. The system can also include a second packaging with a second symbol, such as a turtle, that indicates the staple cartridge in the packaging includes staples that degrade the slowest from among all of the staple cartridges in the system. In various embodiments, the packaging includes a speedometer symbol where the dial of the speedometer indicates relative degradation speed of the staples. Any suitable symbol-based indicia are contemplated by the present disclosure to indicate a relative speed of degradation rates to the clinician.

In various embodiments, the system can include a first packaging with a first letter, such as an 'CA', that indicates that the staple cartridge in the packaging includes staples that degrade the fastest from among all of the staple cartridges in the system. The system can further include a second packaging with a second letter, such as a 'C', that indicates that the staple cartridge in the packaging includes staples that degrade slower than the 'A' packaging staple cartridge. The system can also include a third packaging with a third letter, such as an 'F', that indicates that the staple cartridge in the packaging includes staples that degrade the slowest from among all of the staple cartridges in the system. In various embodiments, the letter-based indicia can be based on a transition from A to F, as referenced above, where A is the fastest, F is the slowest, and letters in between, such as B, C, and D (even including + or –, such as B+ or B–, as an example) can be used to order intermediate speeds. In various embodiments, the letter-based indicia can be based on a transition from A to Z. Any suitable number-based indicia are contemplated by the present disclosure to indicate a relative speed of degradation rates to the clinician.

In one aspect, staples situated in a tissue environment can be in one of three states: a functional state, a non-functional state, or a dissolved state. The functional state can be a state in which the staples perform their intended functions, such as clenching the tissue, to an acceptable level. As one example, a staple can be in a functional state right after the staple has been implanted into the patient in a tissue environment. The non-functional state can be a state in which the staples no longer adequately perform their intended function, but still remain implanted within the tissue environment. As one example, a staple can transition from the functional state to the non-functional state after a period of time, defined as a functional timeframe, has elapsed.

In one aspect, the functional timeframe can be defined as an amount of time in which it takes a staple to fracture, or at least partially fracture, and lose its ability to clench the stapled tissue. In various embodiments, the functional timeframe can be a time it takes for one of the staple legs to fracture. In various embodiments, the functional timeframe can be a time it takes for the base of the staple to fracture. In various embodiments, the functional timeframe can be a time is takes for a staple leg to fracture away from the base of the staple. In various embodiments, the functional timeframe can be a time it takes for any portion of the staple to fracture that would cause a decrease in clenching pressure that the staple provides to the tissue. Accordingly, with an estimated weight loss rate, such as those provided in the Table 1, the functional timeframe of the staples can be estimated and provided to a clinician when selecting a particular staple cartridge to use for a particular stapling operation. This provides the clinician with the ability to select a staple cartridge that includes staples that will be functional in the tissue environment for an estimated amount of time.

In one aspect, the functional timeframe can be correlated to the healing window of the tissue. In various embodiments, a clinician can select a staple cartridge such that the functional timeframe of the staples reaches or exceeds the healing window of the tissue. However, in various embodiments, a clinician can select a staple cartridge such that the functional timeframe of the staples reaches or exceeds the healing window, but does not greatly exceed the healing window such that the staples are not implanted in the tissue longer than is necessary.

In one aspect, the functional timeframe can be defined as an amount of time in which it takes a staple to lose a certain percentage of its weight due to bio-corrosion in the tissue environment. Accordingly, with an estimated weight loss rate, such as those provided in the Table 1, the functional timeframe of the staples can be determined and provided to a clinician when selecting a particular staple cartridge to use for a particular stapling operation. This provides the clinician with the ability to select a staple cartridge that includes staples that will be functional at the stapled tissue for an estimated amount of time. In various embodiments, the estimated amount of time is about 30 days. In various embodiments, the estimated amounted of time is about 60 days. In various embodiments, the estimated amount of time is about 180 days. In various embodiments, the estimated amount of time is less than a year, such as about 6 months or about 9 months, as examples.

In one embodiment, the percentage of weight lost during the functional timeframe is about 25%. In one embodiment, the percentage of weight lost during the functional timeframe is about 50%. In one embodiment, the percentage of weight lost during the functional timeframe is less than about 25%, such as about 5%, 10%, 15%, or 20%, for example. In one embodiment, the percentage of weight lost during the functional timeframe is between about 25% and about 50%, such as about 30%, 35%, 40%, or 45%, for example. In one embodiment, the percentage of weight lost during the functional timeframe is about 75%. In one embodiment, the percentage of weight lost during the functional timeframe is between about 50% and about 75%, such as about 55%, 60%, 65%, or 70%, for example.

Continuing from the above, the dissolved state can be a state in which all of the staple, or at least a substantial amount thereof, has been bio-absorbed by the patient. In various embodiments, a substantial amount means that about 10% of less of the structure of the staple remains. As one example, a staple can transition from the non-functional state to the dissolved state after a period of time, defined as a non-functional timeframe, has elapsed. In one aspect, the non-functional timeframe can be defined as an amount of time it takes all of the staple, or at least a substantial amount thereof, to bio-corrode in the tissue environment after the staple has reached the non-functional state. Accordingly, with an estimated weight loss rate, such as those provided in the Table 1, the non-functional timeframe of the staples can be estimated and provided to a clinician when selecting a particular staple cartridge to use for a particular stapling operation. This provides the clinician with the ability to select a staple cartridge that includes staples that will be present, but non-functional, in the tissue environment for an estimated amount of time.

In one aspect, a staple can transition from the functional state to the dissolved state after a period of time, defined as the life timeframe, has elapsed. The life timeframe, as an example, can be the sum of the functional timeframe and the non-functional timeframe, described above. In one aspect, the life timeframe can be defined as an amount of time in which it takes a staple to bio-corrode completely, or at least substantially bio-corrode, in the tissue environment. Accordingly, with a known weight loss rate, such as those provided in the Table 1, the life timeframe of staples can be estimated and provided to a clinician when selecting a particular staple cartridge to use for a stapling operation. This provides the clinician with the ability to select a staple cartridge that includes staples that will be gone, or at least substantially gone, from stapled tissue within an estimated amount of time.

In one aspect, the life timeframe can be defined as an amount of time in which it takes a staple to lose a certain percentage of its weight due to bio-corrosion in the tissue environment. Accordingly, with a known weight loss rate, such as those provided in the Table 1, the life timeframe of staples can be determined and provided to a clinician when selecting a particular staple cartridge to use for a stapling operation. This provides the clinician with the ability to select a staple cartridge that includes staples that will be gone, or at least substantially gone, from stapled tissue within a known amount of time.

In one embodiment, the percentage of weight lost during the life timeframe is about 50%. In one embodiment, the percentage of weight lost during the life timeframe is about 75%. In one embodiment, the percentage of weight lost during the life timeframe is between about 50% and about 75%, such as about 55%, 60%, 65%, or 70%, for example. In one embodiment, the percentage of weight lost during the life timeframe is about 100%. In one embodiment, the percentage of weight lost during the functional timeframe is between about 75% and about 100%, such as about 80%, 85%, 90%, or 95%, for example.

In various embodiments, the system can include a first packaging with a first table that includes any of the functional timeframe, the non-functional timeframe, and the life timeframe, of the staples positioned in a first staple cartridge in the first packaging. The system can further include a second packaging with a second table that includes any of the functional timeframe, the non-functional timeframe, and the life timeframe, of the staples positioned in a second staple cartridge in the second packaging, where the functional, non-functional, and life timeframes between the first and second staple cartridges are different. These varying timeframes between staple cartridges provides a clinician with the ability to select a staple cartridge from the plurality of staple cartridges provided by the system based on the desired degradation properties of the staples.

A second experiment was performed in which pure magnesium (HP—Mg) and five alloys (AZ31, Mg-0.8Ca, Mg-1Zn, Mg-1Mn, Mg-1.34Ca-3Zn) were immersed in either Earle's balanced salt solution ("EBSS"), minimum essential medium ("MEM"), or MEM-containing 40 g/L bovine serum albumin ("MEMp"). After 21 days, the materials were removed and an assessment of corrosion by weight loss was performed to determine a weight loss rate of the respective materials, as shown below:

TABLE 2

| Second Experiment | | | |
|---|---|---|---|
| Material | In vitro EBSS Weight Loss (mm/year) | In vitro MEM Weight Loss (mm/year) | In vitro MEM Weight Loss (mm/year) |
| Mg—1.34Ca—3Zn | 1.573 | 10.04 | 2.844 |
| Mg—0.8Ca | 0.382 | 0.764 | 1.545 |
| Mg—1Mn | 0.722 | 0.504 | 1.612 |
| AZ31 | 0.546 | 1.192 | 0.944 |
| HP—Mg | 0.382 | 0.659 | 1.37 |
| Mg—1Zn | 0.303 | 0.824 | 1.615 |

More information regarding the experiments can be found in Walker, Jemimah, et al. "Magnesium alloys: predicting in vivo corrosion with in vitro immersion testing." Journal of Biomedical Materials Research Part B: Applied Biomaterials 100.4 (2012): 1134-1141, which is hereby incorporated by reference in its entirety herein.

In light of the results of the experiments, it can be seen that staples perform differently in different environments. For instance, a staple will bio-degrade at a first rate in a first tissue environment and bio-degrade at a second rate different than the first rate in a second tissue environment. Accordingly, an embodiment is disclosed in which a system is provided to a user, such as a clinician, that includes a plurality of staple cartridges. In various embodiments, the staple cartridges are positioned in a respective packaging that includes an indicia thereon, such as a table, a graph, a grid, or an array, as examples, to inform the clinician of the degradation rates of the staples of the respective staple cartridges in a plurality of tissue environments.

In various embodiments, the packaging can have an indicia that includes a first column listing tissue environments, such as stomach tissue, lung tissue, liver tissue, etc., and a second column listing respective bio-corrosion rates for each tissue environment. Accordingly, when determining which staple cartridge to use for a particular stapling operation, a clinician can decide how fast or slow they want the staples to degrade in a particular tissue environment. Based on the decision, the clinician can select a staple cartridge from among the plurality of staple cartridge according to their estimated degradation rates in the plurality of tissue environments. In one embodiment, a clinician intending to staple stomach tissue can decide they want staples to remain in the tissue environment for a particular period of time. Accordingly, the system provides the clinician with the ability to select a staple cartridge from among the plurality of staple cartridge knowing the approximate degradation rates of the staples in the stomach tissue environment.

A third experiment was performed in which pure magnesium (HP—Mg) and two alloys (Mg2Ag and Mg10Gd) were either implanted in vivo in rat femoral bone or immersed in vitro in high-glucose Dulbecco's Modified Eagle's Medium ("DMEM")+10% fetal bovine serum ("FBS"). After 1 week and 4 weeks, an assessment of corrosion by weight loss was performed to determine a weight loss rate of the respective materials, as shown below:

TABLE 3

| Third Experiment | | | | |
|---|---|---|---|---|
| Material | In vitro High glucose DMEM + 10% FBS Week 1 (mm/year) | In vivo rat femoral bone Week 1 (mm/year) | In vitro High glucose DMEM + 10% FBS Week 4 (mm/year) | In vivo rat femoral bone Week 4 (mm/year) |
| HP—Mg | 0.75 | 0.4 | 0.32 | 0.2 |
| Mg2Ag | 1.81 | 0.2 | 0.36 | 0.3 |
| Mg10Gd | 0.56 | 0.7 | 0.56 | 0.5 |

More information regarding the experiment can be found in Myrissa, Anastasia, et al. "In vitro and in vivo comparison of binary Mg alloys and pure Mg." Materials Science and Engineering: C 61 (2016): 865-874, which is hereby incorporated by reference in its entirety herein.

In light of the results of the experiments, it can be seen that the rates of bio-corrosion in staples vary over time in different environments. For instance, a staple will bio-degrade at a first rate for a first period of time in a first tissue environment and bio-degrade at a second rate different than the first rate for a subsequent period of time in the first tissue environment. Accordingly, an embodiment is disclosed in which a system is provided to a user, such as a clinician, that includes a plurality of staple cartridges. In various embodiments, the staple cartridges are positioned in a respective packaging that includes an indicia thereon, such as a table, a graph, a grid, or an array, as examples, to inform the clinician of the degradation rates of the staples of the respective staple cartridges for varying periods of time for a plurality of tissue environments.

In various embodiments, the packaging can have an indicia that includes a first column listing tissue environments, such as stomach tissue, lung tissue, liver tissue, etc., a second column listing a respective bio-corrosion rate in the tissue environment for a first period of time, such as about 1 week, about 2 weeks, about 1 month, or about 3 months, as examples, and a third column listing a respective bio-corrosion rate in the tissue environment for a subsequent period of time after the first period of time, such as about 1 week, about 2 weeks, about 1 month, or about 3 months after the first period of time, as examples. Accordingly, when determining which staple cartridge to use for a particular stapling operation, a clinician can decide how fast or slow they want the staples to degrade for periods of time in a particular tissue environment. Based on the decision, the clinician can select a staple cartridge from among the plurality of staple cartridge according to their estimated degradation rates for particular periods of time in the plurality of tissue environments. It should be understood that the above-provided indicia with varying rates of bio-corrosion can include more than 2 columns of bio-corrosion rates to inform the clinician of the varying bio-corrosion rates of the staples over the life timeframe.

A fourth experiment was performed in which pure magnesium (HP—Mg) and two alloys (Mg2Ag and Mg10Gd) were either implanted in vivo in a rat femur or immersed in vitro in phosphate buffered saline ("PBS"), Hank's balanced salt solution ("HBSS"), or Dulbecco's Modified Eagle's Medium ("DMEM"). An assessment of weight loss and hydrogen evolution used to calculate degradation rate of the respective materials, as shown below:

TABLE 4

| Fourth Experiment | | | | | | |
|---|---|---|---|---|---|---|
| In vitro PBS (mm/year) | | In vitro HBSS (mm/year) | | In vitro DMEM (mm/year) | | In vivo rat femur (mm/year) |
| By mass loss | By $H_2$ evolution | By mass loss | By $H_2$ evolution | By mass loss | By $H_2$ evolution | μCT volume |
| Mg—2Ag (16.7) | Mg—2Ag (15.1) | Mg—10Gd (1.57) | Mg—2Ag (3.5) | Mg—2Ag (2.2) | Mg—2Ag (0.68) | Mg—10Gd (1.11) |
| Mg—10Gd (0.61) | Mg—10Gd (0.4) | Mg—2Ag (5.4) | Mg—10Gd (1.23) | HP—Mg (1.07) | HP—Mg (0.57) | HP—Mg (0.15) |
| HP—Mg (0.28) | HP—Mg (0.19) | HP—Mg (0.72) | HP—Mg (0.57) | Mg—10Gd (0.42) | Mg—10Gd (0.2) | Mg—2Ag (0.13) |

More information regarding the experiment can be found in Marco Pelegrin, Inigo. "Degradation Testing of Magnesium and its Alloys aiming at Biodegradable Implant Applications." (2016) (PhD Thesis), which is hereby incorporated by reference in its entirety herein.

In light of the results of the experiments, it can be seen that the mass loss and $H_2$ evolution in staples vary in different environments. For instance, a staple will bio-degrade at a first rate and a first amount of $H_2$ will be produced in a first tissue environment and bio-degrade at a second rate and a second amount of $H_2$ will be produced in a second tissue environment. Accordingly, an embodiment is disclosed in which a system is provided to a user, such as a clinician, that includes a plurality of staple cartridges. In various embodiments, the staple cartridges are positioned in a respective packaging that includes an indicia thereon, such as a table, a graph, a grid, or an array, as examples, to inform the clinician of the degradation rates and $H_2$ generation rates of the staples in the staple cartridges for a plurality of tissue environments.

Figure 44:
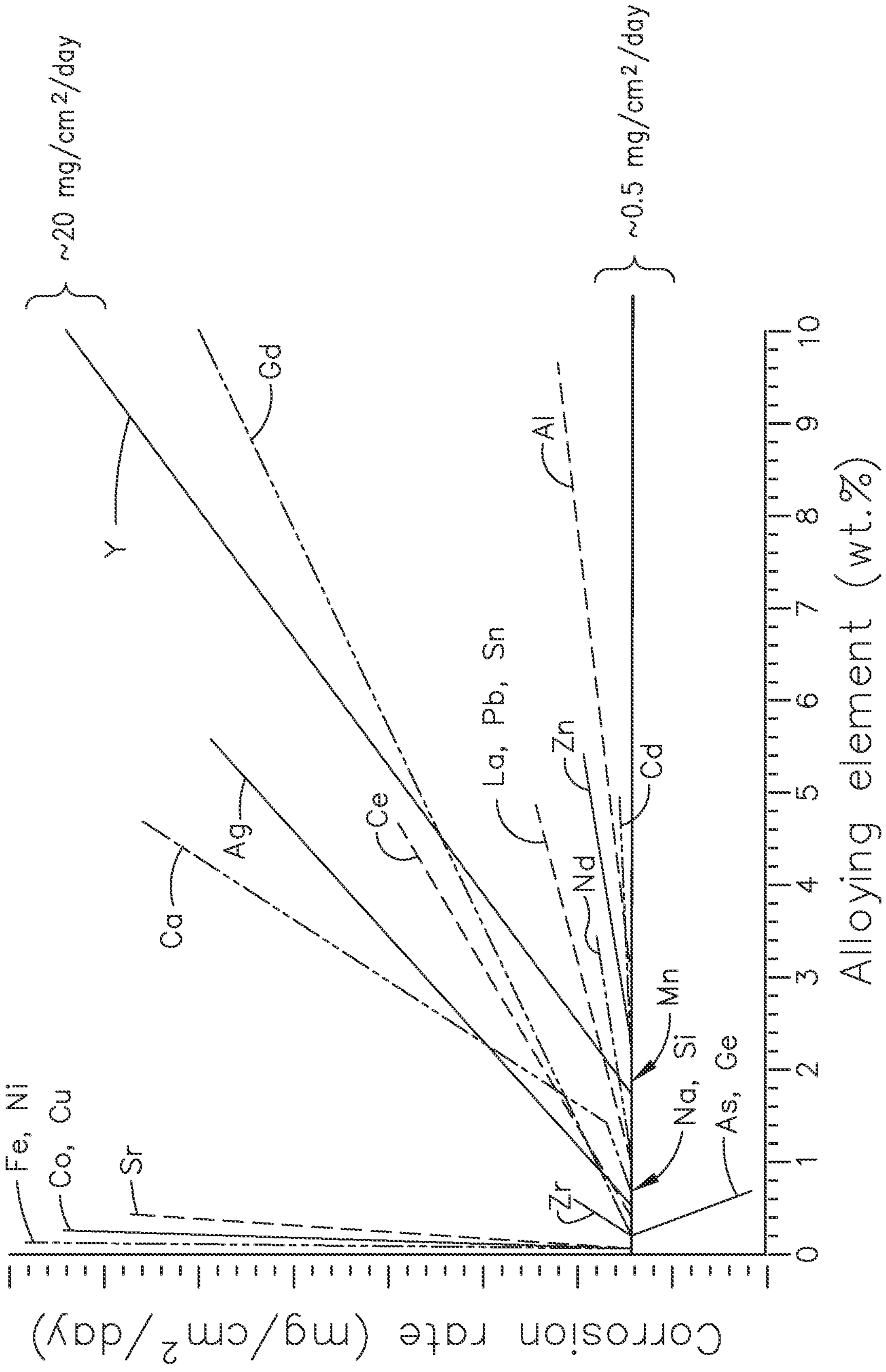
FIG. 44 is a graph depicting the corrosion rate and the alloying percentage of certain metals.

Referring now to FIG. 44, a graph is provided that illustrates corrosion rates (mg/cm$^2$/day) against alloying elements (wt %) for magnesium-based alloys. As can be seen in FIG. 44, increasing wt % of the alloying element affects the corrosion rate of the magnesium-based alloy. As one example, an increase in wt % of an alloying element from a first group of alloying elements (Fe, Ni, Co, Cu, and Sr) results in a large increase in corrosion rate. On the other hand, an increase in wt % of an alloying element from a second group of alloying elements (Zr, Na, Si, Mn, Ca, Ag, Ce, Nd, La, Pb, Sn, Zn, Cd, Y, Gd, and Al) results in a steady, less drastic increase in corrosion rate. In several instances, an increase in wt % of an alloying element from a third group of alloying elements (As and Ge) results in a decrease in corrosion rate of the staples.

In light of this data, a system is provided to a user, such as a clinician, that includes a plurality of staple cartridges comprising a first group of staple cartridges and a second group of staple cartridges. The first group of staple cartridges includes staples comprised of a magnesium-based alloy alloyed with a first alloying element. A first staple cartridge in the first group of staple cartridges includes staples alloyed with a first wt % of the first alloying element and a second staple cartridge in the first group of staple cartridges includes staples alloyed with a second wt % of the first alloying element that is different than the first wt % of the first alloying element.

The second group of staple cartridges includes staples comprised of a magnesium-based alloy alloyed with a second alloying element different than the first alloying element. A first staple cartridge in the second group of staple cartridges includes staples alloyed with a first wt % of the second alloying element and a second staple cartridge in the second group of staple cartridges includes staples alloyed with a second wt % of the second alloying element that is different than the first wt % of the first alloying element.

In various embodiments, each of the staple cartridges in the first and second groups of staple cartridges are positioned in a respective packaging that includes an indicia thereon which informs the clinician of the staple alloying element, the wt % of the alloying element, and the corrosion rate of the staples in the respective packaging. Accordingly, the system provides the clinician with the ability to select a staple cartridge from among the plurality of staple cartridges based on the known alloying element, the wt % of the alloying element, and the corrosion rate of the staples of the staple cartridge. This allows the clinician to select between cartridges with staples comprised of different alloys, such as selecting a cartridge with staples comprised of a first alloy that may be more suitable for a particular tissue environment as opposed to a cartridge with staples comprised of a second alloy.

In one embodiment, for a particular stapling procedure, a clinician may decide that it is more proper to select a staple cartridge from the first group of staple cartridges where the staples are alloyed with the first alloying element as opposed to a staple cartridge from the second group of staple cartridges where the staples are alloyed with the second alloying element. The clinician's decision can be based on a variety of factors, such as the tissue environment, the patient's medical record, or the alloys conductivity in the event that electrosurgery will also be performed in the tissue environment, as examples. Once the clinician has selected which group of staple cartridges to use, the clinician is then able to select a staple cartridge from the group according to the estimated corrosion rates, based on the wt % of the alloying element, giving the clinician the ability to control approximately how long the staples will be situated in the tissue environment.

Figure 43:
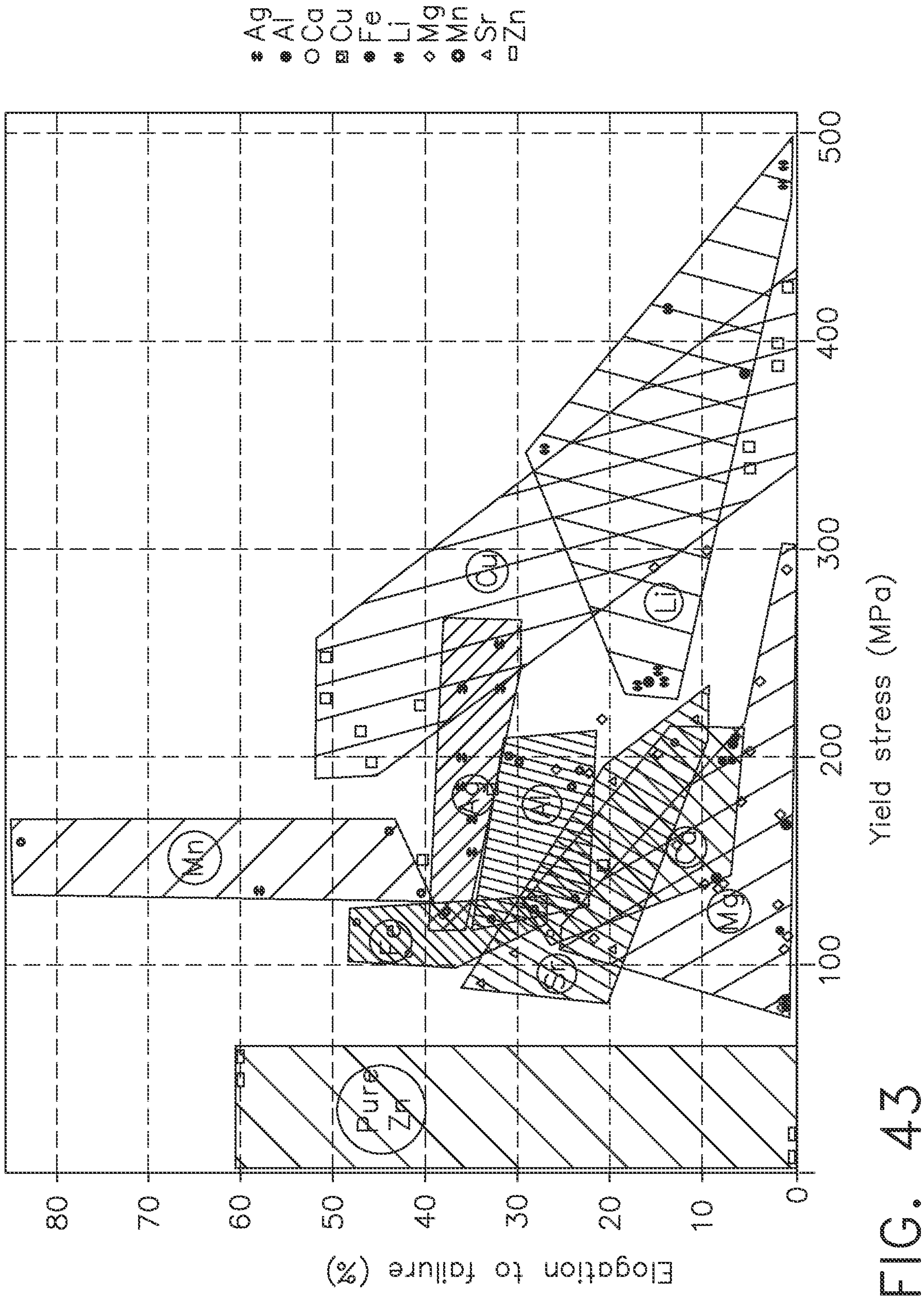
FIG. 43 is a graph depicting the elongation and stress of certain metals.

Referring now to FIG. 43, a graph is provided that illustrates elongation to failure (%) against yield stress (MPa) for pure zinc and a variety of zinc-based alloys. As can be seen in FIG. 43, pure zinc can have a low strength and plasticity, although this depends on how it is processed. Zn—Mg offers good strength, but with ductility dropping beyond ~0.1% Mg. Mn strengthens zinc while maintaining or enhancing ductility. Ca, Sr, and Fe offer low levels of strength with reduced ductility. Zn—Al offers superior that can be increased by processing. Cu improves tensile creep strength while maintaining ductility. Li exhibit remarkable strength (which can be further increased) with reduced ductility; however, ductility can be improved by adding Mn. Ag has high solubility in Mg, so strength is increased without ductility degradation. Ti can be used to improve room temperature creep, especially in Zn—Cu alloys.

In light of this data, a system is provided to a user, such as a clinician, that includes a plurality of staple cartridges. The plurality of staple cartridges includes a first staple cartridge that includes staples comprised of a first zinc-based alloy that has a first stress-strain profile. The plurality of staple cartridges further includes a second staple cartridge that includes staples comprised of a second zinc-based alloy that has a second stress-strain profile that is different than the first stress strain profile. In various embodiments, the first and second staple cartridges are positioned in a respective packaging that includes an indicia thereon which informs the clinician of the staple alloying element and the associated stress-strain profile associated therewith. Accordingly, the system provides the clinician with the ability to select a staple cartridge from among the plurality of staple cartridges based on the known alloying element and their stress-strain profile. This allows the clinician to select between cartridges with staples comprised of different alloys, such as selecting a cartridge with staples comprised of a first alloy that may be more suitable for a particular tissue environment as opposed to a cartridge with staples comprised of a second alloy.

In one embodiment, for a particular stapling procedure, a clinician may decide that it is more appropriate to select a staple cartridge with staples alloyed with a first alloying element as opposed to a staple cartridge with staples alloyed with a second alloying element. The clinician's decision can be based on a variety of factors, such as the stresses that the staples are expected to experience in the tissue environment. Accordingly, the indicia illustrating the stress-strain profile of the staples allows the clinician to have greater confidence that the selected staple cartridge is suitable for the particular tissue environment. The clinician's decision can also be based on other factors, such as the patient's medical record or the alloys conductivity in the event that electrosurgery will also be performed in the tissue environment, as examples. In various embodiments, along with the stress-strain profile, the indicia can indicate suitable tissue environments that the staples are best used for, along with tissue environments that the staples should be avoid being used in.

In various embodiments, further to the above, the bio-corrosion rates of staples can be adjusted by using staples comprised of a zinc-based alloy. Zinc-based alloys have increased mechanical properties when compared to magnesium-based alloys, allowing the staples have a smaller diameter compared to magnesium-based alloy staples. In some embodiments, the diameter of zinc-based alloy staples can be similar to that of diameter of traditional titanium staples. In addition, the modulus of elasticity of zinc-based alloys is considerably higher, and more like titanium, when compared to magnesium-based alloys.

In various embodiments, the staples are comprised of a 3AL-2V titanium alloy, which has an ultimate strength of 76,900-200,000 psi (530-1378 MPa), an elastic modulus of 1450 ksi, and is defined by the following composition: titanium (balance), vanadium (about 2.0 wt % to about 3.0 wt %), aluminum (about 2.5 wt % to about 3.5 wt %), hydrogen (about 0.015 wt % max), nitrogen (about 0.03 wt % max), carbon (about 0.10% max), and iron (about 0.25 wt % max). As shown above, the 3AL-2V titanium alloy has an ultimate strength similar to that of titanium staples, which is 49,900-200,000 psi (344-1378 MPa).

In one aspect, stiffer wires, such as wires comprised of a zinc-based alloy, will effect unfolding or tear open loads of the staples, force to form and un-form the staples (i.e. staple line burst strength, opening partially formed staples), and tip penetration loads of the staples (i.e. penetration thru bronchus and trachea rather than crumple the staple leg). In various embodiments, stiffer wire, such as wire comprised of a zinc-based alloy, enable improved staple leg guidance by the staple cartridge and driver features to better align the staple legs with the target tissue and resist rotation during deployment of the staples from the staple cartridge. In one aspect, stiffer wire staples, such as staples comprised of a zinc-based alloy, are better resistant to forces that can cause mis-alignment during deployment of the staples, such as forces experienced from tissue flow, adjunct skewing forces, or forces as a result of angular closure jaw mis-alignment on the staple trajectory, as examples.

In one aspect, material properties of the staple, such as the yield strength, will control the force required to form and un-form the staple when loaded by sealing tissue layers. In one aspect, material properties of the staple, such as hardness and ductility, control the magnitude of material cracking, fractures, or staple breaking. These harnesses help with yield strength by making the staple harder, but make the material more brittle and crack sensitive. In one aspect, the lower tension properties of magnesium and zinc cause higher work hardening, which makes the staple more brittle. Accordingly, the closer the material properties of the staples are to titanium, such as the 3AL-2V titanium alloy, as discussed above, the better the balance will be between ductility and hardness.

As discussed herein, it is often desirable for implanted staples to dissolve quickly within a patient, or at least faster than titanium and/or stainless steel staples might dissolve, for example. In various instances, staples that dissolve quickly are comprised of metals that are not as strong as titanium and/or stainless steel and, as a result, such quickly dissolvable staples may release the patient tissue sooner than the stronger, slower-dissolving staples. In at least one example, the innermost rows of staples, i.e., the staple rows closest to the longitudinal knife slot, comprise a staple comprised of titanium, a titanium alloy, and/or stainless steel in each staple cavity while the outermost rows of staples and the intermediate rows of staples, i.e., the staple rows intermediate the innermost staple rows and outermost staple rows, have staples comprised of magnesium and/or a magnesium alloy in each staple cavity. In such examples, the outermost staple rows and intermediate staple rows may release the patient tissue before innermost staple rows.

In at least one example, further to the above, the innermost staple rows of a staple cartridge comprise a staple comprised of titanium, a titanium alloy, and/or stainless steel in each staple cavity while the outermost staple rows and the intermediate staple rows have staples comprised of zinc and/or a zinc alloy in each staple cavity. In at least one other example, the intermediate staple rows and the outermost staple rows have staples comprised of iron and/or an iron alloy in each staple cavity. In any of these examples, the outermost staple rows and the intermediate staple rows may release the patient tissue before the innermost staple rows.

In at least one example, further to the above, the innermost staple rows of a staple cartridge include a staple comprised of a first magnesium alloy in each staple cavity, the intermediate staple rows include a staple comprised of a second magnesium alloy in each staple cavity which is different than the first magnesium alloy, and the outermost staple rows include a staple comprised of a third magnesium alloy in each staple cavity that is different than the first magnesium alloy and the second magnesium alloy. The first, second, and third magnesium alloys are selected such that the outermost staple rows release the patient tissue before the intermediate staple rows and the innermost staple rows. Similarly, the intermediate staple rows release the patient tissue before the innermost staple rows. This same approach can be used with zinc alloys in various staple cartridges. This approach could also be used with iron alloys in various staple cartridges. In various embodiments, the first, second, and third magnesium alloys are selected such that the innermost staple rows release the patient tissue before the intermediate staple rows and the outermost staple rows. Similarly, the intermediate staple rows release the patient tissue before the innermost staple rows. This same approach can be used with zinc alloys in various staple cartridges. This approach could also be used with iron alloys in various staple cartridges.

In at least one example, the innermost staple rows of a staple cartridge include staples comprised of pure magnesium and the intermediate staple rows and the outermost staple rows include staples comprised of a magnesium alloy. That said, in other examples, the pure magnesium staples can be placed in any suitable staple row within the staple cartridge. In any event, once implanted, the staples are part of a staple line in the patient where the pure magnesium staples degrade before the magnesium alloy staples. The early degradation of the pure magnesium staples can increase the pH of the environment surrounding the staple line and slow down the degradation of the magnesium alloy staples. Moreover, the pure magnesium staples can act as anodes that draw, redirect, or focus the oxidation and absorption of the staple line toward the pure magnesium staples and away from the magnesium alloy staples, at least temporarily. Such an arrangement would allow the magnesium alloy staples to remain functional for a desired time period. In various other examples, all of the staple rows within a staple cartridge comprise magnesium alloy staples but also include pure magnesium staples interdispersed throughout the staple rows. In at least one example, a staple cartridge comprises one or more staple rows comprised of iron staples and/or iron staples interdispersed throughout the staple rows. In such examples, the iron staples focus the oxidation and absorption away from the magnesium alloy staples. Also, in at least one example, a staple cartridge comprises one ore more staple rows comprised of zinc staples and/or zinc staples interdispersed throughout the staple rows. In such examples, the zinc staples focus the oxidation and absorption away from the magnesium alloy staples.

Figure 75A:
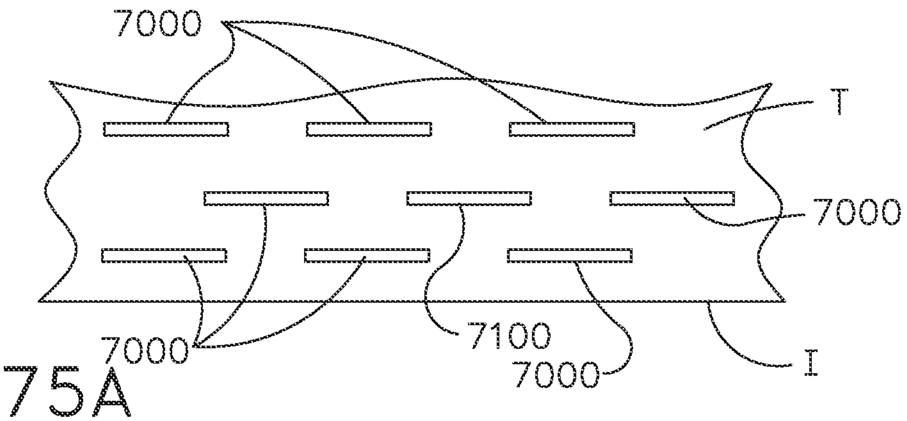
FIG. 75A depicts a staple pattern implanted in patient tissue which also includes a decoy staple configured to be bioabsorbed before the staples in the staple pattern in accordance with at least one embodiment.
Figure 75B:
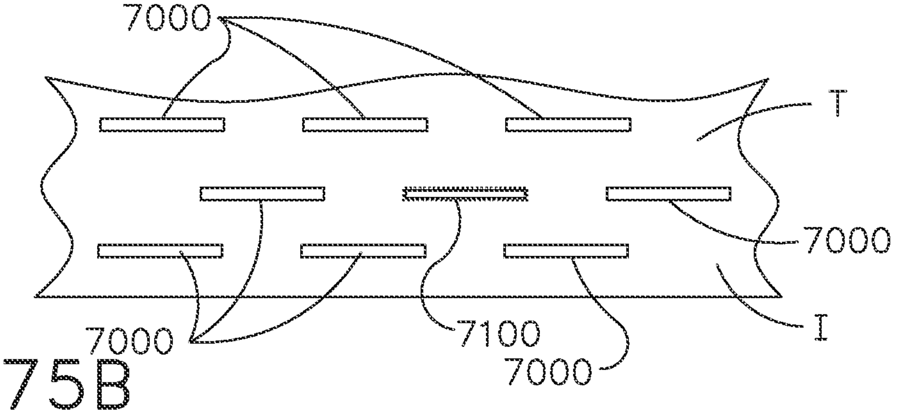
FIG. 75B depicts the staple decoy of FIG. 75A starting to be bioabsorbed before the staples are bioabsorbed.
Figure 75C:
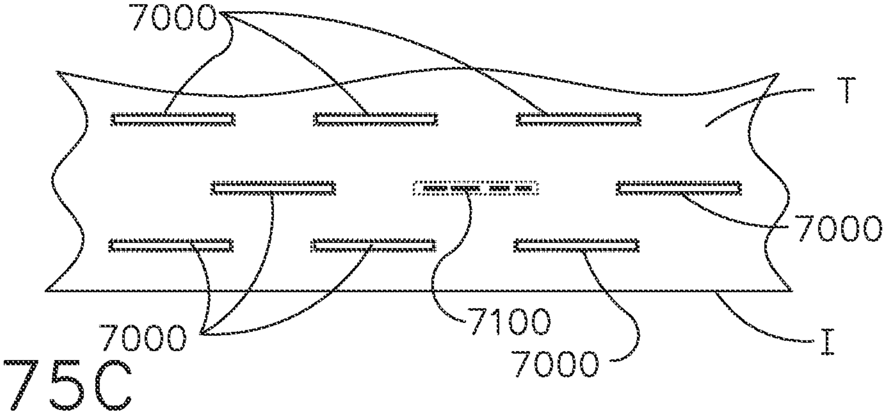
FIG. 75C depicts further bioabsorption of the staple decoy of FIG. 75A while the staples are starting to be bioabsorbed.
Figure 75D:
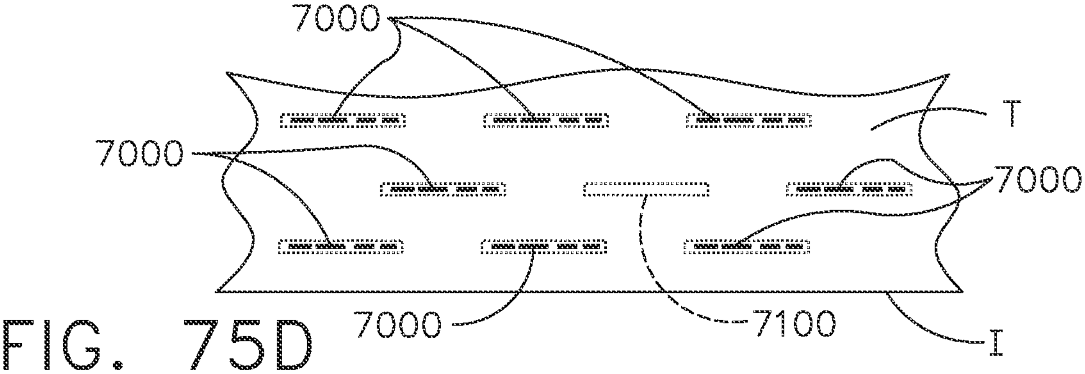
FIG. 75D depicts the dissolution of the staple decoy of FIG. 75A prior to the dissolution of the staples.

As discussed above, one or more staples deployed in a staple line can provide an anodic effect relative to the other staples in the staple line. In various embodiments, implants—other than staples—can be implanted in a patient to provide an anodic effect that at least partially and at least temporarily focuses the oxidation and absorption on the non-staple implants. In various instances, the non-staple implants are comprised of lithium, sodium, and/or potassium, for example. In at least one embodiment, a staple line is comprised of pure magnesium staples and/or magnesium alloy staples and the non-staple implants comprise anodes that allow the magnesium staples and the magnesium alloy staples to remain functional for a desired period of time. In at least one such embodiment, the non-staple implants are comprised of a material that is less noble than magnesium. Referring to FIG. 75A, a staple pattern includes longitudinal rows of staples 7000 implanted in patient tissue T along an incision I. A non-staple implant 7100 is also present in the staple pattern. As can be seen in FIGS. 75A-75D, the non-staple implant 7100 bioabsorbs and dissolves away before the staples 7000.

In various embodiments, in addition to or in lieu of the above, a powder is introduced onto a staple line and/or onto the patient tissue surrounding the staple line that comprises a sacrificial anodic material. In at least one embodiment, the powder comprises magnesium particles. In at least one such embodiment, the magnesium particles are mixed in dry, or at least substantially dry, sodium stearate. In at least one embodiment, a staple cartridge is covered in at least one such powder such that at least some of the powder is transferred to the patient tissue when the patient tissue is clamped against the staple cartridge. In at least one embodiment, the powder is stored in a staple cavity defined in the staple cartridge such that the powder is ejected from the staple cartridge by a staple driver during the staple firing stroke. In various instances, the powder is packed into one or more staple cavities that also have staples stored therein. In other instances, the powder is packed into one or more staple cavities that do not have a staple positioned therein. In at least one such instance, such staple cavities are positioned in the outermost staple rows. In various embodiments, the powder is contained in and/or on an implantable adjunct attached to the deck of the staple cartridge such that the powder is implanted with the adjunct during the staple firing stroke. In at least one embodiment, the sacrificial anodic material is contained in and/or is present on tape adhered to the staple cartridge. In at least one embodiment, the sacrificial anodic material is suspended in a gel, for example, on the staple cartridge.

In various instances, a sacrificial anodic material is applied to the patient tissue before the patient tissue is stapled and/or cut by spraying the sacrificial anodic material onto the patient tissue via a pressurized aerosol, for example, and or deposited onto the patient tissue via a syringe, for example. Similarly, in various instance, the sacrificial anodic material can be applied via these techniques after the patient tissue has been stapled and/or cut.

In various instances, the staples and the anodic material implanted within patient tissue are electrically connected. Such electrical connection can be made by body fluids within the patient. In various embodiments, a powder including sacrificial anodic material, discussed above, electrically interconnects the staples of an implanted staple line. In at least one embodiment, the powder includes silver and/or aluminum powder contained therein, for example. In at least one embodiment, the powder includes an electrically conductive material that is more noble than the magnesium such that the oxidation and bioabsorption processes are not redirected, or at least substantially redirected, to the electrically conductive material. In at least one embodiment, a staple cartridge comprises an electrically conductive wire, such as a wire mesh, for example, on the deck of the staple cartridge that is implanted with the staples. In at least one such embodiment, the wire is comprised of silver and/or aluminum, for example. In various embodiments, a staple cartridge comprises an implantable adjunct including electrically conductive powder contained therein and/or includes an electrically conductive wire mesh that is in contact with the staples once the staples have been fired and implanted in the patient tissue.

As discussed above, a sacrificial material can be used to direct or focus the oxidation and bioabsorption processes of the body away from the staples for a period of time such that the stapled and incised patient tissue has sufficient time to heal. The time in which the sacrificial material provides this effect depends on the mass or amount of sacrificial material that is used. More mass provides more time. In this way, the type and amount of sacrificial material, or materials, can be selected so as to tune the degradation of the staples.

In various instances, galvanic corrosion can occur between staples implanted within a patient that are comprised of different metals. In at least one instance, staples comprised of a first material act as an anode and staples comprised of a second material act as a cathode. In various embodiments, the anodic staples and the cathodic staples are electrically connected by an electrolytic fluid introduced into and/or onto the staple line. In various instances, the electrolytic fluid includes, but is not limited to, $Na+$, $Ca2+$, $K+$, $Mg2+$, $Zn2+$, $Cl-$, and/or $Fl-$, for example. The electrolytic fluid provides a means for ion migration away from the staples to prevent charge build-up that would otherwise stop and/or slow the galvanic reaction between the staples. In various instances, corrosion inhibitors such as sodium nitrite and/or sodium molybdate, for example, can be introduced into the galvanic system to slow the galvanic reaction between the staples.

In various embodiments, a staple is entirely comprised of a single material. For instance, a staple can be entirely comprised of pure magnesium or, alternatively, a magnesium alloy. Also, for instance, a staple can be entirely comprised of a first magnesium alloy or, alternatively, a second alloy. In various other embodiments, a staple is comprised of two or more different materials. For instance, a staple wire can be comprised of an inner core comprised of one metal and an outer portion surrounding the inner core that is comprised of another metal. In at least one such example, the inner core is comprised of pure magnesium and the outer portion is comprised of a magnesium alloy. In another example, the inner core is comprised of a magnesium alloy and the outer portion is comprised of magnesium. An electroplating process, for example, can be used to apply one metal and/or metal alloy onto another. In any event, the rate in which such staples are bioabsorbed can change over time after they have been implanted into a patient owing to the bioabsorption of the outer portion occurring at one rate and the bioabsorption of the inner core occurring at a different rate. For instance, the bioabsorption of a staple can be slower through an outer portion comprised of a magnesium alloy and then faster through an inner core comprised of magnesium, for example. In various embodiments, a galvanic reaction can be present between the inner core and the outer portion of a staple, especially when the outer portion is breached during bioabsorption and electrolytic fluids are in contact with the inner core and the outer portion simultaneously. Such embodiments may have to be used within a given time owing to the ongoing galvanic reaction between the metals, even before the staples are implanted in a patient.

In various embodiments, further to the above, a staple comprises a first portion comprised of a first metal and a second portion comprised of a second metal. In at least one such embodiment, a staple comprises a crown and first and second legs extending from the crown where the crown is comprised of a first material and the legs are comprised of a second material. For instance, in at least one embodiment, the crown is comprised of a magnesium alloy and the legs are comprised of pure magnesium. In various instances, the legs are attached to the crown through a welding process, for example. In at least one such instance, the welds between the crown and the legs occurs in the bends of the staples which creates an interface or weak spot for oxidation and bioabsorption processes of the body to attack. In at least one embodiment, a galvanic reaction can be present between the first and second materials of the crown and legs, especially when the staples are introduced to electrolytic fluids within a patient. The interface between the legs and the crown comprises a galvanic interface which can kickstart the bioabsorption of the staple in that location and can assure that the staples are quickly bioabsorbed and/or quickly made non-functional. Similar to the above, such embodiments may have to be used within a given time owing to the ongoing galvanic reaction between the metals, even before the staples are implanted in a patient.

In various examples, two staples are stored in all of the staple cavities in a staple cartridge, or in at least some of the staple cavities of a staple cartridge. In such instances, the two staples stored in a staple cavity are simultaneously ejected from the staple cartridge and deformed against the anvil during the firing stroke. As discussed below, such examples can be used to obtain various advantages.

As discussed herein, it is often desirable for implanted staples to dissolve quickly within a patient, or at least faster than titanium and/or stainless steel staples might dissolve, for example. In various instances, staples that dissolve quickly are comprised of metals that are not as strong as titanium and/or stainless steel and, as a result, such quickly dissolvable staples may release the patient tissue sooner than the stronger, slower-dissolving staples. In at least one example, the innermost rows of staples, i.e., the staple rows closest to the longitudinal knife slot, comprise two staples in each staple cavity while the outermost rows of staples and the intermediate rows of staples, i.e., the staple rows intermediate the innermost staple rows and outermost staple rows, have only one staple in each staple cavity. In such examples, the outermost staple rows and intermediate staple rows may release the patient tissue before innermost staple rows. In many instances, one staple within a double-staple cluster may release the patient tissue while the other staple in the double-staple cluster continues to clench the patient tissue for at least a while longer. In at least one example, the outermost staple rows and the intermediate staple rows may release the patient tissue in about 20 days while the innermost staple rows release the patient tissue in about 30 days, for example. In at least one example, the outermost staple rows and the intermediate staple rows may release the patient tissue in about 30 days while the innermost staple rows release the patient tissue in about 45 days, for example. In at least one example, the innermost staple rows hold onto the patient tissue about 1.5 times longer than the outermost staple rows and the intermediate staple rows. In other examples, the innermost staple rows hold onto the patient tissue about 2 times longer than the outermost staple rows and the intermediate staple rows. In other examples, the innermost staple rows hold onto the patient tissue about 2.5 times longer than the outermost staple rows and the intermediate staple rows.

In at least one example, further to the above, the innermost staple rows have a single staple in each staple cavity comprised of stainless steel, the intermediate staple rows have two staples in each staple cavity comprised of magnesium, and the outermost staple rows have a single staple in each staple cavity comprised of magnesium. In such examples, the outermost staple rows release the patient tissue, then the intermediate staple rows, and then the innermost staple rows. In such instances, the staple rows closest to the longitudinal incision in the patient tissue holds onto the tissue the longest. Other examples are envisioned in which the intermediate staple rows hold onto the patient to the tissue the longest. In such instances, the early dissolution of the outermost staple rows increases blood flow to the incised tissue margin and the early dissolution of the innermost staple rows directly provides nutrients to the incised tissue margin. In at least one example, all of the staple cavities in a staple cartridge comprises two staples stored therein. In at least one such example, at least some of the staples in the double-staple clusters are comprised of different materials. In at least one example, for instance, the innermost staple cavities of a staple cartridge each has two magnesium or magnesium alloy staples stored therein, the intermediate staple cavities each has one magnesium or magnesium alloy staple and one zinc or zinc alloy staple stored therein, and the outermost staple cavities each as two zinc or zinc alloy staples stored therein.

Figure 78:
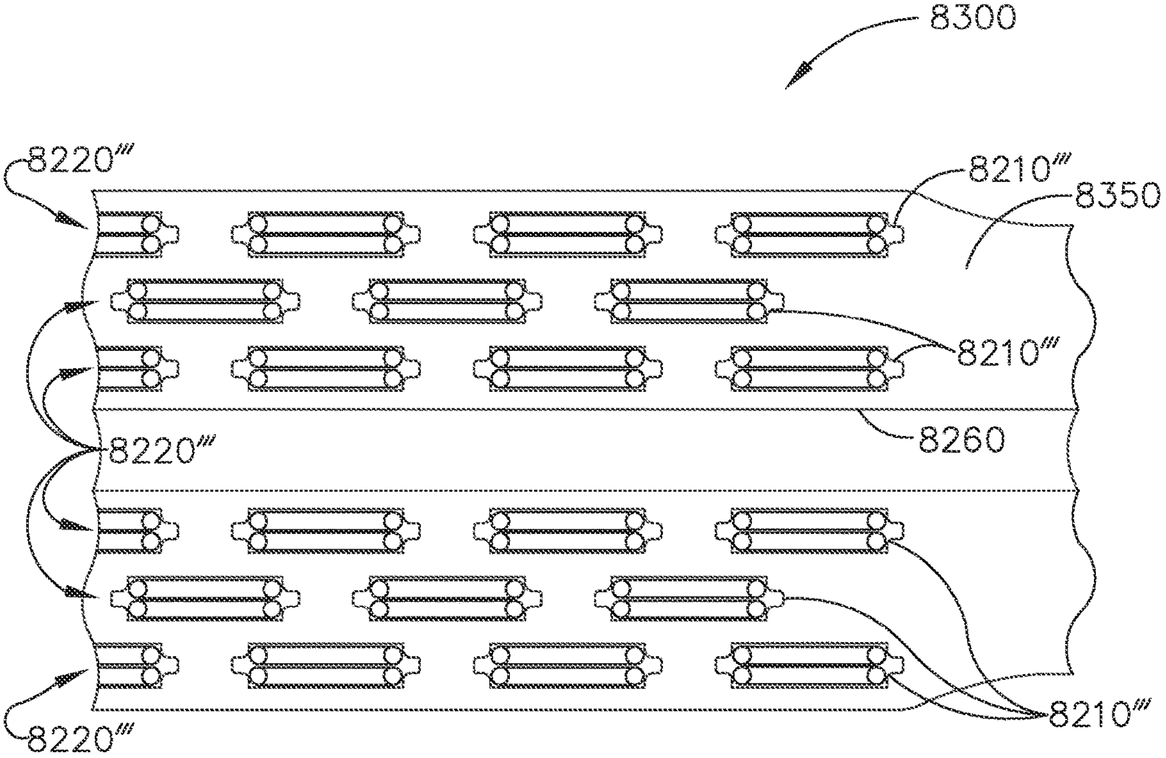
FIG. 78 is a partial plan view of a staple cartridge comprising staple cavities and two staples stored in each staple cavity in accordance with at least one embodiment.
Figure 79:
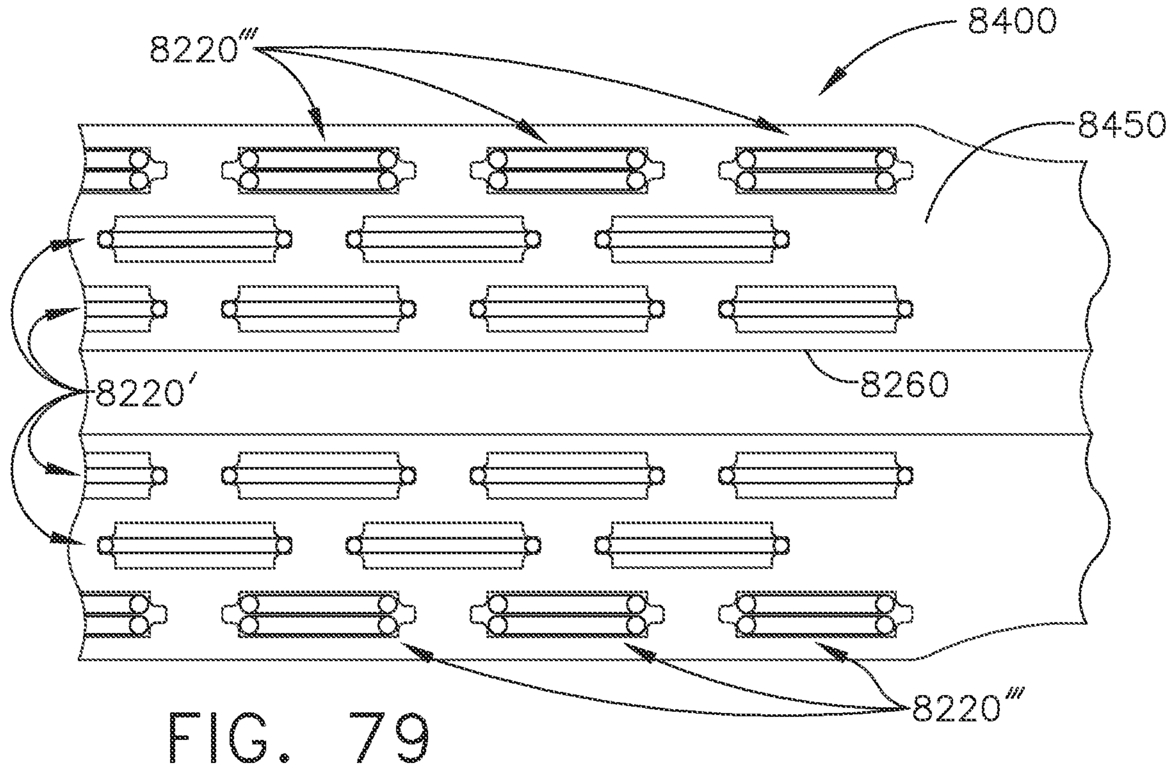
FIG. 79 is a partial plan view of a staple cartridge comprising longitudinal rows of staple cavities which have one staple stored in each staple cavity and a longitudinal row of staple cavities which has two staples stored in each staple cavity in accordance with at least one embodiment.
Figure 80:
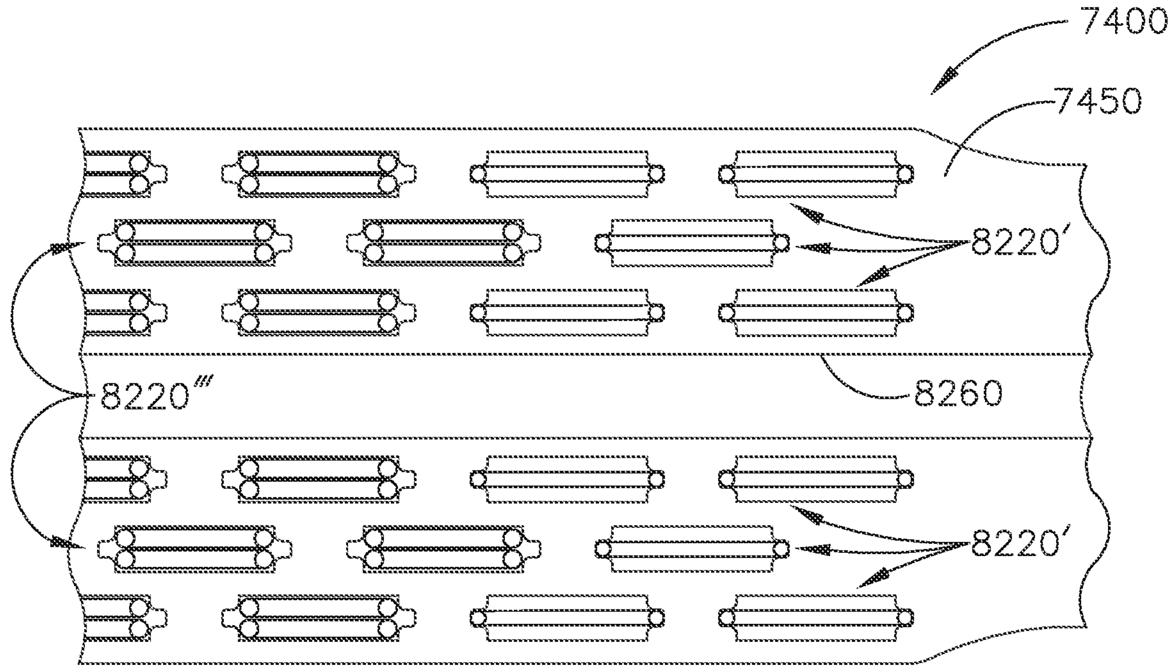
FIG. 80 is a partial plan view of a staple cartridge comprising one staple stored in proximal staple cavities and two staples stored in distal staple cavities in accordance with at least one embodiment.

Referring to FIG. 78, a staple cartridge 8300 comprises a cartridge body 8350 including a deck comprising a proximal end and a distal end and a longitudinal slot 8260 extending from the proximal end toward the distal end. The cartridge body 8350 comprises three longitudinal rows of staple cavities 8210''' defined in the deck on a first lateral side of the longitudinal slot 8260 and three longitudinal rows of staple cavities 8210''' defined in the deck on a second, or opposite, side of the longitudinal slot 8260. Each staple cavity 8210''' has two staples 8220''' removably stored therein. Referring to FIG. 79, a staple cartridge 8400 comprises a cartridge body 8450 including a deck comprising a proximal end and a distal end and a longitudinal slot 8260 extending from the proximal end toward the distal end. The cartridge body 8450 comprises three longitudinal rows of staple cavities defined in the deck on a first lateral side of the longitudinal slot 8260 and three longitudinal rows of staple cavities defined in the deck on a second, or opposite, side of the longitudinal slot 8260. The outermost rows of staple cavities has two staples 8220''' removably stored in each staple cavity, the innermost rows of staple cavities has a single staple 8220' stored in each staple cavity, and the intermediate rows of staple cavities has a single staple 8220' stored in each staple cavity. Referring to FIG. 80, a staple cartridge 7400 comprises a cartridge body 7450 including a deck comprising a proximal end and a distal end and a longitudinal slot 8260 extending from the proximal end toward the distal end. The cartridge body 7450 comprises three longitudinal rows of staple cavities defined in the deck on a first lateral side of the longitudinal slot 8260 and three longitudinal rows of staple cavities defined in the deck on a second, or opposite, side of the longitudinal slot 8260. A proximal group of staple cavities has a single staple 8220' stored in each staple cavity and the staple cavities distal to the proximal group has two staples 9220''' removably stored therein.

As discussed above, the mechanical properties of a staple can be tuned to alter the biodegradation rate of the staple. In various embodiments, the surface of the staple can be modified to increase and/or decrease the biodegradation rate of the staple. In various instances, smoother staples have less exposed surface area than rougher staples and, as a result, smoother staples have less surface area to be exposed to fluids within the patient and less material that can be oxidized at a given time. In at least one process, staples undergo a tumbling and/or polishing process to smoothen the staples so as to decrease the bioabsorption rate of the staples. In other instances, staples undergo an abrading process, for example, to roughen the staples so as to increase the bioabsorption rate of the staples. In various instances, the surfaces of the staples can be broken so as to permit the absorption mechanism to penetrate below the surfaces and/or exterior portions of the staples and increase the bioabsorption rate of the staples. In at least one such instance, the exterior portions of the staples have surface hardening, heat treating, and/or a different grain structure that is different than the interior portions of the staples which can slow the biodegradation process. Such exterior portions can be scored and/or ground, for example, such that the absorption mechanism can penetrate below the exterior portions at the outset of the staples being implanted in the patient. In various instances, the cross-section of certain areas in a staple can be reduced to create an attack point for the biodegradation process which can cause the staple to fail within a desired time frame. Thinner cross-sections fail faster than thicker cross-sections. In at least one instance, one or more portions of the staple wire is knurled, grooved, scored, extruded, and/or rolled, for example, such that the thickness of the staple wire is different in some portions of the staple wire than others.

Figure 18:
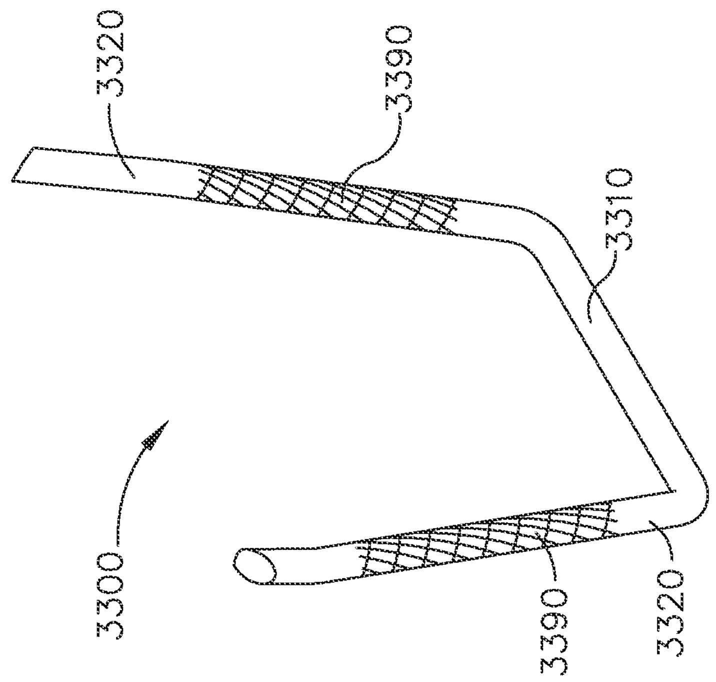
FIG. 18 is a perspective view of a wire staple comprising knurls in accordance with at least one embodiment.
Figure 17:
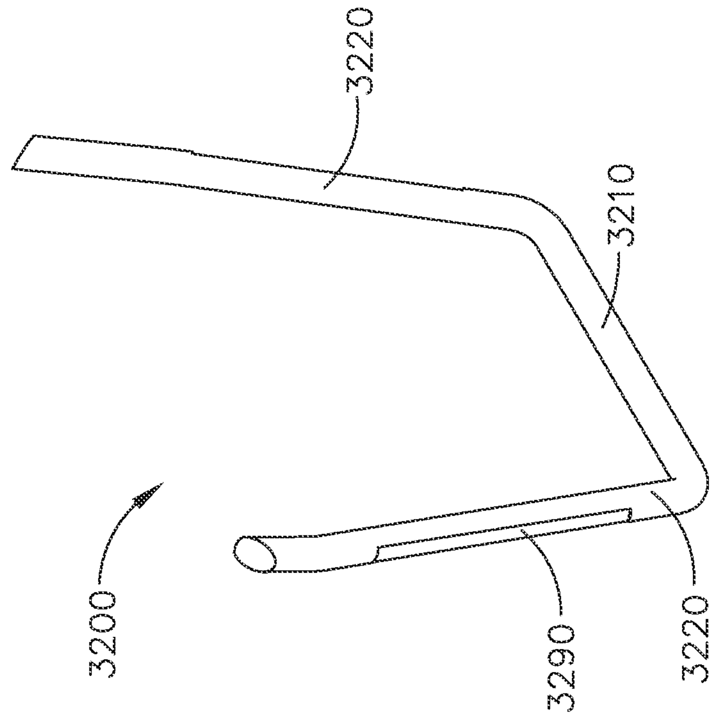
FIG. 17 is a perspective view of a wire staple comprising an abraded surface in accordance with at least one embodiment.

In various embodiments, the entire surface of a staple is roughened while, in other embodiments, only portions of the staple surface are roughened. Referring to FIG. 17, a wire staple 3200 comprises a crown 3210 and legs 3220 extending from the crown 3210. The wire staple 3200 further comprises an abraded region 3290 on each leg 3220 which causes the legs 3220 to fail in the abraded region 3290 before the other regions of the wire staple 3200 during the bioabsorption of the wire staple 3200 in the patient. In at least one such instance, the abraded regions 3290 of the legs 3220 comprise the top of the formed staple configuration which allows the clenched tissue to be released away from the crown 3210 as the wire staple 3200 dissolves. Referring to FIG. 18, a wire staple 3300 comprises a crown 3310 and legs 3320 extending from the crown 3310. The wire staple 3300 further comprises a knurled region 3390 on each leg 3320 which causes the legs 3320 to fail in the abraded region 3390 before the other regions of the wire staple 3300 during the bioabsorption of the wire staple 3300 in the patient. In at least one such instance, the abraded regions 3390 of the legs 3320 comprise the top of the formed staple configuration which allows the clenched tissue to be released away from the crown 3310 as the wire staple 3300 dissolves.

In various embodiments, further to the above, a staple cartridge comprises a first group of staples in the innermost staple rows, a second group of staples in the intermediate staple rows, and a third group of staples in the outermost staple rows. The first group of staples comprises staples having a surface roughness Ra within a first range, the second group of staples comprises staples having a surface roughness Ra within a second range that is different than the first range, and the third group of staples comprises staples have a surface roughness Ra within a third range that is different than the first range and the second range. The first, second, and third ranges of the surface roughness Ra, i.e., average surface roughness, can partially overlap or not overlap at all. In this embodiment, the first range is higher than the second range, and the second range is higher than the third range. That is to say that the first group of staples have a rougher surface than the second group of staples, and the second group of staples have a rougher surface than the first group of staples. In this embodiment, the first group of staples bioabsorbs faster than the second group of staples, and the second group of staples bioabsorbs faster than the third group of staples. In at least one alternative embodiment, the first range is lower than the second range, and the second range is lower than the third range.

In various embodiments, further to the above, a staple cartridge comprises a first group of staples in a proximal-most group of staple cavities, a second group of staples in a distal-most group of staple cavities, and a third group of staples in an intermediate group of staple cavities intermediate the proximal-most group and the distal-most group. The first group of staples comprises staples having a surface roughness Ra within a first range, the second group of staples comprises staples having a surface roughness Ra within a second range that is different than the first range, and the third group of staples comprises staples have a surface roughness Ra within a third range that is different than the first range and the second range. The first, second, and third ranges of the surface roughness Ra, i.e., average surface roughness, can partially overlap or not overlap at all. In this embodiment, the first range is higher than the second range, and the second range is higher than the third range. That is to say that the first group of staples have a rougher surface than the second group of staples, and the second group of staples have a rougher surface than the first group of staples. In this embodiment, the first group of staples bioabsorbs faster than the second group of staples, and the second group of staples bioabsorbs faster than the third group of staples. In at least one alternative embodiment, the first range is lower than the second range, and the second range is lower than the third range. In various embodiments, the first group of staples and the second group of staples bioabsorb faster than the third group of staples. In many instances it is possible that the ends of two consecutive staple firings in the patient tissue will overlap resulting in a high density cluster of staples that makes the patient tissue stiff. In view of the above, the proximal-most and/or the distal-most group of staples can dissolve faster than the other staples so as to permit the patient tissue subjected to the high density staple cluster to become flexible quickly.

In various embodiments, the surface of one or more portions of a staple is roughened to increase the bioabsorption rate of the roughened portions. In at least one embodiment, a staple comprises a crown, first and second legs, and bends connecting the first and second legs to the crown where the surface of the bends is rougher than the crown and the first and second legs. In such embodiments, the bends will deteriorate faster than the crown and the first and second legs when the staple is implanted in a patient. As a result, the staple will fracture at the bends of the staple and release the patient tissue while the crown and first and second staple legs continue to bioabsorb. In at least one other embodiment, the staple legs have a rougher surface than the bends and the crown and, as a result, the staple legs will bioabsorb faster. In view of the above, the staples of a staple cartridge can be subjected to different surface treatments to change the time in which the staples crack, fracture, and/or dissolve once the staples are implanted in a patient.

In various embodiments, further to the above, a staple cartridge can comprise groups of staples stored in the staple cartridge where the staples of each group have a different surface roughness profile. In at least one such embodiment, a staple cartridge includes a first group of staples where each staple has a first surface roughness profile, a second group of staples where each staple has a second surface roughness profile, and a third group of staples where each staple has a third surface roughness profile. In this embodiment, the staples of the first group of staples have not undergone a surface roughening process—the staples of the second group of staples have a crown, first and second legs, and bends connecting the legs to the crown that have been roughened through an abrading process—and the entire exterior surface of the staples in the third group of staples have been roughened through an abrading process. Once implanted in a patient, the staples in the third group of staples bioabsorb faster than the staples in the second group of staples and, likewise, the staples in the second group of staples bioabsorb faster than the staples in the first group of staples. In at least one such embodiment, the first group of staples is stored in the innermost rows of staple cavities defined in a staple cartridge, the second group of staples are stored in the intermediate rows of staple cavities, and the third group of staples are stored in the outermost rows of staple cavities. In another embodiment, the third group of staples are stored in the distal-most staple cavities of a staple cartridge, the second group of staples are stored in the proximal-most staple cavities of the staple cartridge, and the first group of staples are stored in the staple cavities intermediate the second and third groups of staples.

In various embodiments, further to the above, the staples stored in a staple cartridge are comprised of wire having the same diameter, or at least substantially the same diameter. In other embodiments, one or more of the staple rows in a staple cartridge is comprised of wire having a smaller diameter than the other staple rows. In at least one such embodiment, the outermost staple rows in a staple cartridge have staples with a thinner diameter and may provide a smaller, or lighter, clenching force to the patient tissue than the staples closest to the tissue cutline that have a thicker diameter. In at least one such embodiment, the innermost staple rows in a staple cartridge have staples with the thickest diameter and the intermediate staple rows have staples with a diameter in-between the diameters in the inner staple row and the outer staple row. In various instances, the thinner staples will fracture and release the patient tissue before the thicker staples fracture and release the patient tissue. Such an arrangement can place the staples that last the longest along the incision, or margin, in the patient tissue which may be the last portion of the patient to heal after a procedure. In at least one alternative embodiment, the innermost rows of staples in a staple cartridge have the thinnest diameter while the outermost rows of staples have the thickest diameter. In this embodiment, the staples furthest away from the incision in the patient tissue will last the longest and give the tissue margin more space to heal.

Figure 83:
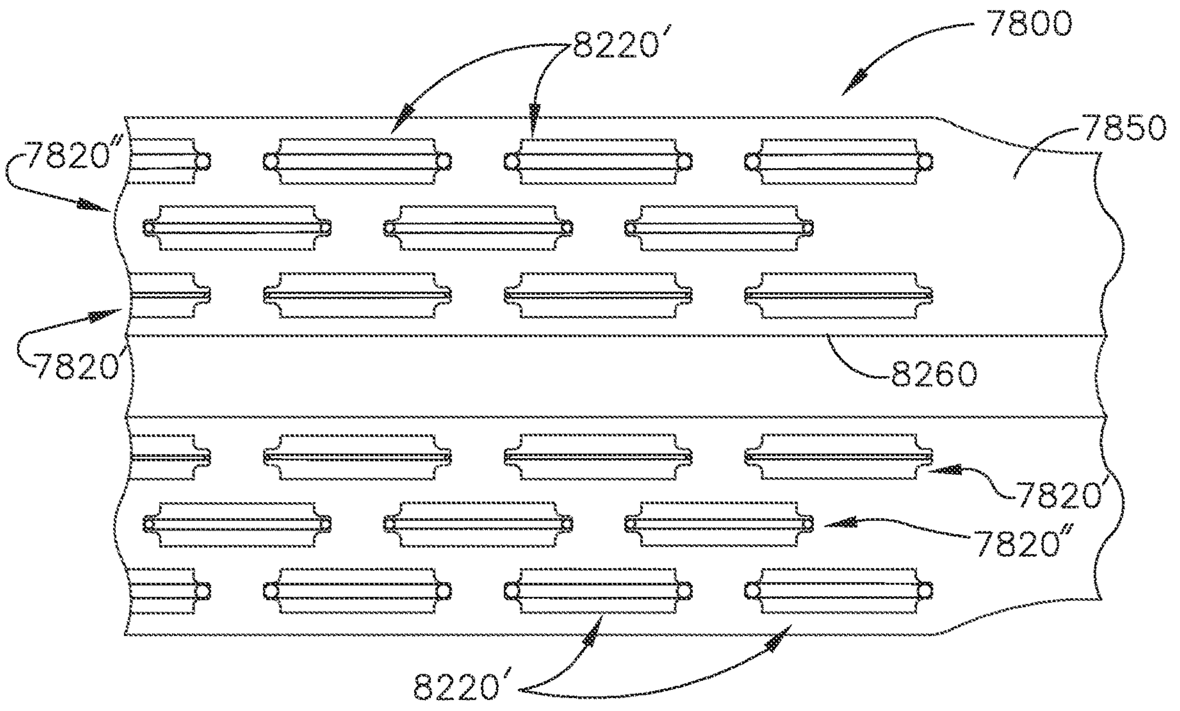
FIG. 83 is a partial plan view of a staple cartridge comprising staples having different wire diameters in accordance with at least one embodiment.
Figure 84:
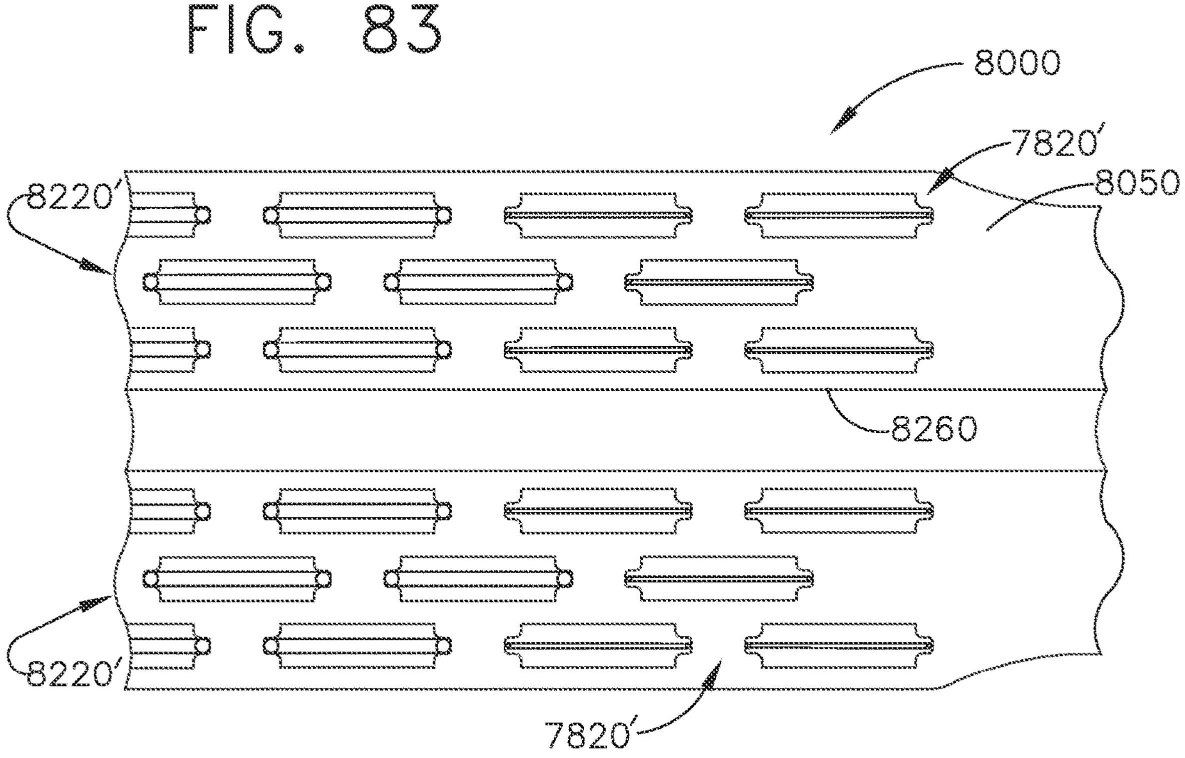
FIG. 84 is a partial plan view of a staple cartridge comprising thin staples in proximal staple cavities and thick staples in distal staple cavities in accordance with at least one embodiment.
Figure 85:
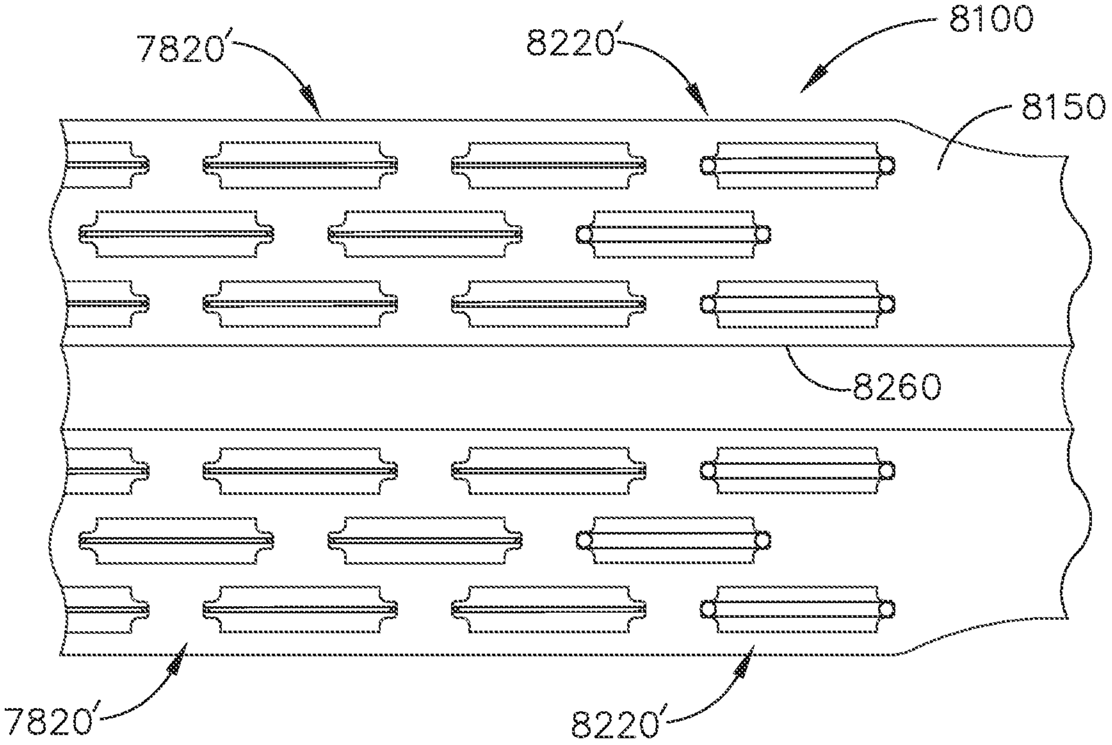
FIG. 85 is a partial plan view of a staple cartridge comprising thick staples in proximal staple cavities and thin staples in distal staple cavities in accordance with at least one embodiment.

Referring to FIG. 83, a staple cartridge 7800 comprises a cartridge body 7850 including a deck comprising a proximal end and a distal end and a longitudinal slot 8260 extending from the proximal end toward the distal end. The cartridge body 7850 comprises three longitudinal rows of staple cavities defined in the deck on a first lateral side of the longitudinal slot 8260 and three longitudinal rows of staple cavities defined in the deck on a second, or opposite, side of the longitudinal slot 8260. The outermost rows of staple cavities has a single staple 8220' stored in each staple cavity, the innermost rows of staple cavities has a single staple 7820' stored in each staple cavity, and the intermediate rows of staple cavities has a single staple 7820" stored in each staple cavity. The staples 7820' are comprised of staple wire that has a smaller diameter than the staples 8220' and the staples 7820" are comprised of staple wire that has a smaller diameter than the staples 7820'. Referring to FIG. 84, a staple cartridge 8000 comprises a cartridge body 8050 including a deck comprising a proximal end and a distal end and a longitudinal slot 8260 extending from the proximal end toward the distal end. The cartridge body 8050 comprises three longitudinal rows of staple cavities defined in the deck on a first lateral side of the longitudinal slot 8260 and three longitudinal rows of staple cavities defined in the deck on a second, or opposite, side of the longitudinal slot 8260. A proximal group of staple cavities has a single staple 7820' stored in each staple cavity and the staple cavities distal to the proximal group has a single staple 8220' removably stored therein. Referring to FIG. 85, a staple cartridge 8100 comprises a cartridge body 8150 including a deck comprising a proximal end and a distal end and a longitudinal slot 8260 extending from the proximal end toward the distal end. The cartridge body 8150 comprises three longitudinal rows of staple cavities defined in the deck on a first lateral side of the longitudinal slot 8260 and three longitudinal rows of staple cavities defined in the deck on a second, or opposite, side of the longitudinal slot 8260. A proximal group of staple cavities has a single staple 8220' stored in each staple cavity and the staple cavities distal to the proximal group has a single staple 7820' removably stored therein.

In various instances, further to the above, the staples implanted into patient tissue from the distal end of one staple cartridge may overlap with staples implanted into the patient tissue from the proximal end of another staple cartridge. Such overlap can make the patient tissue stiff. In order to reduce this effect, the staples stored in the proximal end and/or the distal end of a staple cartridge can have a thinner diameter than the other staples stored in the staple cartridge. In at least one embodiment, a distal group of staples stored in the distal end of a staple cartridge have a thinner wire diameter than the staples stored in the proximal end of the staple cartridge and the intermediate portion of the staple cartridge extending between the proximal end and the distal end. In at least one other embodiment, a proximal group of staples stored in the proximal end of a staple cartridge have a thinner wire diameter than the staples stored in the distal end of the staple cartridge and the intermediate portion of the staple cartridge extending between the proximal end and the distal end. Such embodiments allow the overlap region to normalize quickly by the quick dissolution of the thinner staples in the overlap region such that the stiffness of the overlap region comes to match the stiffness along the rest of the staple line. In at least one instance, the thinner staples release the tissue within 15 days while the thicker staples release the tissue in 30-45 days, for example. In addition to or in lieu of the above, in various embodiments, a staple cartridge comprises anodic elements stored in the proximal end and/or the distal end of the staple cartridge that, once implanted, direct or focus the oxidation and bioabsorption toward the overlap region.

In various other embodiments, the staples stored in the proximal-most staple cavities of a staple cartridge have a thicker wire diameter than the staples stored in the other staple cavities in the staple cartridge. In at least one such embodiment, the deployment of the thicker staples at the beginning of the staple firing stroke pushes the anvil away from the staple cartridge and maintains a desired gap height between the anvil and the staple cartridge. In addition to or in lieu of the above, the staples in the distal-most staple cavities of a staple cartridge have a thicker wire diameter than the staples in the other staple cavities which can assist in maintain a desired gap between the anvil and the staple cartridge at the end of the staple firing stroke. In various embodiments, further to the above, the proximal staples and/or the distal staples can be stiffer than the staples in the middle of the staple cartridge which can assist in positioning the anvil.

Figure 45A:
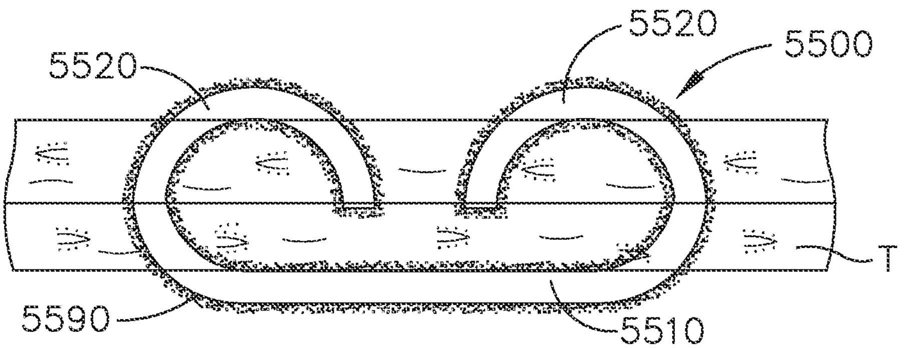
FIG. 45A illustrates a coated wire staple implanted in patient tissue in accordance with at least one embodiment.
Figure 45B:
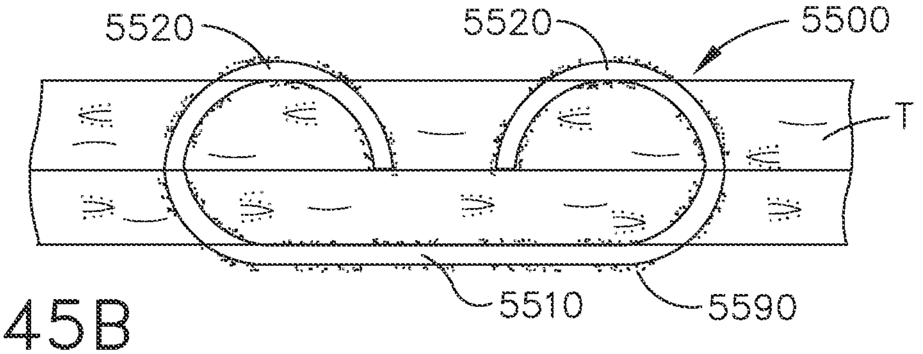
FIG. 45B illustrates the coated wire staple of FIG. 45A in a partially-dissolved functional state.
Figure 45C:
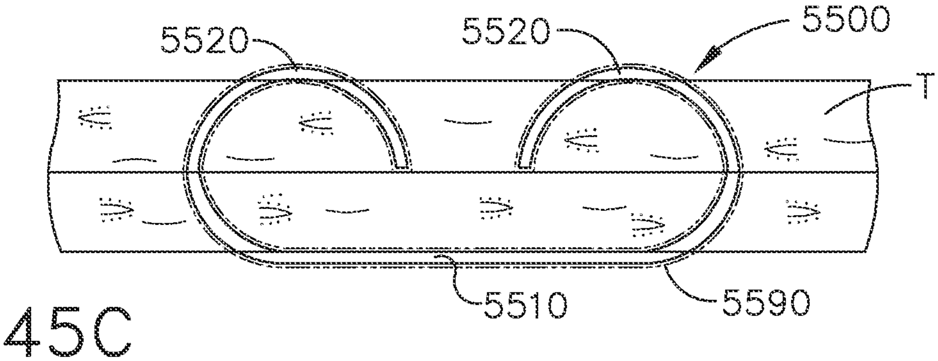
FIG. 45C illustrates the coated wire staple of FIG. 45A in a mostly-dissolved functional state.
Figure 45D:
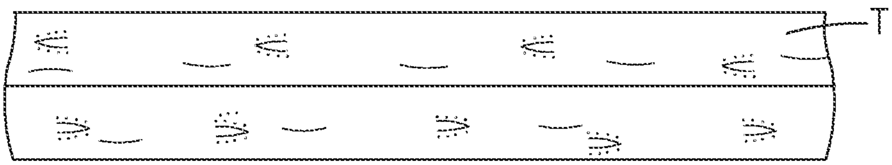
FIG. 45D illustrates the wire staple of FIG. 45A in a completely-dissolved state.

In various embodiments, as discussed herein, the staples of a staple cartridge are coated with at least one coating which delays, slows, and/or otherwise controls the bioabsorption of the substrates, or frames, of the staples. Referring to FIGS. 45A-45D, a wire staple 5500 comprises a substrate including a crown 5510 and legs 5520 extending from the crown 5510. The staple 5500 further comprises a coating 5590 on the substrate. When the staple 5500 is implanted into patient tissue T, referring to FIG. 45A, the coating 5590 is in an unabsorbed state. Thereafter, referring to FIGS. 45B and 45C, the coating 5590 and the substrate bioabsorb until the staple 5500 is completely dissolved, as illustrated in FIG. 45D. As discussed herein, the staples are implanted in the patient tissue at the same time that the tissue is incised and hold the tissue together while the tissue heals. Measured from this point in time, the patient tissue needs a certain amount of time to heal before the staples are no longer needed. This timeframe can be referred to as the healing window. Notably, tissue healing can be long process that can include tissue remodeling over time and can be different from patient to patient and different from tissue type to tissue type. The term healing window as used herein is the amount of time needed before the incised tissue achieves a predicted desirable stability and/or strength. In various instances, the healing window is about 30 days while, in some instances, the healing window is about 60 days, for example. Longer healing windows can be about 100 days, about 180 days, or about 365 days, for example, depending on the type of tissue and the procedure performed, among other things. The time between FIGS. 45A and 45D, i.e., the time between implantation and full dissolution exceeds the healing window. That being said, in various embodiments disclosed herein, it is desirable for the staples to be completely absorbed shortly after the healing window has been exceeded. In many embodiments, the shortest amount of time possible between the end of the healing window and the full dissolution of the staples is desired. Having said that, it is desirable for the staples to retain functionality throughout the healing window and apply a clenching force or pressure to the tissue during the healing window. After the healing window has been exceeded, the functionality can be lost prior to the complete dissolution of the staples. As discussed further below, one or more staple coatings can be used to tune the time in which the staples lose functionality and/or become completely dissolved.

Figure 63:
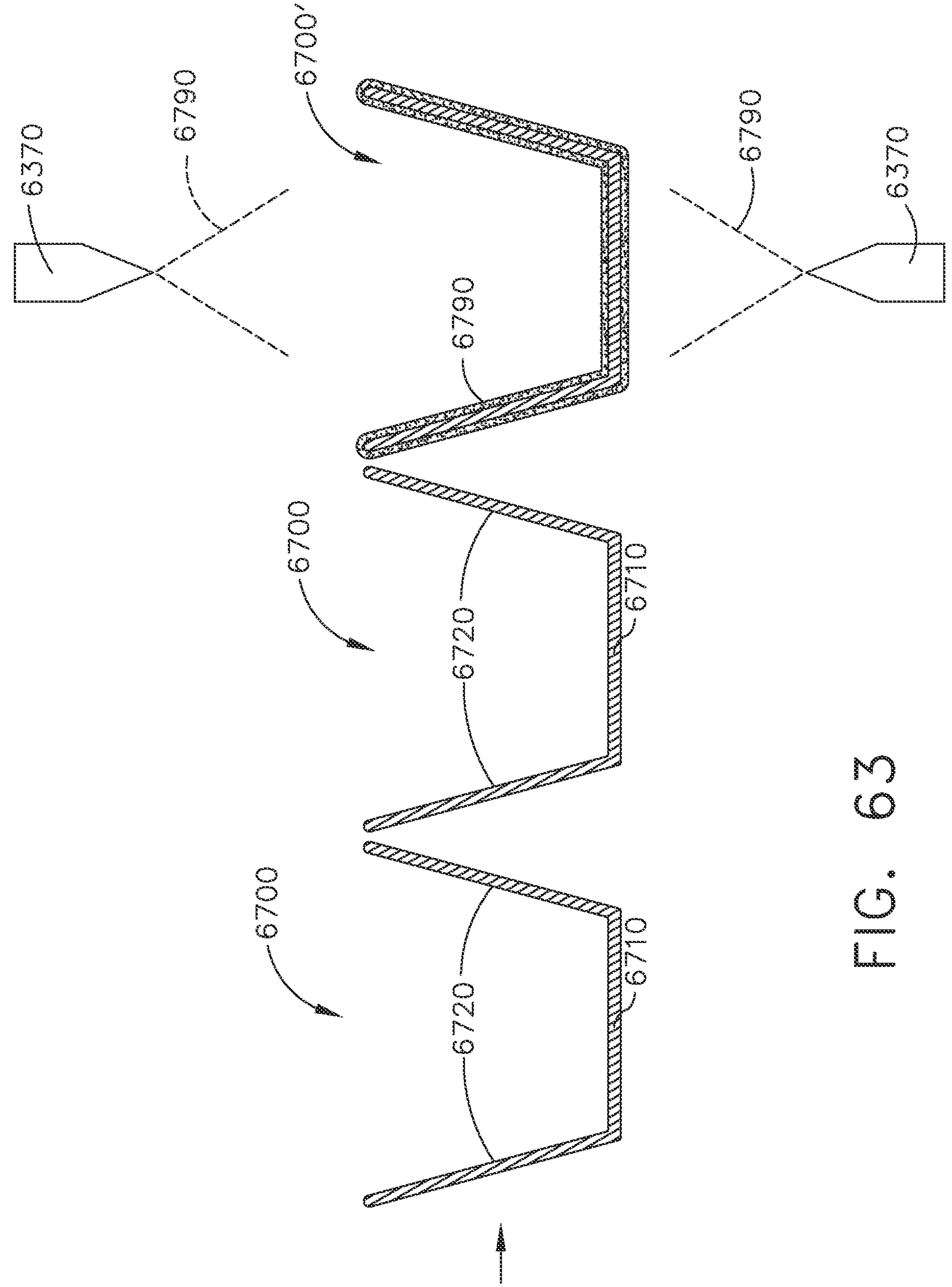
FIG. 63 depicts a staple manufacturing process in accordance with at least one embodiment.

In various embodiments, the substrates of the staples are formed from wire. In at least one embodiment, referring to FIG. 63, the wire is coated after the wire is formed into a staple form. In at least one such embodiment, a length of wire is cut from a spool of wire such that the length of wire has a first end and a second end. In various instances, the length of wire is sheared such that the staple tips are sheared to their final shape and sharpness while, in other instances, the length of wire undergoes additional stamping and/or tip sharpening processes to bring the staple tips into their final shape and sharpness. In either event, the length of wire is bent to create a staple form 6700 including a crown 6710, a first leg 6720 extending from the crown 6710, and a second leg 6720 extending from the crown 6710. That said, other embodiments are envisioned in which a staple form comprises a crown and only one leg. In any event, the length of wire and/or the staple form can undergo one or more treating processes which affect the mechanical properties of the wire substrate and/or prepare the surface of the staple form 6700 to receive a coating 6790.

In various instances, further to the above, a length of wire and/or a staple form is heat treated before it is coated. In various instances, a length of wire and/or a staple form is exposed to phosphoric acid, hydrochloric acid, and/or magnesium fluoride before the coating process. Such processes can clean the surface of the length of wire and/or the staple form, among other things. In addition to or lieu of the above, a length of wire and/or a staple form are ultrasonically cleaned with isopropyl alcohol and/or acetone, for example. In various instances, in addition to or in lieu of the above, the surface of a length of wire and/or a staple form are pre-treated with micro-arc plasma process, a hydrothermal treatment process, and/or a plasma electrolytic oxide process, for example. Once prepared, the staple form is coated with one or more coatings that can mechanically and/or chemically bond to the wire substrate and then loaded into a staple cartridge. In at least one embodiment, the coating is applied to the wire substrate by a spraying process, for example. In various instances, referring to FIG. 63, the coating 6790 is sprayed onto the staple form 6700 using one or more spray jets 6370 to create a coated staple 6700'. In at least one such instance, a spray jet 6370 is positioned on one side of the staple form 6700 and another spray jet 6370 is positioned on the opposite side of the staple form 6700 such that the entire staple form 6700 is coated. In at least one embodiment, the coating is applied the wire substrate by a sputtering process, for example. In at least one embodiment, the coating is applied to the wire substrate by a chemical vapor deposition process, for example. In various instances, paralene, fluoropolymers, and/or silicone, for example, are deposited on the staples using a chemical vapor deposition process. Notably, all of the bending, stamping, and/or tip sharpening processes have already been completed before the staples are coated. Such an approach prevents, or at least reduces the possibility of the coating, or coatings, from cracking and/or delaminating from the substrate of the staple, for example, during the staple manufacturing process.

In various embodiments, further to the above, the staple wire is already coated when the length of wire is cut from the spool of wire. In such embodiments, the coating is applied to the wire substrate and then wound up on a spool. In at least one embodiment, the coating is applied to the wire substrate by a continuous extrusion process, for example. In at least one embodiment, the coating is applied to the wire substrate during a continuous electroplating process, for example. In various instances, the wire substrate is comprised of magnesium and the plating is compatible with the magnesium so as to not initiate corrosion within the magnesium prior to being implanted in a patient. In at least one embodiment, the coating is applied to the wire substrate by a continuous chemical vapor deposition process, for example. In any event, the coatings in these examples are applied to the wire substrate prior the wire substrate being sheared, stamped, bent, and/or sharpened, for example, to make the staples. In various embodiments, the coating comprises a hard shell polymer coating capable of withstanding the stresses and strains created during the staple forming process without cracking and/or delaminating from the wire substrate. In various embodiments, the coating is comprised of polylactic acid (PLA), polyglycolic acid (PGA), poly-L-lactic acid (PLLA), polyurethane (PU), and/or polytrimethylene carbonate (PTMC), for example. PLLA, PLA, and PGA are all synthetic bioabsorbable polymers often used in biomedical applications. PU and PTMC are biocompatible elastomers often used in biomedical applications. In various embodiments, the coating is comprised of poly lactic-co-glycolic acid (PGLA) 65:35, the chemical makeup of which is about 65% glycolide and about 35% lactide, for example. In various embodiments, the coating is comprised of poly(N-vinylcaprolactam) (PNVCL), for example. In various embodiments, the coating is formulated by a sol-gel coating process, for example. In various embodiments, the coating is comprised of carbonate, for example. In any event, such coatings are sufficiently lubricious to undergo the staple manufacturing process without being damaged, or at least significantly damaged. That said, the coated wire can be further coated with sodium stearate and/or a mixture of sodium stearate and ethyl lauroyl arginate (LAE), for example, which can act as a lubricant and reduce the possibility of the coated wire being damaged during the staple manufacturing process. Moreover, the sodium stearate and/or a mixture of sodium stearate and LAE can facilitate the insertion of the staples into the staple cavities of a staple cartridge.

Figure 60:
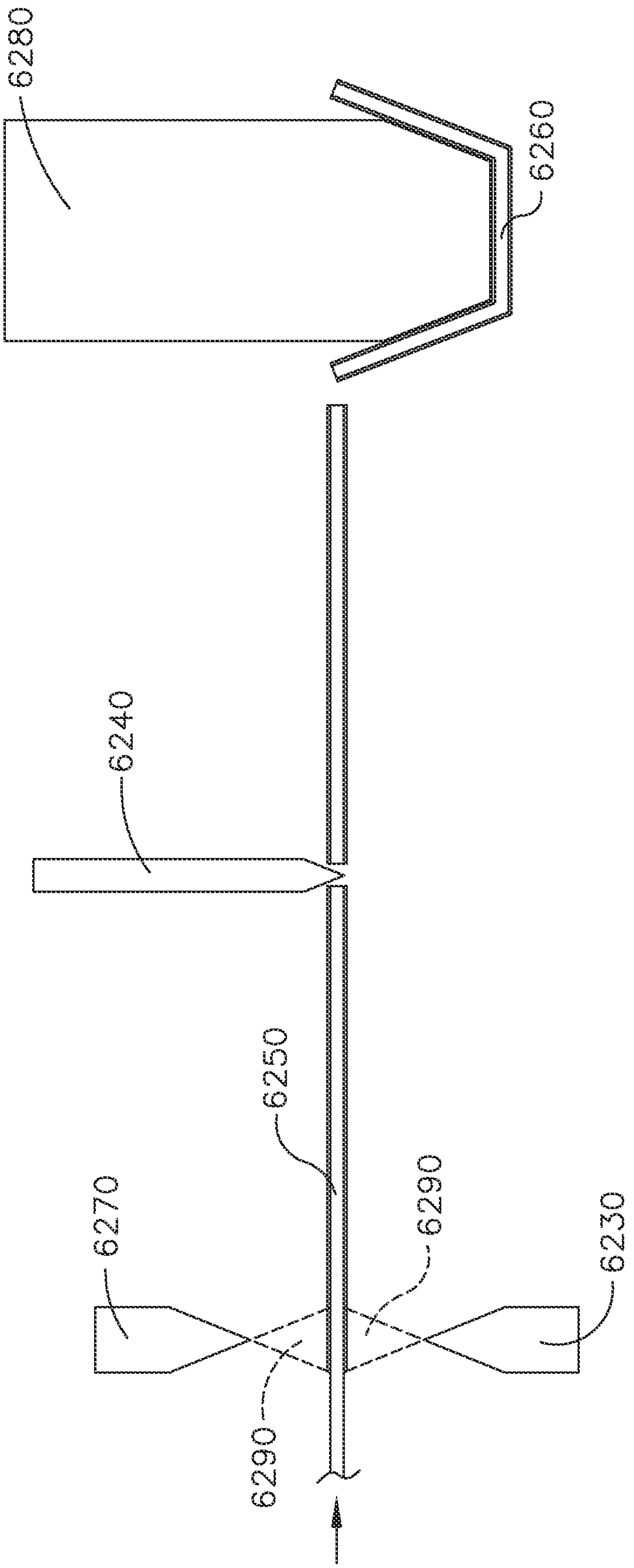
FIG. 60 depicts a wire staple manufacturing process in accordance with at least one embodiment.

In various processes, such as process 6200, referring to FIG. 60, uncoated wire stock 6250 is drawn from a wire spool and then sprayed with a coating 6290 via spray jets 6230 and 6270. In various other embodiments, the coating 6290 is extruded onto the wire stock 6250. In either event, the coated wire stock 6250 is then sheared by a shearing knife 6240 to create a length of wire that is then stamped into a staple form 6260 by a die 6280. That being said, it is possible that the coating 6290 on the wire stock 6250 may become scratched and/or otherwise damaged in the die 6280. Moreover, the shearing process cuts the coating 6290 on the wire stock 6250 and creates uncoated surfaces on the staple tips of the staple form 6260. Absent more, such damage to the coating and/or exposed surfaces of the substrate metal can create focal points, either intentionally or unintentionally, for the oxidation and bioabsorption processes within the patient.

Figure 61:
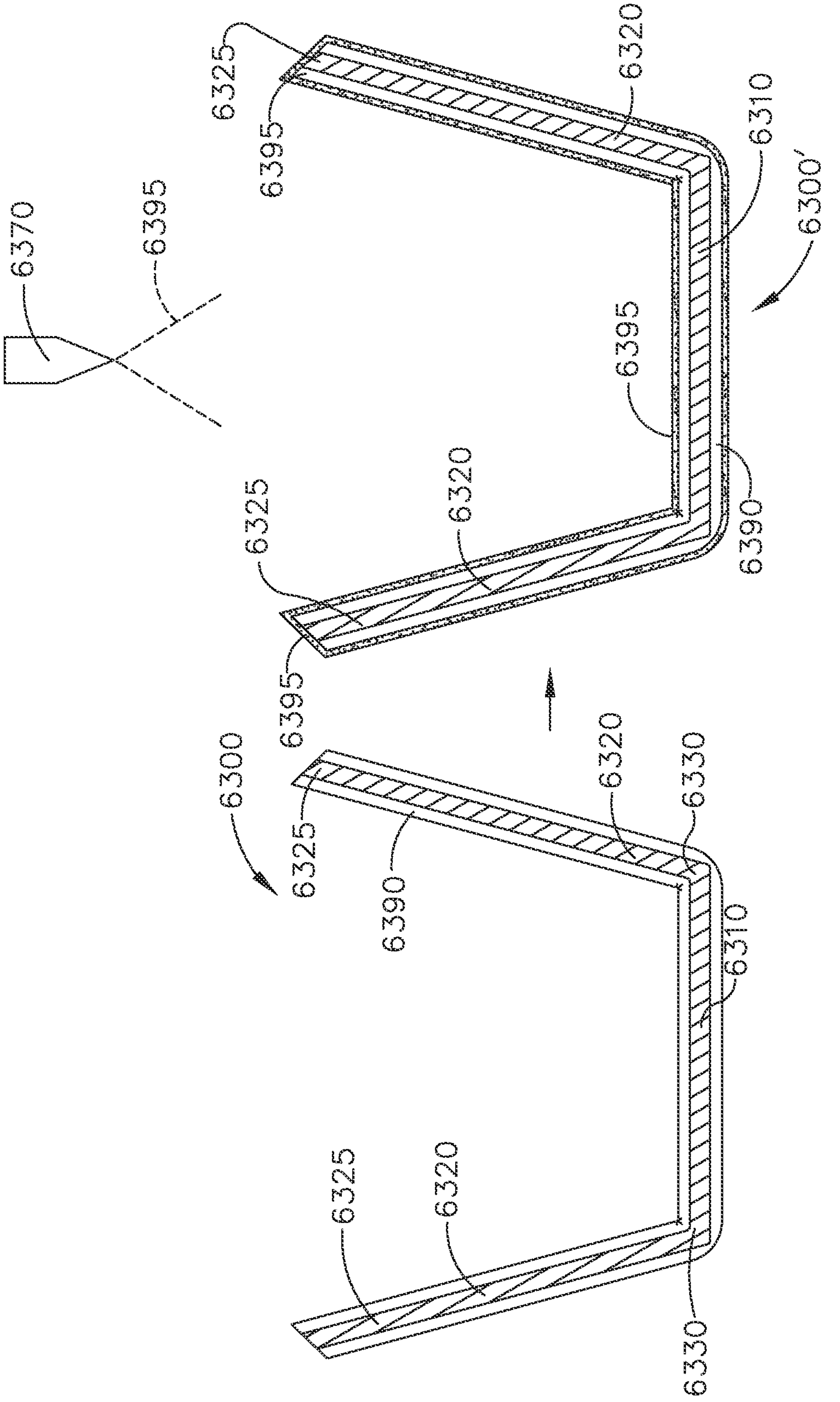
FIG. 61 depicts a staple manufacturing process in which a first coating is applied before a staple forming step in the process and a second coating is applied after the staple forming step in accordance with at least one embodiment.

To address the above, referring to FIG. 61, the coating can be re-applied to a staple after it exits the die 6280. In addition to or in lieu of the above, a second, or different, coating can be applied to the staple after it exits the die 6280. Referring to FIG. 61, a wire staple form 6300 comprises a crown 6310, legs 6320, and bends 6330 connecting the legs 6320 to the crown 6310. As part of forming the wire staple form 6300, the tips 6325 of the staple legs 6320 have exposed metal. Moreover, the coating 6390 on the bends 6330 has become thin, stretched, strained, and/or cracked as a result of the forming process. To address both issues, the wire staple form 6300 is sprayed with coating 6395 via spray jets 6370, for example, which covers the exposed staple tips 6325 and covers up defects in the coating 6390 including any defects present on the staple bends 6330. Further to the above, the coatings 6390 and 6395 can be comprised of the same material or different materials. At such point, staples 6300' have been made from staple forms 6300 and the staples 6300' can be loaded into a staple cartridge.

Figure 62:
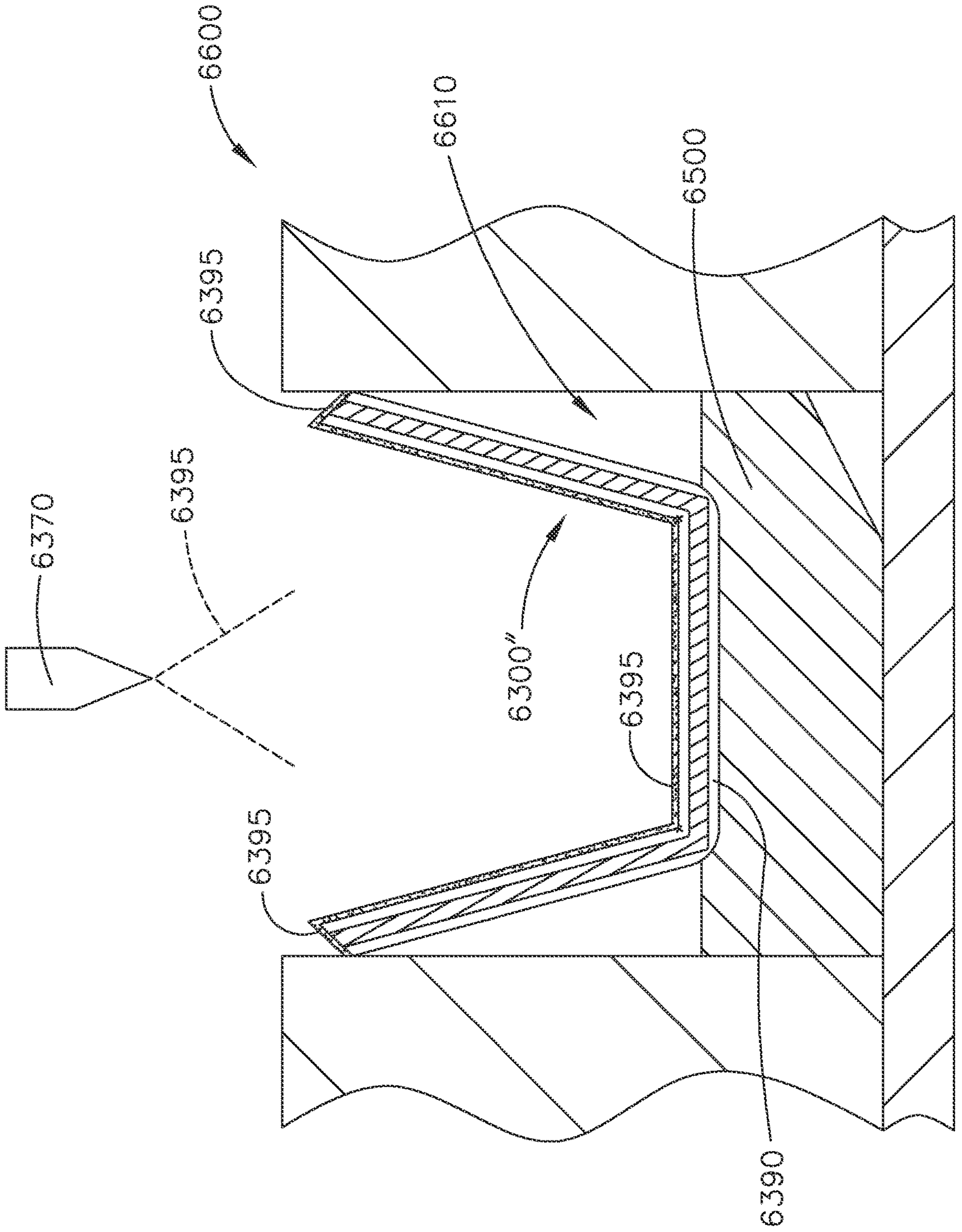
FIG. 62 depicts a process in which a staple is coated while the staple is positioned in a staple cartridge in accordance with at least one embodiment.

In addition to or in lieu of the above, referring to FIG. 62, a plurality of staple forms 6300 are loaded into a staple cartridge 6600 and an additional coating 6395 is applied to the staple forms 6300 while the staple forms 6300 are stored in the staple cartridge 6600 to make staples 6300" out of the staple forms 6300. The staple cartridge 6600 comprises staple cavities 6610 defined therein and drivers 6500 configured to push the staples 6300" out of the staple cavities 6610 during a staple firing stroke. Notably, in this embodiment, the coating 6395 is sprayed down onto the staple forms 6300 from a spray jet 6370 through the top openings of the staple cavities 6610. As a result, the coating 6395 is present on the leg tips, the inner surfaces of the legs and bends, and the top surface of the staple crown of the staples 6300"; however, gaps in the coating may exist on the outside surfaces of the legs and/or on the bottom surface of the staple crown depending on how well the coating 6395 can flow onto those surfaces.

Figure 64:
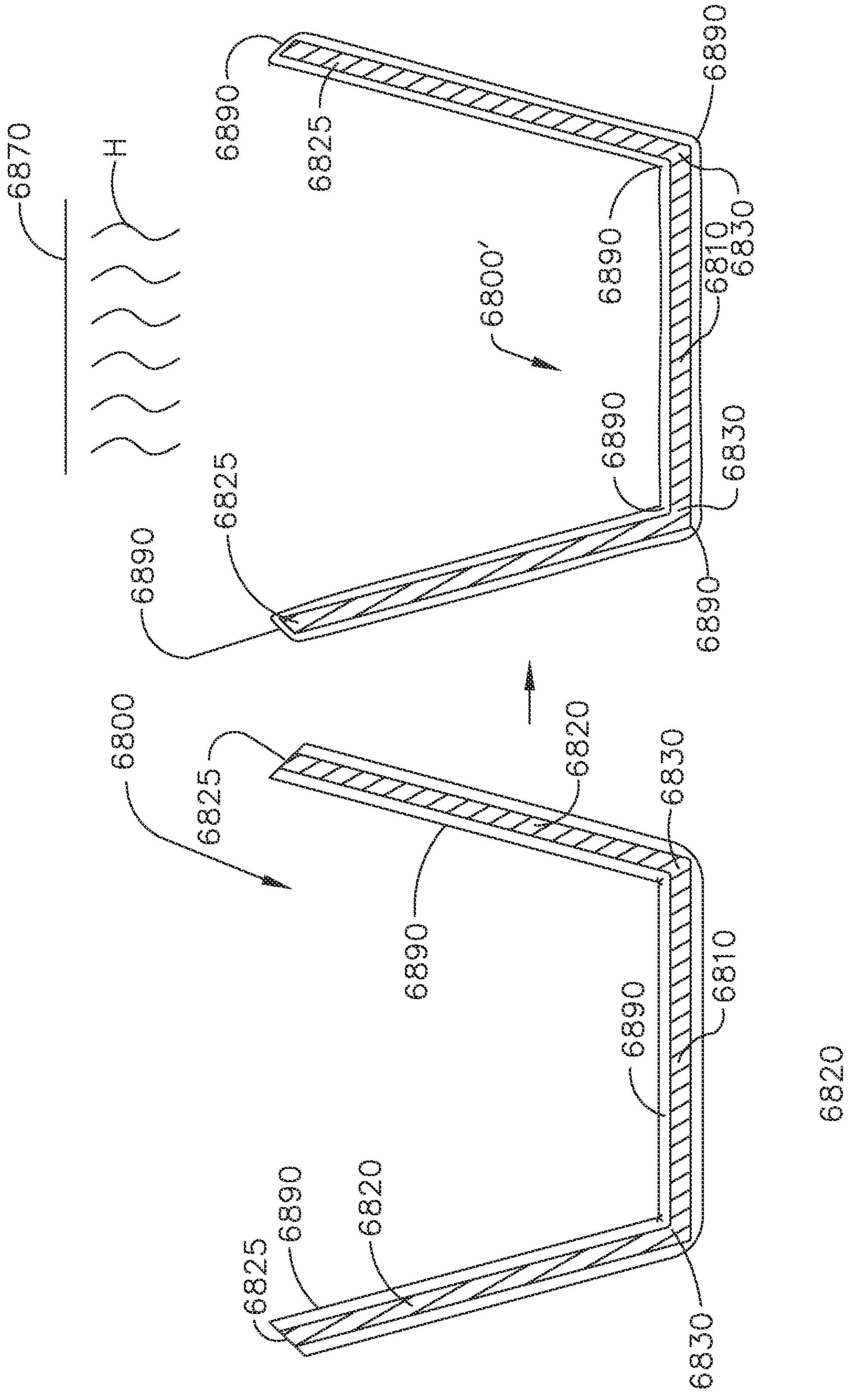
FIG. 64 depicts a staple manufacturing process including a coating reflow process in accordance with at least one embodiment.
Figure 65:
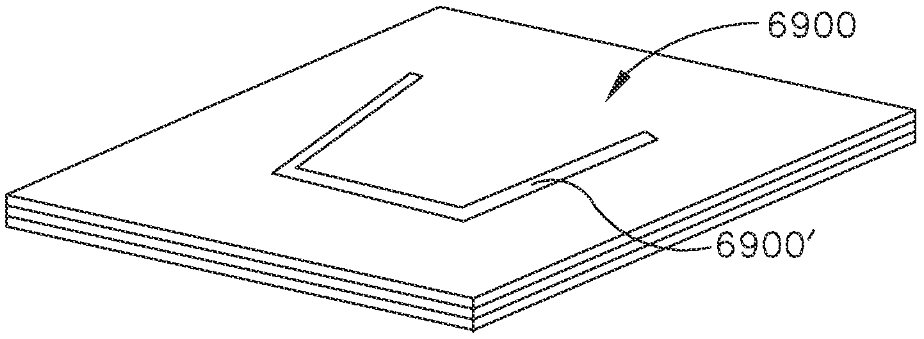
FIG. 65 depicts a staple being cut from a multi-layered sheet of material.
Figure 66:
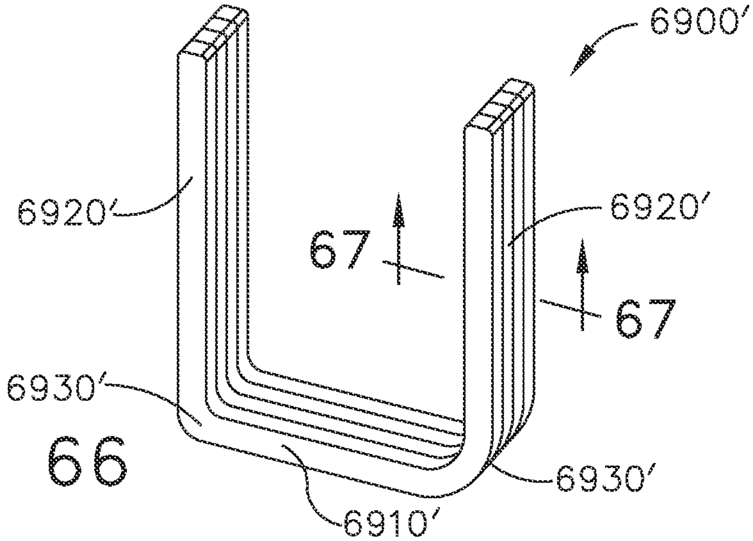
FIG. 66 is a perspective view of the staple of FIG. 65.
Figure 67:
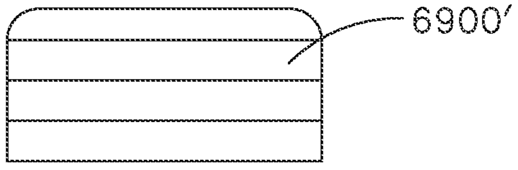
FIG. 67 is a cross-sectional view of the staple of FIG. 66 taken along line 67-67 in FIG. 66.
Figure 67A:
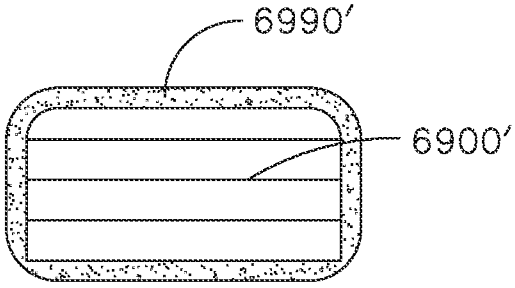
FIG. 67A illustrates a coating on the staple of FIG. 66.

In addition to or in lieu of applying an additional coating to cover the bare surfaces of the staple substrate and/or cracks in the staple coating, the staples can undergo a heating process in which the coating reflows to cover the bare surfaces om the substrate and/or fill-in gaps in the coating. Referring to FIG. 64, a staple form 6800 comprises a substrate including a crown 6810, legs 6820, and bends 6830 connecting the legs 6820 to the crown 6810. The staple form 6800 further comprises a coating 6890 on most of the substrate. More specifically, similar to the above, the leg tips 6825 comprise bare surfaces and the coating 6890 on the bends 6830 may be cracked as a result of the manufacturing process. In various embodiments, the staple form 6800 is heated by a heating element 6870 to partially melt and/or lower the viscosity of the coating 6890 such that the coating 6890 levels itself to fill in the gaps in the coating 6890 and/or even out thin spots in the coating 6890 such as in the bends 6830. At such point, the staple forms 6800 have become staples 6800 and are permitted to cool and/or are actively cooled with a fan and/or a refrigeration process, for example. In various instances, the staples 6800' are reflowed before the staples 6800 are loaded into a staple cartridge. In other instances, the staples 6800 are reflowed after the staples 6800 have been loaded into a staple cartridge. In such instances, defects in the coating created during the staple loading process can be cured by the reflow process.

In addition to or in lieu of the above, the coated wire stock and/or the coated staples can be coated with a lubricant during the staple manufacturing process and/or during the staple loading process. The lubricant can reduce friction between the coated wire stock and/or coated staples and adjacent contact surfaces and/or otherwise reduce damage to the coating on the staples. In various embodiments, the lubricant comprises sodium stearate, LAE, a soap, an antimicrobial agent, and/or combinations thereof, for example.

Figure 46:
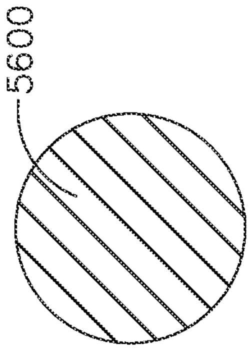
FIG. 46 is a cross-sectional view of a staple wire in accordance with at least one embodiment.
Figure 47:
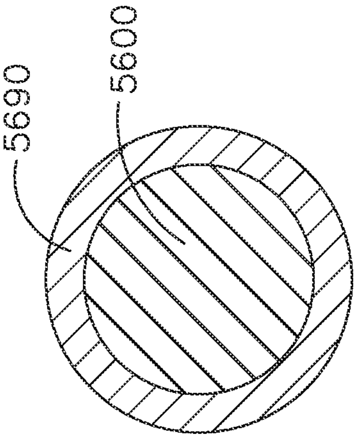
FIG. 47 is a cross-sectional view of a coated staple wire in accordance with at least one embodiment.
Figure 48:
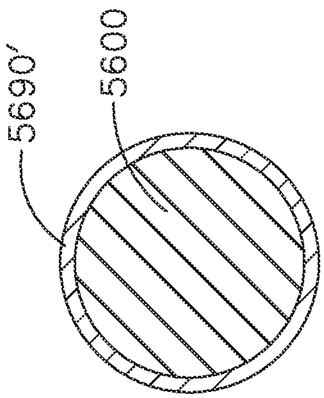
FIG. 48 is a cross-sectional view of a staple wire comprising a thin coating in accordance with at least one embodiment.
Figure 49:
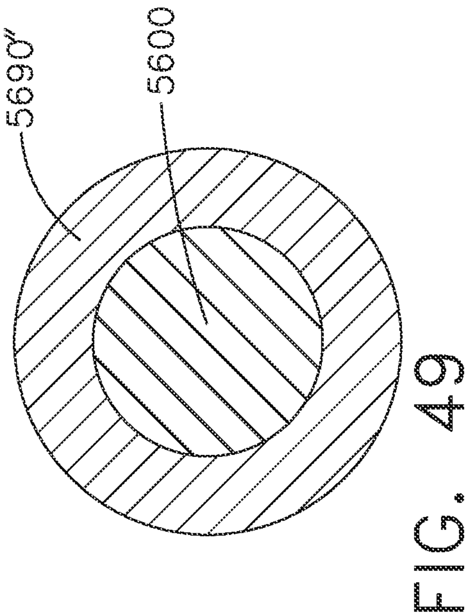
FIG. 49 is a cross-sectional view of a staple wire comprising a thick coating in accordance with at least one embodiment.

Referring to FIG. 46, uncoated staple wire stock 5600 comprises a circular, or an at least substantially circular, cross-section; however, staple wire stock can have any suitable cross-section, such as square and/or rectangular, for example. In various embodiments, referring to FIG. 47, further to the above, the staple wire stock 5600 is coated with a coating 5690. In certain embodiments, referring to FIG. 48, the staple wire stock 5600 is coated with a thinner coating 5690'. Less time is needed to bioabsorb he thinner coating 5690' than the coating 5690 with all other things being equal. As such, the oxidation and bioabsorption of the underlying staple wire stock 5600 will occur sooner once implanted in a patient when the thinner coating 5690' is used. In certain embodiments, referring to FIG. 49, the staple wire stock 5600 is coated with a coating 5690" that is thicker than the coating 5690. More time is needed to bioabsorb the thicker coating 5690" than the coating 5690 with all other things being equal. As such, the oxidation and bioabsorption of the underlying staple wire stock 5600 will occur later once implanted in a patient when the thicker coating 5690" is used.

Figure 50:
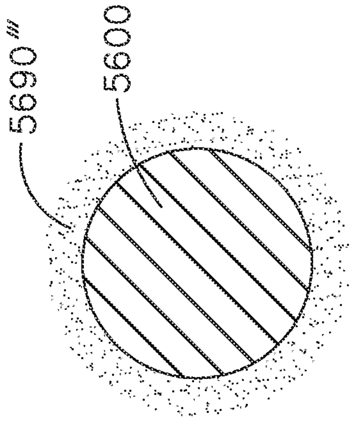
FIG. 50 is a cross-sectional view of a staple wire comprising a powder coating in accordance with at least one embodiment.

In various embodiments, further to the above, the coating applied to the staple wire stock 5600 is sufficiently elastic and/or is sufficiently ductile to move with the underlying wire stock 5600 during the staple manufacturing process and/or staple firing process. In many instances, the coating forms a mechanical bond with the staple wire stock 5600 and, in various instances, the coating forms a chemical bond with the staple wire stock 5600. Referring to FIG. 50, the staple wire stock 5600 can be coated with a dusty coating 5690'''. The dusty coating 5690''' can be adhered to the staple wire stock 5600 via an electrostatic charge and/or a binding medium, for example.

Figure 51:
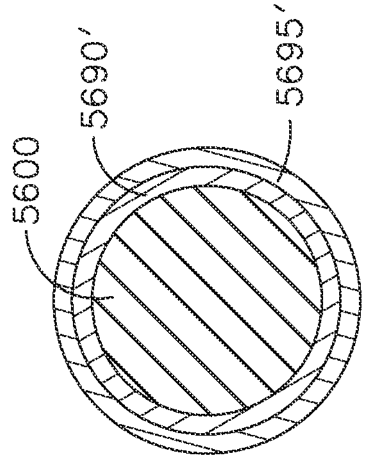
FIG. 51 is a cross-sectional view of a staple wire comprising two coatings in accordance with at least one embodiment.

In various embodiments, referring to FIG. 51, two or more coatings are applied to the staple wire stock 5600. In at least one embodiment, a first coating 5690' is applied to the staple wire stock 5600. In various instances, the entirety of a staple substrate is covered in the first coating 5690'. Likewise, the first coating 5690' is entirely covered with a second coating 5695'. That said, other embodiments are envisioned where only a portion of the staple substrate is covered in the first coating 5690' and/or only a portion of the first coating 5690' is covered with the second coating 5690''. In various embodiments, additional coatings are used.

Figure 52:
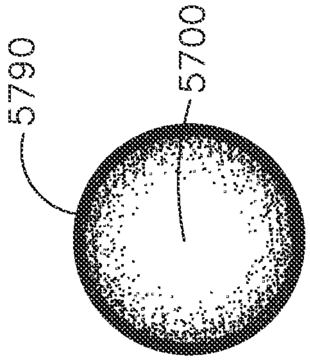
FIG. 52 is a cross-sectional view of a staple wire comprising an impregnated coating in accordance with at least one embodiment.
Figure 53:
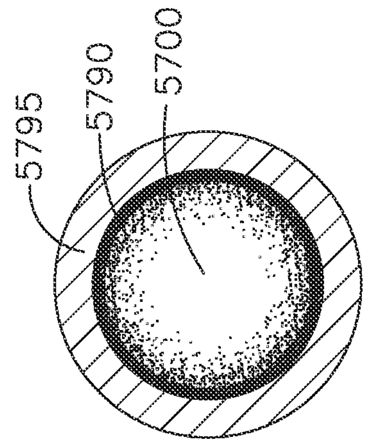
FIG. 53 is a cross-sectional view of a staple wire comprising an impregnated coating and a topical coating in accordance with at least one embodiment.

In various embodiments, further to the above, the penetration depth of a coating into the staple wire stock can be limited and, in many instances, a coating does not penetrate into the staple wire stock below the surface of the staple wire stock. In various embodiments, referring to FIG. 52, the outer portions of a staple wire stock 5700 can be turned into an intrinsic coating 5790. In at least one such embodiment, the intrinsic coating 5790 is the result of heat treating, for example. In various embodiments, referring to FIG. 53, an external coating 5795 can be applied to the intrinsic coating 5790.

Figure 54:
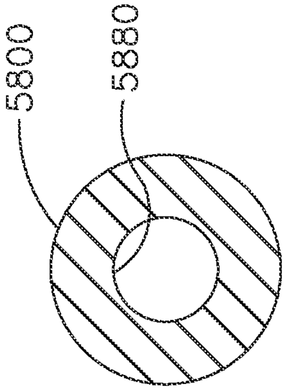
FIG. 54 is a cross-sectional view of a hollow staple wire in accordance with at least one embodiment.
Figure 56:
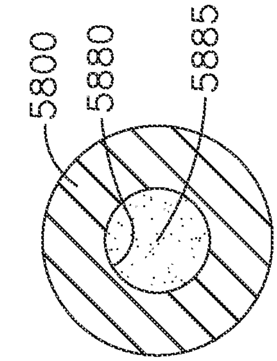
FIG. 56 is a cross-sectional view of a therapeutic-filled staple wire in accordance with at least one embodiment.
Figure 57:
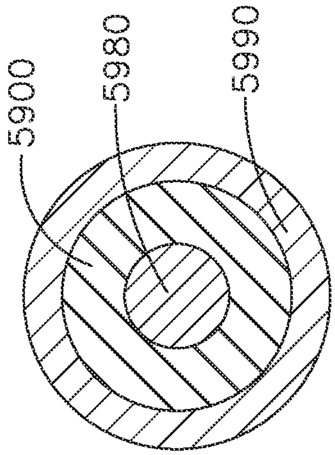
FIG. 57 is a cross-sectional view of the staple wire of FIG. 55 including a coating in accordance with at least one embodiment.

In various embodiments, further to the above, the staple wire stock 5600 comprises solid wire stock. In such embodiments, the staple wire stock 5600 does not have internal openings absent the typical voids in the grain structure and/or the presence of random inclusions, for example. On the other hand, referring to FIG. 54, staple wire stock 5800 is hollow. The staple wire stock 5800 comprises an internal cavity 5880 which is present throughout the length of the staple wire stock 5800. Referring to FIG. 56, a substance can be present in the internal cavity 5880. In at least one embodiment, the internal cavity 5880 is filled, or at least partially filled, with one or more medicaments 5885. In various instances, the medicament 5855 comprises an antibiotic, for example, that is released into the patient once the staple wire stock 5800 has been sufficiently dissolved.

Figure 55:
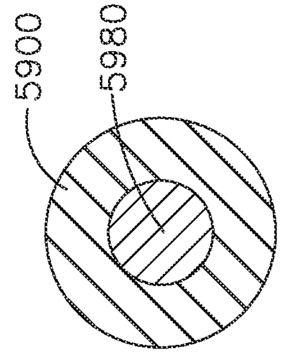
FIG. 55 is a cross-sectional view of a staple wire comprising an internal substrate and an external substrate in accordance with at least one embodiment.

In various embodiments, referring to FIG. 55, a staple wire stock 5980 comprises an internal core 5980. In at least one embodiment, the internal core 5980 is comprised of a first metal and the surrounding portion of the staple wire stock 5980 is comprised of a second, or different, metal. In at least one such embodiment, the internal core 5980 is comprised of pure magnesium while the surrounding portion of the staple wire stock 5980 is comprised of magnesium alloy, for example. As a result, the bioabsorption rate of the surrounding portion is slower than the bioabsorption rate of the internal core 5980. In such embodiments, the strength of a staple comprised of the staple wire stock 5980 may retain its functional strength for a while and then fail quickly. In at least one alternative embodiment, the internal core 5980 is comprised of a magnesium alloy while the surrounding portion of the staple wire stock 5980 is comprised of pure magnesium, for example. As a result, the bioabsorption rate of the surrounding portion is faster than the bioabsorption rate of the internal core 5980. In such embodiments, a staple comprised of the staple wire stock 5980 may bioabsorb quickly down to the internal core 5980 which may provide early strain relief to the stapled tissue.

Figure 58:
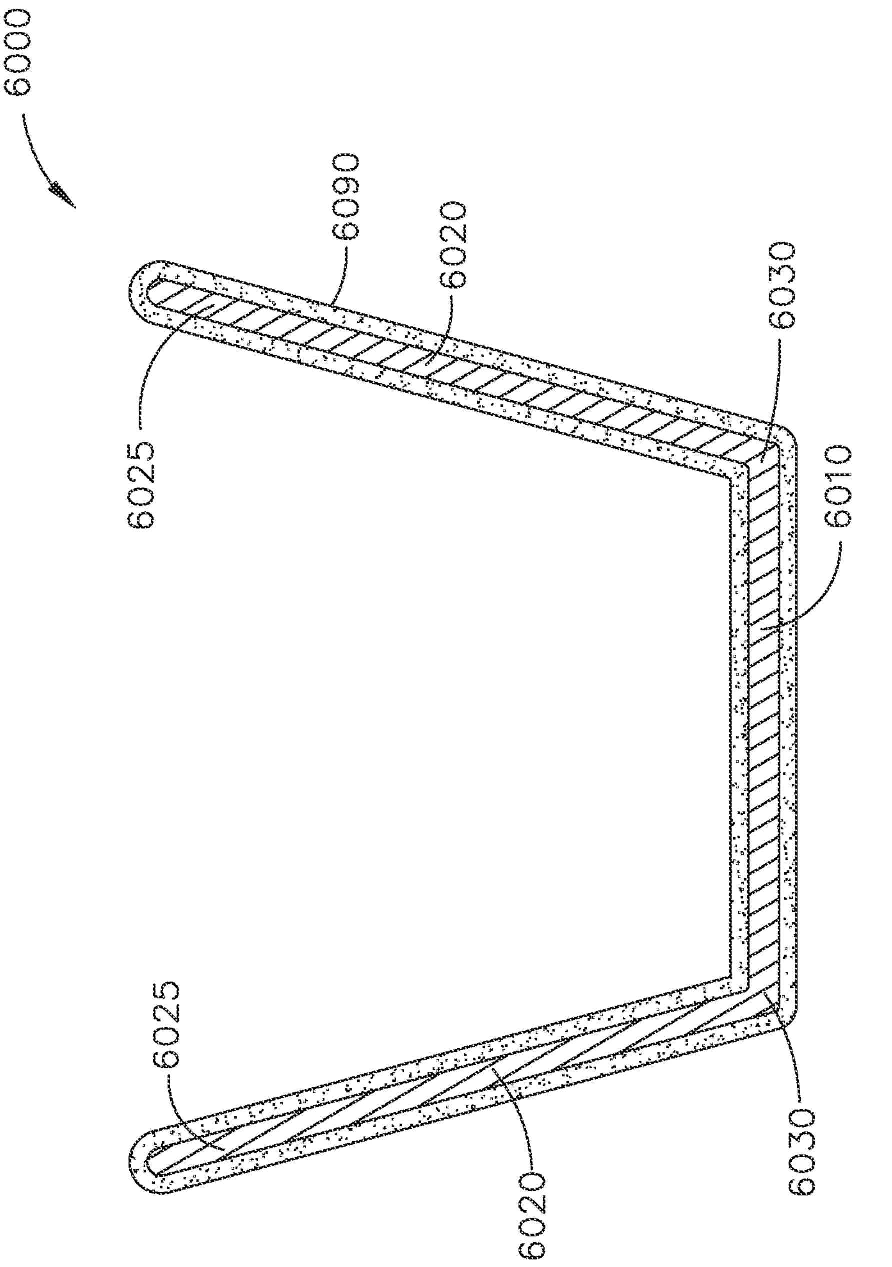
FIG. 58 is a cross-sectional view of a coated staple in accordance with at least one embodiment.
Figure 59:
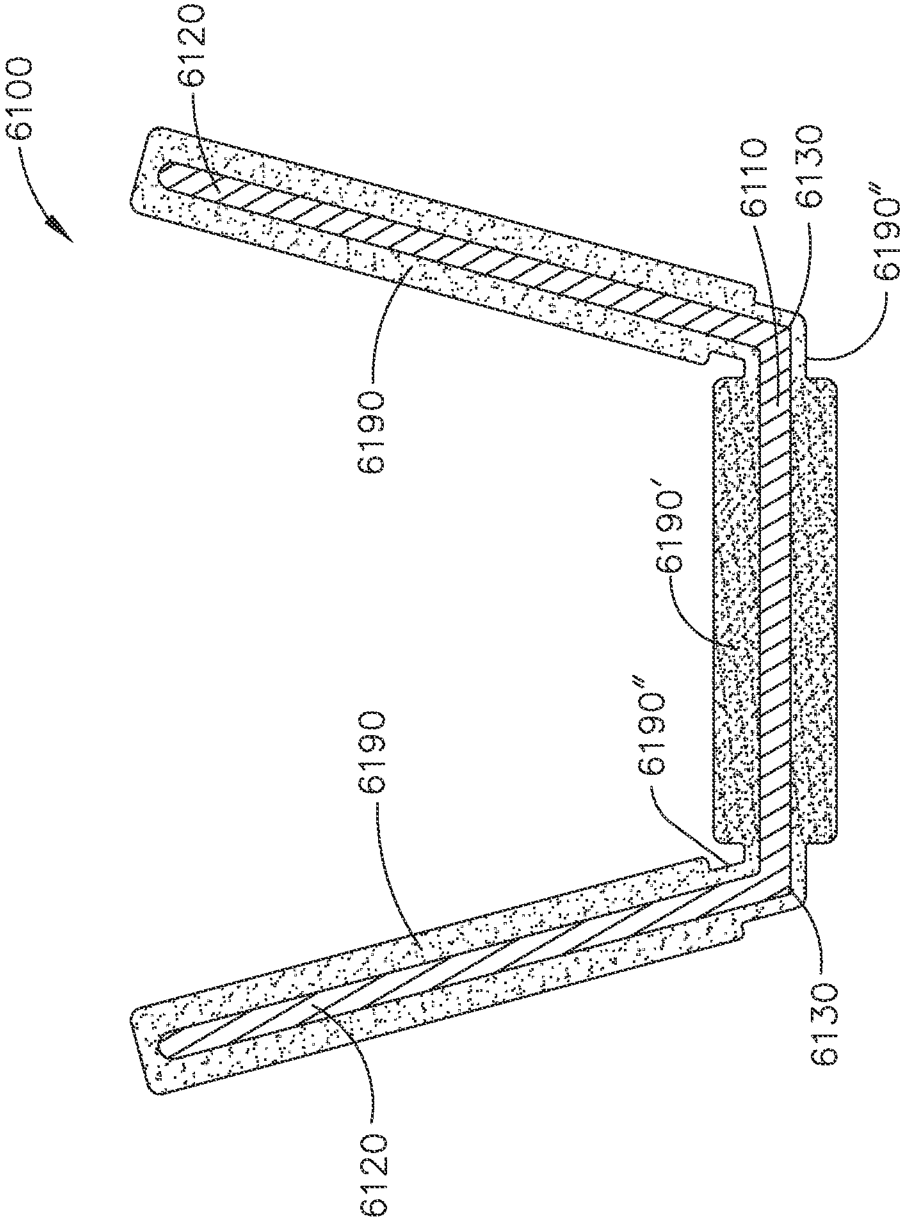
FIG. 59 is a cross-sectional view of a coated staple having different coating thicknesses in accordance with at least one embodiment.

Referring to FIG. 58, a staple 6000 comprises a substrate including a crown 6010, legs 6020, and bends 6030 connecting the legs 6020 to the crown 6010. The staple 6000 further comprises a coating 6090 on the substrate. The coating 6090 has a uniform, or an at least substantially uniform, thickness on the substrate including, further to the above, on the staple tips 6025 and on the inner and outer surfaces of the bends 6030. As a result of the constant thickness of the coating 6090, the oxidation and/or bioabsorption processes may not favor or attack any particular part of the staple 6000 over another. As such, the staple 6000 can bioabsorb evenly. In other embodiments, however, a staple has a non-uniform coating thickness and/or different coatings on different portions of the staple. Referring to FIG. 59, a staple 6100 comprises a substrate including a crown 6110, legs 6120, and bends 6130 connecting the legs 6120 to the crown 6110. The staple 6100 is also coated. The legs 6120 are coated with a first coating 6190 that is comprised of a first material and has a first thickness and the crown 6110 is coated with a second coating 6190' that is comprised of a second material, that is different than the first material, and has a second thickness that is different than the first thickness. The bends 6130 are coated with a third coating 6190'' that is comprised of the first material but has a thickness that is less than the first thickness. In various embodiments, the first material has a faster absorption rate than the second material. Absent other considerations, the time needed to dissolve the coating 6190 on the legs 6120 is less than the time needed to dissolve the coating 6190' on the crown 6110. As a result, the legs 6120 will bioabsorb and/or fracture before the crown 6110 allowing for an early release of the patient tissue. Moreover, the time needed to dissolve the coating 6190'' on the bends 6130 is less than the time needed to dissolve the coating 6190 on the legs 6120 as the material of the 6190'' coating is the same as the 6190 coating but is thinner. As a result, the bends will bioabsorb and/or fracture before the legs 6120 and the crown 6110 providing for an even earlier release of the patient tissue. In various alternative embodiments, the second material of the crown coating 6190' has a faster absorption rate than the first material of the leg coating 6190 and bend coating 6190''. Depending on the difference in bioabsorption rates between the first material and the second material, the time needed to bioabsorb and/or fracture the crown 6110 can be the same as or less than the time needed to bioabsorb and/or fracture the legs 6120 and/or the bends 6130.

In various embodiments, a staple coating comprises polymer surfactant coatings. In at least one embodiment, a staple coating comprises poloxamers including block polymers of poly(ethylene oxide) (PEO) and/or poly(propylene oxide) (PPO), for example. In various embodiments, a staple coating comprises bulky side chains which can limit and/or slow water access to materials in the staple that the water can degrade via steric hindrance effects. In at least one embodiment, a staple coating comprises polymers having bulky side chains. In various embodiments, a staple coating comprises one or more polymers having a polarity. In various embodiments, a staple coating comprises one or more materials that are hydrophobic that slow the degradation of the staple. In at least one such embodiment, a staple coating comprises a polymer that is hydrophobic and has a polarity. In at least one embodiment, a staple is coated with a first layer having a polarity and a second layer on the first layer that has one or more hydrophobic materials. In various embodiments, a staple is coated with a material that mimics gastric mucosa. Such staples may be particularly useful when stapling stomach tissue, for example. In at least one embodiment, a staple is coated with one or more glycoproteins.

In various embodiments, a staple coating includes one or more antimicrobial agents such as triclosan and/or chlorhexidine, for example. In various embodiments, a staple coating includes one or more coagulants. In certain embodiments, a staple coating includes one or more anti-coagulants, such as sirolimus, for example. In various embodiments, a staple coating includes one or more proliferative agents that promotes tissue growth. In various embodiments, a staple coating comprises one or more immuno-suppressants. In various embodiments, a staple coating comprises a cancer treatment, such as paclitaxel, for example. In various embodiments, a staple coating can comprise two or more layers, each of which having a different drug contained therein. For instance, a staple coating can comprise a second layer on the staple substrate that has a second drug contained therein and a first layer on the second layer that has a first drug contained therein. As the staple is bioabsorbed, in such embodiments, the first drug is released as the first layer is being bioabsorbed and then the second drug is released as the second layer is being bioabsorbed. In various instances, there is overlap in the release of the first drug and the release of the second drug.

In various embodiments, a staple includes a hydrogen carbonate coating or a coating layer that includes hydrogen carbonate. In at least one embodiment, the staple coating comprises at least one of $CaHCO_3$, $Mg[OH]CO_2$, and/or strontium, for example. In various embodiments, a staple coating is biodegradable.

In certain embodiments, a staple coating is not biodegradable but is biocompatible. Such coatings can be sufficiently permeable to permit water and/or any other suitable degradation source to access the underlying substrate of the staple. The permeability of the coating can be selected and/or tuned to control the bioabsorption of the underlying substrate. In various embodiments, a staple coating comprises parylene N, parylene C, parylene D, parylene HT and/or combinations thereof, for example. In various instances, parylene can be deposited onto a metal staple substrate using a chemical vapor deposition process. When applied to magnesium staples, whether such staples are comprised of pure magnesium or a magnesium alloy, a coating comprising parylene can sufficiently slow down the bioabsorption of magnesium staples such that the magnesium staples last long enough to remain functional during the tissue healing window.

In various embodiments, magnesium staples comprise radiopaque alloys. In at least one embodiment, magnesium staple alloys include silver and/or barium, for example. In certain embodiments, radiopaque elements, such as silver and/or barium, for example, are present in one or more coatings on the magnesium staples. In such embodiments, the magnesium staples are more readily apparent in radiographs. Moreover, magnesium comprises various naturally occurring isotopes such as Mg-25 and Mg-26, for example, that exist in a natural occurring ratio. In various embodiments, magnesium staples can comprise a higher concentration of Mg-25 and/or Mg-26 such that, when the magnesium of the staples is bioabsorbed and excreted through urine, for example, the increased presence of the magnesium isotopes in the patient's urine can be readily detected which would reveal that the magnesium staples are being or have been bioabsorbed. In certain embodiments, the ratio of the Mg-25 and the Mg-26 in the magnesium staples is different than the naturally occurring ratio and, as a result, the clinician can know that the increased levels of Mg-25 and Mg-26 in the patient's urine is from the implanted staples by verifying that the different ratio of Mg-25 and Mg-26 exists in the urine.

In various embodiments, a staple comprises a substrate and a coating on the substrate which delays the bioabsorption of the substrate and/or slows the bioabsorption of the substrate. In certain embodiments, a staple comprises a substrate and two or more coatings on the substrate. In such embodiments, the coatings can provide different effects and/or work co-operatively to provide an effect.

In various embodiments, a staple comprises a metal substrate and a bioabsorbable coating on only a portion of the substrate. The uncoated portion of the staple is immediately exposed to water and/or other degradation factors in the patient once the staple is implanted in patient tissue. As such, the uncoated portion of the staple starts to bioabsorb right away at the bioabsorption rate of the metal. The coated portion of the staple is impermeable when the staple is implanted and, as a result, the coating prevents the substrate underlying the coating from being bioabsorbed, at least initially. As the coating is bioabsorbed, the coating becomes at least partially permeable and the water and/or other degradation factors can begin to access the substrate underlying the coating. As the coating becomes more and more permeable, water and/or other degradation factors have more and more access to the underlying substrate which increases the effective bioabsorption rate of the underlying substrate. Once the coating has been bioabsorbed, the entire substrate is exposed and can bioabsorb at the bioabsorption rate of the metal. In this embodiment, the degradation of the substrate underlying the coating was delayed and then slowed. In various embodiments, the bioabsorption of the coating can cause the coating to elude into the environment, or tissue, surrounding the implanted staple and effect the tissue environment. In at least one embodiment, the coating is comprised of one or more polymers which, once released into the tissue environment, make the pH of the tissue environment more acidic and/or drive the tissue environment below a pH of 7. In various instances, the tissue environment becomes more and more acidic as more and more coating is bioabsorbed. The increasing acidity of the tissue environment increases the rate in which the exposed portions of the staple substrate are dissolved. Thus, in such embodiments, the staple may be sufficiently functional for a period of time after it has been implanted in the patient tissue and then fail and dissolve suddenly. Such embodiments are useful where it is desired for the staples to hold the patient tissue together during the tissue healing window and then disappear as soon as possible thereafter.

In various embodiments, a staple comprises a metal substrate, a second, or inner, bioabsorbable coating on the metal substrate, and a first, or outer, bioabsorbable coating on the second bioabsorbable coating. The first coating is impermeable when the staple is implanted and protects the second layer and the metal substrate from water and/or degradation factors. Once the first coating starts to bioabsorb, the first coating becomes at least partially permeable and, as a result, the second coating becomes exposed to water and/or degradation factors which begin to bioabsorb the second coating. At this point, the second coating is impermeable and protects the metal substrate from the water and/or degradation factors. As the second coating is bioabsorbed, the water and/or degradation factors can access the metal substrate and begin bioabsorbing the metal substrate. In at least one embodiment, the first coating is comprised of one or more polymers which, once released into the tissue environment, lower the pH, make the pH of the tissue environment more acidic, and/or drive the tissue environment below a pH of 7. In various instances, the tissue environment becomes more and more acidic as more and more first coating is bioabsorbed. The increasing acidity of the tissue environment increases the rate in which the second coating is dissolved. In various embodiments, the second coating is comprised of one or more polymers which, once released into the tissue environment, lower the pH, make the pH of the tissue environment more acidic, and/or drive the tissue environment below a pH of 7. As a result, the dissolution of the first and second coatings can create an environment that quickly dissolves the metal substrate once it is exposed. Thus, in such embodiments, the staple may be sufficiently functional for a period of time after it has been implanted in the patient tissue and then fail and dissolve suddenly. Such embodiments are useful where it is desired for the staples to hold the patient tissue together during the tissue healing window and then disappear as soon as possible thereafter.

In various embodiments, further to the above, the first coating and/or the second coating can comprise hyaluronic acid, lactic acid, and/or hydrochloric acid, for example, which lowers the pH, or increases the acidity of the tissue environment surrounding the staple when the coatings elude into the surrounding tissue environment. In certain embodiments, the first coating and/or the second coating release ionic salts into the tissue environment as they are bioabsorbed which can lower the pH of the tissue environment and/or drive the tissue environment below a pH of 7. In at least one embodiment, the first coating and/or the second coating comprise a substance, such as a drug and/or nutrient, for example, that, once released into the tissue environment, causes a physiologic response in the patient which causes the patient's body to lower the pH in the tissue environment surrounding the staple and/or drive the tissue environment below a pH of 7. In various embodiments, a substance released from the staple coatings can create a pro-inflammation response in the patient that accelerates the bioabsorption of the staple. In any event, the bioabsorption of the first coating can be antagonistic to the second coating and/or the underlying metal substrate. Similarly, the bioabsorption of the second coating can be antagonistic to the underlying metal substrate.

In various embodiments, a staple comprises a metal substrate, a first coating comprised of a first material on the metal substrate, and a second coating comprised of a second, or different, material on the metal substrate. In at least one such embodiment, the first coating is on the legs of the staple and the second coating is on the crown of the staple. In various embodiments, the first coating and the second coating are adjacent to one another and may partially overlap one another. In any event, the first coating is configured to bioabsorb faster than the second coating. Once the staple is implanted, the elution of the first coating can immediately begin to change the tissue environment surrounding the staple which can affect the bioabsorption of the second coating. In various embodiments, the eluded first coating can accelerate or speed up the bioabsorption of the second coating. In other embodiments, however, the eluded first coating can delay, decelerate, and/or slow down the bioabsorption of the second coating and/or underlying metal substrate. In a way, in such embodiments, the first coating can have a protective effect on the second coating and/or the underlying metal substrate even though the bioabsorption of the second coating and/or underlying metal substrate may have already started. In at least one embodiment, the first coating comprises nutrients that increase the pH of the tissue environment surrounding the staple and/or drive the local tissue environment to an alkaline level, i.e., above a pH of 7. In various embodiments, the first coating comprises alkaline phosphate and/or an enzyme that exhibits anti-inflammatory effects by dephosphorylating inflammation triggering moieties (ITMs) like bacterial lipopolysaccharides and extracellular nucleotides, for example. In at least one embodiment, the first coating comprises an alkalizing agent such as bicarbonate, for example. In various embodiments, the first coating comprises a substance that, once eluded into the patient, provokes a physiologic response in the patient that increase the pH of the tissue environment surrounding the staple. In certain embodiments, the first coating comprises electrolyte buffers such as sodium, calcium, and/or potassium, for example, which can bind acids surrounding the staple.

In various embodiments, a staple comprises a metal substrate, a second, or inner, coating on the metal substrate, and a first, or outer, coating on the second coating. As the first coating is being bioabsorbed, the first coating can elude into the tissue environment surrounding the staple and have an alkaline effect in the tissue environment which delays and/or slows the bioabsorption of the second coating and the metal substrate. In such embodiments, the time needed to bioabsorb the staple can be increased by the first coating. In various embodiments, the second coating can elude into the tissue environment and also have an alkaline effect in the tissue environment which further delays and/or slows the bioabsorption of the metal substrate. In various alternative embodiments, the first coating has an alkaline effect on the surrounding tissue environment and the second coating has an acidic effect on the surrounding tissue environment. In such embodiments, the bioabsorption of the staple can begin slowly and then accelerate to fracture and/or dissolve the staple once the second coating begins to elude and countermand the effects of the first coating.

In various embodiments, a staple cartridge comprises a longitudinal row of first staples and a longitudinal row of second staples stored therein. The first staples have a first coating thereon and the second staples have a second coating thereon which is different than first coating. The first coating is configured to bioabsorb faster than the second coating. When the first coating eludes from the first staples during the bioabsorption process, the first coating can affect the tissue environment surrounding the second staples and, thus, affect the bioabsorption of the second staples. In various embodiments, the staple cartridge further comprises a longitudinal slot defined therein which is configured to receive a tissue cutting knife that cuts the patient tissue during the staple firing stroke. In at least one embodiment, the longitudinal row of first staples and the longitudinal row of second staples are stored on the same side of the longitudinal knife slot. In such embodiments, the first staples and the second staples are implanted in the patient tissue on the same side of the tissue incision and are, thus, in close proximity to one another. In various other embodiments, the longitudinal row of first staples and the longitudinal row of second staples are stored on opposite sides of the longitudinal knife slot. In such embodiments, the first staples and the second staples are implanted in the patient tissue on opposite sides of the tissue incision. In either event, the elution of the first coating from the first staples can affect the tissue environment surrounding the second staples and affect the bioabsorption of the second staples.

Further to the above, the bioabsorption of various staple coatings can begin as soon as the staples are implanted in the patient. In other embodiments, the bioabsorption of a staple coating does not begin until a triggering event has occurred. In at least one embodiment, the staple coating is responsive to the presence of an enzyme that, once present in the vicinity of the staple coating, can trigger the bioabsorption process of the staple coating. For instance, the patient's body can release enzymes during the tissue healing response which trigger the bioabsorption of the staple coating. In various embodiments, the triggering event can comprise heat and/or radiation, for example, which can be exposed to the staples once the staples have been implanted in the patient tissue. In certain embodiments, the triggering event can occur after the surgical procedure has been completed. Moreover, although the triggering even can occur in situ, the triggering event can occur ex vivo.

Figure 73A:
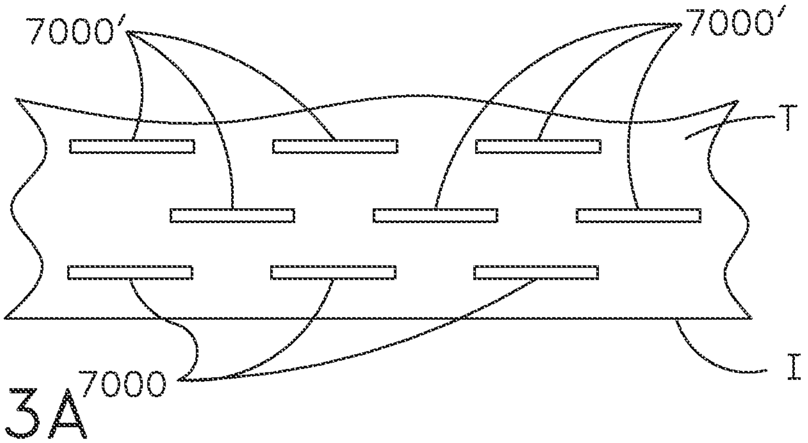
FIG. 73A depicts a staple pattern implanted into patient tissue in an unabsorbed state in accordance with at least one embodiment.
Figure 73B:
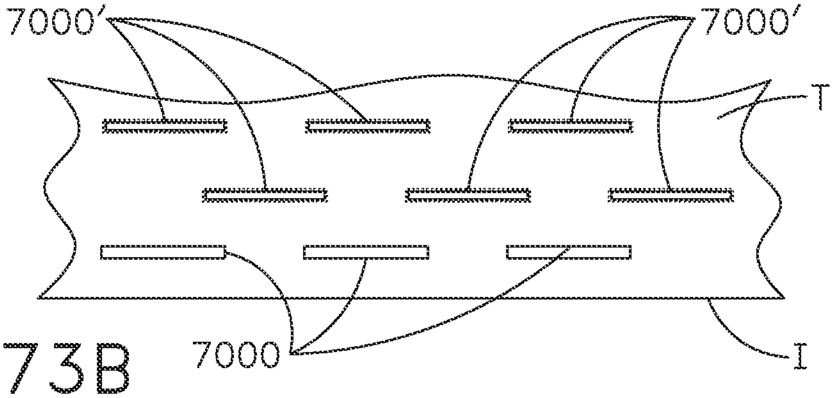
FIG. 73B depicts the staple pattern of FIG. 73A in a partially absorbed state.
Figure 73C:
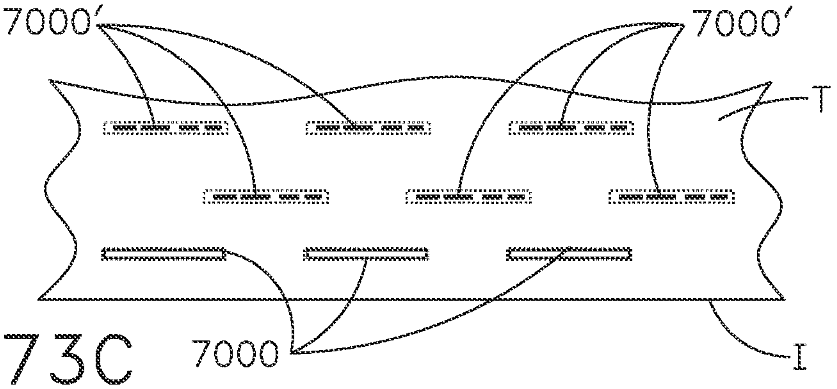
FIG. 73C depicts the staple pattern of FIG. 73A in a further absorbed state as compared to FIG. 73B.
Figure 73D:
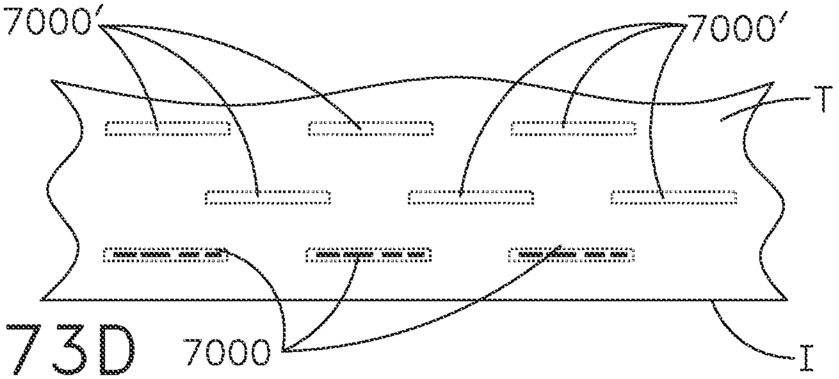
FIG. 73D depicts the staple pattern of FIG. 73A in a further absorbed state as compared to FIG. 73C illustrated with the outer two longitudinal staple rows in a nearly completely absorbed state.

Referring to FIG. 73A, a staple pattern implanted in patient tissue T comprises a longitudinal row of staples 7000 positioned along incision I. The staple pattern further comprises two longitudinal rows of staples 7000' adjacent to the longitudinal row of staples 7000. The staples 7000' are comprised of a substrate and/or coating that causes the staples 7000' to bioabsorb and dissolve faster than the staples 7000. In such embodiments, the staples closest to the incision margin hold onto the patient tissue T longer than the other staples in the staple pattern, as reflected in FIGS. 73B-73D. Such an arrangement allows flexibility in the patient to develop before the incised tissue is finally released. Having said that, other embodiments are envisioned in which the faster-absorbing staples 7000' are closer to the incision I than the staples 7000. In such embodiments, the tissue adjacent the incised tissue margin is released first to provide room for the incised tissue to heal.

Figure 74:
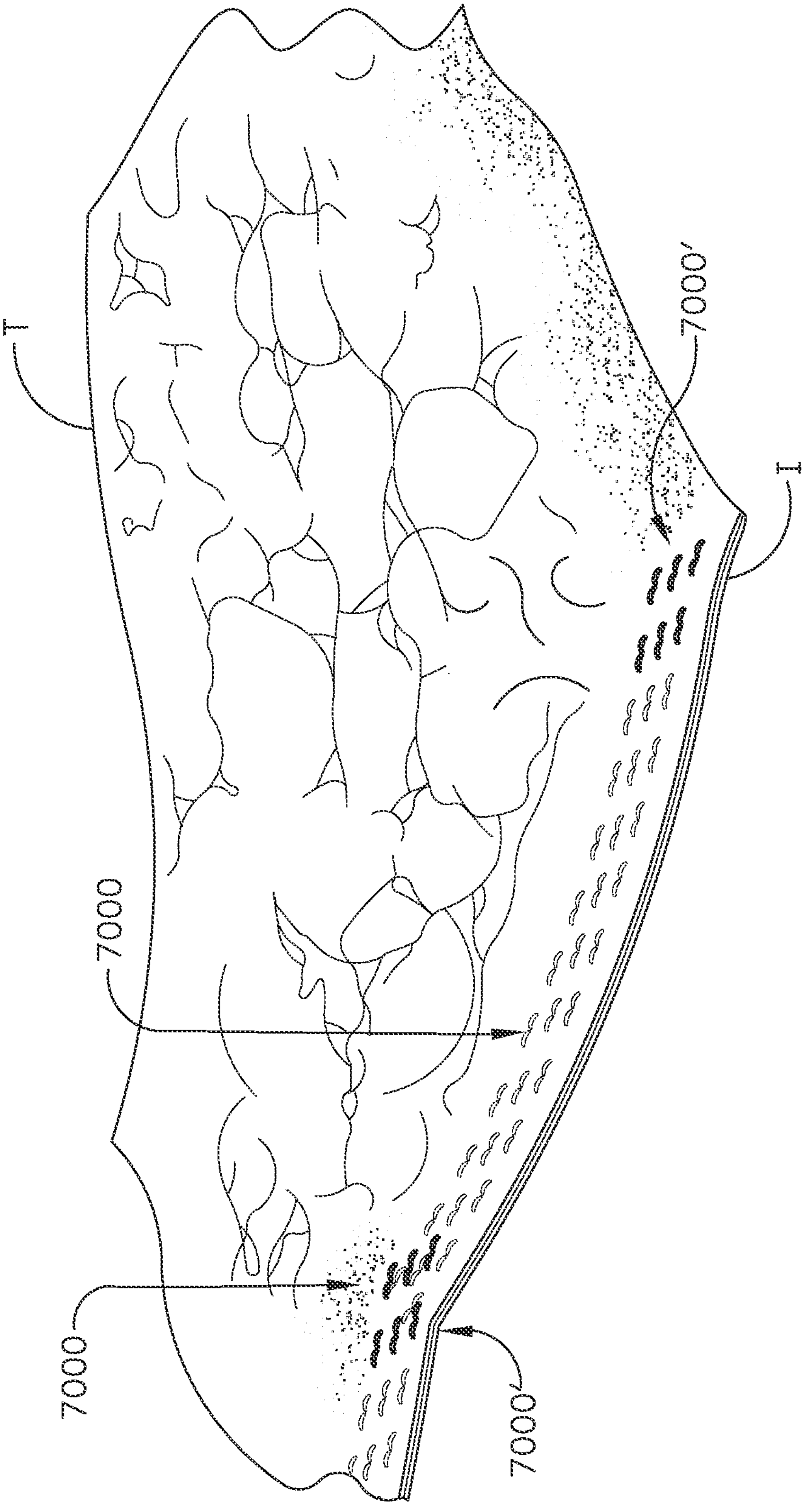
FIG. 74 depicts tissue stapled with multiple staple firings that overlap in accordance with at least one embodiment.
Figure 81:
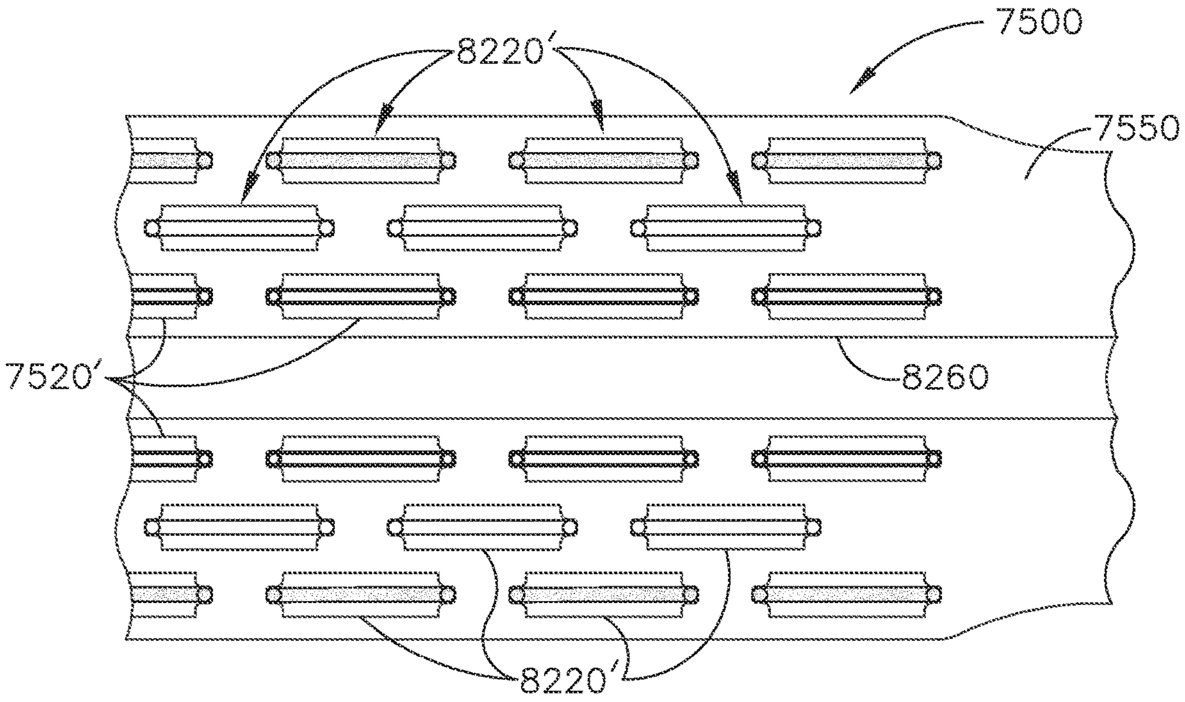
FIG. 81 is a partial plan view of a staple cartridge comprising coated and uncoated staples in accordance with at least one embodiment.
Figure 82:
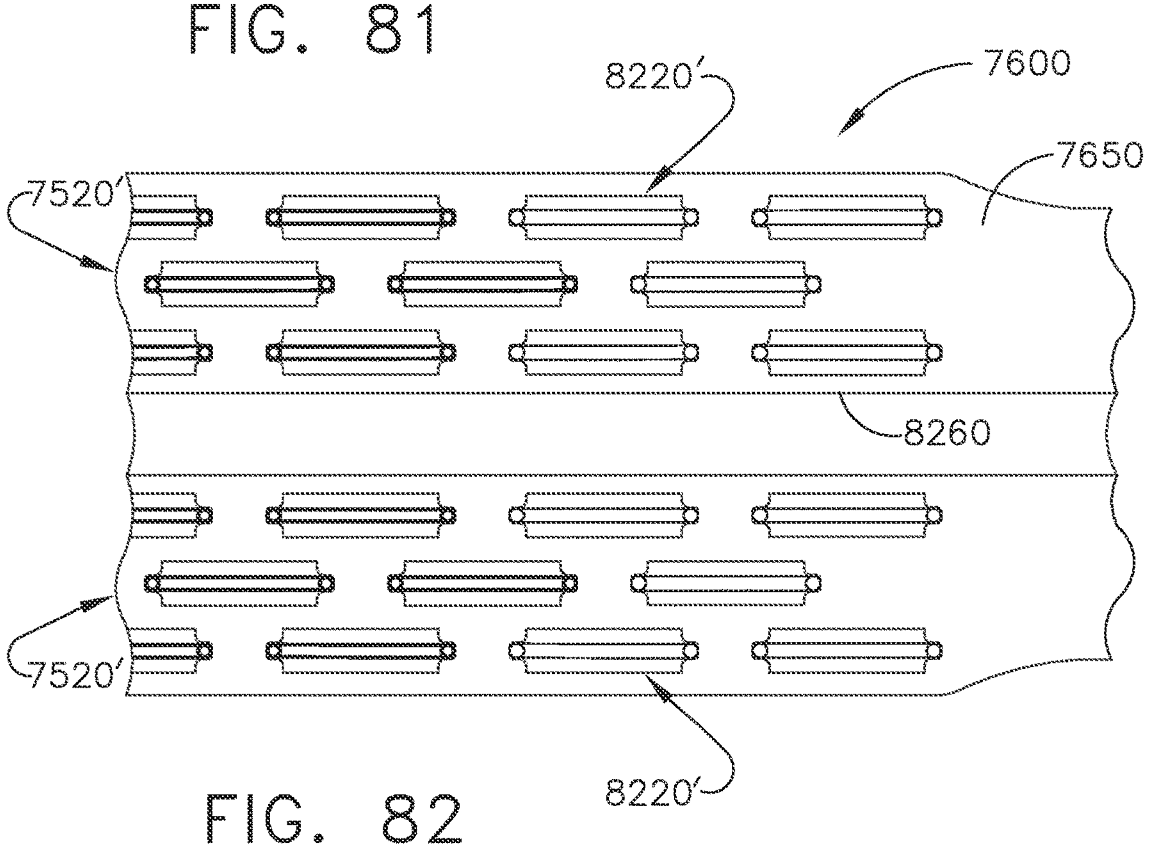
FIG. 82 is a partial plan view of a staple cartridge comprising uncoated staples in proximal staple cavities and coated staples in distal staple cavities in accordance with at least one embodiment.

Referring to FIG. 81, a staple cartridge 7500 comprises a cartridge body 7550 including a deck comprising a proximal end and a distal end and a longitudinal slot 8260 extending from the proximal end toward the distal end. The cartridge body 7550 comprises three longitudinal rows of staple cavities defined in the deck on a first lateral side of the longitudinal slot 8260 and three longitudinal rows of staple cavities defined in the deck on a second, or opposite, side of the longitudinal slot 8260. The innermost rows of staple cavities has a single wire staple 7520' stored in each staple cavity, the outermost rows of staple cavities has a single staple 8220' stored in each staple cavity, and the intermediate rows of staple cavities has a single staple 8220" stored in each staple cavity. The staples 7820' are comprised of a substrate material and/or have a coating that causes the staples 7820' to bioabsorb slower than the staples 8220'. Referring to FIG. 82, a staple cartridge 7600 comprises a cartridge body 7650 including a deck comprising a proximal end and a distal end and a longitudinal slot 8260 extending from the proximal end toward the distal end. The cartridge body 7650 comprises three longitudinal rows of staple cavities defined in the deck on a first lateral side of the longitudinal slot 8260 and three longitudinal rows of staple cavities defined in the deck on a second, or opposite, side of the longitudinal slot 8260. A proximal group of staple cavities has a single staple 8220' stored in each staple cavity and the staple cavities distal to the proximal group has a single staple 7520' removably stored therein. When a staple pattern is created in patient tissue as a result of several consecutive cartridge firings, it is possible for the distal staples of one staple cartridge firing to overlap with the proximal staples of the next staple cartridge firing. In various instances, it is desirable for at least some of the overlapped staples to bioabsorb quickly, or at least bioabsorb faster than the others. For instance, the faster-absorbing staples 8220' can bioabsorb and/or dissolve leaving behind the slower-absorbing staples 7520'. In such instances, the integrity of the entire staple pattern is maintained as at least some staples of the overlapped staples bioabsorb and/or dissolve at the same rate as the non-overlapped staples. Referring to FIG. 74, staples 7000 and 7000' overlap in various locations within a staple pattern to provide such a result. Such arrangements may be particularly useful in lung tissue. Having said that, various embodiments are envisioned in which the bioabsorption of the proximal staples and the distal staples of a staple cartridge can be tuned to achieve a desired result.

Figure 76:
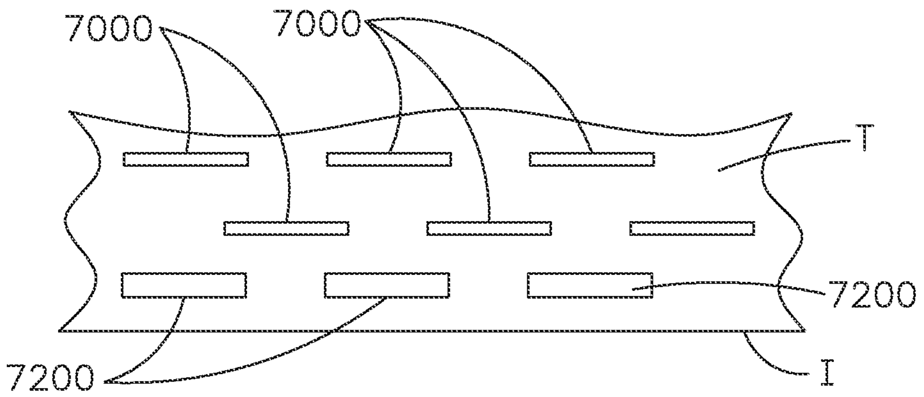
FIG. 76 depicts wire staples having different wire diameters implanted into patient tissue in accordance with at least one embodiment.
Figure 77:
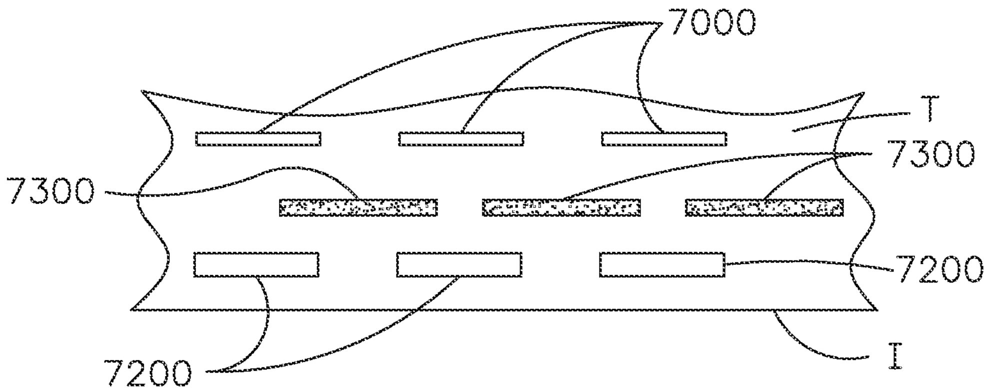
FIG. 77 depicts staples having different sizes and coatings implanted into patient tissue in accordance with at least one embodiment.

Referring to FIG. 76, a staple pattern implanted in patient tissue T comprises a longitudinal row of staples 7200 positioned along an incision I in the patient tissue T. The staple pattern also comprises two outer longitudinal rows of staples 7000 adjacent to the inner longitudinal row of staples 7200. The staples 7200 are larger than the staples 7000 and, absent other considerations, the staples 7200 bioabsorb slower than the staples 7000. Referring to FIG. 77, a staple pattern implanted in patient tissue T is similar to the staple pattern depicted in FIG. 76 except for the intermediate longitudinal row being comprised of staples 7300. The staples 7300 have a different size than the staples 7000 and 7200 and may bioabsorb and/or dissolve at a different rate than the staples 7000 and 7200. Moreover, the staples 7200 are also comprised of a different material than the staples 7000 and 7200 and, as a result, may bioabsorb and/or dissolve at different rate than the staples 7000 and 7200.

In many examples, as discussed above, a staple is comprised of a metal wire. As also discussed above, a staple is stamped from a sheet of material. The teachings provided herein with regard to wire staples are equally applicable to stamped staples. Likewise, the teachings provided herein with regard to stamped staples are equally applicable to wire staples.

In at least one example, further to the above, the sheet of material used to manufacture the stamped staples from is comprised of a homogenous, or an at least substantially homogenous, sheet of material. As discussed further below, in various examples, the sheet of material comprises two or more layers. In either event, a process of manufacturing stamped staples may subject the stamped staples to less cold-working and/or less residual stresses than a process of manufacturing wire staples. Such lower residual stresses in stamped staples may reduce the possibility of cracking and/or fracturing in the stamped staples, especially in the transitions between the crown and the staple legs. In various instances, such transitions may not be bent to form a substantially V-shaped staple, for example, like a wire may be bent to form a similar shape. Moreover, as described above, the diameter of a staple wire can be reduced and/or stamped to create a thinner cross-section in the bends of a wire staple; however, such processes can comprise cold-working of the metal wire to achieve such thinner cross-sections. Stamped staples can be stamped into any suitable configuration with only the cold-working needed during the stamping process, or processes. In at least one example, the transitions between the crown and the staple legs in a stamped staple are thinner than the crown, for example. In at least one example, the legs of a stamped staple are tapered. In at least one such example, the bases of the staple legs are wider than the tips of the staple legs, for example. In another example, the crown is thicker than the staple legs and the transitions, for example.

In various examples, staples are stamped from a sheet of material having two or more layers. In at least one example, the sheet of material comprises three layers—an inner layer positioned intermediate two outer layers. As a result of the stamping process, all of the layers are exposed along the edges of the staple. In at least one example, the outer layers are stiffer than the inner layer. In at least one such example, the inner layer of the staple is comprised of magnesium. Once the staple is implanted in the patient, the inner magnesium layer can act as a sacrificial anode which allows the stamped staple to deteriorate from the inside out. In at least one example, the outer layers of the stamped staple are comprised of a magnesium alloy while the inner layer is comprised of pure magnesium, for example. In such an example, the outer layers can be alloyed such that the inner layer biodegrades slower than the outer layers. In at least one instance, one or both of the outer layers are comprised of a hydrophobic material which delays and/or slows the deterioration of the staple.

In various instances, further to the above, the layers of a stamped staple have different grain directions. In at least one such instance, a first layer has a first grain direction and a second layer has a second grain direction which is different than the first direction. As a result of the different grain directions, the properties of the stamped staple may be isotropic, or at least more isotropic, than either layer alone and/or a staple having only one layer. In at least one example, the first layer and the second layer are comprised of magnesium and/or a magnesium alloy, for example. In at least one example, all of the layers of the stamped staple are comprised of magnesium and/or a magnesium alloy, for example. In at least one example, the first layer and the second layer are comprised of zinc and/or a zinc alloy, for example. In at least one example, all of the layers of the stamped staple are comprised of zinc and/or a zinc alloy, for example. In at least one example, the first layer and the second layer are comprised of iron and/or an iron alloy, for example. In at least one example, all of the layers of the stamped staple are comprised of iron and/or an iron alloy, for example. In at least one example, the first layer is comprised of at least one of magnesium, zinc, and iron and the second layer is comprised of at least one of magnesium, zinc, and iron, for example.

As discussed above, the edges of a stamped staple can immediately expose the internal structure of the stamped staple to a source of biodegradation as soon as the stamped staple is implanted in a patient. In at least one example, the sheet of material that is used to create a stamped staple is not coated prior to the stamped staple being formed and, thereafter, the stamped staple is coated. In this example, the entirety of the stamped staple is coated and any of the coatings disclosed herein can be used. As a result, the biodegradation of the stamped staple can be delayed and/or slowed. In at least one other example, the sheet of material is coated prior to the stamping process and the stamped staples created from the stamping process will have exposed, or uncoated, edges. In order to coat these exposed edges, the stamped staples can be coated after the stamping process. As a result, the stamped staples have a first coating and a second coating. The first coating is comprised out of the same material as the second coating; however, in other examples, the first coating and the second coating are comprised of different materials. In either event, in at least one example, the entirety of the stamped staples are coated during the second coating process which results in the stamped staples having one coating on certain parts of the stamped staples, such as the edges of the stamped staples, for example, and two coatings on the other parts of the stamped staples. In such examples, the entirety of the stamped staples will be coated which will delay and/or slow the bioabsorption of the metal substrate of the stamped staples; however, the overall thickness of the coating on the metal substrate will be uneven. In light of this, in at least one process, the portions of the stamped staples that retain their coating through the stamping process are masked during the second coating process such that few, if any, portions of the stamped staples are double coated.

Figure 72:
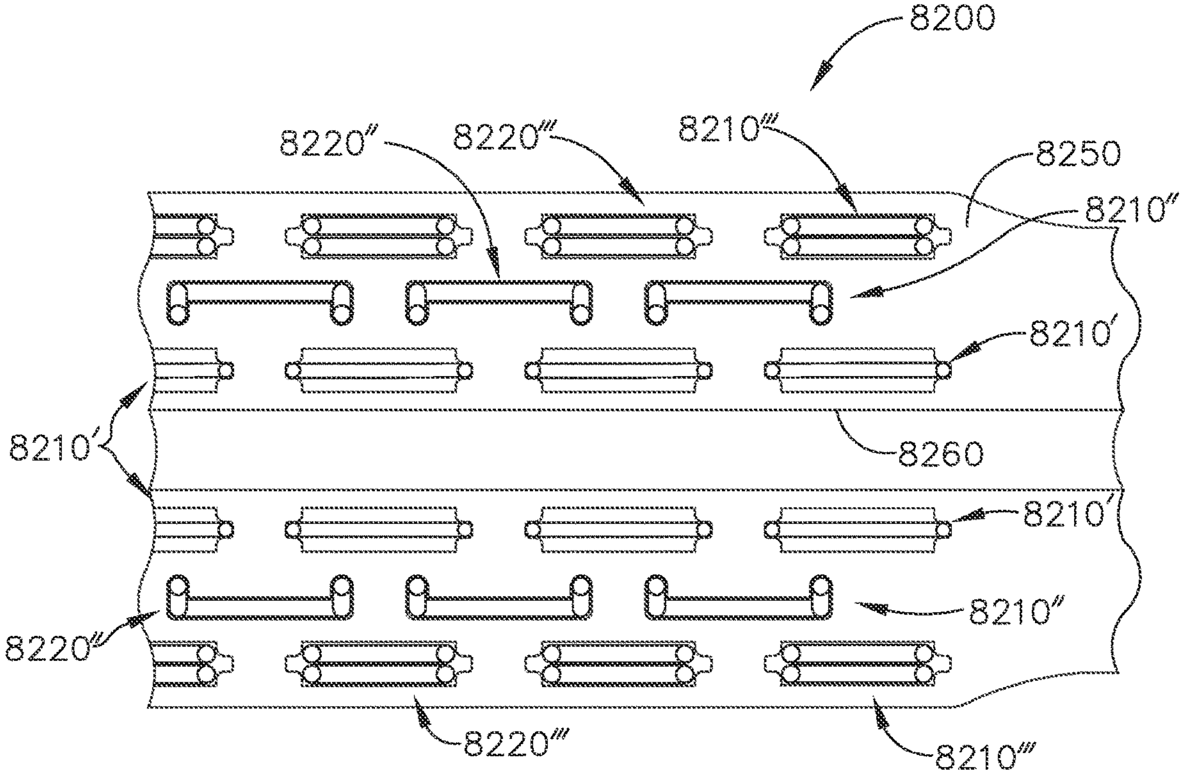
FIG. 72 is a partial plan view of a staple cartridge comprising wire staples and stamped staples stored therein in accordance with at least one embodiment.

Referring to FIG. 72, a staple cartridge 8200 comprises a cartridge body 8250 including a deck comprising a proximal end and a distal end and a longitudinal slot 8260 extending from the proximal end toward the distal end. The longitudinal slot 8260 is configured to receive a firing member, such as a tissue cutting knife, for example, therein during the staple firing stroke. The cartridge body 8250 further comprises three longitudinal rows of staple cavities defined in the deck on a first lateral side of the longitudinal slot 8260 and three longitudinal rows of staple cavities defined in the deck on a second, or opposite, side of the longitudinal slot 8260. The innermost rows of staple cavities include staple cavities 8210', each of which having a single wire staple 8220' stored therein. The intermediate rows of staple cavities include staple cavities 8210", each of which having a single staple 8220" stamped from a sheet of material stored therein. The outermost rows of staple cavities include staple cavities 8210'", each of which having two wire staples 8220' stored therein.

Figure 86:
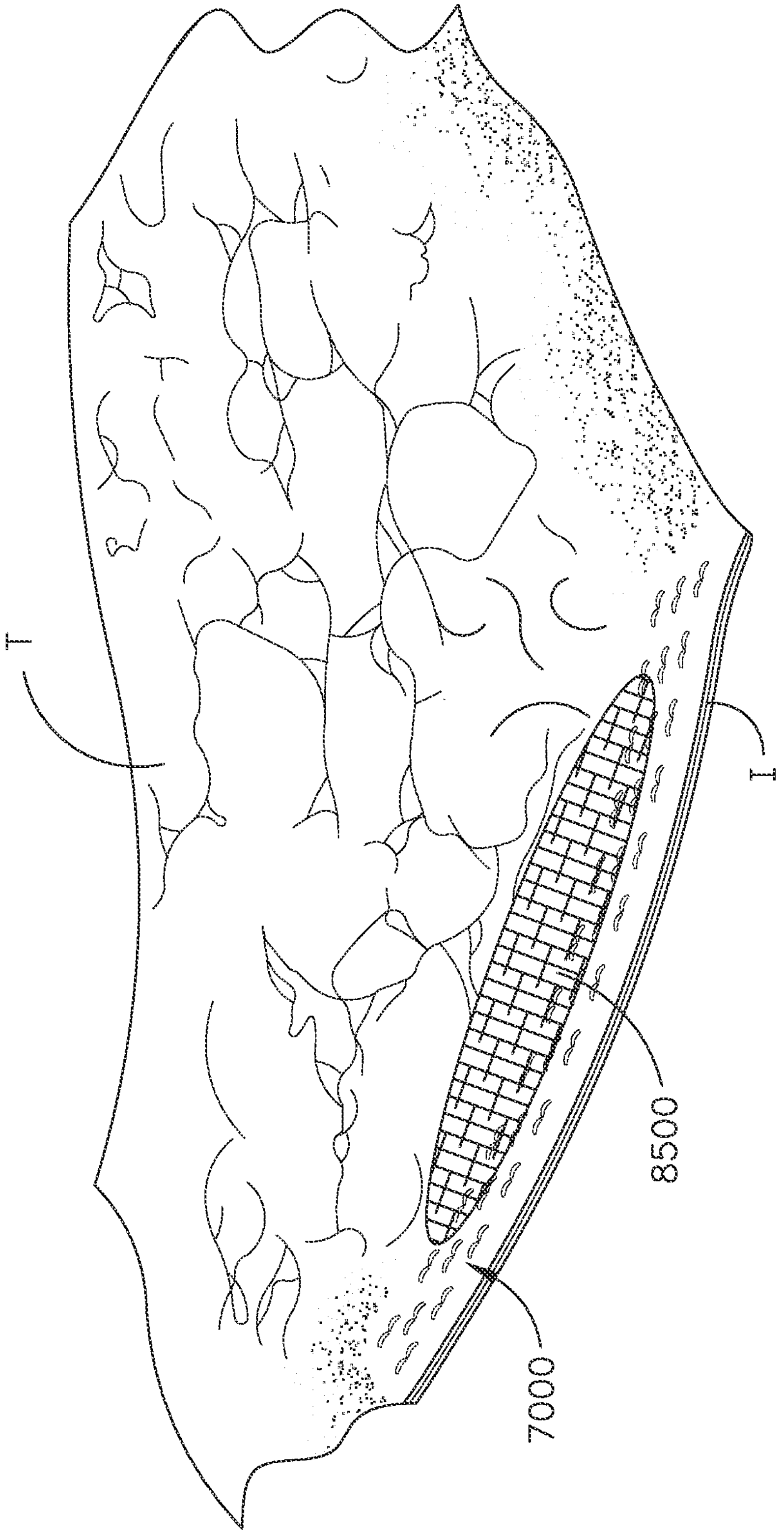
FIG. 86 depicts a bioabsorbable patch applied on top of a staple line in accordance with at least embodiment.

After the patient tissue has been stapled, in various embodiments, a clip can be applied on, over, and/or adjacent to a staple line that directs or focuses the oxidation and bioabsorption processes to the staples in that location. In at least one embodiment, the clip is comprised of zinc, for example. In addition to or in lieu of the above, a patch or covering can be applied on, over, and/or adjacent to a staple line that alters the environment surrounding the tissue. FIG. 86 illustrates a patch 8500 positioned over implanted staples 7000 that seal tissue T along an incision I, for example. In at least one such embodiment, the patch is comprised of one or more polymeric materials, such as PGA and/or PLLA, for example, that eludes compounds that lower the pH of the tissue environment, for example. Applying such a patch can increase the bioabsorption rate of the staples and decrease the time in which the staples are present in the patient. In various embodiments, a staple cartridge comprises more than one groups of staples stored therein which react differently to a patch placed over the staple line. In at least one embodiment, a staple cartridge comprises a first group of staples and a second group of staples where the first group of staples bioabsorb faster than the second staples in response to the presence of the patch. In at least one such embodiment, the second staples are coated with a material that delays and/or slows the bioabsorption of the second staples and the first staples are uncoated. In a least one such embodiment, the first staples are comprised of pure magnesium and the second staples are comprised of a magnesium alloy. In any event, the first group of staples can be stored in the staple cartridge in positions in which, when deployed into the patient tissue, are located where the early absorption of certain staples in the staple line is desired. In at least one example, the first staples are positioned in the distal staple cavities of a staple cartridge.

In at least one example, the outermost staple rows and the intermediate staple rows may release the patient tissue in about 30 days while the innermost staple rows release the patient tissue in about 45 days, for example. In at least one example, the innermost staple rows hold onto the patient tissue about 1.5 times longer than the outermost staple rows and the intermediate staple rows. In other examples, the innermost staple rows hold onto the patient tissue about 2 times longer than the outermost staple rows and the intermediate staple rows. In other examples, the innermost staple rows hold onto the patient tissue about 2.5 times longer than the outermost staple rows and the intermediate staple rows.

FIGS. 149A-149C illustrate a surgical instrument 10500 comprising an elongate shaft 10502 and an end effector 10505 extending from the elongate shaft 10502. The elongate shaft 10502 can extend from a handle our housing, such as those disclose in U.S. Pat. No. 6,978,921, entitled SURGICAL STAPLING INSTRUMENT INCORPORATING AN E-BEAM FIRING MECHANISM, which issued on Dec. 27, 2005 and is herein incorporated by reference in its entirety. Further, the end effector 10505 comprises a first jaw, or anvil jaw 10510, and a second jaw, or cartridge jaw 10520. In at least one embodiment, the anvil jaw 10510 is movable relative to the cartridge jaw 10520 between an open, or unclamped, position and a closed, or clamped, position to capture tissue T therebetween. However, other embodiments are envisioned where the cartridge jaw 10520 moves relative to the anvil jaw 10510 or where both the cartridge jaw 10520 and anvil jaw 10510 are movable relative to one another. In any event, the cartridge jaw 10520 comprises an elongate channel 10522 configured to receive a staple cartridge 10524 therein. The staple cartridge 10524 comprises a plurality of staple cavities which removably store a plurality of staples 10525 therein. In the illustrated embodiment, the staple cartridge 10524 comprises a sled 10540 configured to move from a proximal unfired position to a distal fired position within the staple cartridge 10524 to eject the staples 10525 from the staple cartridge 10524. In at least one embodiment, the staple cartridge 10524 comprises staple drivers upon which the staples 10525 are seated. During a staple firing stroke, the staple drivers are lifted upward toward the anvil jaw 10510 by the sled 10540 to eject the staples 10525. However, other embodiments are envisioned where the staples 10525 comprise integral drivers which are engaged by the sled 10540 to eject the staples 10525.

Further to the above, the surgical instrument 10500 comprises a firing member 10530 configured to move relative to the end effector 10505 from a proximal, or unfired position, illustrated in FIG. 149A to a distal, or fired position, illustrated in FIG. 149B during a staple firing stroke. The firing member 10530 is configured to advance the sled 10540 from the proximal end of the staple cartridge 10524 to the distal end of the staple cartridge 10524 during the staple firing stroke to eject the staples 10525 from the staple cartridge 10524. In at least one embodiment, the sled 10540 remains at the distal end of the staple cartridge 10524 when the firing stroke is completed and the firing member 10530 is retracted toward its proximal, or unfired, position. In at least one embodiment, the firing member 10530 is mechanically advanced through the staple firing stroke in response to actuation of a firing trigger on the handle of the surgical instrument 10500. However, other embodiments are envisioned where the firing member 10530 is advanced through the staple firing stroke using an electric motor and/or any suitable actuation means. The firing member 10530 is an E-Beam firing member similar to the firing members disclosed in U.S. Pat. No. 6,978,921. The firing member 10530 comprises a longitudinal firing bar 10532 and an upstanding distal head portion 10534 extending from the longitudinal firing bar 10532.

Further to the above, the distal head portion 10534 comprises a tissue cutting portion, or knife 10535, positioned at its distal end and configured to cut tissue T positioned in the end effector 10505 during the staple firing stroke of the firing member 10530. The distal head portion 10534 further comprises a lower cam, or lower lateral member 10537, and an upper cam, or upper lateral member 10536. The lower lateral member 10537 and the upper lateral member 10536 extend laterally from either side of the distal head portion 10534 as best shown in FIG. 149C. The distal head portion 10534 further comprises an intermediate lateral member, or lateral tab 10538, extending laterally from either side of the distal head portion 10534. The lateral tab 10538 is positioned intermediate the lower lateral member 10537 and the upper lateral member 10536. The lower lateral member 10537 is configured to engage the cartridge jaw 10520 during the staple firing stroke, the upper lateral member 10536 is configured to engage the anvil jaw 10510 during the staple firing stroke, and the lateral tab 10538 is configured to engage a portion of the anvil jaw 10510 during the staple firing stroke, as discussed in greater detail below.

The anvil jaw 10510 comprises an anvil tissue compression surface 10512 facing the cartridge jaw 10520 and extending from a proximal end of the anvil jaw 10510 to a distal end of the anvil jaw 10510. The anvil jaw 10510 further comprises a plurality of staple forming pockets defined in the anvil tissue compression surface 10512. The staple forming pockets are configured to align with the staple cavities in the staple cartridge 10524 when the staple cartridge 10524 is seated in the elongate channel 10522 and the end effector 10505 is in the closed, or clamped configuration. Further, the anvil jaw 10510 comprises a longitudinal anvil slot 10514 defined therein and extending from the proximal end of the anvil jaw 10510 to the distal end of the anvil jaw 10510. The longitudinal anvil slot 10514 comprises a T-shaped cross-section as best illustrated in FIG. 149C. Further, the elongate channel 10522 of the cartridge jaw 10520 comprises a longitudinal channel slot 10526 defined therein. The longitudinal channel slot 10526 comprises a T-shaped cross-section defined in the elongate channel 10522 as best illustrated in FIG. 149C. Further, the staple cartridge 10524 comprises a longitudinal cartridge slot 10528 defined therein. The longitudinal cartridge slot 10528 is configured to receive a portion of the firing member 10530 to permit the firing member to move through the staple cartridge 10524 during the staple firing stroke.

In use, the lower lateral member 10537 is configured for slideable travel within the longitudinal channel slot 10526 defined in the elongate channel 10522 when the firing member 10530 is distally advanced through the staple firing stroke. Further, the upper lateral member 10536 is configured for slideable travel within the longitudinal anvil slot 10514 define in the anvil jaw 10510 when the firing member 10530 is distally advanced through the staple firing stroke. As such, in at least one embodiment, the lower lateral member 10537 cammingly engages the cartridge jaw 10520 and the upper lateral member 10536 cammingly engages the anvil jaw 10510 to approximate the anvil jaw 10510 and the cartridge jaw 10520 relative to one another during the staple firing stroke. Further, the lateral tab 10538 is configured to slideably engage the anvil tissue compression surface 10512 to maintain a minimum tissue gap MTG (see FIG. 149C) between the anvil tissue compression surface 10512 and the staple cartridge 10524 when the firing member 10530 is distally advanced through the staple firing stroke. The lateral tab 10538 may change the engagement, i.e., wear points between the firing member 10530 and the end effector 10505 during the firing stroke as compared to a firing member without the lateral tab 10538, as discussed in greater detail below.

The end effector 10505 may be utilized to clamp different thicknesses of tissue. Depending on the thickness of the tissue clamped the engagement, or wear points, between the distal head 10534 of the firing member 10530 and the end effector 10505 will vary. For example, if the lateral tab 10538 is not present and the end effector 10505 is used to clamp a thin amount of tissue, the top-most surface of the upper lateral member 10536 will engage a top-most surface 10516 of the longitudinal anvil slot 10514 and the bottom-most surface of the lower lateral member 10537 will engage a bottom-most surface 10517 of the longitudinal channel slot 10526 during the firing stroke. In other words, when thin tissue is present, the anvil jaw 10510 may be over-clamped relative to the staple cartridge 10524. However, in the illustrated embodiment the lateral tab 10538 prevents over-clamping when only a thin amount of tissue is present. Specifically, when the end effector 10505 is used to clamp a thin amount of tissue, a top-most surface 10539 of the lateral tab 10538 will engage the anvil tissue compression surface 10512 and the bottom-most surface of the lower lateral member 10537 will engage the bottom-most surface 10517 of the longitudinal channel slot 10526 during the firing stroke. Further, the distance between top-most surface 10539 of the lateral tab 10538 and bottom-most surface of the lower lateral member 10537 is a fixed distance. As such, the anvil jaw 10510 cannot be approximated relative to the staple cartridge 10524 less than the minimum tissue gap distance MTG. As such, when a thin amount of tissue is present causing the end effector 10505 to over-clamped, the lateral tab 10538 prevents, or at least substantially reduces, the amount of wear experienced by the longitudinal anvil slot 10514.

Further to the above, if the lateral tab 10538 is not present and the end effector 10505 is used to clamp a thick amount of tissue, the distal head 10534 of the firing member 10530 will engage a lower surface 10518 of the longitudinal anvil slot and will engage an upper surface 10519 of the longitudinal channel slot 10526 during the firing stroke. In other words, when thick tissue is present, the anvil jaw 10510 and the cartridge jaw 10520 are pulled away from each and attempt to stretch the firing member 10530 vertically. In the illustrated embodiment with the lateral tab 10538 present, if thick tissue is clamped by the end effector 10505, the top-most surface 10539 of the lateral tab 10538 will engage the anvil tissue compression surface 10512 and the lower lateral member 10537 will engage the lower surface 10519 of the longitudinal channel slot 10526. As such, when a thick amount of tissue is present in the end effector 10505, the lateral tab 10538 prevents the firing member 10530 from engaging, or wearing, against the lower surface 10518 of the anvil slot 10514.

As discussed above, the lateral tab 10538 prevents, or at least substantially reduces, the wearing engagement between the upper lateral member 10536 of the firing member 10530 and the longitudinal anvil slot 10514 during the firing stroke. In the present embodiment, the lateral tab 10538 engages the anvil tissue compression surface 10512 of the anvil jaw 10510 during the firing stroke. Preventing and/or reducing wearing of the longitudinal anvil slot 10514 may be desirable as the inner surfaces of the longitudinal anvil slot 10514 are not easily accessible to coat and/or reinforce against potential wear. In contrast, the anvil tissue compression surface 10512 is more easily accessible and, thus, is easier to coat or reinforce against wear.

Further to the above, in the illustrated embodiment the lateral tab 10538 is positioned proximal to the upper and lower lateral members 10536, 10537. However, other embodiments are envisioned where the lateral tab 10538 is positioned in vertical alignment with the upper and lower lateral members 10536, 10537 or distal to the upper and lower lateral members 10536, 10537, for example. In such instances, the wear points between the firing member 10530 and the anvil and cartridge jaws 10510, 10520 can be modified.

Bioabsorbable metal staples can provide numerous advantages in certain clinical situations. For example, bioabsorbable metal staples can dissolve within the patient at a predetermined rate and/or over a predetermined timeframe to seal the tissue and promote healing without remaining in the patient longer than necessary and without requiring a follow-up removal procedure. In certain instances, bioabsorbable metal staples can be softer and more ductile than conventional metal staples, such as those comprised of titanium or stainless steel, for example. Additionally or alternatively, certain bioabsorbable metal staples can be more prone to cracking and/or malformation during initial formation and/or firing than conventional metal staples. For example, the transitional bend between the staple crown and the staple leg during the initial forming process (e.g. to U-shaped or V-shaped) may result in portions of the staple being in a state of tension and adjacent portions of the staple being in a state of compression, which can weaken the staple at and/or around these adjacent portions. Certain bioabsorbable metal staples can be susceptible to cracking where internal stresses are most concentrated, such as at bends or curvatures in the staple wire.

In various instances, a bioabsorbable buttress can be installed in patient tissue along with the staples. For example, the bioabsorbable buttress can be positioned on a tissue-supporting deck of a staple cartridge and pressed into abutting contact with patient tissue upon clamping and/or firing of the staples from the staple cartridge. Additionally or alternatively, the bioabsorbable buttress can be positioned on a tissue-compressing surface of the anvil. As bioabsorbable staples are deployed from the staple cartridge, the staples are configured to capture the bioabsorbable buttress therein along with the patient's tissue. The buttress and tissue can be captured within the staples to sufficiently compress the tissue and obtain an appropriate seal to reduce bleeding and facilitate healing of the tissue. In various instances, the bioabsorbable buttress can be disengaged from the tissue-supporting deck during the firing stroke. For example, the staple bases and/or drivers in the staple cartridge can push the buttress away from the tissue-supporting deck. In certain instances, the staples can be overdriven by the drivers to further disengage the buttress from the tissue-supporting deck.

The bioabsorbable buttress can mechanically support the bioabsorbable staples during the firing stroke and/or during the degradation life thereof. For example, the bioabsorbable buttress can support the staple legs during firing as the staple legs are pushed through the bioabsorbable buttress to maintain alignment of the staple legs with the forming pockets in the anvil. Additionally or alternatively, the bioabsorbable buttress can support the bioabsorbable staple against the forces exerted by tissue compressed within the staple to resist deflection of the staple legs from the formed configuration within the patient (e.g. away from the desired B-form geometry). The degradation rates and/or degradation lives of the bioabsorbable staples and bioabsorbable buttress can be different. Additionally or alternatively, the degradation rates of the bioabsorbable staples and bioabsorbable buttress may vary during the degradation lives thereof.

As an example, a surgical staple cartridge assembly can include a cartridge body, staples comprised of a bioabsorbable metal alloy, and a buttress layer comprised of a bioabsorbable polymer that is configured to selectively support at least a portion of the staple. The staples can be configured to degrade at a staple degradation rate over an expected staple life in the patient, and the buttress layer can be configured to degrade at a buttress layer degradation rate over an expected buttress layer life in the patient. The staple degradation rate and the buttress degradation rate can be different.

In various instances, the degradation rates of the bioabsorbable buttress and the bioabsorbable staples can be selected such that the bioabsorbable buttress supports the bioabsorbable staples as the staples weaken, degrade, and/or dissolve within the patient's tissue. For example, the staples can absorb faster than the buttress at one or more time periods during the degradation lives thereof. In such instances, the buttress can support the weakened staples to ensure proper sealing of tissue until the tissue has sufficiently healed.

Figure 87:
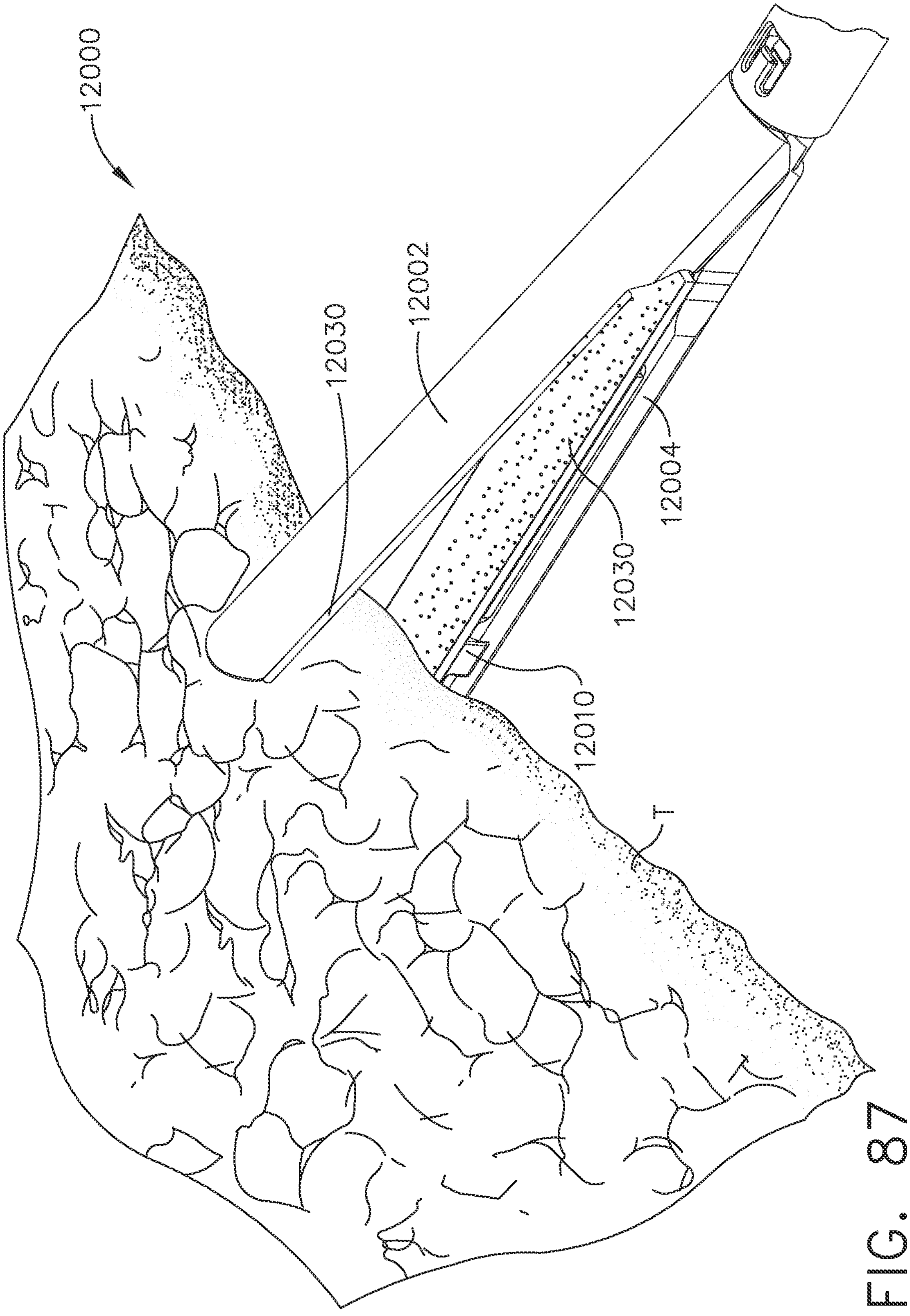
FIG. 87 is perspective view of a surgical stapling assembly and tissue prior to incision and stapling of the tissue, according to various aspects of the present disclosure.
Figure 88:
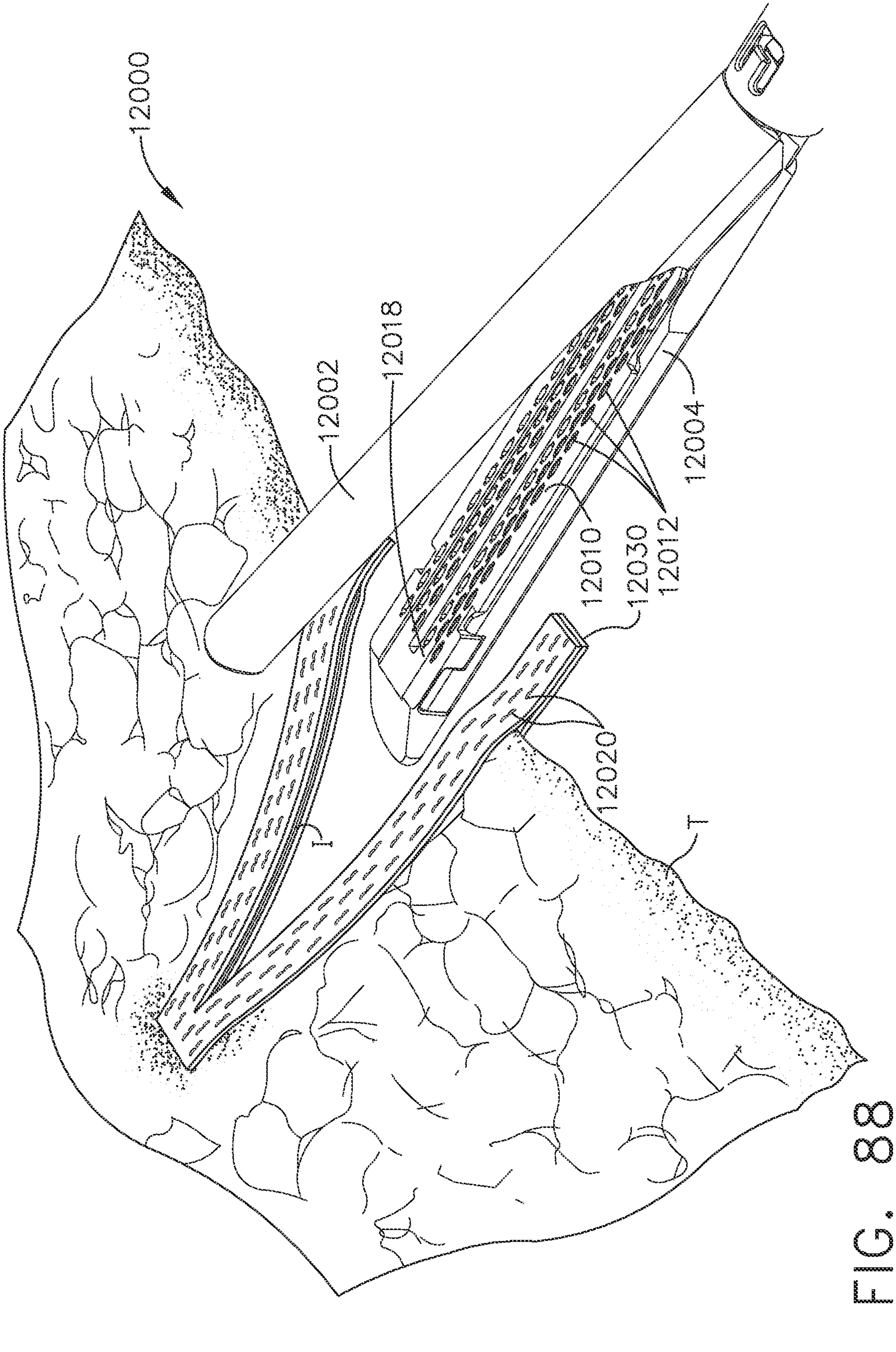
FIG. 88 is a perspective view of the surgical stapling assembly and tissue of FIG. 87 after incision and stapling of the tissue and depicting layers of buttress stapled to the tissue, according to various aspects of the present disclosure.
Figure 89:
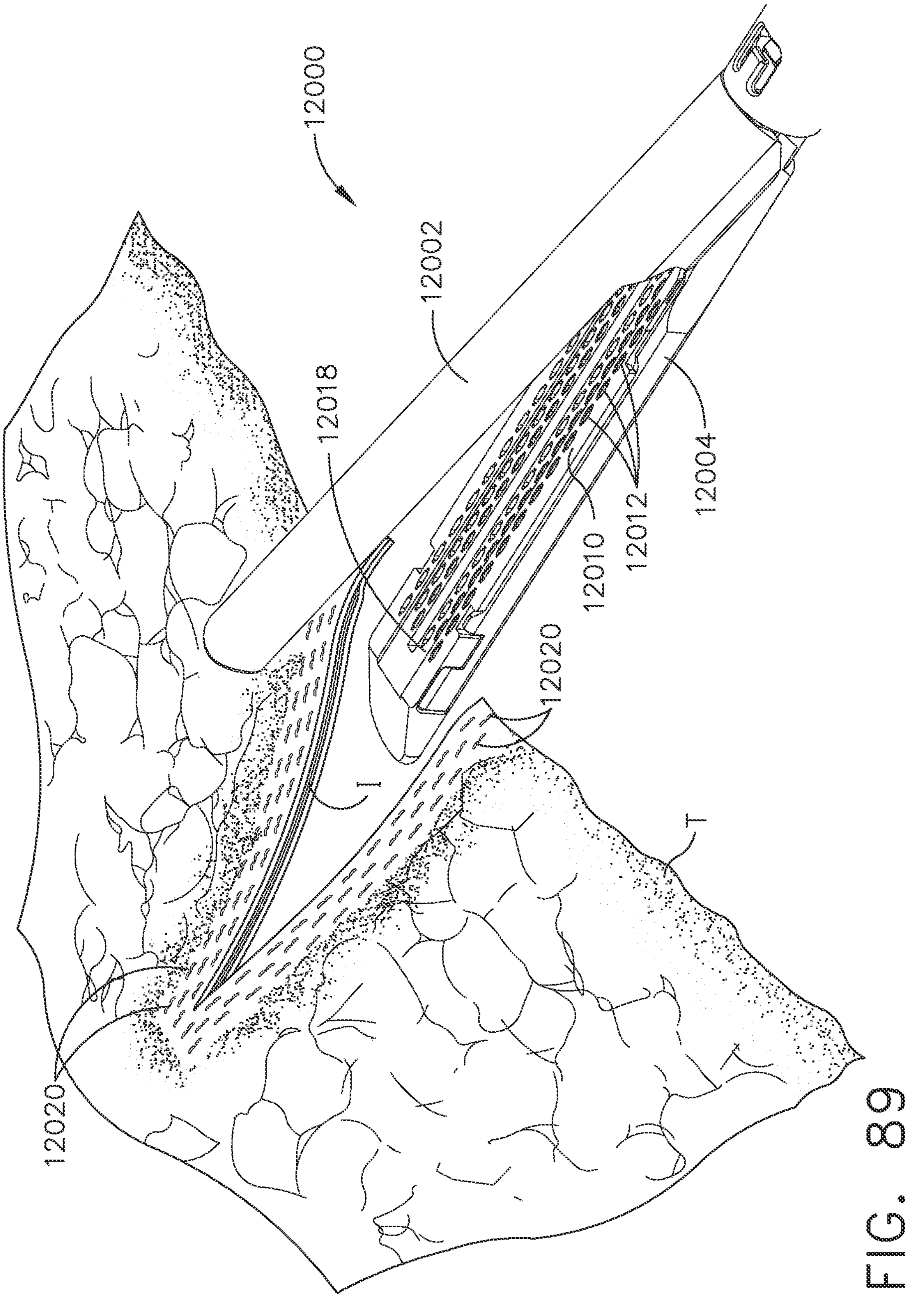
FIG. 89 is a perspective view of the surgical stapling assembly and tissue of FIG. 87 after the incision and stapling of the tissue and after dissolution of the layers of buttress into the patient, according to various aspects of the present disclosure.

A surgical stapling assembly 12000 for cutting and stapling tissue is shown in FIGS. 87-89. The surgical stapling assembly can be a distal portion of a handheld surgical instrument, robotic surgical tool, disposable loading unit, or multi-use loading unit, for example. The surgical stapling assembly includes an end effector comprised of a first jaw 12002 and a second jaw 12004. The end effector is configured to receive a staple cartridge 12010 therein. As further described herein, the staple cartridge 12010 can comprise a disposable staple cartridge in certain instances and a reloadable staple cartridge in other instances. The staple cartridge 12010 is installed in the elongate channel of the second jaw 12004 in FIGS. 87-89. The staple cartridge 12010 includes staple cavities 12012 arranged in a plurality of longitudinal rows. Layers of buttress 12030 are releasably attached to the surgical stapling assembly 12000. More specifically, a first layer of buttress 12030 is releasably attached to a tissue-facing surface of the first jaw 12002, and a second layer of buttress 12030 is releasably attached to a tissue-facing surface of the staple cartridge 12010. The buttress 12030 can be referred to as an implantable layer, an adjunct, or a tissue thickness compensator, for example. Materials and properties for such layers of material, as well as techniques and methods for releasably attaching the layers of material to a staple cartridge and/or an anvil, are further described, for example, in U.S. Pat. No. 8,393,514, titled SELECTIVELY-ORIENTABLE IMPLANTABLE FASTENER CARTRIDGE, which issued Mar. 12, 2014, and in U.S. Pat. No. 9,211,120, titled TISSUE THICKNESS COMPENSATOR COMPRISING A PLURALITY OF MEDICAMENTS, which issued Dec. 15, 2015, which are both incorporated by reference herein in their respective entireties.

Figure 97:
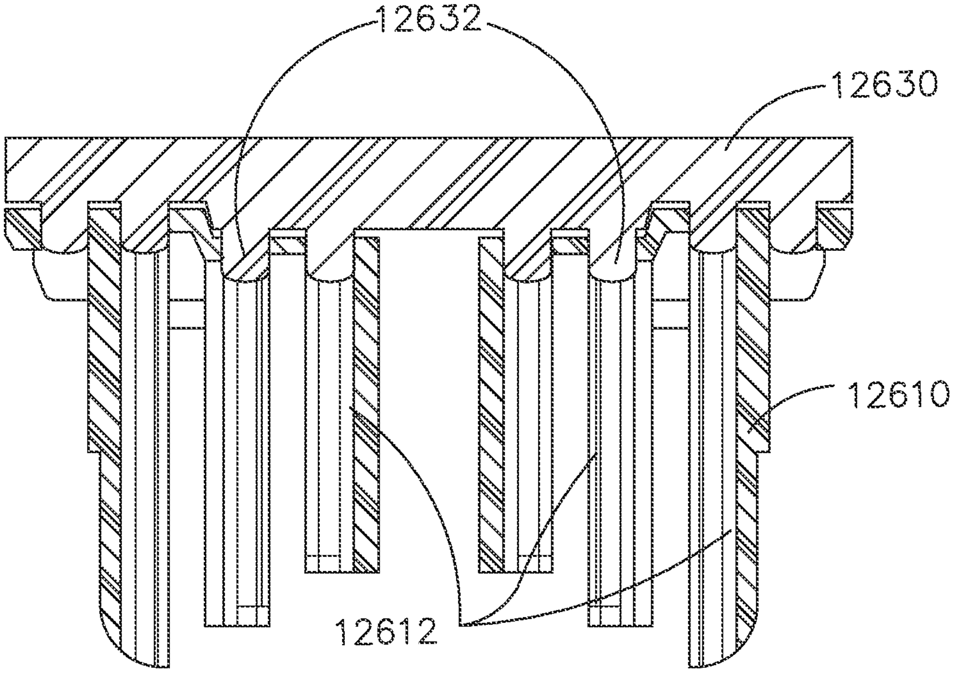
FIG. 97 is a cross-sectional elevation view of a staple cartridge and a buttress releasably secured to the staple cartridge, according to various aspects of the present disclosure.

In certain instances, the buttress 12030 can be releasably secured to the staple cartridge 12010 with extensions that extend into the staple cavities. Referring now to FIG. 97, a staple cartridge 12610 and a buttress 12630 are shown. The staple cartridge 12610 is similar in many aspects to the staple cartridge 12010. Moreover, the buttress 12630 is similar in many aspects to the buttress 12030; however, the buttress 12630 includes a cartridge-facing surface with a geometry that complements that tissue-supporting deck 12618 of the cartridge 12610. More specifically, the buttress 12630 includes a stepped underside that complements the stepped geometry of the tissue-supporting deck 12618 and further includes an array of extensions 12632 that extend at least partially into the staple cavities 12612. The extensions 12632 can frictionally engage the staple cavities 12612 to releasably secure the buttress 12630 to the staple cartridge 12610. In various instances, the extensions 12632 can be press-fit into the staple cavities 12612. The firing action of the staples and drivers within the staple cartridge 12610 is configured to overcome the friction fit between the extensions 12632 and the staple cavities 12612 to release the buttress 12630 from the staple cartridge 12610. In certain instances, only certain staple cavities 12612 receive extensions 12632 from the buttress 12630. For example, extensions 12632 can secure the buttress 12630 to the staple cartridge 12610 at the proximal and distal ends of the buttress 12630 and/or intermittently along the length thereof.

In certain aspects of the present disclosure, extension from a buttress are configured to be received between projections from the tissue-supporting deck of the staple cartridge. For example, the tissue-supporting deck can include a plurality of projections, as further described herein, and extensions from the buttress are configured to frictionally engage the projections to releasably secure the buttress to the staple cartridge. Frictional engagement between the buttress and the tissue-supporting deck can limit axial and/or lateral skewing of the staples during firing and, thus, can minimize the likelihood of inadvertent malformation or bending of the staples during firing.

In other instances, one or both of the jaws 12002, 12004 can include multiple overlapping and/or staggered layers of buttress 12030. In still other instances, the layer of buttress 12030 can only be positioned on one side of the tissue. For example, the layer of buttress 12030 may only be on the side of the first jaw 12002 or only be on the side of the second jaw 12004.

To effect tissue, the jaws 12002 and 12004 are clamped onto the tissue. Clamping the tissue can compress tissue and/or the layer(s) of buttress 12030 between the jaws 12002 and 12004. Thereafter, firing of the surgical stapling assembly 12000 can drive a firing member longitudinally therethrough to fire the staples 12020 from the staple cartridge 12010 into forming engagement with staple forming pockets in the anvil surface of the first jaw 12002. Tissue and the layer(s) of buttress 12030 are captured within the staples, as shown in FIG. 88. Thereafter, the surgical stapling assembly 12000 can be unclamped to release the tissue clamped therebetween. Referring primarily to FIG. 88, the staples 12020 ejected from the staple cartridge 12010 are configured to hold the layer(s) of buttress 12030 against the stapled tissue T. A knife is further configured to incise the tissue along an incision I between the rows of staples 12020. In other instances, the tissue T and/or buttress 12030 may not be severed by a knife.

The staple cartridge 12010 includes different types of bioabsorbable components. For example, the staples 12020 can be bioabsorbable metal staples, as further described herein, and the layer of buttress 12030 can be a bioabsorbable polymer buttress. In various instances, the staples 12020 and the layer of buttress 12030 can breakdown within a patient at different rates and/or within different timeframes. For example, the staples 12020 and the buttress 12030 can have different degradation rates. Referring now to FIG. 89, the buttress 12030 has completely dissolved within the patient while the staples 12020 remain undissolved within the patient. In other instances, the staples 12020 can completely dissolve before the buttress 12030 and, in still other instances, the staples 12020 can dissolve faster than the buttress 12030 initially, but later the buttress 12030 can dissolve faster than the staples, or vice versa. Relative dissolution rates and timeframes are further described herein.

Figure 90:
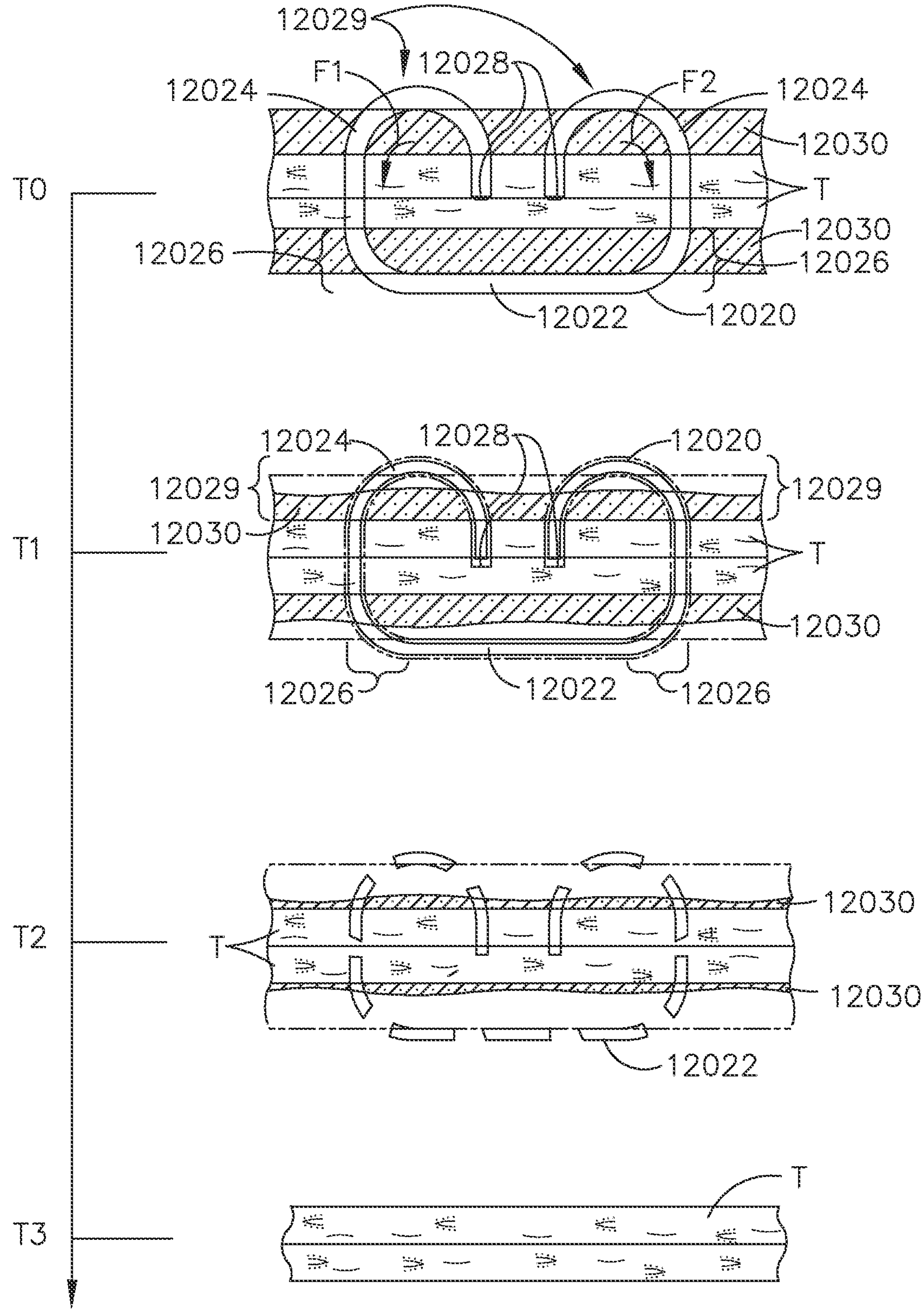
FIG. 90 is a timeline schematic depicting degradation and bioabsorption of a staple and buttress of the surgical stapling assembly of FIG. 87, according to various aspects of the present disclosure.

Referring primarily to FIG. 90, the staple 12020 and buttress 12030 are shown in various stages of degradation and bioabsorption. Time T0 shows the staple 12020 and the buttress 12030 upon initial implantation in the patient. More specifically, the staple 12020 has just been deformed to a B-form configuration and has captured the tissue T and buttress 12030 within the B-form configuration. In various instances, the tissue T and the buttress 12030 can fill the entire space within the formed staple 12020. In such instances, the tissue T and/or the buttress 12030 can be suitably compressed within the formed staple 12020 to encourage healing.

The formed staple 12020 includes a base 12022 and two legs 12024. Each leg 12024 extends away from the base 12020 at a transition 12026, which is generated during the initial forming process. The transition 12026 defines a radius of curvature, which directs the legs 12024 away from the base and toward the staple-forming pockets in the anvil. The tips 12028 of the legs 12024, upon making forming contact with the staple-forming pockets, are turned toward a centerline of the staple 12020. As shown in FIG. 90, the tips 12028 are turned toward each other at a curvature 12027 along one or more radii of curvature defined by the forming pocket geometry. In various instances, depending on the type of tissue (e.g. thickness, toughness, etc.) pierced by the staple 12020, the tips 12028 can be bent back toward the base 12022. In certain instances, the tips 12028 can meet at or near the centerline of the staple 12020, which extends through a midpoint of the base 12022 equidistant between the legs 12024. In still other instances, the tips 12028 of the staple 12020 can cross or overlap longitudinally.

The formed staple 12020 is subjected to forces F1 and F2 by the tissue T and/or buttress 12030 compressed therein. The forces F1 and F2 can seek to splay the staple 12020 by pushing the legs 12024 outward and away from each other. In various instances, the forces F1 and F2 can generate a torque at the transition 12026. Furthermore, the forces F1 and F2 can seek to rotate the tips 12028 away from their formed configurations and/or reduce the curve in the curvatures 12027 in response to the compressive load from the tissue T and/or buttress 12030.

The staple 12020 is a bioabsorbable metal staple, which is more ductile than a non-bioabsorbable metal staple. For example, the staple 12020 can be substantially comprised of a bioabsorbable metal alloy. The staple 12020 can be substantially comprised of a magnesium-based alloy, a zinc-based alloy, an iron-based alloy, or combinations thereof, as further described herein. In certain instances, the staple 12020 can further be comprised of magnesium, lithium, zinc, calcium, and manganese, for example.

The forces F1 and F2 within more ductile staples, such as the various bioabsorbable metal staples described herein, for example, may be more prone to cause deformation of the staple 12020 away from the desired B-form configuration. To counter such forces, the buttress 12030 is configured to mechanically support the staples 12020. In various instances, the combination of a bioabsorbable buttress 12030 with bioabsorbable staples 12020 can increase the staple's stability and improve the strength and structural integrity of the deployed staple line in patient's tissue.

The buttress 12030 from the cartridge-side of the surgical stapling assembly 12000 can be configured to support the staple 12020 adjacent to the base 12022 thereof and at the transition 12026 by at least partially surrounding the transition 12026. Referring primarily to the staple 12020 and the buttress 12030 at time T0, the buttress 12030 surrounds a substantial portion of the staple 12020 at the transition 12026 to resist splaying or torqueing of the legs 12024 outward at the transition 12026. In various instances, the buttress 12030 can define a thickness that is sufficient to support the portion of the transition 12026 at regions of weakness therein, such as where the legs 12024 are stained during the initial forming process.

The buttress 12030 from the anvil-side of the surgical stapling assembly 12000 can be configured to support the staple 12020 at the curvature 12029 by at least partially surrounding the curvature 12029. The buttress 12030 at time T0 in FIG. 90 surrounds a substantial portion of the staple 12020 at the curvature 12029 to resist unbending of the legs 12024 from the desired B-form configuration. In various instances, the buttress 12030 can define a thickness that is sufficient to support the portion of the curvature 12029 at regions of weakness therein, such as where the legs 12024 are stained during the forming process by the radii of curvature of the forming pockets in the anvil. By engaging the legs 12024 at and/or adjacent to the top of the formed staple, the buttress 12030 can further hold and support the legs 12024 to resist outward splaying at the transition 12026, in various instances.

Figure 91:
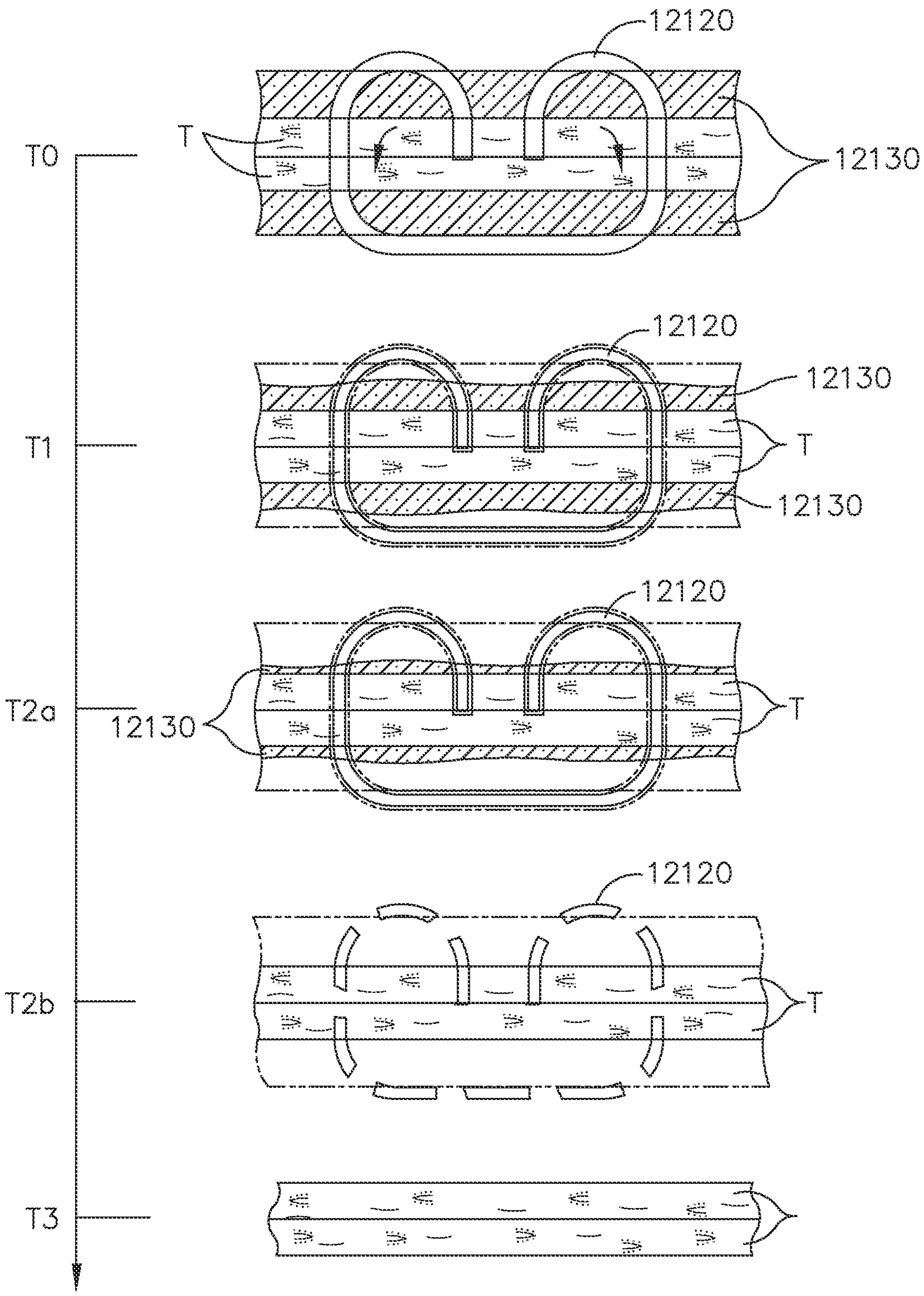
FIG. 91 is a timeline schematic depicting degradation and bioabsorption of a staple and buttress of anther surgical stapling assembly, according to various aspects of the present disclosure.

As shown in FIGS. 90 and 91, the staple 12020 and the buttress 12030 can define different degradation rates and/or timeframes. In FIG. 90, both the staple 12020 and the buttress 12030 are installed in patient's tissue T at time T0 and both degrade simultaneously. More specifically, the wire of the staple 12020 and the buttress 12030 are thinner at time T1. In such instances, as the buttress 12030 begins to degrade, the tissue T and the buttress 12030 may not fill the entire space within the formed staple 12020. In other instances, the tissue T can at least partially expand to refill the space within the formed staple 12020 as the staple 12020 and/or buttress 12030 become thinner. At time T2, the buttress 12030 is thinner still and the wire of the staple 12020 has fractured into segments and no longer exerts a compressive force on the patient's tissue T. In certain instances, the buttress 12030 can also break into smaller pieces as it degrades. At time T3, both the staple 12020 and the buttress 12030 have entirely dissolved.

The reader will understand that alterative degradation timeframes are contemplated. For example, the buttress 12030 can dissolve entirely before the staple 12020 begins its degradation process. In other instances, the staple 12020 can dissolve entirely before the buttress 12030 begins its degradation process. In still other instances, the buttress 12030 and the staple 12020 can degrade simultaneously, at least during a portion of their degradation life, however, the degradations rates can be different. For example, the staple 12020 can initially degrade faster (e.g. an outer layer thereof can have a fast degradation rate), then degradation of the buttress 12030 can surpass that of the staple 12020. Layers and coatings, which can adjust the absorption rate of the staples and/or buttress, are further described herein.

Figure 95:
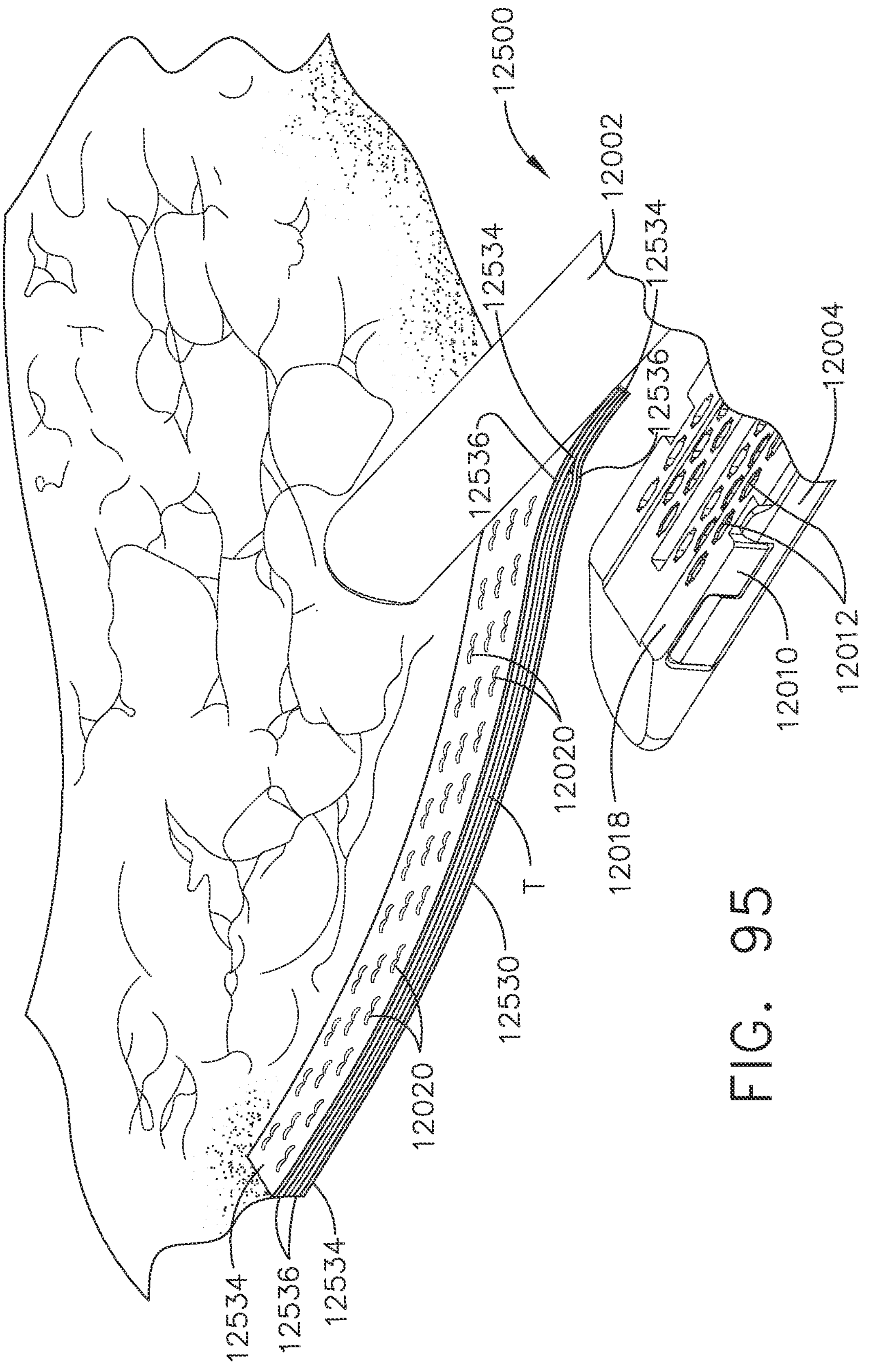
FIG. 95 is a perspective view of a surgical stapling assembly and tissue, further depicting multilayer buttresses releasably secured to the tissue, according to various aspects of the present disclosure.

In other instances, the buttress 12020 can initially degrade faster (e.g. an outer layer thereof can have a fast degradation rate), then degradation of the staple 12020 can surpass that of the buttress 12030. For example, referring to FIG. 95, a surgical stapling assembly 12500 similar in many aspects to the surgical stapling assembly 12000 is shown. However, the surgical stapling assembly 12500 deployed a buttress 12530 having multiple layers 12534, 12536. More specifically, inner layers 12536 and outer layers 12534 are installed on both sides of the tissue T. In other instances, multiple layers may be positioned on a single side of the patient tissue T and/or the multiple layers can include more than two layers. The different layers can have different properties. In one instance, the inner layers 12536 positioned adjacent to the tissue T can degrade faster than the outer layers 12534 and, in other instances, the outer layers 12534 can degrade faster than the inner layers 12536. For example, the outer layers 12534, which are positioned adjacent to higher stress regions in the bioabsorbable metal staples (e.g. regions of transition/curvature), can be configured to degrade more slowly than the staples 12020 to support the staples 12020 as they weaken and degrade, while the inner layers 12526 adjacent to the patient tissue T can degrade faster than the staples 12020.

As described herein, the degradation rates can change at least once during the degradation lifespan dependent on the properties of the staple 12020, the buttress 12030, and the interaction thereof. In certain instances, the degradation rates can depend, at least in part, on the tissue type (e.g. thick tissue versus thin tissue, tissue with limited blood flow versus tissue with optimized blood flow, etc.) Moreover, the degradation rates can be selected and customized for different tissue types. For example, a staple cartridge having particular staple and buttress properties can be selected for a particular type of tissue or a particular surgical procedure, whereas a different staple cartridge having different staple and/or buttress properties can be selected for another type of tissue or surgical procedure.

For example, referring now to FIG. 91, a staple 12120 and buttress 12130 for a surgical stapling assembly are shown. The staple 12120 can be similar in many aspects to the staple 12020 and the buttress 12130 can be similar in many aspects to the buttress 12030; however, the degradation rates can be different from those in FIG. 90. Both the staple 12120 and the buttress 12130 are installed in patient's tissue at time T0 and both degrade simultaneously. More specifically, the wire of the staple 12120 and the buttress 12130 are thinner at time T1. At time T2*a*, the buttress 12130 is thinner still; however, degradation of the staple 12120 has slowed down. More specifically, the staple 12120 is not thinner at time T2*a* than time T1. In certain instances, the staple 12120 can include a coating, as further described herein, which can control the initial degradation rate of the staple 12120 from time t0 to time t1. Upon degradation of the coating, the material of the staple body and/or an inner coating on the staple 12120 can control the subsequent degradation rate, for example. At time T2*b*, the buttress 12130 is entirely dissolved while the staple 12120 continues to breakdown. More specifically, the wire of the staple 12120 has broken into segments and no longer exerts a compressive force on the patient's tissue at time T2*b*. At time T3, both the staple 12120 and the buttress 12130 have entirely dissolved.

Referring again to FIGS. 87-89, the buttress 12030 can be configured to protect the staples 12020 upon deployment into tissue. For example, the buttress 12030 can include a film or similar material for protecting the staples 12020. The buttress 12030 can protect certain portions of the staples 12020 to control the degradation rates thereof. For example, contact with patient tissue can accelerate degradation of the staples 12030. In such instances, the buttress 12030 can form a film around portions of the staple 12030 to slow down degradation thereof. The buttress 12030 can degrade first, followed by those portions of the staple 12030 previously covered or protected by the buttress 12030, for example.

The buttress 12030 can mechanically support the staples 12020 within the patient tissue, as further described herein. Additionally or alternatively, the buttress 12030 can mechanically support the staples 12020 during deployment of the staples 12020 into patient's tissue. In various instances, upon compression of tissue between the jaws 12002, 12004 of the surgical stapling assembly 12000, fluid can flow out of the tissue away from the compressed tissue within the jaws 12002, 12004. Additionally or alternatively, tissue can be pushed in the direction of the firing motion (e.g. distally during a proximal-to-distal firing stroke). The flow of tissue during clamping and/or firing can exert additional forces on the bioabsorbable metal staples 12020, which can lead to malformation and/or misfiring thereof. As one example, the staple legs can be deformed distally out of alignment with the staple forming pockets in the anvil, for example, during a distal firing stroke. Bioabsorbable metal staples, as further described herein, are generally softer than conventional non-bioabsorbable metal staples and, thus, more prone to shifting and/or skewing during firing, which may increase incidences of staple malformation under certain conditions.

In various instances, positioning buttress 12030 adjacent to the tissue T can reduce the effects of tissue flow during staple formation. For example, the buttress 12030 can be secured to the tissue-supporting deck 12018 of the staple cartridge 12010 to isolate the staples 12020 from tissue flow as the tips 12028 of the staples 12020 leave the staple cavities in the staple cartridge 12010. In such instances, the buttress 12030 can maintain proper alignment of the staples 12020 with the staple-forming pockets in the anvil. Stated differently, the buttress 12030 can exert effective counter forces to balance the distal or outward flow of tissue and the staples 12020 engaged therewith during firing. For example, the buttress 12030 can resist stretching or elongation during the firing motion to resist distal or outward forces applied thereto.

In various aspects of the present disclosure, the buttress 12030 can include features that can enable the buttress 12030 to resist planar forces relative thereto during clamping and/or firing. For example, the buttress 12030 can include holes, ridges, slots, extensions, protrusions, and/or varying surface textures to counter forces applied to the staple 12020 and forces within the staple 12020 during firing and/or upon installation into patient tissue T. In various instances, integration of the buttress 12030 with bioabsorbable staples 12020 can enhance the collective behavior of the buttress 12030 and the staples 12020 over their individual capabilities in isolation. Integration of the buttress 12030 with bioabsorbable staples 12020 can be advantageous in certain clinical applications, such as where bioabsorbable staples 12020 are beneficial and where thick and/or otherwise tough-to-seal tissue applies significant forces to the staples 12020 during formation and/or upon installation in patient tissue.

In various instances, the buttress 12030 can include one or more medicaments, which can be administered to tissue upon installation and/or during the dissolution of the buttress, as further described herein. Additionally or alternatively, the buttress 12030 can incorporate Barium for radiopaque purposes. For example, the buttress 12030 can be covered or impregnated with Barium to make the overall structured embedded in patient's tissue radiopaque and more visible to the clinician during certain procedures.

Figure 92:
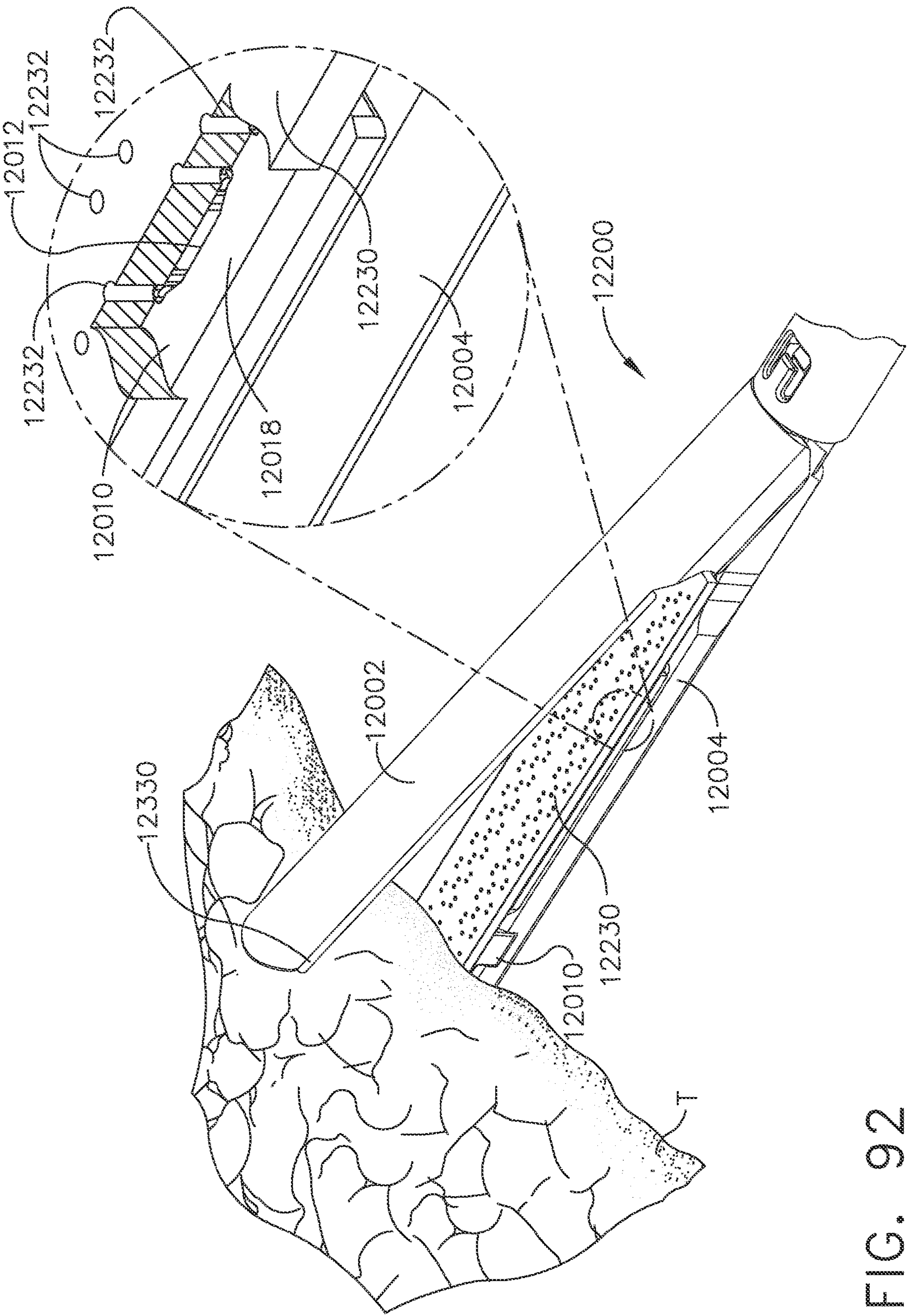
FIG. 92 is a perspective view of a surgical stapling assembly and tissue, further depicting layers of buttress releasably secured to the surgical stapling assembly, in which the layers of buttress include an array of through-holes aligned with the staple legs, according to various aspects of the present disclosure.

Referring now to FIG. 92, a surgical stapling assembly 12200 similar in many aspects to the surgical stapling assembly 12000 is shown. However, the surgical stapling assembly 12200 includes a buttress 12230 having an array of staple support features 12232 for improving the integration of the buttress 12230 with the staples 12020. The staple support features 12232 are aligned with the staples 12020 in the staple cartridge 12010. More specifically, the staple support features 12232 are through-holes from the cartridge-facing side of the buttress 12230 to the tissue-facing side of the buttress 12230. The through-holes are dimensioned and positioned to receive the staple legs therein upon deployment of the staples 12020 from the staple cartridge 12010. Each staple leg is aligned with a through-hole. The through-holes are configured to guide the staple legs through the buttress 12230 to maintain the desired shape of the staple 12020 during firing. In various aspects of the present disclosure, the interaction between the staple support features 12232 and the staples 12020 is configured to stabilize the staples 12020 during firing and/or upon implantation of the staples 12020 within patient tissue. For example, the staple support features 12232 allows the buttress 12230 to grip or hold the staples legs. In various instances, the buttress 12230 resists stretching and, thus, can resist lateral and/or longitudinal skew of the staple legs to guide the staple legs along the intended tissue penetration pathway into forming engagement with the forming pockets in the anvil.

Figure 93:
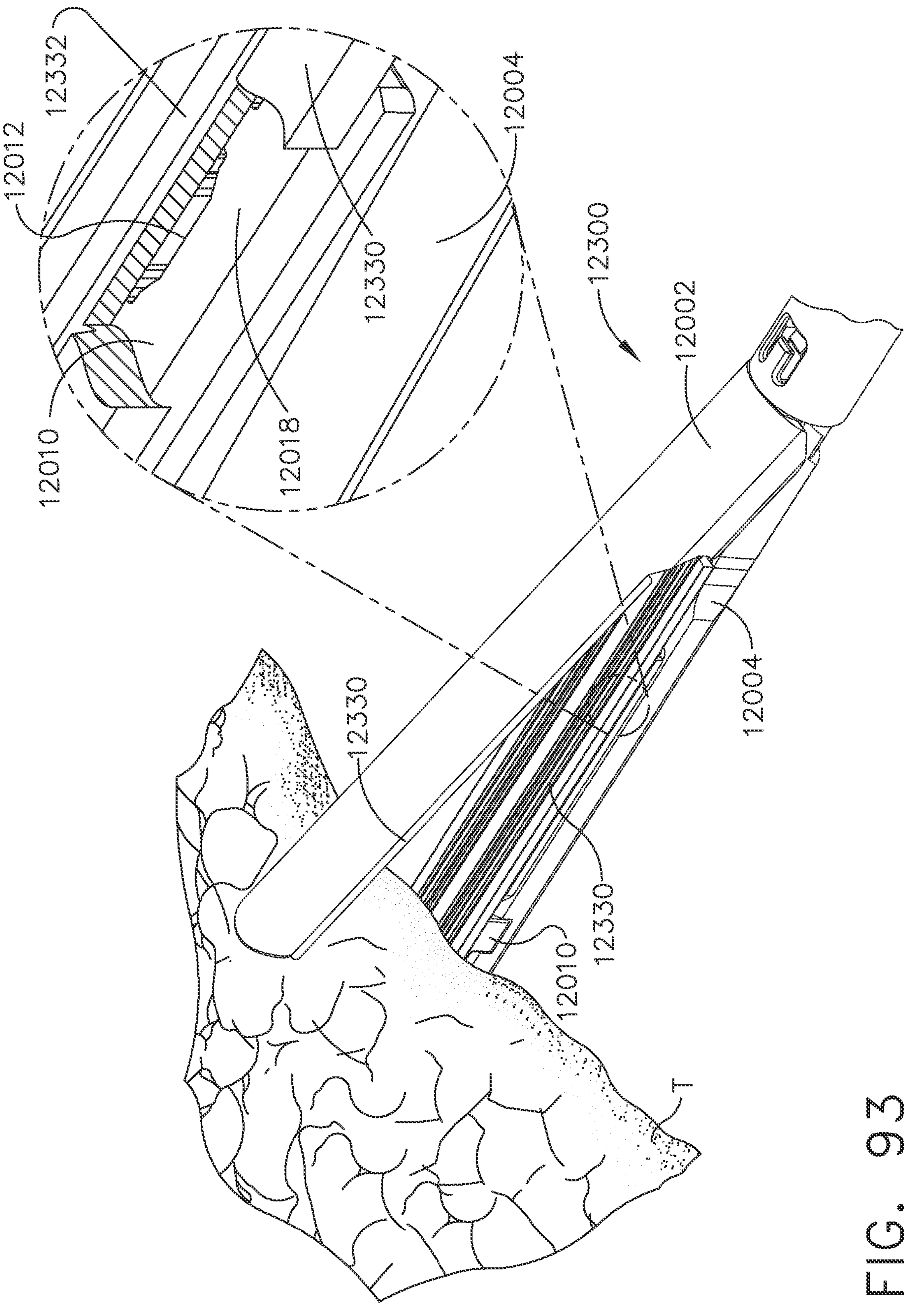
FIG. 93 is a perspective view of a surgical stapling assembly and tissue, further depicting layers of buttress releasably secured to the surgical stapling assembly, in which the layers of buttress include an array of longitudinal ridges aligned with the rows of staples, according to various aspects of the present disclosure.

Referring now to FIG. 93, a surgical stapling assembly 12300 similar in many aspects to the surgical stapling assembly 12000 is shown. The surgical stapling assembly 12300 includes a buttress 12230 having an array of staple support features 12232 for improving the integration of the buttress 12330 with the staples 12020. The staple support features 12332 are aligned with the staples 12020 in the staple cartridge 12010. More specifically, the staple support features 12332 are longitudinal ridges in the buttress 12330 defining regions of a reduced thickness. The thinner regions of the buttress 12330 are dimensioned and positioned to receive the staple legs therein upon ejection of the staples 12020 from the staple cartridge 12010. In such instances, the staple legs can penetrate through the thinner regions in the buttress 12330 with a reduced force in comparison to the force required to penetrate the thicker, adjacent portions of the buttress 12330. In such instances, the risk of bending or otherwise misdirecting the staple legs from their intended pathway can be reduced.

Figure 94:
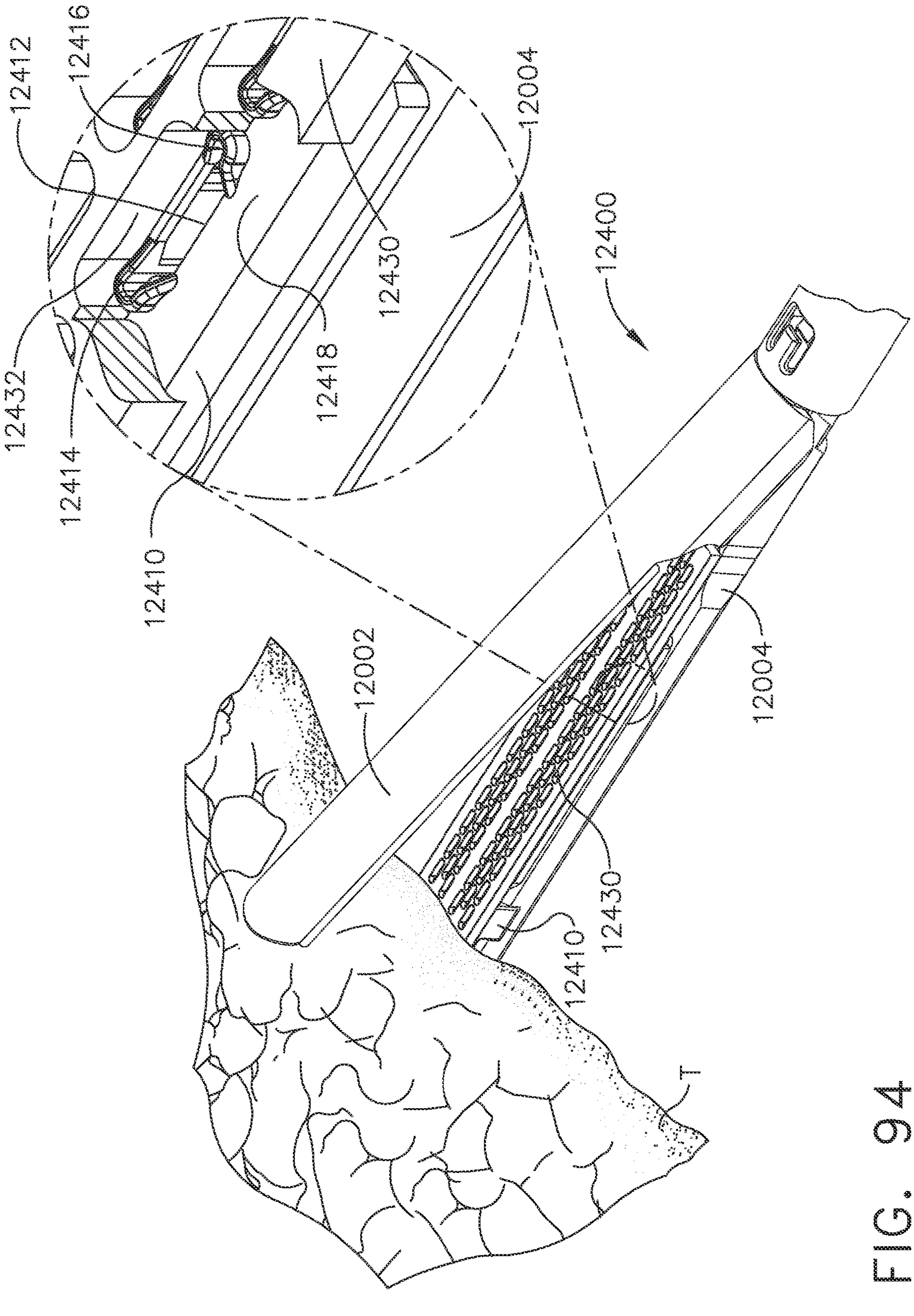
FIG. 94 is a perspective view of a surgical stapling assembly and tissue, further depicting layers of buttress releasably secured to the surgical stapling assembly, in which the layers of buttress include an array of slots positioned and dimensioned to accommodate projections from the deck, according to various aspects of the present disclosure.

Referring now to FIG. 94, a surgical stapling assembly 12400 similar in many aspects to the surgical stapling assembly 12000 is shown. However, the surgical stapling assembly 12400 includes a staple cartridge 12410, which is similar to the staple cartridge 12010 but further includes an array of projections 12414, 12416 extending from a tissue-supporting deck 12418 thereof. Proximal projections 12416 extend around the proximal ends of staple cavities 12412 defined in the tissue-supporting deck 12418, distal projections 12414 extend around the distal ends of staple cavities 12412 defined in the tissue-supporting deck 12418. In various instances, the projections 12414, 12418 are configured to guide the staples and/or grip tissue during clamping and/or firing to improve staple formation. For example, the projections can guide the tips of the bioabsorbable metals staples that are further described herein to maintain the proper alignment of the tips despite the softer material thereof. In certain instances, projections may only extend around the distal ends of the staple cavities 12412 and, in other instances, the projections may only extend around the proximal ends of the staple cavities 12412. In still other instances, the projections can define discrete projections entirely surrounding each staple cavity 12412. The projections are positioned within the rows of staple cavities 12412 and between adjacent staples cavities 12412 in each row.

The surgical stapling assembly 12400 further includes a buttress 12430 having an array of staple support features 12432 for improving the integration of the buttress 12430 with the staples 12020. The staple support features 12432 are aligned with the staples 12020 in the staple cartridge 12010. More specifically, the staple support features 12432 are longitudinal through-slots in the buttress 12430 that overlap the staple cavities 12412. Each through-slot is aligned with a staple cavity 12412 and overlaps the cavity 12412 and the projections 12414, 12416 extending around the cavity 12412. The through-slots can facilitate alignment of the buttress 12430 with the staple cartridge 12410 in various instances. Moreover, due to the absence of material overlapping the pathway of the staples 12020, a reduced force may be required to fire the staples 12020 from the staple cavities 12412.

Figure 96:
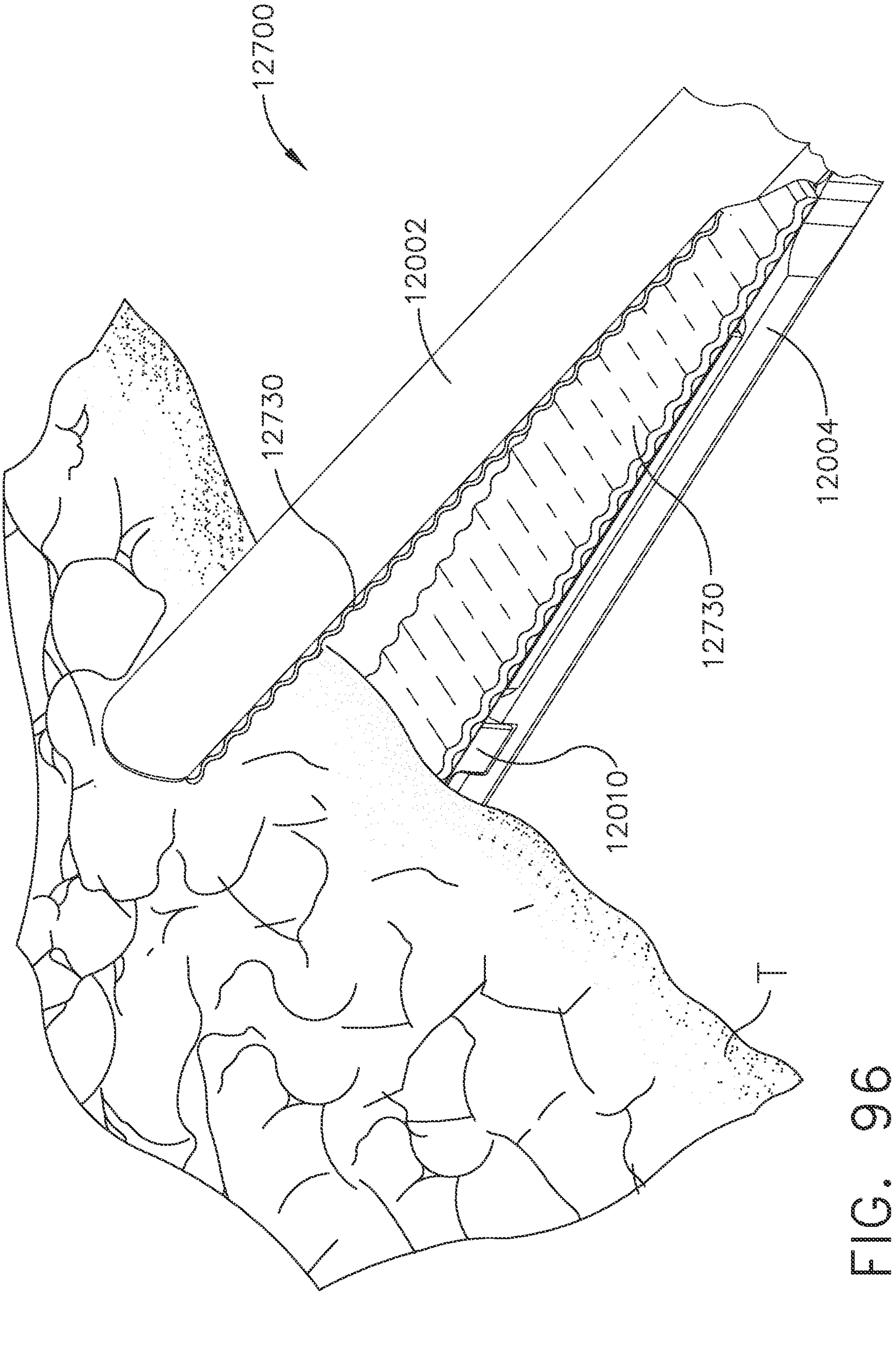
FIG. 96 is a perspective view of a surgical stapling assembly and tissue, further depicting corrugated buttresses releasably secured to the surgical stapling assembly, according to various aspects of the present disclosure.

Referring now to FIG. 96, a surgical stapling assembly 12700 similar in many aspects to the surgical stapling assembly 12000 is shown. The surgical stapling assembly 12700 includes a corrugated buttress 12730. The corrugated buttress 12730 includes undulating proximal-to-distal peaks and valleys along the length thereof. In other instances, the peaks and valleys can undulate laterally along the width of the corrugated buttress 12730. In certain instances, only a portion of the corrugated buttress 12730 can include a corrugated surface texture. The corrugated buttress 12730 can be configured to grip patient's tissue T during clamping and firing to reduce the effects of tissue flow on staple misfiring and/or malformation, as further described herein.

Various staple cartridge assemblies described herein apply buttress to opposing sides of the tissue T. The reader will appreciate that the various buttresses described herein can be interchangeable in various instances. For example, the corrugated buttress 12730 on the first jaw 12002 in FIG. 96 can be interchanged with one of the other buttresses described herein such that dissimilar buttresses are installed on opposing sides of the stapled tissue T. In other instances, buttress may only be applied to one side of the stapled tissue T.

Figure 98:
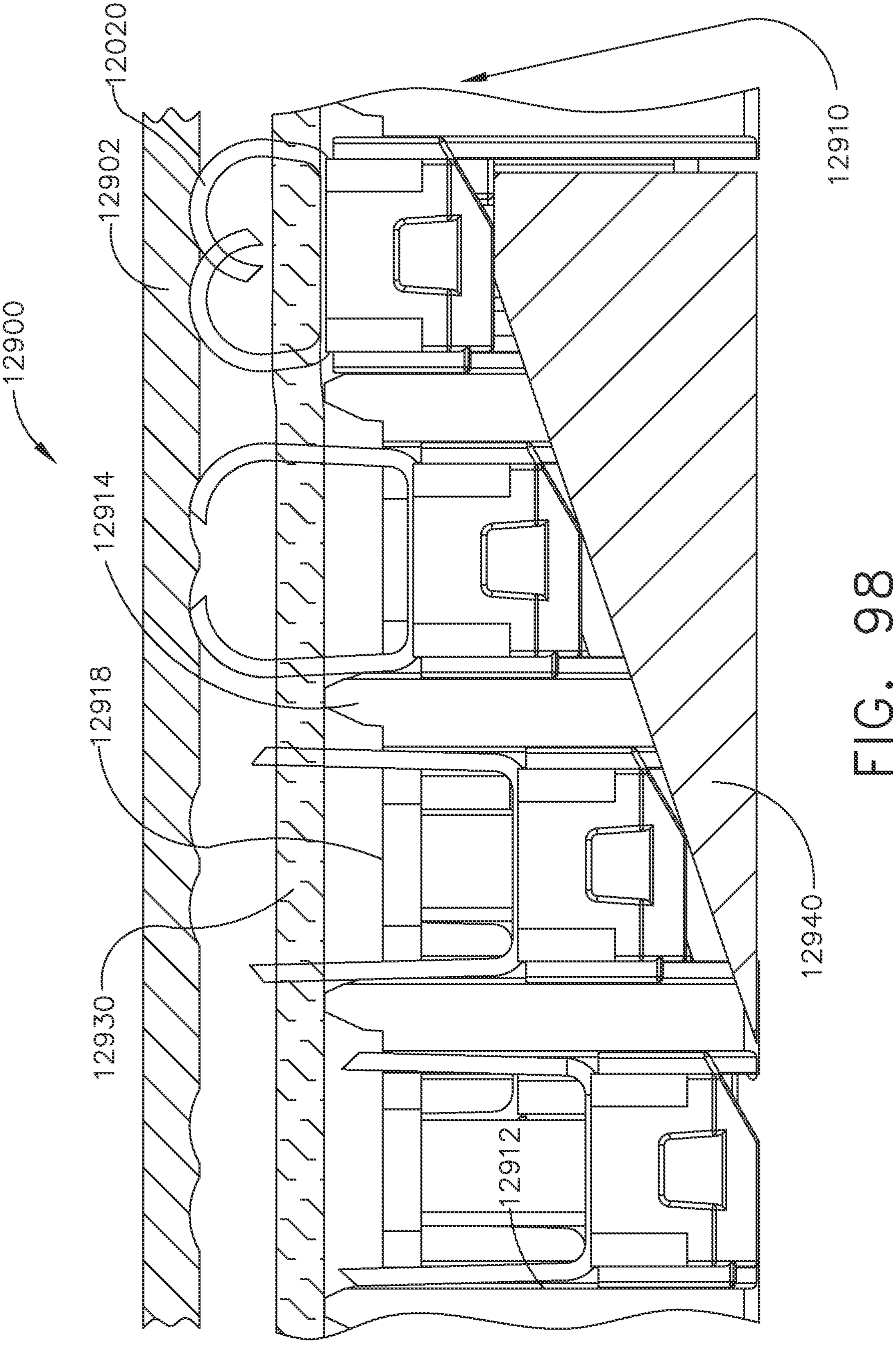
FIG. 98 is a cross-sectional elevation view of a portion of a surgical stapling assembly including a staple cartridge, a buttress releasably secured to the staple cartridge, and an anvil, depicting a firing element within the staple cartridge mid-firing stroke, according to various aspects of the present disclosure.

Referring now to FIG. 98, a portion of a surgical stapling assembly 12900 is shown. The surgical stapling assembly 12900 is similar in many aspects to the surgical stapling assembly 12000; however, the surgical stapling assembly 12900 includes a staple cartridge 12910 having an array of projections 12914 extending from a tissue-supporting deck 12918 thereof. Though the projections 12914 are only shown along the distal end of the staple cavities 12912 therein, the reader will appreciate that alternative arrangements are contemplated, such as projections being positioned at both the proximal and distal ends of one or more cavities 12912, or projections entirely surrounding one or more cavities 12912, for example. The buttress 12930, which is similar in many aspects to the buttress 12030, is secured to the top edge of the projections 12914. A firing member 12940 is being advanced distally during a firing stroke to lift the staples 12020 (and drivers) toward the anvil of the second jaw 12902. The staples 12020 are being moved through the buttress 12930 into forming contact with the anvil.

The staples 12020 are subjected to significant forces during firing thereof as a result of, for example, the outward flow of fluid/tissue from the surgical stapling assembly 12900 and the distal pushing force applied by the firing member 12940 and knife movable along with the firing member 12940 during the firing stroke. The projections 12914 are positioned and structured to guide the staple legs along a predefined path through the buttress 12930 and toward the anvil. For example, the abutting contact between the projections 12914 and the buttress 12930 can ensure the staple legs pierce the buttress 12930 at the appropriate location and minimizing incidences of buckling. Upon moving through the buttress 12930, the buttress 12930 can grip or otherwise guide the staple legs. Traction between the buttress 12930 and the staple 12020 provides buttress purchase on the staple legs to minimize lateral and/or longitudinal skew thereof. In such instances, interactions between the projections 12914 and the buttress 12930 can improve the stability of the staples 12020 during firing.

In other instances, the buttress 12930 can include a plurality of alignment and/or retention features for securing the buttress 12930 to the staple cartridge 12910. For example, the buttress 12930 can include friction-fit extensions extending into the staple cavities 12912 and/or between adjacent projections 12914, as further described herein. Additionally or alternatively, the buttress 12930 can include a cartridge-facing surface having a geometry that complements the geometry of the tissue-supporting deck 12918. For example, the buttress 12930 can include a stepped underside and/or apertures or recesses structured and positioned to accommodate the projections 12914.

Figure 99:
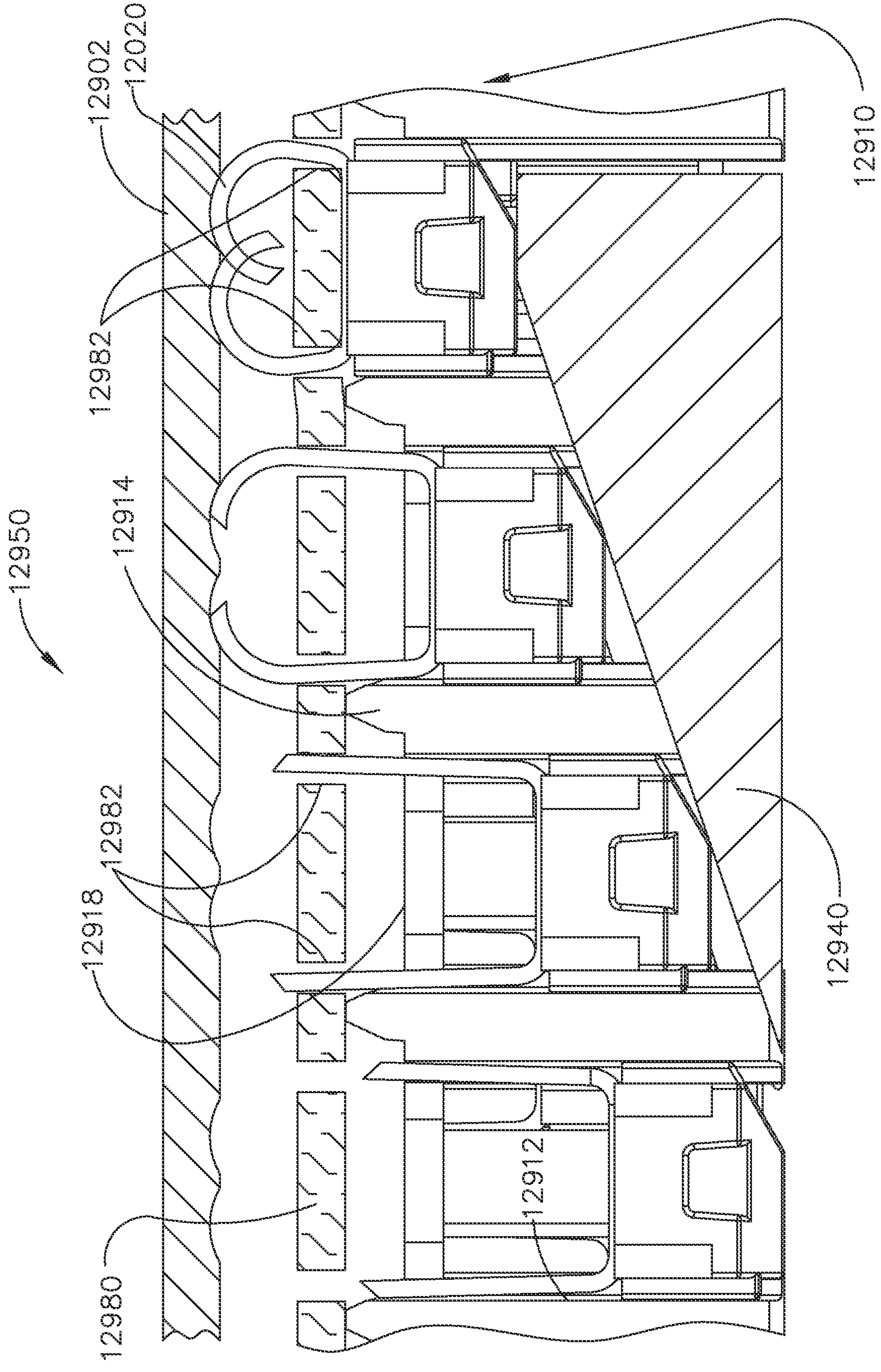
FIG. 99 is a cross-sectional elevation view of a portion of a surgical stapling assembly including the staple cartridge and anvil of FIG. 98 mid-firing stroke, the surgical stapling assembly further including a buttress releasably secured to the staple cartridge, in which the buttress includes through-holes adapted to receive staple legs therethrough during the firing stroke, according to various aspects of the present disclosure.

Referring now to FIG. 99, a surgical stapling assembly 12950 is shown, which is similar in many aspects to the surgical stapling assembly 12900; however, the surgical stapling assembly 12950 includes a buttress 12980 having an array of through-holes 12982 positioned and dimensioned to receive the legs of the staples 12020 therethrough during the firing stroke. The through-holes 12982 can reduce the amount of forces exerted on the staples 12020 as the staples 12020 are fired through the buttress 12980 and/or can be configured to guide the staples 12020 along the predefined staple formation pathway into piercing engagement with the tissue T at the desired location. Additionally, the through-holes 12982 can facilitate alignment of the buttress 12980 with the staple cartridge 12910. In various instances, the buttress 12980 can interface with the projections 12914, as further described herein, to stabilize the staples 12020 during the firing stroke.

As further described herein, a staple cartridge assembly can include a bioabsorbable component such as a bioabsorbable metal staple and/or a bioabsorbable buttress, for example. In certain instances, the staple cartridge assembly can include multiple dissimilar bioabsorbable components such as both a bioabsorbable metal staple and a bioabsorbable polymer buttress. Bioabsorbable components can include unique properties, as further described herein. For example, the staples can be softer and/or more ductile than conventional metal staples and/or the implantable layer can be prone to shifting during certain firing control programs. A single firing control program or algorithm may not accommodate the array of different conditions in the surgical stapling assembly and/or adjacent tissue where multiple, different bioabsorbable components are present. Instead of a one-size-fits-all algorithm, the firing control program (e.g. firing speed(s), timing, number and/or duration of pauses, etc.) can be adjusted or modified based on the bioabsorbable components present in the surgical stapling assembly. For example, a first adjustment to a standard firing control program can be implemented for bioabsorbable staples, a second adjustment to the standard firing control program can be implemented for a bioabsorbable buttress, and a third adjustment to the standard firing control program can be implemented for both bioabsorbable staples and a bioabsorbable buttress. The first adjustment, second adjustment, and third adjustment can be different. Moreover, the third adjustment can be different than the summation or simple combination of the first adjustment and the second adjustment.

The firing control program for surgical stapling assemblies adapted for use with dissimilar staple cartridges having one or more different bioabsorbable components can be adaptive firing programs. The programs can adapt in response to one or more conditions detected during firing and the adaptions can be based, at least in part, on the type of staple cartridge and/or bioabsorbable components thereof. Adaptive firing programs for surgical instruments are further described in, for example, U.S. Patent Application Publication No. 2019/0206003, titled ADAPTIVE CONTROL PROGRAM UPDATES FOR SURGICAL DEVICES, which is incorporated by reference herein in its entirety. Adaptive firing programs can be implemented by a control circuit internal to the surgical instrument and/or in signal communication with a motor adapted to drive a firing component in the surgical instrument. The reader will appreciate that adaptive firing programs can be implemented by a variety of surgical devices, such as handheld surgical instruments (e.g. staplers) and robotic surgical tools releasably mounted to a motor housing, for example.

Figure 100:
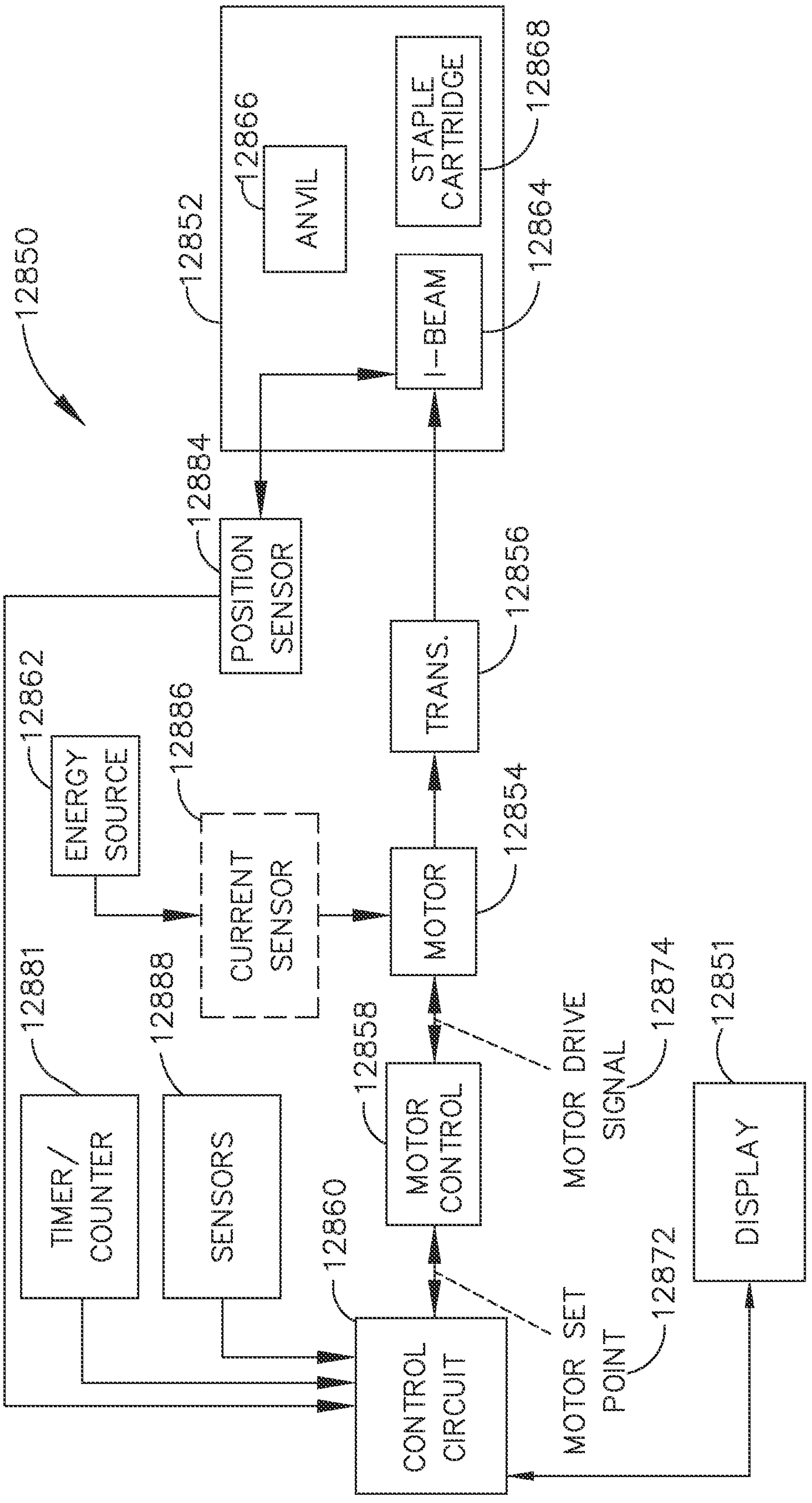
FIG. 100 is a block diagram of a surgical instrument programmed to control the distal translation of a displacement member, according to various aspects of the present disclosure.

Referring now to FIG. 100, a block diagram of a surgical instrument 12850 programmed to control the distal translation of a displacement member is shown. In one aspect, the surgical instrument 12850 is programmed to control the distal translation of a displacement member such as the I-beam 12864. The surgical instrument 12850 includes a surgical stapling assembly, or end effector, 12852 that includes an anvil 12866, an I-beam 12864 (including a sharp cutting edge), and a removable or replaceable staple cartridge 12868. The surgical stapling assembly 12852 can be similar in many aspects to the surgical stapling assembly 12000, for example.

The position, movement, displacement, and/or translation of a linear displacement member, such as the I-beam 12864, for example, can be measured by an absolute positioning system, sensor arrangement, and/or position sensor 12884. Because the I-beam 12864 is coupled to a longitudinally movable drive member, the position of the I-beam 12864 can be determined by measuring the position of the longitudinally movable drive member employing the position sensor 12884.

A control circuit 12860 can be programmed to control the translation of the displacement member, such as the I-beam 12864. The control circuit 12860, in some examples, can comprise one or more microcontrollers, microprocessors, or other suitable processors for executing instructions that cause the processor or processors to control the displacement member, e.g., the I-beam 12864, in the manner described. The control circuit 12860 is coupled to a display 12851, which can provide information to a clinician. In certain instances, the display 12851 can include an input (e.g. a touchscreen), which is configured to receive input from a clinician, such as the type of staple cartridge installed in the surgical stapling assembly 12852.

In one aspect, a timer/counter 12881 provides an output signal, such as the elapsed time or a digital count, to the control circuit 12860 to correlate the position of the I-beam 12864 as determined by the position sensor 12884 with the output of the timer/counter 12881 such that the control circuit 12860 can determine the position of the I-beam 12864 at a specific time relative to a starting position. The timer/counter 12881 can be configured to measure elapsed time, count external events, or time external events. A position sensor, like the position sensor 12884, is further described in U.S. Patent Application Publication No. 2019/0206003, titled ADAPTIVE CONTROL PROGRAM UPDATES FOR SURGICAL DEVICES, for example.

The control circuit 12860 can generate a motor set point signal 12872. The motor set point signal 12872 can be provided to a motor controller 12858. The motor controller 12858 can comprise one or more circuits configured to provide a motor drive signal 12874 to the motor 12854 to drive the motor 12854 as described herein. In some examples, the motor 12854 can be a brushed DC electric motor. For example, the velocity of the motor 12854 can be proportional to the motor drive signal 12874. In some examples, the motor 12854 can be a brushless DC electric motor and the motor drive signal 12874 can comprise a pulse width modulation (PWM) signal provided to one or more stator windings of the motor 12854. Also, in some examples, the motor controller 12858 can be omitted or incorporated into the control circuit 12860, and the control circuit 12860 can generate the motor drive signal 12874 directly.

The motor 12854 can receive power from an energy source 12862. The energy source 12862 can be or include a battery, a super capacitor, or any other suitable energy source. The motor 12854 can be mechanically coupled to the I-beam 12864 via a transmission 12856. The transmission 12856 can include one or more gears or other linkage components to couple the motor 12854 to the I-beam 12864.

The control circuit 12860 can be in communication with one or more sensors 12888. The sensors 12888 can be positioned on the end effector 12852 and adapted to operate with the surgical instrument 12850 to measure the various derived parameters such as gap distance versus time, tissue compression versus time, and anvil strain versus time. The sensors 12888 can comprise a magnetic sensor, a magnetic field sensor, a strain gauge, a pressure sensor, a force sensor, an inductive sensor such as an eddy current sensor, a resistive sensor, a capacitive sensor, an optical sensor, and/or any other suitable sensor for measuring one or more parameters of the end effector 12852. The sensors 12888 can include one or more sensors. The sensors 788 can be configured to measure forces exerted on the anvil 12866 by a closure drive system, for example. Sensors, like the sensors 12888, are further described in, for example, U.S. Patent Application Publication No. 2019/0206003, titled ADAPTIVE CONTROL PROGRAM UPDATES FOR SURGICAL DEVICES.

A current sensor 12886 can be employed to measure the current drawn by the motor 12854. The force required to advance the I-beam 12864 corresponds to the current drawn by the motor 12854. The force is converted to a digital signal and provided to the control circuit 12860.

The control circuit 12860 can be configured to simulate the response of the actual system of the instrument in the software of the controller. A displacement member can be actuated to move the I-beam 12864 in the end effector 12852 at or near a target velocity. The surgical instrument 12850 can include a feedback controller, which can be one of any feedback controllers, including, but not limited to a proportional-integral-derivative (PID) controller, a state feedback controller, linear-quadratic regulator (LQR) controller, and/or an adaptive controller, for example. The surgical instrument 12850 can include a power source to convert the signal from the feedback controller into a physical input such as case voltage, PWM voltage, frequency modulated voltage, current, torque, and/or force, for example.

In various aspects of the present disclosure, the motor 12854 can drive a displacement member distally and proximally along a longitudinal axis of the end effector 12852.

The end effector 12852 can be configured to grasp tissue between the anvil 12866 and the staple cartridge 12868, as further described herein. When ready to use the instrument 12850, the clinician may provide a firing signal, for example by depressing a trigger of the instrument 12850. In response to the firing signal, the motor 12854 may drive the displacement member distally along the longitudinal axis of the end effector 12852 from a stroke begin position to a stroke end position that is distal to the stroke begin position. As the displacement member translates distally, the I-beam 12864 with a cutting element positioned at a distal end thereof, can cut the tissue clamped between the staple cartridge 12868 and the anvil 12866.

The control circuit 12860 can be programmed to sense one or more conditions of the tissue and/or end effector 12852. The control circuit 12860 can be programmed to select a firing control program or algorithm based on tissue conditions. A firing control program may control the distal motion of the displacement member. Different firing control programs can be selected based on the staple cartridge 12868 installed in the end effector 12852. In various instances, the firing control program, or firing algorithm, can be optimized for different combinations of bioabsorbable materials in the staple cartridge 12868 and/or surgical stapling assembly.

In one aspect of the present disclosure, referring again to FIGS. 87-89, the surgical stapling assembly 12000 can be configured to implement an adaptive firing control program. The various surgical stapling assemblies described herein can incorporate one or more aspects of the control circuit in FIG. 100, for example, to implement an adaptive firing control program.

In various instances, a powered surgical stapling device like the surgical instrument 12850 (FIG. 100), for example, can include the surgical stapling assembly 12000 (FIGS. 87-89) having a first jaw 12002 comprising an anvil and a second jaw 12004 configured to sequentially receive a plurality of dissimilar staple cartridges. For example, the powered surgical stapling device can include a control circuit (like control circuit 12860) and a motor control circuit (like motor control circuit 12858), as further described herein with respect to FIG. 100. Dissimilar staple cartridges for the surgical stapling assembly can include a first staple cartridge having a first bioabsorbable component (e.g. a bioabsorbable staple), a second staple cartridge having a second bioabsorbable component that is a different type of component (e.g. a bioabsorbable buttress), and a third staple cartridge having the first bioabsorbable component and the second bioabsorbable component. The powered surgical stapling device can further include a firing member (like the I-beam 12864) for deploying staples from the staple cavities. The powered surgical stapling device can be coupled to a motor (like the motor 12854) drivingly coupled to the firing member and to the control circuit/motor control circuit communicatively coupled to the motor. The motor control circuit can be configured to implement one of a plurality of motor control programs based on which of the dissimilar staple cartridges is received in the second jaw 12002. The implemented motor control program can including a first algorithm for the first staple cartridge, a second algorithm for the second staple cartridge, and a third algorithm for the third staple cartridge, wherein the third algorithm is not a summation of the first algorithm and the second algorithm. In various instances, the firing control program or algorithm(s) thereof can depend on threshold triggers, which can vary depending on which staple cartridge is installed in the surgical stapling assembly.

In various instances, the surgical stapling device can be configured to detect the type of staple cartridge installed into the surgical stapling assembly. For example, one or more sensors can detect a feature, characteristic, or marking on the staple cartridge identifying the type of staple cartridge and/or the bioabsorbable component(s) thereof. In still other instances, the clinician can input the type of staple cartridge and/or the bioabsorbable components thereof into the control circuit via an input device, such as a display screen, for example. Various features and techniques for identification of staple cartridges and bioabsorbable components thereof are further described herein.

For a staple cartridge that includes a bioabsorbable buttress (e.g. the buttress 12030), the firing control program could implement adjustments to the firing speed to improve stabilization of the bioabsorbable buttress within the jaws 12002, 12004 and/or minimize the longitudinal force that seeks to push the uncut buttress distally, for example. Additionally or alternatively, for a staple cartridge that includes bioabsorbable metal staples (e.g. the staples 12020), adjustments to pre-firing wait time and/or the implementation of pauses and/or pulsing of the firing member can accommodate the creep or flow of compressed tissue and, thus, minimize the effects of tissue flow on the formation of the bioabsorbable metal staples, for example. In yet another example, for a staple cartridge that includes bioabsorbable metal staples and a bioabsorbable buttress and where the staples have penetrated or pierced the buttress before being formed in the tissue, the firing control program could be adjusted to further adjust the timing and duration of pauses to the firing stroke. In such instances, the staples could be significantly affected by the shifting of the buttress during deployment and formation and, thus, it can be beneficial to pause the firing stroke once mid-stroke for a longer period of time in comparison to the firing of staple cartridges without this combination of bioabsorbable components.

In certain instances, the firing control program can contemplate threshold triggers and, upon reaching or exceeding a threshold trigger, for example, the firing control program can implement an adjustment thereto. In such instances, the firing control program can be adaptive or interactive depending on the conditions experienced by the surgical stapling assembly during firing. A threshold trigger can correspond to the force-to-fire the firing member, for example. The adjustment can be a variation to the target speed of the firing member and/or the timing, number, and/or duration of wait times/pauses of the firing member. For example, upon reaching a threshold trigger, the target firing speed can be adjusted. In other instances, a firing pause can be initiated or extended upon reaching a threshold trigger. In still other instances, a firing pause can be shortened or canceled from the firing control program.

As described herein, the threshold trigger for adapting a firing control program can be the force-to-fire detected during the firing stroke. In various instances, the threshold trigger can be a direct measurement of the force-to-fire. For example, the force-to-fire can be detected by a force gauge, a strain gauge on a component subjected to a firing load, and/or the current drawn by the motor and detected by a current sensor (e.g. the current sensor 12886), which can be proportional to the firing force. In other instances, the threshold trigger can be an indirect measurement as indicated by differences in actual firing speed in comparison to the desired or target firing speed. An indirect measurement of the force-to-fire can further be indicated by differences in a predicted PWM scheme for achieving a desired or target speed in comparison to the actual PWM scheme required to achieve the desired or target firing speed. Adjustments to the firing control program can be implemented based on one or more direct and/or indirect measurements of the force-to-fire, for example.

Different threshold triggers can be associated with different bioabsorbable components. For example, a first threshold trigger can be associated with a staple cartridge without bioabsorbable staples and without bioabsorbable buttress, a second threshold trigger can be associated with a staple cartridge having a bioabsorbable buttress but without bioabsorbable staples, and a third threshold trigger can be associated with a staple cartridge having bioabsorbable staples but without a bioabsorbable buttress. Moreover, in instances where the staple cartridge includes both bioabsorbable staples and a bioabsorbable buttress, a fourth threshold can be utilized, which is different than the first threshold, the second threshold, and the third threshold. The fourth threshold can be a percentage of the second threshold and the third threshold in certain instances.

As an example, the first threshold trigger can be a threshold force, the second threshold trigger can correspond to a 20% reduction to the threshold force, the third threshold trigger can correspond to a 30% reduction to the threshold force, and the fourth threshold trigger can correspond to a 35% to 40% reduction to the threshold force, which is different than a 20% reduction plus a 30% reduction. As another example, the first threshold trigger for force-to-fire can be 100 pounds, the reduced threshold trigger for a staple cartridge having a bioabsorbable buttress can be 80 pounds (i.e., a 20% reduction), and the reduced threshold trigger for a staple cartridge having bioabsorbable staples can be 70 pounds (i.e., a 30% reduction). Moreover, the reduced threshold for a staple cartridge having both bioabsorbable components (the staples and the buttress) can be 60 pounds or 65 pounds (i.e., a 40% or 35% reduction, respectively). In such instances, the reduced threshold for the staple cartridge having a combination of bioabsorbable components is the summation of a percentage of the reduction for the staple cartridges having a single type of bioabsorbable component.

As further described herein, a staple cartridge having bioabsorbable components can perform differently during clamping and/or firing compared to a staple cartridge without bioabsorbable components. Moreover, different bioabsorbable components can have different effects, and the collective behavior of multiple, dissimilar bioabsorbable components in a staple cartridge can be different than the summation of their individual effects. A surgical stapling assembly can include one or more features for integrating different bioabsorbable components and/or balancing the forces exerted during clamping and firing. Additionally or alternatively, a control circuit can be configured to interactively adapt the firing control program based on one or more detected threshold triggers depending on which bioabsorbable component(s) are present in the surgical stapling assembly. In instances in which a surgical stapling assembly includes multiple types of bioabsorbable components, adaption of the operational parameters can be cooperative or cancelling in nature.

In various instances, the physiological and/or environmental response of a patient can affect the corrosion process of the staples implanted within the patient. Various fluids in the local environment around the staples can influence the biocorrosion of the staples. In various embodiments, staple corrosion, or deterioration, after deployment into tissue can be controlled, or tuned, by introduction of an implantable adjunct into and/or around the stapled tissue. The implantable adjunct can be configured to adjust, or modify, the local environment around the stapled tissue in a manner that changes one or more characteristics of the corrosion of the staples.

In some implementations, the modification to the local environment comprises a physical modification. In other implementations, the modification comprises a chemical modification. In other implementations, the modification comprises physical and chemical modifications.

In some implementations, the change to the corrosion of the staples comprises changing a rate of corrosion of the staples by increasing or decreasing a normal rate of corrosion, for example. In some implementations, the change to the corrosion of the staples comprises preserving a rate of corrosion of the staples. In some implementations, the change to the corrosion of the staples comprises causing an initial delay of the corrosion of the staples.

Figure 101:
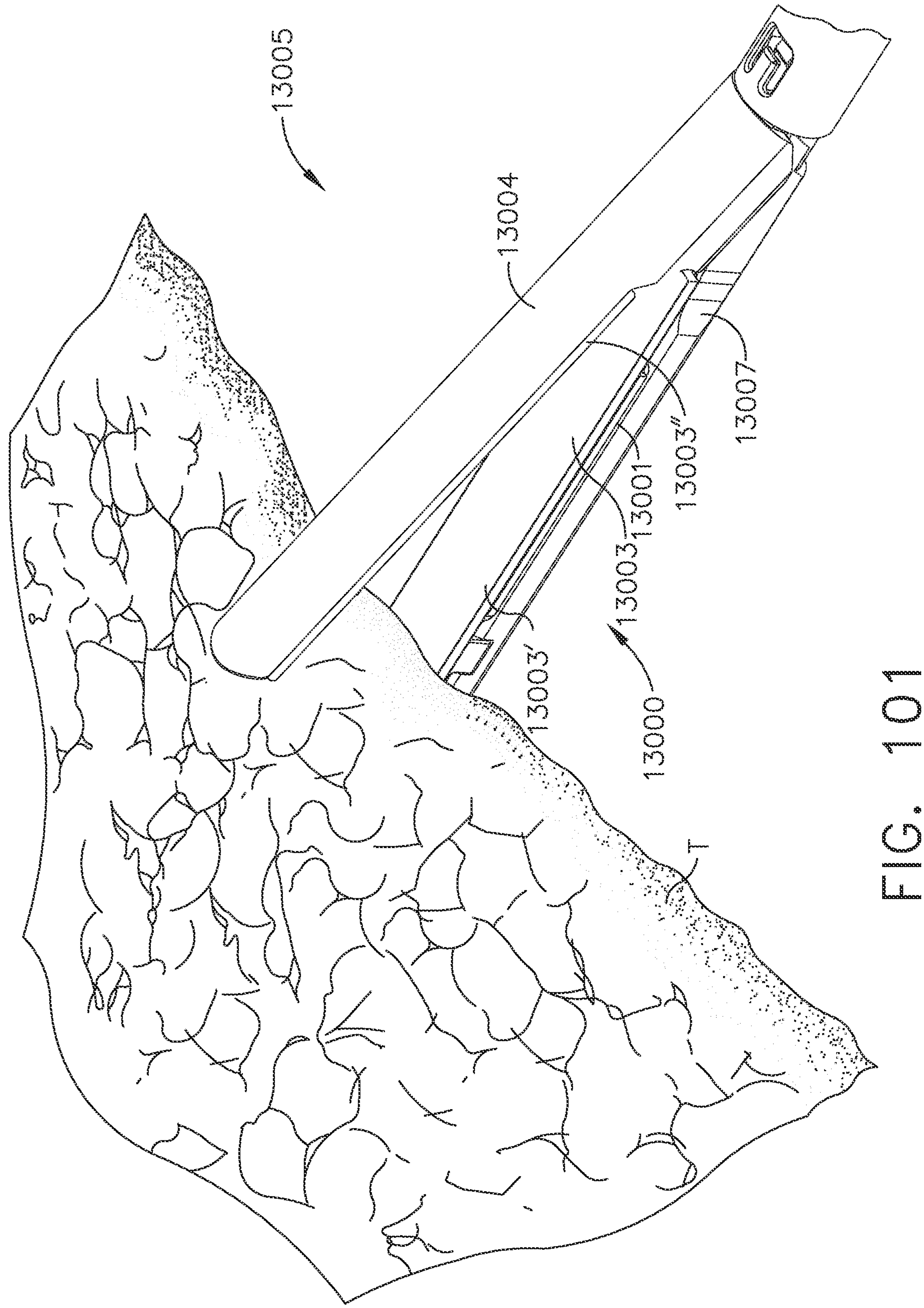
FIG. 101 is a perspective view of an end effector assembly configured to engage, cut, staple, and apply an implantable adjunct material to tissue, in accordance with at least one aspect of the present disclosure.
Figure 102:
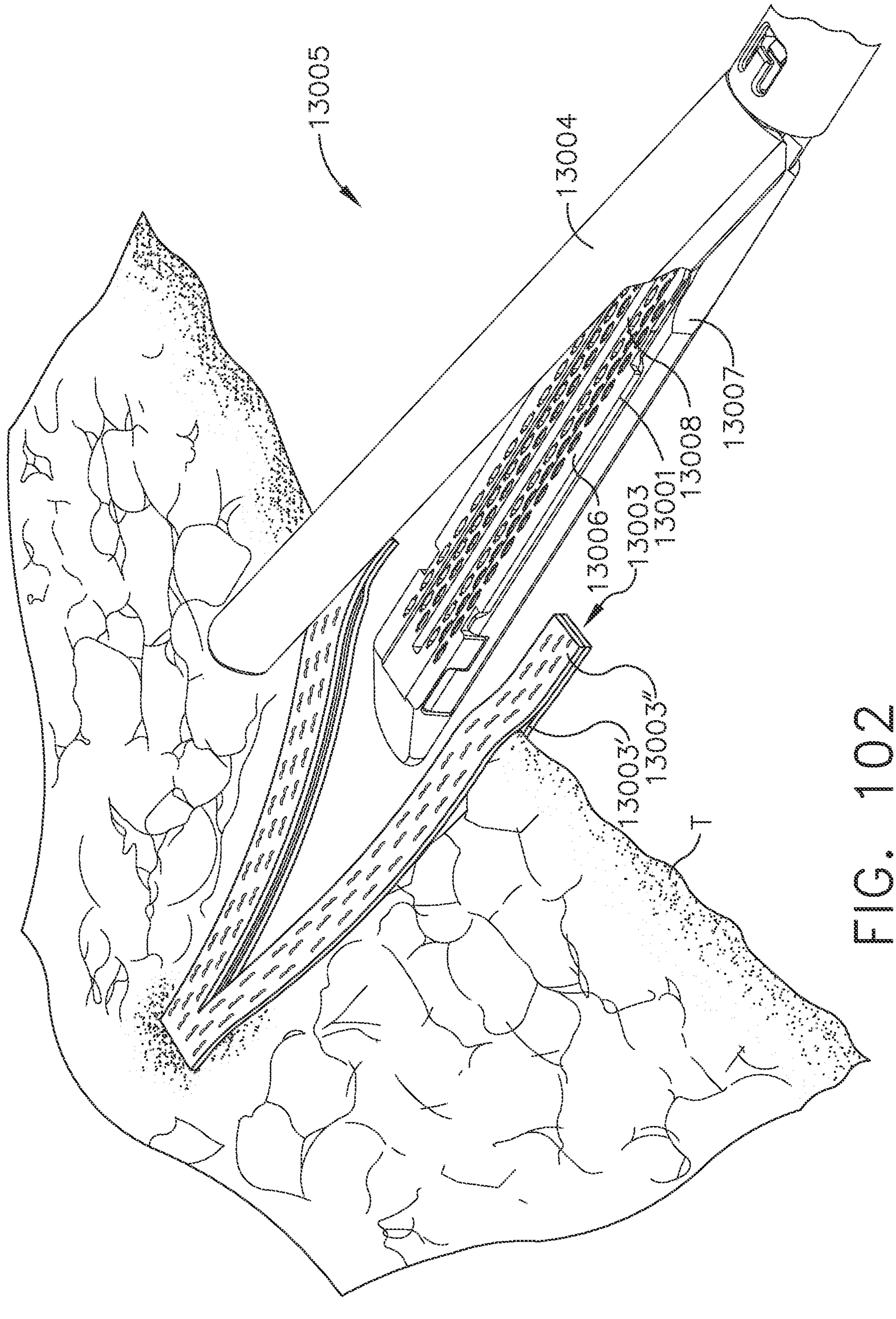
FIG. 102 is a perspective view of the end effector assembly of FIG. 101 after the end effector has been utilized to engage, cut, staple, and apply an implantable adjunct material to the tissue.

Referring to FIGS. 101 and 102, a staple cartridge assembly 13000 includes a staple cartridge 13001 that houses metal bioabsorbable staples 13002, and an implantable adjunct 13003 including a bioabsorbable material such as, for example, a bioabsorbable polymer. The implantable adjunct 13003 can be assembled with the staple cartridge 13001 and/or an anvil 13004 of an end effector. In some implementations, the implantable adjunct 13003 includes a first implantable adjunct portion 13003' positionable onto, or attachable to, a cartridge deck 13006 and/or a second implantable adjunct portion 13003" positionable onto, or attachable to, a tissue contacting surface of the anvil 13004. In some implementations, the staple cartridge 13001 is assembled with an end effector 13005 of a surgical instrument by insertion into a longitudinal channel 13007 of the end effector 13005. The first implantable adjunct portion 13003' can be assembled with the staple cartridge 13001 before or after insertion into the longitudinal channel 13007, for example. Techniques and methods for releasably attaching layers of material, such as buttress, for example, to a staple cartridge and an anvil are further described in U.S. Pat. No. 8,393,514, titled SELECTIVELY-ORIENTABLE IMPLANTABLE FASTENER CARTRIDGE, which issued Mar. 12, 2014, and in U.S. Pat. No. 9,211,120, titled TISSUE THICKNESS COMPENSATOR COMPRISING A PLURALITY OF MEDICAMENTS, which issued Dec. 15, 2015, which are both incorporated by reference herein in their respective entireties.

In some implementations, as described in connection with FIGS. 101 and 102, the implantable adjunct 13003 includes a buttress that is deployed with the staples 13002. In other implementations, the implantable adjunct 13003 can be deployed separately from the staples 13002, before and/or after deploying the staples 13002 into tissue (T). In some implementations, the implantable adjunct 13003 can be in the form of a gel, a sponge-like scaffold, a mesh, a film, a foam, an injection molded thermoplastic, a vacuum thermoformed material, or a fibrous structure, for example, or suitable combinations thereof.

Figure 103:
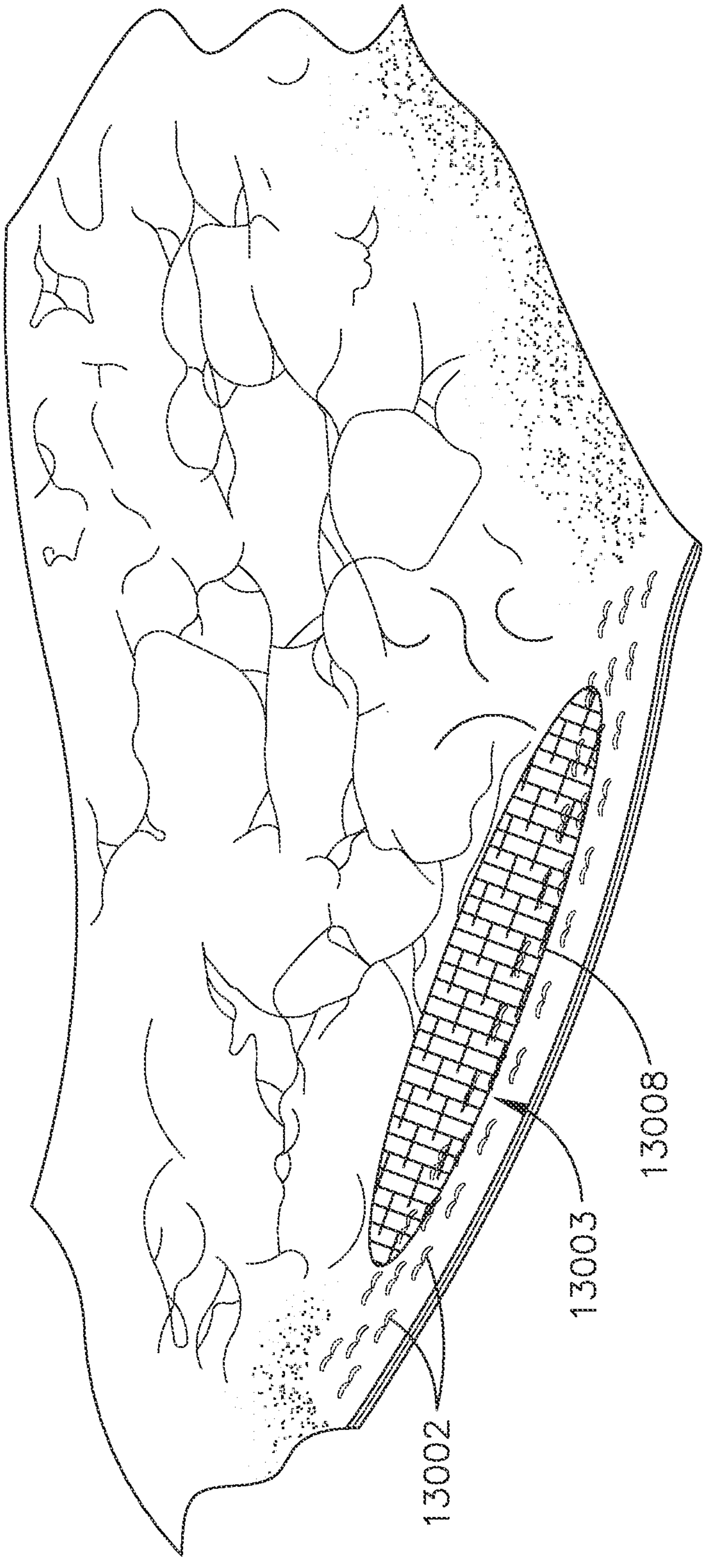
FIG. 103 is a perspective view of a stapled tissue and an implantable adjunct applied to the stapled tissue, in accordance with at least one aspect of the present disclosure.

FIG. 103 illustrates an example where the implantable adjunct 13003 is in the form of a mesh 13008 that is manually placed on the stapled tissue after the staples 13002 are deployed into the tissue (T). In some implementations, the mesh 13008 is selectively disposed onto specific subsets of the staples 13002 to change a biocorrosion profile of such subsets of staples. Different meshes can be placed on different subsets of the staples 13002 to yield different biocorrosion profiles for such subsets of the staples 13002. In at least one example, a first mesh is placed onto a proximal subset of the staples 13002, and a second mesh is placed onto a distal subset of the staples 13002 to yield different biocorrosion profiles for the proximal and distal subsets, for example.

As illustrated in FIG. 102, the staples 13002 are deployed from the staple cartridge 13001 into the implantable adjunct 13003, and into tissue (T) grasped by the end effector 13005. The deployed staples 13002 hold the implantable adjunct 13003 to the tissue (T). In the illustrated example, the staples 13002 hold the first implantable adjunct portion 13003' to a first side of the tissue (T), and the second implantable adjunct portion 13003' to a second side of the tissue (T) opposite the first side. In other examples, the deployed staples 13002 only hold the implantable adjunct to one side of the tissue, for example, or to one or more portions of one or both sides of the tissue (T), for example. Accordingly, the implantable adjunct 13003 can be selectively placed against certain tissue portions of the stapled tissue to control, or tune, staple deterioration at the selected tissue portions. For example, the implantable adjunct 13003 can be selectively placed against peripheral tissue portion(s) of the stapled tissue. In another examples, the implantable adjunct 13003 can be selectively placed against a central tissue portion of the stapled tissue.

In various aspects, the staples 13002 are made of metal that biocorrodes in a patient. In some implementations, the staples 13002 comprise magnesium, iron, zinc, and/or alloys thereof, for example. Various metals and metal alloys suitable for use with the staples 13002 are described in greater detail elsewhere in the present disclosure. Nonetheless, the following discussion mainly describes the staples 13002 as being comprised of a magnesium alloy, for brevity.

In various aspects, further to the above, the implantable adjunct 13003 can be formed from various materials. The materials can be selected in accordance with a desired biocorrosion rate of the staples 13002 in the stapled tissue. Moreover, the materials described can be used to form an implantable adjunct 13003 in any desired combination.

The materials can include bioabsorbable and biocompatible polymers, including homopolymers and copolymers. Non-limiting examples of homopolymers and copolymers include p-dioxanone (PDO or PDS), polyglycolic acid (PGA), poly(lactic-co-glycolic acid) (PLGA), polycaprolactone (PCL), trimethylene carbonate (TMC), and polylactic acid (PLA), poly(glycolic acid-co-lactic acid) (PLA/PGA) (e.g., PLA/PGA materials used in Vicryl, Vicryl Rapide, PolySorb, and Biofix), polyurethanes (such as Elastane, Biospan, Tecoflex, Bionate, and Pellethane fibers), polyorthoesters, polyanhydrides (e.g., Gliadel and Biodel polymers), polyoxaesters, polyesteramides, and tyrosine-based polyesteramides. The copolymers can also include poly (lactic acid-co-polycaprolactone) (PLA/PCL), poly(L-lactic acid-co-polycaprolactone) (PLLA/PCL), poly(glycolic acid-co-trimethylene carbonate) (PGA/TMC) (e.g., Maxon), Poly (glycolic acid-co-caprolactone) (PCL/PGA) (e.g., Monocryl and Capgly), PDS/PGA/TMC (e.g., Biosyn), PDS/PLA, PGA/PCL/TMC/PLA (e.g., Caprosyn), and LPLA/DLPLA (e.g., Optima).

Figure 104:
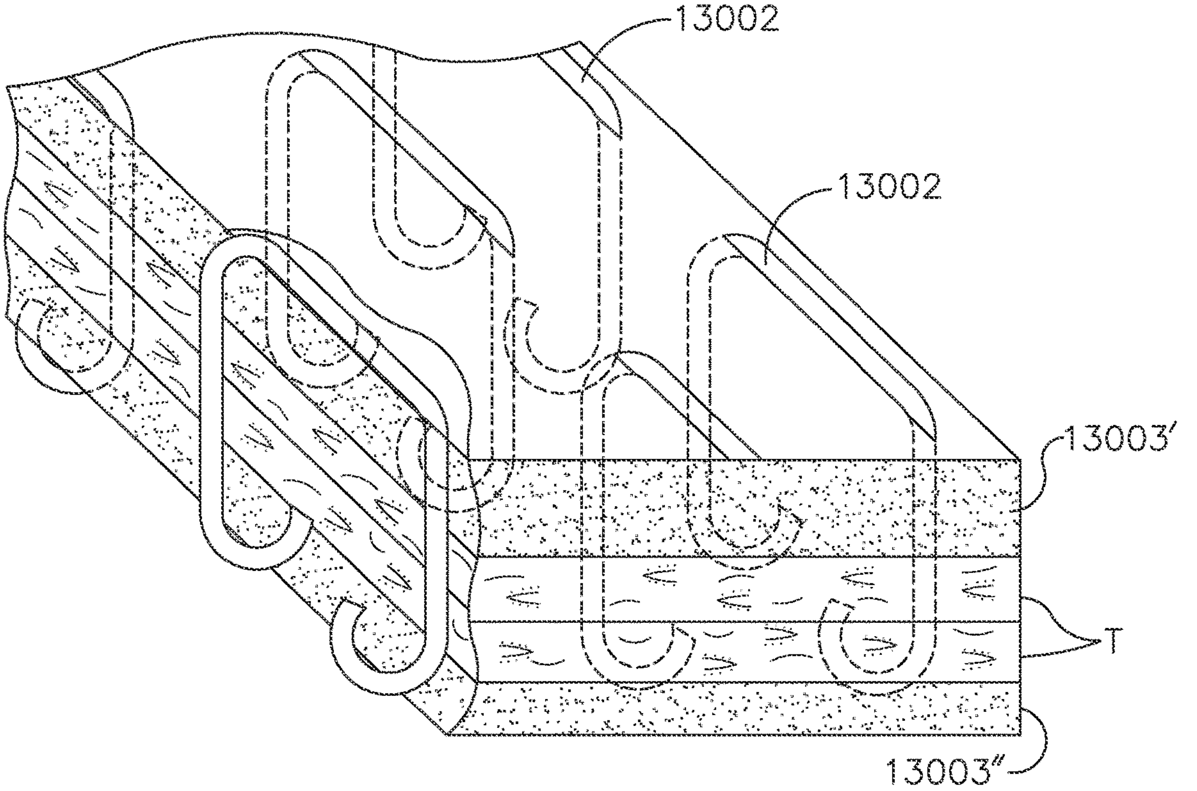
Figure 105:
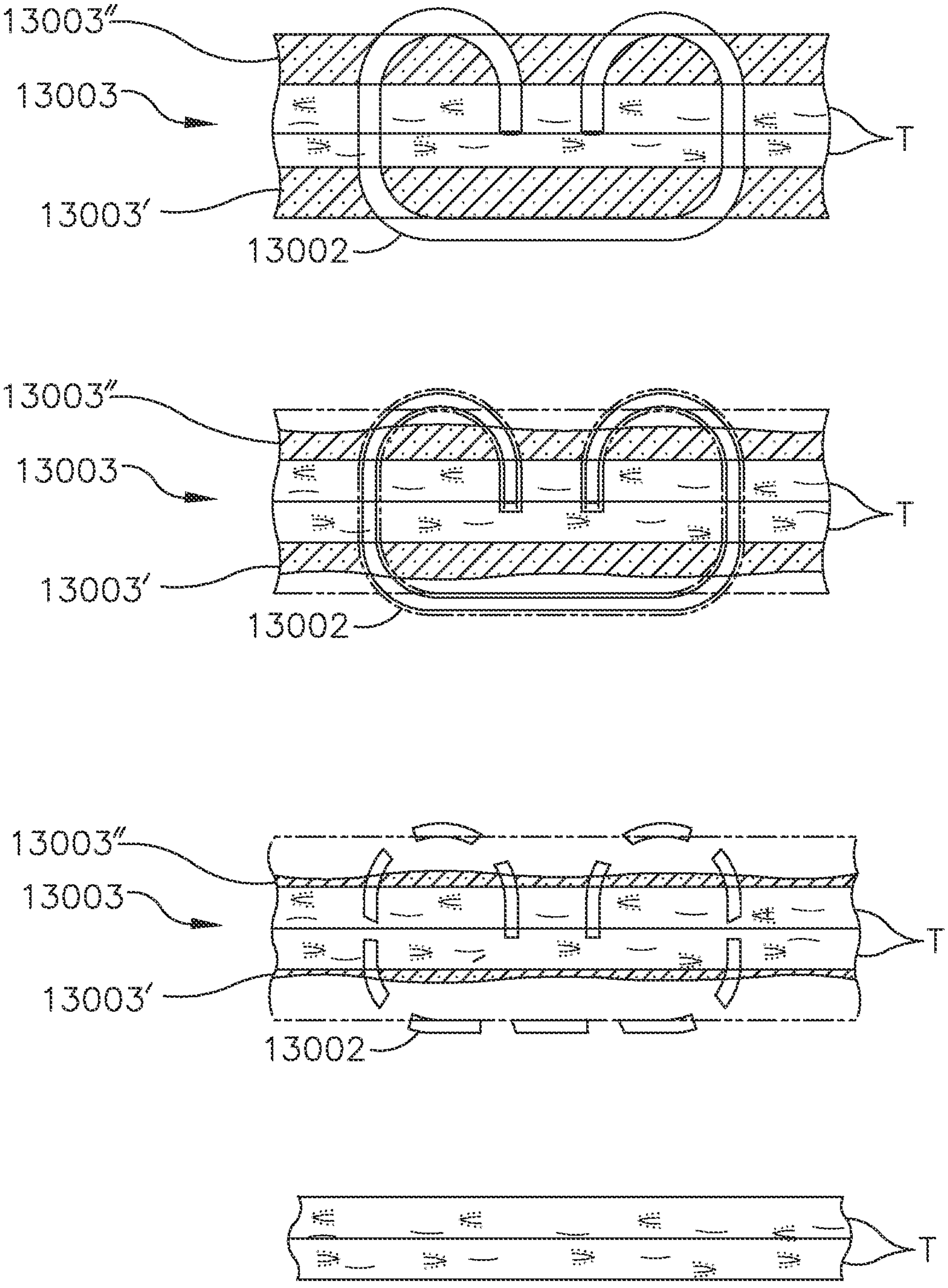

In various aspects, as best illustrated in FIGS. 104 and 105, the implantable adjunct 13003 initially acts as a physical barrier, or shield, between portions of the staples 13002 in contact therewith and the local environment surrounding the staples 13002 in the patient. In doing so, the implantable adjunct 13003 initially physically delays biocorrosion of the portions of the staples 13002 in contact therewith in the patient.

As time passes, the implantable adjunct 13003 begins to degrade compromising the physical barrier. Consequently, the staple portions initially shielded by the implantable adjunct become exposed to the local environment surrounding the stapled tissue, and begin to corrode. In various implementations, an implantable adjunct 13003 with a suitable bioabsorption profile can be selected based on a desired initial delay of the staple biocorrosion. In other embodiments, an implantable adjunct 13003 can be designed with sufficient porosity to eliminate, or at least reduce, the initial delay.

In certain instances, degradation products of the implantable adjunct 13003 modify the local environment surrounding the stapled tissue in a manner that changes the biocorrosion profile of the staples 13002 following the initial delay. In certain instances, the degradation products increase or decrease a normal, or expected, biocorrosion rate of the staples 13002 after the initial delay. Accordingly, the material composition of the implantable adjunct 13003 can be selected based the ability of the degradation products of the material composition to yield a desired biocorrosion rate of the staples 13002.

In certain instances, the biocorrosion of the staples 13002 and the degradation of the implantable adjunct 13003 are synchronized to protect the structural integrity of the staples 13002 for a predetermined time period (the initial delay), which is followed by an increased biocorrosion rate. In at least one example, the implantable adjunct 13003 includes a bioabsorbable polymer, or co-polymer. In at least one example, the implantable adjunct 13003 includes polylactic acid (PLA), polylactic-co-glycolic acid (PLGA), polyglycolic acid (PGA), or combinations thereof, for example, and the staples are comprised of a magnesium alloy. Immediately after deployment of the staples, the implantable adjunct 13003 protects the metal (e.g. magnesium allow) in portions of the staples 13002 in contact with the implantable adjunct 13003 from biocorrosion by forming a physical barrier around such portions. As the bioabsorbable polymer degrades, its degradation products cause the local environment around the staples 13002 to become acidic, or to comprise a lower pH, which improves the solubility of the corrosion products and minerals, thereby preserving, or increasing, the corrosion rate of the staples 13002.

Different bioabsorbable polymers comprise different degradation rates. Accordingly, the degradation rate of the implantable adjunct 13003 and, in turn, the biocorrosion rate of the staples 13002 can be controlled, or tuned, based on the material composition of the implantable adjunct 13003. For example, PLA comprises a slower degradation rate than PGA. Accordingly, the initial delay in the biocorrosion of the staples 13002 can be controlled by selectively adjusting the ratio of PLA to PGA in the implantable adjunct 13003. In some implementations, a first PLA/PGA ratio can be selected to achieve a first biocorrosion delay, and a second PLA/PGA ratio can be selected to achieve a second biocorrosion delay different from the first biocorrosion delay.

In some implementations, a staple cartridge assembly kit includes the staple cartridge 13001, a first implantable adjunct, and a second implantable adjunct. The first and second implantable adjuncts are configured to yield different biocorrosion profiles of the staples of the staple cartridge 13001 in a patient.

In at least one example, the first implantable adjunct is comprised of a first material composition that has a first bioabsorption profile, and the second implantable adjunct is comprised of a second material composition that has a second bioabsorption profile different than the first bioabsorption profile. The first bioabsorption profile yields a first biocorrosion profile of the staples 13002, and the second bioabsorption profile yields a second biocorrosion profile, different than the first bioabsorption profile. Accordingly, a user may select between the first implantable adjunct and the second implantable adjunct, for assembly with the staple cartridge 13001, based on a desired biocorrosion profile of the staples 13002 in the patient.

Further to the above, in at least one example, the first bioabsorption profile yields a first delay in biocorrosion of the staples 13002, and the second bioabsorption profile yields a second delay, different than the second delay. Accordingly, a user may select between the first implantable adjunct and the second implantable adjunct, for assembly with the staple cartridge 13001, based on a desired initial delay in the biocorrosion of the staples 13002.

In at least one example, the first implantable adjunct and the second implantable adjunct include bioabsorbable materials such as, for example, bioabsorbable polymers, or copolymers, with different bioabsorption profiles. Various examples of suitable bioabsorbable polymers are described elsewhere in the present disclosure, and are not repeated herein for brevity. In at least one example, the first implantable adjunct and the second implantable adjunct are copolymers. In at least one example, the first implantable adjunct and the second implantable adjunct are copolymers of polyglycolic acid (PGA) and polylactic acid (PLA). In at least one example, the first implantable adjunct and the second implantable adjunct comprise different molar ratios of PLA/PGA selected from the group including 90/10, 80/20, 70/30, 60/40, 50/50, 40/60, 30/70, 20/80, and 10/90, for example. Other suitable molar ratios of PLA/PGA are contemplated by the present disclosure.

In at least one example, the first implantable adjunct has a first material composition that is higher in polyglycolic acid (PGA) than polylactic acid (PLA), and the second implantable adjunct has a second material composition that is higher in polylactic acid (PLA) than polyglycolic acid (PGA). Since PLA has a slower bioabsorption rate than PGA, the higher PLA content in the second implantable adjunct reduces the bioabsorption rate of the second implantable adjunct relative to the first implantable adjunct, which allows the second implantable adjunct to shield the staples 13002 from degradation sources that cause staple biocorrosion in the patient longer than the first implantable adjunct, for example.

In various aspects, an implantable adjunct can be designed to selectively, or differently, control, or tune, biocorrosion profiles of subsets of the staples 13002 deployed into the tissue (T) from different locations, or positions, in the staple cartridge 13001. In some implementations, an implantable adjunct includes implantable adjunct portions with different bioabsorption profiles designed to yield different biocorrosion profiles for different subsets of the staples 13002.

Figure 106:
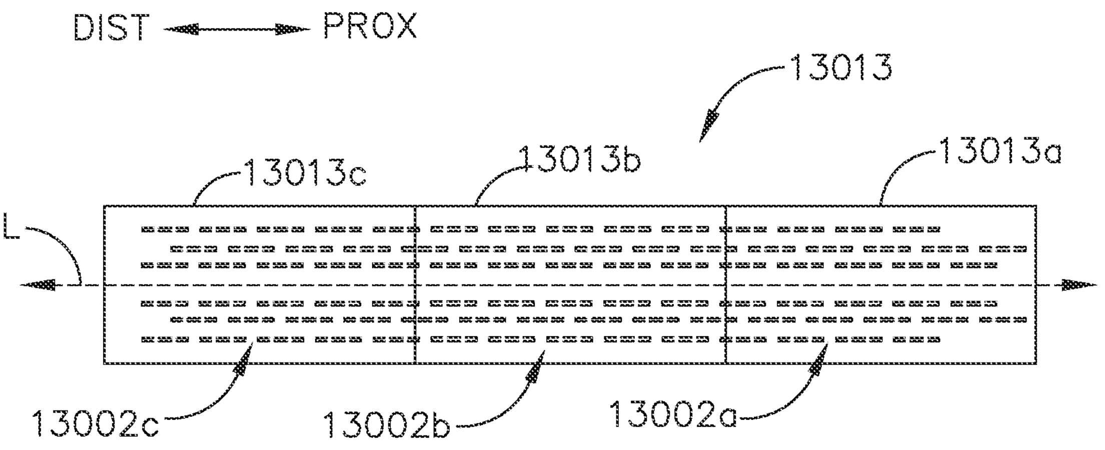

Referring to FIG. 106, an implantable adjunct 13013 is illustrated with the staples 13002 deployed into different portions thereof. The implantable adjunct 13013 is similar in many respects to the implantable adjunct 13003, which are not repeated herein for brevity. In addition, the implantable adjunct 13013 includes different portions **13013*a*, 13013*b*, 13013*c* arranged along a longitudinal axis (L) extending longitudinally through the implantable adjunct 13013. In the illustrated example, the implantable adjunct 13013 includes a first implantable adjunct portion 13013*a* comprised of a first material composition that has a first bioabsorption profile, and a second implantable adjunct portion 13013*b* comprised of a second material composition that has a second bioabsorption profile. The first implantable adjunct portion 13013*b* is configured to receive a first subset 13002*a* of the staples of the staple cartridge 13001, and the second implantable adjunct portion is configured to receive a second subset 13002*b* of the staples of the staple cartridge 13001, distal to the first subset 13002*a* of the staples 13002**.

The first bioabsorption profile of the first material composition yields a first biocorrosion profile of the first subset **13002*a* of the staples 13002*a* in contact with, or near, the first implantable adjunct portion 13002*a* in the patient, and the second bioabsorption profile of the second material composition yields a second biocorrosion profile, different than the first bioabsorption profile, of the second subset 13002*b* of the staples 13002 in contact with, or near, the second implantable adjunct portion 13002*b*. In at least one example, the first bioabsorption profile yields a first delay in biocorrosion of the first subset 13002*a*, while the second bioabsorption profile yields a second delay, different than the first delay, in biocorrosion of the second subset 13002*b***.

In at least one example, the first implantable adjunct portion **13013*a* and the second implantable adjunct portion 13013*b*** include bioabsorbable materials such as, for example, bioabsorbable polymers, or copolymers, with different bioabsorption profiles. Various examples of suitable bioabsorbable polymers are described elsewhere in the present disclosure, and are not repeated herein for brevity.

In at least one example, the first implantable adjunct portion **13013*a* and the second implantable adjunct portion 13013*b* are copolymers. In at least one example, the first implantable adjunct portion 13013*a* and the second implantable adjunct portion 13013*b* are copolymers of polyglycolic acid (PGA) and polylactic acid (PLA). In at least one example, the first implantable adjunct portion 13013*a* and the second implantable adjunct portion 13013*b*** comprise different molar ratios of PLA/PGA selected from the group including 90/10, 80/20, 70/30, 60/40, 50/50, 40/60, 30/70, 20/80, and 10/90, for example. Other suitable molar ratios PLA/PGA are contemplated by the present disclosure.

In at least one example, the first implantable adjunct portion **13013*a* has a first material composition that is higher in polyglycolic acid (PGA) than polylactic acid (PLA), and the second implantable adjunct portion 13013*b* has a second material composition that is higher in polylactic acid (PLA) than polyglycolic acid (PGA). Since PLA has a slower bioabsorption rate than PGA, the higher PLA content in the second implantable adjunct portion 13013*b* reduces the bioabsorption rate of the second implantable adjunct portion 13013*b* relative to the first implantable adjunct portion 13013*a*, which allows the second implantable adjunct portion 13013*b* to shield the staples longer than the first implantable adjunct portion 13013*a*** from degradation sources that cause staple biocorrosion in the patient.

Referring still to FIG. 106, the first implantable adjunct portion **13013*a* is proximal to the second implantable adjunct portion 13013*b*. Moreover, the first implantable adjunct portion 13013*a* is a peripheral implantable adjunct portion, while the second implantable adjunct portion 13013*b* is a central implantable adjunct portion. In certain instances, a third implantable adjunct portion 13013*c* forms another peripheral implantable adjunct portion such that the second implantable adjunct portion 13013*b* extends longitudinally between the first implantable adjunct portion 13013*a* and the third implantable adjunct portion 13013*c***.

In at least one example, the first implantable adjunct portion **13013*a* and the third implantable adjunct portion 13013*c* are configured to yield a faster biocorrosion rate in peripheral subsets 13002*a*, 13002*c* of the staples 13002 in the patient, and the second implantable adjunct portion 13013*b* is configured to yield a slower biocorrosion rate in a central subset 13002*b* of the staples 13002 in the patient. In other examples, the first implantable adjunct portion 13013*a* and the third implantable adjunct portion 13013*c* are configured to yield a slower biocorrosion rate in peripheral subsets 13002*a*, 13002*c* of the staples 13002 in the patient, and the second implantable adjunct portion 13013*b* is configured to yield a faster biocorrosion rate in a central subset 13002*b* of the staples 13002** in the patient.

In at least one example, the peripheral implantable adjunct portions **13013*a*, 13013*c* have higher levels of polyglycolic acid (PGA) than polylactic acid (PLA), and the central implantable adjunct portion 13013*b* has a higher level of polylactic acid (PLA) than polyglycolic acid (PGA). In other examples, the peripheral implantable adjunct portions 13013*a*, 13013*c* have lower levels of polyglycolic acid (PGA) than polylactic acid (PLA), and the central implantable adjunct portion 13013*b*** has a lower level of polylactic acid (PLA) than polyglycolic acid (PGA).

Figure 108:
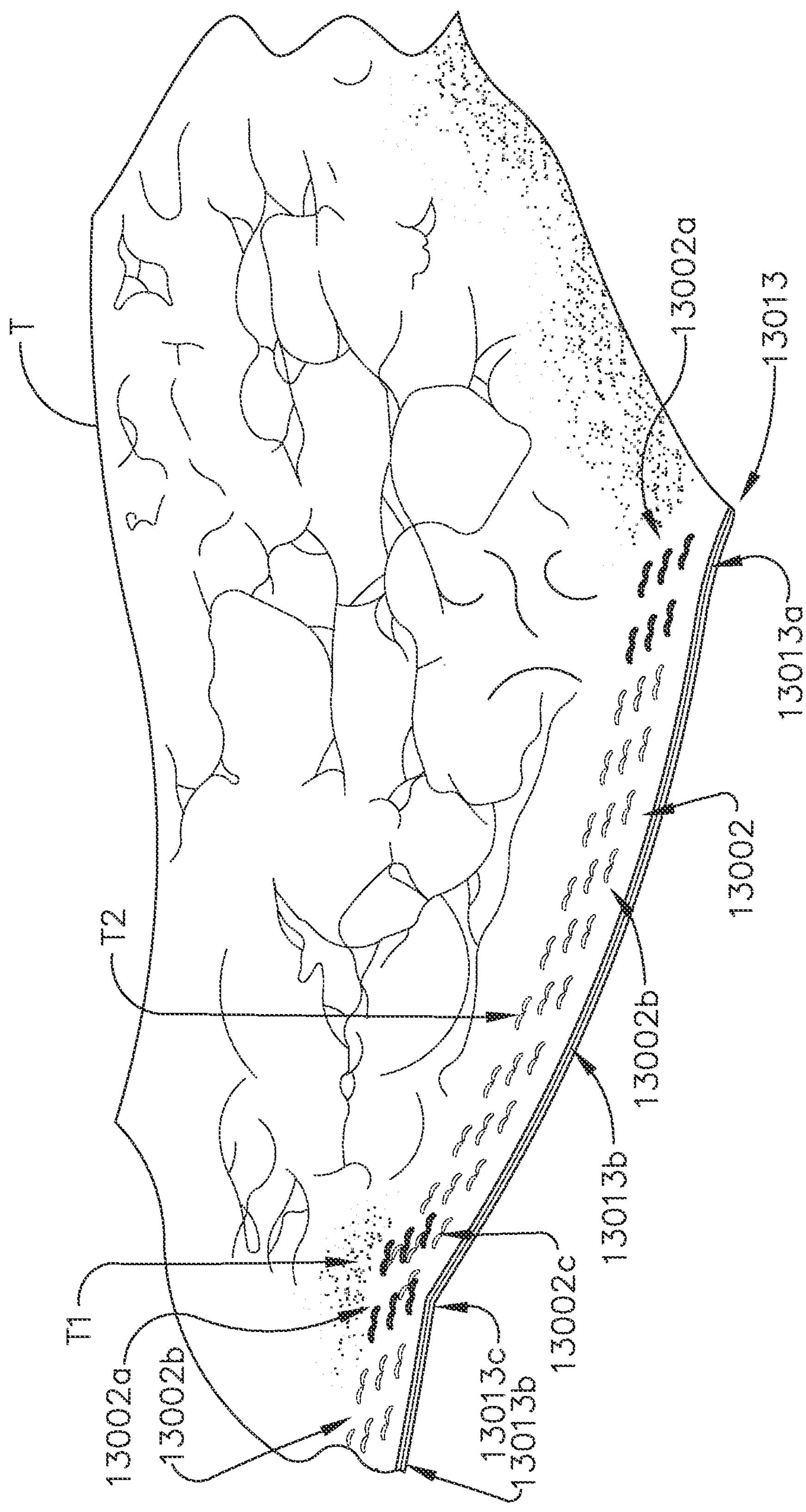

Referring primarily to FIGS. 106 and 108, in surgical procedures where a surgical stapler is fired multiple times to staple tissue along a line too long to be stapled in a single firing, clinicians typically overlap peripheral subsets of staples deployed in subsequent firings to ensure a proper seal. Consequently, some tissue portions (e.g. T1), where the overlapping occurs, include a higher number of staples 13002 than other tissue portions (e.g. T2), where overlapping does not occur. In such instances, an implantable adjunct can be employed to synchronize staple biocorrosion of the staples by increasing the biocorrosion rate of the peripheral subsets of staples, which experience the overlap, and decreasing the biocorrosion rate of the central subset of the staples, which do no experience the overlap. Consequently, staple biocorrosion will commence faster in regions with overlapping staple lines and more material to degrade, than in regions without overlapping staple lines and less material to degrade. Accordingly, an implantable adjunct can be selected to synchronize staple biocorrosion between areas with different numbers of staples to achieve a uniform, or at least substantially uniform, breakdown of the structural support provided by the staples, for example.

In at least one example, as illustrated in FIGS. 106 and 108, the biocorrosion synchronization is achieved by selecting an implantable adjunct 13013 for use with the staple cartridge 13001. In each firing of the surgical stapler, an implantable adjunct 13013 is deployed with rows of the staples 13002. In the illustrated example, the bioabsorption rate of first and third implantable adjunct portions **13013*a*, 13013*c* (i.e. peripheral portions) is faster than the bioabsorption rate of the second implantable adjunct portion 13013*b*. The faster bioabsorption rate yields a faster biocorrosion in the first and third subsets 13002*a*, 13002*c* (i.e. proximal and distal) of the staples 13002 than the second subset 13002*b* (i.e. central) of the staples 13002**.

Figure 107:
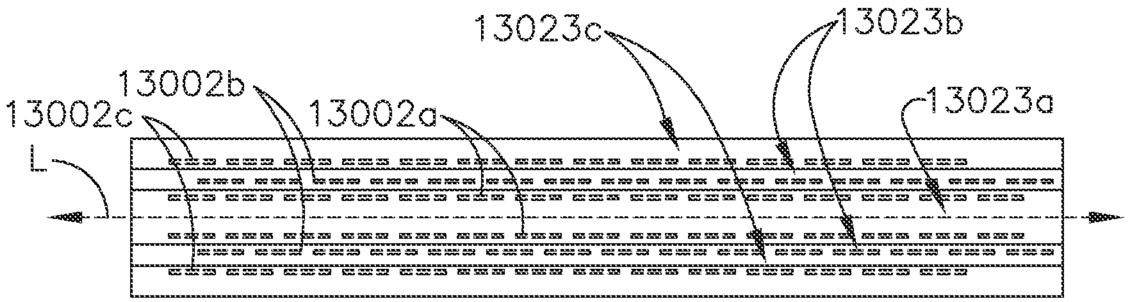

Referring to FIG. 107, an implantable adjunct 13023 is illustrated with the staples 13002 deployed into different portions thereof. The implantable adjunct 13023 is similar in many respects to the implantable adjuncts 13003, 13013, which are not repeated herein for brevity. In addition, the implantable adjunct 13023 includes different implantable adjunct portions **13023*a*, 13023*b*, 13023*c*** arranged laterally, and extend longitudinally next to one another.

When the implantable adjunct 13023 is assembled with the staple cartridge 13001, by positioning onto the cartridge deck 13006, the first implantable adjunct portion **13023*a* extends over a longitudinal slot 13008, and is cut with tissue during firing. The first implantable adjunct portion 13023*a* is configured to receive inner rows 13002***d* of the staples 1302, and the second implantable adjunct portion 13023*b* is configured to receive intermediate rows 13002*e* of the staples 13002, and is positioned laterally peripheral to the first implantable portion 13023*a*. Additionally, the third implantable adjunct portion 13023*c* is configured to receive outer rows 13002*f* of the staples 13002, and is positioned laterally peripheral to the first and second implantable portions 13023*a*, 13023*b*.

In various aspects, the implantable adjunct portions 13023*a*, 13023*b*, 13023*c* synchronize staple biocorrosion of staples 13002 in the same row by causing the staples 13002 in the same row to have the same, or substantially the same, biocorrosion profile. Since all the staples in the same row are received in the same implantable adjunct portion, the bioabsorption profile of the implantable adjunct portions can be configured to control, modify, or tune the local environment surrounding the staples in the same row to achieve a uniform biocorrosion profile for the staples in the same row.

In various aspects, the implantable adjunct portions 13023*a*, 13023*b*, 13023*c* yield different staple biocorrosion profiles for different rows of the staples of the staple cartridge 13001. This can be achieved by selecting different bioabsorption profiles for the implantable adjunct portions 13023*a*, 13023*b*, 13023*c*, for example.

In at least one example, the implantable adjunct portion 13023*a* includes a faster bioabsorption rate than the implantable adjunct portion 13023*b*, and the implantable adjunct portion 1303*b* includes a faster bioabsorption rate than the implantable adjunct portion 13023*c*. Consequently, the inner row 13002*a*, received by the implantable adjunct portion 13023*a*, will have a faster biocorrosion rate than the intermediate row 13002*b*, received by the implantable adjunct portion 13023*b*. Additionally, the inner row 13002*a*, received by the implantable adjunct portion 13023*a*, will have a faster biocorrosion rate than the outer row 13002*c*, received by the implantable adjunct portion 13023*c*.

In other examples, the implantable adjunct portion 13023*a* includes a slower bioabsorption rate than the implantable adjunct portion 13023*b*, and the implantable adjunct portion 13023*b* includes a slower bioabsorption rate than the implantable adjunct portion 13023*c*. In such examples, the inner row 13002*a* will have a slower biocorrosion rate than the intermediate row 13002*b*. Additionally, the inner row 13002*a* will have a slower biocorrosion rate than the outer row 13002*c*.

In at least one example, the implantable adjunct 13023 comprises a PLA/PGA copolymer. In at least one example, the first implantable adjunct portion 13023*a* includes higher levels of polyglycolic acid than the second implantable adjunct portion 13023*b*. Additionally, the second implantable adjunct portion 13023*b* includes higher levels of polyglycolic acid than the third implantable adjunct portion 13023*c*.

Several of the previously-described implantable adjuncts include three different implantable adjunct portions. This, however, is not limiting. In other implementations, the previously-described implantable adjuncts may each include more or less than three different implantable adjunct portions. Moreover, in various instances, instead of discrete portions comprising different bioabsorption rates, an implantable adjunct can be designed with a gradation of bioabsorption rates configured to yield a gradation of biocorrosion rates of staples in contact therewith in the patient.

In at least one example, an implantable adjunct includes a longitudinal gradation of bioabsorption rates. The longitudinal gradation may include a highest bioabsorption rate at the longitudinal center of the implantable adjunct, and a lowest bioabsorption rate at longitudinal peripherals of the implantable adjunct, for example. Alternatively, the longitudinal gradation may include a lowest bioabsorption rate at the longitudinal center of the implantable adjunct, and a highest bioabsorption rate at longitudinal peripherals of the implantable adjunct, for example In at least one example, an implantable adjunct includes a longitudinal gradation of PLLA in an PLLA-PGA copolymer mix, with higher PLLA levels in portions of the implantable adjunct configured to receive a central subset of the staples, and lower PLLA levels in proximal and distal subsets of the staples, to direct degradation of the staples in regions most likely to have overlapping staple lines, and thus more material to degrade. Alternatively, in other examples, an implantable adjunct includes a longitudinal gradation of PLLA in an PLLA-PGA copolymer mix, with lower PLLA levels in portions of the implantable adjunct configured to receive a central subset of the staples, and higher PLLA levels in proximal and distal subsets of the staples.

In some implementations, an implantable adjunct can be designed with a lateral gradation of bioabsorption rates. The lateral gradation may include a highest bioabsorption rate at the lateral center of the implantable adjunct, and a lowest bioabsorption rate at the lateral peripherals of the implantable adjunct. Alternatively, the lateral gradation may include a lowest bioabsorption rate at the lateral center of the implantable adjunct, and a highest bioabsorption rate at the lateral peripherals of the implantable adjunct.

In at least one example, an implantable adjunct includes a lateral gradation of PLLA in an PLLA-PGA copolymer mix, with higher PLLA levels in portions of the implantable adjunct configured to receive outer rows the staples 13002, and lower PLLA levels in portions of the implantable adjunct configured to receive intermediate and inner rows of the staples. In other examples, an implantable adjunct includes a lateral gradation of PLLA in an PLLA-PGA copolymer mix, with lower PLLA levels in portions of the implantable adjunct configured to receive outer rows the staples 13002, and higher PLLA levels in portions of the implantable adjunct configured to receive intermediate and inner rows of the staples.

In some implementations, an implantable adjunct with multiple portions each having a different material composition can be prepared by separately preparing the different portions, then assembling the different portions into the implantable adjunct. In at least one example, the different portions can be attached to one another in a predetermined arrangement using any suitable biodegradable sealant or glue.

In some implementations, an implantable adjunct with multiple portions each having a different material composition can be prepared using a lyophilization process. A scaffold or a foam can be prepared by lyophilizing a solution including a first bioabsorbable polymer such as, for example, PGA. Then, a solution including a second bioabsorbable polymer such as, for example, PLA can be selectively applied to specific regions of the scaffold or foam to form different portions with different material compositions, or to form a longitudinal gradation or a lateral gradation, for exmaple. The scaffold can then be subjected to a second round of lyophilization.

In other examples, a mesh or fibers comprised of a first bioabsorbable polymer (e.g. PGA) can be selectively deposited in a mold containing a solution including a second bioabsorbable polymer (e.g. PLA) prior to lyophilization. The resulting implantable adjunct includes portions with the mesh/fibers and portions without the mesh/fibers. Other suitable techniques for preparing suitable implantable adjuncts are disclosed in U.S. Pat. No. 10,617,418, titled IMPLANTABLE LAYERS FOR A SURGICAL INSTRUMENT, and granted Apr. 14, 2020, which is hereby incorporated by reference in its entirety.

In various aspects, the implantable adjunct and/or the staples can releasably retain therein at least one medicament that can be selected from a large number of different medicaments. Medicaments include, but are not limited to, drugs or other agents included within, or associated with, the implantable adjunct, which have a desired functionality. The medicaments include, but are not limited to, for example, antimicrobial agents such as antibacterial and antibiotic agents, antifungal agents, antiviral agents, anti-inflammatory agents, growth factors, analgesics, anesthetics, tissue matrix degeneration inhibitors, anti-cancer agents, hemostatic agents, and other agents that elicit a biological response.

Various suitable bioabsorbable polymers, active agents, and medicaments are disclosed in U.S. Pat. No. 10,569,071, issued Feb. 25, 2020, and titled Medicament eluting adjuncts and methods of using medicament eluting adjuncts, and/or U.S. Patent Publication No. 2018/0353174, titled SURGICAL STAPLER WITH CONTROLLED HEALING, and published Dec. 13, 2018, which are both hereby incorporated by reference herein in their entireties.

In various aspects, one or more portions of an implantable adjunct (e.g. implantable adjuncts 13003, 13013, 13023) and/or one or more portions of the staples 13002 can include active agents, such as active cell culture (e.g., diced autologous tissue, agents used for stem cell therapy (e.g., Biosutures and Cellerix S. L.), hemostatic agents, and tissue healing agents. Non-limiting examples of hemostatic agents can include cellulose such as oxidized Regenerated Cellulose (ORC) (e.g., Surgicel and Interceed), fibrin/thrombin (e.g., Thrombin-JMI, TachoSil, Tiseel, Floseal, Evicel, TachoComb, Vivostat, and Everest), autologous platelet plasma, gelatin (e.g., Gelfilm and Gelfoam), hyaluronic acid such as microfibers (e.g., yarns and textiles) or other structures based on hyaluronic acid, or hyaluronic acid-based hydrogels. The hemostatic agents can also include polymeric sealants such as, for example, bovine serum albumin and glutarldehyde, human serum albumin and polyethylene cross-linker, and ethylene glycol and trimethylene carbonate. The polymeric sealants can include FocalSeal surgical sealant developed by Focal Inc.

In various aspects, one or more portions of an implantable adjunct (e.g. implantable adjuncts 13003, 13013, 13023) and/or one or more portions of the staples 13002 can be associated with at least one medicament in a number of different ways, so as to provide a desired effect in a desired manner.

The at least one medicament can be configured to be released from the implantable adjunct and/or the staples in multiple spatial and temporal patterns to trigger a desired staple biocorrosion of the staples and/or a desired healing process of the stapled tissue at a treatment site. In some implementations, the release profile of one or more medicaments from the implantable adjunct and/or the staples can be based on the degradation profile of the implantable adjunct and/or the staples.

In some implementations, the medicament can be disposed within, bonded to, incorporated within, dispersed within, or otherwise associated with the implantable adjunct and/or the staples. For example, the implantable adjunct and/or the staples can have one or more regions releasably retaining therein one or more different medicaments. The regions can be distinct reservoirs of various sizes and shapes and retaining medicaments therein in various ways, or other distinct or continuous regions within the implantable adjuncts and/or the staples. In some aspects, a specific configuration of the implantable adjunct and/or staples allows them to releasably retain therein medicaments. Regardless of the way in which the at least one medicament is disposed within the implantable adjunct and/or the staples, an effective amount thereof can be encapsulated within a vessel, such as a pellet which can be in the form of microcapsules, microbeads, or any other vessel. The vessels can be formed from a bioabsorbable polymer. The vessels can be incorporated into a coating.

Targeted delivery and release of at least one medicament from an implantable adjunct and/or staples can be accomplished in a number of ways which depend on various factors. In general, the at least one medicament can be released from the adjunct material and/or the staples as a bolus dose such that the medicament is released substantially immediately upon delivery of the adjunct material to tissue. Alternatively, the at least one medicament can be released from the adjunct and/or the staples over a certain duration of time, which can be minutes, hours, days, or more. A rate of the timed release and an amount of the medicament being released can depend on various factors, such as a degradation rate of a region from which the medicament is being released, a degradation rate of one or more coatings or other structures used to retains the medicament within the adjuncts and/or staples, environmental conditions at a treatment site, and various other factors.

In some implementations, the implantable adjunct is configured to release the medicament per a timeline based on the degradation rate of the staples. In at least one example, the material composition of the implantable adjunct is bioabsorbable, and the timeline for releasing the medicament from the implantable adjunct is based on the bioabsorption profile of the implantable adjunct. In such examples, the material composition of the implantable adjunct is selected based on the biocorrosion profile of the staples.

In some aspects, when the adjunct and/or staples have more than one medicament disposed therein, a bolus dose release of a first medicament can regulate a release of a second medicament that commences release after the first medicament is released. For example, the staples can include a first medicament that regulates a release of a second medicament from the implantable adjunct. Alternatively, the implantable adjunct can include a first medicament that regulates a release of a second medicament from the staples. In at least one example, the staples can include a medicament that regulates a bioabsorption of the implantable adjunct. Alternatively, the implantable adjunct can include a medicament that regulates a biocorrosion of the staples. In various aspects, the adjunct and/or staples can include multiple medicaments, each of which can affect the release of one or more other medicaments in any suitable way. Release of at least one medicament as a bolus dose or as a timed release can occur or begin either substantially immediately upon delivery of the adjunct material to tissue, or it can be delayed until a predetermined time. The delay can depend on structure and/or other properties of the adjunct and/or the staples.

In some implementations, a medicament can be stored at, or near, the center of an implantable adjunct and/or staples. The implantable adjunct and/or staples can be impregnated with the medicament by injection, for example. In some implementations, various medicaments can be stored in, or on, the implantable adjunct and/or staples in solid form such as, for example, in the form of a powder. The solid medicaments can be stored in pockets or reservoirs that control a rate of dissolving of the solid medicaments into a surrounding local environment within the patient.

In some implementations, the pockets or reservoirs can be selectively positioned on, or near, specific portions of the staples such as, for example, staple crowns, sides of staple crowns, and/or staple legs. In some implementations, the pockets or reservoirs storing the medicaments can form protrusions extending from selected portions of the staples such as, for example, staple crowns, sides of staple crowns, and/or staple legs. Additionally, or alternatively, the pockets or reservoirs storing the medicaments can be incorporated into the implantable adjunct, for example.

In some implementations, the implantable adjunct and/or staples coordinate the release of multiple medicaments into the local environment surrounding the staples in the patient based on the degradation profile of the implantable adjunct and/or staples. In at least one example, a hemostat is incorporated into a coating on the implantable adjunct and/or staples. A quick release of the hemostat can reduce bleeding from the stapled tissue. Additionally, or alternatively, one or more medicaments such as, for example, an anti-inflammatory agent, a pain management agent, and/or a medicament that increases delayed perfusion can be released by the staples and/or the implantable adjunct, in a predetermined release profile, after the quick release of the hemostat, for example. In some implementations, one or more medicaments can be stored in pockets or reservoirs within the implantable adjunct and/or staples, for example.

Figure 109:
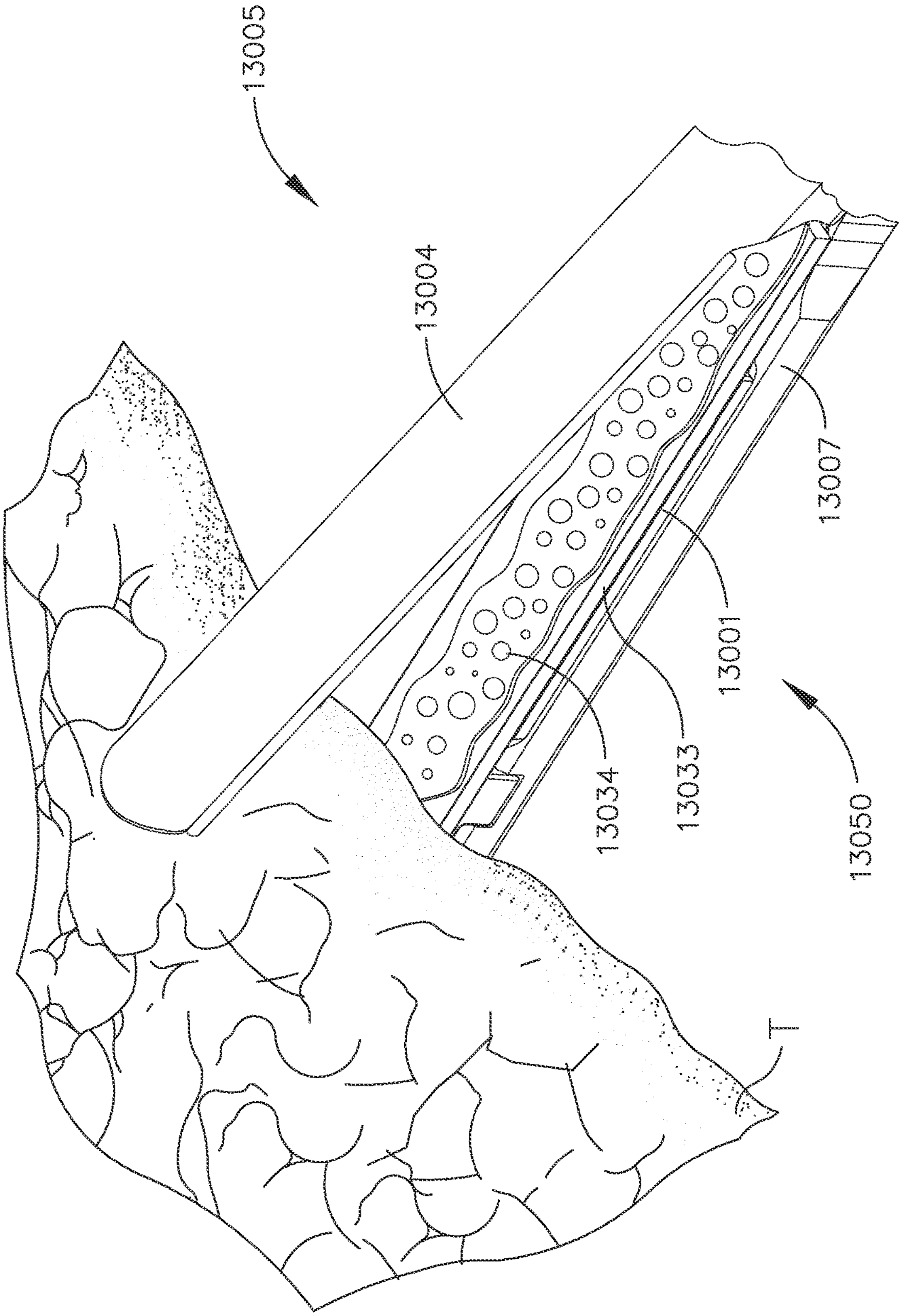

FIG. 109 is a perspective view of an end effector assembly 13005 configured to engage, cut, staple, and apply an implantable adjunct 13033 to tissue, in accordance with at least one aspect of the present disclosure. The implantable adjunct 13033 stores a medicament in a number of reservoirs 14034 dispersed through the implantable adjunct 13033. The medicament is released from the reservoirs 14034 as the implantable adjunct is bioabsorbed. In at least one example, the medicament is stored in the reservoirs 14034 in solid form such as, for example, a powder. In other examples, the medicament is stored in the reservoirs 14034 in the other forms such as, for example, a liquid or a gel.

In the illustrated example, the medicament is released from the reservoirs 14034 in a preset manner based on the bioabsorption profile of the implantable adjunct 13033. In some implementations, as it is released, the medicament modifies a biocorrosion profile of the staples 13002 in the patient. Accordingly, the predetermined release profile of the medicament form the reservoirs can be adjusted, based on the bioabsorption profile of the implantable adjunct 13022, to yield a desirable biocorrosion profile of the staples 13002, for example.

In various implementations, the biocorrosion of the staples 13002 can be synchronized, or coordinated, with a tissue healing response of the stapled tissue by the additional cooperative behavior of an active agent and/or a medicament. The staples and/or the implantable adjunct can releasably retain one or more medicaments that can be timely released to tailor the tissue healing response of the stapled tissue to the biocorrosion profile of the staples, for example.

In various aspects, the implantable adjunct and/or the staples can include one or more Matrix metalloproteinase (MMP) inhibitors. MPPs are a family of proteases that breakdown components of the extracellular matrix (ECM) of tissue under a variety of physiological and pathological conditions, including during wound healing. These enzymes remove dead and devitalized tissue, help to remodel the underlying connective tissue of the ECM, promote inflammatory cell migration into the wound site, and assist in angiogenesis. MPPs allow a healing cascade of the stapled tissue to be controlled. That said, without being bound to theory, it is believed that delivering substances capable of inhibiting MMPs to wound sites in tissue (for example, intestinal tissue) immediately after staple insertion can prevent or minimize the ECM degeneration associated with the initial stages of wound healing, thereby strengthening the staple insertion site and making it less likely to leak or rupture.

In various implementations, one or more MMP inhibitors can be controllably released, in a predetermined release profile, from the staples and/or the implantable adjunct to synchronize staple biocorrosion with cellular remodeling. In some implementations, the implantable adjunct includes one or more MMP inhibitors that are released into the local environment surrounding the stapled tissue immediately after deployment of the staples. The MMP inhibitors cause an initial delay in the tissue healing response. In at least one example, the implantable adjunct is coated with the one or more MMP inhibitors.

Further to the above, the predetermined release profile may include a pause following the initial release of the MMP inhibitors. Alternatively, the predetermined release profile may include a gradual release following the initial release at a rate slowed than the initial release, for example. Various MPP inhibitors suitable for use in accordance with the present disclosure are described in U.S. Patent Publication No. 2018/0353174, titled SURGICAL STAPLER WITH CONTROLLED HEALING, and published Dec. 13, 2018, which is hereby incorporated by reference herein in its entirety.

In at least one example, one or more of the MMP inhibitors can be initially released, in a predetermined release profile, from a coating on one or more of the staples, and then later released from the implantable adjunct. In other examples, the one or more of the MMP inhibitors can be initially released, in a predetermined release profile, from the implantable adjunct, then later released from a coating on one or more of the staples.

In various implementations, one or more calcification inhibitors such as Fetuin A, citrate, and/or a chelating agent, such as phytic acid, for example, can be controllably released, in a predetermined release profile, from the staples and/or the implantable adjunct to control, or modify, staple biocorrosion. After such staples have been implanted, the calcification inhibitor can slowly release from the staples and/or the implantable adjunct. The calcification inhibitor binds with calcium and phosphate ions to form calciprotein particles (CPP). These keep the ions in solution and prevent, or at least significantly decrease, the extent of mineral deposition on the staples, thereby preserving and/or increasing the corrosion rate thereof.

In various embodiments, the calcification inhibitor and/or the chelating agent can be embedded within an absorbable polymer substrate. In at least one such embodiment, the calcification inhibitor and/or chelating agent are continuously released as the absorbable polymer substrate is bioabsorbed. In certain instances, the bioabsorbable polymer substrate can be utilized to form a coating onto the staples and/or the implantable adjunct. In certain instances, an implantable adjunct can be comprised of one or more bioabsorbable polymers that incorporate one or more calcification inhibitors and/or chelating agents configured to be released from the implantable adjunct as the implantable adjunct is bioabsorbed.

In at least one example, the calcification inhibitor and/or chelating agent can be initially released, in a predetermined release profile, from a coating on one or more of the staples, and then later released from the implantable adjunct. In other examples, the calcification inhibitor and/or chelating agent can be initially released, in a predetermined release profile, from the implantable adjunct, then later released from a coating on one or more of the staples.

In at least one example, an implantable adjunct is configured to delay the biocorrosion of staples in contact therewith, by physically shielding the staples from a biocorrosion agent, in a patient, for a predetermined time period. Then, after the predetermined time period is lapsed, the implantable adjunct is configured to chemically modify, or change, the biocorrosion of the staples by chemically maintaining the biocorrosion agents away from the staples, for example. In at least one example, the chemical modification is achieved by the release of a calcification inhibitor and/or chelating agent from the implantable adjunct as the implantable adjunct is bioabsorbed.

In various aspects, a surgical stapler can be utilized to staple and excise tissue to remove a cancerous tissue from a patient. The clinician often employs various techniques, e.g. imaging techniques, to identify the cancerous tissue. The surgical stapler is then utilized to staple and cut tissue at a safe margin from the cancerous tissue to ensure a complete removal of the cancerous tissue form the patient. In certain instances, however, it is difficult to ascertain the safe margin. Consequently, the remaining tissue can become cancerous overtime.

Figure 110:
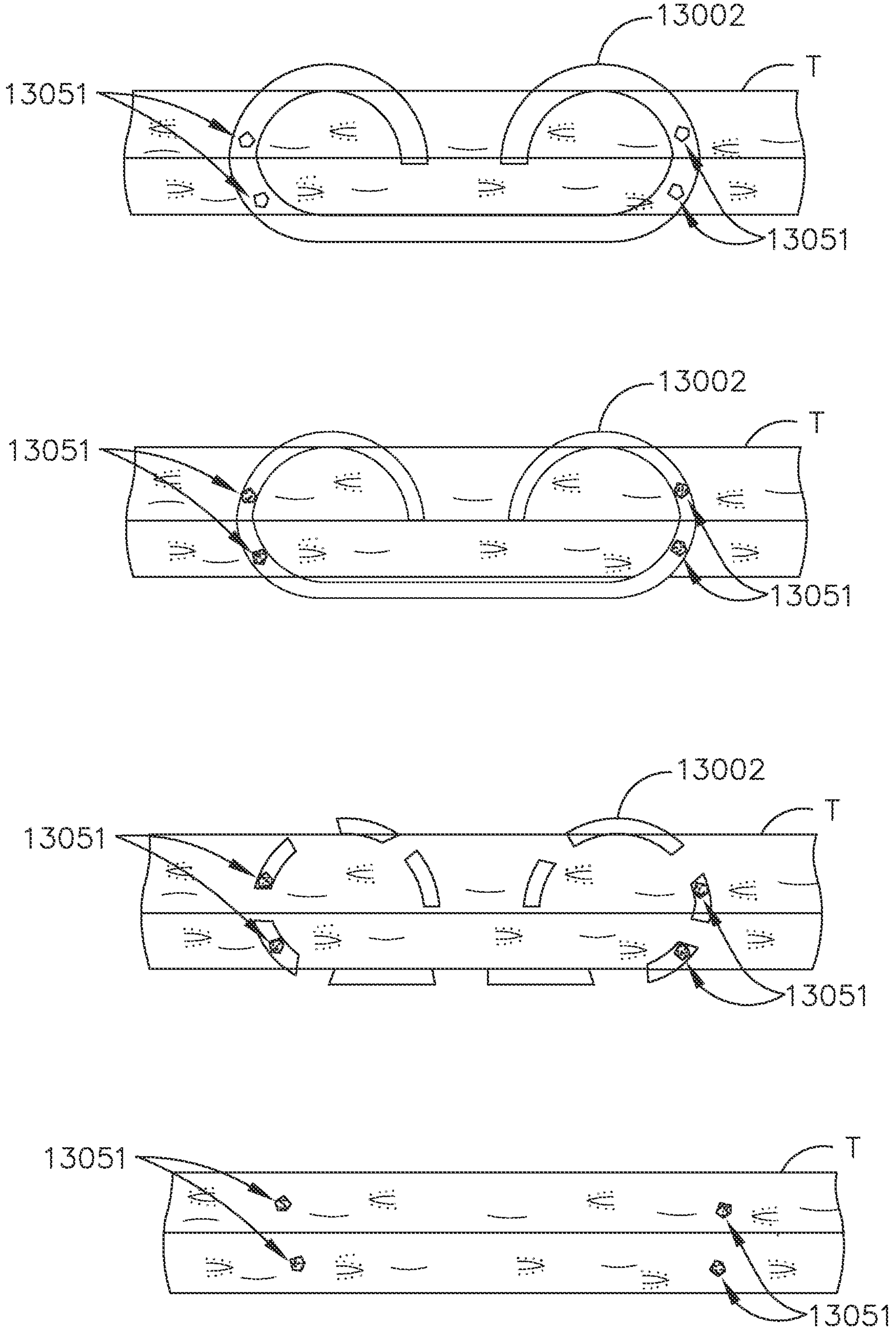

Referring primarily to FIG. 110, staples 13002' deployed by the surgical stapler into the tissue of the patient are configured to provide a radiotherapy as a preventative measure and/or a treatment therapy for the remaining tissue to ensure a complete remission. In some implementations, a staple cartridge 13001 is modified to include one or more of the staples 13002' that include a material configured to deliver a radiotherapy to the stapled-tissue in the patient.

The staples 13002' are similar in many respects to the staples 13002, which are not repeated herein at the same level of detail for brevity. For example, like the staples 13002, the staples 13002' include a substrate having a metal that degrades when exposed to a degradation source in the patient. Additionally, the substrate of the staples 13002' also includes a material configured to deliver a radiotherapy to the tissue stapled by the staples 13002'. Accordingly, in addition to fastening the tissue, the staples 13002' are configured to provide a radiotherapy as a preventative measure and/or a treatment therapy to the stapled tissue.

In some implementations, the metal of the substrate of one or more staples 13002' comprises magnesium, iron, zinc, and/or alloys thereof, for example. Various metals and metal alloys suitable for use with the staples 13002' are described in greater detail elsewhere in the present disclosure.

In some implementations, the material configured to deliver a radiotherapy to the tissue stapled by the staples 13002' is an alpha particle emitter 130051. As illustrated in FIG. 110, in some implementations, the alpha particle emitter 130051 is dispersed in the substrate of the staples 13002'.

In at least one example, the metal of the staples 13002' is doped with the alpha particle emitter 130051. In at least one example, the alpha particle emitter 130051 is introduced into a melt of the metal, prior to producing the staples 13002', in quantities sufficient to achieve a therapeutic effect in tissue stapled by the staples 13002'. In at least one example, the staples 13002' are comprised of a doped alloy including the alpha particle emitter 130051 at levels capable of alpha emissions that achieve a therapeutic effect in tissue stapled by the staples 13002'.

In some implementations, the metal of the substrate of one or more staples 13002' biocorrodes in the patient over a predetermined time period, as described in greater detail in connection with the staples 13002, which causes the alpha particle emitter 130051 to be gradually released from the staples 13002' over a predetermined timeline. Additionally, or alternatively, the alpha particle emitter 130051 can be incorporated into a coating applied to staples. Various suitable coatings are disclosed elsewhere in the present disclosure. As the coating degrades, the alpha particle emitter 130051 is gradually released into the stapled tissue.

In some implementations, the alpha particle emitter 130051 is Thorium 232, Radium 223, Radium 224, or combinations thereof, for example. In at least one example, the concentration of the alpha particle emitter 130051 in the metal can be tuned to provide different doses of radiotherapy, up to the solubility of the alpha particle emitter in the metal melt. Dosing can also be controlled based on the number of individual staples, staple rows, or staple lines with the doped alloy, deployed into the tissue of a patient.

In at least on example, a staple cartridge 13001 is configured to include staples 13002 and staples 13002', wherein the staples 13002 and the staples 13002' are selectively arranged to achieve a predetermined radiotherapeutic effect in the stapled tissue in a patient. In at least one example, the staples 13002' are positioned in a first row of staples, but not a second row of staples, of the staple cartridge 13001. The first row can be an inner row of staples, and the second row can be an intermediate or outer row of staples. In at least one example, the first row is closer to the longitudinal slot 13008 than the second row. This arrangement causes the staples 13002' to be deployed in close proximity to a cutline, or a tumor margin, of the tissue, where cancer is more likely to occur.

In various aspects, instead of the alpha particle emitter 130051, or in addition to it, the staples 13002' may include a radiosensitizer such as, for example, hafnium oxide. Radiosensitizers are compounds that enhance the lethal effects of radiation on cancerous tissue. In some implementations, the therapeutic effect of the radiosensitizer is realized after the staples are deployed into the tissue by activation of benefits of the radiosensitizer with the application of radiotherapy. For example, the radiotherapy can be applied to the stapled tissue one day, one week, one month, two months, and/or six months following the deployment of the staples into the tissue. The radiotherapy can be employed as a preventative measure, or as an additional treatment, for example, to ensure a complete remission.

The radiosensitizer is retained in the staples, near the stapled tissue, until the staples degrade. Accordingly, the radiosensitizer is configured to provide a targeted, or localized, enhancement to the effects of a radiotherapy applied to tissue of a patient at a later time after the surgical procedure that deployed the staples into the tissue.

In some implementations, the radiosensitizer (e.g. hafnium oxide) is introduced into a melt of the metal, prior to producing the staples 13002', in quantities sufficient to achieve an enhanced therapeutic effect when radiotherapy is applied to the stapled tissue. In some implementations, the metal of the substrate of one or more staples 13002' biocorrodes in the patient over a predetermined time period, as described in greater detail in connection with the staples 13002, which causes the radiosensitizer to be gradually released from the staples 13002' over a predetermined timeline. Additionally, or alternatively, the radiosensitizer can be incorporated into a coating applied to staples. Various suitable coatings are disclosed elsewhere in the present disclosure. As the coating degrades, the radiosensitizer is gradually released into the stapled tissue.

Figure 1:
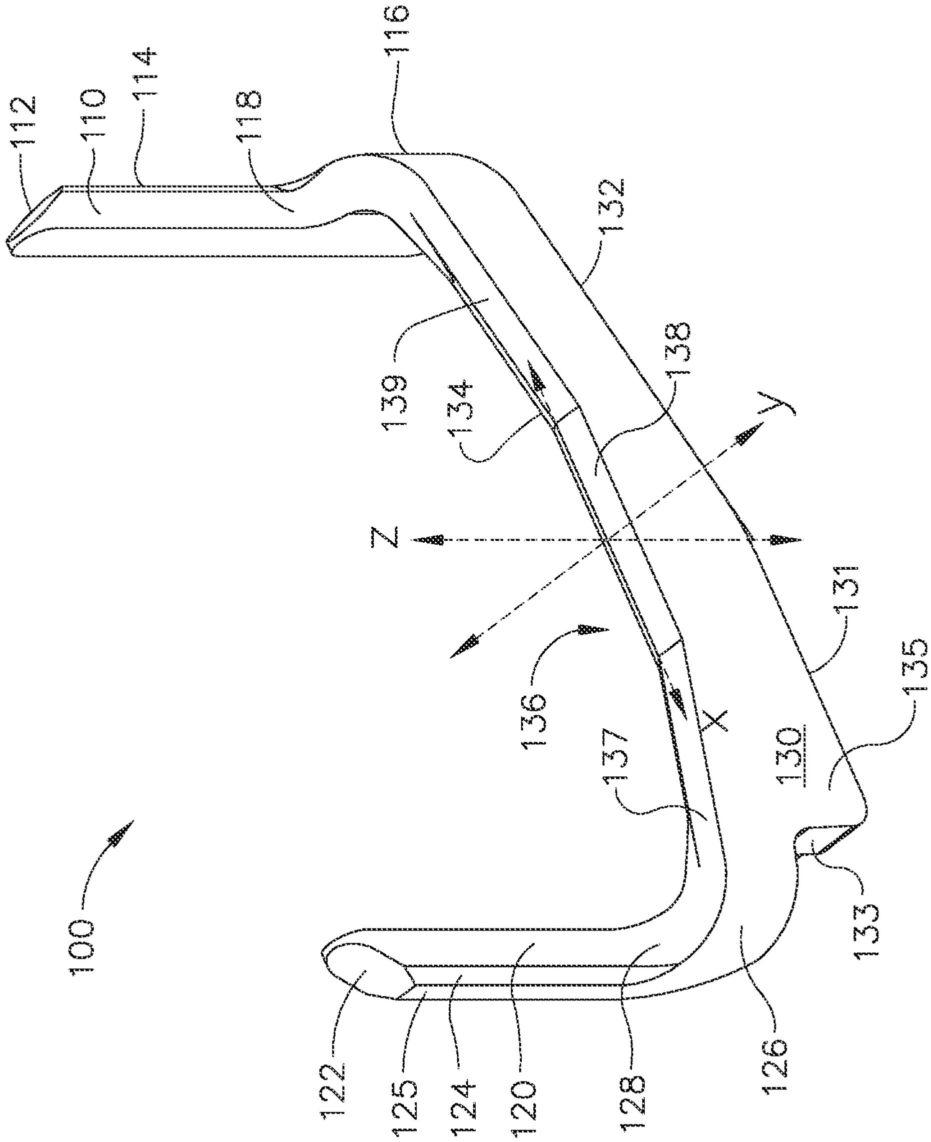
FIG. 1 is a perspective view of a staple for use with a surgical stapling instrument.
Figure 2:
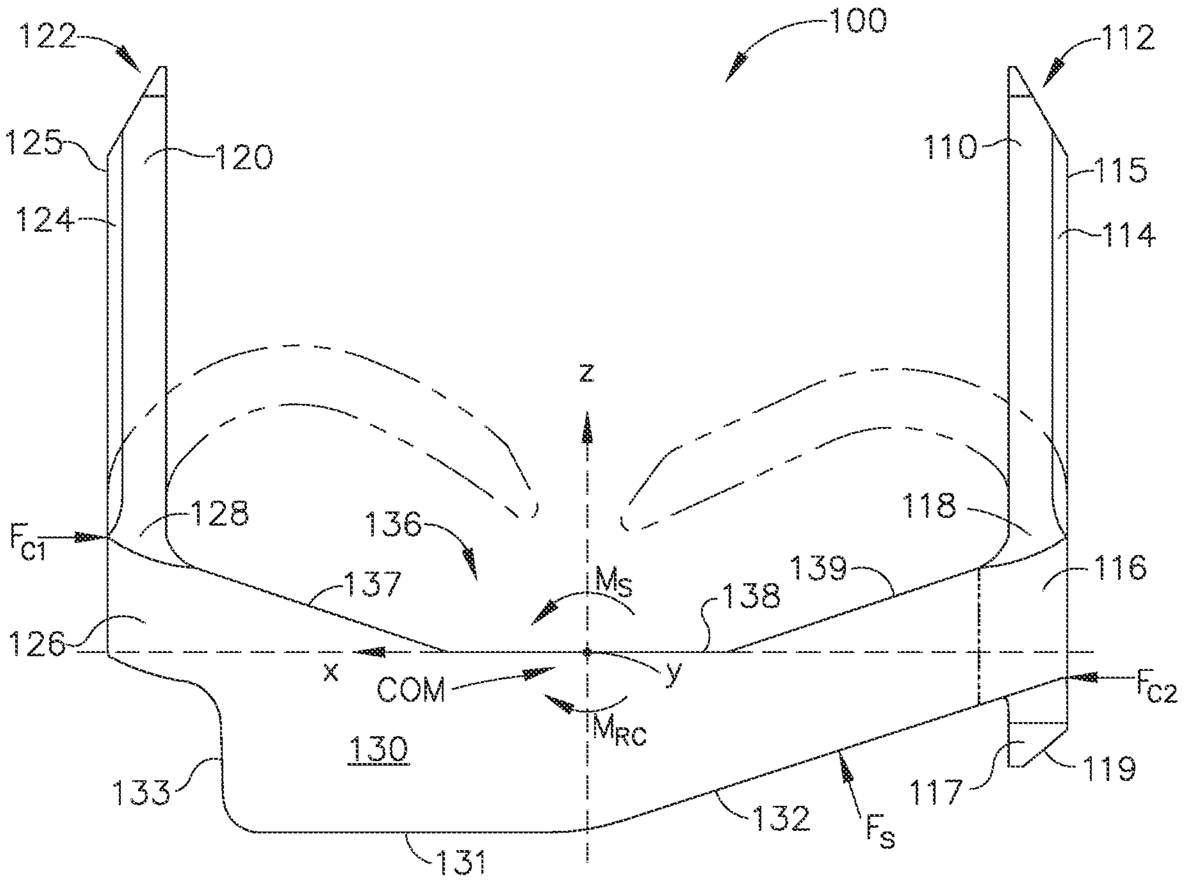
FIG. 2 is a side elevation view of the staple of FIG. 1.
Figure 3:
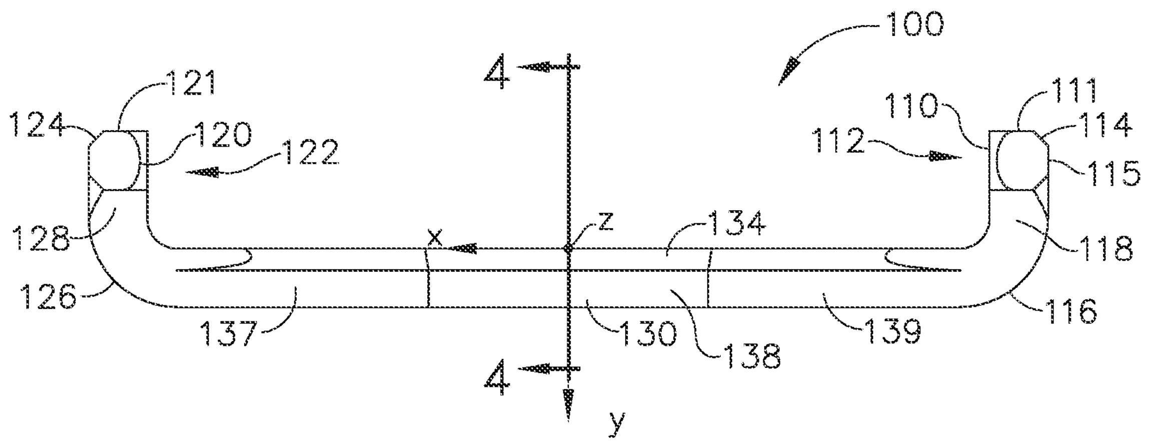
FIG. 3 is a top view of the staple of FIG. 1.
Figure 4:
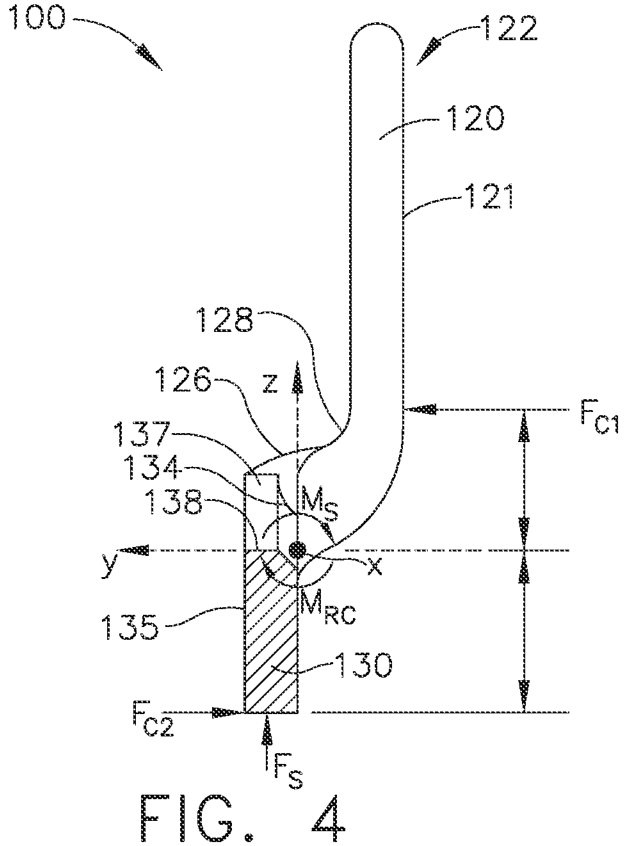
FIG. 4 is a cross-sectional view of the staple of FIG. 1 taken along line 4-4 in FIG. 3.
Figure 111:
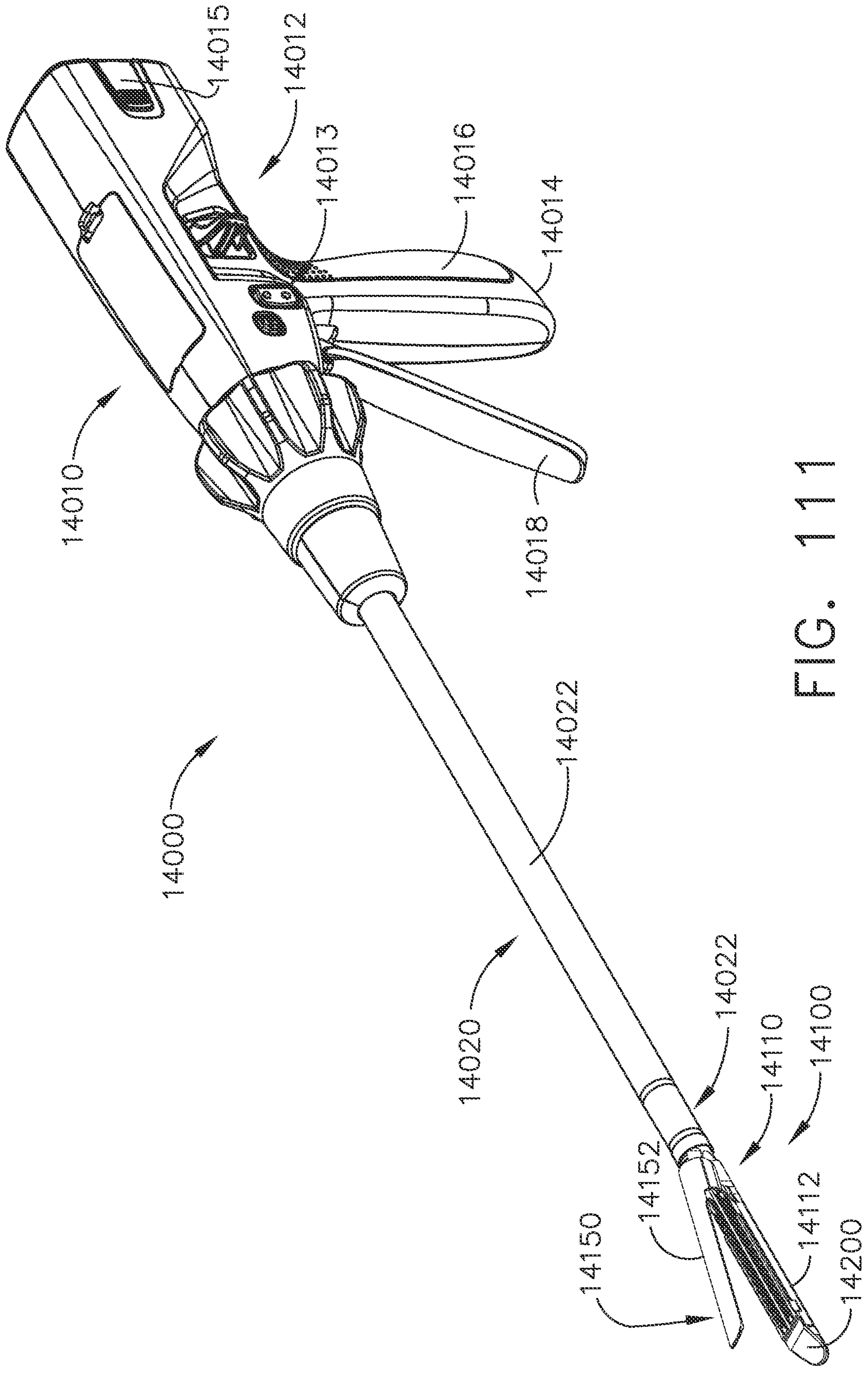
Figure 112:
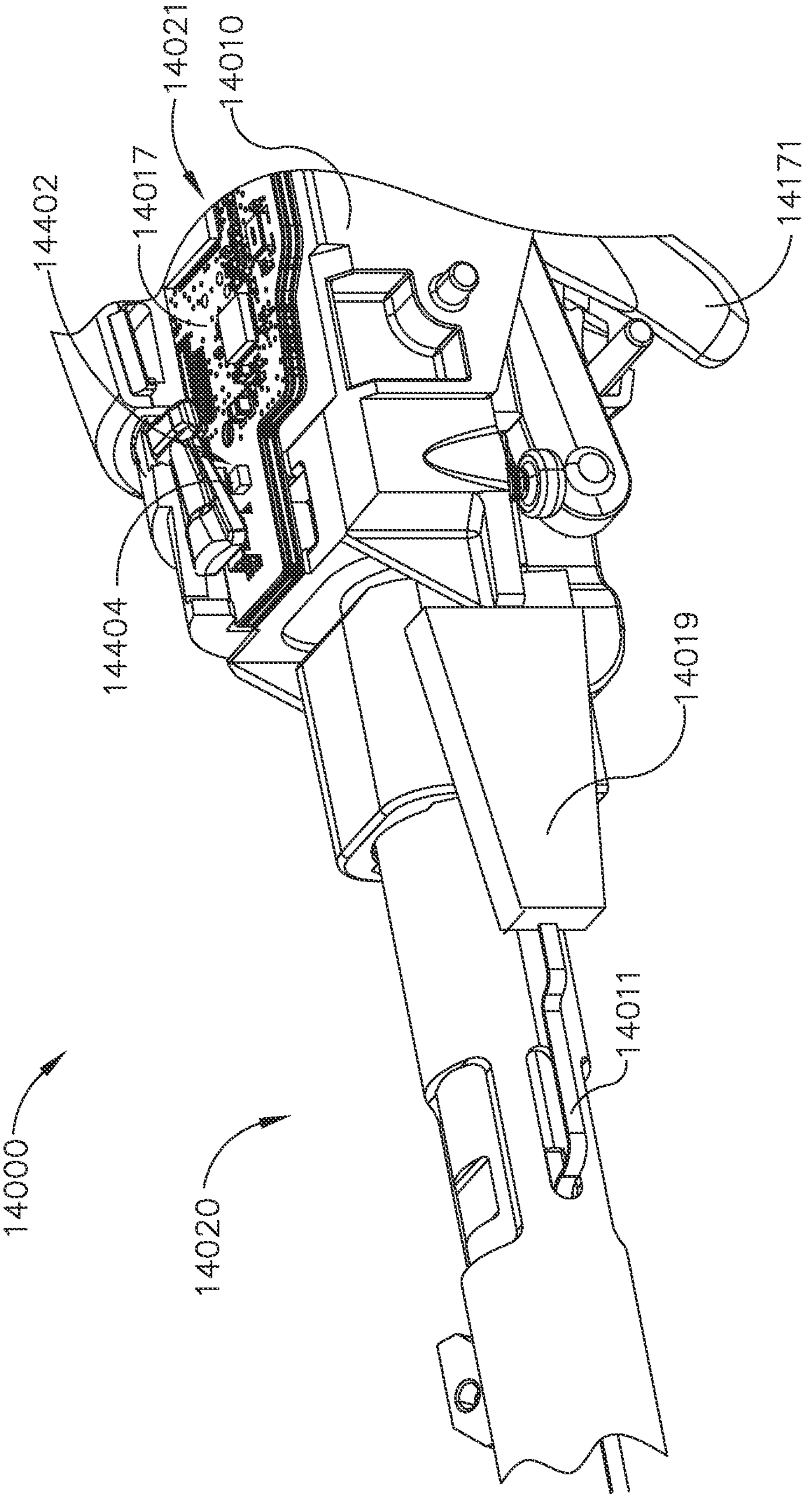

FIGS. 111-4 depict a surgical stapling instrument 14000 that is configured to cut and staple tissue of a patient. The surgical stapling instrument 14000 comprises a handle assembly 14010, a shaft assembly 14020 attached to the handle assembly 14010, and a surgical end effector 14100. The handle assembly 14010 comprises a housing 14012 that is configured to house various components therein such as, for example, electronics, motors, and/or drive train components. The handle assembly 14010 comprises a pistol grip portion 14014 comprising a handle 14016 that is configured to be held by a user, a closure trigger 14018 that is configured to clamp tissue within the surgical end effector 14100, and a firing trigger 14171 (FIG. 112) located forward of the closure trigger 14018 and which controls actuation of a firing system that is configured to cut and staple tissue that is clamped within the surgical end effector 14100. The handle assembly 14010 further comprises a plurality of actuators and/or buttons 14013 that are configured to electronically actuate various functions of the surgical stapling instrument 14000.

In at least one instance, the handle assembly 14010 comprises a plurality of motors positioned therein that are configured to drive one or more functions of the surgical stapling instrument 14000. The handle assembly 14010 further comprises one or more power sources such as, for example, batteries 14015 that are configured to power onboard electronics or control system 14021 that comprises, for example, the printed circuit boards 14017, 14019 which control the motor(s) positioned within the handle assembly 14010. See FIG. 112. In at least one instance, the handle assembly 14010 comprises one or more onboard memories, processors, and/or control circuits that are configured to analyze sensor data and/or control various electronic systems of the surgical stapling instrument 14000 such as, for example, motor control programs. The handle assembly 14010 may be in wireless communication with a surgical hub and/or various other components of a surgical operating suite to communicate various data between the handle assembly 14010 and the surgical hub, for example.

In the illustrated arrangement, the shaft assembly 14020 is attached to the handle assembly 14010. In at least one instance, the shaft assembly 14020 is modular and can be replaced with another shaft assembly of another surgical instrument attachment, for example. In at least one instance, the shaft assembly 14020 comprises one or more of the printed circuit boards 14017, 14019. The shaft assembly 14020 is configured to house a plurality of components of the surgical stapling instrument 14000 such as, for example, drive shafts, electronics, sensors, wires, and/or frame components, for example. Such components are configured to be coupled to corresponding components that are positioned within the handle assembly 14010 such as, for example, motors, supply leads, wires, and/or drive train components, for example. The shaft assembly 14020 houses such components and transfers such components to the surgical end effector 14100 to drive various functions of the shaft assembly 14020 and/or surgical end effector 14100 and/or transfer electrical signals between the shaft assembly 14020 and the surgical end effector 14100 and to/from the handle assembly 14010, for example. The shaft assembly 14020 comprises electrical leads 14011 electrically coupled with one or more of the printed circuit board's 14017, 14019 and one or more components within the shaft assembly 14020 and/or the surgical end effector 14100. Further details regarding the surgical stapling instrument 14000 may be found in U.S. patent application Ser. No. 17/513,690, filed Oct. 28, 2021, entitled ELECTRICAL LEAD ARRANGEMENTS FOR SURGICAL INSTRUMENTS, the entire disclosure of which is hereby incorporated by reference herein.

In one form, the surgical end effector 14100 comprises a first jaw 14110 and a second jaw 14150 that is movable relative to the first jaw 14110 to grasp and ungrasp tissue therebetween. The first jaw 14110 comprises a cartridge-receiving channel 14112 that is configured to receive a surgical staple cartridge 14200 therein. The second jaw 14150 comprises an anvil 14152 that is configured to clamp onto tissue upon actuation of the closure trigger 14018 and form staples removably stored within the surgical staple cartridge 14200 upon actuation of the firing trigger 14171. As discussed above, the surgical stapling instrument 14000 may comprise various electronics. Such electronics may be wireless, wired, passively powered, and/or actively powered, for example. In various instances, such electronics may be positioned within the surgical staple cartridge 14200, on one or more components of the surgical end effector 14100 such as the cartridge-receiving channel 14112 and/or the anvil 14152, within the shaft assembly 14020, and/or within the handle assembly 14010.

Figure 113:
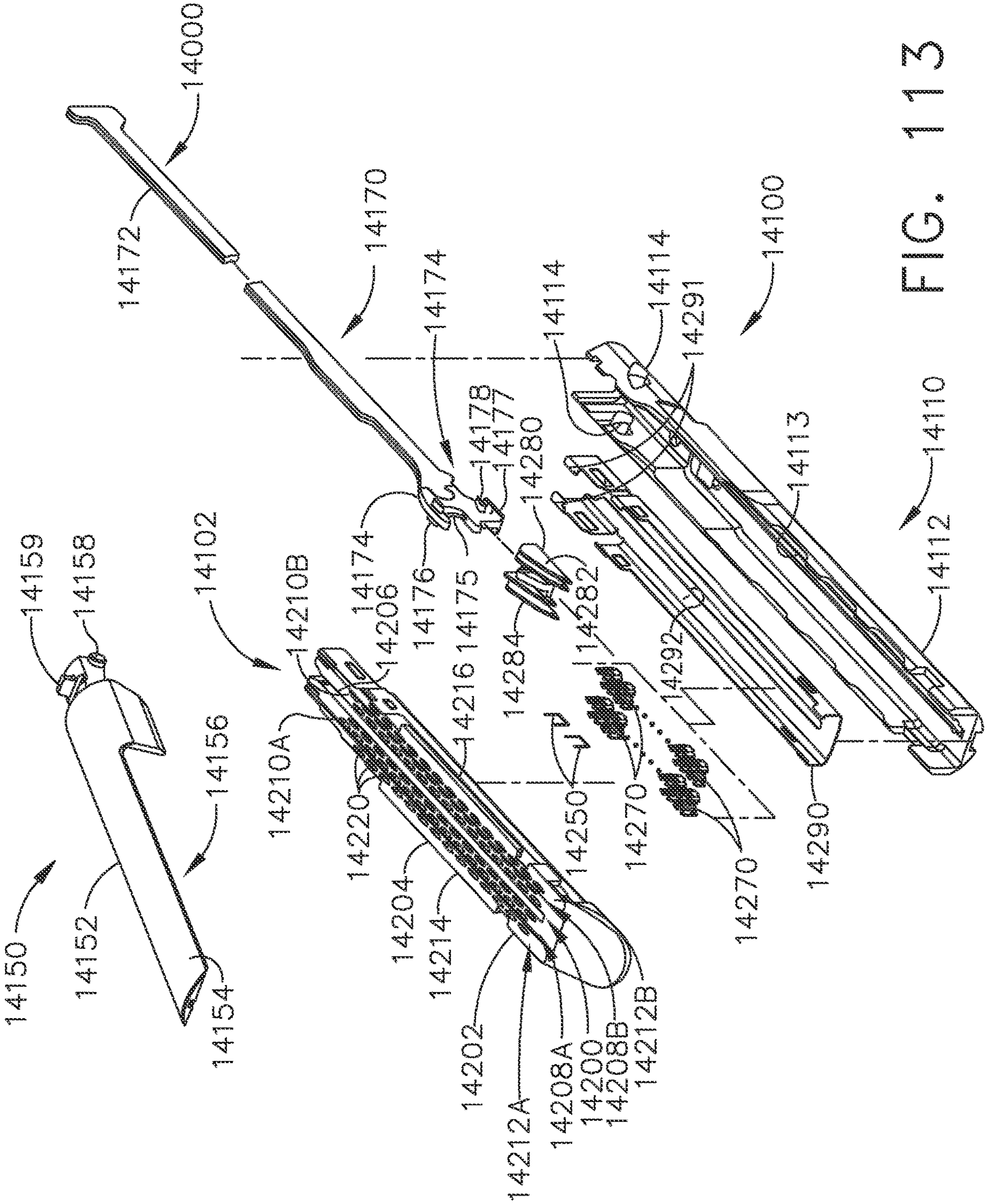

In various embodiments, a surgical staple cartridge 14200 comprises a cartridge body 14202 that defines a deck surface 14204. A longitudinal slot 14206 splits the deck surface 14204 and is configured to receive a tissue-cutting knife or E-beam member 14174 that has a tissue-cutting surface 14175 thereon. The E-beam member 14174 comprises a portion of a firing assembly 14170. See FIG. 113. The deck surface 14204 further defines longitudinal rows of staple cavities 14220 in the cartridge body 14202 located on both sides of the longitudinal slot 14206. For instance, a surgical staple cartridge 14200 can comprise three longitudinal rows 14208A, 14210A, 14212A of staple cavities 14220 on a first side 14214 of the longitudinal slot 14206 and three longitudinal rows 14208B, 14210B, 14212B of staple cavities 14220 on a second, or opposite, side 14216 of the longitudinal slot 14206. On the first side 14214 of the longitudinal slot 14206, in at least one such embodiment, the longitudinal rows of staple cavities 14220 are arranged in an inner row 14208A adjacent the longitudinal slot 14206, an intermediate row 14210A adjacent the inner row 14208A, and an outer row 14212A adjacent the intermediate row 14210A. Similarly, on the second side 14216 of the longitudinal slot 14206, the longitudinal rows of staple cavities 14220 are arranged in an inner row 14208B adjacent the longitudinal slot 14206, an intermediate row 14210B adjacent the inner row 14212B, and an outer row 14212B adjacent the intermediate row 14210B.

A staple 14250 is positioned in each staple cavity 14220. Each staple 14250 is supported on a corresponding staple driver 14270 that is slidably supported with the staple cavity 14220. In various embodiments, the staples 14250 that are positioned in the inner rows, intermediate rows, and outer rows are comprised of the same material. The staples 14250 may comprise any of the various bio-absorbable staple compositions/configurations disclosed herein as well as incorporated by reference herein, including but not limited to, absorbable metal staples, coated staples, etc. In at least one such instance, all of the staples 14250 in the surgical staple cartridge 14200 are comprised of the same alloy, for example. In still other instances, each staple 14250 may comprise its own integrally-formed driver as disclosed herein.

In at least one arrangement, the staples 14250 are driven from unfired positions within the cartridge body 14202 to fired positions by a firing member, such as sled 14280, for example. The sled 14280 comprises wedges 14282 which are configured to directly engage the staple drivers 14270 or the driver portion of the staples (whichever the case may be) and lift the staple drivers 14270 and staples 14250 toward the anvil 14152. The sled 14280 comprises a wedge, or rail, 14282 that corresponds to each longitudinal row of staples 14250; however, the sled 14280 may have any suitable number of wedges 14282. Each wedge 14282 comprises an angled drive surface 14284 which slides under the staple drivers 14270 or staples as the sled 14280 is advanced from a proximal end of the surgical staple cartridge 14200 toward a distal end of the surgical staple cartridge 14200.

In various arrangements, the staple drivers 14270 may be installed in the staple cavities 14220 in the cartridge body 14202 and the sled 14280 may be positioned in the cartridge body 14202 through openings the bottom of the cartridge body 14202. A metal pan 14290 may be attached to the cartridge body 14202 by tabs 14291 formed therein that are configured to retainingly engage the cartridge body 14202. The metal pan 14290 serves to retain the staple drivers 14270 and the sled 14280 within the cartridge body 14202. Each staple cavity 14220 opens through the deck surface 14204. The staples 14250 may be inserted onto their respective driver 14270 through the staple cavity opening in the deck surface 14204 or they may be installed with their corresponding staple driver through the bottom of the cartridge body 14202, for example.

In the illustrated example, the anvil 14152 comprises an elongate anvil body 14154 that has a staple-forming undersurface 14156. The staple-forming undersurface 14156 may comprise a series of staple-forming pockets that correspond to each staple 14250 in a corresponding surgical staple cartridge 14200 that is operably seated in the cartridge-receiving channel 14112. The anvil body 1454 further comprises a pair of anvil trunnions or pivot pins 14158 that are pivotally received in corresponding slots 14114 in the channel 14112 to facilitate pivotal travel of the anvil 14152 relative to the channel 14112 between an open position and a closed position.

A variety of methods and components exist for applying opening and closing motions to the anvil 14152. In one instance, for example, such opening and closing motions are applied to the anvil 14152 by an axially moving closure member or closure tube 14022. For example, the closure tube 14022 may be moved distally by compressing the closure trigger 14018. After the firing stroke has been completed, the closure tube 14022 may be moved proximally back to the starting position by releasing the closure trigger 14018 which may actuate the closure system in reverse. As the closure tube moves proximally, the closure tube 14022 may interact with an anvil opening feature or tab 14159 on the anvil 14152 to apply opening motions thereto. In addition, a spring (not shown) may be employed to apply opening motions to the anvil 14152.

The sled 14280 is configured to be actuated through a firing stroke by the firing assembly 14170 to deploy the staples 14250 from the surgical staple cartridge 14200 and cut tissue that is clamped between the jaws 14100, 14150. In various arrangements, the firing assembly 14170 may comprise an axially movable firing beam 14172 that interfaces with a firing system within the housing 14012. Once the anvil 14152 has been closed, actuation of a firing trigger 14171 causes the firing beam 14172 to move distally. The firing beam 14172 is coupled to the firing member 14174 that has a tissue-cutting surface 14175 thereon. In addition, the firing member 14174 further comprises a pair of anvil engaging tabs 14176 that are configured to be slidably received within corresponding slots in the anvil 14152. Stated another way, the anvil engaging tabs 14176 are configured to slidably engage ledges or shoulders (not shown) in the anvil 14152 and serve to maintain the staple-forming undersurface 14156 of the anvil 14152 at a desired spacing relative to the surgical staple cartridge 14200 during the firing stroke. The firing member 14174 extends through an elongate slot 14292 in the metal pan 14290 and a slot 14113 in the channel 14112. The firing member 14174 further comprises a pair of channel-engaging tabs 14177 that are located on the bottom of the firing member 14174. In addition, the firing member 14174 may comprise a pair of laterally-extending central tabs 14178 configured to slidably engage portions of the cartridge body 14202. As the firing member 14174 is driven distally during the firing stroke, the firing member 14174 contacts the sled 14280 and drives the sled 14280 distally. As the sled 14280 moves distally, the angled drive surface 14284 on each wedge 14282 cammingly interfaces with the corresponding staple drivers 14270 and causes the staple drivers 14270 to move toward the anvil 14152 which causes the staples 14250 to be ejected from the surgical staple cartridge 14200 into forming contact with the staple-forming undersurface 14156 of the anvil 14152.

In those instances wherein the staples 14250 are designed to be bio-absorbable within a desired period of time, it is desirable for the staples 14250 to be protected from physical and environmental influences that might cause premature degradation of the unfired staples 14250 during shipping and storage of the surgical staple cartridge 14200. FIG. 116 illustrates one form of a packaging assembly, generally designated as 14300, for packaging, storing, and shipping a sterile surgical staple cartridge 14200 that operably stores staples 14250 that comprise any of the various bio-absorbable staples disclosed herein.

For example, in one embodiment, each of the staples 14250 in the surgical staple cartridge 14200 or at least some of the staples 14250 in the surgical staple cartridge 14200 may comprise a zinc-based alloy that is configured to accelerate corrosion of the staples. In another instance, each of the staples 14250 in the surgical staple cartridge 14200 or at least some of the staples 14250 in the surgical staple cartridge 14200 may comprise a magnesium-based alloy and be coated with a coating comprised of an absorbable polymer and a calcification inhibitor. In still another instance, for example, each of the staples 14250 in the surgical staple cartridge 14200 or at least some of the staples 14250 in the surgical staple cartridge 14200 may be hollow and comprise a magnesium-based alloy. In yet another example, each of the staples 14250 in the surgical staple cartridge 14200 or at least some of the staples 14250 in the surgical staple cartridge 14200 may comprise a magnesium-based alloy, wherein an alloying element of the magnesium-based alloy is selected to lower an electrode potential of the staples. In yet another arrangement, each of the staples 14250 in the surgical staple cartridge 14200 or at least some of the staples 14250 in the surgical staple cartridge 14200 may comprise a magnesium-based alloy, wherein an alloying element of the magnesium-based alloy is selected to accelerate anodic corrosion of magnesium of the magnesium-based alloy. In another arrangement, at least a portion of each staple 14250 in the surgical staple cartridge 14200 or at least some of the staples 14250 in the surgical staple cartridge 14200 is coated in Fetuin A. In other instances, at least a portion of each staple 14250 in the surgical staple cartridge 14200 or at least some of the staples 14250 in the surgical staple cartridge 14200 is coated by one or more proteins. In still other embodiments, at least a portion of each staple 14250 in the surgical staple cartridge 14200 or at least some of the staples 14250 in the surgical staple cartridge 14200 is coated in citrate. In another arrangement, at least a portion of each staple 14250 in the surgical staple cartridge 14200 or at least some of the staples 14250 in the surgical staple cartridge 14200 is coated in a chelating agent. In another arrangement, at least a portion of each staple 14250 in the surgical staple cartridge 14200 or at least some of the staples 14250 in the surgical staple cartridge 14200 is coated in phytic acid. In various alternatives, at least a portion of each staple 14250 in the surgical staple cartridge 14200 or at least some of the staples 14250 in the surgical staple cartridge 14200 is coated in pyrophosphate. In another arrangement, at least a portion of each staple 14250 in the surgical staple cartridge 14200 or at least some of the staples 14250 in the surgical staple cartridge 14200 is coated in a bisphosphonate. In still other arrangements, at least a portion of each staple 14250 in the surgical staple cartridge 14200 or at least some of the staples 14250 in the surgical staple cartridge 14200 is coated in a polyphosphate. In another embodiment, at least a portion of each staple 14250 in the surgical staple cartridge 14200 or at least some of the staples 14250 in the surgical staple cartridge 14200 is coated in a co-polymer of acrylic acid. In still another embodiment, at least a portion of each staple 14250 in the surgical staple cartridge 14200 or at least some of the staples 14250 in the surgical staple cartridge 14200 is coated in a polycarboxylic acid. In another instance, at least a portion of each staple 14250 in the surgical staple cartridge 14200 or at least some of the staples 14250 in the surgical staple cartridge 14200 is coated in a polymer coating. In another arrangement, at least a portion of each staple 14250 in the surgical staple cartridge 14200 or at least some of the staples 14250 in the surgical staple cartridge 14200 is coated in osteopontin. In still another arrangement, at least a portion of each staple 14250 in the surgical staple cartridge 14200 or at least some of the staples 14250 in the surgical staple cartridge 14200 is coated in magnesium ions.

After the staples 14250 have been installed in the surgical staple cartridge 14200, the surgical staple cartridge 14200 may then be sterilized utilizing, for example, gamma radiation, x-rays, high-energy electrons, beta radiation, ethylene oxide, plasma peroxide, steam etc. In one arrangement, the packaging assembly 14300 comprises a staple retainer 14310 that is removably coupled to the surgical staple cartridge 14200 to form a cartridge/retainer assembly 14330. See FIG. 114. When coupled to the surgical staple cartridge 14200, the staple retainer 14310 covers the staple cavities 14220 and serves to retain the staples 14250 within each staple cavity 14220 during shipping and storage of the surgical staple cartridge 14200. The staple retainer 14310 is configured to be removed from the surgical staple cartridge 14200 prior to use of the surgical staple cartridge 14200. For example, the staple retainer 14310 may be removed from the surgical staple cartridge 14200 prior to installation in the cartridge-receiving channel 14112 or the cartridge/retainer assembly 14330 may be installed in the channel 14112 and thereafter, the staple retainer 14310 is removed prior to use of the surgical stapling instrument 14000. See FIG. T-5. The staple retainer 14310 may be separately sterilized prior to installation on the surgical staple cartridge 14200 or the staple retainer 14310 may be installed onto the surgical staple cartridge 14200 and the entire cartridge/retainer assembly 14330 may then be sterilized. After sterilization, the cartridge/retainer assembly 14330 is then placed into a hermetically-sealed (airtight and fluidtight) sterile container 14320 for shipping and storage. See FIG. 116.

In various embodiments, one form of a staple retainer 14310 may be fabricated from a polymer material and comprise an elongate body portion 14312 that is configured to be received on the deck surface 14204 of the surgical staple cartridge 14200. See FIG. 119. The elongate body portion 14312 is sized relative to the deck surface 14204 such that when the staple retainer 14310 is received thereon, the elongate body portion 14312 covers all of the staple cavities 14220 in the cartridge body 14202. In various instances, the body portion 14312 of the staple retainer 14310 may be formed with instructional indicia 14319 and/or identifying indicia that relates to a particular surgical staple cartridge. To facilitate positioning of the staple retainer 14310 on the deck 14204, a downwardly extending locator keel or locator member 14314 may protrude downward from a deck-facing surface 14313 of the elongate body portion 14312 and is configured to be received within the elongate slot 14206 in the cartridge body 14202. See FIG. 119. In at least one arrangement, the staple retainer 14310 is formed with a plurality of attachment tabs 14316 that are configured to retainingly engage corresponding portions of the cartridge body 14202 to removably affix the staple retainer 14310 to the cartridge body 14202. In at least one instance, the staple retainer 14310 is configured to prevent the staples 14250 from falling out of their respective staple cavities 14220 during shipping and/or installation of the surgical staple cartridge 14200 into the channel 14112 of the surgical stapling instrument 14000 as well as prevents infiltration of debris into the staple cavities 14220 prior to use.

The staple retainer 14310 is configured to be removed prior to use of the surgical stapling instrument 14000 and the surgical staple cartridge 14200. To facilitate such removal, the staple retainer 14310 may comprise a removal tab 14318 that protrudes from a distal end of the staple retainer 14310 to facilitate prying of the staple retainer 14310 from the cartridge body 14202 of the surgical staple cartridge 14200. Various other staple retainer arrangements are disclosed in U.S. Pat. No. 11,185,330, entitled FASTENER CARTRIDGE ASSEMBLIES AND STAPLE RETAINER COVER ARRANGEMENTS, and U.S. Pat. No. 9,839,420, entitled TISSUE THICKNESS COMPENSATOR COMPRISING AT LEAST ONE MEDICAMENT, the entire disclosures of each are hereby incorporated by reference herein.

In various embodiments, the packaging assembly 14300 further comprises a hermetically-sealable (airtight and fluidtight) container 14320 that is configured to temporarily store one or more cartridge/retainer assemblies 14330 therein prior to use. See FIG. 116. Such hermetically-sealable container 14320 is configured to store and protect the cartridge/retainer assemblies 14330 after being manufactured and sterilized until the container 14320 is opened in the operating room, for example. As described in U.S. Patent Application Publication No. 2020/0405296, entitled PACKAGING FOR A REPLACEABLE COMPONENT OF A SURGICAL STAPLING SYSTEM, the entire disclosure of which is hereby incorporated by reference herein, various container arrangements may comprise peel-pouches, woven and/or non-woven material wrappers, rigid containers, etc.

In the examples illustrated in FIGS. 116, 117, 123, 124, 125, 128, 129, 131, 135, and 136, the container 14320 comprises a hermetically-sealable peel-pouch 14322 that is fabricated from a gas and moisture impermeable foil or plastic material. In at least one arrangement, for example, the container 14320 comprises a first layer 14324 and a second layer 14326. The first layer 14324 and the second layer 14326 form a protective barrier around a cartridge/retainer assembly 14330. An adhesive bonds the first layer 14324 and the second layer 14326 together to form an airtight and fluidtight sealed pouch around the cartridge/retainer assembly 14330. The adhesive forms a seal without creases, wrinkles, and/or gaps. The seal created by the adhesive prevents contaminants from coming into contact with the cartridge/retainer assembly 14330 as well as prevents air/gas/fluid from infiltrating into the interior of the container 14320. As discussed in U.S. Patent Application Publication No. 2020/0405296, the first layer 14324 may comprise a first corner 14325 positioned outside of the seal, and the second layer 14326 may comprise a second corner 14327 positioned outside of the seal. The clinician can expose the cartridge/retainer assembly 14330 by peeling the first layer 14324 apart from the second layer 14326. In various instances, the clinician can expose the sealed cartridge/retainer assembly 14330 by holding the first corner 14325 and the second corner 14327 in separate hands and pulling the first corner 14325 in a direction away from the second layer 14326, although any suitable opening method could be used.

The first layer 14324 and the second layer 14326 may be comprised of a material such as, for example, paper with a laminated inner surface. The laminated inner surface provides a gas impermeable and a fluid impermeable barrier to prevent contaminants from entering the sealed portion of the container 14320. In one arrangement, the first layer 14324 and the second layer 14326 are comprised of foil. In another arrangement, the first layer 14324 and the second layer 14326 are comprised of plastic. In various arrangements, the first layer 14324 and/or the second layer 14326 can be comprised of a material with a particular degree of transparency to allow a clinician, for example, to observe the contents of the container 14320. Additionally, the container 14320 may comprise any of the various identification features/indicia described in U.S. Patent Application Publication No. 2020/0405296.

In various instances, the container 14320 may be sized relative to a cartridge/retainer assembly 14330 such that when the cartridge/retainer assembly 14330 is received therein, the cartridge/retainer assembly 14330 is substantially non-movably retained in position within the container 14320. Although FIG. 116 illustrates a container 14320 that is sized to contain one cartridge/retainer assembly 14330 therein, the container 14320 may be sized to contain a plurality of cartridge/retainer assemblies 14330 or surgical staple cartridges 14200 therein. In either case, the container 14320 may be sized relative to the cartridge/retainer assemblies 14330 to substantially prevent movement therein once the container 14320 is sealed.

As discussed above, in those instances wherein the staples 14250 are designed to be bio-absorbable within a desired period of time, it is desirable for the staples 14250 to be protected from physical and environmental influences that might cause premature degradation of the unfired staples 14250 during shipping and storage of the surgical staple cartridge 14200. For example, should the staples 14250 be exposed to moisture prior to use, the staples 14250 may begin to undesirably degrade. Thus, it is desirable to prevent the staples from being exposed to moisture while being stored and shipped prior to use. In the arrangement depicted in FIG. 116, the packaging assembly 14300 further comprises a desiccant element 14340 that is sealed in the container 14320 with the cartridge/retainer assembly 14330. In one arrangement, the desiccant element 14340 comprises a pouch 14342 that contains a desiccant material such as, for example, silica gel, activated alumina, etc. that are configured to absorb and ultimately reduce the moisture within the hermetically-sealed container 14320. In still other arrangements, the desiccant element 14340 comprises 220 $g/m^2$+/−5% Invercote T2 paper per P-02-003 (Adaptiv) or other commercially available moisture absorbent boards.

In various instances, the desiccant element 14340 may be configured to change color in the presence of moisture. In such instance, the desiccant element 14340 would provide the clinician with an indication that moisture was present within the container 14320 and could have caused premature degradation of the bio-absorbable staples 14250 allowing the clinician to avoid use of the surgical staple cartridge 14200. For example, in at least one arrangement, the desiccant element 14340 may comprise a blue desiccant material containing cobalt chloride which will change to a pink color when the desiccant material has reached its maximum adsorption capacity. This change in color would indicate a compromised package. In another arrangement, for example, the desiccant element 14340 may comprise a PH sensitive dye that changes color upon exposure to basic environments which may indicate corrosion of Mg to Mg(OH)2. In another arrangement, the desiccant element 14340 may be treated with an irreversible hydrochromic dye such as, for example, patent blue V (tryphenylmethane) dye, cobalt II chloride or methyl violet, for example.

In other arrangements, the packaging assembly 14300 may additionally comprise a tray 14302 that is configured with a cartridge retention receptacle 14304 or other retention features that non-movably retain one or more cartridge/retainer assemblies 14330 or surgical staple cartridges 14200 in position on the tray 14302. See FIG. 117. In addition, a desiccant element 14340 may be received within the receptacle 14304 on top of the cartridge/retainer assembly 14330 or otherwise positioned therein. When the clinician is ready to use a surgical staple cartridge 14200, the container 14320 is opened and the tray 14302 is removed or otherwise positioned to allow the clinician to again access to the cartridge/retainer assembly 14330 and pry or otherwise remove the cartridge/retainer assembly 14330 out of retaining engagement within the receptacle 14304 in the tray 14302. In certain instances, the surgical staple cartridge 14200 or the cartridge/retainer assembly 14330 may be attached to the tray 14302 during the sterilization process. The tray 14302, as well as the staple retainer 14310, provides air/fluid paths for a sterilization medium to invade around the surgical staple cartridge 14200 and be flushed from the interior portions of the cartridge body 14202.

FIG. 118 illustrates an alternative packaging assembly 14300 that comprises a container 14320' that comprises a tray 14302 of the type and construction described above with a top layer 14306 removably sealed thereto so as to create a hermetic seal between the top layer 14306 and the tray 14302. In various instances, the tray may comprise a gas and moisture impermeable material and the top layer may comprise a gas and moisture impermeable foil material, for example. The top layer 14306 may be sealed to the tray 14302 by an adhesive, for example.

In another embodiment, the packaging assembly 14300 may comprise a desiccant element 14350 that is configured to be received between the deck surface 14204 and the deck-facing surface 14313 of the staple retainer 14310. See FIG. 119. In one arrangement the desiccant element 14350 comprises a 220 $g/m^2$+/−5% Invercote T2 paper per P-02-003 (Adaptiv) or other commercially available moisture absorbent board that has a slot 14352 therein that is configured to accommodate insertion of the retainer keel 14314 therethrough. In another arrangement, the desiccant element 14350 comprises a compliant desiccant material. For example, the desiccant element 14350 may comprise an adjunct material or buttress material of the various types and constructions disclosed in the various disclosures that have been herein incorporated by reference that comprises or is infused with a desiccant material. In all of the foregoing arrangements, the desiccant element 14350 is sized to cover the deck surface 14204 such that the desiccant element 14350 covers all of the staple cavities 14220. In one arrangement, the desiccant element 14350 is placed onto the deck surface 14204 and is held in place by the staple retainer 14310. That is, the desiccant element 14350 is trapped between the deck-facing surface 14313 of the staple retainer 14310 and the deck surface 14204. In such instance, the desiccant element 14350 covers each staple cavity 14220 and serves to absorb moisture occurring therein (if any). The staple retainer 14310 and the desiccant element 14350 are removed before the surgical staple cartridge 14200 can be used. In another arrangement, the desiccant element 14350 is attached to the deck-facing surface 14313 of the staple retainer 14310 with an appropriate adhesive, for example. In such arrangement, the desiccant element 14350 is removed from the surgical staple cartridge 14200 when the staple retainer 14310 is detached therefrom. In another embodiment, the desiccant element 14350 may comprise an adhesive strip (not shown) that is configured to be removably attached to the deck surface 14204. In such arrangement, a staple retainer 14310 may or may not be removably attached to the surgical staple cartridge 14200 in the above-described manner.

In at least one arrangement, the desiccant element 14350 may comprise a blue desiccant material containing cobalt chloride which will change to a pink color when the desiccant material has reached its maximum adsorption capacity. This change in color would indicate a compromised package. In another arrangement, for example, the desiccant element 14350 may comprise a PH sensitive dye that changes color upon exposure to basic environments which may indicate corrosion of Mg to Mg(OH)2. In another embodiment, the desiccant element 14350 may be treated with an irreversible hydrochromic dye such as, for example, patent blue V (tryphenylmethane) dye, cobalt II chloride or methyl violet, for example.

FIG. 121 illustrates another desiccant element 14360 that may comprise a portion of the packaging assembly 14300. As can be seen in FIG. 121, the desiccant element 14360 is configured to be received between the deck surface 14204 and the deck-facing surface 14313 of the staple retainer 14310. In one arrangement the desiccant element 14360 comprises a 220 $g/m^2$+/−5% Invercote T2 paper per P-02-003 (Adaptiv) or other commercially available moisture absorbent board that has a slot 14362 therein that is configured to accommodate insertion of the retainer keel 14314 therethrough. Additionally, the desiccant element 14360 is formed with a plurality of individual staple retention protrusions 14364 that protrude downward from a deck-facing surface 14362 of the desiccant element 14360. In the illustrated arrangement, each retention protrusion is 14364 is configured to protrude into a corresponding staple cavity 14220 such that each staple cavity 14220 has a corresponding staple retention protrusion 14364 protruding therein when the desiccant element 14360 is received on the deck 14204. Each staple retention protrusion 14364 is configured to non-movably retain the corresponding staple 14250 on the corresponding staple driver 14270 within the corresponding staple cavity 14220. See FIG. 122. Such desiccant element 14360 immovably restrains the staples 14250 within their respective staple cavities 14220 and prevents their movement which might damage or compromise the staple and/or staple coating.

In at least one arrangement, the desiccant element 14360 may comprise a blue desiccant material containing cobalt chloride which will change to a pink color when the desiccant material has reached its maximum adsorption capacity. This change in color would indicate a compromised package. In another arrangement, for example, the desiccant element 14360 may comprise a PH sensitive dye that changes color upon exposure to basic environments which may indicate corrosion of Mg to Mg(OH)2. In another embodiment, the desiccant element 14360 may be treated with an irreversible hydrochromic dye such as, for example, patent blue V (tryphenylmethane) dye, cobalt II chloride or methyl violet, for example.

FIG. 123 illustrates use of another desiccant element 14370 that is formed as an adhesive strip that is configured to be attached to an upper surface 14315 of the staple retainer 14310. The desiccant element 14370 may comprise a blue desiccant material containing cobalt chloride which will change to a pink color when the desiccant material has reached its maximum adsorption capacity. This change in color would indicate a compromised package. In another arrangement, for example, the desiccant element 14360 may comprise a PH sensitive dye that changes color upon exposure to basic environments which may indicate corrosion of Mg to Mg(OH)2. In another embodiment, the desiccant element 14360 may be treated with an irreversible hydrochromic dye such as, for example, patent blue V (tryphenylmethane) dye, cobalt II chloride or methyl violet, for example.

FIG. 124 illustrates a cartridge retainer assembly 14330 sandwiched between an upper desiccant element 14372 and a lower desiccant element 14380. The upper desiccant element 14372 and the lower desiccant element 14380 may each comprise a 220 $g/m^2$+/−5% Invercote T2 paper per P-02-003 (Adaptiv) or other commercially available moisture absorbent board. In other arrangements, the upper desiccant element 14372 and the lower desiccant element 14380 may each comprise a compliant desiccant material that offers some cushioning protection to the cartridge/retainer assembly 14330. For example, the upper desiccant element 14372 and lower desiccant element 14380 may each comprise an adjunct material or buttress material of the various types and constructions disclosed in the various disclosures that have been herein incorporated by reference that has a cushioning attribute and comprises or is infused with a desiccant material. Such arrangement may additionally provide the cartridge retainer assembly 14330 with cushioning and physical protection from external impacts to the container 14320. In one arrangement, the upper desiccant element 14372 may be affixed to an inner surface of the first layer 14324 of the container 14320 by an adhesive. Similarly, the lower desiccant element 14380 may be affixed to an inner surface of the second layer 14326 in registration with the upper desiccant element 14372 such that the cartridge/retainer assembly 14330 may be positioned therebetween within the container 14320. In other arrangements, the upper desiccant element 14372 may be attached to the upper surface 14315 of the staple retainer 14310 with an adhesive and the lower desiccant element 14380 may be removably attached to the bottom surface of the metal pan 14290. In such instance, the clinician would remove the staple retainer 14310 and the lower desiccant element 14380 before use. When installed in the container 14320, the upper desiccant element 14372 and the lower desiccant element 14380 may serve to substantially immovably constrain the cartridge/retainer assembly 14330 within the container 14320. In an alternative arrangement, the cartridge/retainer assembly 14330 and the upper desiccant element 14372 and lower desiccant element 14380 are inserted into a retainer tube 14374. In one arrangement, the retainer tube 14374 may be formed from a transparent polymer material that permits the cartridge/retainer assembly 14330 to be viewed through the retainer tube 14374 for identification purposes. Retainer tube 14374 serves to hold the upper desiccant element 14372 and lower desiccant element 14380 in registration with the cartridge/retainer assembly 14330 within the container 14320 and affords added protection to the cartridge/retainer assembly 14330. See FIG. 125.

In at least one arrangement, the upper desiccant element 14372 and/or the lower desiccant element 14380 may comprise a blue desiccant material containing cobalt chloride which will change to a pink color when the desiccant material has reached its maximum adsorption capacity. This change in color would indicate a compromised package. In another arrangement, for example, the upper desiccant element 14372 and/or the lower desiccant element 14380 may comprise a PH sensitive dye that changes color upon exposure to basic environments which may indicate corrosion of Mg to Mg(OH)2. In another embodiment, the upper desiccant element 14372 and/or the lower desiccant element 14380 may be treated with an irreversible hydrochromic dye such as, for example, patent blue V (tryphenylmethane) dye, cobalt II chloride or methyl violet, for example.

FIGS. 126 and 127 illustrate another desiccant element 14390 that comprises a tubular-shaped member 14391 that is configured to receive a surgical staple cartridge 14200 therein. The desiccant element 14390 may comprise a 220 $g/m^2$+/−5% Invercote T2 paper per P-02-003 (Adaptiv) or other commercially available moisture absorbent board. For example, the desiccant element 14390 comprises a top portion 14392 that is adapted to cover the staple cavities 14220 in the deck surface 14204 when the surgical staple cartridge 14200 has been inserted therein. The top portion 14392 is attached to a bottom portion 14394 by a first side 14393 that corresponds to a first side 14203 of the cartridge body 14202 and a second side 14395 that corresponds to a second side 14205 of the cartridge body 14202 to form a tubular structure sized to receive a surgical staple cartridge 14200 therein. The bottom portion 14394 of the desiccant element 14390 may be substantially coextensive with a bottom portion 14207 of the cartridge body 14202 which is defined by the pan 14290. A slot 14396 is provided through the top portion 14392 to accommodate passage of the retainer keel 14314 therethrough. The surgical staple cartridge 14200 is inserted into the desiccant element 14390 until the slot 14396 in the top portion 14392 is in registration with the longitudinal slot 14206 in the surgical staple cartridge 14200. The staple retainer 14310 may then be attached to the cartridge/element assembly by inserting the retainer keel 13314 into the slots 14396 and 14206. The proximal-most attachment tabs 14316 are in registration with corresponding windows 14397 in the first side 14393 and the second side 14395 to engage the cartridge body 14202. The desiccant element 14390 stops short of the distal-most attachment tabs 14316 such that the distal-most attachment tabs 14316 may engage the surgical staple cartridge 14200. In other instances, the desiccant element 14390 may be used without a staple retainer 14310. In such instance, for example, the top portion 14392 would not include the longitudinal slot 14396 and the windows 14397 would not be provided in first side 14393 and the second side 14395. The surgical staple cartridge 14200 would be similarly inserted into the desiccant element 14390 for storage therein. The entire unit is then sealed within a hermetically-sealed container 14320.

The desiccant element 14390 may comprise a blue desiccant material containing cobalt chloride which will change to a pink color when the desiccant material has reached its maximum adsorption capacity. This change in color would indicate a compromised package. In another arrangement, for example, the desiccant element 14390 may comprise a PH sensitive dye that changes color upon exposure to basic environments which may indicate corrosion of Mg to Mg(OH)2. In another embodiment, the desiccant element 14390 may be treated with an irreversible hydrochromic dye such as, for example, patent blue V (tryphenylmethane) dye, cobalt II chloride or methyl violet, for example.

FIG. 128 illustrates use of a desiccant element 14376 that is formed as a hollow tube that is sized to receive a cartridge/retainer assembly 14330 therein. The cartridge/retainer assembly 14330 is inserted into the desiccant element 14376 and the entire unit is inserted into the container 14320 for storage and shipping. The desiccant element 14376 may comprise a blue desiccant material containing cobalt chloride which will change to a pink color when the desiccant material has reached its maximum adsorption capacity. This change in color would indicate a compromised package. In another arrangement, for example, the desiccant element 14376 may comprise a PH sensitive dye that changes color upon exposure to basic environments which may indicate corrosion of Mg to Mg(OH)2. In another arrangement, the desiccant element 14376 may be treated with an irreversible hydrochromic dye such as, for example, patent blue V (tryphenylmethane) dye, cobalt II chloride or methyl violet, for example.

FIG. 129 illustrates another desiccant element embodiment 14832 that is supported or stored in a hermetically-sealable container 14320. In various instances, the desiccant element 14382 is configured to be removably attached to the deck surface 14204 of the surgical staple cartridge 14200. The desiccant element 14382 is sized to cover all of the staple cavities 14220 in the surgical staple cartridge 14200 and, as such, eliminates a need to employ a separate staple retainer. Stated another way, the desiccant element 14382 functions as a staple retainer while also providing an additional advantage of moisture absorption. In one arrangement, the desiccant element 14382 includes two opposing side portions 14385 that extend downwardly from a top portion 14383. The side portions 14385 may be configured to releasably engage the corresponding sides of the surgical staple cartridge 14200. In addition or in the alternative, the desiccant element 14382 may be removably coupled to the deck surface 14204 by an adhesive, for example. In alternative embodiments, the desiccant element 14382 may comprise the top portion 14383 and not include the side portions 14385. In such instance, the desiccant element may be removably attached to the deck surface 14204 by an adhesive. In various arrangements, the adhesive may comprise a "double stick" or double-sided tape. However, other adhesive materials may be employed to removably or temporarily affix the desiccant element 14382 to the deck surface 14204. In another arrangement, the desiccant element 14382 may additionally comprise a plurality of staple retention protrusions (see FIG. 122) that protrude from the underside of the desiccant element 14382 and are configured to extend into the staple cavities 14220 as was discussed above. In one arrangement, the staple retention protrusions serve to non-movably retain the staples 14250 within their respective cavities 14220 as well as retain the desiccant element on the deck surface 14204 during storage and shipping. In other arrangements, however, an adhesive may be employed to removably adhere the desiccant element to the deck surface 14204, for example.

The desiccant element 14382 may comprise a 220 $g/m^2$+/−5% Invercote T2 paper per P-02-003 (Adaptiv) or other commercially available moisture absorbent board. The desiccant element 14382 may further comprise a blue desiccant material containing cobalt chloride which will change to a pink color when the desiccant material has reached its maximum adsorption capacity. This change in color would indicate a compromised package. In another arrangement, for example, the desiccant element 14382 may comprise a PH sensitive dye that changes color upon exposure to basic environments which may indicate corrosion of Mg to Mg(OH)2. In another embodiment, the desiccant element 14382 may be treated with an irreversible hydrochromic dye such as, for example, patent blue V (tryphenylmethane) dye, cobalt II chloride or methyl violet, for example.

FIG. 130 illustrates another desiccant element 14384 that is formed to immovably support a surgical staple cartridge 14200 or a cartridge/retainer assembly 14330 during storage and shipping of a cartridge/retainer assembly 14330 within a hermetically-sealable container 14320'. The hermetically-sealable container 14320' may be fabricated from rigid plastic or other suitable material that may or may not be transparent. The hermetically-sealable container 14320 may be configured to support one or a plurality of cartridge/retainer assemblies 14330 and their respective desiccant elements 14384, for example. The hermetically-sealable container 14320' may include sides 14321 that form hermetic seals with each other. One side 14323 may be hinged or otherwise configured to facilitate opening of the hermetically-sealable container 14320'. In other arrangements, for example, the cartridge/retainer assembly 14330 and desiccant support element 14384 may be supported in a hermetically-sealable pouch 14322 or other hermetically-sealable container arrangement, for example.

As can be seen in FIG. 130, the desiccant element 14384 is configured to immovably support the cartridge/retainer assembly 14330 and serves to protect the cartridge/retainer assembly 14330 (or surgical staple cartridge 14200) and minimize movement thereof during shipping and storage within a hermetically-sealable container 14320', for example. In various instances, the desiccant element 14384 comprises a 220 $g/m^2$+/−5% Invercote T2 paper per P-02-003 (Adaptiv) or other commercially available moisture absorbent board that can be folded or otherwise fashioned into a supportive structure for the surgical staple cartridge 14200 or cartridge/retainer assembly 14330. The desiccant element 14384 may further comprise a blue desiccant material containing cobalt chloride which will change to a pink color when the desiccant material has reached its maximum adsorption capacity. This change in color would indicate a compromised package. In another arrangement, for example, the desiccant element 14382 may comprise a PH sensitive dye that changes color upon exposure to basic environments which may indicate corrosion of Mg to Mg(OH)2. In another embodiment, the desiccant element 14384 may be treated with an irreversible hydrochromic dye such as, for example, patent blue V (tryphenylmethane) dye, cobalt II chloride or methyl violet, for example. Those of ordinary skill in the art will appreciate that the desiccant element 14384 may be fashioned into a variety of different supportive structures and configurations configured to non-movably support the surgical staple cartridge 14200 or cartridge/retainer assembly 14330, yet facilitate easy removal therefrom. For example, the desiccant element may comprise a moisture absorbent board that can be folded into a desired shape and retained in that shape by inserting tab portions into corresponding slots and/or using adhesive materials.

Turning next to FIG. 131, in one arrangement, the surgical staple cartridge 14200 comprises an RFID (radio frequency identification) chip or tag 14410 that is positioned in the cartridge body 14202. In the illustrated arrangement for example, the RFID chip 14410 is positioned in one of the lateral walls 14403 of the cartridge body 14202. A variety of RFID chips/tag configurations and systems are disclosed in further detail in U.S. Patent Application Publication No. 2020/0405296 which has been incorporated by reference in its entirety herein. Other RFID chips/tag configurations and systems are disclosed in U.S. Patent Application Publication 2021/0393268, entitled METHOD OF USING MULTIPLE RFID CHIPS WITH A SURGICAL ASSEMBLY, the entire disclosure of which is hereby incorporated by reference herein.

The RFID chip 14410 is associated with and RFID system 14402 that comprises a scanner 14404 that is associated with the control system 14021. See FIG. 112. The RFID system 14402 can either be an active system, a passive system or comprise a combination of active and passive attributes. In passive systems, the onboard RFID chip does not comprise an internal power source and requires a reader or scanner to send a first signal, such as, for example an interrogation signal to the RFID chip. Active radio frequency identification systems also comprise an RFID chip and an RFID scanner. However, the RFID chip in an active RFID system comprises an internal power source. Active RFID systems utilize battery-powered RFID chips that are configured to continuously broadcast their own signal. One type of active RFID chip is commonly referred to as a “beacon.” Such beacon RFID chips do not wait to receive a first signal from an RFID scanner. Instead, the beacon RFID chip continuously transmits its stored information. For example, the beacon can send out its information at an interval of every 3-5 seconds. Another type of active RFID chip comprises a transponder. In such systems, the RFID scanner transmits a signal first. The RFID transponder chip then sends a signal back to the RFID scanner with the relevant information. Such RFID transponder tag systems are efficient, as they conserve battery life when, for example, the RFID chip is out of range of the RFID scanner.

In the illustrated example, the RFID chip 14410 comprises or is associated with a sensor 14420 that is configured to track an environmental parameter within the container 14320. In one arrangement, for example, the sensor 14420 comprises a moisture sensor that is configured to monitor a moisture level within the container 14320. The RFID chip 14410 then transmits the moisture-level information to the scanner 14404 of the control system 14021. This transmission of information may occur when the surgical staple cartridge has been seated in the channel 14112 of the surgical stapling instrument 14000 or it may be transmitted to the control system 14021 prior to being seated in the channel 14112. To prevent the use of a surgical staple cartridge 14200 that has been exposed to a moisture level within the container 14320 that could have conceivably caused premature degrading of the bio-absorbable staples 14250 therein, in at least one arrangement, the control system 14021 is configured to prevent a staple firing stroke or other operation from being performed or permit the staple firing stroke or other operation to be performed based on feedback from the RFID system 14402. For example, the control system 14021 can execute the process 14023 illustrated in FIG. 132. Accordingly, the control circuit 14021 receives 14025 the detected moisture level information from the RFID chip 14410. The detected moisture level information $M_D$ is then compared 14027 to a minimum acceptable level or compatible information $M_A$ (which may be substantially zero or some other level determined to not cause premature degradation of the bio-absorbable staples 14250). If the detected moisture level information $M_D$ is at or below the acceptable moisture level $M_A$, the control system 14021 permits 14029 operation of the surgical instrument systems (firing system, closure system). If the detected moisture level information $M_D$ exceeds the acceptable moisture level $M_A$, the control system 14021 prevents 14031 operation of one or more of the surgical instrument systems.

In various instances, depending upon the particular composition of the staples 14250 stored in a particular surgical staple cartridge 14200, exposure of the staples 14250 to certain temperatures may, for example, result in age hardening of the staples 14250 or annealing of the staples 14250 and/or damage (melting of) to the staple coating. Thus, it is desirable to monitor the temperature level within the container 14320 while the surgical staple cartridge 14200 is being stored and shipped therein to ensure that the temperature level has not attained undesirable levels that could cause premature degradation of the staples 14250.

In another arrangement, for example, the sensor 14420 comprises a temperature sensor that is configured to monitor a temperature level within the container 14320. The RFID chip 14410 then transmits the temperature-level information $T_D$ to the scanner 14404 of the control system 14021. This transmission of information may occur when the surgical staple cartridge 14200 has been seated in the cartridge-receiving channel 14112 of the surgical stapling instrument 14000 or it may be transmitted to the control system 14021 prior to being seated in the channel 14112. To prevent the use of a surgical staple cartridge 14200 that has been exposed to a temperature level within the container 14320 that could have conceivably caused premature degrading of the staples 14250 therein, in at least one arrangement, the control system 14021 is configured to prevent a staple firing stroke or other operation from being performed or permit the staple firing stroke or other operation to be performed based on feedback from the RFID system 14402. For example, the control system 14021 can execute the process 14033 illustrated in FIG. 133. Accordingly, the control system 14021 receives 14035 the detected temperature level information $T_D$ from the RFID chip 14410. The detected temperature level information $T_D$ is then compared 14037 to a minimum acceptable level or compatible information $T_A$ (determined to not cause premature degradation of the staples 14250). If the detected temperature level information $T_D$ is at or below the acceptable temperature level $T_A$, the control system 14021 permits 14039 operation of the surgical instrument systems (firing system, closure system, etc.).

In another arrangement, for example, the sensor 14420 is configured to monitor a temperature level as well as a moisture level within the container 14320. In other arrangements, a separate temperature sensor and a separate moisture sensor may be used. The separate temperature sensor and the separate moisture sensor may be associated with the RFID chip 14410 or the separate temperature sensor and the separate moisture sensor may each be associated with a dedicated RFID chip. In either case, the RFID chips would be configured to transmit the detected temperature level information $T_D$ and detected moisture level information $M_D$ to the scanner 14404/control system 14021. This transmission of information may occur when the surgical staple cartridge 14200 has been seated in the cartridge-receiving channel 14112 of the surgical stapling instrument 14000 or it may be transmitted to the control system 14021 prior to being seated in the channel 14112. To prevent the use of a surgical staple cartridge 14200 that has been exposed to a temperature level and/or a moisture level within the container 14320 that could have conceivably caused premature degrading of the staples 14250 therein, in at least one arrangement, the control system 14021 is configured to prevent a staple firing stroke or other operation from being performed or permit the staple firing stroke or other operation to be performed based on feedback from the RFID system 14402. For example, the control system 14021 can execute the process 14043 illustrated in FIG. 134. Accordingly, the control system 14021 receives 14045 the detected temperature level information $T_D$ and the detected moisture level information $M_D$ from the RFID chip(s) 14410. The detected temperature level information $T_D$ is then compared 14047 to a minimum acceptable level or compatible information $T_A$ (which may be determined to not cause premature degradation of the staples 14250). If the detected temperature level information $T_D$ exceeds the acceptable temperature level $T_A$, the control system 14021 prevents 14041 operation of one or more of the surgical instrument systems. If the detected temperature level information $T_D$ is at or below the acceptable temperature level $T_A$, the control system 14021 then compares 14051 the detected moisture level information $M_D$ to a minimum acceptable level or compatible information $M_A$ (determined to not cause premature degradation of the staples 14250). If the detected moisture level information Mo exceeds the acceptable moisture level $M_A$, the control system 14021 prevents 14049 operation of one or more of the surgical instrument systems. If the detected moisture level information $M_D$ is at or below the acceptable moisture level $M_A$, the control system 14021 permits 14053 operation of the surgical instrument systems (firing system, closure system).

As discussed herein, the staples 14250 may comprise a variety of different compositions and configurations disclosed herein. In certain instances, each composition of the staples 14250 may have unique sensitivities to a particular moisture level and/or temperature level. Thus, the staples 14250 in one surgical staple cartridge 14200 may be more sensitive to a particular moisture and/or temperature level than the staples 14250 in another surgical staple cartridge that may also be employed in the surgical stapling instrument 14000. In such instances, the surgical staple cartridge 14200 may comprise another RFID chip/tag (not shown) that contains identification information regarding the surgical staple cartridge 14200 including the particular composition of the staples 14250 stored therein. This information is then transmitted by the RFID chip/tag to the control system 14021. In other arrangements, such information could also be transmitted by RFID chip 14110. Various RFID system arrangements and configurations that are configured to transmit cartridge information to a surgical instrument controller or control system are disclosed in various documents that have been incorporated herein by reference. In either case, the control system 14021 then looks up/determines the acceptable temperature and/or moisture level information (compatible information) for the particular surgical cartridge 14200 that has been seated in the channel 14112 or is slated to be used with the surgical stapling instrument 14000. That compatible information for that particular surgical staple cartridge 14200 is used during the implementation of the processes described herein to determine whether the surgical staple cartridge 14200 was exposed to unacceptable temperature and/or moisture levels (for the bio-absorbable staples in that particular cartridge) within the container.

FIG. 135 illustrates a container 14320 that comprises an indicator member 14500 that has a sensor 14510 associated therewith. In one arrangement, the sensor 14510 comprises a moisture sensor that is configured to detect a moisture level within the container 14320 and provide a signal to the indicator member 14500 if the sensed moisture level exceeds a predetermined level which could cause, for example, premature degradation of the bio-absorbable staples 14250 that are stored in the surgical staple cartridge 14200. In one arrangement, the indicator member 14500 comprises a light emitting diode (LED). The indicator member 14500 and the sensor 14510 may each have an onboard power source such that when the moisture level inside of the container 14320 has exceeded the predetermined level, the LED is illuminated. The clinician would then be informed that the integrity of the staples 14250 may have been compromised due to exposure to moisture and then avoid use of the surgical staple cartridge 14200.

In an alternative arrangement, the sensor 14510 comprises a temperature sensor that is configured to detect a temperature level within the container 14320 and provide a signal to the indicator member 14500 if the sensed temperature level exceeds a predetermined level which could cause, for example, premature degradation of the staples 14250 that are stored in the surgical staple cartridge 14200. In one arrangement, the indicator member 14500 comprises a light emitting diode (LED). The indicator member 14500 and the sensor 14510 may each have an onboard power source such that when the temperature level inside of the container 14320 has exceeded the predetermined acceptable level, the LED 14500 is illuminated. The clinician would then be informed that the integrity of the staples 14250 may have been compromised due to an undesirable temperature within the container 14320 and then avoid use of the surgical staple cartridge.

In still another arrangement, the sensor 14510 (or separate sensors) is configured to sense a moisture level and a temperature level within the container 14320. If the moisture level exceeds the predetermined level or the temperature exceeds the predetermined level, an LED 14500 would be illuminated. In other embodiments, after the control system 14021 compares the transmitted moisture level that was detected within the container 14320 and/or the transmitted temperature level that was detected within the container, the control system 14021 may activate another indicator that may be onboard the surgical stapling instrument 14000. For example, the indicator may comprise an LED, speaker, buzzer, haptic feedback system, notification screed onboard the surgical stapling instrument 14000 or otherwise associated with the surgical stapling instrument 14000, etc. to provide the clinician with an indication that the surgical staple cartridge 14200 may have been compromised and should not be used. In other instances, the control system may be configured to provide the clinician with an indication of the environmental history of a particular container and the cartridge/retainer assemblies or surgical staple cartridge retained therein. Such environmental history may be presented in table or graph form, for example, that is displayed on a display (not shown) associated with the surgical stapling instrument.

Turning to FIG. 136, in various examples, the container 14320 may be filled with a gas 14520 to provide the interior of the container 14320 with a desired environment. For example, the gas 14520 may comprise dry nitrogen or argon which serves to provide the interior of the container with an extremely low moisture and oxygen environment.

FIG. 137 and FIG. 138 illustrate an alternative staple retainer 14310' that is substantially similar to staple retainer 14310 described above, except that the staple retainer 14310' additionally comprises a plurality of staple retention protrusions 14317 that protrude downwardly from the deck-facing surface 14313 of the elongate body portion 14312. The staple retainer 14310' may or may not comprise a locator keel 14314 as described above. In the illustrated arrangement, each retention protrusion 14317 is configured to protrude into a corresponding staple cavity 14220 such that each staple cavity 14220 has a corresponding staple retention protrusion 14364 protruding therein when the staple retainer 14310' is received on the deck 14204 of the surgical staple cartridge 14200. Each retention protrusion 14317 is configured to non-movably retain the corresponding staple 14250 on the corresponding staple driver 14270 within the corresponding staple cavity 14220. See FIG. 138. Such staple retainer 14310' immovably restrains the staples 14250 within their respective staple cavities 14220 and prevents their movement which might damage or compromise the staple and/or staple coating.

FIG. 139 illustrates a staple 14250 within a staple cavity 14220 in the cartridge body 14202 of a surgical staple cartridge 14200. The staple 14250 is supported on a staple driver 14270 that is slidably supported in the staple cavity 14220. In the illustrated example, the staple 14250 comprises any one of the staple configurations disclosed herein that include a staple coating component 14251. The staple coating 14251 may comprise any of the various staple coating compositions disclose herein that may be somewhat softened (melted) when exposed to an appropriate amount of heat. In various instances, the staples 14250 may be manufactured and coated as described herein and are then inserted into a corresponding staple cavity 14220 in a surgical staple cartridge wherein it is supported on a corresponding staple driver 14270. In one embodiment, the staples 14250 are exposed to a heat source 14600 that is configured to apply an amount of heat to the staple 14250 that is sufficient to cause the coating 14251 on the staple 14250 to become sticky or tacky without degrading or causing significant migration of the coating on the underlying staple material which might otherwise lead to the premature degradation of the staple 14250. Those tacky portions 14253 of the coating 14251 that contact the inner walls 14221 of the staple cavity 14220 serve to temporarily adhere the staple 14250 to the inner walls 14221 if the staple cavity 14220. Similarly, the tacky portion 14255 of the coating 14251 that contacts the staple driver 14270 serves to temporarily adhere the staple 14250 to the staple driver 14270. Those of ordinary skill in the art will understand that the connections formed between the tacky portions 14253 and the inner walls 14221 and the connection formed between the tacky portion 14255 and the staple driver 14270 are easily defeated when the staple driver 14270 drives the staple 14250 into forming contact with the staple-forming undersurface 14156 of the anvil 14152. However, such temporary connections between the staple 14250 and the inner walls 14221 and/or the staple driver 14270 serve to prevent movement of the staple 14250 within the staple cavity 14220 during storage and shipping of the surgical staple cartridge 14200 which might otherwise damage the staple coating 14251 and lead to premature degradation of the staple 14250. Such arrangement may be particularly advantageous when the shape of the staple 14250 normally does not afford much retaining engagement with the inner walls of the corresponding staple cavity. For example, when the staple 14250 is generally U-shaped and not V-shaped and the staple legs do not retainingly engage the inner walls of the staple cavity. When the above-described method is employed, a staple retainer may not be needed, for example. However, in various instances, a staple retainer 14310 may be attached to the cartridge body 14202 to prevent debris from entering the staple cavities 14220 and provide an additional degree of protection to the staples 14250 contained therein.

FIG. 140 illustrates a staple 14250 within a staple cavity 14220 in the cartridge body 14202 of a surgical staple cartridge 14200. The staple 14250 is supported on a staple driver 14270 that is slidably supported in the staple cavity 14220. In the illustrated example, the staple 14250 comprises any one of the bio-absorbable staples disclosed herein. In the illustrated arrangement, after the staples 14250 have been inserted into their corresponding staple cavity 14220, the staples 14250 may be coated in place with a Vapor Corrosion Inhibitor (VCI) 14610. Thereafter, the surgical staple cartridge 14200 is sealed in a container 14320. Vapor corrosion inhibitors (VCIs) are substances that slowly release a corrosion preventative compound into a sealed air space, effectively protecting exposed metal surfaces. VCIs are often used in situations where it is impractical or undesired to use rust preventative liquids or other surface treatments. VCI's can be built into films, papers or be emitted by a specific diffuser. In other arrangements, any one of the desiccant element configurations disclosed herein may be fabricated from a material configured to diffuse a vapor corrosion inhibitor therefrom in place of the desiccant material and in other instances in addition to the desiccant material. In other arrangements, the staples 14250 may be treated with a VCI coating before being installed in the cartridge body 14202.

In various instances, when using surgical staple cartridges that employ bio-absorbable staples, it may be desirable to "pre-treat" the staple-forming undersurface 14156 of the anvil 14512 prior to use. Stated another way, it may be desirable to clean off body fluid and waters (since the bio-absorbable staples 14250 may be water interactive) from the staple-forming undersurface 14156 and also lubricate the staple-forming undersurface 14156 to prevent erosion of the bio-absorbable staple 14250 or its coating during the staple-forming process. Further to the above, the absorption of the staples 14250 may be driven by the exposure level to $O_2$, $CO_2$, and $H_2O$, which allows the staples 14250 to first form oxidation product and then be converted into salts and absorbed. In various instances, the staples 14250 may include a coating as disclosed herein to slow these processes. If the forming motion of the staple tips through the staple-forming pocket in the staple-forming undersurface 14156 of the anvil 14152 either damages or rubs off the coating, it may "initiate" the processes faster than intended. In various arrangements, the anvil 14152 is fabricated from stainless steel. If the stainless steel staple-forming pockets in the anvil gouge, gall, or otherwise create defects in the surface of the staple 14250, premature degradation of the staples 14250 may occur. The speed of the degradation, as well as the structural integrity of the staple 14250, may be dependent upon the amount of surface area of the underlying staple member or core that is undesirably exposed during the forming process.

FIG. 141 illustrates use of a pretreatment element or adjunct cassette 14700 for pretreating the staple-forming undersurface 14156 of an anvil 14152 to address many if not all of the foregoing challenges. In at least one embodiment, the pretreatment element 14700 comprises a fabric or sponge body material 14702 that is saturated with a pre-treatment medium 140704 that may comprise, for example, sodium sterates, silicones, absorbable polymers, etc. The body material 14702 may include an absorbent attributes for absorbing water and body fluids out of the staple-forming pockets in the staple-forming undersurface 14156. In various instances, the pretreatment element 14700 may be configured to fill or introduce each of the staple-forming pockets in the staple-forming undersurface 14156 with a soft hydrogel, an absorbable polymer (polyethylene glycol (PEG), polyglycolic acid (PGA), etc.). Such arrangements would enable the material to coat the anvil 14152 as well as portions of the staples 14250 when they are deployed through the staple-forming pockets. The pretreatment mediums 14704 may additionally have a hydrophobic aspect that would further inhibit $H_2O$ from being attracted to the staple 14250 during or after the staple-forming process.

In the example depicted in FIG. 141, the pretreatment element or adjunct cassette 14700 is attached to a staple retainer 14310. The staple retainer 14310 is then attached to a surgical staple cartridge 14200 to form a cartridge/retainer assembly 14330. FIGS. 142A and 142B illustrate installation of the cartridge/retainer assembly 14330 into the channel 14112 of the surgical end effector 14100. Once the cartridge/retainer assembly 14330 has been at least partially seated in the channel 14112, the surgical stapling instrument 14000 may be actuated to move the anvil 14152 to a closed position. As the anvil 14152 moves toward the cartridge/retainer assembly 14330, the staple-forming undersurface 14156 of the anvil 14152 contacts the pretreatment element 14700 and may complete the seating of the cartridge/retainer assembly 14330 into the cartridge-receiving channel 14112. As the staple-forming undersurface 14156 contacts the pre-treatment element 14700, the pretreatment medium 14704 therein is transferred to or "pretreats" the staple-forming undersurface 14156 of the anvil 14152. See FIG. 142C. Thereafter, the anvil 14152 is moved to the open position and the staple retainer 14310 is removed from the seated surgical staple cartridge 14200. The surgical end effector 14100 is then ready for use. See FIG. 142D.

FIG. 143 illustrates an alternative arrangement wherein the pretreatment element 14700 is not attached to a staple retainer 14310. In such instance, a cartridge/retainer assembly 14330 may be seated in the cartridge-receiving channel 14112 of the surgical end effector 14100 and thereafter the staple retainer 14310 is detached from the surgical staple cartridge 14200. See FIGS. 144A-144C. After the staple retainer 14310 has been removed from the surgical staple cartridge 14200, the pretreatment element 14700 is positioned on the deck surface 14204 of the surgical staple cartridge 14200. See FIGS. 143 and 144D. After the pre-treatment element 14700 has been positioned on the deck surface 14204, the surgical stapling instrument 14000 may be actuated to move the anvil 14152 to a closed position. As the anvil 14152 moves toward the surgical staple cartridge 14200, the staple-forming undersurface 14156 of the anvil 14152 contacts the pretreatment element 14700 thereby transferring the pretreatment medium 14704 to the staple-forming undersurface of the anvil 14152. See FIG. 144E. Thereafter, the anvil 14152 is moved to the open position and the pretreatment element 14700 is removed from the seated surgical staple cartridge 14200. The surgical end effector 14100 is then ready for use. See FIG. 144F.

In various examples described herein, the container 14320 comprises a hermetically-sealable peel-pouch that is fabricated from an air/gas impermeable and moisture impermeable foil or plastic material. In other examples, the container 14320 is constructed of other suitable materials that can provide a hermetic seal. In view of the teachings herein, other materials for use in constructing the container 14320 of packaging assembly 14300 will be apparent to those of ordinary skill in the art. The container 14320 may also comprise other hermetically-sealable structures that are fabricated from a gas and moisture impermeable material and are configured to store one or more surgical staple cartridges 14200 and/or one or more of the various cartridge/retainer assemblies 14330 disclosed herein. Such other container configurations may be fabricated from rigid material such as a plastic and may be formed with cartridge retention cavities or retention features for non-movably retaining one or more surgical staple cartridges 14200 and/or one or more cartridge/retainer assemblies 14330 therein while facilitating easy removal therefrom after the container has been opened. In various arrangements, a container may be fabricated from a transparent material or otherwise be configured to permit the contents of the container to be viewed without opening the container. In addition, or in the alternative, identifying indicia, such as, for example RFID tags, bar codes, QR codes, labels etc. may be applied to the outer surface of the container.

The various packaging assemblies, containers, staple retainers, desiccant elements disclosed herein offer solutions to many if not all of the challenges associated with storing and shipping surgical staple cartridges that contain bio-absorbable staples that are designed to degrade within a desired period of time after being formed in tissue. As was discussed above, the absorption of the staples may be driven by the exposure level to $O_2$, $CO_2$, and $H_2O$, which allows the staples to first form oxidation product and then be converted into salts and absorbed. If the staples are exposed to $O_2$, $CO_2$, and $H_2O$, for example, while being stored, shipped and otherwise prior to use, they may prematurely begin to degrade which could detrimentally affect their ability to properly form and retain tissue after deployment into the body for a desired period of time. The various embodiments disclosed herein serve to prevent the surgical staple cartridges containing such bio-absorbable staples from exposure to such elements prior to use while facilitating easy access thereto.

The various bio-absorbable staples disclosed herein may begin to prematurely deteriorate if exposed to moisture and/or higher temperatures. The various packaging assemblies and packaging systems disclosed herein may comprise sensors configured to monitor the moisture level and/or temperature level experienced by the surgical staple cartridge(s) or cartridge/retainer assemblies stored within the hermetically-sealable container. Such sensor arrangements may be associated with indicator members, LED's, etc. in the container and/or be associated with an RFID system in the surgical stapling instrument that is configured to prevent operation of the surgical stapling instrument when the moisture level and/or temperature level within the container has exceeded level(s) that might result in the premature degradation of the bio-absorbable staples. The various desiccant elements disclosed herein may also change color in the presence of moisture to provide the user with an indication that the staples in the surgical staple cartridge have been exposed to moisture and may have begun to prematurely degrade. In other instances, the staples may be treated with a vapor corrosion inhibitor and/or any one of the desiccant element configurations disclosed herein may be fabricated from a material configured to diffuse a vapor corrosion inhibitor therefrom in place of the desiccant material and in other instances in addition to the desiccant material.

Further to the above, some of the bio-absorbable staples disclosed herein are provided with a coating to slow oxidation process. Thus, various container, staple retainers, desiccant elements, and methods disclosed herein serve to non-movably retain the surgical staple cartridges within their respective container and/or non-movably retain each staple within its respective staple cavity. In one arrangement for example, the staples are heated within their respective cavities to cause the coating on the portions of the staples that are in contact with the cavity walls and/or the staple driver to melt the coating to temporarily adhere the staples to the inner walls and/or the staple driver. Such arrangements and methods prevent movement and/or migration of the individual staples and cartridges during storage and shipping which could otherwise damage the staple coating and cause the staples to prematurely degrade. It will also be appreciated that while the various packaging assemblies and methods disclosed herein are particularly well suited for use with surgical staple cartridge that contain bio-absorbable staples, the person of ordinary skill in the art will appreciate that the various packaging assemblies and methods disclosed herein may find equal utility when used in connection with surgical staple cartridges containing other forms of staples and/or fasteners.

As mentioned above, in many instances, after the staples have been installed in the surgical staple cartridge, the surgical staple cartridge is then sterilized utilizing, for example, gamma radiation, x-rays, high-energy electrons, beta radiation, ethylene oxide, plasma peroxide, steam etc. The various staple retainers, desiccant elements, adjuncts and cassettes disclosed herein may be coupled to a surgical staple cartridge prior to sterilization. In such instances, the staple retainers, desiccant elements, adjuncts and cassettes provide air/fluid paths for a sterilization medium to invade and be flushed from the interior portions of the cartridge base.

As indicated above, various bio-absorbable staples disclose herein may be coated with a coating to slow the oxidation of the staple core material. Thus, it may be advantageous to prevent or minimize damage to that coating as the staple is being formed through contain with a corresponding staple pocket in the anvil. Thus, any of the packaging assemblies and packaging systems disclosed herein may comprise or additionally comprise a pretreatment element that is configured to apply a pretreatment medium to the staple pockets prior to forming the staples. The pretreatment medium may comprise sodium sterates, silicones, absorbable polymers, and hydrogels. The pretreatment element may be associated with a staple retainer or be separate from the staple retainer and placed between the cartridge deck surface and the anvil after the staple retainer has been detached from the staple cartridge. The pretreatment element may be packaged in a dedicated package/pouch and included in the hermetically-sealable container with the surgical staple cartridge(s) or cartridge/retainer assemblies contained therein.

The various packaging assemblies and packaging systems disclosed herein may include a hermetically-sealable container and a staple retainer. The staple retainer may be configured to prevent movement of each staple within their individual cavity. The packaging assemblies and packaging systems may include a desiccant element contained within the container to absorb and reduce moisture within the container and/or the surgical staple cartridge(s). The desiccant element may be configured to be removably trapped between a staple retainer and a surgical staple cartridge and/or attached to the staple retainer or removably attached to the surgical staple cartridge and used without a staple retainer. The desiccant element may be configured to prevent movement of each staple within their individual cavity. The desiccant element may be configured to change color in the presence of moisture. Multiple desiccant elements may be employed within the container to also isolate the surgical staple cartridge or cartridge/reload assembly from vibration and shock. In other instances, the desiccant element may be configured to non-movably support a surgical staple cartridge or cartridge/retainer assembly therein. The container may be equipped with sensor(s) to detect the moisture level and/or temperature levels in the container and provide indications thereof. The detected levels may be used by the stapling instrument controller to prevent operation of the surgical stapling instrument if the levels exceed acceptable levels.

As discussed herein, different staple cartridges can have different types of staples stored therein. In various embodiments, a staple cartridge is sold and delivered to a clinician with one or more indicia thereon which indicate to the clinician the type of staples stored in the staple cartridge. In at least one embodiment, the indicia include words that inform the clinician that pure magnesium and magnesium alloy staples are contained therein. In various embodiments, the indicia include visual representations of the types of staples and their locations with the staple cartridge. In at least one such embodiment, the indicia comprises a staple pattern than mimics the staples the pattern of staples stored in the enclosed staple cartridge. For instance, if the pure magnesium staples are stored in the proximal end and the distal end of the staple cartridge and the magnesium alloy staples are stored in between the proximal end and the distal end, solid black lines can be used as representations of the magnesium alloy staples while dashed black lines can be used as representations of the pure magnesium alloy staples. The dashed black lines, as opposed to the solid black lines, signify that the pure magnesium staples may bioabsorb faster than the magnesium alloy staples. Similarly, thick solid lines can be used to represent staples having a thicker wire diameter while thin solid lines can be used to represent staple staples having a thinner wire diameter, for example.

Once the staple cartridge is removed from its packaging and the packaging is discarded, however, the clinician may not be able to discern, absent more, what type of staples and/or the arrangement of the staples stored in the staple cartridge. In various embodiments, the staple pattern indicia discussed above is present on the staple retainer attached to the staple cartridge. A staple cartridge assembly 8600 is depicted in FIG. 145 which comprises, among other things, a cartridge body 8610, staples 8630 (FIG. 146) removably stored in the cartridge body 8610, and a staple retainer 8650 removably attached to the cartridge body 8610 that prevents the staples 8630 from falling out of the top of the staple cavities. The staple retainer 8650 comprises latch arms 8655 which releasably hold the staple retainer 8650 to the cartridge body 8610. To install the staple cartridge assembly 8600 in a stapling instrument, a clinician can grab a distal end 8652 of the staple retainer 8650 and guide the staple cartridge assembly 8600 into position in a cartridge jaw of the stapling instrument. Once the staple cartridge assembly 8600 is positioned in the cartridge jaw, the clinician can push down on a top portion 8654 of the staple retainer 8650 to seat the staple cartridge assembly 8600 into the cartridge jaw. At such point, the clinician can lift upwardly on the distal end 8652 of the staple retainer 8650 to detach the staple retainer 8650 from the staple cartridge. Up until that point, the staple pattern indicia is present on the staple cartridge assembly 8600 and, in the event that several staple cartridges are unpackaged simultaneously during a surgical procedure, the clinician can still discern the difference between staple cartridges that otherwise look the same. As illustrated in FIG. 145, the staple retainer 8650 has indicia 8656 molded into the top portion 8654 of the staple retainer 8650 and, in various instances, the staple pattern indicia can be molded into the staple retainer 8650 and/or printed on the staple retainer 8650 using ink, for example. A staple cartridge assembly 8700, which is similar to the staple cartridge assembly 8600 in many respects, includes a staple retainer 8750 including two longitudinal row indicia 8760 marked thereon which signify to the clinician that the staples underlying the row indicia 8760 are highly bioabsorbable staples which can bioabsorb within 30 days, for example. Such longitudinal row indicia could alternatively be used to signify a different aspect of the underlying staples. In any event, the staple cartridge 8600 further comprises a chip 8660, such as an RFID tag, for example, which can be read by a stapling instrument to identify the staple cartridge, as discussed further below.

Once a staple retainer is removed from a staple cartridge and the staple retainer is discarded, the clinician may not be able to discern what type of staples and/or the arrangement of the staples stored in the staple cartridge, absent more. As discussed below, various staple cartridges comprise indicia thereon which indicate the type and/or arrangement of staples contained therein.

FIG. 146A illustrates a staple cartridge 9200 comprising, among other things, a cartridge body 9202 and a cartridge pan 9204. The cartridge body 9202 comprises a plurality of staple cavities defined therein which are each configured to removably store one or more staples therein. The cartridge pan 9204 is assembled to the cartridge body 9202 and is configured to at least partially retain the staples within the staple cavities. The cartridge body 9202 comprises an identification feature 9206 on its distal end. The identification feature 9206 comprises a shiny dot that visually stands out compared to the rest of the cartridge body 9202. Various embodiments are envisioned where the identification feature 9206 is a reflective metallic dot that is shiny compared to the rest of the cartridge body 9202. In at least one embodiment, the identification feature 9206 identifies the type of staples contained within the staple cartridge. For example, the identification feature can 9206 can indicate the staples are magnesium staples, zinc staples, iron staples, titanium staples, stainless steel staples, stamped staples, wire staples, or combinations thereof. In such instances, the type of staples identified includes the size of the staples, the manufacturing process used to create the staples, the materials that the staples are constructed from, the coatings applied to the staples, the lubricants on the staples, and/or whether the staples are comprised of wire and/or are stamped from a sheet of material, among other things.

FIG. 146B illustrates a staple cartridge 9300 comprising a cartridge body 9302 and a cartridge pan 9304. The cartridge body 9302 is comprised of plastic and metal flakes molded into or embedded within the plastic. In such instances, the cartridge body 9302 is visually different as compared to a cartridge body molded without metal flakes, for example. As a result, the cartridge body 9302 is configured to reflect light better than a cartridge body molded without metal flakes and, as a result, the two staple cartridges are readily discernable to a clinician. As discussed above, the cartridge body 9302 with metal flakes identifies the type of staple cartridge and/or the type of staples within the staple cartridge 9300. In at least one instance, a staple cartridge without metal particles embedded in the cartridge body indicates that stainless steel staples are contained therein while a staple cartridge with metal particles embedded in the cartridge body indicates that magnesium staples are contained therein, for example.

FIG. 146C illustrates a staple cartridge 9400 comprising a cartridge body 9402 and a cartridge pan 9404. The staples stored within the cartridge body 9402 are identifiable by text or a symbol, such as the text 9406 on the cartridge body 9402. The text 9406 reads "Mg" which indicates that magnesium staples are stored within the staple cartridge 9400. In at least one other embodiment, the text 9406 reads "Zn" to indicate that zinc staples are stored within the staple cartridge. The text and/or symbol can be placed in any suitable location on the cartridge body and can be applied to the staple cartridge using any suitable method. In the illustrated embodiment, the text is applied onto the staple cartridge using ink. Other embodiments are envisioned where the text and/or symbol is engraved into the cartridge body 9402 using a laser engraving process, for example, such that the text and/or symbol is cut into the cartridge body 9402. Various embodiments are envisioned where the text and/or symbol is created during the injection molding process of the cartridge body 9402 where the text and/or symbol can extend from and/or extend into the distal end of the cartridge body 9402.

FIG. 146E illustrates a staple cartridge 9600 comprising a cartridge body 9602 and a cartridge pan 9604. The cartridge pan 9604 comprises text 9606 written on its proximal end which reads "Mg", for example, indicating that magnesium staples are stored within the staple cartridge 9600. In at least one other embodiment, the text 9606 reads "Zn" to indicate that zinc staples are stored within the staple cartridge. In the illustrated embodiment, the text is applied onto the cartridge pan 9604 using an ink spraying process, for example, although any suitable process may be used. Other embodiments are envisioned where the text and/or symbol is stamped into the cartridge pan 9604 such that the text and/or symbol creates an indentation in the cartridge pan 9604.

FIG. 146D illustrates a staple cartridge 9500 comprising a cartridge body 9502 and a cartridge pan 9504. The cartridge body 9502 comprises a deck configured to support patient tissue and staple cavity extensions 9506 extending from the deck which at least partially surround at least some of the staple cavities. The amount, position, and/or shape of the protrusions 9506 can be used by a clinician to identify the type of staple cartridge 9500 and/or the type of staples contained within the staple cartridge 9500. In the illustrated embodiment, some of the proximal-most staple cavities of the cartridge body 9502 do not have staple cavity extensions 9506 surrounding the staple cavities. Such a staple cartridge 9500 is visually different than a staple cartridge with all of the staple cavities having extensions. In at least one such embodiment, the presence of all the staple cavity extensions 9506 on a staple cartridge indicates that stainless steel staples are contained therein and the absence of the proximal staple cavity extensions 9506 on a staple cartridge indicates that magnesium staples are contained therein, for example. Other embodiments are envisioned where the staple cavity extensions 9506 are positioned solely along the outermost longitudinal rows of staple cavities in the cartridge body. Such embodiments could indicate that stainless steel staples are contained in the outermost longitudinal rows while magnesium staples are contained in the longitudinal rows not having staple cavity extensions 9506, for example. Oher embodiments are envisioned where the staple cavity extensions 9506 laterally interconnect with one another from one row of staple cavities to the next. Such embodiments could indicate that coated staples are contained therein, for example. Other embodiments are envisioned where the staple cavity extensions 9506 longitudinally interconnect within a longitudinal row of staple cavities. Further, other embodiments are envisioned with staple cavity extensions 9506 positioned distally with respect to the distal-most staple cavities (i.e., beyond the staple line). Such embodiments could indicate that zinc staples are stored therein, for example. In any event, a clinician can identify the type of staple cartridge and/or the type of staples within the staple cartridge based on the presence or absence of staple cavity protrusions or extensions 9506.

FIG. 146F illustrates a staple cartridge assembly 9700 comprising a cartridge body 9702, a cartridge pan 9704 attached to the cartridge body 9702, and an implantable layer 9708 positioned on the deck of the cartridge body 9702. The implantable layer 9708 comprises a symbol 9709 that is configured to visually identify the type of staple cartridge and/or the type of staples stored within the staple cartridge. When the staples are fired from the staple cartridge assembly 9700 in use, the staples implant the layer 9708 against the patient tissue and, as a result, the symbol 9709 on the implanted layer 9708 can be reviewed and referenced by the clinician during the surgical procedure to verify the type of staples that have been implanted. In addition, the cartridge body 9702 comprises a symbol 9706 that matches the symbol 9709 on the layer 9708. When the clinician removes the stapling instrument from the patient after firing the staples and implanting the layer 9708, the symbol 9706 is still visible on the cartridge body 9702 and can be reviewed and referenced by the clinician to verify the type of staples just implanted.

In at least one embodiment, the type of staple cartridge and/or the type of staples stored within a staple cartridge is identified during the installation of the staple cartridge into a stapling instrument. For example, audible and/or tactile feedback is given to a user of the stapling instrument through the stapling instrument when the staple cartridge is installed to alert the user that the staple cartridge installed is not compatible with the stapling instrument. Embodiments are also envisioned where audible and/or tactile feedback is given to a user of the stapling instrument through the stapling instrument when the staple cartridge is installed to alert the user that the staple cartridge installed is compatible with the stapling instrument.

In at least one embodiment, text and/or symbols such as those described herein are placed onto the anvil of a stapling instrument. In such instances, the symbol on the anvil identifies the type of staple cartridge that is compatible for use with that specific instrument and anvil. Other embodiments are envisioned where the text and/or symbol is placed on the elongate shaft of a stapling instrument. Similarly, the text and/or symbol identifies the type of staple cartridge that is compatible for use with that specific instrument.

Once staples have been implanted into patient tissue, the clinician may not be able to discern what the implanted staples are comprised of. In various embodiments, the types of the staples implanted in the patient tissue are visually discernable based on the color of the staples. In at least one such embodiment, fast-absorbing staples comprise a color, such as a purple hue, for example, and slower-absorbing staples comprise different colors, such as a black hue, for example. After the clinician has stapled patient tissue with a staple cartridge, the clinician can unclamp the staple cartridge from the patient tissue and visually confirm—either directly or via an endoscope—that the appropriate staples had been implanted in the patient tissue. In various instances, faster-absorbing staples release the patient tissue within 30 days while slow-absorbing staples release the patient tissue within 60 days, for example. Any other suitable time frames could be used.

In various embodiments, further to the above, the staples are electroplated to have a specific color, or colors. In certain instances, a coating is applied to the staples that has a specific color, or colors, and/or includes a dye to have a specific color, colors. In at least one embodiment, a staple cartridge includes staples having pure magnesium staples and magnesium alloy staples which are both covered with the same coating. In such embodiments, the coating on the pure magnesium staples is dyed with a first dye to make a first color and the coating on the magnesium alloy staples is dyed with a second dye to a make a second color that is different than the first color. In these embodiments, the colors comprise visible colors under ordinary surgical room lighting, white light, and/or yellow light, for example. In other embodiments, the dyes comprise fluorescent inks that are clear, or at least not readily noticeable, unless exposed to ultraviolet light in which the dyes appear colorized.

Figure 71:
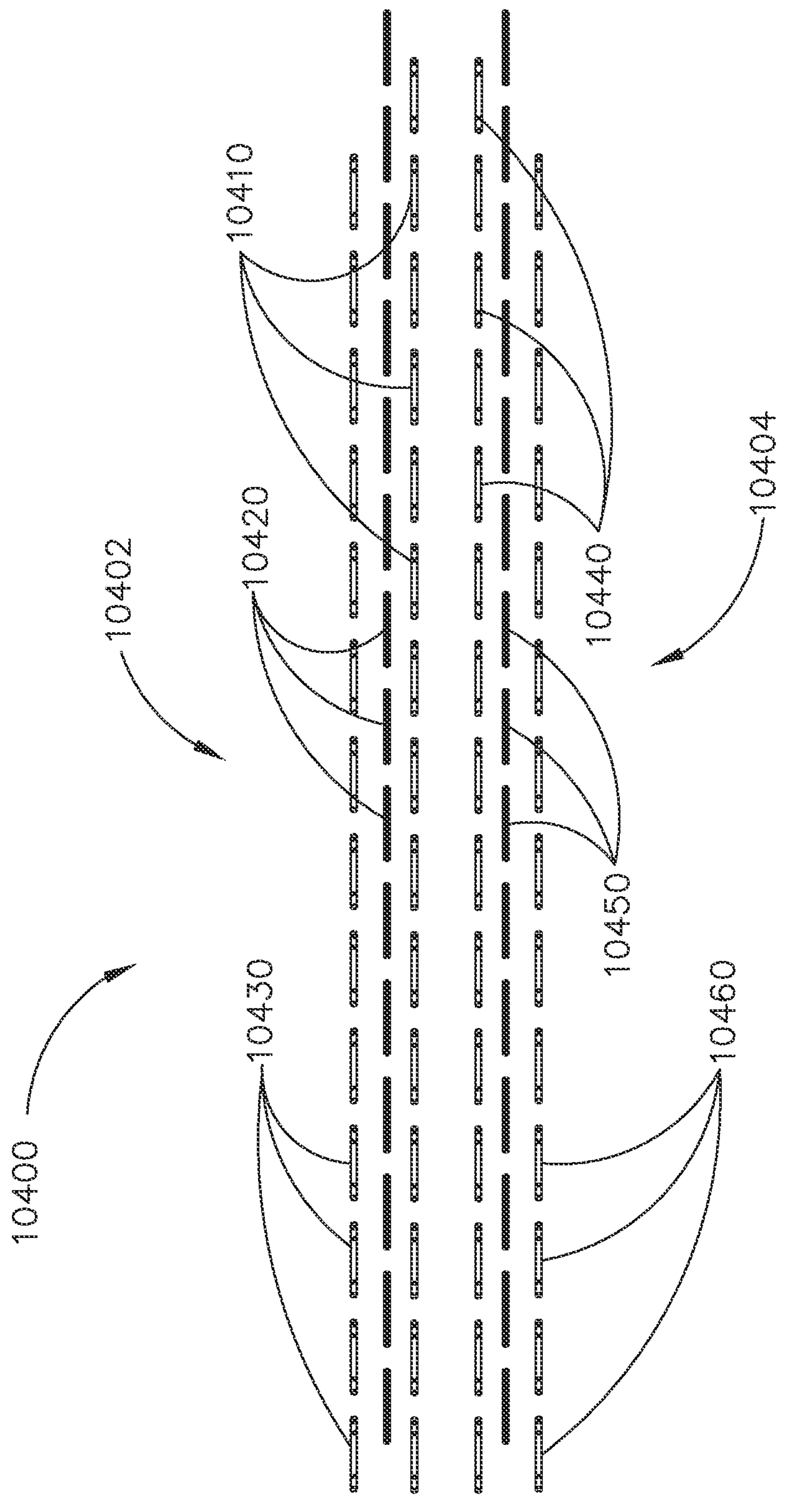
FIG. 71 is a plan view of a plurality of staple lines after being implanted into the tissue of a patient.

FIG. 71 illustrates a staple pattern including staple lines 10400 implanted into patient tissue. The staple lines 10400 comprise a first staple line 10410 on a first side 10402 of a tissue incision, a second staple line 10420 on the first side 10402 of the tissue incision, and a third staple line 10430 on the first side 10402 of the tissue incision. The second staple line 10420 is positioned intermediate the first staple line 10410 and the third staple line 10430. Further, the staple lines 10400 comprise a fourth staple line 10440 on a second side 10404 of the tissue incision opposite the first side 10402, a fifth staple line 10450 on the second side 10404 of the tissue incision, and a sixth staple line 10460 on the second side 10404 of the tissue incision. The fifth staple line 10450 is positioned intermediate the fourth staple line 10440 and the sixth staple line 10460. In the illustrated embodiment, the staples on the first side 10402 of the tissue incision and the staples on the second side 10404 of the tissue incision are mirror images of each other. However, other embodiments are envisioned with different numbers of staple lines, different staples, and/or a different number of staples on the different sides of the tissue incision.

Further to the above, the second staple line 10420 and the fifth staple line 10450 are visibly different than the other staple lines 10410, 10430, 10440, 10460. In at least one embodiment, the second staple line 10420 and the fifth staple line 10450 comprise fast-absorbing staples and the remaining staple lines comprise slow-absorbing staples and/or non-absorbable staples. That said, other embodiments are envisioned where the staple lines 10410, 10430, 10440, 10460 comprise fast-absorbing staples and the staple lines 10420, 10450 comprise slow-absorbing and/or non-absorbable staples. In any event, the staple lines 10400 vary in their visual appearance due to the types of staples within each row. Different staples can have different colors due to their absorbability, unformed size, formed size, coating, and/or lubrication, for example. Staples having different colors can signal other attributes about the staples. For instance, staples can have different colors to signify different unformed staple heights and/or different formed staple heights. Also, for instance, staples can have different colors to signify different hardnesses and/or different strengths of the staple substrates.

In at least one embodiment, the implanted staples 10400 are the same color as the staple cartridge from which they were ejected. For example, a staple cartridge comprising a green cartridge body comprises green staples stored therein which produces a staple line 10400 of green staples. In many instances, the cartridge body is a specific color, such as green, to indicate the unformed height of the staples contained therein, such as 4 mm, for example. Thus, once the green staples have been fired from the green staple cartridge of this embodiments into patient tissue, the clinician can visibly discern that the unformed height of the green staples was 4 mm. In a similar embodiment, the staples and cartridge body are black to signify an unformed staple height of 5 mm. In at least one embodiment, the implanted staples 10400 are the same color as the staple retainer attached to a staple cartridge from which the staples are ejected. As discussed herein, staple retainers retain the staples in the staple cartridge.

In various embodiments, the type of staples within an implanted staple pattern is visually indicated by a dye or stain that eludes from the implanted staples onto the tissue surrounding the staple line. In at least one embodiment, a dye is transferred to the surrounding tissue but the staples themselves are not colored. However, other embodiments are envisioned where a dye stains the surrounding tissue as a result of the dye on the staples, as discussed above, such that the staple color and dye color visually indicate the type of staples within a given staple line.

In at least one embodiment, the transferrable dye is applied to the staples prior to placing the staples in the cartridge. In other embodiments, the transferrable dye is applied to the staples while the staples are in the staple cartridge. In any event, once the staples are implanted in the tissue, the dye bleeds into and/or stains the tissue surrounding the staple line such that the dyed tissue is visually different than the surrounding undyed tissue. In such instances, the color of the dye used is indicative of the type of staple within a particular staple line. In various aspects, different color dyes are used for different cartridge types such that the stained tissue provides a visual representation of the type of staple cartridge used to create the staple lines. In various embodiments, different color dyes are used within the same staple cartridge such that the tissue stained with different color dyes provides a visual representation of the type of staple within the dye stain. For example, a staple cartridge comprising fast-absorbing staples dyed with a first color dye and slow-absorbing staples dyed with a second color dye are implantable into patient tissue. The first and second colors are different and, once the dyed staples are implanted, the dyes elude from the staples to stain the surrounding tissue different colors in different areas which visually indicate which staples are fast-absorbing and which staples are slow-absorbing.

In at least one embodiment, the dye is blended into an adhesive soap coating or lubricant, such as those discussed herein, and applied to the staples prior to inserting the staples into a staple cartridge. In such instances, when the staples are deployed into tissue, the dye bleeds into and stains the tissue surrounding the staple line. The color of the dye is indicative of the type of staple within the staple line and/or indicative of the type of lubricant being used, for example. Other embodiments are envisioned where the dye is blended into a lubricant, such as those discussed herein, and applied to the staples and staple cartridge after the staples are positioned in the staple cartridge. In such instances, the die may seep between the staples and the staple cavities prior to staple ejection. Once the staples are ejected into the tissue, the dye bleeds into and stains the tissue surrounding the staple line. Other embodiments are envisioned where the dye is blended into a lubricant, such as those discussed herein, and applied to only the degradable metal tips of the staples after the staples are positioned in the staple cartridge. Once the staples are ejected into the tissue, the dye positioned on the staple tips bleeds into and stains the tissue making the tissue surrounding the staple line visually different.

In at least one embodiment, the staple drivers within a staple cartridge are coated with a dye which is transferred to the tissue when the staples are ejected. Specifically, staple drivers, such as drivers 10130, for example, will contact portions of the tissue surrounding the staple line when the staples are ejected. As such, the drivers 10130 coated with the dye will contact tissue and transfer the dye to the tissue such that the dyed tissue is visually different than the surrounding undyed tissue. As such, different color dyes can be used to indicate the type of staples within a given staple line and/or the type of staple cartridge used to produce a given staple line. In at least one embodiment, a dye is applied to the deck surface of a staple cartridge such that when tissue is clamped against the deck surface, the dye transfers to and stains the tissue. As such, the dye positioned on the deck surface may visually represent the type or types of staples within the cartridge, and/or the type of staple cartridge, for example. In various embodiments, the dye used to stain the tissue comprises a colored dye which increases the contrast between the dyed tissue and the undyed tissue. In at least one embodiment, blood is readily apparent against the backdrop of the dyed tissue.

In various embodiments, the type of staple cartridge is identified via the packaging, such as the packaging described herein, in which the staple cartridge is packaged. In at least one embodiment, a first staple cartridge comprising absorbable staples is packaged in a first type of packaging and a second staple cartridge comprising non-absorbable staples is packaged in a second type of packaging that is different than the first type of packaging. In at least one embodiment, the first packaging comprises a foil pouch which encapsulates the first staple cartridge, and the foil pouch is housed within a tube. In at least one embodiment, the second packaging comprises plastic packaging having at least a portion being see-through. In various embodiments, the packaging for the staple cartridges described herein is moisture proof. In at least one embodiment, the first packaging is moisture proof and the second packaging is non-moisture proof, for example.

In at least one embodiment, a first packaging for a first staple cartridge provides a first audible sound when the first staple cartridge is removed from the first packaging. Further, a second packaging for a second staple cartridge provides a second audible sound when the second staple cartridge is removed from the second packaging. The first audible sound and the second audible sound are different and indicative of the type of staple cartridge within the first and second packaging. In at least one embodiment, the first and second packaging each comprise a power source and a circuit including an audio segment including a speaker, for example. The circuit within the packaging is interrupted when the cartridge is removed from the packaging resulting in the audio segment of the circuit playing the audible sound. In at least one embodiment, a first staple cartridge comprising absorbable staples is packaged in a first type of packaging configured to play a first audible sound when the first staple cartridge is removed from the first packaging. Further, a second staple cartridge comprising non-absorbable staples is packaged in a second type of packaging configured to play a second audible sound when the second staple cartridge is removed from the second packaging. The first audible sound and the second audible sound are different and, thus, audibly indicate to a user whether the staples are absorbable or non-absorbable, for example.

In various embodiments, a surgeon, or other clinician, is provided with a set of staple cartridges for use with a surgical stapling instrument from which the surgeon can select that contains staples that perform and bioabsorb in a desired way. In at least one embodiment, the set of staple cartridges includes staple cartridges having uncoated staples, staple cartridges having coated staples, and staple cartridges having both uncoated staples and coated staples, for example. In addition to or in lieu of the above, the set of staple cartridges includes staple cartridges having staples with thin coatings that bioabsorb quickly, staple cartridges having staples with thick coatings that bioabsorb slowly, and staple cartridges having staples with thin coatings and staples with thick coatings, for example. In addition to or in lieu of the above, the set of staple cartridges includes staple cartridges having staples with no surface treatments, staple cartridges having staples with surface treatments, and staple cartridges having staples with surface treatments and staples without surface treatments, for example. In addition to or in lieu of the above, the set of staple cartridges includes staple cartridges having staples with smaller wire diameters, staple cartridges having staples with larger wire diameters, and staple cartridges having staples with smaller wire diameters and staples with larger wire diameters, for example. In addition to or in lieu of the above, the set of staple cartridges comprises staple cartridges having magnesium staples, staple cartridges having zinc staples, staple cartridges having iron staples, and staple cartridges having magnesium staples, zinc staples, and iron staples, for example. In addition to or in lieu of the above, the set of staple cartridges comprises staple cartridges having metal staples, staple cartridges having staples comprised of a first alloy of the metal, staple cartridges having staples of a second alloy of the metal, and staple cartridges having staples comprised of the metal, the first metal alloy, and the second metal alloy, for example. The set of staple cartridges can include any of the staples disclosed herein.

In various instances, further to the above, some staple cartridges may not be compatible with certain stapling instruments. For instance, the drive systems of certain stapling instruments may be too powerful to be used with staple cartridges having weak and/or brittle staples while the drive systems of other stapling instruments may not be powerful enough to be used with staple cartridges having strong or stiff staples. In various embodiments, a stapling instrument and/or the staple cartridges are configured such that a wrong staple cartridge is prevented from being used with a stapling instrument. Referring to FIGS. 147 and 148, a stapling instrument 8900 comprises a handle, a shaft extending from the handle, and an end effector including a cartridge jaw 8910 and an anvil jaw 8920. The cartridge jaw 8910 comprises a channel including a bottom portion 8912 and sidewalls 8914 extending upwardly from the bottom portion 8912. The channel is sized and configured to receive, in the alternative, a staple cartridge 8800 including first staples stored therein, a staple cartridge 9000 including second staples stored therein, and a staple cartridge 9100 including third staples stored therein. Although the first staples, the second staples, and third staples are different, the staple cartridges 8800, 9000, and 9100 are all compatible for use with the stapling instrument 8900. Notably, the staple cartridge 8800 includes a cartridge body, staples removably stored in the cartridge body, and a pan 8840 attached to the cartridge body where the pan 8840 includes a key, or projection, 8860 extending laterally from each lateral side of the staple cartridge 8800. The sidewalls 8914 of the cartridge jaw 8910 comprise slots 8960 defined therein which are aligned with and configured to receive the keys 8860 when the staple cartridge 8800 is seated in the cartridge jaw 8910. Similarly, the staple cartridge 9000 comprises two keys 9060 extending laterally from each lateral side of the staple cartridge 9000 which are aligned with and configured to receive the keys 9060 when the staple cartridge 9000 is seated in the cartridge jaw 8910. A staple cartridge having three keys extending laterally from a staple cartridge, or keys positioned at the distal end of a staple cartridge, for example, could not be seated in the cartridge jaw 8910. To the extent that there are staple cartridges that are incompatible with the stapling instrument 8900, such arrangements could be used to prevent the incompatible staple cartridges from being used with the stapling instrument 8900.

A stapling instrument 8900' is illustrated in FIG. 149 and is different than the stapling instrument 8900 in several respects. For instance, the electric motor that drives the staple firing drive of the stapling instrument 8900' is operated at a higher torque than the electric motor of the staple firing drive of the stapling instrument 8900. The staple cartridges 8800 and 9000 are incompatible with the higher torque and firing force transmitted through the staple firing drive of the stapling instrument 8900'. In at least one instance, the staple cartridge 8800 comprises magnesium staples and the staple cartridge 9000 comprises zinc staples, for example. To prevent the staple cartridges 8800 and 9000 from being used with the stapling instrument 8900', the channel sidewalls of the stapling instrument 8900' do not have slots 8960 defined therein such that, if a clinician were to attempt to seat the staple cartridge 8800 or the staple cartridge 9000 in the stapling instrument 8900', the keys 8860 or keys 9060, respectively, would abut the sidewalls of the channel thereby preventing the staple cartridge 8800 or 9000 from being seated in the channel. The staple cartridge 9100, however, is compatible with both the stapling instrument 8900 and the stapling instrument 8900'. The staple cartridge 9100 does not have keys extending laterally therefrom and, thus, is not blocked from being used with the stapling instrument 8900 or the stapling instrument 8900'. In at least one such instance, the staples of the staple cartridge 9100 are comprised of stainless steel, for example.

Various aspects of the present disclosure relate to surgical staples that compress and appose patient tissue. During a surgical procedure, a clinician can utilize a surgical stapling instrument to staple, and cut, the patient tissue. The surgical stapling instrument can include a staple cartridge that includes staples removably stored therein that are deployed into the patient tissue by a firing drive of the surgical stapling instrument. When deployed, the staples puncture a first side of the tissue and are then deformed by an anvil of the surgical stapling instrument positioned on a second, or opposite, side of the tissue. The deformed staples clench, or compress, the tissue to prevent, or at least reduce, bleeding from the incision created by the stapling instrument. In one aspect, the surgical stapling instrument is a motor operated and includes a control circuit to control various functional aspects of the surgical stapling instrument. The surgical stapling instrument may be a hand held instrument or may be a surgical robot operated instrument. In the latter implementation, the control circuit may be located in the surgical robot, in a portion of the surgical stapling instrument downstream from a robotic interface, or both. Functional aspects of the surgical stapling instrument controlled by the control circuit include adaptive clamping and firing and in various aspects includes controlling speed, wait periods, load forces, closure forces, firing forces, without limitation.

A surgical stapling system can comprise a shaft and an end effector extending from the shaft. The end effector comprises a first jaw and a second jaw. The first jaw comprises a staple cartridge. The staple cartridge is insertable into and removable from the first jaw; however, other embodiments are envisioned in which a staple cartridge is not removable from, or at least readily replaceable from, the first jaw. The second jaw comprises an anvil configured to deform staples ejected from the staple cartridge. The second jaw is pivotable relative to the first jaw about a closure axis; however, other embodiments are envisioned in which the first jaw is pivotable relative to the second jaw. The surgical stapling system further comprises an articulation joint configured to permit the end effector to be rotated, or articulated, relative to the shaft. The end effector is rotatable about an articulation axis extending through the articulation joint. Other embodiments are envisioned which do not include an articulation joint.

The staple cartridge comprises a cartridge body. The cartridge body includes a proximal end, a distal end, and a deck extending between the proximal end and the distal end. In use, the staple cartridge is positioned on a first side of the tissue to be stapled and the anvil is positioned on a second side of the tissue. The anvil is moved toward the staple cartridge to compress and clamp the tissue against the deck. Thereafter, staples removably stored in the cartridge body can be deployed into the tissue. The cartridge body includes staple cavities defined therein wherein staples are removably stored in the staple cavities. The staple cavities are arranged in six longitudinal rows. Three rows of staple cavities are positioned on a first side of a longitudinal slot and three rows of staple cavities are positioned on a second side of the longitudinal slot. Other arrangements of staple cavities and staples may be possible.

The staples are supported by staple drivers in the cartridge body. The drivers are movable between a first, or unfired position, and a second, or fired, position to eject the staples from the staple cavities. The drivers are retained in the cartridge body by a staple retainer which extends around the bottom of the cartridge body and includes resilient members configured to grip the cartridge body and hold the staple retainer to the cartridge body. The drivers are movable between their unfired positions and their fired positions by a sled. The sled is movable between a proximal position adjacent the proximal end and a distal position adjacent the distal end. The sled comprises a plurality of ramped surfaces configured to slide under the drivers and lift the drivers, and the staples supported thereon, toward the anvil.

Further to the above, the sled is moved distally by a firing member. The firing member is configured to contact the sled and push the sled toward the distal end. The longitudinal slot defined in the cartridge body is configured to receive the firing member. The anvil also includes a slot configured to receive the firing member. The firing member further comprises a first cam which engages the first jaw and a second cam which engages the second jaw. As the firing member is advanced distally, the first cam and the second cam can control the distance, or tissue gap, between the deck of the staple cartridge and the anvil. The firing member also comprises a knife configured to incise the tissue captured intermediate the staple cartridge and the anvil. It is desirable for the knife to be positioned at least partially proximal to the ramped surfaces such that the staples are ejected ahead of the knife.

Various staples disclosed herein comprise a flat-formed staple which can be cut and/or stamped from a sheet of material, for example. The sheet of material can be metallic and can comprise stainless steel and/or titanium, for example. In at least one instance, outlines can be traced, etched, and/or cut into the sheet of material which are machined and/or laser cut to form the staples into a manufactured shape. The staples comprise a pair of staple legs and a staple base portion, or crown, from which the staple legs extend. Each staple leg comprises a staple tip, or piercing portion, which is configured to pierce the tissue and contact a corresponding forming pocket of the anvil of the surgical stapling instrument. The staple legs are configured to be deformed to assume a formed configuration to fasten the tissue. The staple legs define a plane which is laterally offset from but at least substantially parallel to a plane defined by the base of the staple. Embodiments are envisioned where the first and second planes are not parallel.

The staples can be made of a bioabsorbable material such that the staples can dissolve and release the tissue after a sufficient amount of time has elapsed following the surgical procedure. While it is desirable that the staples ultimately dissolve and release the tissue, the staples must maintain their structural integrity for an amount of time, i.e., the biocorrosion timeframe, to allow for sufficient healing of the tissue. When selecting appropriate bioabsorbable materials such that the staples can meet the biocorrosion timeframe, many factors are considered, such as the stiffness of the staples, the strength of the staples, the ductility of the staple materials, the safety of the materials being utilized (such as toxicity concerns), and/or the compatibility of the materials with electrosurgical instruments, for example. Comparatively, stents which are often implanted to hold open an artery, for example, are often comprised of alloys which resist or impede biocorrosion of the underlying structure eventhough a surface of the stent may comprise a dissolvable coating.

Magnesium (Mg) staples can be manufactured using one or more manufacturing methods. As discussed herein, the manufacturing method used to create a magnesium staple can affect, if not greatly affect, the mechanical properties of the magnesium staple and the performance characteristics of the magnesium staple in situ. In at least one example, magnesium staples can be created by a casting process. The magnesium staples can comprise a base, or crown, and one or more legs extending from the crown and, in at least one example, the tips of the legs can be shaped by a stamping process and then sharpened by a grinding process, for example. In various instances, cast magnesium can have a fairly large grain structure and can be anisotropic. In another example, magnesium is drawn into a wire, the wire is cut, or sheared, to length to create a wire portion, and then the wire portion is bent into a staple shape, or pre-form, having a crown and one or more staple legs.

Similar to the above, the staple legs, or at least the tips of the staple legs, can be shaped by a stamping process and then sharpened by a grinding process, for example. In at least one example, a wire having a first, or larger, diameter is drawn down into a second, or smaller, diameter. Such cold working or plastic straining of the magnesium wire can reduce the grain size within the magnesium wire and/or create isoptropic, or at least substantially isotropic, properties within the magnesium wire. Moreover, as a result, such processes can increase the ductility of the magnesium wire and improve the magnesium wire's resistance to cracking and/or fracturing when the wire is bent into the pre-form staple shape. Similarly, such processes can reduce the possibility of the magnesium staple cracking and/or fracturing during the staple firing process.

In at least one example, magnesium wire can be plastically strained by an equal channel angular extrusion process to improve the ductility of the wire before the wire is formed into staples. In such a process, the magnesium wire is fed into an inlet aperture in a die and exits the die through an outlet aperture having the same diameter as the inlet aperture. A passage in the die extends between the inlet aperture and the outlet aperture and includes an angled portion, such as a right angle, for example, that causes the magnesium wire to plastically strain as the magnesium wire passes through the passage. This process can be repeated several times. In at least one instance, the process can be repeated until the wire has been plastically strained between about 600% and about 800%, for example. In various instances, an equal channel angular extrusion process can reduce the grain structure in the magnesium wire to 10 micrometers or below, for example. In at least one instance, an equal channel angular extrusion process can reduce the grain structure in the magnesium wire below 1 micrometer, for example. Once the magnesium wire has been suitably worked, the wire can be cut and bent into shape. In various instances, one or more stamping processes can be used to shape the wire and can further plastically strain the wire. Moreover, one or more stamping or shearing processes can be used to make the tips of the staple legs sufficiently hard enough and sharp enough to suitably puncture the patient tissue and deform into a desired shape during the staple firing process.

By way of background, magnesium is an-isotropic element and the strain it is exposed to, the strain rate it is applied at, the stress level, and the work hardness of the material dramatically change the functional properties of the resulting metal construct. The most common of these issues would occur during the staple manufacturing process where the magnesium wire is drawn down and then sheared and bent into staple pre-form shapes. However, the deployment forming of a magnesium staple could amplify these flaws or impacts further making the staple brittle, lower compressive capable, or more easily fracturable. These failures would first manifest as cracks in the staple which would propagate and lead to staple wire fractures. The most likely zones for these failures would be the bend between the crown and the leg, the crown itself, and leg close to the crown intersection and the final resulting "b" bend areas.

Equal channel angular extrusion (ECAE) is a relatively new metal working process which is capable of producing ultrafine sub-micron grain (SMG) structure by means of intense plastic straining without a change in shape or dimensions of the worked material. In the current research work, the influence of ECAE processing on the room temperature mechanical properties of Al—Cu—Li—Mg—Ag—Zr alloys were investigated in the T4 and T6 temper conditions. A conventionally processed alloy via rolling with similar compositions to those ECAE processed was also investigated for comparison purposes. Microstructural analysis were assessed by means of optical microscopy (OM) and transmission electron microscopy (TEM). An ultrafine SMG structure of 0.2 to 0.4 μm was produced for the ECAE processed alloys from initial grain size of >100 μm, while a minimum of 1.2 μm was revealed for the rolled alloy. A significant improvement in the mechanical properties at room temperatures were accomplished by ECAE processing in comparison with conventional processing. Additional disclosure of the influence of intense plastic straining on room temperature mechanical properties of Al—Cu—Li bases alloys is described in The Influence Of Intense Plastic Straining On Room Temperature Mechanical Properties Of Al—Cu—Li Bases Alloys, by Salem H. A. and Goforth R. E., in Current Advances in Mechanical Design and Production VII, 2000, which is herein incorporated by reference.

Accordingly, in order to obtain the smallest microstructural sizes plastic strains of more than 600 to 800% are necessary. Such high degrees of plastic deformation are possible because one sample can be subjected several times to severe plastic deformation (SPD) in order to accumulate the total amount of plastic strain. ECAP is one of the most employed methods of SPD; it can be applied to a variety of metals and alloys in order to obtain ultrafine grains and good mechanical and physical properties. The recent literature shows intense and growing interest in some fundamental aspects of SPD techniques, viz., the generation of ultrafine grains and the mechanisms underlying the high levels of strength observed. Aluminum and its alloys, Cu and Ti are the most employed materials in SPD-ECAP studies, with Ti being seriously considered for orthopedic implants. In addition, the stress-strain behavior of magnesium wire demonstrates deformation twinning, which can be dependent on strain rate. Deformation twinning can cause undesirable mechanical properties like tension compression asymmetry or softening.

Furthermore, because a magnesium staple is absorbable, it is likely the staple will be coated in at least one coating, and more likely several coatings. Because the coatings are on the outside diameter of the staple wire they will experience higher strains and strain rates than the core bulk of the wire. These coatings, while usually at least partially elastic, also will experience similar an-isotropic behavior. If the coating cracks or flakes off, the magnesium wire will be prematurely exposed to the outside local environment which will likely accelerate its degradation. Additional alloys may include fine grain micro-alloyed (<10 μm, preferably sub-micrometer), isotropic grain orientation, highly formable materials, and/or lean alloys.

Further to the above, a magnesium wire can comprise pure magnesium or a magnesium alloy. Moreover, all of the staple forming processes described herein can be used to create staples made from titanium, a titanium alloy, stainless steel, silver, aluminum, an aluminum alloy, copper, a copper alloy, zinc, a zinc alloy, iron, and/or an iron alloy, for example. Regardless of the metal used to create the staples for a staple cartridge, it is understood that the force and/or momentum needed to properly form the staples from an unfired configuration to a fired configuration will depend on the staple material, material hardness, material ductility, and/or geometry of the staples, for example. For instance, staples that are more brittle than others may need to be fired at a slower speed, for example, to prevent cracking and/or fracturing within the staples. Similarly, staples that are more ductile than other may be fired a faster speed, for example. Also, for instance, magnesium staples may require less force to be fired than titanium staples and/or stainless steel staples, for example. Another factor to be considered when controlling and/or changing the force and/or speed of the staple firing process is whether or not a coating is present on the staples. If staples with coatings are fired too quickly, and/or with too much force, the coatings may crack and/or delaminate in an undesirable manner. As discussed below, the force and/or speed of a staple firing member used to fire the staples can be controlled or changed by a surgical stapling instrument to properly form the staples.

Adaptive firing programs for surgical stapling instruments are described in, for example, U.S. Patent Application Publication No. 2019/0206003, titled ADAPTIVE CONTROL PROGRAM UPDATES FOR SURGICAL DEVICES, which is incorporated by reference herein in its entirety. Adaptive firing programs can be implemented by a control circuit internal to the surgical instrument and/or in signal communication with a motor adapted to drive a firing component in the surgical instrument. The reader will appreciate that adaptive firing programs can be implemented by varied surgical devices, such as handheld surgical instruments (e.g. staplers) and robotic surgical tools releasably mounted to a motor housing, for example.

For conciseness and clarity of disclosure, the following description will reference FIG. 98, which describes a schematic block diagram of a surgical stapling instrument 12850 programmed to control the distal translation of a displacement member. In one aspect, the surgical stapling instrument 12850 is programmed to control the distal translation of a displacement member such as the I-beam 12864 (or E-beam). The surgical stapling instrument 12850 includes a surgical stapling assembly, or end effector 12852 that may comprise an anvil 12866, an I-beam 12864 (including a sharp cutting edge), or an E-beam, and a removable staple cartridge 12868. The surgical stapling assembly 12852 can be similar in many aspects to the surgical stapling assembly 12000. Further reference is made to FIGS. 114-121, which describes an embodiment of a surgical stapling instrument 1400, which is shown schematically as surgical stapling instrument 12850 in FIG. 98.

The position, movement, displacement, and/or translation of a linear displacement member, such as the I-beam 12864, for example, can be measured by an absolute positioning system, sensor arrangement, and/or position sensor 12884. Because the I-beam 12864 is coupled to a longitudinally movable drive member, the position of the I-beam 12864 can be determined by measuring the position of the longitudinally movable drive member employing the position sensor 12884.

A control circuit 12860 may be programmed to control the translation of the displacement member, such as the I-beam 12864. The control circuit 12860, in some examples, may comprise one or more microcontrollers, microprocessors, or other suitable processors for executing instructions that cause the processor or processors to control the displacement member, e.g., the I-beam 12864, in the manner described. The control circuit 12860 is coupled to a display 12851, which can provide information to a clinician. In certain instances, the display 12851 can include an input (e.g. a touchscreen), which is configured to receive input from a clinician.

In one aspect, a timer/counter 12881 provides an output signal, such as the elapsed time or a digital count, to the control circuit 12860 to correlate the position of the I-beam 12864 as determined by the position sensor 12884 with the output of the timer/counter 12881 such that the control circuit 12860 can determine the position of the I-beam 12864 at a specific time relative to a starting position. The timer/counter 12881 may be configured to measure elapsed time, count external events, or time external events. A position sensor, like the position sensor 12884, is further described in U.S. Patent Application Publication No. 2019/0206003, titled ADAPTIVE CONTROL PROGRAM UPDATES FOR SURGICAL DEVICES, for example.

The control circuit 12860 can generate a motor set point signal 12872. The motor set point signal 12872 can be provided to a motor controller 12858. The motor controller 12858 can comprise one or more circuits configured to provide a motor drive signal 12874 to the motor 12854 to drive the motor 12854 as described herein. In some examples, the motor 12854 may be a brushed DC electric motor. For example, the velocity of the motor 12854 may be proportional to the motor drive signal 12874. In some examples, the motor 12854 may be a brushless DC electric motor and the motor drive signal 12874 may comprise a pulse width modulation (PWM) signal provided to one or more stator windings of the motor 12854. Also, in some examples, the motor controller 12858 may be omitted or incorporated into the control circuit 12860, and the control circuit 12860 may generate the motor drive signal 12874 directly.

The motor 12854 may receive power from an energy source 12862. The energy source 12862 may be or include a battery, a super capacitor, or any other suitable energy source. The motor 12854 may be mechanically coupled to the I-beam 12864 via a transmission 12856. The transmission 12856 may include one or more gears or other linkage components to couple the motor 12854 to the I-beam 12864.

The control circuit 12860 may be in communication with one or more sensors 12888. The sensors 12888 may be positioned on the end effector 12852 and adapted to operate with the surgical stapling instrument 12850 to measure the various derived parameters such as gap distance versus time, tissue compression versus time, and anvil strain versus time. The sensors 12888 may comprise a magnetic sensor, a magnetic field sensor, a strain gauge, a pressure sensor, a force sensor, an inductive sensor such as an eddy current sensor, a resistive sensor, a capacitive sensor, an optical sensor, and/or any other suitable sensor for measuring one or more parameters of the end effector 12852. The sensors 12888 may include one or more sensors. The sensors 12888 may be configured to measure forces exerted on the anvil 12866 by a closure drive system, for example. Sensors, like the sensors 12888, are further described in, for example, U.S. Patent Application Publication No. 2019/0206003, titled ADAPTIVE CONTROL PROGRAM UPDATES FOR SURGICAL DEVICES. In various aspects, the sensors 12888 may be configured to detect the type of staple cartridge 12868 loaded in the end effector 12852.

A current sensor 12886 can be employed to measure the current drawn by the motor 12854. The force required to advance the I-beam 12864 corresponds to the current drawn by the motor 12854. The force is converted to a digital signal and provided to the control circuit 12860.

The control circuit 12860 can be configured to simulate the response of the actual system of the instrument in the software of the controller. A displacement member can be actuated to move the I-beam 12864 in the end effector 12852 at or near a target velocity. The surgical stapling instrument 12850 can include a feedback controller, which can be one of any feedback controllers, including, but not limited to a proportional-integral-derivative (PID) controller, a state feedback controller, linear-quadratic regulator (LQR) controller, and/or an adaptive controller, for example. The surgical stapling instrument 12850 can include a power source to convert the signal from the feedback controller into a physical input such as case voltage, PWM voltage, frequency modulated voltage, current, torque, and/or force, for example.

In various aspects of the present disclosure, the motor 12854 can drive a displacement member distally and proximally along a longitudinal axis of the end effector 12852. The end effector 12852 can be configured to grasp tissue between the anvil 12866 and the staple cartridge 12868, as described herein. When ready to use the instrument 12850, the clinician may provide a firing signal, for example by depressing a trigger of the instrument 12850. In response to the firing signal, the motor 12854 may drive the displacement member distally along the longitudinal axis of the end effector 12852 from a stroke begin position to a stroke end position that is distal to the stroke begin position. As the displacement member translates distally, the I-beam 12864 with a cutting element positioned at a distal end, can cut the tissue clamped between the staple cartridge 12868 and the anvil 12866.

The control circuit 12860 can be programmed to sense one or more conditions of the tissue, end effector 12852, and/or staple cartridge 12868. The control circuit 12860 can be programmed to select a firing control program or algorithm based on tissue conditions, type of staple cartridge 12868, among others. A firing control program may control the distal motion of the displacement member. Different firing control programs can be selected based on the staple cartridge 12868 installed in the end effector 12852. In various instances, the firing control program, or firing algorithm, can be optimized for different combinations of bioabsorbable materials in the staple cartridge 12868 and/or surgical stapling assembly.

The disclosure now turns to the description of various identifiable aspects of staple cartridges 12868 to intuitively differentiate absorbable and non-absorbable staple cartridges described herein. In one aspect, a staple wire material identifier may be employed to enable adaptation of the deployment of a staple. The staple wire material, for example, may comprise, consist essentially of, or consist of titanium, titanium alloy, stainless steel, silver, aluminum, aluminum alloy, copper, copper alloy, zinc, zinc alloy, iron, and/or iron alloy. Based on the identified staple material, the control circuit 12860 adaptively controls the operation of the surgical stapling instrument 12850.

FIG. 150 illustrates a logic diagram of a control system 15470 of a surgical instrument or tool in accordance with one or more aspects of the present disclosure. The system 15470 comprises a control circuit, which is one implementation of the control circuit 12860 shown in FIG. 98. The control circuit includes a microcontroller 15461 comprising a processor 15462 and a memory 15468. One or more of sensors 15472, 15474, 15476, for example, provide real-time feedback to the processor 15462. A motor 15482, driven by a motor driver 15492, operably couples a longitudinally movable displacement member to drive the I-beam knife element. A tracking system 15480 is configured to determine the position of the longitudinally movable displacement member. The position information is provided to the processor 15462, which can be programmed or configured to determine the position of the longitudinally movable drive member as well as the position of a firing member, firing bar, and I-beam knife element. Additional motors may be provided at the tool driver interface to control I-beam firing, closure tube travel, shaft rotation, and articulation. In one aspect, a display displays a variety of operating conditions of the instruments and may include touch screen functionality for data input. Information displayed on the display may be overlaid with images acquired via endoscopic imaging modules.

In one aspect, the microcontroller 15461 may be any single-core or multicore processor such as those known under the trade name ARM Cortex by Texas Instruments. In one aspect, the main microcontroller 15461 may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle SRAM, and internal ROM loaded with StellarisWare® software, a 2 KB EEPROM, one or more PWM modules, one or more QEI analogs, and/or one or more 12-bit ADCs with 12 analog input channels, details of which are available for the product datasheet.

In one aspect, the microcontroller 15461 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The microcontroller 15461 may be programmed to perform various functions such as precise control over the speed and position of the knife and articulation systems. In one aspect, the microcontroller 15461 includes a processor 15462 and a memory 15468. The electric motor 15482 may be a brushed direct current (DC) motor with a gearbox and mechanical links to an articulation or knife system. In one aspect, a motor driver 15492 may be an A3941 available from Allegro Microsystems, Inc. Other motor drivers may be readily substituted for use in the tracking system 15480 comprising an absolute positioning system. A detailed description of an absolute positioning system is described in U.S. Patent Application Publication No. 2017/0296213, titled SYSTEMS AND METHODS FOR CONTROLLING A SURGICAL STAPLING AND CUTTING INSTRUMENT, which published on Oct. 19, 2017, which is herein incorporated by reference in its entirety.

The microcontroller 15461 may be programmed to provide precise control over the speed and position of displacement members and articulation systems. The microcontroller 15461 may be configured to compute a response in the software of the microcontroller 15461. The computed response is compared to a measured response of the actual system to obtain an "observed" response, which is used for actual feedback decisions. The observed response is a favorable, tuned value that balances the smooth, continuous nature of the simulated response with the measured response, which can detect outside influences on the system.

In one aspect, the motor 15482 may be controlled by the motor driver 15492 and can be employed by the firing system of the surgical instrument or tool. In various forms, the motor 15482 may be a brushed DC driving motor having a maximum rotational speed of approximately 25,000 RPM. In other arrangements, the motor 15482 may include a brushless motor, a cordless motor, a synchronous motor, a stepper motor, or any other suitable electric motor. The motor driver 15492 may comprise an H-bridge driver comprising field-effect transistors (FETs), for example. The motor 15482 can be powered by a power assembly releasably mounted to the handle assembly or tool housing for supplying control power to the surgical instrument or tool. The power assembly may comprise a battery which may include a number of battery cells connected in series that can be used as the power source to power the surgical instrument or tool. In certain circumstances, the battery cells of the power assembly may be replaceable and/or rechargeable. In at least one example, the battery cells can be lithium-ion batteries which can be couplable to and separable from the power assembly.

The motor driver 15492 may be an A3941 available from Allegro Microsystems, Inc. The A3941 motor driver 15492 is a full-bridge controller for use with external N-channel power metal-oxide semiconductor field-effect transistors (MOSFETs) specifically designed for inductive loads, such as brush DC motors. The driver 15492 comprises a unique charge pump regulator that provides full (>10 V) gate drive for battery voltages down to 7 V and allows the A3941 to operate with a reduced gate drive, down to 5.5 V. A bootstrap capacitor may be employed to provide the above battery supply voltage required for N-channel MOSFETs. An internal charge pump for the high-side drive allows DC (100% duty cycle) operation. The full bridge can be driven in fast or slow decay modes using diode or synchronous rectification. In the slow decay mode, current recirculation can be through the high-side or the low-side FETs. The power FETs are protected from shoot-through by resistor-adjustable dead time. Integrated diagnostics provide indications of under voltage, over temperature, and power bridge faults and can be configured to protect the power MOSFETs under most short circuit conditions. Other motor drivers may be readily substituted for use in the tracking system 15480 comprising an absolute positioning system.

The tracking system 15480 comprises a controlled motor drive circuit arrangement comprising a position sensor 15472 according to one aspect of this disclosure. The position sensor 15472 for an absolute positioning system provides a unique position signal corresponding to the location of a displacement member. In one aspect, the displacement member represents a longitudinally movable drive member comprising a rack of drive teeth for meshing engagement with a corresponding drive gear of a gear reducer assembly. In other aspects, the displacement member represents the firing member, which could be adapted and configured to include a rack of drive teeth. In yet another aspect, the displacement member represents a firing bar or the I-beam, each of which can be adapted and configured to include a rack of drive teeth. Accordingly, as used herein, the term displacement member is used generically to refer to any movable member of the surgical instrument or tool such as the drive member, the firing member, the firing bar, the I-beam, or any element that can be displaced. In one aspect, the longitudinally movable drive member is coupled to the firing member, the firing bar, and the I-beam. Accordingly, the absolute positioning system can, in effect, track the linear displacement of the I-beam by tracking the linear displacement of the longitudinally movable drive member. In various other aspects, the displacement member may be coupled to any position sensor 15472 suitable for measuring linear displacement. Thus, the longitudinally movable drive member, the firing member, the firing bar, or the I-beam, or combinations thereof, may be coupled to any suitable linear displacement sensor. Linear displacement sensors may include contact or non-contact displacement sensors. Linear displacement sensors may comprise linear variable differential transformers (LVDT), differential variable reluctance transducers (DVRT), a slide potentiometer, a magnetic sensing system comprising a movable magnet and a series of linearly arranged Hall effect sensors, a magnetic sensing system comprising a fixed magnet and a series of movable, linearly arranged Hall effect sensors, an optical sensing system comprising a movable light source and a series of linearly arranged photo diodes or photo detectors, an optical sensing system comprising a fixed light source and a series of movable linearly, arranged photo diodes or photo detectors, or any combination thereof.

The electric motor 15482 can include a rotatable shaft that operably interfaces with a gear assembly that is mounted in meshing engagement with a set, or rack, of drive teeth on the displacement member. A sensor element may be operably coupled to a gear assembly such that a single revolution of the position sensor 15472 element corresponds to some linear longitudinal translation of the displacement member. An arrangement of gearing and sensors can be connected to the linear actuator, via a rack and pinion arrangement, or a rotary actuator, via a spur gear or other connection. A power source supplies power to the absolute positioning system and an output indicator may display the output of the absolute positioning system. The displacement member represents the longitudinally movable drive member comprising a rack of drive teeth formed thereon for meshing engagement with a corresponding drive gear of the gear reducer assembly. The displacement member represents the longitudinally movable firing member, firing bar, I-beam, E-beam, or combinations thereof.

A single revolution of the sensor element associated with the position sensor 15472 is equivalent to a longitudinal linear displacement d1 of the of the displacement member, where d1 is the longitudinal linear distance that the displacement member moves from point "a" to point "b" after a single revolution of the sensor element coupled to the displacement member. The sensor arrangement may be connected via a gear reduction that results in the position sensor 15472 completing one or more revolutions for the full stroke of the displacement member. The position sensor 15472 may complete multiple revolutions for the full stroke of the displacement member.

A series of switches, where n is an integer greater than one, may be employed alone or in combination with a gear reduction to provide a unique position signal for more than one revolution of the position sensor 15472. The state of the switches are fed back to the microcontroller 15461 that applies logic to determine a unique position signal corresponding to the longitudinal linear displacement d1+d2+ . . . dn of the displacement member. The output of the position sensor 15472 is provided to the microcontroller 15461. The position sensor 15472 of the sensor arrangement may comprise a magnetic sensor, an analog rotary sensor like a potentiometer, or an array of analog Hall-effect elements, which output a unique combination of position signals or values.

The position sensor 15472 may comprise any number of magnetic sensing elements, such as, for example, magnetic sensors classified according to whether they measure the total magnetic field or the vector components of the magnetic field. The techniques used to produce both types of magnetic sensors encompass many aspects of physics and electronics. The technologies used for magnetic field sensing include search coil, fluxgate, optically pumped, nuclear precession, SQUID, Hall-effect, anisotropic magnetoresistance, giant magnetoresistance, magnetic tunnel junctions, giant magnetoimpedance, magnetostrictive/piezoelectric composites, magnetodiode, magnetotransistor, fiber-optic, magneto-optic, and microelectromechanical systems-based magnetic sensors, among others.

In one aspect, the position sensor 15472 for the tracking system 15480 comprising an absolute positioning system comprises a magnetic rotary absolute positioning system. The position sensor 15472 may be implemented as an AS5055EQFT single-chip magnetic rotary position sensor available from Austria Microsystems, AG. The position sensor 15472 is interfaced with the microcontroller 15461 to provide an absolute positioning system. The position sensor 15472 is a low-voltage and low-power component and includes four Hall-effect elements in an area of the position sensor 15472 that is located above a magnet. A high-resolution ADC and a smart power management controller are also provided on the chip. A coordinate rotation digital computer (CORD IC) processor, also known as the digit-by-digit method and Volder's algorithm, is provided to implement a simple and efficient algorithm to calculate hyperbolic and trigonometric functions that require only addition, subtraction, bitshift, and table lookup operations. The angle position, alarm bits, and magnetic field information are transmitted over a standard serial communication interface, such as a serial peripheral interface (SPI) interface, to the microcontroller 15461. The position sensor 15472 provides 12 or 14 bits of resolution. The position sensor 15472 may be an AS5055 chip provided in a small QFN 16-pin 4×4×0.85 mm package.

The tracking system 15480 comprising an absolute positioning system may comprise and/or be programmed to implement a feedback controller, such as a PID, state feedback, and adaptive controller. A power source converts the signal from the feedback controller into a physical input to the system: in this case the voltage. Other examples include a PWM of the voltage, current, and force. Other sensor(s) may be provided to measure physical parameters of the physical system in addition to the position measured by the position sensor 15472. In some aspects, the other sensor(s) can include sensor arrangements such as those described in U.S. Pat. No. 9,345,481, titled STAPLE CARTRIDGE TISSUE THICKNESS SENSOR SYSTEM, which issued on May 24, 2016, which is herein incorporated by reference in its entirety; U.S. Patent Application Publication No. 2014/0263552, titled STAPLE CARTRIDGE TISSUE THICKNESS SENSOR SYSTEM, which published on Sep. 18, 2014, which is herein incorporated by reference in its entirety; and U.S. Patent Application Ser. No. 15/628,175, titled TECHNIQUES FOR ADAPTIVE CONTROL OF MOTOR VELOCITY OF A SURGICAL STAPLING AND CUTTING INSTRUMENT, filed Jun. 20, 2017, which is herein incorporated by reference in its entirety. In a digital signal processing system, an absolute positioning system is coupled to a digital data acquisition system where the output of the absolute positioning system will have a finite resolution and sampling frequency. The absolute positioning system may comprise a compare-and-combine circuit to combine a computed response with a measured response using algorithms, such as a weighted average and a theoretical control loop, that drive the computed response towards the measured response. The computed response of the physical system takes into account properties like mass, inertial, viscous friction, inductance resistance, etc., to predict what the states and outputs of the physical system will be by knowing the input.

The absolute positioning system provides an absolute position of the displacement member upon power-up of the instrument, without retracting or advancing the displacement member to a reset (zero or home) position as may be required with conventional rotary encoders that merely count the number of steps forwards or backwards that the motor 15482 has taken to infer the position of a device actuator, drive bar, knife, or the like.

A sensor 15474, such as, for example, a strain gauge or a micro-strain gauge, is configured to measure one or more parameters of the end effector, such as, for example, the amplitude of the strain exerted on the anvil during a clamping operation, which can be indicative of the closure forces applied to the anvil. The measured strain is converted to a digital signal and provided to the processor 15462. Alternatively, or in addition to the sensor 15474, a sensor 15476, such as, for example, a load sensor, can measure the closure force applied by the closure drive system to the anvil. The sensor 15476, such as, for example, a load sensor, can measure the firing force applied to an I-beam in a firing stroke of the surgical instrument or tool. The I-beam is configured to engage a wedge sled, which is configured to upwardly cam staple drivers to force out staples into deforming contact with an anvil. The I-beam also includes a sharpened cutting edge that can be used to sever tissue as the I-beam is advanced distally by the firing bar. Alternatively, a current sensor 15478 can be employed to measure the current drawn by the motor 15482. The force required to advance the firing member can correspond to the current drawn by the motor 15482, for example. The measured force is converted to a digital signal and provided to the processor 15462.

In one form, the strain gauge sensor 15474 can be used to measure the force applied to the tissue by the end effector. A strain gauge can be coupled to the end effector to measure the force on the tissue being treated by the end effector. A system for measuring forces applied to the tissue grasped by the end effector comprises a strain gauge sensor 15474, such as, for example, a micro-strain gauge, that is configured to measure one or more parameters of the end effector, for example. In one aspect, the strain gauge sensor 15474 can measure the amplitude or magnitude of the strain exerted on a jaw member of an end effector during a clamping operation, which can be indicative of the tissue compression. The measured strain is converted to a digital signal and provided to a processor 15462 of the microcontroller 15461. A load sensor 15476 can measure the force used to operate the knife element, for example, to cut the tissue captured between the anvil and the staple cartridge. A magnetic field sensor can be employed to measure the thickness of the captured tissue. The measurement of the magnetic field sensor also may be converted to a digital signal and provided to the processor 15462.

The measurements of the tissue compression, the tissue thickness, and/or the force required to close the end effector on the tissue, as respectively measured by the sensors 15474, 15476, can be used by the microcontroller 15461 to characterize the selected position of the firing member and/or the corresponding value of the speed of the firing member. In one instance, a memory 15468 may store a technique, an equation, and/or a lookup table which can be employed by the microcontroller 15461 in the assessment.

In various aspects, the sensors 15472, 15474, 15476 may be implemented as optical sensors, scanners, light sensor, lasers, optical light, RFID circuits, etc., to "read" a predefined location of the staple cartridge 12868 to identify the staple cartridge type. The sensors 15472, 15474, 15476 may optical sensors incorporated or integrated in the staple cartridge 12868 to detect the color of the staple cartridge 12868 or staple retainer where different colors indicate the presence of a different staple cartridge type, e.g., absorbable or conventional non-absorbable staple cartridge. In other aspects, the sensors 15472, 15474, 15476 may comprise a magnetic sensor, a magnetic field sensor, a strain gauge, a pressure sensor, a force sensor, an inductive sensor such as an eddy current sensor, a resistive sensor, a capacitive sensor, an optical sensor, and/or any other suitable sensor for measuring one or more parameters of the end effector 12852. The sensors 15472, 15474, 15476 may include one or more sensors. The sensors 15472, 15474, 15476 may be configured to measure forces exerted on the anvil 12866 by a closure drive system, for example. Sensors, like the sensors 15472, 15474, 15476, are further described in, for example, U.S. Patent Application Publication No. 2019/0206003, titled ADAPTIVE CONTROL PROGRAM UPDATES FOR SURGICAL DEVICES. In various aspects, the sensors 15472, 15474, 15476 may be configured to detect the type of staple cartridge 12868 loaded in the end effector 12852.

FIG. 151 illustrates a method 15000 of adaptively controlling a surgical stapling instrument 12850 based on the type of staple cartridge 12868 identified by a clinician or the control circuit 12860. As described above, the control circuit may be part of the control system 15470 including a microcontroller 15461, as described in FIG. 150. With reference to FIGS. 98, 150, and 151, the microcontroller 15461 may be programmed or configured to identify and/or distinguish different staple cartridges 12868 and adapt the operation of the surgical stapling system 12850 based on the type of staple cartridge 12868 detected. In accordance with the method 15000, a first staple cartridge may include a first set of staples made of, comprising, consisting essentially of, or consisting of a first material. The characteristics useful for detecting and identifying the first staple cartridge and its material properties may be stored in the memory 15468 for later comparison by the processor 15462 to detected staple cartridges. A second staple cartridge may include a second set of staples made of, comprising, consisting essentially of, or consisting of a second material. The characteristics useful for detecting and identifying the second staple cartridge and its material properties also may be stored in the memory 15468 for later comparison by the processor 15462 to detected staple cartridges. The first and second materials are different and have substantially different material properties. The first and second staple cartridges each comprise an identifier to identify and distinguish one staple cartridge from another staple cartridge.

With reference to FIGS. 98, 150, and 151, according to the method 15000, the staple cartridge 12868 type is identified 15002 based on a unique identifier or indicia placed on or associated with the staple cartridge 12868 or the package in which the staple cartridge 12868 is stored. The staple cartridge type may be identified by a clinician or a sensor 15472, 15474, 15476 coupled to the microcontroller 15461. The identify aspect of the difference of the first and second staple cartridges may be a visual or digital identifier. The unique identifier has the ability to be used in conjunction with the deployment surgical stapling instrument 12850 to configure 15004 the operation of the surgical stapling instrument 12850 based on the identified type of staple cartridge 12868. Once the staple cartridge 12868 has been identified 15002 by the control circuit 12860, the operation/functionality of the surgical stapling instrument 12850 is adaptively controlled 15006 by the control circuit 12860 based on the configuration 15004 of the surgical stapling instrument 12850 loaded with the identified 15002 staple cartridge type.

If the staple cartridge 12868 is identified 15002 by the clinician, the staple cartridge type may be entered or programmed into the surgical stapling instrument 12850 configured 15004 manually by the clinician. Thereafter, the operation/functionality of the surgical stapling instrument 12850 is adaptively controlled 15006 by the control circuit 12860 based on the configuration 15004 of the surgical stapling instrument 12850 loaded with the identified 15002 staple cartridge type.

Accordingly, after the staple cartridge type is identified 15002 and the surgical stapling instrument 12850 is configured 15004 according to the identified 15002 staple cartridge type, the control circuit 12860 adaptively controls 15006 the speed, wait periods, load forces, closure forces, and/or firing forces, among other operations/functionalities of the surgical stapling instrument 12850, based on the identified type of staple cartridge 12868. In accordance with this disclosure, the surgical stapling instrument 12850 may be a handheld surgical stapling instrument or a robotic surgical stapling instrument. In instances where the surgical stapling instrument 12850 determines the type of staple cartridge 12868 being employed based on readings from a variety of sensors 12888, the control circuit 12860 may be configured to determine the staple cartridge type and adaptively clamp the anvil 12866 and fire the I-beam 12864/E-beam of the surgical stapling instrument 12850 based on the type of staple cartridge 12868 detected by the sensors 12888, clinicians, or other means of detecting the type of staple cartridge 12868 loaded in the end effector 12852.

With continued reference to FIGS. 98, 150, and 151, according to the method 15000, aspects of the present disclosure are generally directed to adaptively clamping the anvil 12866 and firing the I-beam 12864/E-beam of the surgical stapling instrument 12850 based on the type of staple cartridge 12868 being used in the end effector 12852. Stainless steel or titanium staples may need different forces (e.g., current) to fire the I-beam 12864 and hold the jaws of the end effector 12852 in position as compared to magnesium or zinc staples, for example. As described generally above, the end effector 12852 comprises a first jaw and a second jaw. The first jaw comprises the staple cartridge 12868 and the second jaw comprises the anvil 12866, for example. The firing speed of the surgical stapling instrument 12850 also may be adaptively controlled by the control circuit 12860 though the motor control circuit 12858, motor 12854, and transmission elements 12856 coupled to the I-beam 12864. For example, magnesium, zinc, or coated staples may have to be fired at a slower speed to avoid cracking the staples. In various aspects, the present disclosure also provides techniques for the surgical stapling instrument 12850, or at least the clinician, to determine the type of staple cartridge 12868 is being used in the surgical stapling instrument 12850. The determination may occur before, during, or after inserting the staple cartridge 12868 in the end effector 12852. The reader may appreciate that although the packaging storing the staple cartridge 12868 prior to use may identify the type of staple cartridge 12868 as magnesium, zinc, or stainless steel, for example, once the staple cartridge 12868 is removed from the packaging, the type of staple cartridges 12868 may be substantially indistinguishable to the untrained eye. Therefore, there is a need to identify the type of staple cartridge 12868 before, during, and after inserting the staple cartridge 12868 in the end effector 12852.

With continued reference to FIGS. 98, 150, and 151, according to the method 15000, aspects of the present disclosure are generally directed to intuitively indicating absorbable staples relative to non-absorbable staples. The indication may be provided on the staple cartridge 12868 itself, as part of the staple retainer 14310 shown in FIG. 114, as part of the residual staple lines themselves, and/or as part of the packaging such as sterile container 14320, shown in FIG. 116, for example. In some aspects, the indication may be provided in the form of tissue staining or releasable tissue dye that colors the surrounding tissue but not the staples themselves. In other aspects, the surgical stapling instrument 12850 provides feedback on which staple cartridge 12868 was fired.

In one aspect, the indication may be provided on the staple cartridge 12868 itself. In one implementation, an absorbable staple cartridge identification may be provided on the body of the staple cartridge 12868. For example, on the elongate body portion 14312 of staple retainer 14312 of surgical staple cartridge 14200, as shown in FIG. 119, for example. Returning to the block diagram of a surgical stapling instrument 12850 shown in FIG. 98, in one aspect, a combination of indicators may be employed to enable positive identification of the staple cartridge type by a clinician, such as, for example, a circulating nurse (packaging indicator), scrub nurse/surgical tech (staple cartridge/staple retainer indicator), and surgeon (cartridge or staple line indicator). Consistency amongst the different types of staple cartridge 12868 indicators facilitates positive identification of a staple cartridge type located in or out of its original packaging. For example, a unique color "racing stripe" incorporated or integrated with the staple cartridge packaging, staple retainer clip, cartridge, and/or staple line may be employed to identify whether the staple cartridge 12868 comprises absorbable or non-absorbable staples. In another example, the middle row of a staple line can be anodized to provide a visually distinctive color, e.g., a distinct darker gray color, of metal to distinguish an absorbable staple from a non-absorbable staple and thus identify the staple cartridge type.

In another aspect, a staple cartridge type, e.g., absorbable or non-absorbable staple cartridge, identification indication may be presented to the users before the deployment of the staples. In one example, a metallic dot or indicator may be situated at the distal end of the staple cartridge 12868 to provide a shiny appearance set against the rest of the staple cartridge 12868. In another example, the color of the staple cartridge 12868 may distinguish an absorbable staple cartridge from a non-absorbable staple cartridge. For example, a plastic body portion of the staple cartridge 12868 may include a sparkly glitter to identify an absorbable staple cartridge, for example. In another example, text or image may be provided on the staple cartridge 12868 to identify an absorbable type staple cartridge 12868. The text or image may be formed by laser marking to etch a racing stripe along the length of the staple cartridge 12868, etch text on the tip of the staple cartridge 12868 such as "Mg" or "AB", or etch an image on the tip of the staple cartridge 12868. The text or image may be formed by raised plastic on the staple cartridge 12868. The text or image also may be provided on the staple cartridge metal pan 14290, as shown in FIG. 119, for example.

In another example, gripping surface technology (GST) bumps may be configured differently enough to enable visually identification of the absorbable staple cartridge. The GST bumps may be formed from the outer row extent to the edge of the staple cartridge, may connect lateral rows, or connect longitudinal pockets. No GST bumps may be provided on proximal-most pockets to identify an absorbable type staple cartridge. A GST gripping pattern may be provided distal of pockets to hold tissue distal of the staple line. In another example, installation of a staple cartridge may provide an indication that the staple cartridge is different from a conventional staple cartridge. The indication may be audible or tactile. In another example, the identification may be provided by a different staple retainer such a different colors, text, or symbols. Text or symbols may be provided on the anvil or shaft. The color of the staple cartridge or a color change on the plastic on the proximal end of the shaft may be used to identify the staple cartridge type. In view of the above, providing the absorbable staple cartridge identification indication to the users before the deployment of the staples may drive use changes for the surgical stapling instrument 12850 shown in FIG. 98. For example, the indication could include images of combinations that contraindicate like adjuncts that would interact poorly with the absorbable staples. Highly acidic pH exuding adjuncts could decrease the longevity of the absorbable staple prematurely. Accordingly, if these were noted, the adjunct and the staple cartridge could have icons that indicate the acceptability of using them together or not. In another aspect, the absorbable staple cartridge identification indication may be provided to the users after the deployment of the staples. In one example, post deployment indication may include providing different color drivers as contrasted with the GST.

In yet another aspect, the absorbable staple cartridge identification indication may be provided to the surgical stapling instrument 12850 or digital assistant. In one example, electronic communication means may be employed to uniquely identify the staple cartridge 12868 to the surgical stapling instrument 12850. This may include staple cartridge color, staple material, staple wire thickness, integrated adjunct, and the fired status of the staple cartridge. The electronic communication may be in the form of a radio frequency identification (RFID) circuit. Alternatively, electronic communication means may located on the staple cartridge or staple retainer while also having a feature in the staple retainer inhibits removal before insertion. Integration of an RFID circuit into a staple cartridge or staple retainer is described in commonly owned U.S. Pat. No. 11,229,437 and U.S. Patent Application Ser. No. 17/186,269, each of which is herein incorporated by reference in its entirety. In another example, an integrated circuit ("chip") may be incorporated or integrated in the staple cartridge to tell the surgical stapling instrument 12850 that the staple cartridge type is absorbable, for example. The surgical stapling instrument 12850 may require acknowledgment of the staple cartridge type before firing. In another example, a capacitive or resistance element may be incorporated or integrated into the staple cartridge which can be read by the control circuit 12860 of the surgical stapling instrument 12850. Each of the staple cartridges has a distinctly different mean value of capacitance or resistance such that the staple cartridge type can be easily distinguished electrically by monitoring the measured value of capacitance and resistance across electrical contacts in the staple cartridge. In another example, the end effector 12852 or the digital hub may comprise a light sensor (laser, optical light, etc.) to "read" a pre-defined location of the staple cartridge 12868 to identify the staple cartridge type.

In another aspect, an absorbable staple cartridge identification indication may be provided as part of the staple retainer. In one implementation, the absorbable staple cartridge identification is provided on the staple retainer. In one example, the absorbable staple cartridge may be identified on the staple retainer by the color of the staple retainer, which may be clear or translucent. In another example, the absorbable staple cartridge may be identified by text on the staple retainer, such as "Absorbable," which may be laser marked or in raised plastic. In another example, a vertical fin may be added to the staple retainer and text or symbols may be added to the fin. In another example, the absorbable staple cartridge may be identified by an image on the staple retainer that may be laser marked or pad printed and may include an image of a staple or the text "Mg," for example, or other symbol identifying the staple cartridge type as absorbable or non-absorbable. In another example, a staple cartridge type (e.g., absorbable or non-absorbable) may be identified by a light emitting diode (LED) added to the staple retainer. In another example, a staple cartridge type (e.g., absorbable or non-absorbable) may be identified by a quick response (QR) code. The QR code may be read by a smart phone (sterile nurse holds the staple cartridge up and non-sterile nurse reads code with the phone) and identifies the staple cartridge type. The QR code may be read by a code reader in the sterile filed and linked to a surgical hub, which tells the user the staple cartridge type.

In another example, a staple cartridge type (e.g., absorbable or non-absorbable) may be identified by a staple retainer that can be removed in a different way. Several two step methods may be employed to accomplish this task. In a first two step method, a first step includes snapping the staple cartridge into the surgical stapling instrument and using a tool in the packaging to remove the retainer. In a second two step method, a first step includes snapping the staple cartridge into the surgical stapling instrument and twisting off the retainer. In a third two step method, a first step includes snapping the staple cartridge into the surgical stapling instrument and pressing releases on top of the retainer to release from the surgical stapling instrument. In a fourth two step method, a moisture resistant or desiccant based adhesive film is applied between the staple cartridge deck and the staple retainer clip with the adhesive portion facing the staple cartridge deck requires an additional step prior to firing of removing the film after removing the staple retainer clip. Thus, a first step includes removing the staple retainer clip and a second step includes removing the protective film. In one example, the film can be transparent with a tongue section at the distal end of the staple cartridge that is a different color to indicate where to pull to remove. The film can be a translucent color different than the staple cartridge or staple retainer to provide contract and awareness of the presence of the film. Alternatively, the staple retainer at the bottom of staple cartridge (in addition to the staple retainer on top of the staple cartridge) has to be removed before the staple cartridge can be installed into surgical stapling instrument 12850 that makes user acknowledge the difference in staple cartridges.

In another aspect, the indication of the staple cartridge type (e.g., absorbable or non-absorbable) is provided as part of the packaging. In one example, an absorbable staple cartridge may be packaged in a moisture proof package, which looks different than a traditional staple cartridge package. The absorbable staple cartridge may be located in a reload tube within a foil pouch or foil pack. In another example, an absorbable staple cartridge package may be configured to give an audible signal when touched or opened to indicate the staple cartridge type.

In other aspects, the surgical stapling instrument 12850 provides feedback on which staple cartridge 12868 was fired. In one implementation, the staple cartridge type identification (e.g., absorbable or non-absorbable) is provided via surgical stapling instrument 12850 feedback. For example, the surgical stapling instrument 12850 may be configured to read an identification of the staple cartridge type either directly or through another device (e.g., surgical hub) and gives the user audible, visual, or haptic feedback that differs from that given during firing of a durable (non-absorbable) staple line as compared to an absorbable staple line.

With continued reference to FIGS. 98, 150, and 151, according to the method 15000, aspects of the present disclosure are generally directed to preventing incompatibility of operation of the surgical stapling instrument 12850 or the surgical procedure based on the identified 15002 staple cartridge type. In various implementations, the method comprises preventing insertion of an incompatible staple cartridge into the surgical stapling instrument 12850. In one example, this technique may utilize a poka-yoke staple cartridge and channel, as described herein. In another implementation, the method comprises preventing the closure of the anvil 12866 in the clamped state of an incompatible staple cartridge 12868 in the end effector 12852. In yet another implementation, the method comprises preventing energization of a powered firing system (e.g., motor control circuit 12858, motor 12854, and transmission 12856) if an incompatible staple cartridge 12868nis inserted in the end effector 12852. In yet another implementation, the method comprises locking-out the firing member, sled, or prevent I-beam 12864/E-beam advancement when an incompatible staple cartridge 12868 is inserted in the end effector 12854. In yet another implementation, the method comprises preventing retraction of the I-beam 12864/E-beam or unclamping until confirmation from the user of the presence of the presence of just deployed absorbable staples.

With continued reference to FIGS. 98, 150, and 151, according to the method 15000, aspects of the present disclosure are generally directed to adapting the use-case of the surgical stapling instrument 12850 if the use of the staples/staple cartridges require modification or adaptation of the surgical stapling instrument 12850. In one implementation, the method comprises pre-coating the anvil 12866 to minimize staple metal depositing. In another implementation, the method comprises controlling or minimizing part of the staple cartridge 12868 for inadvertent contact with the tissue or patient.

With continued reference to FIGS. 98, 150, and 151, according to the method 15000, aspects of the present disclosure are generally directed to indicating special waste stream, disposal, or lifecycle pathways of the staple cartridge 12868 based on the identified 15002 based on the identified staple cartridge type. In one implementation, the method provides determining inadvertent exposure to exceeding functional limits of the degradation or shelf life of the staple cartridge 12868. In another implementation, the method provides indicating the magnitude of the amount of absorption or shelf life left in the staple cartridge 12868. In yet another implementation, the method provides indicating the magnitude of the effect on staple strength based on life or environmental exposure of the staple cartridge 12868.

With continued reference to FIGS. 98, 150, and 151, according to the method 15000, aspects of the present disclosure are generally directed to identifying the introduction of an absorbable staple cartridge type within a smart powered device, such as the surgical stapling instrument 12850, and the control circuit 12860 adjusting the functionality of the surgical stapling instrument 12850 including, for example, clamping, firing rate, and/or algorithms to pause firing based on the detection or introduction of an absorbable staple cartridge. In one implementation, the rate of firing absorbable staples may be slower or the pauses may be longer than firing traditional staples in order to limit the strain rate on the absorbable staples, its protecting coating, or to minimize lateral or longitudinal tissue flow to limit tangential forces on the softer absorbable staple wire as it is being deployed. Several examples of adjusting the functionality of the surgical stapling instrument 12850 include reducing cracking of the absorbable staple wire and coatings to reduce coating cracking by adjusting the rate of firing, increasing the elasticity of the absorbable staple, and reducing the local strain. In other examples, the method comprises reducing tissue flow in the end effector 12852 and thereby reducing tangential loading that would have a greater bending or deflecting impact as compared to traditional stainless steel (SS) or titanium, (Ti) staples.

With continued reference to FIGS. 98, 150, and 151, according to the method 15000, aspects of the present disclosure are generally directed to adapting the limits or operation/functionality of algorithms executed by the control circuit 12860 for the motor powered surgical stapling instrument 12850 based on the combined use of a magnesium staple cartridge with the powered surgical stapling instrument 12850. In one aspect, the powered surgical stapling instrument 12850 may be adapted and configured to detect or determine the use of an absorbable alloy staple cartridge, such as magnesium, for example, with various sensors 12888 on the surgical stapling instrument 12850. Once the use of an absorbable staple cartridge is determined, the presence of such absorbable cartridge can be communicated to the powered surgical stapling instrument 12850 or surgical hub system. As used herein, a powered surgical stapling instrument 12850 or system may be a handheld surgical stapling instrument or a robotic surgical stapling instrument. In either case, the powered surgical stapling instrument 12850 comprises communications and control circuits 12860 configured to detect the type of staple cartridge currently employed, communicate the staple cartridge information, and configure the operation of the powered surgical stapling instrument 12850 based on the detected staple cartridge type.

In various implementations, one of the sensors 12888 may be a RFID circuit incorporated or integrated in the staple cartridge 12868 to identify the type of staple cartridge 12868 loaded in the end effector 12852. The staple cartridge type may be determined and/or communicated by the RFID circuit and read by the control circuit 12860 of the powered surgical stapling instrument 12850. In other examples, the sensors 12888 may include resistors incorporated or integrated on a side of the staple cartridge 12868 where the resistances are read by the control circuit 12860 of the powered surgical stapling instrument 12850 and where different resistance values indicate the presence of different staple cartridge types, e.g., absorbable or conventional non-absorbable staple cartridge. In other examples, the sensors 12888 may include an optical sensor incorporated or integrated in the staple cartridge 12868 to detect the color of the staple cartridge 12868 or staple retainer where different colors indicate the presence of a different staple cartridge type, e.g., absorbable or conventional non-absorbable staple cartridge. In another example, the staple cartridge 12868 may be scanned (e.g., the packaging or on the staple cartridge itself) to identify the staple cartridge type and the information may be communicated to the control circuit 12860 of the powered surgical stapling instrument 12850 or surgical hub system. Accordingly, the functionality or behavior of the powered surgical stapling instrument 12850 changes based on the staple cartridge type code read by the control circuit 12850.

In various implementations, the identification of the staple cartridge 12850 may be determined by detecting an absorbable cartridge, such as, for example, a magnesium staple cartridge, through a mechanical interaction. In one example, the absorbable cartridge may be detected as the I-beam 12864 knife breaks through a barrier that causes a force spike that is detected by the current sensor 12886 of the surgical stapling instrument 12850. In another example, the absorbable staple cartridge may be detected by punch card style holes read by micro-switches in the end effector 12852. In yet another example, the absorbable cartridge may be detected by differentiating the material that the staple cartridge pan is made of. For example, a titanium staple cartridge has a steel ferromagnetic pan while a magnesium staple cartridge has non-ferromagnetic pan (e.g., aluminum, austenitic stainless steel, plastic, or titanium). The surgical stapling instrument 12850 comprises sensors 12888 configured to sense the ferromagnetic or non-ferromagnetic properties of the staple cartridge pan to determine whether the staple cartridge 12868 contains absorbable or non-absorbable staples. In some examples, steel ball bearings may be used for detection purposes. In yet another example, a second retention bump for the sled may used by the surgical stapling instrument 12850 to sense the presence or absence of absorbable or non-absorbable staple cartridges.

In another aspect, the surgical stapling instrument 12850 may be adapted and configured to drive improved operation. In one implementation, the surgical stapling instrument 12850 may be configured to operate at different adaptive firing speeds based on the type of staple cartridge 12868 loaded in the end effector 12852. For example, the surgical stapling instrument 12850 may be configured to fire at slower overall speeds, control the firing speed based on closure load and/or speed, fire at slower speed in thicker tissue, fire at faster speed in thinner tissue, and/or adjust firing speeds based on wait time between anvil closure and firing. In another example, the surgical stapling instrument may be configured with more aggressive adjustments by an algorithm when a trigger is reached to slow the firing speed. The speed reduction is greater when the staples are strain rate sensitive (e.g., magnesium alloy). In a first example, a surgical stapling instrument 12850 configured with three firing speeds where the first is a top speed, the second is a middle speed, and the third is a slow speed may be configured with adaptive firing speeds based on reload cartridge type. When the surgical stapling instrument 12850 operating at the first speed reaches a current (e.g., force) trigger, as measured by the current sensor 12886, signaling it to slow down, a second speed is adopted that is slower when the staple cartridge 12868 is identified to have absorbable staples, e.g., magnesium alloy staples, as compared to a staple cartridge comprising conventional staples, e.g., titanium alloy staples. In a second example, a surgical stapling instrument 12850 configured to pause when it reaches a current (e.g., force) threshold, as measured by the current sensor 12886, may be configured to extend the length of a pause when the staple cartridge 12886 comprises absorbable staples, e.g., magnesium alloy staples, as compared to a staple cartridge comprising non-absorbable staples, e.g., titanium alloy staples.

In various other examples, the surgical stapling instrument 12850 may be adapted and configured to operate at different anvil 12866 closure speeds based on staple cartridge type and/or different anvil 12866 powered closure force based on staple cartridge type. In addition, the surgical stapling instrument 12850 may be adapted and configured to operate with a variable adaptable time between anvil 12886 closure and firing to provide the surgeon with the staple cartridge 12868 type information or apply a force wait period based on the staple cartridge type. The surgical stapling instrument 12850 may be adapted and configured with a variable amount of time that the jaws are held closed after firing is complete, again, to provide the surgeon with the staple cartridge type information or apply a forced wait period based on the staple cartridge type. Finally, the surgical stapling instrument 12850 may be adapted and configured to calculate tissue thickness based on force to close information.

The surgical instrument systems described herein have been described in connection with the deployment and deformation of staples; however, the embodiments described herein are not so limited. Various embodiments are envisioned which deploy fasteners other than staples, such as clamps or tacks, for example. Moreover, various embodiments are envisioned which utilize any suitable means for sealing tissue. For instance, an end effector in accordance with various embodiments can comprise electrodes configured to heat and seal the tissue. Also, for instance, an end effector in accordance with certain embodiments can apply vibrational energy to seal the tissue.

EXAMPLES

Example 1

A surgical staple cartridge comprising a cartridge body comprising a base, a deck, a longitudinal slot defined in the deck, and staple cavities defined in the deck. The surgical staple cartridge further comprises staples removably stored in the staple cavities, wherein the staples are comprised of a magnesium-based alloy, and wherein the magnesium-based alloy is configured to accelerate corrosion of the staples.

Example 2

A surgical staple cartridge comprising a cartridge body comprising a base, a deck, a longitudinal slot defined in the deck, and staple cavities defined in the deck. The surgical staple cartridge further comprises staples removably stored in the staple cavities, wherein the staples are comprised of a zinc-based alloy, and wherein the zinc-based alloy is configured to accelerate corrosion of the staples.

Example 3

A surgical staple cartridge assembly comprising a cartridge body comprising a base, a deck, a longitudinal slot defined in the deck, and staple cavities defined in the deck. The surgical staple cartridge assembly further comprises staples removably stored in the staple cavities, wherein the staples are deployable from the staple cavities into tissue of a patient, and wherein the staples are comprised of a magnesium-based alloy. The surgical staple cartridge assembly further comprises a buttress, wherein the staples are configured to hold the buttress to the tissue, and wherein the buttress is comprised of an absorbable polymer and a calcification inhibitor.

Example 4

A surgical staple cartridge comprising a cartridge body comprising a base, a deck, a longitudinal slot defined in the deck, and staple cavities defined in the deck. The surgical staple cartridge further comprises staples removably stored in the staple cavities, wherein the staples are deployable from the staple cavities into tissue of a patient, wherein the staples are comprised of a magnesium-based alloy, and wherein the staples comprise a coating comprised of an absorbable polymer and a calcification inhibitor.

Example 5

A surgical staple cartridge comprising a cartridge body comprising a base, a deck, a longitudinal slot defined in the deck, and staple cavities defined in the deck. The surgical staple cartridge further comprises staples removably stored in the staple cavities, wherein the staples are deployable from the staple cavities into tissue of a patient, wherein the staples are comprised of a magnesium-based alloy, and wherein the staples comprise hollow staples defining a recess therein.

Example 6

The surgical staple cartridge of Example 5, further comprising a filler positioned in the recess, wherein the filler is configured to mitigate a physiological response within the patient.

Example 7

A surgical staple cartridge comprising a cartridge body comprising a base, a deck, a longitudinal slot defined in the deck, and staple cavities defined in the deck. The surgical staple cartridge further comprises staples removably stored in the staple cavities, wherein the staples are deployable from the staple cavities into tissue of a patient, wherein the staples are comprised of a magnesium-based alloy, and wherein an alloying element of the magnesium-based alloy is selected to lower an electrode potential of the staples.

Example 8

The surgical staple cartridge of Example 7, wherein the alloying element comprises lithium.

Example 9

A surgical staple cartridge comprising a cartridge body comprising a base, a deck, a longitudinal slot defined in the deck, and staple cavities defined in the deck. The surgical staple cartridge further comprises staples removably stored in the staple cavities, wherein the staples are deployable from the staple cavities into tissue of a patient, wherein the staples are comprised of a magnesium-based alloy, and wherein an alloying element of the magnesium-based alloy is selected to accelerate anodic corrosion of magnesium of the magnesium-based alloy.

Example 10

The surgical staple cartridge of Example 9, wherein the alloying element comprises iron.

Example 11

The surgical staple cartridge of Examples 9 or 10, wherein the alloying element comprises zinc.

Example 12

A surgical staple cartridge comprising a cartridge body comprising a base, a deck, and a staple cavity defined in the deck. The surgical staple cartridge further comprises a staple removably stored in the staple cavity, wherein at least a portion of the staple is coated in Fetuin A.

Example 13

The surgical staple cartridge of Example 12, wherein the staple is comprised of a magnesium alloy.

Example 14

The surgical staple cartridge of Example 12, wherein the staple is comprised of a zinc alloy.

Example 15

The surgical staple cartridge of any one of Examples 12-14, wherein the Fetuin A is infused in a polymer coating on the staple.

Example 16

A surgical staple cartridge comprising a cartridge body comprising a base, a deck, and a staple cavity defined in the deck. The surgical staple cartridge further comprises a staple removably stored in the staple cavity, wherein at least a portion of the staple is coated by one or more proteins.

Example 17

The surgical staple cartridge of Example 16, wherein the staple is comprised of a magnesium alloy.

Example 18

The surgical staple cartridge of Example 16, wherein the staple is comprised of a zinc alloy.

Example 19

The surgical staple cartridge of any one of Examples 16-18, wherein the proteins are infused in a polymer coating on the staple.

Example 20

A surgical staple cartridge comprising a cartridge body comprising a base, a deck, and a staple cavity defined in the deck. The surgical staple cartridge further comprises a staple removably stored in the staple cavity, wherein at least a portion of the staple is coated in citrate.

Example 21

The surgical staple cartridge of Example 20, wherein the staple is comprised of a magnesium alloy.

Example 22

The surgical staple cartridge of Example 20, wherein the staple is comprised of a zinc alloy.

Example 23

The surgical staple cartridge of any one of Examples 20-22, wherein the citrate is infused in a polymer coating on the staple.

Example 24

A surgical staple cartridge comprising a cartridge body comprising a base, a deck, and a staple cavity defined in the deck. The surgical staple cartridge further comprises a staple removably stored in the staple cavity, wherein at least a portion of the staple is coated in a chelating agent.

Example 25

The surgical staple cartridge of Example 24, wherein the staple is comprised of a magnesium alloy.

Example 26

The surgical staple cartridge of Example 24, wherein the staple is comprised of a zinc alloy.

Example 27

The surgical staple cartridge of any one of Examples 24-26, wherein the chelating agent is infused in a polymer coating on the staple.

Example 28

A surgical staple cartridge comprising a cartridge body comprising a base, a deck, and a staple cavity defined in the deck. The surgical staple cartridge further comprises a staple removably stored in the staple cavity, wherein at least a portion of the staple is coated in phytic acid.

Example 29

The surgical staple cartridge of Example 28, wherein the staple is comprised of a magnesium alloy.

Example 30

The surgical staple cartridge of Example 28, wherein the staple is comprised of a zinc alloy.

Example 31

The surgical staple cartridge of any one of Examples 28-30, wherein the phytic acid is infused in a polymer coating on the staple.

Example 32

A surgical staple cartridge comprising a cartridge body comprising a base, a deck, and a staple cavity defined in the deck. The surgical staple cartridge further comprises a staple removably stored in the staple cavity, wherein at least a portion of the staple is coated in pyrophosphate.

Example 33

The surgical staple cartridge of Example 32, wherein the staple is comprised of a magnesium alloy.

Example 34

The surgical staple cartridge of Example 32, wherein the staple is comprised of a zinc alloy.

Example 35

The surgical staple cartridge of any one of Examples 32-34, wherein the pyrophosphate is infused in a polymer coating on the staple.

Example 36

A surgical staple cartridge comprising a cartridge body comprising a base, a deck, and a staple cavity defined in the deck. The surgical staple cartridge further comprises a staple removably stored in the staple cavity, wherein at least a portion of the staple is coated in a bisphosphonate.

Example 37

The surgical staple cartridge of Example 36, wherein the staple is comprised of a magnesium alloy.

Example 38

The surgical staple cartridge of Example 36, wherein the staple is comprised of a zinc alloy.

Example 39

The surgical staple cartridge of any one of Examples 36-38, wherein the bisphosphonate is infused in a polymer coating on the staple.

Example 40

A surgical staple cartridge comprising a cartridge body comprising a base, a deck, and a staple cavity defined in the deck. The surgical staple cartridge further comprises a staple removably stored in the staple cavity, wherein at least a portion of the staple is coated in a polyphosphate.

Example 41

The surgical staple cartridge of Example 40, wherein the staple is comprised of a magnesium alloy.

Example 42

The surgical staple cartridge of Example 40, wherein the staple is comprised of a zinc alloy.

Example 43

The surgical staple cartridge of any one of Examples 40-42, wherein the polyphosphate is infused in a polymer coating on the staple.

Example 44

A surgical staple cartridge comprising a cartridge body comprising a base, a deck, and a staple cavity defined in the deck. The surgical staple cartridge further comprises a staple removably stored in the staple cavity, wherein at least a portion of the staple is coated in a co-polymer of acrylic acid.

Example 45

The surgical staple cartridge of Example 44, wherein the staple is comprised of a magnesium alloy.

Example 46

The surgical staple cartridge of Example 44, wherein the staple is comprised of a zinc alloy.

Example 47

A surgical staple cartridge comprising a cartridge body comprising a base, a deck, and a staple cavity defined in the deck. The surgical staple cartridge further comprises a staple removably stored in the staple cavity, wherein at least a portion of the staple is coated in a polycarboxylic acid.

Example 48

The surgical staple cartridge of Example 47, wherein the staple is comprised of a magnesium alloy.

Example 49

The surgical staple cartridge of Example 47, wherein the staple is comprised of a zinc alloy.

Example 50

The surgical staple cartridge of any one of Examples 47-49, wherein the polycarboxylic acid is infused in a polymer coating on the staple.

Example 51

A surgical staple cartridge comprising a cartridge body comprising a base, a deck, and a staple cavity defined in the deck. The surgical staple cartridge further comprises a staple removably stored in the staple cavity, wherein at least a portion of the staple is coated in a polymer coating.

Example 52

The surgical staple cartridge of Example 51, wherein the staple is comprised of a magnesium alloy.

Example 53

The surgical staple cartridge of Example 51, wherein the staple is comprised of a zinc alloy.

Example 54

The surgical staple cartridge of any one of Examples 51-53, wherein the polymer coating is comprised of at least one of PLA, PLGA, and PGA.

Example 55

A surgical staple cartridge comprising a cartridge body comprising a base, a deck, and a staple cavity defined in the deck. The surgical staple cartridge further comprises a staple removably stored in the staple cavity, wherein at least a portion of the staple is coated in osteopontin.

Example 56

The surgical staple cartridge of Example 55, wherein the staple is comprised of a magnesium alloy.

Example 57

The surgical staple cartridge of Example 55, wherein the staple is comprised of a zinc alloy.

Example 58

The surgical staple cartridge of any one of Examples 55-57, wherein the osteopontin is infused in a polymer coating on the staple.

Example 59

A surgical staple cartridge comprising a cartridge body comprising a base, a deck, and a staple cavity defined in the deck. The surgical staple cartridge further comprises a staple removably stored in the staple cavity, wherein at least a portion of the staple is coated in magnesium ions.

Example 60

The surgical staple cartridge of Example 59, wherein the staple is comprised of a magnesium alloy.

Example 61

The surgical staple cartridge of Example 59, wherein the staple is comprised of a zinc alloy.

Example 62

The surgical staple cartridge of any one of Examples 59-61, wherein the magnesium ions are infused in a polymer coating on the staple.

The entire disclosures of:

U.S. Pat. No. 5,403,312, entitled ELECTROSURGICAL HEMOSTATIC DEVICE, which issued on Apr. 4, 1995;

U.S. Pat. No. 7,000,818, entitled SURGICAL STAPLING INSTRUMENT HAVING SEPARATE DISTINCT CLOSING AND FIRING SYSTEMS, which issued on Feb. 21, 2006;

U.S. Pat. No. 7,422,139, entitled MOTOR-DRIVEN SURGICAL CUTTING AND FASTENING INSTRUMENT WITH TACTILE POSITION FEEDBACK, which issued on Sep. 9, 2008;

U.S. Pat. No. 7,464,849, entitled ELECTRO-MECHANICAL SURGICAL INSTRUMENT WITH CLOSURE SYSTEM AND ANVIL ALIGNMENT COMPONENTS, which issued on Dec. 16, 2008;

U.S. Pat. No. 7,670,334, entitled SURGICAL INSTRUMENT HAVING AN ARTICULATING END EFFECTOR, which issued on Mar. 2, 2010;

U.S. Pat. No. 7,753,245, entitled SURGICAL STAPLING INSTRUMENTS, which issued on Jul. 13, 2010;

U.S. Pat. No. 8,393,514, entitled SELECTIVELY ORIENTABLE IMPLANTABLE FASTENER CARTRIDGE, which issued on Mar. 12, 2013;

U.S. patent application Ser. No. 11/343,803, entitled SURGICAL INSTRUMENT HAVING RECORDING CAPABILITIES, now U.S. Pat. No. 7,845,537;

U.S. patent application Ser. No. 12/031,573, entitled SURGICAL CUTTING AND FASTENING INSTRUMENT HAVING RF ELECTRODES, filed Feb. 14, 2008;

U.S. patent application Ser. No. 12/031,873, entitled END EFFECTORS FOR A SURGICAL CUTTING AND STAPLING INSTRUMENT, filed Feb. 15, 2008, now U.S. Pat. No. 7,980,443;

U.S. patent application Ser. No. 12/235,782, entitled MOTOR-DRIVEN SURGICAL CUTTING INSTRUMENT, now U.S. Pat. No. 8,210,411;

U.S. patent application Ser. No. 12/235,972, entitled MOTORIZED SURGICAL INSTRUMENT, now U.S. Pat. No. 9,050,083.

U.S. patent application Ser. No. 12/249,117, entitled POWERED SURGICAL CUTTING AND STAPLING APPARATUS WITH MANUALLY RETRACTABLE FIRING SYSTEM, now U.S. Pat. No. 8,608,045;

U.S. patent application Ser. No. 12/647,100, entitled MOTOR-DRIVEN SURGICAL CUTTING INSTRUMENT WITH ELECTRIC ACTUATOR DIRECTIONAL CONTROL ASSEMBLY, filed Dec. 24, 2009, now U.S. Pat. No. 8,220,688;

U.S. patent application Ser. No. 12/893,461, entitled STAPLE CARTRIDGE, filed Sep. 29, 2012, now U.S. Pat. No. 8,733,613;

U.S. patent application Ser. No. 13/036,647, entitled SURGICAL STAPLING INSTRUMENT, filed Feb. 28, 2011, now U.S. Pat. No. 8,561,870;

U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535;

U.S. patent application Ser. No. 13/524,049, entitled ARTICULATABLE SURGICAL INSTRUMENT COMPRISING A FIRING DRIVE, filed on Jun. 15, 2012, now U.S. Pat. No. 9,101,358;

U.S. patent application Ser. No. 13/800,025, entitled STAPLE CARTRIDGE TISSUE THICKNESS SENSOR SYSTEM, filed on Mar. 13, 2013, now U.S. Pat. No. 9,345,481;

U.S. patent application Ser. No. 13/800,067, entitled STAPLE CARTRIDGE TISSUE THICKNESS SENSOR SYSTEM, filed on Mar. 13, 2013, now U.S. Patent Application Publication No. 2014/0263552;

U.S. Patent Application Publication No. 2007/0175955, entitled SURGICAL CUTTING AND FASTENING INSTRUMENT WITH CLOSURE TRIGGER LOCKING MECHANISM, filed Jan. 31, 2006; and U.S. Patent Application Publication No. 2010/0264194, entitled SURGICAL STAPLING INSTRUMENT WITH AN ARTICULATABLE END EFFECTOR, filed Apr. 22, 2010, now U.S. Pat. No. 8,308,040, are hereby incorporated by reference herein.

The entire disclosures of:

U.S. Provisional Patent Application Ser. No. 63/186,519, entitled ABSORBABLE METAL STAPLE, filed on May 10, 2021;

U.S. patent application Ser. No. 15/621,572, entitled SURGICAL STAPLER WITH CONTROLLED HEALING, filed Jun. 13, 2017;

U.S. Pat. No. 10,569,071, entitled MEDICANT ELUTING ADJUNCTS AND METHODS OF USING MEDICANT ELUTING ADJUNCTS, which issued on Feb. 25, 2020;

U.S. Pat. No. 9,561,308, entitled BIODEGRADABLE COMPOSITE WIRE FOR MEDICAL DEVICES, which issued on Feb. 7, 2017;

International Application Serial No. PCT/US2020/035731, entitled MAGNESIUM-BASED ABSORBABLE ALLOY, filed on Jun. 2, 2020;

U.S. Pat. No. 11,229,437, entitled METHOD FOR AUTHENTICATING THE COMPATIBILITY OF A STAPLE CARTRIDGE WITH A SURGICAL INSTRUMENT, which issue on Jan. 25, 2022;

U.S. patent application Ser. No. 17/186,269, entitled METHOD OF POWERING AND COMMUNICATING WITH A STAPLE CARTRIDGE, filed on Feb. 26, 2021;

U.S. Pat. No. 10,939,911, entitled SURGICAL STAPLER WITH END EFFECTOR COATING, which issued on Mar. 9, 2021;

U.S. Pat. No. 9,307,989, entitled TISSUE STAPLER HAVING A THICKNESS COMPENSATOR INCORPORATING A HYDROPHOBIC AGENT, which issued on Apr. 12, 2016;

U.S. Pat. No. 9,700,311, entitled TISSUE INGROWTH MATERIALS AND METHOD OF USING THE SAME, which issued on Jul. 11, 2017;

U.S. Pat. No. 10,390,829, entitled STAPLES COMPRISING A COVER, which issued on Aug. 27, 2019;

U.S. Pat. No. 8,365,976, entitled SURGICAL STAPLES HAVING DISSOLVABLE, BIOABSORBABLE OR BIOFRAGMENTABLE PORTIONS AND STAPLING INSTRUMENTS FOR DEPLOYING THE SAME, which issued on Feb. 5, 2013;

U.S. Patent Application Publication No. 2006/0052825, entitled SURGICAL IMPLANT ALLOY, which published on Mar. 9, 2006;

U.S. Pat. No. 7,905,902, entitled SURGICAL IMPLANT WITH PREFERENTIAL CORROSION ZONE, which issued on Mar. 15, 2011;

International Publication No. WO 2020/038800 A1, entitled IMPROVING THE POLYMER LAYER ON DEGRADABLE DEVICES, which published on Feb. 27, 2020;

U.S. Pat. No. 9,861,361, entitled RELEASABLE TISSUE THICKNESS COMPENSATOR AND FASTENER CARTRIDGE HAVING THE SAME, which issued on Jan. 9, 2018;

U.S. patent application Ser. No. 17/246,017, entitled STAPLE CARTRIDGE COMPRISING STAPLE DRIVERS AND STABILITY SUPPORTS, filed on Apr. 30, 2021;

U.S. Pat. No. 7,673,781, entitled SURGICAL STAPLING DEVICE WITH STAPLE DRIVER THAT SUPPORTS MULTIPLE WIRE DIAMETER STAPLES, which issued on Mar. 9, 2010;

U.S. Pat. No. 10,702,270, entitled STAPLING SYSTEM FOR USE WITH WIRE STAPLES AND STAMPED STAPLES, which issued on Jul. 7, 2020;

U.S. Design Patent No. D836,198, entitled STAPLE CARTRIDGE FOR A SURGICAL STAPLER, which issued on Dec. 18, 2018;

U.S. Design Patent No. D833,608, entitled STAPLING HEAD FEATURE FOR SURGICAL STAPLER, which issued on Nov. 13, 2018;

U.S. Design Patent No. D926,318, entitled SURGICAL STAPLER DECK WITH TISSUE ENGAGEMENT RECESS FEATURES, which issued on Jul. 27, 2021;

U.S. Design Patent Application Ser. No. 29/736,648, entitled STAPLE CARTRIDGE, filed on Jun. 2, 2020;

U.S. Design Patent Application Ser. No. 29/736,653, entitled STAPLE CARTRIDGE, filed on Jun. 2, 2020;

U.S. Pat. No. 9,833,241, entitled SURGICAL FASTENER CARTRIDGES WITH DRIVER STABILIZING ARRANGEMENTS, which issued on Dec. 5, 2017;

U.S. Pat. No. 9,924,944, entitled STAPLE CARTRIDGE COMPRISING AN ADJUNCT MATERIAL, which issued on Mar. 27, 2018;

U.S. Patent Application Publication Serial No. 2018/0140299 A1, entitled FASTENER CARTRIDGE COMPRISING A TISSUE THICKNESS COMPENSATOR AND A GAP SETTING ELEMENT, which published on May 24, 2018;

U.S. Pat. No. 10,098,642, entitled SURGICAL STAPLES COMPRISING FEATURES FOR IMPROVED FASTENING OF TISSUE, which issued on Oct. 16. 2018; and U.S. Pat. No. 6,978,921, entitled SURGICAL STAPLING INSTRUMENT INCORPORATING AN E-BEAM FIRING MECHANISM, which issued on Dec. 27, 2005 are incorporated by reference herein.

Although various devices have been described herein in connection with certain embodiments, modifications and variations to those embodiments may be implemented. Particular features, structures, or characteristics may be combined in any suitable manner in one or more embodiments. Thus, the particular features, structures, or characteristics illustrated or described in connection with one embodiment may be combined in whole or in part, with the features, structures or characteristics of one or more other embodiments without limitation. Also, where materials are disclosed for certain components, other materials may be used. Furthermore, according to various embodiments, a single component may be replaced by multiple components, and multiple components may be replaced by a single component, to perform a given function or functions. The foregoing description and following claims are intended to cover all such modification and variations.

The devices disclosed herein can be designed to be disposed of after a single use, or they can be designed to be used multiple times. In either case, however, a device can be reconditioned for reuse after at least one use. Reconditioning can include any combination of the steps including, but not limited to, the disassembly of the device, followed by cleaning or replacement of particular pieces of the device, and subsequent reassembly of the device. In particular, a reconditioning facility and/or surgical team can disassemble a device and, after cleaning and/or replacing particular parts of the device, the device can be reassembled for subsequent use. Those skilled in the art will appreciate that reconditioning of a device can utilize a variety of techniques for disassembly, cleaning/replacement, and reassembly. Use of such techniques, and the resulting reconditioned device, are all within the scope of the present application.

The devices disclosed herein may be processed before surgery. First, a new or used instrument may be obtained and, when necessary, cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, and/or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta radiation, gamma radiation, ethylene oxide, plasma peroxide, and/or steam.

While this invention has been described as having exemplary designs, the present invention may be further modified within the spirit and scope of the disclosure. This application is therefore intended to cover any variations, uses, or adaptations of the invention using its general principles.

What is claimed is:

1. A surgical staple cartridge assembly, comprising:

a cartridge body, comprising:

a deck;

a longitudinal slot defined in the deck; and staple cavities defined in the deck; and staples removably stored in the staple cavities, wherein the staples are deployable from the staple cavities into tissue of a patient, and wherein the staples comprise substrates comprised of metal that degrades when exposed to a degradation source in the patient, the staples comprising a first subset defining a first plurality of staples and a second subset defining a second plurality of staples; and an implantable adjunct releasably secured to the deck and comprising a first portion and a second portion, wherein the staples are configured to hold the implantable adjunct to the tissue, wherein the first portion of the implantable adjunct is configured to delay an initiation of the degradation of regions of the first subset of staples at a first degradation rate, wherein the second portion of the implantable adjunct is configured to delay an initiation of the degradation of regions of the second subset of staples at a second degradation rate, different from the first degradation rate, wherein the first portion and the second portion are configured to chemically modify a local environment surrounding the staples to control the first and second degradation rates of the staples after the initial delay, and wherein the first portion and the second portion comprise at least one of a calcification inhibitor or a chelating agent, and the chemical modification is in response to a release of the at least one of the calcification inhibitor or the chelating agent from the implantable adjunct.

2. The surgical staple cartridge assembly of claim 1, wherein the first and second portions are configured to delay the initiation of the degradation by physically shielding the regions of the metal from the degradation source.

3. The surgical staple cartridge assembly of claim 1, wherein after the initial delay, the implantable adjunct is configured to reduce mineral deposition on the staples.

4. The surgical staple cartridge assembly of claim 1, wherein the implantable adjunct comprises a bioabsorbable polymer.

5. The surgical staple cartridge assembly of claim 4, wherein a degradation of the bioabsorbable polymer changes a pH of the local environment.

6. The staple surgical cartridge assembly of claim 1, wherein the implantable adjunct preserves or increases the degradation rate of the staples after the initial delay.

7. The surgical staple cartridge assembly of claim 1, wherein the first portion and the second portion of the implantable adjunct are coplanar.

8. The surgical staple cartridge assembly of claim 1, wherein:

the first portion is configured to receive the first subset of staples;

the second portion is configured to receive the second subset of staples; and the first portion and the second extend along a longitudinal axis of the implantable adjunct; and the first portion is positioned medial to the second portion with respect to the longitudinal axis.

9. A surgical staple cartridge assembly, comprising:
a cartridge body, comprising:
a deck;
a longitudinal slot defined in the deck; and
staple cavities defined in the deck;
staples removably stored in the staple cavities, wherein the staples are deployable from the staple cavities into tissue of a patient, and wherein the staples comprise substrates comprised of metal that degrades when exposed to a degradation source in the patient; and
an implantable adjunct releasably secured to the deck, wherein the staples are configured to hold the implantable adjunct to the tissue, and wherein the implantable adjunct comprises:
a first portion configured to receive a first subset of the staples, wherein the first portion yields a first biocorrosion profile of the first subset of the staples in the patient; and
a second portion configured to receive a second subset of the staples, wherein the second portion yields a second biocorrosion profile of the second subset of the staples in the patient, and wherein the first biocorrosion profile is different than the second biocorrosion profile,
wherein the first biocorrosion profile causes a first degradation rate for the first subset of staples, and the second biocorrosion profile causes a second degradation rate for the second subset of staples, and
wherein the first portion and the second portion are configured to chemically modify a local environment surrounding the staples to control the first and second degradation rates of the staples after an initial delay.

10. The staple cartridge assembly of claim 9, wherein the first subset of staples is proximal to the second subset of staples.

11. The staple cartridge assembly of claim 9, wherein the first subset of staples defines a first row of staples, wherein the second subset of staples defines a second row of staples further away from the longitudinal slot than the first row of staples.

12. The staple cartridge assembly of claim 9, wherein the first portion yields the first biocorrosion profile by causing a first initial delay in a biocorrosion of the first subset of the staples.

13. The staple cartridge assembly of claim 12, wherein the first portion causes the first initial delay by physically shielding regions of the first subset of staples in contact with the first portion from a degradation source in the patient.

14. The staple cartridge assembly of claim 13, wherein the second portion yields the second biocorrosion profile by causing a second initial delay in a biocorrosion of the second subset of the staples, wherein the second initial delay is different than the first initial delay.

15. The staple cartridge assembly of claim 14, wherein the second portion causes the second initial delay by physically shielding regions of the second subset of staples in contact with the second portion from the degradation source in the patient.

16. The staple cartridge assembly of claim 15, wherein after the first initial delay, the first portion is configured to reduce mineral deposition on the first subset of staples.

17. The surgical staple cartridge assembly of claim 9, wherein the first portion and the second portion of the implantable adjunct are coplanar.

18. The surgical staple cartridge assembly of claim 9, wherein the first portion and the second portion comprise at least one of a calcification inhibitor or a chelating agent, and the chemical modification is in response to a release of the at least one of the calcification inhibitor or the chelating agent from the implantable adjunct.

19. The surgical staple cartridge assembly of claim 9, wherein:
the first portion and the second extend along a longitudinal axis of the implantable adjunct; and
the first portion is positioned medial to the second portion with respect to the longitudinal axis.

* * * * *